(12) United States Patent
Maddaford et al.

(10) Patent No.: US 8,173,813 B2
(45) Date of Patent: May 8, 2012

(54) QUINOLONE AND TETRAHYDROQUINOLONE AND RELATED COMPOUNDS HAVING NOS INHIBITORY ACTIVITY

(75) Inventors: Shawn Maddaford, Mississauga (CA); Jailall Ramnauth, Brampton (CA); Suman Rakhit, Mississauga (CA); Joanne Patman, Mississauga (CA); Subhash C. Annedi, Mississauga (CA); John Andrews, Mississauga (CA); Peter Dove, Toronto (CA); Sarah Silverman, Toronto (CA); Paul Renton, Toronto (CA)

(73) Assignee: NeurAxon, Inc., Mississauga (CA)

( * ) Notice: Subject to any disclaimer, the term of this patent is extended or adjusted under 35 U.S.C. 154(b) by 556 days.

(21) Appl. No.: 12/054,083

(22) Filed: Mar. 24, 2008

(65) Prior Publication Data

US 2008/0234237 A1    Sep. 25, 2008

Related U.S. Application Data

(60) Provisional application No. 60/896,829, filed on Mar. 23, 2007.

(51) Int. Cl.
C07D 215/00 (2006.01)
C07D 487/00 (2006.01)
(52) U.S. Cl. .......................... 546/158; 540/523
(58) Field of Classification Search .................. 546/158; 540/523
See application file for complete search history.

(56) References Cited

U.S. PATENT DOCUMENTS

| 4,100,278 | A | | 7/1978 | Nedelec et al. |
| 4,963,677 | A | * | 10/1990 | Sellin et al. ................ 544/247 |
| 5,854,234 | A | * | 12/1998 | Hansen et al. ............ 514/211.01 |
| 6,174,924 | B1 | * | 1/2001 | Goldin et al. ................ 514/634 |
| 7,375,219 | B2 | | 5/2008 | Maddaford et al. |
| 2006/0258721 | A1 | | 11/2006 | Maddaford et al. |
| 2008/0249302 | A1 | | 10/2008 | Maddaford et al. |

FOREIGN PATENT DOCUMENTS

| CA | 1069753 | | 1/1980 |
| CA | 1081222 | | 7/1980 |
| CA | 1169423 | | 6/1984 |
| CA | 1169428 | | 6/1984 |
| CA | 1253497 | | 5/1989 |
| CA | 2615007 | | 1/2007 |
| EP | 0322746 | * | 7/1989 |
| JP | 53073571 | | 6/1978 |
| NZ | 563191 | | 11/2009 |
| WO | WO98/23610 | | 6/1998 |
| WO | WO 02100327 | * | 12/2002 |
| WO | WO03/045313 | | 6/2003 |

(Continued)

OTHER PUBLICATIONS

Hagen et al. Journal of Medicinal Chemistry, 1998, 41, 3675-3683.*

(Continued)

*Primary Examiner* — Nizal Chandrakumar
(74) *Attorney, Agent, or Firm* — Clark & Elbing LLP

(57) ABSTRACT

The present invention features quinolones, tetrahydroquinolines, and related compounds that inhibit nitric oxide synthase (NOS), particularly those that selectively inhibit neuronal nitric oxide synthase (nNOS) in preference to other NOS isoforms. The NOS inhibitors of the invention, alone or in combination with other pharmaceutically active agents, can be used for treating or preventing various medical conditions.

17 Claims, 16 Drawing Sheets

Standard Test Method for the Chung SNL Model of Thermal Hyperalgesia

FOREIGN PATENT DOCUMENTS

WO    WO03/076405    9/2003

OTHER PUBLICATIONS

Dorwald F. A. Side Reactions in Organic Synthesis, 2005, Wiley: VCH, Weinheim p. IX of Preface p. 1-15.*
Sato et al.. STN Document No. 89:197350, Abstract of JP 53073570, Jun. 30, 1978.*
Richardson et al. Journal of Organic Chemistry (1965), 30(8), 2589-93.*
Winkelmann et al. STN Document No. 72:41258. Abstract of Arzneimittel-Forschung (1969), 19(4), 543-58.*
Wolf, Solid State Chemistry and Its Applications, john Wiley & Sons, 1984.*
Abdel-Majid et al., "Reductive Amination of Aldehydes and Ketones with Sodium Triacetoxyborohydride. Studies on Direct and Indirect Reductive Amination Procedures[1]," *J. Org. Chem.* 61(11):3849-3862, 1996.
Beletskaya and Cheprakov, "The Heck Reaction as a Sharpening Stone of Palladium Catalysis," *Chem. Rev.* 100(8):3009-3066, 2000.
Grice et al., "The SAR of 4-substituted (6,6-Bicyclic) Piperidine Cathepsin S Inhibitors," *Bioorg. Med. Chem. Lett.* 16(8):2209-2212, 2006.
Huang and Buchwald, "New Ammonia Equivalents for the Pd-Catalyzed Amination of Aryl Halides," *Org. Lett.* 3(21):3417-3419, 2001.
Ogawa et al., "Orally Active, Nonpeptide Vasopressin V1 Antagonists. A Novel Series of 1-(1-Substituted 4-Piperidyl)-3,4-Dihdyro-2(1H)-Quinolinone," *J. Med. Chem.* 36(14):2011-2017, 1993.
Richardson, "The Chemistry of 7-Aminoindoline and Certain Pyrrolo- and Pyrido [1,2,3-de]Quinoxalines," *J. Org. Chem.* 30(8):2589-2593, 1965.
Winkelmann et al., "Tuberculostatic Active N,N'-Diarylthioureas. 1," *Arzneimittelforschung* 19(4):543-558, 1969 (German).
Wolfe et al., "Simple, Efficient Catalyst System for the Palladium-Catalyzed Amination of Aryl Chlorides, Bromides, and Triflates," *J. Org. Chem.* 65(4):1158-1174, 2000.
Zaveri et al., "A Novel Series of Piperidin-4-yl-1,3-Dihydroindo1-2-ones as Agonist and Antagonist Ligands at the Nociceptin Receptor," *J. Med. Chem.* 47(12):2973-2976, 2004.
International Search Report for PCT/CA2008/000569 (mailed Jul. 11, 2008).
Examination Report from New Zealand Patent Application No. 580618, dated Oct. 1, 2010.
Written Opinion from Singapore Patent Application No. 200906309-0, mailed Sep. 30, 2010.
Extended European Search Report for European Application No. 08748081, dated Feb. 24, 2011 (6 pages).
International Preliminary Report on Patentability for International Application No. PCT/CA2008/000569, dated Sep. 29, 2009 (8 pages).

* cited by examiner

Figure 1. Standard Test Method for the Chung SNL Model of Thermal Hyperalgesia
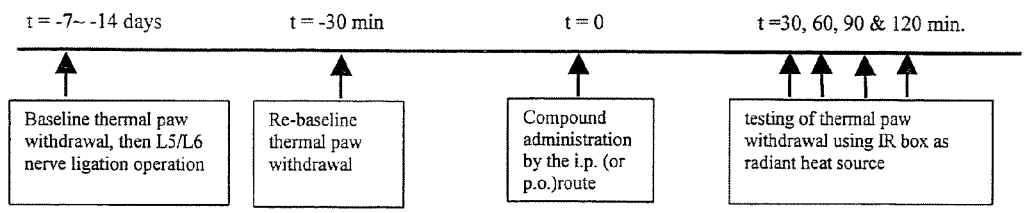
Figure 2. Dose response relationship for i.p. injection of Compound 11 of the invention after 30 and 60 minutes of dosing in the Chung Model of neuropathic pain.
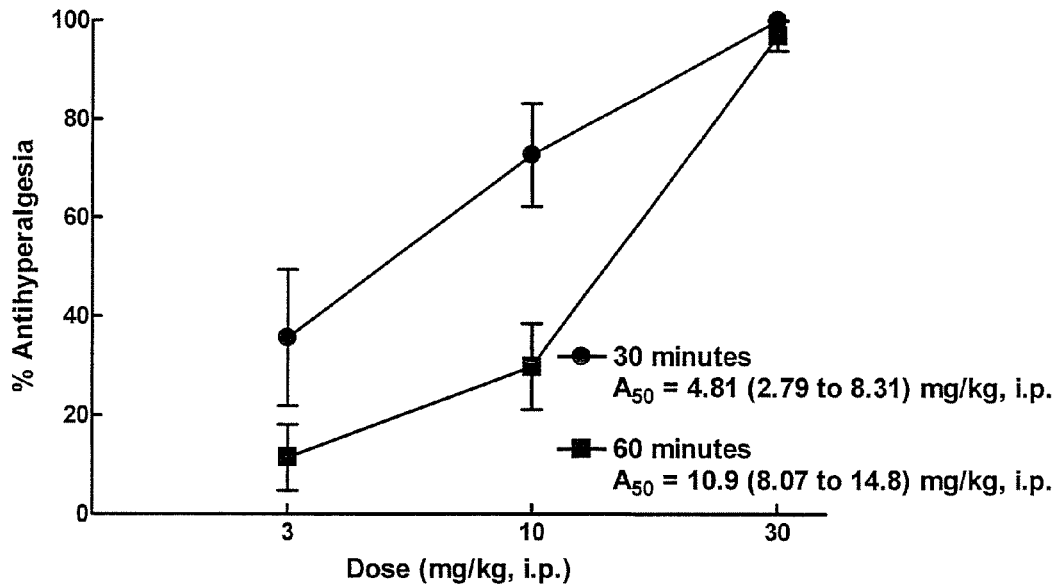

Figure 3. Response of Compound of Example 3 in Chung Model
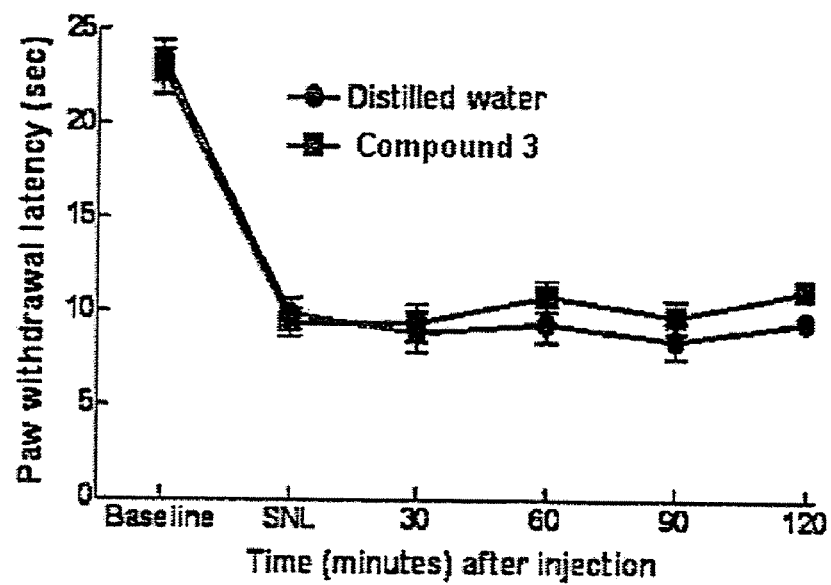

Figure 4. Antihyperalgesia Response of Compound from Example 23 in Chung Model after i.p. dosing at 30 mg/kg.
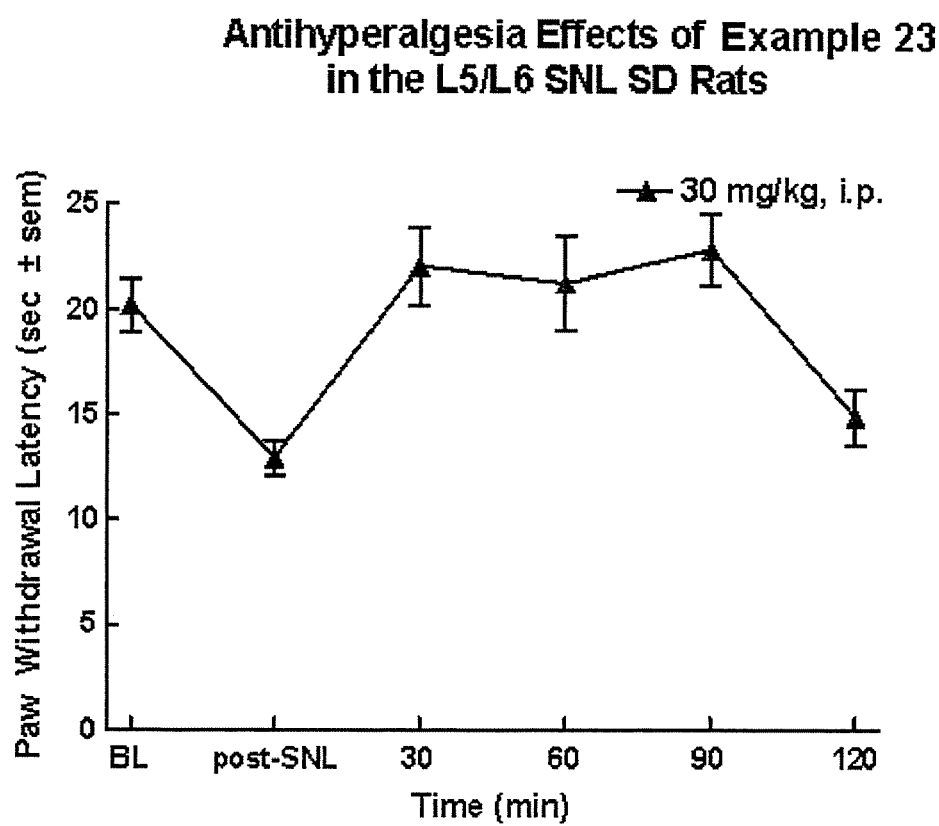

Figure 5. Standard Test Method for the Chung (SNL) Model of Tactile Hypersensitivity
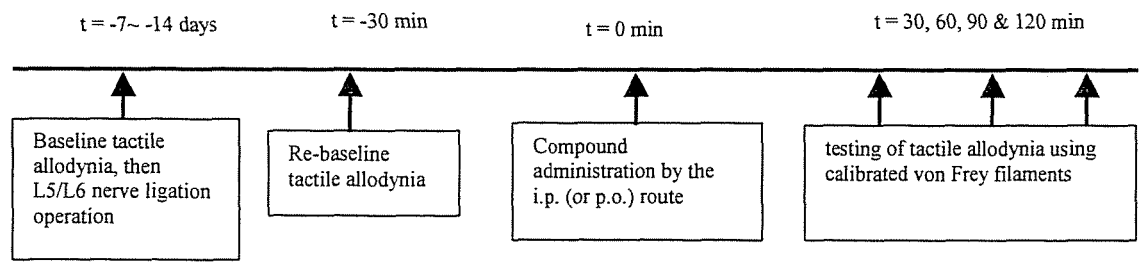

Figure 6. Antiallodynic Response of Compound from Example 23 in Chung Model after i.p. dosing at 30 mg/kg.
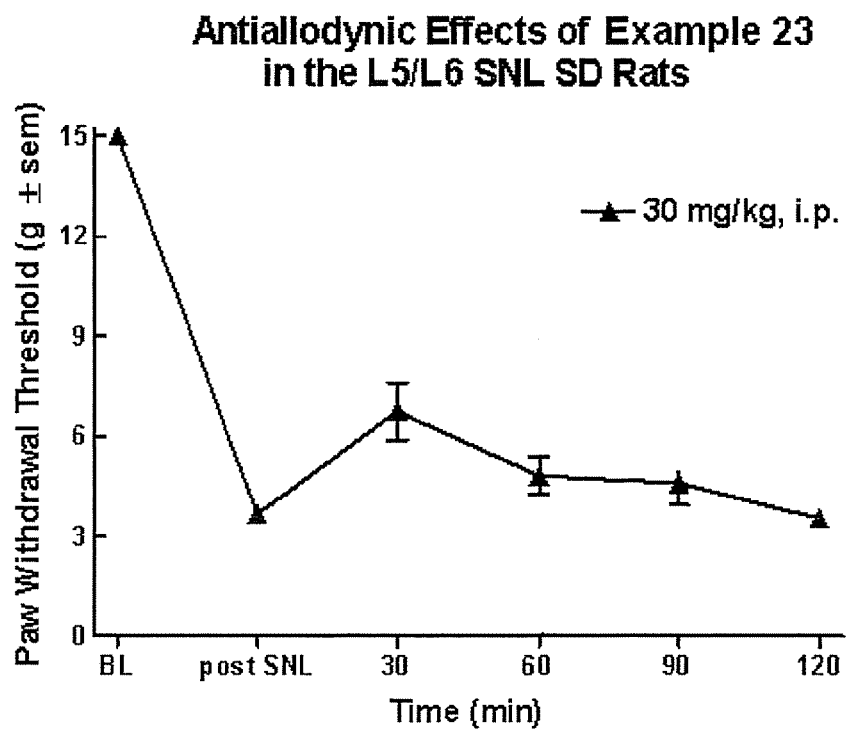

Figure 7. Method for the Porreca Model of Tactile Hypersensitivity
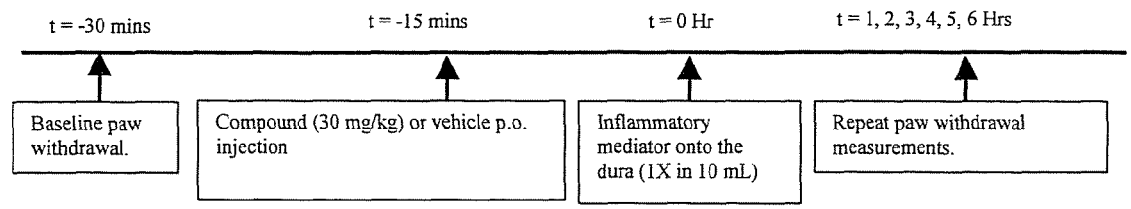

Figure 8. Antiallodynic Response of Compound from Example 23 in a Migraine Model after i.p. dosing at 30 mg/kg Administered 15 Minutes Prior to Inflammatory Soup (Dural Stimulation).
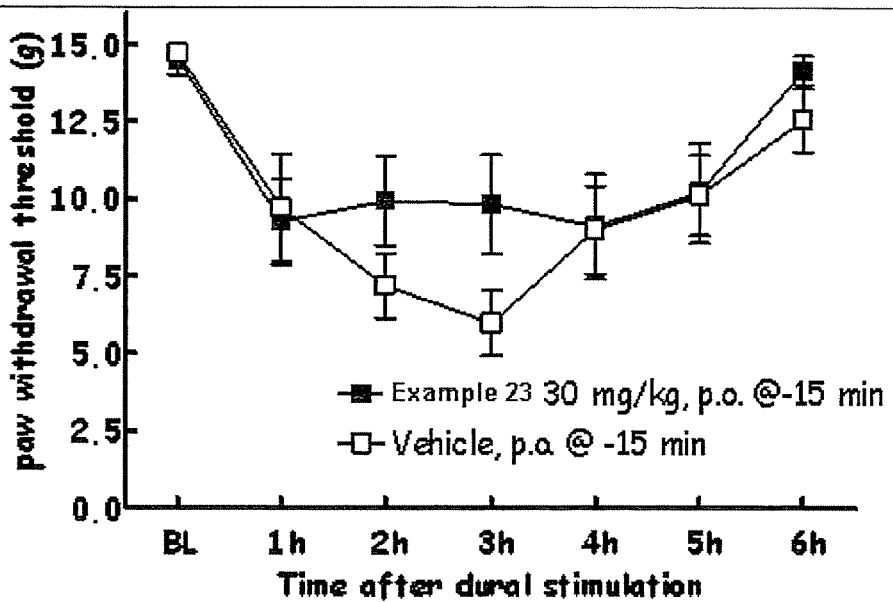

Figure 9. Antiahyperalgesic Response of Compound from Example 37 in Chung Model after i.p. dosing at 30 mg/kg.
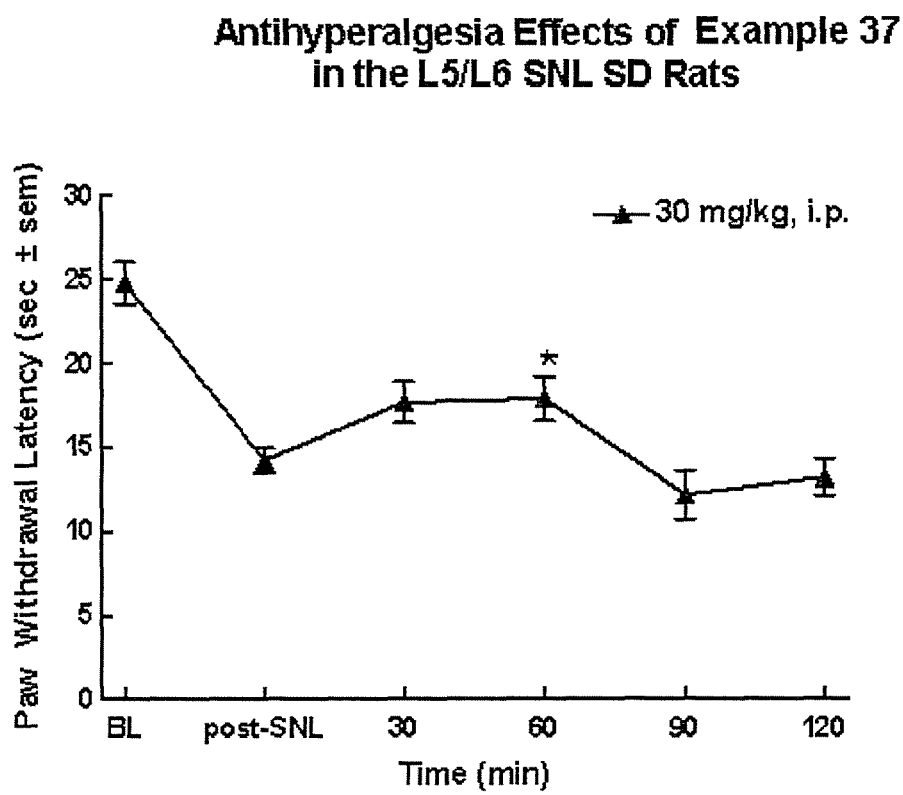

Figure 10. Antiallodynic Response of Compound from Example 47 in Chung Model after i.p. dosing at 30 mg/kg.
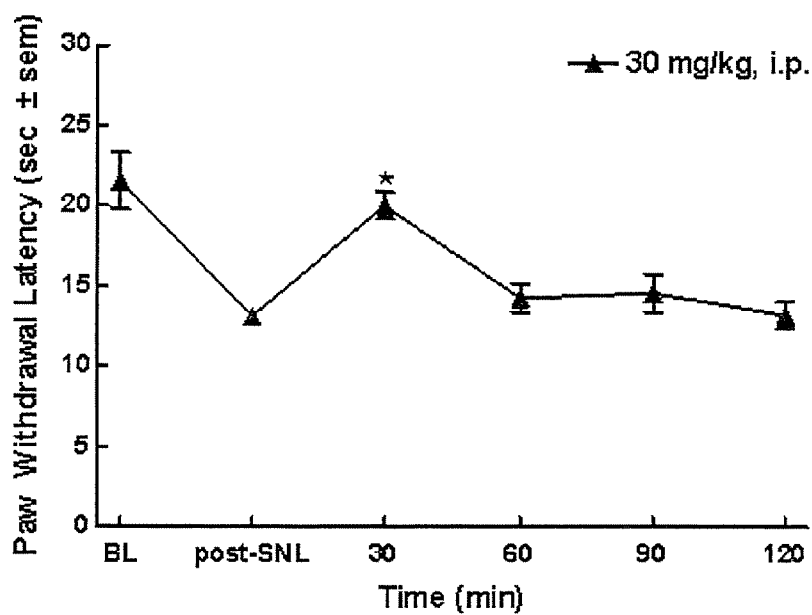

Figure 11. Antiallodynic Response of Compound from Example 54 in Chung Model after i.p. dosing at 30 mg/kg.
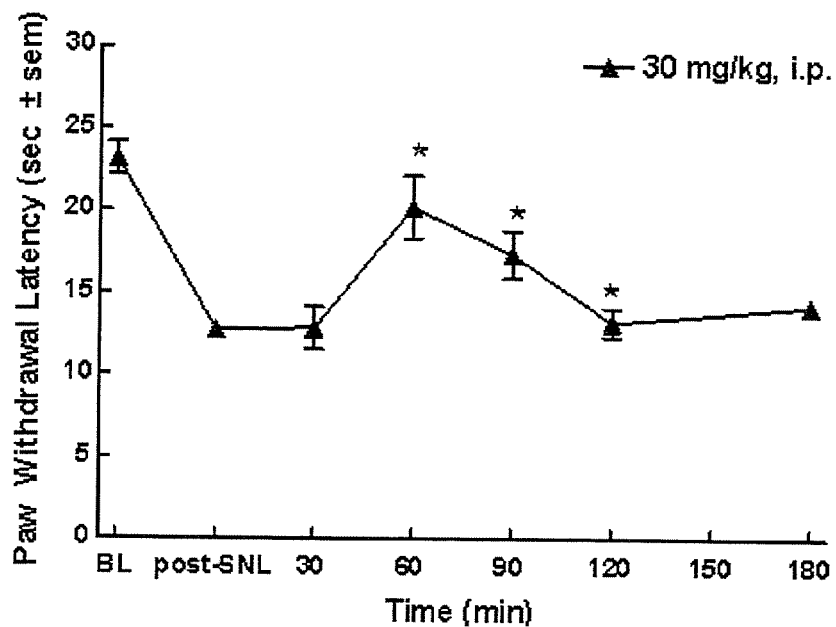

Figure 12. Antihyperalgesic Response of Compound from Example 28 in the Chung (SNL) Model of Neuropathic Pain after i.p. dosing at 30 mg/kg.
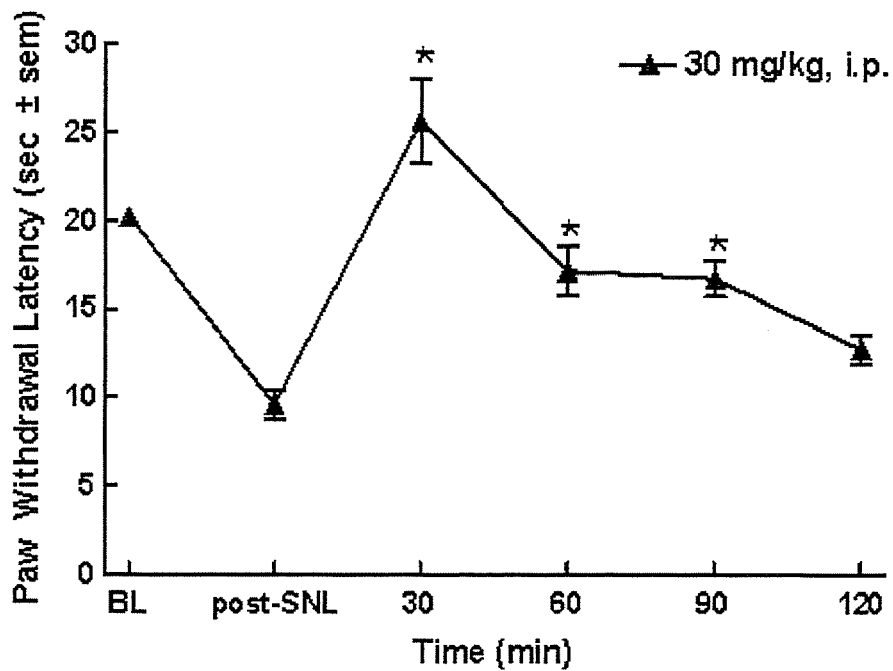

Figure 13. Antiallodynic Response of Compound from Example 28 in a Migraine Model after p.o. Dosing at 30 mg/kg Administered 15 Minutes Prior to Inflammatory Soup (Dural Stimulation).
Example 28 (30mg/kg, p.o.) Produces Attenuation of Tactile Hyperesthesia of the Hindpaw in Rats with Inflammation of the Dura (p value = 0.01; 2 Factor ANOVA).
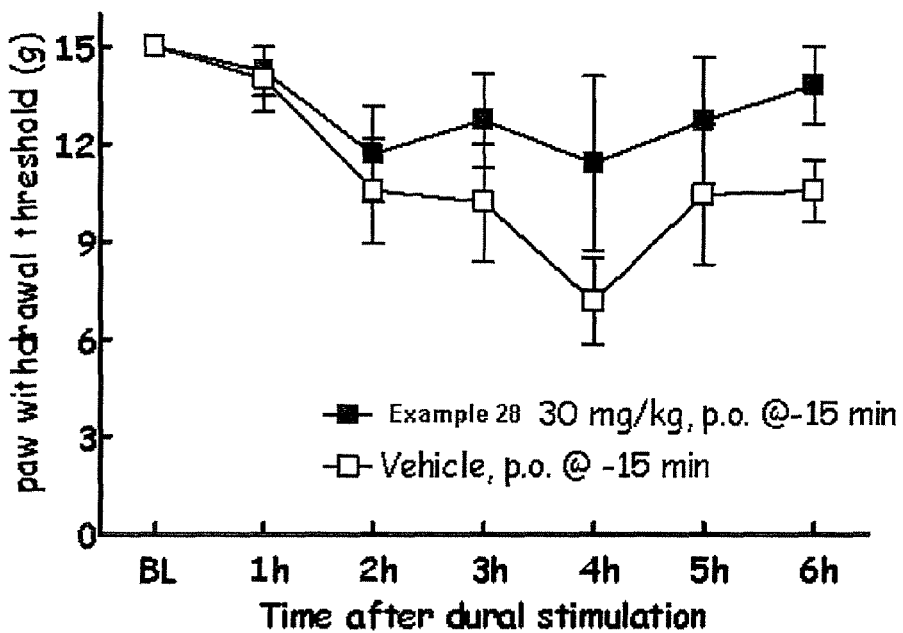

Figure 14. Antiallodynic Response of Compound from Example 11 in the Sciatic Nerve Cuff Model of Neuropathic Pain after a single dose at 30 mg/kg (i.p.).
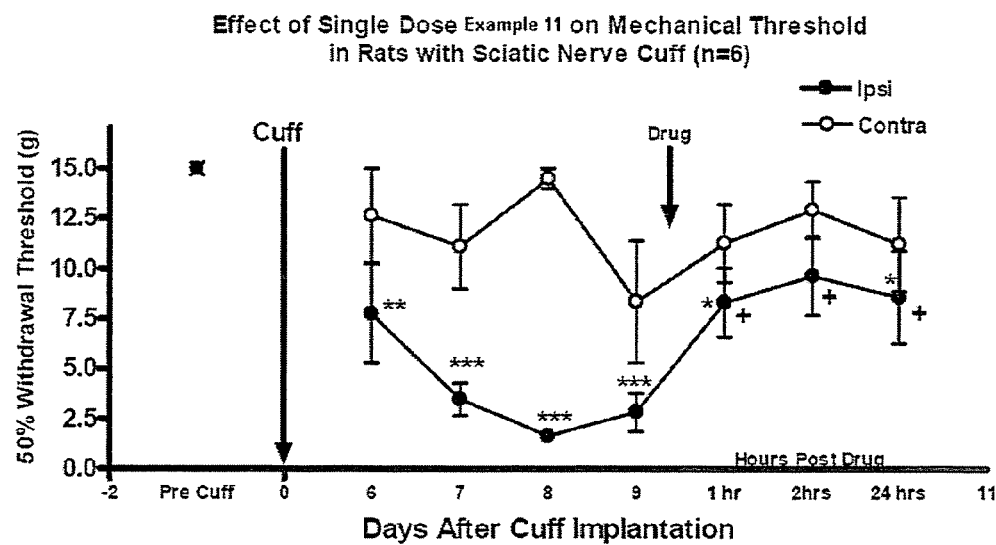
Figure 15. Antiallodynic Response of Compound from Example 11 in the Sciatic Nerve Cuff Model of Neuropathic Pain after i.p. dosing at 30 mg/kg.
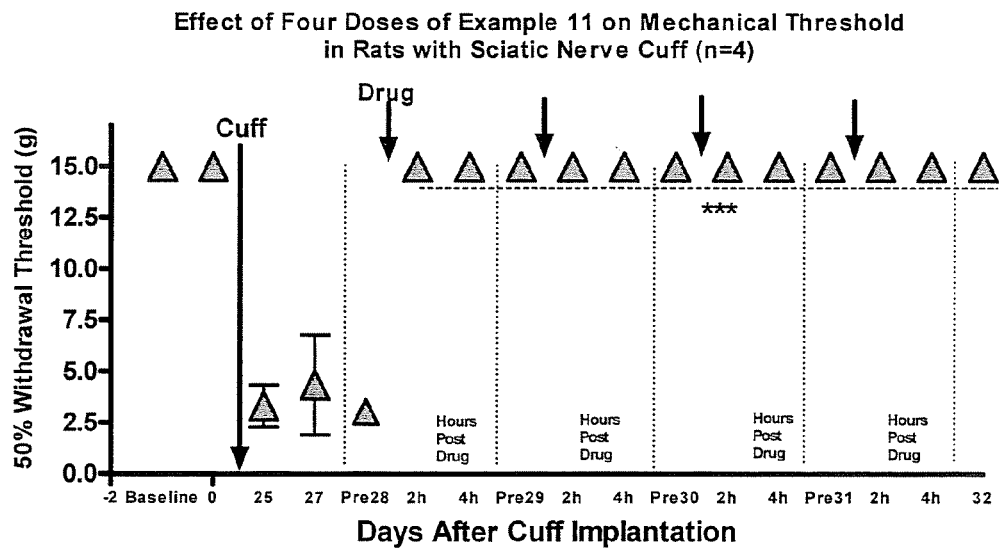

Figure 16. Effect of Administration of Example 11 on the frequency of paw lifts on a cold platform in the rat sciatic cuff model of neuropathic pain.
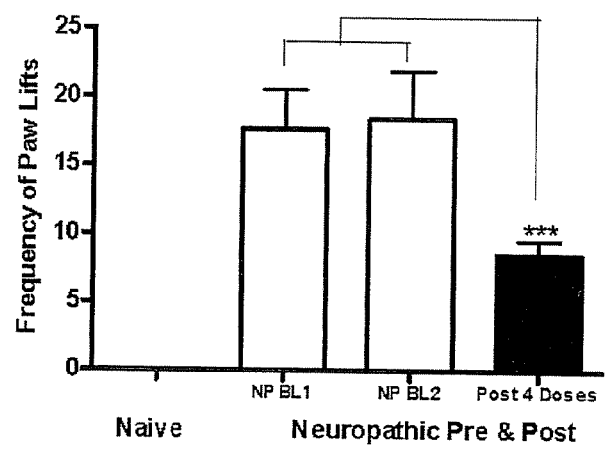
Figure 17. Effect of Administration of Example 11 (i.p. 30 mg/kg) hind leg weight distribution in the rat sciatic cuff model of neuropathic pain.
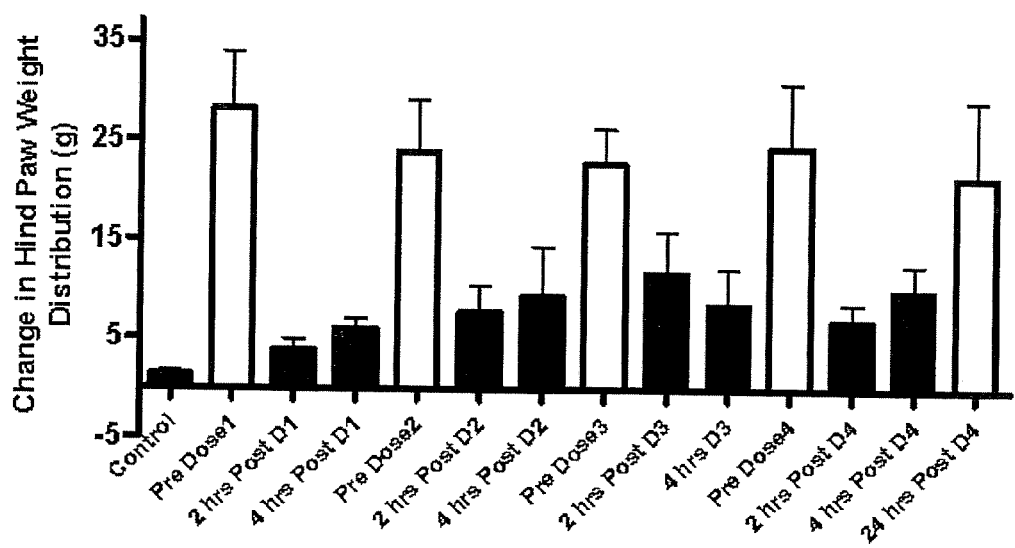

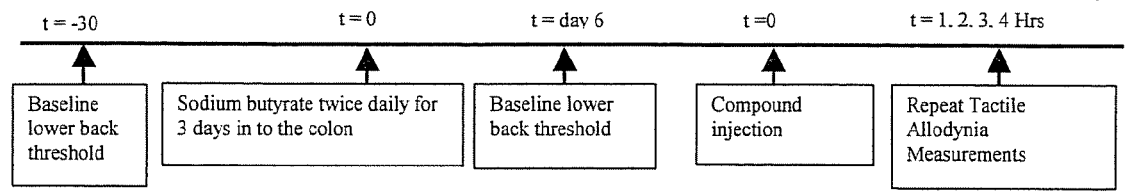
Figure 18. Standard Test Method for the Visceral Pain Model of Tactile Hypersensitivity Figure 19. Effect of Administration of Example 11 (i.p. 30 mg/kg) in a Rat Model of Visceral Pain Produced by Inflammation of the Bowel (IBS).
Compound 11 (30mg/kg, i.p.) Produces Attenuation of Tactile Allodynia of the Lower Back in Rats with IBS
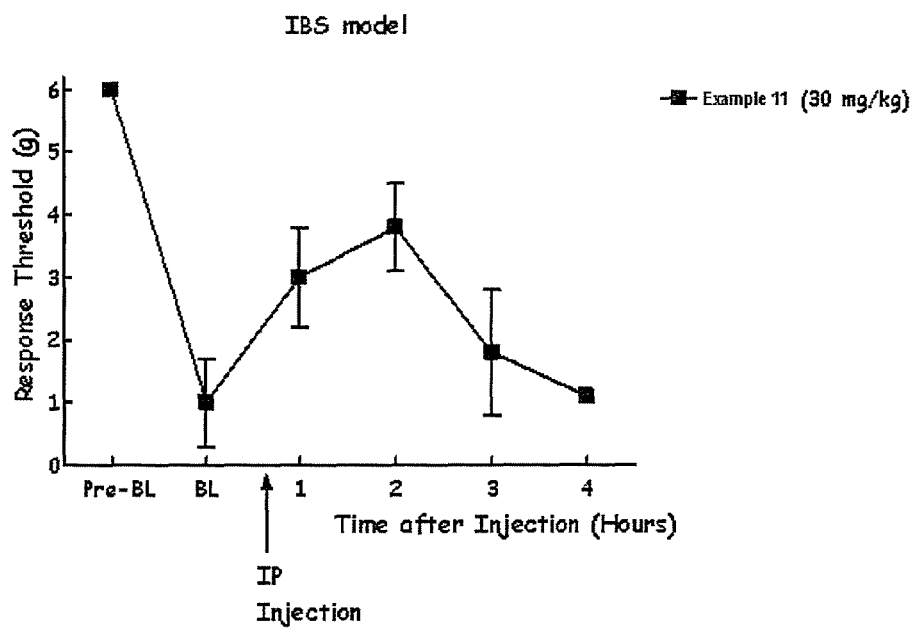

QUINOLONE AND TETRAHYDROQUINOLONE AND RELATED COMPOUNDS HAVING NOS INHIBITORY ACTIVITY

CROSS-REFERENCE TO RELATED APPLICATIONS

This application claims benefit of U.S. Provisional Application No. 60/896,829, filed Mar. 23, 2007, which is hereby incorporated by reference.

BACKGROUND OF THE INVENTION

The field of the present invention relates to quinolones, tetrahydroquinolines, and related compounds and to their medical use.

Nitric oxide (NO) has diverse roles both in normal and pathological processes, including the regulation of blood pressure, in neurotransmission, and in the macrophage defense systems (Snyder et al., *Scientific American*, May 1992:68). NO is synthesized by three isoforms of nitric oxide synthase, a constitutive form in endothelial cells (eNOS), a constitutive form in neuronal cells (nNOS), and an inducible form found in macrophage cells (iNOS). These enzymes are homodimeric proteins that catalyze a five-electron oxidation of L-arginine, yielding NO and citrulline. The role of NO produced by each of the NOS isoforms is quite unique. Overstimulation or overproduction of individual NOS isoforms especially nNOS and iNOS, plays a role in several disorders, including septic shock, arthritis, diabetes, ischemia-reperfusion injury, pain, and various neurodegenerative diseases (Kerwin, et al., *J. Med. Chem.* 38:4343, 1995), while eNOS inhibition leads to unwanted effects such as enhanced white cell and platelet activation, hypertension and increased atherogenesis (Valance and Leiper, *Nature Rev. Drug Disc.* 2002, 1, 939).

NOS inhibitors have the potential to be used as therapeutic agents in many disorders. However, the preservation of physiologically important nitric oxide synthase function suggests the desirability of the development of isoform-selective inhibitors that preferentially inhibit nNOS over eNOS.

SUMMARY OF THE INVENTION

The invention features a compound having the formula:

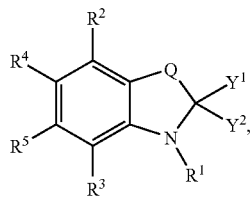

(I)

wherein,

Q is $(CHR^6)_{1-3}$;

$R^1$ and each $R^6$ is, independently, H, optionally substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl;

each of $R^2$ and $R^3$ is, independently, H, Hal, optionally substituted $C_{1-6}$ alkyl, optionally substituted $C_{6-10}$ aryl, optionally substituted $C_{1-6}$ alkaryl, optionally substituted $C_{2-9}$ heterocyclyl, hydroxy, optionally substituted $C_{1-6}$ alkoxy, optionally substituted $C_{1-6}$ thioalkoxy, $(CH_2)_{r2}NHC(NH)R^{2A}$, or $(CH_2)_{r2}NHC(S)NHR^{2A}$, or optionally substituted $C_{1-4}$ alkheterocyclyl, wherein r2 is an integer from 0 to 2, $R^{2A}$ is optionally substituted $C_{1-6}$ alkyl, optionally substituted $C_{6-10}$ aryl, optionally substituted $C_{1-4}$ alkaryl, optionally substituted $C_{2-9}$ heterocyclyl, optionally substituted $C_{1-4}$ alkheterocyclyl, optionally substituted $C_{1-6}$ thioalkoxy, optionally substituted $C_{1-4}$ thioalkaryl, optionally substituted aryloyl, optionally substituted $C_{1-4}$ thioalkheterocyclyl, or optionally substituted amino;

each of $R^4$ and $R^5$ is independently H, Hal, $(CH_2)_{r2}NHC(NH)R^{2A}$, or $(CH_2)_{r2}NHC(S)NHR^{2A}$;

wherein $Y^1$ and $Y^2$ are each H, or $Y^1$ and $Y^2$ together are =O, or $Y^1$ and $Y^2$ are independently H, optionally substituted $C_{1-6}$ alkyl, optionally substituted $C_{6-10}$ aryl, optionally substituted $C_{1-6}$ alkaryl, optionally substituted $C_{2-9}$ heterocyclyl, hydroxy, optionally substituted $C_{1-6}$ alkoxy, optionally substituted $C_{1-6}$ thioalkoxy, or optionally substituted $C_{1-4}$ alkheterocyclyl;

wherein only one of $R^2$, $R^3$, $R^4$, and $R^5$ is $(CH_2)_{r2}NHC(NH)R^{2A}$ or $(CH_2)_{24}NHC(S)NHR^{2A}$;

or a pharmaceutically acceptable salt or prodrug thereof.

In certain embodiments, Q is $(CHR^6)_{1-3}$;

$R^1$ and each $R^6$ is, independently, H, optionally substituted $C_{1-6}$ alkyl, optionally substituted $C_{1-4}$ alkaryl, optionally substituted $C_{1-4}$ alkheterocyclyl, or optionally substituted $C_{2-9}$ heterocyclyl;

each of $R^2$ and $R^3$ is, independently, H, Hal, optionally substituted $C_{1-6}$ alkyl, optionally substituted $C_{6-10}$ aryl, optionally substituted $C_{1-6}$ alkaryl, optionally substituted $C_{2-9}$ heterocyclyl, or optionally substituted $C_{1-4}$ alkheterocyclyl;

each of $R^4$ and $R^5$ is, independently, H, $(CH_2)_{r2}NHC(NH)R^{2A}$, or $(CH_2)_{r2}NHC(S)NHR^{2A}$ wherein $Y^1$ and $Y^2$ are each H, or $Y^1$ and $Y^2$ together are =O;

wherein one, but not both, of $R^4$ and $R^5$ is H;

or a pharmaceutically acceptable salt or prodrug thereof.

In certain embodiments, $Y^1$ and $Y^2$ together are =O, and Q is $(CHR^6)_2$; or $Y^1$ and $Y^2$ are each H, and Q is $(CHR^6)_2$; or $Y^1$ and $Y^2$ together are =O, and Q is $CHR^6$; or $Y^1$ and $Y^2$ are each H, and Q is $CHR^6$; or $Y^1$ and $Y^2$ together are =O, and Q is $(CHR^6)_3$; or $Y^1$ and $Y^2$ are each H, and Q is $(CHR^6)_3$.

In certain embodiments, $R^2$, $R^3$, $R^4$ or $R^5$ has the formula:

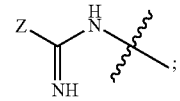

(II)

wherein Z is $R^{2A}$, e.g., wherein $R^{2A}$ has the formula:

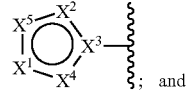

(III)

each of $X^1$, $X^2$, $X^4$, and $X^5$ is independently selected from O, S, $NR^7$, N, or $CR^8$; $X^3$ is selected from N or $CR^8$;

$R^7$ is H or optionally substituted $C_{1-6}$ alkyl;

$R^8$ is H, Hal, optionally substituted $C_{1-6}$ alkyl, hydroxy, optionally substituted $C_{1-6}$ alkoxy, or optionally substituted $C_{1-6}$ thioalkoxy, wherein at least one of $X^1$, $X^2$, $X^4$, and $X^5$ is not $CR^8$.

$R^{2A}$ may also have the formula:

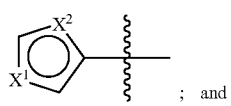

(III)

; and each of $X^1$ and $X^2$ is independently selected from O, S, NH, N, or CH; wherein at least one of $X^1$ and $X^2$ is not CH.

In exemplary compounds, $X^1$ is CH, and $X^2$ is S.

Exemplary compounds are shown in Table 2.

The invention also features a pharmaceutical composition comprising a compound of formula (I) or a pharmaceutically acceptable salt or prodrug thereof, and a pharmaceutically acceptable excipient.

The invention further features a method of treating or preventing a condition in a mammal caused by the action of nitric oxide synthase (NOS), wherein said method comprises administering an effective amount of a compound of the invention or a pharmaceutically acceptable salt or prodrug thereof to said mammal, e.g., a human. Exemplary conditions include migraine headache (with or without aura), chronic tension type headache (CTTH), migraine with allodynia, medication overuse headache, neuropathic pain, AIDS associated painful neuropathy, chronic headache, central post-stroke pain (CPSP), medication-induced hyperalgesia or allodynia, acute pain, chronic pain, diabetic neuropathy, trigeminal neuralgia, chemotherapy induced neuropathic pain, bone cancer pain, chemical dependencies or addictions, CNS disorders, neurodegenerative diseases or nerve injury, cardiovascular related conditions, diabetic nephropathy, inflammatory diseases, or gastrointestinal disorders. Specific examples of these conditions are described herein. Preferred conditions are neuropathic pain, CTTH, visceral pain, and IBS.

The method may further include administering to the mammal an opioid, an antidepressant, an antiepileptic, a non-steroidal anti-inflammatory drug (NSAID), an antiarrhythmic, a GABA-B antagonist, an alpha-2-adrenergic receptor agonist, a serotonin $5HT_{1B/1D}$ agonist, an N-methyl-D-aspartate antagonist, a cholecystokinin B antagonist, a substance P antagonist, an anti-inflammatory compound, a DHP-sensitive L-type calcium channel antagonist, omega-conotoxin-sensitive N-type calcium channel antagonist, a P/Q-type calcium channel antagonist, an adenosine kinase antagonist, an adenosine receptor $A_1$ agonist, an adenosine receptor $A_{2a}$ antagonist, an adenosine receptor $A_3$ agonist, an adenosine deaminase inhibitor, an adenosine nucleoside transport inhibito, a vanilloid VR1 receptor agonist, a cannabinoid CB1/CB2 agonist, an AMPA receptor antagonist, a kainate receptor antagonist, a sodium channel blocker, a nicotinic acetylcholine receptor agonist, a $K_{ATP}$ potassium channel, $K_{v1.4}$ potassium channel, $Ca^{2+}$-activated potassium channel, SK potassium channel, BK potassium channel, IK potassium channel, KCNQ2/3 potassium channel opening agent, a muscarinic M3 antagonist, a muscarinic M1 agonist, a muscarinic M2/M3 partial agonist/antagonist, an antioxidant, an antipsychotic agent, or a dopamine receptor antiparkinson's agent. Specific examples of these compounds are provided herein.

Preferably, a compound of the invention selectively inhibits neuronal nitric oxide synthase (nNOS), particularly over endothelial nitric oxide synthase (eNOS) or inducible nitric oxide synthase (iNOS) or both.

Preferably, the $IC_{50}$ or $K_i$ value observed for the compound is at least 2 times lower for nNOS than for eNOS and/or iNOS. More preferably, the $IC_{50}$ or $K_i$ value is at least 5, 20, 50, or 100 times lower. In one embodiment, the $IC_{50}$ or $K_i$ value is between 2 times and 100 times lower. In another embodiment, the $IC_{50}$ or $K_i$ in eNOS is greater than 10 µM. More preferably eNOS $IC_{50}$ is greater than 20 µM, most preferably eNOS $IC_{50}$ or Ki is greater than 30 µM, as a threshold level of eNOS may be needed to avoid any direct eNOS mediated constriction of human vascular tissue.

Exemplary compounds are described herein.

The invention also features a pharmaceutical composition that includes a compound of the invention and a pharmaceutically acceptable excipient.

The invention further features a method of treating or preventing a condition in a mammal, such as, for example, a human, caused by the action of nitric oxide synthase (NOS), e.g., nNOS, that includes administering an effective amount of a compound of the invention to the mammal. Examples of such conditions include migraine headache (with or without aura), chronic tension type headache (CTTH), migraine with allodynia, medication overuse headache, neuropathic pain, AIDS associated painful neuropathy, chronic headache, central post-stroke pain (CPSP), medication-induced hyperalgesia and/or allodynia, e.g., opioid-induced hyperalgesia or triptan (5-HT1D/1B agonists)-induced hyperalgesia/allodynia, acute pain, chronic pain, diabetic neuropathy, trigeminal neuralgia, chemotherapy induced neuropathic pain (e.g., Paclitaxol, cis-Platin, Doxorubicin etc.), bone cancer pain, chemical dependencies or addictions (e.g., drug addiction, cocaine addiction, nicotine addiction, methamphetamine-induced neurotoxicity, ethanol tolerance, dependence, or withdrawal, or morphine/opioid induced tolerance, dependence, hyperalgesia, or withdrawal), CNS disorders (e.g., epilepsy, anxiety, depression (alone or in combination), attention deficit hyperactivity disorder (ADHD), psychosis, or dementia), neurodegenerative diseases or nerve injury (e.g., acute spinal cord injury, AIDS associated dementia, Parkinson's disease, Alzheimer's disease, amyotrophic lateral sclerosis (ALS), Huntington's disease, multiple sclerosis, neurotoxicity, or head trauma), cardiovascular related conditions (e.g., stroke, coronary artery bypass graft (CABG) associated neurological damage, hypothermic cardiac arrest (HCA), post-stroke pain, cardiogenic shock, reperfusion injury, or vascular dementia), diabetic nephropathy, inflammatory diseases (e.g., osteoarthritis or neuroinflammation), or gastrointestinal disorders (e.g., ileostomy-associated diarrhea, dumping syndrome, or visceral pain).

A compound of the invention can also be used in combination with one or more other therapeutic agents for the prevention or treatment of one of the aforementioned conditions.

Exemplary agents useful in combination with a compound of the invention, include opioids, antidepressants, antiepileptics, non-steroidal anti-inflammatory drugs (NSAIDs), antiarrhythmics, GABA-B antagonists, alpha-2-adrenergic receptor agonists, serotonin $5HT_{1B/1D}$ agonists, N-methyl-D-aspartate antagonists, cholecystokinin B antagonists, substance P antagonists (NK1), anti-inflammatory compounds, DHP-sensitive L-type calcium channel antagonists, omega-conotoxin-sensitive N-type calcium channel antagonists, P/Q-type calcium channel antagonists, adenosine kinase antagonists, adenosine receptor $A_1$ agonists, adenosine receptor $A_{2a}$ antagonists, adenosine receptor $A_3$ agonists, adenosine deaminase inhibitors, adenosine nucleoside transport inhibitors, vanilloid VR1 receptor agonists, cannabinoid CB1/CB2 agonists, AMPA receptor antagonists, kainate receptor antagonists, sodium channel blockers (e.g., Nav1.8 blocker for neuropathic pain), nicotinic acetylcholine receptor agonists, a $K_{ATP}$ potassium channel, $K_{v1.4}$ potassium channel, $Ca^{2+}$-activated potassium channel, SK potassium channel, BK potassium channel, IK potassium channel, or KCNQ2/3 potassium channel opening agents, muscarinic M3 antagonists, muscarinic M1 agonists, muscarinic M2/M3 partial agonists/antagonists, and antioxidants. Specific examples of therapeutic agents that are useful in combination with a compound of the invention are listed in Table 1. Other classes include CB1/CB2 agonists, e.g., dexanabinol (HU-211), fatty acid amide hydrolase inhibitors, P2X purinergic blockers, and NGF antagonists.

TABLE 1

Therapeutic agents useful in combination with compounds of the invention

| Class | Examples |
|---|---|
| Opioid | alfentanil, butorphanol, buprenorphine, codeine, dextromoramide, dextropropoxyphene, dezocine, dihydrocodeine, diphenoxylate, etorphine, fentanyl, hydrocodone, hydromorphone, ketobemidone, levorphanol, levomethadone, methadone, meptazinol, morphine, morphine-6-glucuronide, nalbuphine, naloxone, oxycodone, oxymorphone, pentazocine, pethidine, piritramide, remifentanil, sulfentanyl, tilidine, or tramadol |
| Antidepressant (selective serotonin reuptake inhibitor) | alaproclate, citalopram, chlomipramine, escitalopram, femoxetine, fluoxetine, fluvoxamine, paroxetine, sertraline, or zimelidine |
| Antidepressant (norepinephrine-reuptake inhibitor) | adinazolam, amiltriptylinoxide, amineptine, amoxapine, atomoxetine, bupropion, butriptyline, desipramine, doxepin, desipramine, maprotiline, nortriptyline (desmethylamitriptyline), demexiptiline, dothiepin, fluacizine, imipramine, imipramine oxide, iprindole, lofepramine, maprotiline, melitracen, metapramine, norclolipramine, noxiptilin, opipramol, perlapine, pizotyline, propizepine, quinupramine, reboxetine, or tianeptine, tomoxetine, trimipramine or viloxazine |
| Antidepressant (dual serotonin/norepinephrine reuptake inhibitor) | duloxetine, milnacipran, mirtazapine, nefazodone, or venlafaxine |
| Antidepressant (monoamine oxidase inhibitor) | amiflamine, iproniazid, isocarboxazid, M-3-PPC (Draxis), moclobemide, pargyline, phenelzine, tranylcypromine, or vanoxerine |
| Antidepressant (reversible monoamine oxidase type A inhibitor) | bazinaprine, befloxatone, brofaromine, cimoxatone, or clorgyline |
| Antidepressant (tricyclic) | amitriptyline, amoxapine, buriptyline, clomipramine, desipramine, dibenzepin, dothiepin, doxepin, imipramine, iprindole, , lofepramine, melitracen, opipramol, nortryptyline, protriptyline, or trimipramine |
| Antidepressant (other) | adinazolam, alaproclate, amineptine, amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dothiepin, droxidopa, enefexine, estazolam, etoperidone, femoxetine, fengabine, fezolamine, fluotracen, idazoxan, indalpine, indeloxazine, iprindole, levoprotiline, lithium, litoxetine; lofepramine, medifoxamine, metapramine, metralindole, mianserin, milnacipran, minaprine, mirtazapine, montirelin, nebracetam, nefopam, nialamide, nomifensine, norfluoxetine, orotirelin, oxaflozane, pinazepam, pirlindone, pizotyline, |

TABLE 1-continued

Therapeutic agents useful in combination with compounds of the invention

| Class | Examples |
|---|---|
| | ritanserin, rolipram, sercloremine, setiptiline, sibutramine, sulbutiamine, sulpiride, teniloxazine, thozalinone, thymoliberin, tianeptine, tiflucarbine, trazodone, tofenacin, tofisopam, toloxatone, tomoxetine, veralipride, viloxazine, viqualine, zimelidine, or zometapine |
| Antiepileptic | carbamazepine, flupirtine, gabapentin, lamotrigine, oxcarbazepine, phenyloin, pregabalin, retigabine, topiramate, or valproate |
| Non-steroidal anti-inflammatory drug (NSAID) | acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one). |
| $5HT_{1B/1D}$ agonist | eletriptan, frovatriptan, naratriptan, rizatriptan, sumatriptan, almotriptan, donitriptan, or zolmitriptan |
| Anti-inflammatory compounds | aspirin, celecoxib, cortisone, deracoxib, diflunisal, etoricoxib, fenoprofen, ibuprofen, ketoprofen, naproxen, prednisolone, sulindac, tolmetin, piroxicam, mefenamic acid, meloxicam, phenylbutazone, rofecoxib, suprofen, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3(2H)-pyridazinone, or 2-(3,5-difluorophenyl)-3-[4-(methylsulfonyl)phenyl]-2-cyclopenten-1-one |
| N-methyl-D-aspartate antagonist and other glutamate receptor antagonists (e.g., AMPA/kainite (GluR5), MGluR, and iGluR) (Medicinal Research Reviews, 2007; 27(2): 239-278 and Basic & Clinical. Pharmacol. Toxicol. 2005, 97: 202-213) | amantadine; aptiganel; besonprodil; budipine; conantokin G; delucemine; dexanabinol; dextromethorphan; dextropropoxyphen; felbamate; fluorofelbamate; gacyclidine; glycine; ipenoxazone; kaitocephalin; ketamine; ketobemidone; lanicemine; licostinel; midafotel; memantine; D-methadone; D-morphine; milnacipran; neramexane; orphenadrine; remacemide; sulfazocine; FPL-12,495 (racemide metabolite); topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H-,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3,4-dihydro-3- |

TABLE 1-continued

Therapeutic agents useful in combination with compounds of the invention

| Class | Examples |
|---|---|
| | [4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; efenprodil, CP101606, Ro256981, or 3,6,7-tetrahydro-2,3-dioxo-N-phenyl-1H,5H-pyrido[1,2,3-de]quinoxaline-5-acetamide |

NMDA antagonists in combination with nNOS inhibitors may be particularly useful in treating conditions such as inflammatory and neuropathic pain, traumatic brain injury and Parkinson's Disease (see Drug Discovery Today 2002: 7(7) 403-406).

Asymmetric or chiral centers may exist in any of the compounds of the present invention. The present invention contemplates the various stereoisomers and mixtures thereof. Individual stereoisomers of compounds of the present invention are prepared synthetically from commercially available starting materials which contain asymmetric or chiral centers or by preparation of mixtures of enantiomeric compounds followed by resolution well-known to those of ordinary skill in the art. These methods of resolution are exemplified by (1) attachment of a racemic mixture of enantiomers, designated (+/−), to a chiral auxiliary, separation of the resulting diastereomers by recrystallization or chromatography and liberation of the optically pure product from the auxiliary or (2) direct separation of the mixture of optical enantiomers on chiral chromatographic columns. Alternatively, chiral compounds can be prepared by an asymmetric synthesis that favours the preparation of one enantiomer over the other. Alternatively a chiral pool synthesis (starting with an enantiomerically pure building block) can be used wherein the chiral group or center is retained in the intermediate or final product. Enantiomers are designated herein by the symbols "R," or "S," depending on the configuration of substituents around the chiral atom. Alternatively, enantiomers are designated as (+) or (−) depending on whether a solution of the enantiomer rotates the plane of polarized light clockwise or counterclockwise, respectively.

Geometric isomers may also exist in the compounds of the present invention. The present invention contemplates the various geometric isomers and mixtures thereof resulting from the arrangement of substituents around a carbon-carbon double bond and designates such isomers as of the Z or E configuration, where the term "Z" represents substituents on the same side of the carbon-carbon double bond and the term "E" represents substituents on opposite sides of the carbon-carbon double bond. It is also recognized that for structures in which tautomeric forms are possible, the description of one tautomeric form is equivalent to the description of both, unless otherwise specified. For example, amidine structures of the formula —C(=NR$^Q$)NHR$^T$ and —C(NHR$^Q$)=NR$^T$, where R$^T$ and R$^Q$ are different, are equivalent tautomeric structures and the description of one inherently includes the other.

It is understood that substituents and substitution patterns on the compounds of the invention can be selected by one of ordinary skill in the art to provide compounds that are chemically stable and that can be readily synthesized by techniques known in the art, as well as those methods set forth below, from readily available starting materials. If a substituent is itself substituted with more than one group, it is understood that these multiple groups may be on the same carbon or on different carbons, so long as a stable structure results.

Other features and advantages will be apparent from the following description and the claims.

Definitions

The terms "acyl" or "alkanoyl," as used interchangeably herein, represent an alkyl group, as defined herein, or hydrogen attached to the parent molecular group through a carbonyl group, as defined herein, and is exemplified by formyl, acetyl, propionyl, butanoyl and the like. Exemplary unsubstituted acyl groups include from 2 to 7 carbons.

The terms "$C_{x-y}$ alkaryl" or "$C_{x-y}$ alkylenearyl," as used herein, represent a chemical substituent of formula -RR', where R is an alkylene group of x to y carbons and R' is an aryl group as defined elsewhere herein. Similarly, by the terms "$C_{x-y}$ alkheteroaryl" or "$C_{x-y}$ alkyleneheteroaryl," is meant a chemical substituent of formula -RR", where R is an alkylene group of x to y carbons and R" is a heteroaryl group as defined elsewhere herein. Other groups preceded by the prefix "alk-" or "alkylene-" are defined in the same manner. Exemplary unsubstituted alkaryl groups are of from 7 to 16 carbons.

The term "alkcycloalkyl" represents a cycloalkyl group attached to the parent molecular group through an alkylene group.

The term "alkenyl," as used herein, represents monovalent straight or branched chain groups of, unless otherwise specified, from 2 to 6 carbons containing one or more carbon-carbon double bonds and is exemplified by ethenyl, 1-propenyl, 2-propenyl, 2-methyl-1-propenyl, 1-butenyl, 2-butenyl, and the like.

The term "alkheterocyclyl" represents a heterocyclic group attached to the parent molecular group through an alkylene group. Exemplary unsubstituted alkheterocyclyl groups are of from 2 to 14 carbons.

The term "alkoxy" represents a chemical substituent of formula —OR, where R is an alkyl group of 1 to 6 carbons, unless otherwise specified.

The term "alkoxyalkyl" represents an alkyl group which is substituted with an alkoxy group. Exemplary unsubstituted alkoxyalkyl groups include between 2 to 12 carbons.

The terms "alkyl" and the prefix "alk-," as used herein, are inclusive of both straight chain and branched chain saturated groups of from 1 to 6 carbons, unless otherwise specified. Alkyl groups are exemplified by methyl, ethyl, n- and iso-propyl, n-, sec-, iso- and tert-butyl, neopentyl, and the like, and may be optionally substituted with one, two, three or, in the case of alkyl groups of two carbons or more, four substituents independently selected from the group consisting of: (1) alkoxy of one to six carbon atoms; (2) alkylsulfinyl of one to six carbon atoms; (3) alkylsulfonyl of one to six carbon atoms; (4) amino; (5) aryl; (6) arylalkoxy; (7) aryloyl; (8) azido; (9) carboxaldehyde; (10) cycloalkyl of three to eight carbon atoms; (11) halo; (12) heterocyclyl; (13) (heterocycle)oxy; (14) (heterocycle)oyl; (15) hydroxyl; (16) N-protected amino; (17) nitro; (18) oxo; (19) spirocyclyl of three to eight carbon atoms; (20) thioalkoxy of one to six carbon atoms; (21) thiol; (22) —CO$_2$R$^A$, where R$^A$ is selected from the group consisting of (a) alkyl, (b) aryl, (c) alkaryl, and (d) hydrogen, where the alkylene group is of one to six carbon atoms; (23) —C(O)NR$^B$R$^C$, where each of R$^B$ and R$^c$ is, independently, selected from the group consisting of (a) hydrogen, (b) alkyl, (c) aryl and (d) alkaryl, where the alkylene group is of one to six carbon atoms; (24) —SO$_2$R$^D$, where $R^D$ is selected from the group consisting of (a) alkyl, (b) aryl and (c) alkaryl, where the alkylene group is of one to six carbon atoms; (25) —SO$_2$NR$^E$R$^F$, where each of R$^E$ and R$^F$ is, independently, selected from the group consisting of (a) hydrogen, (b) alkyl, (c) aryl and (d) alkaryl, where the alkylene group is of one to six carbon atoms; and (26) —NR$^G$R$^H$, where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group.

The term "alkylene," as used herein, represents a saturated divalent hydrocarbon group derived from a straight or branched chain saturated hydrocarbon by the removal of two hydrogen atoms, and is exemplified by methylene, ethylene, isopropylene, and the like.

The term "alkylsulfinyl," as used herein, represents an alkyl group attached to the parent molecular group through an —S(O)— group. Exemplary unsubstituted alkylsulfinyl groups are of from 1 to 6 carbons.

The term "alkylsulfonyl," as used herein, represents an alkyl group attached to the parent molecular group through an —SO$_2$— group. Exemplary unsubstituted alkylsulfonyl groups are of from 1 to 6 carbons.

The term "alkylsulfinylalkyl," as used herein, represents an alkyl group, as defined herein, substituted by an alkylsulfinyl group. Exemplary unsubstituted alkylsulfinylalkyl groups are of from 2 to 12 carbons.

The term "alkylsulfonylalkyl," as used herein, represents an alkyl group, as defined herein, substituted by an alkylsulfonyl group. Exemplary unsubstituted alkylsulfonylalkyl groups are of from 2 to 12 carbons.

The term "alkynyl," as used herein, represents monovalent straight or branched chain groups of from two to six carbon atoms containing a carbon-carbon triple bond and is exemplified by ethynyl, 1-propynyl, and the like.

The term "amidine," as used herein, represents a —C(=NH)NH$_2$ group.

The term "amino," as used herein, represents an —NH$_2$ group, or an —NHR$^{N1}$ wherein R$^{N1}$ can be a OH, NO$_2$, NH$_2$, NR$^{N2}$$_2$, SO$_2$OR$^{N2}$, SO$_2$R$^{N2}$, SOR$^{N2}$, and wherein R$^{N2}$ can be a H, an alkyl group, or an aryl group.

The term "aminoalkyl," as used herein, represents an alkyl group, as defined herein, substituted by an amino group.

The term "aryl," as used herein, represents a mono- or bicyclic carbocyclic ring system having one or two aromatic rings and is exemplified by phenyl, naphthyl, 1,2-dihydronaphthyl, 1,2,3,4-tetrahydronaphthyl, fluorenyl, indanyl, indenyl, and the like, and may be optionally substituted with one, two, three, four, or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, (c) alkaryl, and (d) hydrogen, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The term "arylalkoxy," as used herein, represents an alkaryl group attached to the parent molecular group through an oxygen atom. Exemplary unsubstituted arylalkoxy groups are of from 7 to 16 carbons.

The term "aryloxy" represents a chemical substituent of formula —OR', where R' is an aryl group of 6 to 18 carbons, unless otherwise specified.

The terms "aryloyl" and "aroyl" as used interchangeably herein, represent an aryl group that is attached to the parent molecular group through a carbonyl group. Exemplary unsubstituted aryloyl groups are of 7 or 11 carbons.

The term "azido" represents an N$_3$ group, which can also be represented as N=N=N.

The term "azidoalkyl" represents an azido group attached to the parent molecular group through an alkyl group.

The term "carbonyl," as used herein, represents a C(O) group, which can also be represented as C=O.

The term "carboxaldehyde" represents a CHO group.

The term "carboxaldehydealkyl" represents a carboxaldehyde group attached to the parent molecular group through an alkylene group.

The term "cycloalkyl," as used herein represents a monovalent saturated or unsaturated non-aromatic cyclic hydrocarbon group of from three to eight carbons, unless otherwise specified, and is exemplified by cyclopropyl, cyclobutyl, cyclopentyl, cyclohexyl, cycloheptyl, bicyclo[2.2.1.]heptyl and the like. The cycloalkyl groups of this invention can be optionally substituted with (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —(CH$_2$)$_q$CO$_2$R$^A$, where q is an integer of from zero to four, and R$^A$ is selected from the group consisting of (a) alkyl, (b) aryl, (c) alkaryl, and (d) hydrogen, where the alkylene group is of one to six carbon atoms; (36) —(CH$_2$)$_q$CONR$^B$R$^C$, where q is an integer of from zero to four and where R$^B$ and R$^C$ are independently selected from the group consisting of (a) hydrogen, (b) alkyl, (c) aryl, and (d) alkaryl, where the alkylene group is of one to six carbon atoms; (37) —(CH$_2$)$_q$SO$_2$R$^D$, where q is an integer of from zero to four and where R$^D$ is selected from the group consisting of (a) alkyl, (b) aryl, and (c) alkaryl, where the alkylene group is of one to six carbon atoms; (38) —(CH$_2$)$_q$SO$_2$NR$^E$R$^F$, where q is an integer of from zero to four and where each of R$^E$ and R$^F$ is, independently, selected from the group consisting of (a) hydrogen, (b) alkyl, (c) aryl, and (d) alkaryl, where the alkylene group is of one to six carbon atoms; (39) —(CH$_2$)$_q$NR$^G$R$^H$, where q is an integer of from zero to four and where each of R$^G$ and R$^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, with the proviso that no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "cycloalkyloxy" or "cycloalkoxy", as used interchangeably herein, represent a cycloalkyl group, as defined herein, attached to the parent molecular group through an oxygen atom. Exemplary unsubstituted cycloalkyloxy groups are of from 3 to 8 carbons.

The term an "effective amount" or a "sufficient amount" of an agent, as used herein, is that amount sufficient to effect beneficial or desired results, such as clinical results, and, as such, an "effective amount" depends upon the context in which it is being applied. For example, in the context of administering an agent that is an inhibitor of NOS, an effective amount of an agent is, for example, an amount sufficient to achieve a reduction in NOS activity as compared to the response obtained without administration of the agent.

The terms "halide" or "halogen" or "Hal" or "halo," as used herein, represent bromine, chlorine, iodine, or fluorine.

The term "heteroaryl," as used herein, represents that subset of heterocycles, as defined herein, which are aromatic: i.e., they contain 4n+2 pi electrons within the mono- or multicyclic ring system.

The terms "heterocycle" or "heterocyclyl," as used interchangeably herein represent a 5-, 6- or 7-membered ring, unless otherwise specified, containing one, two, three, or four heteroatoms independently selected from the group consisting of nitrogen, oxygen and sulfur. The 5-membered ring has zero to two double bonds and the 6- and 7-membered rings have zero to three double bonds. The term "heterocyclyl" also represents a heterocyclic compound having a bridged multicyclic structure in which one or more carbons and/or heteroatoms bridges two non-adjacent members of a monocyclic ring, e.g., a quinuclidinyl group. The term "heterocycle" includes bicyclic, tricyclic and tetracyclic groups in which any of the above heterocyclic rings is fused to one, two, or three rings, e.g., an aryl ring, a cyclohexane ring, a cyclohexene ring, a cyclopentane ring, a cyclopentene ring and another monocyclic heterocyclic ring, such as indolyl, quinolyl, isoquinolyl, tetrahydroquinolyl, benzofuryl, benzothienyl and the like. Examples of fused heterocycles include tropanes and 1,2,3,5,8,8a-hexahydroindolizine. Heterocyclics include pyrrolyl, pyrrolinyl, pyrrolidinyl, pyrazolyl, pyrazolinyl, pyrazolidinyl, imidazolyl, imidazolinyl, imidazolidinyl, pyridyl, piperidinyl, homopiperidinyl, pyrazinyl, piperazinyl, pyrimidinyl, pyridazinyl, oxazolyl, oxazolidinyl, isoxazolyl, isoxazolidinyl, morpholinyl, thiomorpholinyl, thiazolyl, thiazolidinyl, isothiazolyl, isothiazolidinyl, indolyl, quinolinyl, isoquinolinyl, benzimidazolyl, benzothiazolyl, benzoxazolyl, furyl, thienyl, thiazolidinyl, isothiazolyl, isoindazolyl, triazolyl, tetrazolyl, oxadiazolyl, uricyl, thiadiazolyl, pyrimidyl, tetrahydrofuranyl, dihydrofuranyl, tetrahydrothienyl, dihydrothienyl, dihydroindolyl, tetrahydroquinolyl, tetrahydroisoquinolyl, pyranyl, dihydropyranyl, dithiazolyl, benzofuranyl, benzothienyl and the like. Heterocyclic groups also include groups of the formula

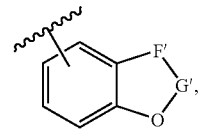

where

F' is selected from the group consisting of —CH$_2$—, —CH$_2$O— and —O—, and G' is selected from the group consisting of —C(O)— and —(C(R')(R''))$_v$—, where each of R' and R'' is, independently, selected from the group consisting of hydrogen or alkyl of one to four carbon atoms, and v is one to three and includes groups, such as 1,3-benzodioxolyl, 1,4-benzodioxanyl, and the like. Any of the heterocycle groups mentioned herein may be optionally substituted with one, two, three, four or five substituents independently selected from the group consisting of: (1) alkanoyl of one to six carbon atoms; (2) alkyl of one to six carbon atoms; (3) alkoxy of one to six carbon atoms; (4) alkoxyalkyl, where the alkyl and alkylene groups are independently of one to six carbon atoms; (5) alkylsulfinyl of one to six carbon atoms; (6) alkylsulfinylalkyl, where the alkyl and alkylene groups are independently of one to six carbon atoms; (7) alkylsulfonyl of one to six carbon atoms; (8) alkylsulfonylalkyl, where the alkyl and alkylene groups are independently of one to six carbon atoms; (9) aryl; (10) amino; (11) aminoalkyl of one to six carbon atoms; (12) heteroaryl; (13) alkaryl, where the alkylene group is of one to six carbon atoms; (14) aryloyl; (15) azido; (16) azidoalkyl of one to six carbon atoms; (17) carboxaldehyde; (18) (carboxaldehyde)alkyl, where the alkylene group is of one to six carbon atoms; (19) cycloalkyl of three to eight carbon atoms; (20) alkcycloalkyl, where the cycloalkyl group is of three to eight carbon atoms and the alkylene group is of one to ten carbon atoms; (21) halo; (22) haloalkyl of one to six carbon atoms; (23) heterocyclyl; (24) (heterocyclyl)oxy; (25) (heterocyclyl)oyl; (26) hydroxy; (27) hydroxyalkyl of one to six carbon atoms; (28) nitro; (29) nitroalkyl of one to six carbon atoms; (30) N-protected amino; (31) N-protected aminoalkyl, where the alkylene group is of one to six carbon atoms; (32) oxo; (33) thioalkoxy of one to six carbon atoms; (34) thioalkoxyalkyl, where the alkyl and alkylene groups are independently of one to six carbon atoms; (35) —$(CH_2)_q CO_2 R^A$, where q is an integer of from zero to four, and $R^A$ is selected from the group consisting of (a) alkyl, (b) aryl, (c) alkaryl, and (d) hydrogen where the alkylene group is of one to six carbon atoms; (36) —$(CH_2)_q CONR^B R^C$, where q is an integer of from zero to four and where $R^B$ and $R^C$ are independently selected from the group consisting of (a) hydrogen, (b) alkyl, (c) aryl, and (d) alkaryl, where the alkylene group is of one to six carbon atoms; (37) —$(CH_2)_q SO_2 R^D$, where q is an integer of from zero to four and where $R^D$ is selected from the group consisting of (a) alkyl, (b) aryl, and (c) alkaryl, where the alkylene group is of one to six carbon atoms; (38) —$(CH_2)_q SO_2 NR^E R^F$, where q is an integer of from zero to four and where each of $R^E$ and $R^F$ is, independently, selected from the group consisting of (a) hydrogen, (b) alkyl, (c) aryl, and (d) alkaryl, where the alkylene group is of one to six carbon atoms; (39) —$(CH_2)_q NR^G R^H$, where q is an integer of from zero to four and where each of $R^G$ and $R^H$ is, independently, selected from the group consisting of (a) hydrogen; (b) an N-protecting group; (c) alkyl of one to six carbon atoms; (d) alkenyl of two to six carbon atoms; (e) alkynyl of two to six carbon atoms; (f) aryl; (g) alkaryl, where the alkylene group is of one to six carbon atoms; (h) cycloalkyl of three to eight carbon atoms; and (i) alkcycloalkyl, where the cycloalkyl group is of three to eight carbon atoms, and the alkylene group is of one to ten carbon atoms, wherein in one embodiment no two groups are bound to the nitrogen atom through a carbonyl group or a sulfonyl group; (40) thiol; (41) perfluoroalkyl; (42) perfluoroalkoxy; (43) aryloxy; (44) cycloalkoxy; (45) cycloalkylalkoxy; and (46) arylalkoxy.

The terms "heterocyclyloxy" and "(heterocycle)oxy," as used interchangeably herein, represent a heterocycle group, as defined herein, attached to the parent molecular group through an oxygen atom.

The terms "heterocyclyloyl" and "(heterocycle)oyl," as used interchangeably herein, represent a heterocycle group, as defined herein, attached to the parent molecular group through a carbonyl group.

The term "hydroxy" or "hydroxyl," as used herein, represents an —OH group.

The term "hydroxyalkyl," as used herein, represents an alkyl group, as defined herein, substituted by one to three hydroxy groups, with the proviso that no more than one hydroxy group may be attached to a single carbon atom of the alkyl group and is exemplified by hydroxymethyl, dihydroxypropyl, and the like.

The terms "inhibit" or "suppress" or "reduce," as relates to a function or activity, such as NOS activity, means to reduce the function or activity when compared to otherwise same conditions except for a condition or parameter of interest, or alternatively, as compared to another condition.

The term "N-protected amino," as used herein, refers to an amino group, as defined herein, to which is attached an N-protecting or nitrogen-protecting group, as defined herein.

The terms "N-protecting group" and "nitrogen protecting group," as used herein, represent those groups intended to protect an amino group against undesirable reactions during synthetic procedures. Commonly used N-protecting groups are disclosed in Greene, "Protective Groups In Organic Synthesis," $3^{rd}$ Edition (John Wiley & Sons, New York, 1999), which is incorporated herein by reference. N-protecting groups include acyl, aroyl, or carbamyl groups such as formyl, acetyl, propionyl, pivaloyl, t-butylacetyl, 2-chloroacetyl, 2-bromoacetyl, trifluoroacetyl, trichloroacetyl, phthalyl, o-nitrophenoxyacetyl, α-chlorobutyryl, benzoyl, 4-chlorobenzoyl, 4-bromobenzoyl, 4-nitrobenzoyl, and chiral auxiliaries such as protected or unprotected D, L or D, L-amino acids such as alanine, leucine, phenylalanine, and the like; sulfonyl groups such as benzenesulfonyl, p-toluenesulfonyl, and the like; carbamate forming groups such as benzyloxycarbonyl, p-chlorobenzyloxycarbonyl, p-methoxybenzyloxycarbonyl, p-nitrobenzyloxycarbonyl, 2-nitrobenzyloxycarbonyl, p-bromobenzyloxycarbonyl, 3,4-dimethoxybenzyloxycarbonyl, 3,5-dimethoxybenzyl oxycarbonyl, 2,4-dimethoxybenzyloxycarbonyl, 4-methoxybenzyloxycarbonyl, 2-nitro-4,5-dimethoxybenzyloxycarbonyl, 3,4,5-trimethoxybenzyloxycarbonyl, 1-(p-biphenylyl)-1-methylethoxycarbonyl, α,α-dimethyl-3,5-dimethoxybenzyloxycarbonyl, benzhydryloxy carbonyl, t-butyloxycarbonyl, diisopropylmethoxycarbonyl, isopropyloxycarbonyl, ethoxycarbonyl, methoxycarbonyl, allyloxycarbonyl, 2,2,2-trichloroethoxycarbonyl, phenoxycarbonyl, 4-nitrophenoxy carbonyl, fluorenyl-9-methoxycarbonyl, cyclopentyloxycarbonyl, adamantyloxycarbonyl, cyclohexyloxycarbonyl, phenylthiocarbonyl, and the like, arylalkyl groups such as benzyl, triphenylmethyl, benzyloxymethyl, and the like and silyl groups such as trimethylsilyl, and the like. Preferred N-protecting groups are formyl, acetyl, benzoyl, pivaloyl, t-butylacetyl, alanyl, phenylsulfonyl, benzyl, t-butyloxycarbonyl (Boc), and benzyloxycarbonyl (Cbz).

The term "nitro," as used herein, represents an —$NO_2$ group.

The term "oxo" as used herein, represents =O.

The term "perfluoroalkyl," as used herein, represents an alkyl group, as defined herein, where each hydrogen radical bound to the alkyl group has been replaced by a fluoride radical. Perfluoroalkyl groups are exemplified by trifluoromethyl, pentafluoroethyl, and the like.

The term "perfluoroalkoxy," as used herein, represents an alkoxy group, as defined herein, where each hydrogen radical bound to the alkoxy group has been replaced by a fluoride radical.

The term "pharmaceutically acceptable salt," as use herein, represents those salts which are, within the scope of sound medical judgment, suitable for use in contact with the tissues of humans and animals without undue toxicity, irritation, allergic response and the like and are commensurate with a reasonable benefit/risk ratio. Pharmaceutically acceptable salts are well known in the art. For example, S. M Berge et al. describe pharmaceutically acceptable salts in detail in *J. Pharmaceutical Sciences* 66:1-19, 1977. The salts can be prepared in situ during the final isolation and purification of the compounds of the invention or separately by reacting the free base group with a suitable organic acid. Representative acid addition salts include acetate, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, fumarate, glucoheptonate, glycerophosphate, hemisulfate, heptonate, hexanoate, hydrobromide, hydrochloride, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, toluenesulfonate, undecanoate, valerate salts and the like. Representative alkali or alkaline earth metal salts include sodium, lithium, potassium, calcium, magnesium and the like, as well as nontoxic ammonium, quaternary ammonium, and amine cations, including, but not limited to ammonium, tetramethylammonium, tetraethylammonium, methylamine, dimethylamine, trimethylamine, triethylamine, ethylamine and the like.

The term "pharmaceutically acceptable prodrugs" as used herein, represents those prodrugs of the compounds of the present invention which are, within the scope of sound medical judgment, suitable for use in contact with the tissues of humans and animals with undue toxicity, irritation, allergic response, and the like, commensurate with a reasonable benefit/risk ratio, and effective for their intended use, as well as the zwitterionic forms, where possible, of the compounds of the invention.

The term "Ph" as used herein means phenyl.

The term "prodrug," as used herein, represents compounds which are rapidly transformed in vivo to the parent compound of the above formula, for example, by hydrolysis in blood. Prodrugs of the compounds of the invention may be conventional esters. Some common esters which have been utilized as prodrugs are phenyl esters, aliphatic ($C_7$-$C_8$ or $C_8$-$C_{24}$) esters, cholesterol esters, acyloxymethyl esters, carbamates, and amino acid esters. For example, a compound of the invention that contains an OH group may be acylated at this position in its prodrug form. A thorough discussion is provided in T. Higuchi and V. Stella, Pro-drugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and Judkins et al., *Synthetic Communications* 26(23):4351-4367, 1996, each of which is incorporated herein by reference.

Each of the terms "selectively inhibits nNOS" or "a selective nNOS inhibitor" refers to a substance that inhibits or binds the nNOS isoform more effectively than the eNOS and/or iNOS isoform as measured by an in vitro assay, such as, for example, those assays described herein. Selective inhibition can be expressed in terms of an $IC_{50}$ value, a $K_i$ value, or the inverse of a percent inhibition value which is lower, or conversely a higher % inhibition when the substance is tested in an nNOS assay than when tested in an eNOS and/or iNOS assay. Preferably, the $IC_{50}$ or $K_i$ value is 2 times lower. More preferably, the $IC_{50}$ or $K_i$ value is 5, 10, 50, or even more than 100 times lower.

The term "solvate" as used herein means a compound of the invention wherein molecules of a suitable solvent are incorporated in the crystal lattice. A suitable solvent is physiologically tolerable at the dosage administered. Examples of suitable solvents are ethanol, water and the like. When water is the solvent, the molecule is referred to as a "hydrate."

The term "spirocycle," as used herein, represents an alkylene diradical, both ends of which are bonded to the same carbon atom of the parent group to form a spirocyclic group and also heteroalkylene diradical, both ends of which are bonded to the same atom.

The term "sulfonyl," as used herein, represents an —$S(O)_2$— group.

The term "thioalkheterocyclyl," as used herein, represents a thioalkoxy group substituted with a heterocyclyl group.

The term "thioalkoxy," as used herein, represents an alkyl group attached to the parent molecular group through a sulfur atom. Exemplary unsubstituted alkylthio groups are of from 1 to 6 carbons.

The term "thiol" represents an —SH group.

As used herein, and as well understood in the art, "treatment" is an approach for obtaining beneficial or desired results, such as clinical results. Beneficial or desired results can include, but are not limited to, alleviation or amelioration of one or more symptoms or conditions; diminishment of extent of disease, disorder, or condition; stabilized (i.e. not worsening) state of disease, disorder, or condition; preventing spread of disease, disorder, or condition; delay or slowing the progress of the disease, disorder, or condition; amelioration or palliation of the disease, disorder, or condition; and remission (whether partial or total), whether detectable or undetectable. "Treatment" can also mean prolonging survival as compared to expected survival if not receiving treatment. "Palliating" a disease, disorder, or condition means that the extent and/or undesirable clinical manifestations of the disease, disorder, or condition are lessened and/or time course of the progression is slowed or lengthened, as compared to the extent or time course in the absence of treatment. The term also includes prophylactic treatment or treatment that prevents one or more symptoms or conditions of a disease, disorder, or condition.

BRIEF DESCRIPTION OF THE DRAWINGS

FIG. 1 is a schematic depiction of the Chung model of thermal hyperalgesia.

FIG. 2 is a graph showing the dose response of the compound of Example 11 on hyperalgesia in the Chung model.

FIG. 3 is a graph showing the effect of the compound of Example 3 on hyperalgesia in the Chung model.

FIG. 4 is a graph showing the effect of the compound of Example 23 on hyperalgesia in the Chung model.

FIG. 5 is a schematic depiction of the Chung model of tactile hypersensitivity.

FIG. 6 is a graph showing the effect of the compound of Example 23 on allodynia in the Chung model.

FIG. 7 is a schematic depiction of the Porreca model of tactile hypersensitivity.

FIG. 8 is a graph showing the effect of the compound of Example 23 on allodynia in the Porreca model.

FIG. 9 is a graph showing the effect of the compound of Example 37 on hyperalgesia in the Chung model.

FIG. 10 is a graph showing the effect of the compound of Example 47 on hyperalgesia in the Chung model.

FIG. 11 is a graph showing the effect of the compound of Example 54 on hyperalgesia in the Chung model.

FIG. 12 is a graph showing the effect of the compound of Example 28 on hyperalgesia in the Chung model.

FIG. 13 is a graph showing the effect of compound 28 on allodynia in the Porreca model.

FIG. 14 is a graph showing the effect a single dose of compound 11 on allodynia in the Sciatic Nerve Cuff model.

FIG. 15 is a graph showing the effect a multiple doses of compound 11 on allodynia in the Sciatic Nerve Cuff model.

FIG. 16 is a graph showing the effect of compound 11 on the frequency of paw lifts in the Sciatic Nerve Cuff model.

FIG. 17 is a graph showing the effect of compound 11 on the hind leg weight bearing in the Sciatic Nerve Cuff model.

FIG. 18 is a schematic depiction of a model for visceral pain.

FIG. 19 is a graph showing the effect of compound 11 in a rat model of visceral pain.

DETAILED DESCRIPTION

The invention features novel quinolones, tetrahydroquinolines, and related compounds having nitric oxide synthase (NOS) inhibitory activity, pharmaceutical and diagnostic compositions containing them, and their medical use. Exemplary compounds of the invention are shown in Table 2.

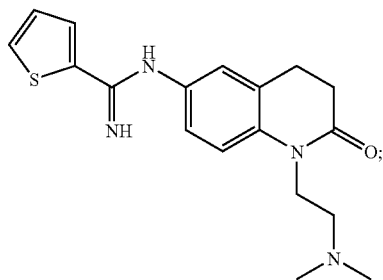

TABLE 2

TABLE 2-continued
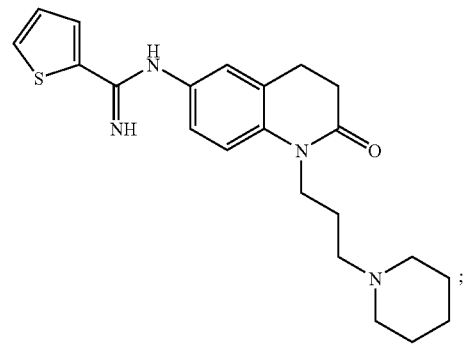
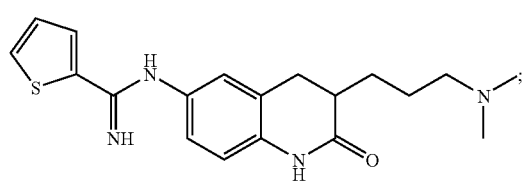
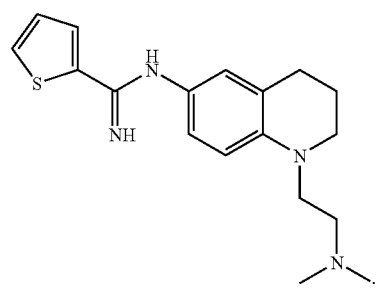
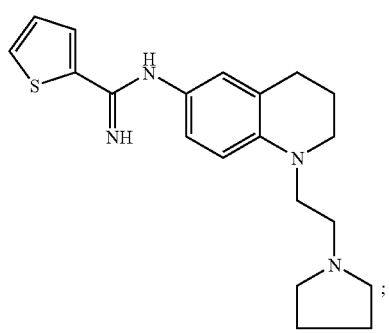
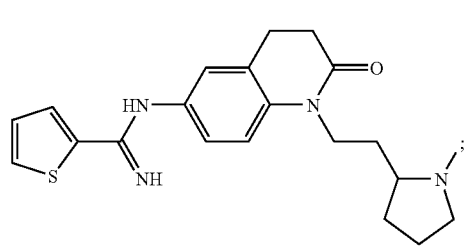
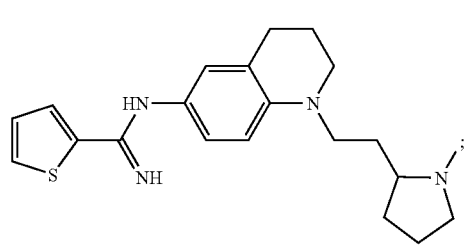
TABLE 2-continued
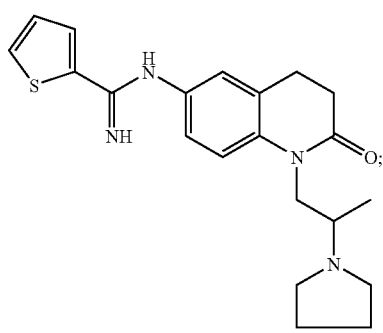
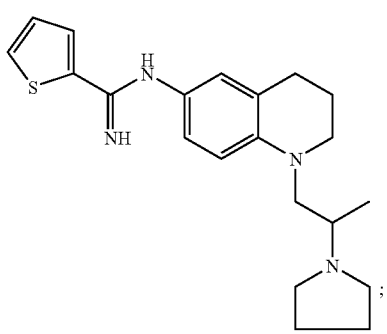
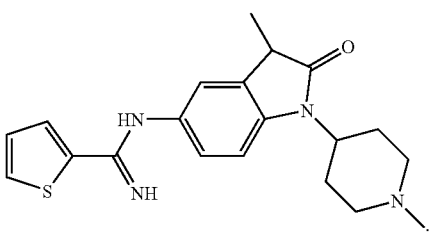
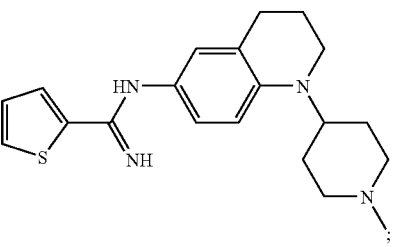
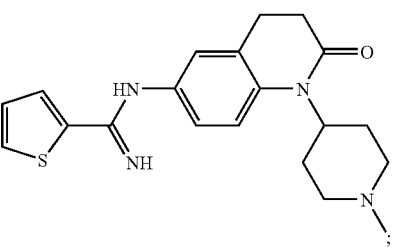

TABLE 2-continued
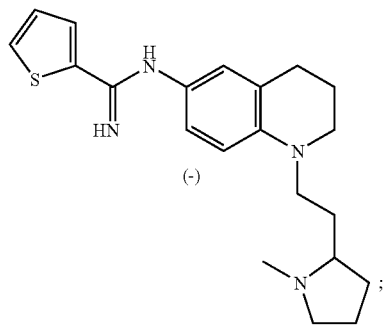
(-)
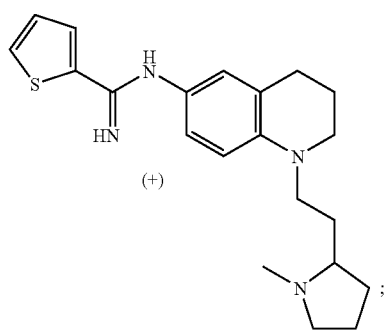
(+)
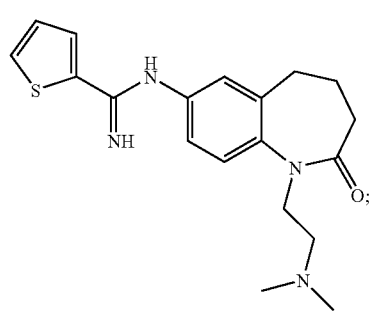
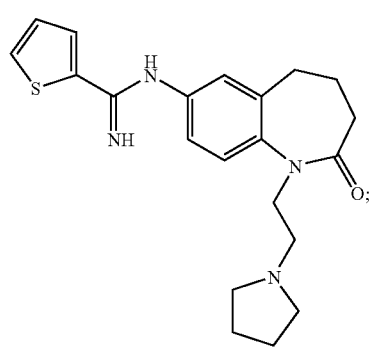
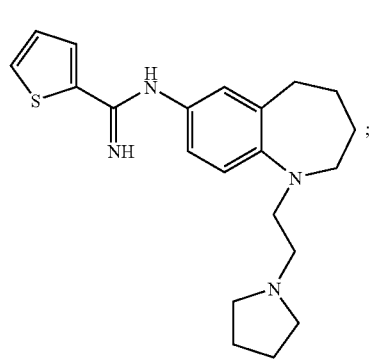
TABLE 2-continued
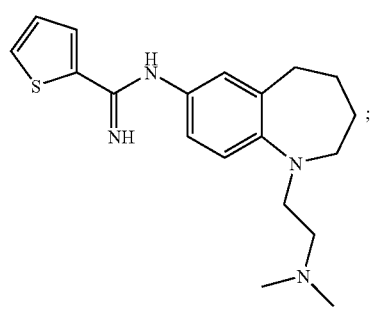
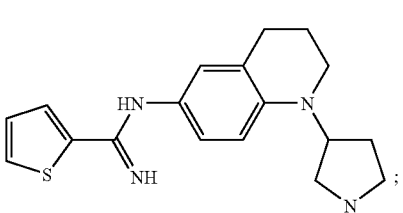
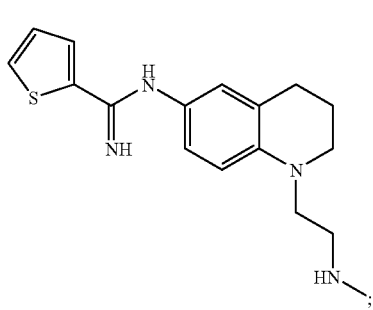
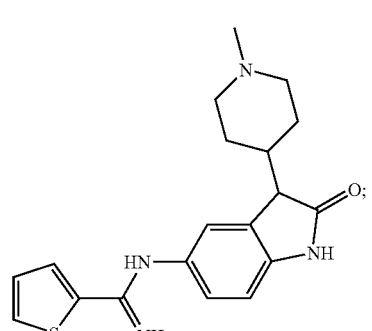
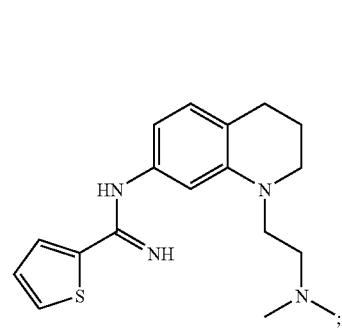

TABLE 2-continued
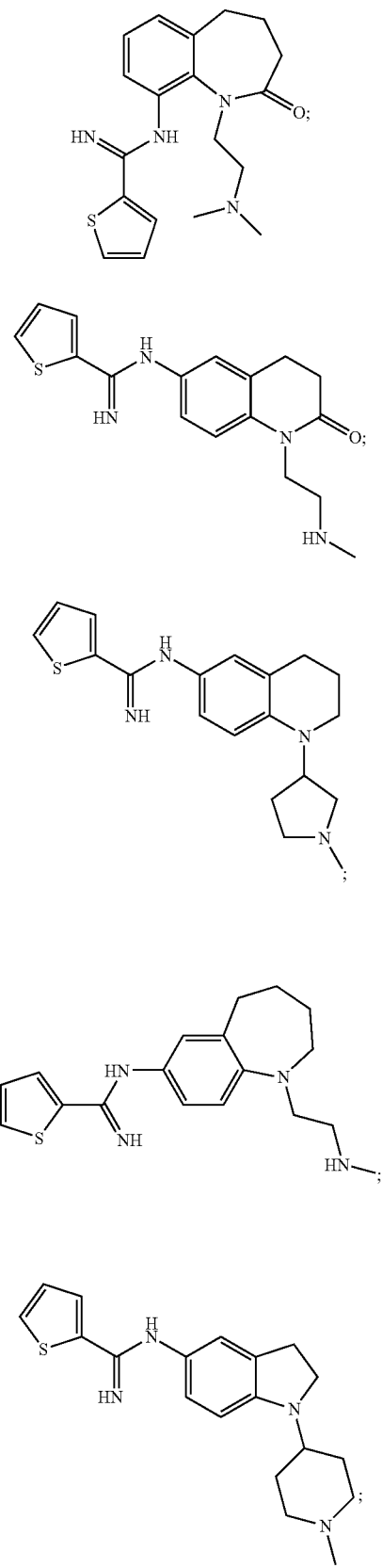
TABLE 2-continued
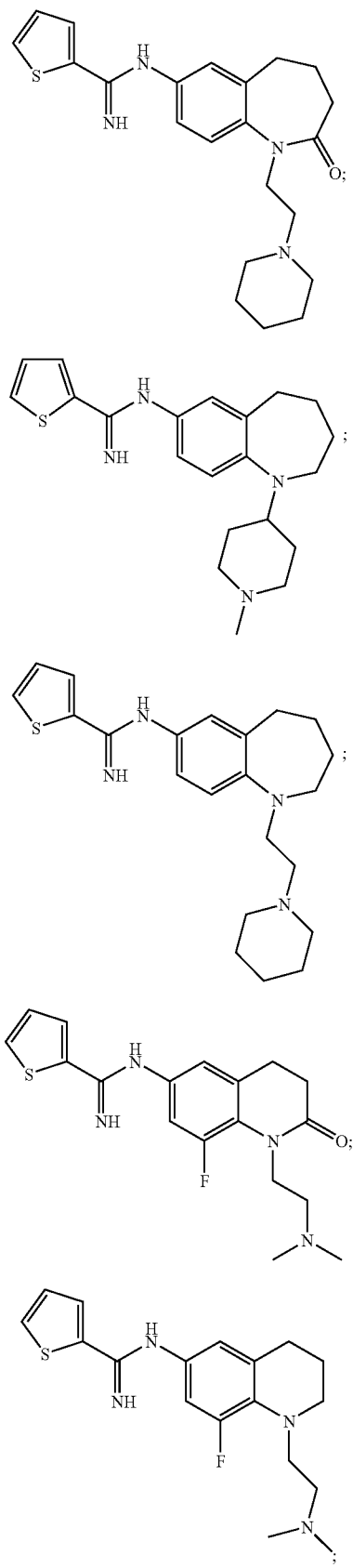

TABLE 2-continued
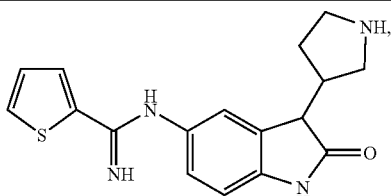
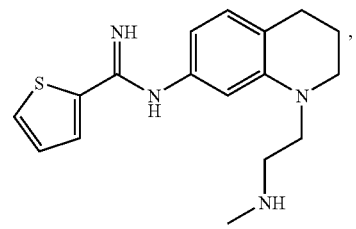
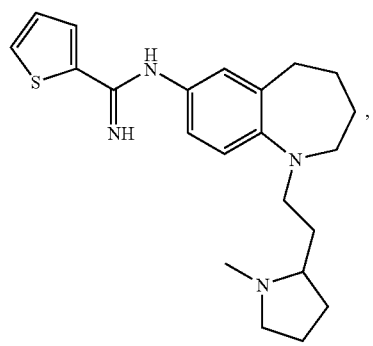
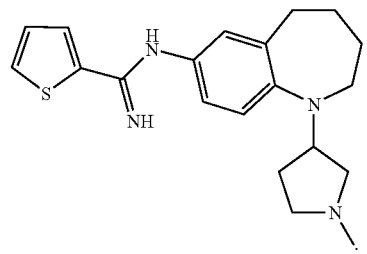
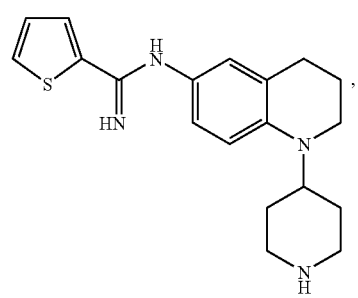
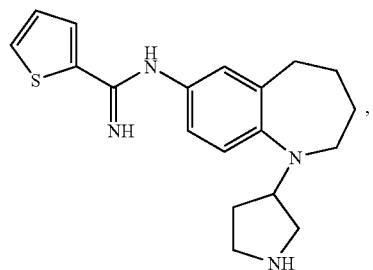
TABLE 2-continued
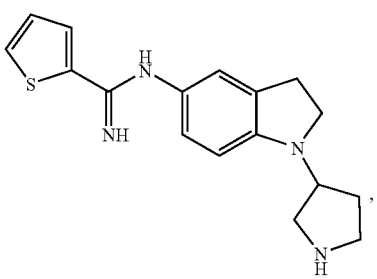
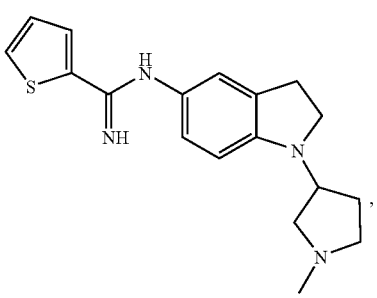
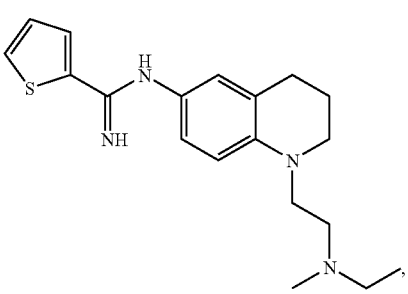
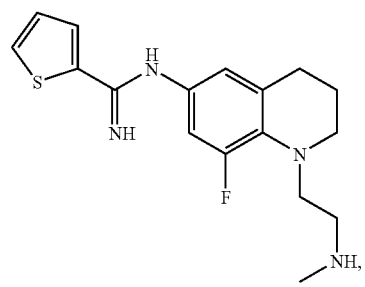
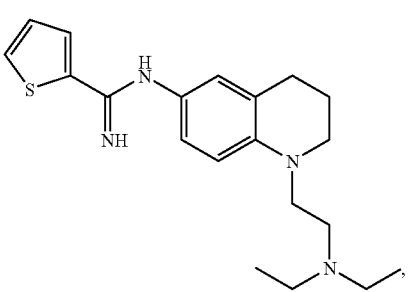

TABLE 2-continued
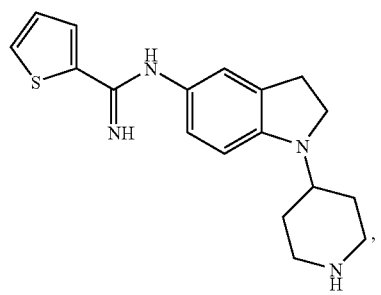
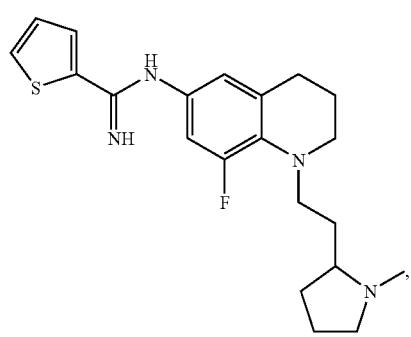
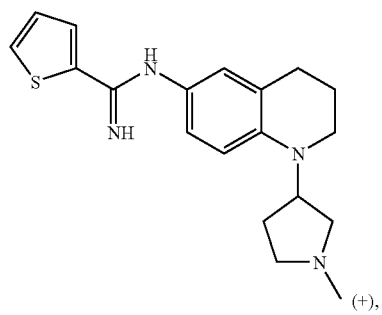
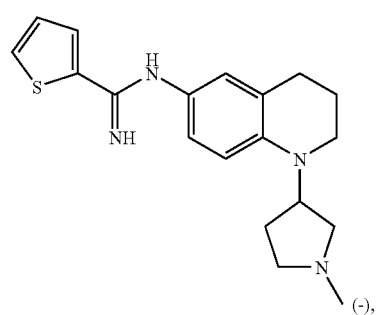
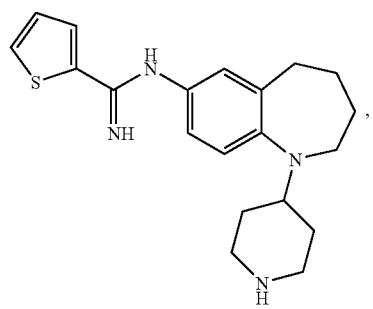
TABLE 2-continued
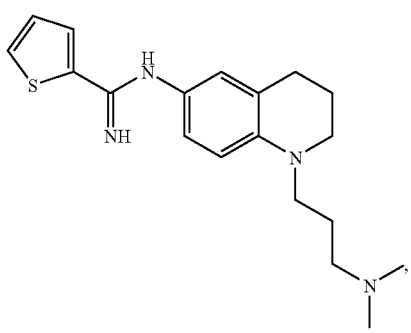
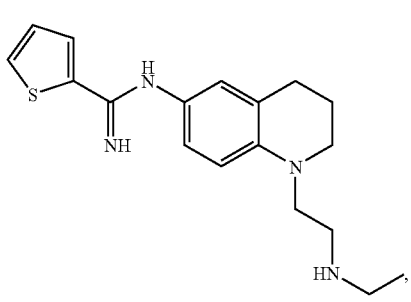
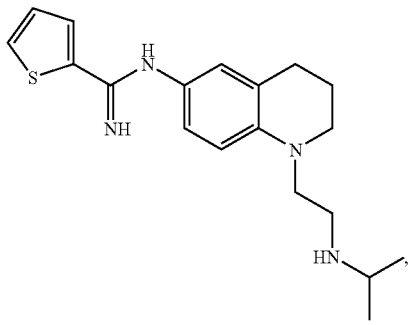
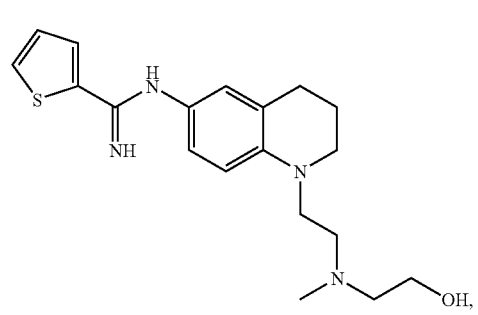
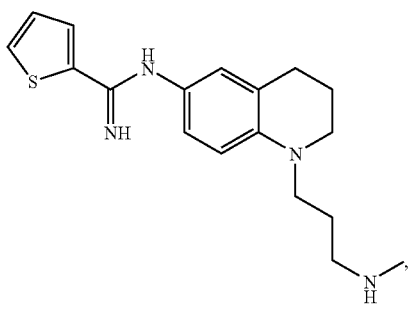

TABLE 2-continued
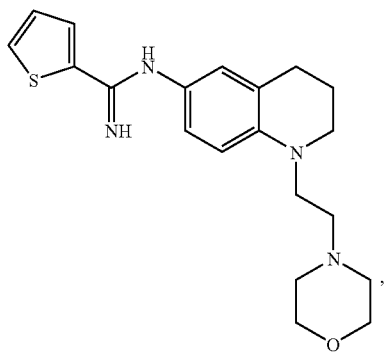
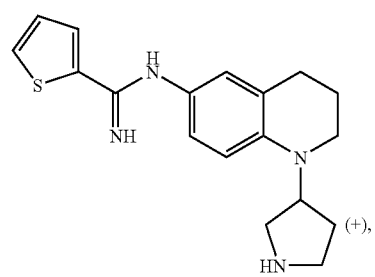 (+),
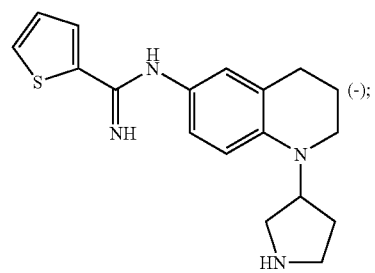 (−);
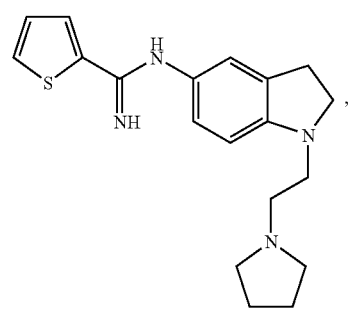,
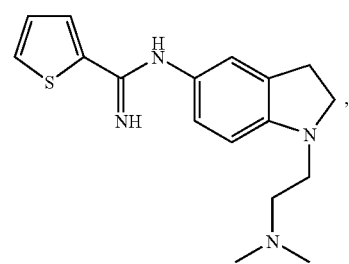,
TABLE 2-continued
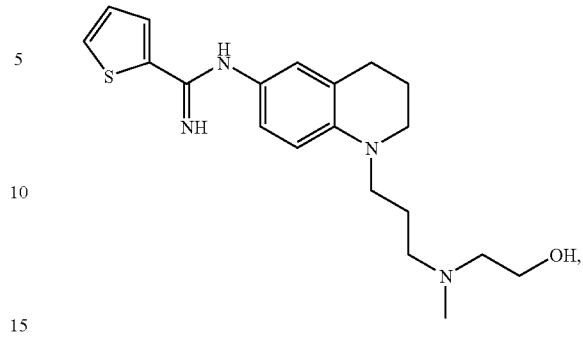
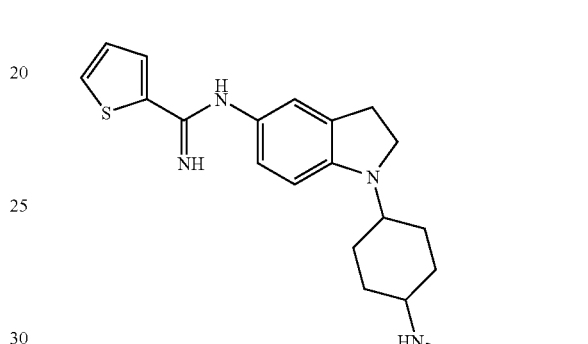, Diastereomer 1,
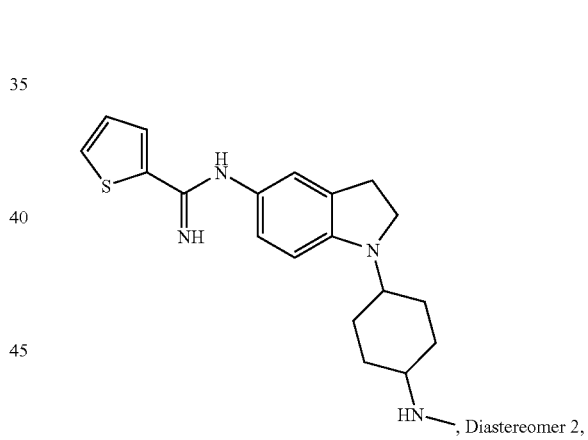, Diastereomer 2,
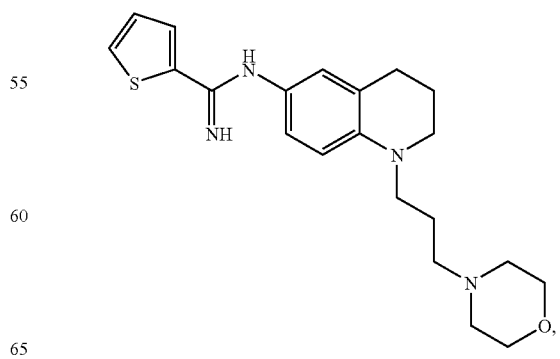,

TABLE 2-continued

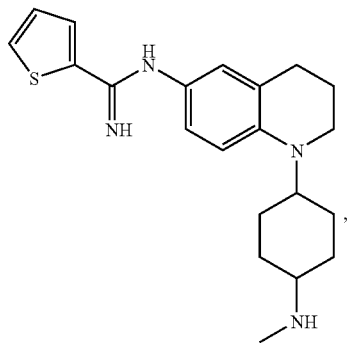

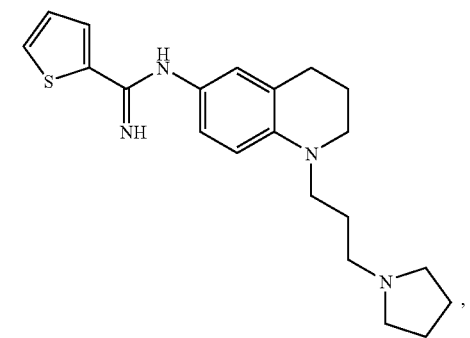

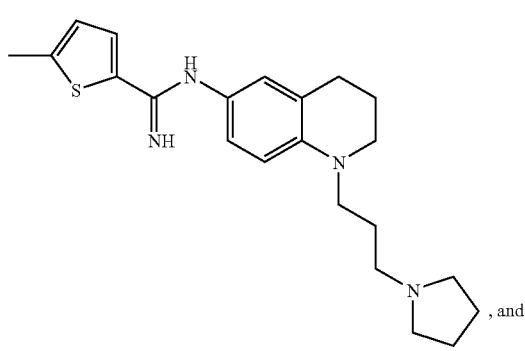

TABLE 2-continued

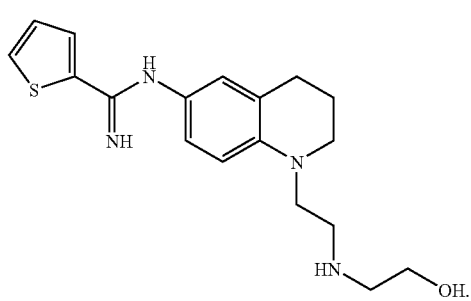

Exemplary methods for synthesizing compounds of the invention are described herein.

Methods of Preparing Compounds of the Invention

The compounds of the invention can be prepared by processes analogous to those established in the art, for example, by the reaction sequences shown in Schemes 1-8.

A compound of formula 3, where $R^1$ and Q is as defined elsewhere herein, can be prepared under standard alkylating conditions by treating a compound of formula 1 with a compound of formula 2, or a suitably protected derivative thereof, where $R^1$ is as defined above, with the exception that $R^1$ is not H, and "LG" is a leaving group, such as, for example, chloro, bromo, iodo, or sulfonate (e.g., mesylate, tosylate, or triflate). Conditions to effect the alkylation of a compound of formula 1 with a compound of formula 2 may include, for example, heating a compound of formula 1 and a compound of formula 2, with or without a solvent, optionally in the presence of a suitable base (see Scheme 1). Preferred conditions include, for example, heating a compound of formula 1 and 2 in the presence of a solvent, such as DMF, and potassium carbonate.

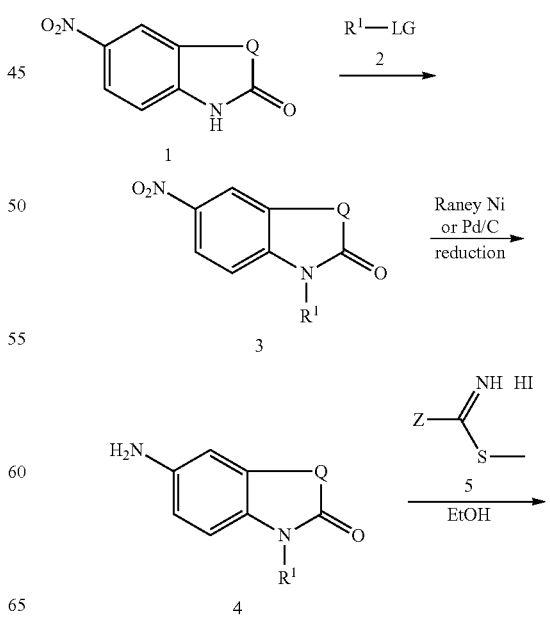

Scheme 1-General reaction scheme for the preparation of Oxaza Compounds

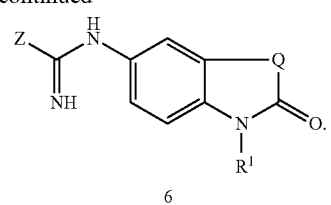

6

A compound of formula 4 can be prepared by reduction of the nitro group of a compound of formula 3 or a suitably protected derivative, under standard conditions as shown in Scheme 1. In one example, standard reduction conditions include the use of Raney Nickel in a polar solvent, such as, for example, methanol or ethanol at refluxing temperatures. Alternatively, a compound of formula 4 can be prepared by the hydrogenation of a compound of formula 3 using a suitable catalyst, such as palladium on charcoal in ethanol or another solvent or combinations of solvents.

As shown in Scheme 1, a compound of formula 6 can be prepared by reacting a compound of formula 5 with a compound of formula 4 according to a previous procedure (US 2006/0258721 A1).

Alternatively, compound of formula 3 in which $R^1$ is $(CH_2)_n X^1$, where $X^1$ is

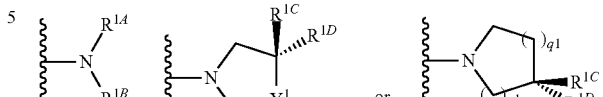

with $R^{1A}, R^{1B}, R^{1C}, R^{1D}, Y^1$ is $CH_2$, O, S, $NR^1$, n1, p1, and q1 as defined by example herein, involves the reaction of a compound of formula 7, wherein LG is a suitable leaving group, such as, for example, chloro, bromo, iodo, or sulfonate (e.g., mesylate, tosylate, or triflate), with compounds of formula 8, where $X^1$ is as defined above, under standard alkylation conditions as shown in Scheme 2. When LG is an aldehyde or ketone group, standard reductive amination conditions (Abdel-Majid et al. *J. Org. Chem.* 61:3849-3862, 1996) may be employed using a suitable reducing agent, such as $NaBH_4$, $NaBH(OAc)_3$, $NaCNBH_4$, and the like, in an alcoholic solvent, such as ethanol, to produce a compound of formula 9. The reductive amination may be performed in one reaction or the imine resulting from mixing a compound of formula 7 with a compound of formula 8 can be preformed in situ, followed by sequential reduction with a suitable reducing agent. Compound 9 is converted to compound 11 by nitro reduction followed by amidation in a similar fashion as described in Scheme 1.

When alkylation produces a compound of formula 9 wherein $R^{1A}$ or $R^{1B}$ is H, then a suitable protecting group, for example a Boc group, may be required before the reduction of the nitro group. The protecting group can then be removed under standard conditions (e.g., under acidic conditions when a Boc group is used) to produce compounds of the invention. Alternatively, when $R^{1A}$ and/or $R^{1B}$ is a methyl group, compounds of 9 can be treated with a demethylating agent such as a chloroformate reagent, for example, phenyl chloroformate, chloromethylchlorformate, and the like. After reduction and amidation, the protecting group can be removed by cleavage under standard conditions. A preferred protecting group is the phenyl carbamate, and preferred deprotection conditions include reaction under basic conditions (e.g., sodium hydroxide) in a suitable solvent such as water in the presence of a cosolvent such as methanol or ethanol.

Scheme 2-General reaction scheme for the preparation of compounds with a proplyamino-sidechain.

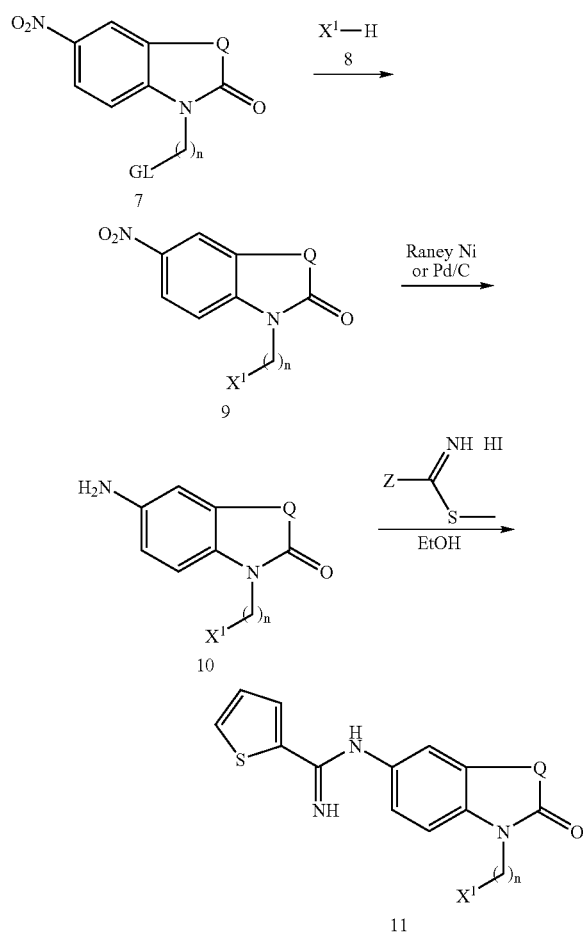

Scheme 3-General reacton scheme for the preparation of reduced compounds.

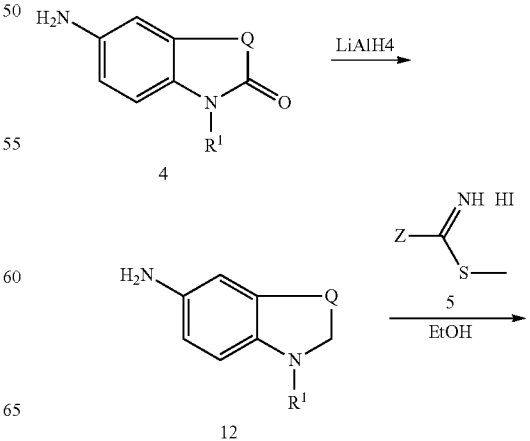

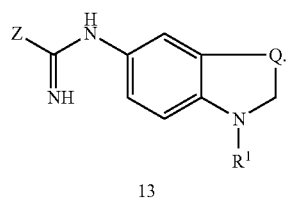

13

Compound of general formula 12 can be prepared from a compound of formula 4 by amide reduction with lithium aluminum hydride in aprotic solvents, such as, THF, ether, and the like. Alternatively, a compound of formula 12 can be reduced using a suitable reducing agent, such as, $BH_3$, in a suitable aprotic solvent, such as THF. These compounds are then converted to compound of formula 13 by coupling with reagent 5 as described in Scheme 1.

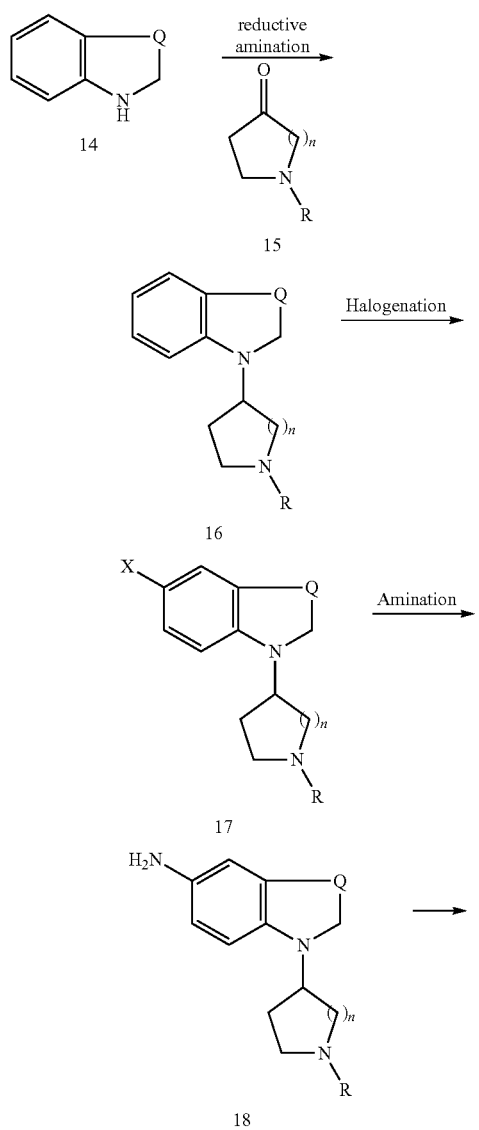

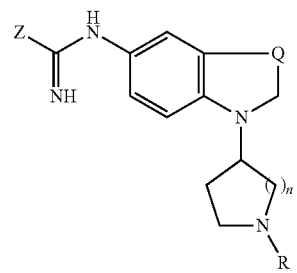

19

R = alkyl, PG

Compounds of general formula 16 can be prepared from compound 14 and compound of general formula 15 under standard reductive amination conditions (Abdel-Majid et al. *J. Org. Chem.* 61:3849-3862, 1996). Compounds of general formula 17 can be prepared by aromatic halogenation of a compound of general formula 16 according to established procedures (de la Mare, "Electrophilic Halogenation," Cambridge University Press, Cambridge (1976)). The preferred condition is reacting compounds of general formula 16 with N-Bromosuccinimide under neutral conditions. A compound of formula 18 can be prepared by metal catalyzed amination of a compound of formula 17 where X is chloro, bromo, or iodo (Wolfe, et al. *J. Org. Chem.* 65:1158-1174, 2000) in the presence of a suitable ammonia equivalent, such as benzophenone imine, $LiN(SiMe_3)_2$, $Ph_3SiNH_2$, $NaN(SiMe_3)_2$, or lithium amide (Huang and Buchwald, *Org. Lett.* 3(21):3417-3419, 2001). A preferred halogen is bromo in the presence of palladium (0) or palladium (II) catalyst. Examples of suitable metal catalysts include, for example, a palladium catalyst coordinated to suitable ligands. Suitable palladium catalysts include tris-dibenzylideneacetone dipalladium ($Pd_2dba_3$) and palladium acetate ($PdOAc_2$), preferably $Pd_2dba_3$. Suitable ligands for palladium can vary greatly and may include, for example, XantPhos, BINAP, DPEphos, dppf, dppb, DPPP, (o-biphenyl)-$P(t-Bu)_2$, (o-biphenyl)-$P(Cy)_2$, $P(t-Bu)_3$, $P(Cy)_3$, and others (Huang and Buchwald, *Org. Lett.* 3(21): 3417-3419, 2001). Preferably, the ligand is $P(t-Bu)_3$. The Pd-catalyzed amination is performed in a suitable solvent, such as THF, dioxane, toluene, xylene, DME, and the like, at temperatures between room temperature and reflux. Conversion of compound 18 to 19 was done under conditions in Scheme 1. Compounds wherein R=H can be prepared by cleavage of a suitable protecting group PG. A suitable protecting group includes a t-butoxycarbonyl (Boc) group that can be cleaved under acidic conditions, for example, aqueous HCl with an optional cosolvent.

Scheme 5-General reaction scheme for the preparation of quinolones with a cyclic group.

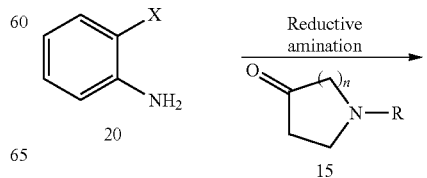

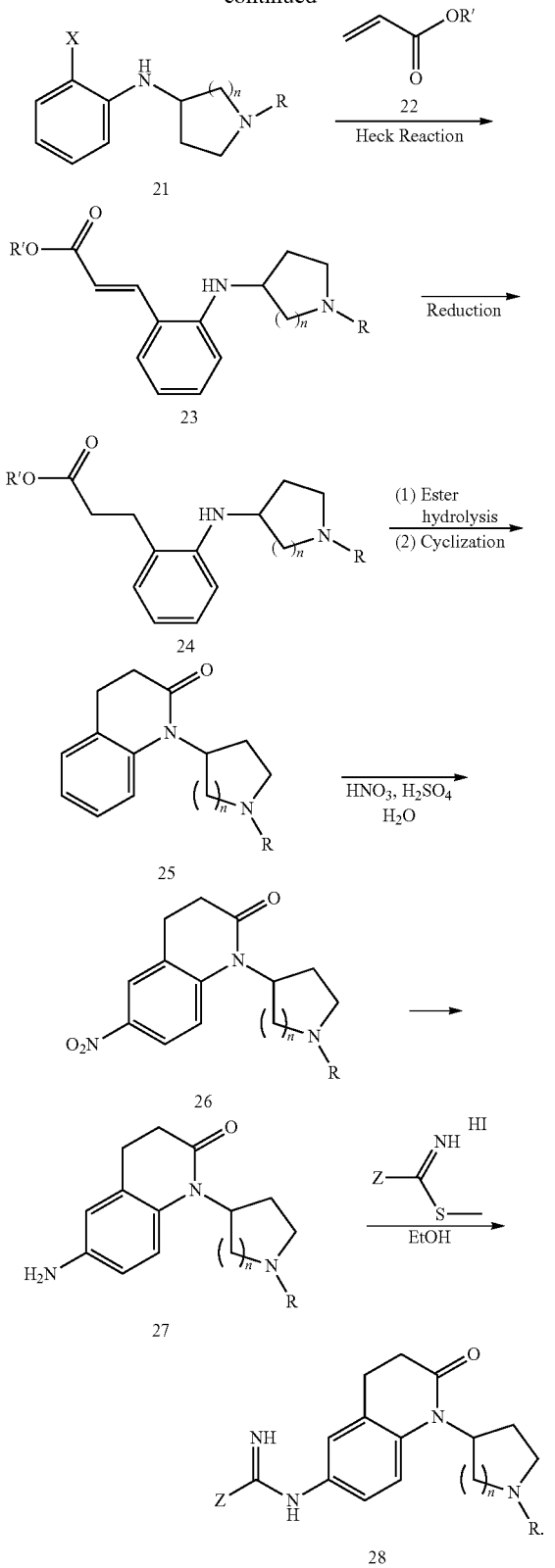

ditions (Abdel-Majid et al. *J. Org. Chem.* 61:3849-3862, 1996). Compounds of general formula 23 can be prepared by cross-coupling of acrylic ester 22 with a compound of general formula 21 under Heck reaction conditions using a suitable palladium catalyst (Beletskaya and Cheprakov. *Chem. Rev.* 100:3009-3066, 200). A preferred halogen is iodo in the presence of palladium (0) or palladium (II) catalyst. Suitable palladium catalysts include tris-dibenzylideneacetone dipalladium ($Pd_2dba_3$) and palladium acetate ($PdOAc_2$), preferably $PdOAc_2$. Suitable ligands for palladium can vary greatly and may include, for example, $(o\text{-tolyl})_3P$, XantPhos, BINAP, DPEphos, dppf, dppb, DPPP, $(o\text{-biphenyl})\text{-}P(t\text{-}Bu)_2$, $(o\text{-biphenyl})\text{-}P(Cy)_2$, $P(t\text{-}Bu)_3$, $P(Cy)_3$, and others.

A compound of formula 24 can be prepared by the hydrogenation of a compound of formula 23 using a suitable catalyst, such as palladium on charcoal in ethanol or another solvent or combination of solvents. A number of different hydrogenation conditions can also be employed in the transformation of 23 to 24 (see Rylander, "Hydrogenation Methods," Academic Press, New York (1985), Chpt 2).

A compound of general formula 25 can be prepared by hydrolysis of the ester 24 under standard conditions, such as, for example, aqueous sodium hydroxide in methanol. The subsequent cyclization can be performed by heating under aqueous acidic conditions (Ogawa et al *J. Med. Chem.* 36:2011-2017, 1993) or coupling with a dehydrating agent such as EDCI as previously reported (Grice et al *Bioorg. Med. Chem. Lett.* 16:2209-2212, 2006). The nitration of compound of general structure 25 under conditions previously reported (Devita et al. WO03/045313) gives compound of general structure 26. Conversion of compound of general structure 26 to compounds of general structure 28 can be carried out according to procedures as described in Scheme 1.

Scheme 6-General reaction scheme for the preparation of oxindoles

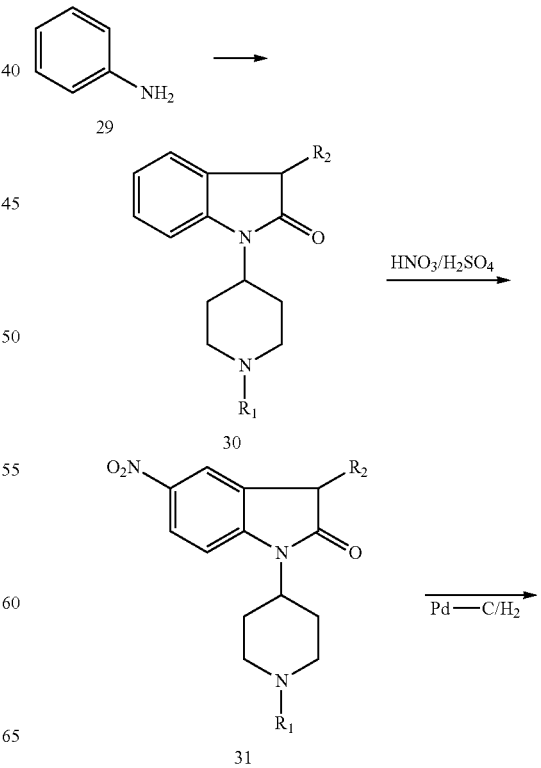

Compounds of general formula 21, where X can be chloro, bromo, or iodo and R is defined herein, can be prepared by reacting compound of general formula 20 with compound of general formula 15 under standard reductive amination con-

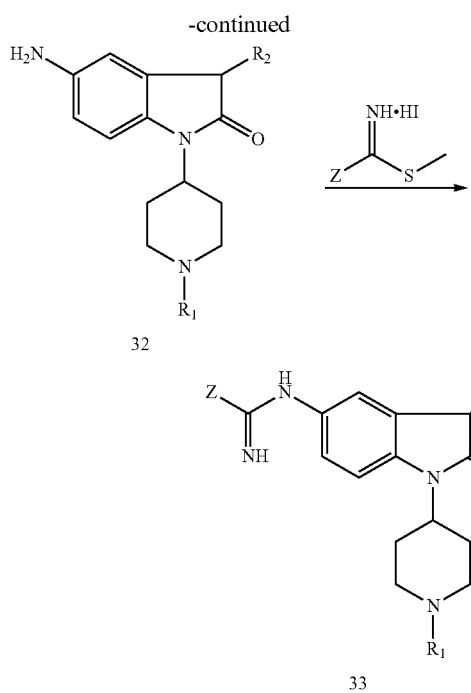

Compounds having general structure 35, can be prepared starting from 32 in two steps using LiAlH$_4$ reduction, followed by amidine coupling reactions described earlier (US 2006/0258721 A1).

Scheme 8-General reaction scheme for the preparation of indolones.

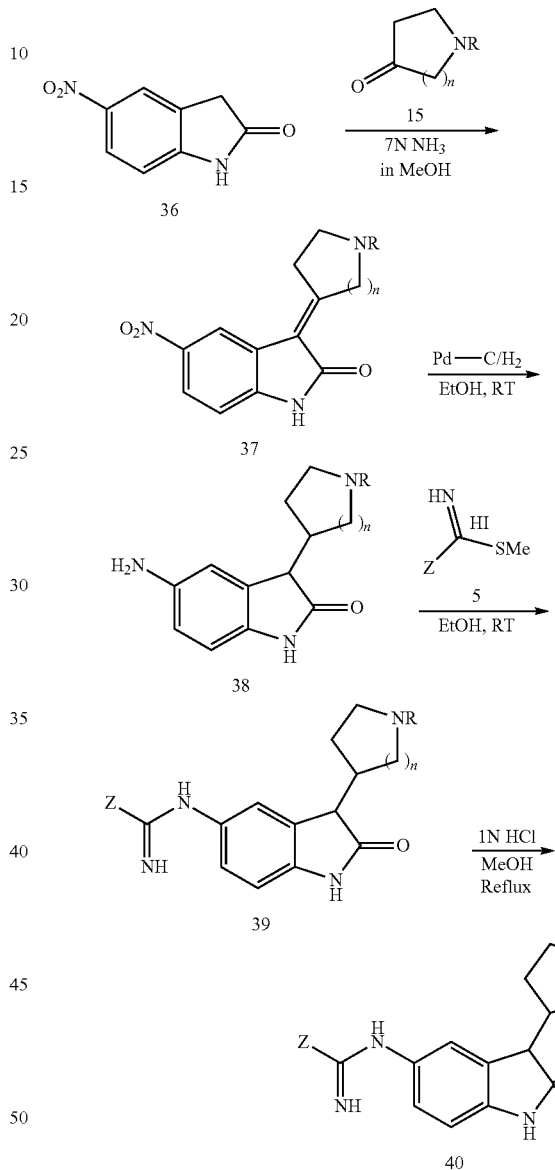

Compounds having general structure 30 can be prepared according to the known procedure in *J. Med. Chem.* 2004, 47, 2973-2976, from anilines such as 29. The nitration on compound 30 was carried according to procedure reported in International Publication No. WO03/045313. The reduction of nitro group followed by coupling with an amidine reagent was carried out according to a previous reported procedure (US 2006/0258721 A1).

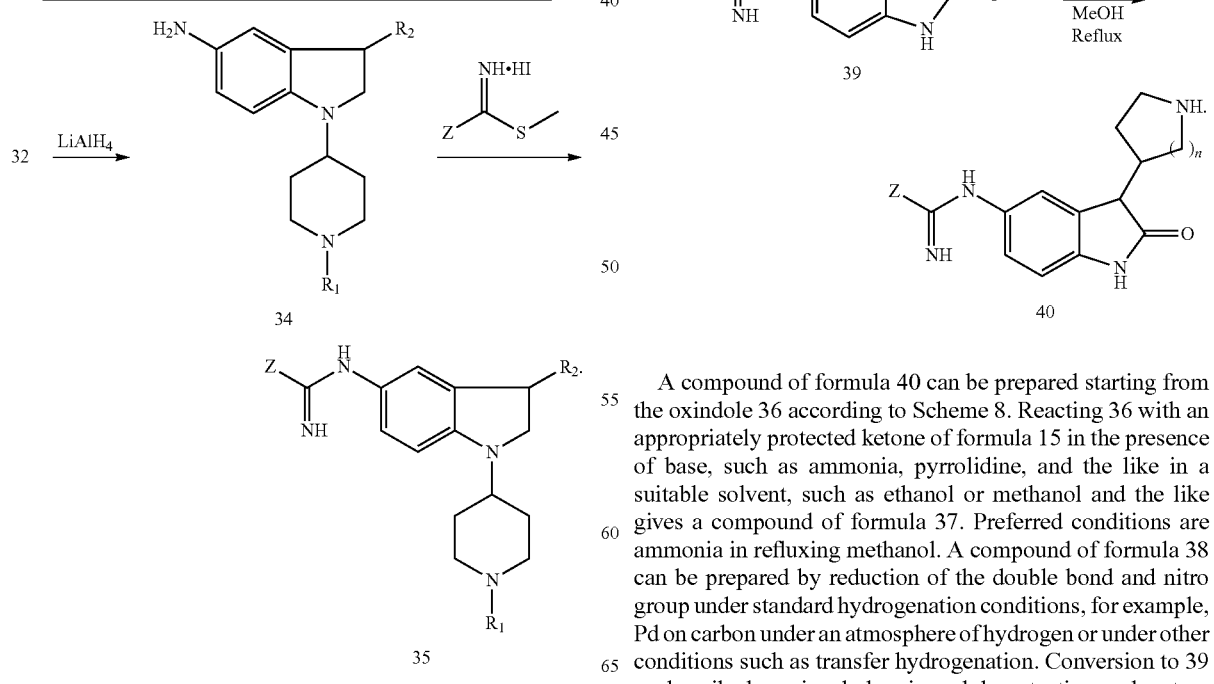

A compound of formula 40 can be prepared starting from the oxindole 36 according to Scheme 8. Reacting 36 with an appropriately protected ketone of formula 15 in the presence of base, such as ammonia, pyrrolidine, and the like in a suitable solvent, such as ethanol or methanol and the like gives a compound of formula 37. Preferred conditions are ammonia in refluxing methanol. A compound of formula 38 can be prepared by reduction of the double bond and nitro group under standard hydrogenation conditions, for example, Pd on carbon under an atmosphere of hydrogen or under other conditions such as transfer hydrogenation. Conversion to 39 as described previously herein and deprotection under standard conditions provide compounds of formula 40. A preferred protecting group is the Boc protecting group, which can be cleaved under acidic conditions, such as refluxing in methanolic HCl solution.

In some cases the chemistries outlined above may have to be modified, for instance, by the use of protective groups to prevent side reactions due to reactive groups, such as reactive groups attached as substituents. This may be achieved by means of conventional protecting groups as described in "Protective Groups in Organic Chemistry," McOmie, Ed., Plenum Press, 1973 and in Greene and Wuts, "Protective Groups in Organic Synthesis," John Wiley & Sons, $3^{rd}$ Edition, 1999.

The compounds of the invention, and intermediates in the preparation of the compounds of the invention, may be isolated from their reaction mixtures and purified (if necessary) using conventional techniques, including extraction, chromatography, distillation, and recrystallization.

The formation of a desired compound salt is achieved using standard techniques. For example, the neutral compound is treated with an acid in a suitable solvent and the formed salt is isolated by filtration, extraction, or any other suitable method.

The formation of solvates of the compounds of the invention will vary depending on the compound and the solvate. In general, solvates are formed by dissolving the compound in the appropriate solvent and isolating the solvate by cooling or adding an antisolvent. The solvate is typically dried or azeotroped under ambient conditions.

Preparation of an optical isomer of a compound of the invention may be performed by reaction of the appropriate optically active starting materials under reaction conditions which will not cause racemization. Alternatively, the individual enantiomers may be isolated by separation of a racemic mixture using standard techniques, such as, for example, fractional crystallization or chiral HPLC.

A radiolabeled compound of the invention may be prepared using standard methods known in the art. For example, tritium may be incorporated into a compound of the invention using standard techniques, such as, for example, by hydrogenation of a suitable precursor to a compound of the invention using tritium gas and a catalyst. Alternatively, a compound of the invention containing radioactive iodine may be prepared from the corresponding trialkyltin (suitably trimethyltin) derivative using standard iodination conditions, such as [$^{125}$I] sodium iodide in the presence of chloramine-T in a suitable solvent, such as dimethylformamide. The trialkyltin compound may be prepared from the corresponding non-radioactive halo, suitably iodo, compound using standard palladium-catalyzed stannylation conditions, such as, for example, hexamethylditin in the presence of tetrakis(triphenylphosphine) palladium (0) in an inert solvent, such as dioxane, and at elevated temperatures, suitably 50-100° C.

Pharmaceutical Uses

The present invention features all uses for compounds of the invention, including use in therapeutic methods, whether alone or in combination with another therapeutic substance, their use in compositions for inhibiting NOS activity, e.g., nNOS, their use in diagnostic assays, and their use as research tools.

The compounds of the invention have useful NOS inhibiting activity, and therefore are useful for treating, or reducing the risk of, diseases or conditions that are ameliorated by a reduction in NOS activity. Such diseases or conditions include those in which the synthesis or oversynthesis of nitric oxide plays a contributory part.

Accordingly, the present invention features a method of treating, or reducing the risk of, a disease or condition caused by NOS activity that includes administering an effective amount of a compound of the invention to a cell or animal in need thereof. Such diseases or conditions include, for example, migraine headache (with or without aura), chronic tension type headache (CTTH), migraine with allodynia, medication overuse headache, neuropathic pain, AIDS associated painful neuropathy, chronic headache, central post-stroke pain (CPSP), medication-induced hyperalgesia and/or allodynia, e.g., opioid-induced hyperalgesia or triptan (5-HT1D/1B agonists)-induced hyperalgesia/allodynia, acute pain, chronic pain, diabetic neuropathy, trigeminal neuralgia, chemotherapy induced neuropathic pain (e.g., Taxol, cis-Platin, Doxorubicin etc.), bone cancer pain, chemical dependencies or addictions, e.g., drug addiction, cocaine addition, nicotine addition, methamphetamine-induced neurotoxicity, ethanol tolerance, dependence, or withdrawal, or morphine/opioid induced tolerance, dependence, hyperalgesia, or withdrawal, CNS disorders including but not limited to, e.g., epilepsy, anxiety, depression (alone or in combination), attention deficit hyperactivity disorder (ADHD), psychosis, or dementia, neurodegenerative diseases or nerve injury, e.g., acute spinal cord injury, AIDS associated dementia, Parkinson's disease, Alzheimer's disease, ALS, Huntington's disease, multiple sclerosis, neurotoxicity, or head trauma, cardiovascular related conditions, e.g., stroke, CABG associated neurological damage, HCA, post-stroke pain, cardiogenic shock, reperfusion injury, or vascular dementia, diabetic nephropathy, inflammatory diseases, e.g., osteoarthritis or neuroinflammation, or gastrointestinal disorders, e.g., ileostomy-associated diarrhea, dumping syndrome, or visceral pain.

The following description is a summary and a basis for the link between NOS inhibition and some of these conditions.

Migraine with or without Aura

The first observation by Asciano Sobrero in 1847 that small quantities of nitroglycerine, an NO releasing agent, causes severe headache lead to the nitric oxide hypothesis of migraine (Olesen et al., *Cephalagia* 15:94-100, 1995). Serotonergic $5HT_{1D/1B}$ agonists, such as sumatriptan, which are used clinically in the treatment of migraine, are known to prevent the cortical spreading depression in the lissencephalic and gyrencephalic brain during migraine attack, a process resulting in widespread release of NO. Indeed, it has been shown that sumatriptan modifies the artificially enhanced cortical NO levels following infusion of glyceryl trinitate in rats (Read et al., *Brain Res.* 847:1-8, 1999; ibid, 870(1-2):44-53, 2000). In a human randomized double-blinded clinical trial for migraine, a 67% response rate after single i.v. administration of L-N$^G$ methylarginine hydrochloride (L-NMMA, an NOS inhibitor) was observed. The effect was not attributed to a simple vasoconstriction since no effect was observed on transcranial doppler determined velocity in the middle cerebral artery (Lassen et al., *Lancet* 349:401-402, 1997). In an open pilot study using the NO scavenger hydroxycobalamin, a reduction in the frequency of migraine attack of 50% was observed in 53% of the patients and a reduction in the total duration of migraine attacks was also observed (van der Kuy et al., *Cephalgia* 22(7):513-519, 2002).

Migraine with Allodynia

Clinical studies have shown that as many as 75% of patients develop cutaneous allodynia (exaggerated skin sensitivity) during migraine attacks and that its development during migraine is detrimental to the anti-migraine action of triptan $5HT_{1B/1D}$ agonists (Burstein et al., *Ann. Neurol.* 47:614-624, 2000; Burstein et al., *Brain*, 123:1703-1709, 2000). While the early administration of triptans such as sumatriptan can terminate migraine pain, late sumatriptan intervention is unable to terminate migraine pain or reverse the exaggerated skin sensitivity in migraine patients already associated with allodynia (Burstein et al., *Ann. Neurol. DOI:* 10.1002/ana.10785, 2003; Burstein and Jakubowski, *Ann. Neurol.*, 55:27-36, 2004). The development of peripheral and central sensitization correlates with the clinical manifestations of migraine. In migraine patients, throbbing occurs 5-20 minutes after the onset of headache, whereas cutaneous allodynia starts between 20-120 minutes (Burstein et al., *Brain*, 123:1703-1709, 2000). In the rat, experimentally induced peripheral sensitization of meningeal nociceptors occurs within 5-20 minutes after applying an inflammatory soup (I.S.) to the dura (Levy and Strassman, *J. Physiol.*, 538:483-493, 2002), whereas central sensitization of trigeminovascular neurons develops between 20-120 minutes (Burstein et al., *J. Neurophysiol.* 79:964-982, 1998) after I.S. administration. Parallel effects on the early or late administration of antimigraine triptans like sumatriptan on the development of central sensitization have been demonstrated in the rat (Burstein and Jakubowski, vide supra). Thus, early but not late sumatriptan prevents the long-term increase in I.S.-induced spontaneous activity seen in central trigeminovascular neurons (a clinical correlate of migraine pain intensity). In addition, late sumatriptan intervention in rats did not prevent I.S.-induced neuronal sensitivity to mechanical stimulation at the periorbital skin, nor decreased the threshold to heat (a clinical correlate of patients with mechanical and thermal allodynia in the periorbital area). In contrast, early sumatriptan prevented I.S. from inducing both thermal and mechanical hypersensitivity. After the development of central sensitization, late sumatriptan intervention reverses the enlargement of dural receptive fields and increases in sensitivity to dural indentation (a clinical correlate of pain throbbing exacerbated by bending over) while early intervention prevents its development.

Previous studies on migraine compounds such as sumatriptan (Kaube et al., *Br. J. Pharmacol.* 109:788-792, 1993), zolmitriptan (Goadsby et al., *Pain* 67:355-359, 1996), naratriptan (Goadsby et al., *Br. J. Pharmacol.*, 328:37-40, 1997), rizatriptan (Cumberbatch et al., *Eur. J. Pharmacol.*, 362:43-46, 1998), or L-471-604 (Cumberbatch et al., *Br. J. Pharmacol.* 126:1478-1486, 1999) examined their effects on nonsensitized central trigeminovascular neurons (under normal conditions) and thus do not reflect on their effects under the pathophysiological conditions of migraine. While triptans are effective in terminating the throbbing of migraine whether administered early or late, the peripheral action of sumatriptan is unable to terminate migraine pain with allodynia following late intervention via the effects of central sensitization of trigeminovascular neurons. The limitations of triptans suggest that improvement in the treatment of migraine pain can be achieved by utilizing drugs that can abort ongoing central sensitization, such as the compounds of the present invention.

It has been shown that systemic nitroglycerin increases nNOS levels and c-Fos-immunoreactive neurons (a marker neuronal activation) in rat trigeminal nucleus caudalis after 4 hours, suggesting NO likely mediates central sensitization of trigeminal neurons (Pardutz et al., *Neuroreport* 11(14):3071-3075, 2000). In addition, L-NAME can attenuate Fos expression in the trigeminal nucleus caudalis after prolonged (2 hrs) electrical stimulation of the superior sagittal sinus (Hoskin et al. *Neurosci. Lett.* 266(3):173-6, 1999). Taken together with ability of NOS inhibitors to abort acute migraine attack (Lassen et al., *Cephalalgia* 18(1):27-32, 1998), the compounds of the invention, alone or in combination with other antinociceptive agents, represent excellent candidate therapeutics for aborting migraine in patients after the development of allodynia.

Chronic Headache (CTTH)

NO contributes to the sensory transmission in the peripheral (Aley et al., *J. Neurosci.* 1:7008-7014, 1998) and central nervous system (Meller and Gebhart, *Pain* 52:127-136, 1993). Substantial experimental evidence indicates that central sensitization, generated by prolonged nociceptive input from the periphery, increases excitability of neurons in the CNS and is caused by, or associated with, an increase in NOS activation and NO synthesis (Bendtsen, *Cephalagia* 20:486-508, 2000; Woolf and Salter, *Science* 288:1765-1769, 2000). It has been shown that experimental infusion of the NO donor, glyceryl trinitrate, induces headache in patients. In a double-blinded study, patients with chronic tension-type headache receiving L-NMMA (an NOS inhibitor) had a significant reduction in headache intensity (Ashina and Bendtsen, *J. Headache Pain* 2:21-24, 2001; Ashina et al., *Lancet* 243 (9149):287-9, 1999). Thus the NOS inhibitors of the present invention may be useful for the treatment of chronic tension-type headache.

Acute Spinal Cord Injury, Chronic or Neuropathic Pain

In humans, NO evokes pain on intracutaneous injection (Holthusen and Arndt, *Neurosci. Lett.* 165:71-74, 1994), thus showing a direct involvement of NO in pain. Furthermore, NOS inhibitors have little or no effect on nociceptive transmission under normal conditions (Meller and Gebhart, *Pain* 52:127-136, 1993). NO is involved in the transmission and modulation of nociceptive information at the periphery, spinal cord and supraspinal level (Duarte et al., *Eur. J. Pharmacol.* 217:225-227, 1992; Haley et al., *Neuroscience* 31:251-258, 1992). Lesions or dysfunctions in the CNS may lead to the development of chronic pain symptoms, known as central pain, and includes spontaneous pain, hyperalgesia, and mechanical and cold allodynia (Pagni, *Textbook of Pain*, Churchill Livingstone, Edinburgh, 1989, pp. 634-655; Tasker In: *The Management of Pain*, pp. 264-283, J. J. Bonica (Ed.), Lea and Febiger, Philadelphia, Pa., 1990; Casey, Pain and Central Nervous System Disease: The Central Pain Syndromes, pp. 1-11 K. L. Casey (Ed.), Raven Press, New York, 1991). It has been demonstrated that systemic administration (i.p.) of the NOS inhibitors 7-NI and L-NAME relieve chronic allodynia-like symptoms in rats with spinal cord injury (Hao and Xu, *Pain* 66:313-319, 1996). The effects of 7-NI were not associated with a significant sedative effect and were reversed by L-arginine (NO precursor). The maintenance of thermal hyperalgesia is believed to be mediated by nitric oxide in the lumbar spinal cord and can be blocked by intrathecal administration of a nitric oxide synthase inhibitor like L-NAME or soluble guanylate cyclase inhibitor methylene blue (*Neuroscience* 50(1):7-10, 1992). Thus the NOS inhibitors of the present invention may be useful for the treatment of chronic or neuropathic pain.

Diabetic Neuropathy

The endogenous polyamine metabolite agmatine is a metabolite of arginine that is both an NOS inhibitor and N-methyl-D-aspartate (NMDA) channel antagonist. Agmatine is effective in both the spinal nerve ligation (SNL) model of neuropathic pain as well as the streptozotocin model of diabetic neuropathy (Karadag et al., *Neurosci. Lett.* 339(1):88-90, 2003). Thus compounds possessing NOS inhibitory activity, such as, for example, a compound of formula I, a combination of an NOS inhibitor and an NMDA antagonist should be effective in treating diabetic neuropathy and other neuropathic pain conditions.

Inflammatory Diseases and Neuroinflammation

LPS, a well-known pharmacological tool, induces inflammation in many tissues and activates NFκB in all brain regions when administered intravenously. It also activates pro-inflammatory genes when injected locally into the striatum (Stern et al., *J. Neuroimmunology*, 109:245-260, 2000). Recently it has been shown that both the NMDA receptor antagonist MK801 and the brain selective nNOS inhibitor 7-NI both reduce NFκB activation in the brain and thus reveal a clear role for glutamate and NO pathway in neuroinflammation (Glezer et al., *Neuropharmacology* 45(8):1120-1129, 2003). Thus, the administration of a compound of the invention, either alone or in combination with an NMDA antagonist, should be effective in treating diseases arising from neuroinflammation.

Stroke and Reperfusion Injury

The role of NO in cerebral ischemia can be protective or destructive depending on the stage of evolution of the ischemic process and on the cellular compartment producing NO (Dalkara et al., *Brain Pathology* 4:49, 1994). While the NO produced by eNOS is likely beneficial by acting as a vasodilator to improve blood flow to the affected area (Huang et al., *J. Cereb. Blood Flow Metab.* 16:981, 1996), NO produced by nNOS contributes to the initial metabolic deterioration of the ischemic penumbra, resulting in larger infarcts (Hara et al., *J. Cereb. Blood Flow Metab.* 16:605, 1996). The metabolic derangement that occurs during ischemia and subsequent reperfusion results in the expression and release of several cytokines that activate iNOS in several cell types including some of the central nervous system. NO can be produced at cytotoxic levels by iNOS, and increased levels of iNOS contribute to progressive tissue damage in the penumbra, leading to larger infarcts (Parmentier et al., *Br. J. Pharmacol.* 127:546, 1999). Inhibition of i-NOS has been shown to ameliorate cerebral ischemic damage in rats (*Am. J. Physiol.* 268:R286, 1995).

It has been shown that a synergistic neuroprotective effect is observed upon the combined administration of an NMDA antagonist (e.g., MK-801 or LY293558) with nNOS selective inhibitors (7-NI or ARL17477) in global cerebral ischemia (Hicks et al., *Eur. J. Pharmacol.* 381:113-119, 1999). Thus the compounds of the invention, administered either alone or in combination with NMDA antagonists, or compounds possessing mixed nNOS/NMDA activity, may be effective in treating conditions of stroke and other neurodegenerative disorders.

Complications Resulting from Coronary Artery Bypass Surgery

Cerebral damage and cognitive dysfunction still remains as a major complication of patients undergoing coronary artery bypass surgery (CABG) (Roch et al., *N. Eng. J. Med.* 335:1857-1864, 1996; Shaw et al., *Q. J. Med.* 58:59-68, 1986). This cerebral impairment following surgery is a result of ischemia from preoperative cerebral microembolism. In a randomized trial of the NMDA antagonist remacemide, patients showed a significant overall postoperative improvement in learning ability in addition to reduced deficits (Arrowsmith et al., *Stroke* 29:2357-2362, 1998). Given the involvement of excitotoxicity produced by excessive release of glutamate and calcium influx, it is expected that a neuroprotective agent, such as a compound of the invention or an NMDA antagonist, either alone or in combination (as discussed above), may have a beneficial effect improving neurological outcomes after CABG.

AIDS-Associated Dementia

HIV-1 infection can give rise to dementia. The HIV-1 coat protein gp-120 kills neurons in primary cortical cultures at low picomolar levels and requires external glutamate and calcium (Dawson et al., *Proc. Natl. Acad. Sci.* 90(8):3256-3259, 1993). This toxicity can be attenuated by administration of a neuroprotective agent, e.g., a compound of the invention, either alone or in combination with another therapeutic agent, such as, for example, an NMDA antagonist (as discussed above).

Examples of other compounds, e.g., NMDA antagonists, useful for any of the combinations of the invention include aptiganel; besonprodil; budipine; conantokin G; delucemine; dexanabinol; felbamate; fluorofelbamate; gacyclidine; glycine; ipenoxazone; kaitocephalin; lanicemine; licostinel; midafotel; milnacipran; neramexane; orphenadrine; remacemide; topiramate; (αR)-α-amino-5-chloro-1-(phosphonomethyl)-1H-benzimidazole-2-propanoic acid; 1-aminocyclopentane-carboxylic acid; [5-(aminomethyl)-2-[[[(5S)-9-chloro-2,3,6,7-tetrahydro-2,3-dioxo-1H,5H-pyrido[1,2,3-de]quinoxalin-5-yl]acetyl]amino]phenoxy]-acetic acid; α-amino-2-(2-phosphonoethyl)-cyclohexanepropanoic acid; α-amino-4-(phosphonomethyl)-benzeneacetic acid; (3E)-2-amino-4-(phosphonomethyl)-3-heptenoic acid; 3-[(1E)-2-carboxy-2-phenylethenyl]-4,6-dichloro-1H-indole-2-carboxylic acid; 8-chloro-2,3-dihydropyridazino[4,5-b]quinoline-1,4-dione 5-oxide salt with 2-hydroxy-N,N,N-trimethyl-ethanaminium; N'-[2-chloro-5-(methylthio)phenyl]-N-methyl-N-[3-(methylthio)phenyl]-guanidine; N'-[2-chloro-5-(methylthio)phenyl]-N-methyl-N-[3-[(R)-methylsulfinyl]phenyl]-guanidine; 6-chloro-2,3,4,9-tetrahydro-9-methyl-2,3-dioxo-1H-indeno[1,2-b]pyrazine-9-acetic acid; 7-chlorothiokynurenic acid; (3S,4aR,6S,8aR)-decahydro-6-(phosphonomethyl)-3-isoquinolinecarboxylic acid; (−)-6,7-dichloro-1,4-dihydro-5-[3-(methoxymethyl)-5-(3-pyridinyl)-4-H-1,2,4-triazol-4-yl]-2,3-quinoxalinedione; 4,6-dichloro-3-[(E)-(2-oxo-1-phenyl-3-pyrrolidinylidene)methyl]-1H-indole-2-carboxylic acid; (2R,4S)-rel-5,7-dichloro-1,2,3,4-tetrahydro-4-[[(phenylamino)carbonyl]amino]-2-quinolinecarboxylic acid; (3R,4S)-rel-3',4-dihydro-3-[4-hydroxy-4-(phenylmethyl)-1-piperidinyl-]-2H-1-benzopyran-4,7-diol; 2-[(2,3-dihydro-1H-inden-2-yl)amino]-acetamide; 1,4-dihydro-6-methyl-5-[(methylamino)methyl]-7-nitro-2,3-quinoxalinedione; [2-(8,9-dioxo-2,6-diazabicyclo[5.2.0]non-1(7)-en-2-yl)ethyl]-phosphonic acid; (2R,6S)-1,2,3,4,5,6-hexahydro-3-[(2S)-2-methoxypropyl]-6,11,11-trimethyl-2,6-methano-3-benzazocin-9-ol; 2-hydroxy-5-[[(pentafluorophenyl)methyl]amino]-benzoic acid; 1-[2-(4-hydroxyphenoxy)ethyl]-4-[(4-methylphenyl)methyl]-4-piperidinol; 1-[4-(1H-imidazol-4-yl)-3-butynyl]-4-(phenylmethyl)-piperidine; 2-methyl-6-(phenylethynyl)-pyridine; 3-(phosphonomethyl)-L-phenylalanine; and 3,6,7-tetrahydro-2,3-dioxo-N-phenyl-1H,5H-pyrido[1,2,3-de]quinoxaline-5-acetamide or those described in U.S. Pat. Nos. 6,071,966; 6,034,134; and 5,061,703.

Cardiogenic Shock

Cardiogenic shock (CS) is the leading cause of death for patients with acute myocardial infarction that is consistent with increased levels of NO and inflammatory cytokines. High levels of NO and peroxynitrite have many effects, including a direct inhibition on myocardial contractability, suppression of mitochondrial respiration in myocardium, alteration in glucose metabolism, reduced catecholamine responsivity, and induction of systemic vasodilation (Hochman, *Circulation* 107:2998, 2003). In a clinical study in 11 patients with persistent shock, administration of the NOS inhibitor L-NMMA resulted in increases in urine output and blood pressure and survival rate of 72% up to 30 days (Cotter et al., *Circulation* 101:1258-1361, 2000). In a randomized trial of 30 patients, it was reported that L-NAME reduced patient mortality from 67% to 27% (Cotter et al., *Eur. Heart. J.* 24(14):1287-95, 2003). Similarly, administration of a compound of the invention, either alone or in combination with another therapeutic agent, may be useful for the treatment of cardiogenic shock.

Anxiety and Depression

Recent studies of rats and mice in the forced swimming test (FST) indicate that NOS inhibitors have antidepressant activity in mice (Harkin et al. *Eur. J. Pharm.* 372:207-213, 1999) and that their effect is mediated by a serotonin dependent mechanism (Harkin et al., *Neuropharmacology* 44(5):616-623, 1993). 7-NI demonstrates anxiolytic activity in the rat plus-maze test (Yildiz et al., *Pharmacology, Biochemistry and Behavior* 65:199-202, 2000), whereas the selective nNOS inhibitor TRIM is effective in both the FST model of depression and anxiety in the light-dark compartment test (Volke et al., *Behavioral Brain Research* 140(1-2):141-7, 2003). Administration of a compound of the invention to an afflicted individual, either alone or in combination with another therapeutic agent, such as, for example, an antidepressant, may be useful for the treatment of anxiety or depression.

Attention Deficit Hyperactivity Disorder

Non-selective attention (NSA) to environmental stimuli in Spontaneously Hypertensive (SHR) and Naples Low-Excitability (NHE) rats has been used as an animal model of Attention-Deficit Hyperactivity Disorder (ADHD) (Aspide et al., *Behav. Brain Res.* 95(1):23-33, 1998). These genetically altered animals show increased episodes of rearing that have a shorter duration than observed in normal animals. A single injection of L-NAME at 10 mg/kg produced an increase in rearing duration. Similarly, using the more neuronally selective 7-NINA, an increase in the rearing duration was observed after rapid administration (i.p.), while a slow release single release dose or a slow multiple release dose (s.c. in DMSO) resulted in the opposite effect. Thus, administration of a compound of the invention may be useful for the treatment of ADHD.

Psychosis

Phencyclidine (PCP) is a non-competitive NMDA channel blocker that produces behavioral side effects in human and mammals consistent with those observed in patients with psychosis. In two animal models of psychosis, the nNOS selective inhibitor AR-R17477 antagonized PCP-induced hyperlocomotion and PCP-induced deficit in prepulse inhibition of the acoustic response startle (Johansson et al., *Pharmacol. Toxicol.* 84(5):226-33, 1999). These results suggest the involvement of nNOS in psychosis. Therefore, administration of a compound of the invention to an afflicted individual may be useful for the treatment of this or related diseases or disorders.

Head Trauma

The mechanism of neurological damage in patients with head trauma parallels that of stroke and is related to excitotoxic calcium influx from excessive glutamate release, oxidative stress and free radical production from mitochondrial dysfunction and inflammation (*Drug & Market Development* 9(3):60-63, 1998). Animals treated with nitric oxide synthase (NOS) inhibitors, such as 7-NI and 3-bromo-7-nitroindazole, have shown an improvement in neurological deficits after experimental traumatic brain injury (TBI) (Mesenge et al., *J. Neurotrauma* 13:209-14, 1996). Administration of a compound of the invention to an afflicted individual may also be useful for the treatment of neurological damage in head trauma injuries.

Hypothermic Cardiac Arrest

Hypothermic cardiac arrest (HCA) is a technique used to protect from ischemic damage during cardiac surgery when the brain is sensitive to damage during the period of blood flow interruption. Various neuroprotective agents have been used as adjunct agents during HCA and reducing nitric oxide production during HCA is predicted to result in improvements in neurological function. This is based on previous studies that showed glutamate excitotoxicity plays a role in HCA-induced neurologic damage (Redmond et al., *J. Thorac. Cardiovasc. Surg.* 107:776-87, 1994; Redmond et al., *Ann. Thorac. Surg.* 59:579-84, 1995) and that NO mediates glutamate excitotoxicity (Dawson and Snyder, *J. Neurosci.* 14:5147-59, 1994). In a study of 32 dogs undergoing 2 hours of HCA at 18° C., a neuronal NOS inhibitor was shown to reduce cerebral NO production, significantly reduce neuronal necrosis, and resulted in superior neurologic function relative to controls (Tseng et al., *Ann. Thorac. Surg.* 67:65-71, 1999). Administration of a compound of the invention may also be useful for protecting patients from ischemic damage during cardiac surgery.

Neurotoxicity and Neurodegenerative Diseases

Mitochondrial dysfunction, glutamate excitotoxicity, and free radical induced oxidative damage appear to be the underlying pathogenesis of many neurodegenerative diseases, including amyotrophic lateral sclerosis (ALS), Parkinson's disease (PD), Alzheimer's disease (AD), and Huntington's disease (HD) (Schulz et al., *Mol. Cell. Biochem.* 174(1-2):193-197, 1997; Beal, *Ann. Neurol.* 38:357-366, 1995), and NO is a primary mediator in these mechanisms. For example, it was shown by Dawson et al., in *PNAS* 88(14):6368-6371, 1991, that NOS inhibitors like 7-NI and L-NAME prevent neurotoxicity elicited by N-methyl-D-aspartate and related excitatory amino acids.

(a) Parkinson's Disease

Studies have also shown that NO plays an important role in 1-methyl-4-phenyl-1,2,3,6-tetrahydropyridine (MPTP) neurotoxicity, a commonly used animal model of Parkinson's disease (Matthews et al., *Neurobiology of Disease* 4:114-121, 1997). MPTP is converted to MPP+ by MAO-B and is rapidly taken up by the dopamine transporter into the mitochondria of dopamine containing neurons with subsequent activation of nNOS resulting in neuronal death. Mutant mice lacking the nNOS gene, but not the eNOS gene, have reduced lesions in the substantia nigra after MPP+ injection into the striatum. In primate studies, 7-NI exerts a profound neuroprotective and antiparkinsonium effect after MPTP challenge (Hantraye et al., *Nature Med.* 2:1017-1021, 1996) as did the non-specific inhibitor L-NAME (T. S. Smith et. al. Neuroreport 1994, 5, 2598-2600). These results suggest that administration of an appropriate dose of an NOS inhibitor, such as, for example, a compound of the invention, can be beneficial in the treatment of Parkinson's Disease.

(b) Alzheimer's Disease (AD)

The pathology of AD is associated with β-amyloid plaques infiltrated with activated microglia and astrocytes. When cultured rat microglia are exposed to beta-amyloid, there is a prominent microglial release of nitric oxide, especially in the presence of gamma-interferon (Goodwin et al., *Brain Research* 692(1-2):207-14, 1995). In cortical neuronal cultures, treatment with nitric oxide synthase inhibitors provides neuroprotection against toxicity elicited by human beta-amyloid (Resink et al., *Neurosci. Abstr.* 21:1010, 1995). Consistent with the glutamate hypothesis of excitoxicity in neurodegerative disorders, the weak NMDA antagonist amantadine increases the life expectancy of PD patients (Uitti et al., *Neurology* 46(6):1551-6, 1996). In a preliminary, placebocontrolled study of patients with vascular- or Alzheimer's-type dementia, the NMDA antagonist memantine was associated with improved Clinical Global Impression of Change and Behavioral Rating Scale for Geriatric Patients scores (Winblad and Poritis, *Int. J. Geriatr. Psychiatry* 14:135-46, 1999). These results suggest that administration of an appropriate dose of an NOS inhibitor, such as, for example, a compound of the invention, can be beneficial in the treatment of AD.

(c) Amyotrophic Lateral Sclerosis

Amyotrophic lateral sclerosis (ALS) is a fatal neurodegenerative disease characterized by selective motor neuronal death. Accumulating evidence suggests that the pathogenesis of ALS is the insufficient clearance of glutamate through the glutamate transporter, and the specific distribution of $Ca^{2+}$-permeable AMPA receptors in spinal motor neurons, indicates a glutamate-induced neurotoxicity. Increased nNOS immunoreactivity is found in the spinal cords (Sasaki et al., *Acta Neuropathol. (Berl)* 101(4):351-7, 2001) and glial cells (Anneser et al., *Exp. Neurol.* 171(2):418-21, 2001) of ALS patients, implicating NO as an important factor in the pathogenesis of ALS. These results suggest that administration of an appropriate dose of an NOS inhibitor, such as, for example, a compound of the invention, can be beneficial in the treatment of ALS.

(d) Huntington's Disease

The pathogenesis of Huntington's disease (HD) arising from a mutation in the Htt protein is linked to excitotoxicity, oxidative stress and apoptosis, in all of which excessive NO has a clear role (Peterson et al., *Exp. Neurol.* 157:1-18, 1999). Oxidative damage is one of the major consequences of defects in energy metabolism and is present in HD models after injection of excitotoxins and mitochondrial inhibitors (A. Petersen et. al., *Exp. Neurol.* 157:1-18, 1999). This mitochondrial dysfunction is associated with the selective and progressive neuronal loss in HD (Brown et al., *Ann. Neurol.* 41:646-653, 1997). NO can directly impair the mitochondrial respiratory chain complex IV (Calabrese et al., *Neurochem. Res.* 25:1215-41, 2000). Striatal medium spiny neurons appear to be the primary target for the generation of motor dysfunction in HD. Hyperphosphorylation and activation of NMDA receptors on these neurons likely participates in the generation of motor dysfunction. It has been shown clinically that the NMDA antagonist amantadine improves choreiform dyskinesias in HD (Verhagen Metman et al., *Neurology* 59:694-699, 2002). Given the role of nNOS in NMDA mediated neurotoxicity, it is expected that nNOS inhibitors, especially those with mixed nNOS/NMDA, or combinations of drugs with nNOS and NMDA activity will also be useful in ameliorating the effects and or progression of HD. For example, pretreatment of rats with 7-nitroindazole attenuates the striatal lesions elicited by stereotaxic injections of malonate, an injury that leads to a condition resembling Huntington's disease (Hobbs et. al., *Ann. Rev. Pharm. Tox.* 39:191-220, 1999). In a R6/1 transgenic mouse model of HD expressing a human mutated htt exon1, a 116 CAG repeat, mice at 11, 19 and 35 weeks show a progressive increase in lipid peroxidation with normal levels of superoxide dismutase (SOD) at 11 weeks similar to wild type (WT) mice; a maximum level at 19 weeks, above that observed in WT mice and corresponding to the early phase of disease progression; and finally, decreasing levels at 35 weeks below that observed in WT mice (Pérez-Sevriano et al., *Brain Res.* 951:36-42, 2002). The increase in SOD activity is attributable to a compensatory neuroprotective mechanism, with decreased levels at 35 weeks corresponding to a failed protective mechanism. Concomitant with the levels of SOD, levels of calcium dependent NOS was the same for 11 week mice in both WT and R6/1 mice, but increased significantly at 19 weeks and decreased at 35 weeks relative to WT control mice. Levels of nNOS expression also increased dramatically relative to controls at 19 weeks but were decreased significantly relative to controls at 35 weeks. No significant differences were observed in levels of eNOS expression, nor could iNOS protein be detected during progression of the disease. The progressive phenotypic expression of the disease, as measured by increased weight loss, feet clasping behavior, and horizontal and vertical movements, are consistent with changes in NOS activity and nNOS expression. Finally, the effects of L-NAME administration to both R6/2 transgenic HD mice and WT mice showed improved levels of clasping behavior at a 10 mg/kg dose similar to controls, which worsened at the highest dose of 500 mg/kg (Deckel et al., *Brain Res.* 919 (1):70-81, 2001). An improvement in weight increase in HD mice was also significant at the 10 mg/kg dose, but decreased relative to controls at high dose levels of L-NAME. These results demonstrate that administration of an appropriate dose of an NOS inhibitor, such as, for example, a compound of the invention, can be beneficial in the treatment of HD.

(e) Multiple Sclerosis (MS)

MS is in an inflammatory demyelinating disease of the CNS involving cytokines and other inflammatory mediators. Many studies suggest that NO and its reactive derivative peroxynitrite are implicated in the pathogenesis of MS (Acar et al. *J. Neurol.* 250(5):588-92, 2003; Calabrese et al., *Neurochem. Res.* 28(9):1321-8, 2003). In experimental autoimmune encephalomyelitis (EAE), a model of MS, nNOS levels are slightly increased in the spinal cord of EAE rats and treatment with 7-nitroindazole results in a significant delay in the onset of EAE paralysis (Shin, *J. Vet. Sci.* 2(3):195-9, 2001). These results suggest that administration of an appropriate dose of an NOS inhibitor, such as, for example, a compound of the invention, can be beneficial in the treatment of MS.

(f) Methamphetamine-Induced Neurotoxicity

Methamphetamine is neurotoxic by destroying dopamine nerve terminals in vivo. It has been shown that methamphetamine-induced neurotoxicity can be attenuated by treatment with NOS inhibitors in vitro (Sheng et al., *Ann. N.Y. Acad. Sci.* 801:174-186, 1996) and in in vivo animal models (Itzhak et al., *Neuroreport* 11(13):2943-6, 2000). Similarly, the nNOS selective inhibitor AR-17477AR, at 5 mg/kg s.c in mice, was able to prevent the methamphetamine-induced loss of the neurofilament protein NF68 in mouse brain and prevent the loss of striatal dopamine and homovanillic acid (HVA) (Sanchez et al., *J. Neurochem.* 85(2):515-524, 2003). These results suggest that administration of an appropriate dose of an NOS inhibitor, such as, for example, a compound of the invention, can be beneficial in the treatment of methamphetamine-induced neurotoxicity.

Administration of a compound of the invention, either alone or in combination with another therapeutic agent, such as, for example, an NMDA antagonist, may be useful for the protection or treatment of any of the neurodegenerative diseases described herein. Further, the compounds of the invention may be tested in standard assays used to assess neuroprotection (see for example, *Am. J. Physiol.* 268:R286, 1995). Chemical Dependencies and Drug Addictions (e.g., Dependencies on Drugs, Alcohol and Nicotine)

A key step in the process of drug-induced reward and dependence is the regulation of dopamine release from mesolimbic dopaminergic neurons. Chronic application of cocaine alters the expression of the key protein controlling the synaptic level of dopamine—the dopamine transporter (DAT).

(a) Cocaine Addiction

Studies have shown that animals reliably self-administer stimulants intravenously and that dopamine is critical in their reinforcing effects. Recently NO containing neurons have been shown to co-localize with dopamine in areas of the striatum and ventral tegmental area and that NO can modulate stimulant-evoked dopamine (DA) release. Administration of dopamine D1 receptor antagonists decrease the levels of striatal NADPH-diaphorase staining, a marker for NOS activity, while D2 antagonists produce the opposite effect. L-Arginine, the substrate of NOS, is also a potent modulator of DA release. Also, multiple NO-generating agents increase DA efflux or inhibit reuptake both in vitro and in vivo. L-NAME has been shown to significantly alter cocaine reinforcement by decreasing the amount of self-administration and by increasing the inter-response time between successive cocaine injections (Pudiak and Bozarth, *Soc. Neurosci. Abs.* 22:703, 1996). This indicates that NOS inhibition by compounds of the invention may be useful in the treatment of cocaine addiction.

(b) Morphine/Opioid Induced Tolerance and Withdrawal Symptoms

There is much evidence supporting the role of both the NMDA and NO pathways in opioid dependence in adult and infant animals. Adult or neonatal rodents injected with morphine sulfate develop behavioral withdrawal after precipitation with naltrexone. The withdrawal symptoms after naltrexone initiation can be reduced by administration of NOS inhibitors, such as 7-NI or L-NAME (Zhu and Barr, *Psychopharmacology* 150(3):325-336, 2000). In a related study, it was shown that the more nNOS selective inhibitor 7-NI attenuated more of the morphine induced withdrawal symptoms including mastication, salivation and genital effects than the less selective compounds (Vaupel et al., *Psychopharmacology (Berl.)* 118(4):361-8, 1995). This indicates that NOS inhibition by compounds of the invention may be useful in the treatment of morphine/opioid induced tolerance and withdrawal symptoms.

(c) Ethanol Tolerance and Dependence

Among the factors that influence alcohol dependence, tolerance to the effects of ethanol is an important component because it favors the exaggerated drinking of alcoholic beverages (Lê and Kiianmaa, *Psychopharmacology (Berl.)* 94:479-483, 1988). In a study with rats, ethanol tolerance to motor incoordination and hypothermia develop rapidly and can be blocked by i.c.v. administration of 7-NI without altering cerebral ethanol concentrations (Wazlawik and Morato, *Brain Res. Bull.* 57(2):165-70, 2002). In other studies, NOS inhibition with L-NAME (Rezvani et al., *Pharmacol. Biochem. Behav.* 50:265-270, 1995) or by i.c.v. injection of nNOS antisense (Naassila et. al., Pharmacol. Biochem. Behav. 67:629-36, 2000) reduced ethanol consumption in these animals. This indicates that NOS inhibition by compounds of the invention may be useful in the treatment of ethanol tolerance and dependence.

Administration of a compound of the invention, either alone or in combination with another therapeutic agent, such as, for example, an NMDA antagonist, may be useful for the treatment of chemical dependencies and drug addictions.

Epilepsy

Co-administration of 7-NI with certain anticonvulsants, such as carbamazepine, shows a synergistic protective effect against amygdala-kindled seizures in rats at concentrations that do not alter roto-rod performance (Borowicz et al., *Epilepsia* 41(9:112-8, 2000). Thus, an NOS inhibitor, such as, for example, a compound of the invention, either alone or in combination with another therapeutic agent, such as, for example, an antiepileptic agent, may be useful for the treatment of epilepsy or a similar disorder. Examples of antiepileptic agents useful in a combination of the invention include carbamazepine, gabapentin, lamotrigine, oxcarbazepine, phenyloin, topiramate, and valproate.

Diabetic Nephropathy

Urinary excretion of NO byproducts is increased in diabetic rats after streptozotocin treatment and increased NO synthesis has been suggested to be involved in diabetic glomerular hyperfiltration. The neuronal isoform nNOS is expressed in the loop of Henle and mucula densa of the kidney and inhibition of this isoform using 7-NI reduces glomerular filtration without affecting renal arteriole pressure or renal blood flow (Sigmon et al., *Gen. Pharmacol.* 34(2):95-100, 2000). Both the non-selective NOS inhibitor L-NAME and the nNOS selective 7-NI normalize renal hyperfiltration in diabetic animals (Ito et al., *J. Lab Clin. Med.* 138(3):177-185, 2001). Therefore, administration of a compound of the invention may be useful for the treatment of diabetic nephropathy.

Medication Overuse Headache

Medication overuse headache (MOH) is associated with excessive use of combination analgesics, opioids, barbiturates, aspirin, NSAIDS, caffeine and triptans and is a common problem that limits the usefulness of these types of medications (Diener and Limmroth. Medication-overuse headache: a worldwide problem. *Lancet Neurol.* 2004: 3, 475-483). It is generally defined as headaches that present >15 days per month (Headache Classification Committee. The International Classification of Headache Disorders ($2^{nd}$ Ed). *Cephalalgia* 2004: 24 (Supple. 1); 9-160). It is well documented that acute treatment of patients for migraine or tension type headache are at increased risk of headache aggravation, develop daily headache, or may become refractory to treatment if the acute medication is taken excessively (Zeeberg et. al. *Cephalalgia* 2006: 26, 1192-1198). MOH patients generally are unresponsive to prophylactic medications while overusing medications. Currently the treatment of choice for MOH is discontinuation of medication although this often associated with withdrawal symptoms such as nausea, vomiting and sleep disturbances. While migraine or tension-type headache patients suffering from MOH that discontinue medication for 2 months have a reduction in headache frequency (45%), many patients were either unchanged (48%) following withdrawal or had an aggravation of headache (Zeeberg et. al. *Cephalalgia* 2006: 26, 1192-1198). Thus there remains a large unmet need for patients suffering from MOH.

It is believed that certain features of MOH, such as increased headache frequency, expansion of headache area and the development of cutaneous allodynia are a result of medication-induced central sensitization of trigeminal nociceptive pathways and periaqueductal grey area (Waeber and Moskowitz. Therapeutic implications of central and peripheral neurologic mechanisms in migraine. *Neurology:* 2003, 61(Suppl. 4); S9-20). Similar to behavioral sensitization to psychostimulants, the repeated administration of headache medications (e.g., triptans) results in cross-sensitization among different drugs used to treat headache. Changes in synaptic plasticity involve changes in intracellular calcium and nitric oxide levels. Patients suffering from chronic headache, migraine and MOH patients show increased levels of platelet nitrate levels. Thus the development of the sensitization in MOH is likely mediated by the changes in NO and calcium levels in the CNS (Sarchielli et. al. Nitric oxide pathway, Ca2+, and serotonin content in platelets from patients suffering from chronic daily headache. *Cephalalgia* 1999: 19; 810-816). Given that the development of central sensitization is mediated by nNOS (Cizkova et. al. *Brain. Res. Bull.* 2002; 58(2): 161-171, Choi et. al. *J. Neurol. Sci.* 1996; 138(1-2): 14-20, as such, it is expected that neuronal nitric oxide synthase inhibitors, such as the compounds of the invention, will be useful in the prevention and treatment of MOH if used in concomitantly with other headache medications. It is also expected that both CTTH and migraine treatment with nNOS inhibitors will not result in the development of MOH.

Gastrointestinal Disorders nNOS constitutes more than 90% of the total NOS in the small intestine. Although iNOS is constitutively present, it accounts for less than 10% of the total NOS activity, and eNOS is essentially undetectable in the intestine (Qu X W et. al. Type I nitric oxide synthase (NOS) is the predominant NOS in rat small intestine. Regulation by platelet-activating factor. *Biochim Biophys Acta* 1999; 1451: 211-217). The main function of nNOS in the intestine is believed to be regulation of gut motility via neuronal signal transmission in the NANC components of the nervous system. NO regulates the muscle tone of the sphincter in the lower esophagus, pylorus, sphincter of Oddi, and anus. NO also regulates the accommodation reflex of the fundus and the peristaltic reflex of the intestine. NOS inhibitors are known to delay gastric emptying and colonic transit (T. Takahashi J. *Gastroenterol.* 2003; 38(5):421-30). Thus nNOS inhibitors can be therapeutic in GI disorders that would benefit from the delay of gastric emptying or slowing of colonic transit. Dumping syndrome is a disorder that in which food is emptied too quickly from the stomach, filling the small intestine with undigested food that is not adequately prepared to permit efficient absorption of nutrients in the small intestine and is often observed after gastrectomy. Therefore, administration of a compound of the invention may be useful for the treatment of gastrointestinal disorders such as dumping syndrome.

Combination Formulations, and Uses Thereof

In addition to the formulations described above, one or more compounds of the invention can be used in combination with other therapeutic agents. For example, one or more compounds of the invention can be combined with another NOS inhibitor. Exemplary inhibitors useful for this purpose include, without limitation, those described in U.S. Pat. No. 6,235,747; U.S. patent application Ser. Nos. 09/127,158, 09/325,480, 09/403,177, 09/802,086, 09/826,132, 09/740,385, 09/381,887, 10/476,958, 10/483,140, 10/484,960, 10/678,369, 10/819,853, 10/938,891; International Publication Nos. WO 97/36871, WO 98/24766, WO 98/34919, WO 99/10339, WO 99/11620, and WO 99/62883.

In another example, one or more compounds of the invention can be combined with an antiarrhythmic agent. Exemplary antiarrhythmic agents include, without limitation, lidocaine and mixiletine.

GABA-B agonists, alpha-2-adrenergic receptor agonists, cholecystokinin antagonists, $5HT_{1B/1D}$ agonists, or CGRP antagonists can also be used in combination with one or more compounds of the invention. Non-limiting examples of alpha-2-adrenergic receptor agonists include clonidine, lofexidine, and propanolol. Non-limiting examples of cholecystokinin antagonists include L-365, 260; CI-988; LY262691; S0509, or those described in U.S. Pat. No. 5,618,811. Non-limiting examples of $5HT_{1B/1D}$ agonists that may be used in combination with a compound of the invention include dihydroergotamine, eletriptan, frovatriptan, naratriptan, rizatriptan, sumatriptan, donitriptan, or zolmitriptan. Non-limiting examples of CGRP antagonists that may be used in combination with a compound of the invention include quinine analogues as described in International Publication No. WO9709046, non-peptide antagonists as described in International Publication Nos. WO0132648, WO0132649, WO9811128, WO9809630, WO9856779, WO0018764, or other antagonists such as SB-(+)-273779 or BIBN-4096BS.

Substance P antagonists, also known as $NK_1$ receptor antagonists, are also useful in combination with one or more compounds of the invention. Exemplary inhibitors useful for this purpose include, without limitation, those compounds disclosed in U.S. Pat. Nos. 3,862,114, 3,912,711, 4,472,305, 4,481,139, 4,680,283, 4,839,465, 5,102,667, 5,162,339, 5,164,372, 5,166,136, 5,232,929, 5,242,944, 5,300,648, 5,310,743, 5,338,845, 5,340,822, 5,378,803, 5,410,019, 5,411,971, 5,420,297, 5,422,354, 5,446,052, 5,451,586, 5,525,712, 5,527,811, 5,536,737, 5,541,195, 5,594,022, 5,561,113, 5,576,317, 5,604,247, 5,624,950, and 5,635,510; International Publication Nos. WO 90/05525, WO 91/09844, WO 91/12266, WO 92/06079, WO 92/12151, WO 92/15585, WO 92/20661, WO 92/20676, WO 92/21677, WO 92/22569, WO 93/00330, WO 93/00331, WO 93/01159, WO 93/01160, WO 93/01165, WO 93/01169, WO 93/01170, WO 93/06099, WO 93/10073, WO 93/14084, WO 93/19064, WO 93/21155, WO 94/04496, WO 94/08997, WO 94/29309, WO 95/11895, WO 95/14017, WO 97/19942, WO 97/24356, WO 97/38692, WO 98/02158, and WO 98/07694; European Patent Publication Nos. 284942, 327009, 333174, 336230, 360390, 394989, 428434, 429366, 443132, 446706, 484719, 499313, 512901, 512902, 514273, 514275, 515240, 520555, 522808, 528495, 532456, and 591040.

Suitable classes of antidepressant agents that may be used in combination with a compound of the invention include, without limitation, norepinephrine re-uptake inhibitors, selective serotonin re-uptake inhibitors (SSRIs), selective noradrenaline/norepinephrine reuptake inhibitors (NARIs), monoamine oxidase inhibitors (MAOs), reversible inhibitors of monoamine oxidase (RIMAs), dual serotonin/noradrenaline re-uptake inhibitors (SNRIs), α-adrenoreceptor antagonists, noradrenergic and specific serotonergic antidepressants (NaSSAs), and atypical antidepressants.

Non-limiting examples of norepinephrine re-uptake inhibitors include tertiary amine tricyclics and secondary amine tricyclics, such as, for example, adinazolam, amineptine, amoxapine, butriptyline, demexiptiline, desmethylamitriptyline, desmethylclomipramine, demexiptiline, desipramine, doxepin, dothiepin, fluacizine, imipramine, imipramine oxide, iprindole, lofepramine, maprotiline, melitracen, metapramine, norclolipramine, nortriptyline, noxiptilin, opipramol, perlapine, pizotifen, pizotyline, propizepine, protriptyline, quinupramine, tianeptine, trimipramine, trimipramineamiltriptylinoxide, and pharmaceutically acceptable salts thereof.

Non-limiting examples of selective serotonin re-uptake inhibitors include, for example, clomipramine, femoxetine, fluoxetine, fluvoxamine, paroxetine, and sertraline, and pharmaceutically acceptable salts thereof.

Non-limiting examples of selective noradrenaline/norepinephrine reuptake inhibitors include, for example, atomoxetine, bupropion; reboxetine, tomoxetine, and viloxazine and pharmaceutically acceptable salts thereof.

Non-limiting examples of selective monoamine oxidase inhibitors include, for example, isocarboxazid, phenazine, tranylcypromine and selegiline, and pharmaceutically acceptable salts thereof. Other monoamine oxidase inhibitors useful in a combination of the invention include clorgyline, cimoxatone, befloxatone, brofaromine, bazinaprine, BW-616U (Burroughs Wellcome), BW-1370U87 (Burroughs Wellcome), CS-722 (RS-722) (Sankyo), E-2011 (Eisai), harmine, harmaline, moclobemide, PharmaProjects 3975 (Hoechst), RO 41-1049 (Roche), RS-8359 (Sankyo), T-794 (Tanabe Seiyaku), toloxatone, K-Y 1349 (Kalir and Youdim), LY-51641 (Lilly), LY-121768 (Lilly), M&B 9303 (May & Baker), MDL 72394 (Marion Merrell), MDL 72392 (Marion Merrell), sercloremine, and MO 1671, and pharmaceutically acceptable salts thereof. Suitable reversible inhibitors of monoamine oxidase that may be used in the present invention include, for example, moclobemide, and pharmaceutically acceptable salts thereof.

Non-limiting examples of dual serotonin/norepinephrine reuptake blockers include, for example, duloxetine, milnacipran, mirtazapine, nefazodone, and venlafaxine.

Non-limiting examples of other antidepressants that may be used in a method of the present invention include adinazolam, alaproclate, amineptine, amitriptyline amitriptyline/chlordiazepoxide combination, atipamezole, azamianserin, bazinaprine, befuraline, bifemelane, binodaline, bipenamol, brofaromine, caroxazone, cericlamine, cianopramine, cimoxatone, citalopram, clemeprol, clovoxamine, dazepinil, deanol, demexiptiline, dibenzepin, dimetacrine, dothiepin, droxidopa, enefexine, estazolam, etoperidone, fengabine, fezolamine, fluotracen, idazoxan, indalpine, indeloxazine, levoprotiline, litoxetine; medifoxamine, metralindole, mianserin, minaprine, montirelin, nebracetam, nefopam, nialamide, nomifensine, norfluoxetine, orotirelin, oxaflozane, pinazepam, pirlindone, ritanserin, rolipram, sercloremine, setiptiline, sibutramine, sulbutiamine, sulpiride, teniloxazine, thozalinone, thymoliberin, tiflucarbine, tofenacin, tofisopam, toloxatone, veralipride, viqualine, zimelidine, and zometrapine, and pharmaceutically acceptable salts thereof, and St. John's wort herb, or Hypencuin perforatum, or extracts thereof.

In another example, opioids can be used in combination with one or more compounds of the invention. Exemplary opioids useful for this purpose include, without limitation, alfentanil, butorphanol, buprenorphine, dextromoramide, dezocine, dextropropoxyphene, codeine, dihydrocodeine, diphenoxylate, etorphine, fentanyl, hydrocodone, hydromorphone, ketobemidone, loperamide, levorphanol, levomethadone, meperidine, meptazinol, methadone, morphine, morphine-6-glucuronide, nalbuphine, naloxone, oxycodone, oxymorphone, pentazocine, pethidine, piritramide, propoxyphene, remifentanil, sulfentanyl, tilidine, and tramadol.

In yet another example, anti-inflammatory compounds, such as steroidal agents or non-steroidal anti-inflammatory drugs (NSAIDs), can be used in combination with one or more compounds of the invention. Non-limiting examples of steroidal agents include prednisolone and cortisone. Non-limiting examples of NSAIDs include acemetacin, aspirin, celecoxib, deracoxib, diclofenac, diflunisal, ethenzamide, etofenamate, etoricoxib, fenoprofen, flufenamic acid, flurbiprofen, lonazolac, lornoxicam, ibuprofen, indomethacin, isoxicam, kebuzone, ketoprofen, ketorolac, naproxen, nabumetone, niflumic acid, sulindac, tolmetin, piroxicam, meclofenamic acid, mefenamic acid, meloxicam, metamizol, mofebutazone, oxyphenbutazone, parecoxib, phenidine, phenylbutazone, piroxicam, propacetamol, propyphenazone, rofecoxib, salicylamide, suprofen, tiaprofenic acid, tenoxicam, valdecoxib, 4-(4-cyclohexyl-2-methyloxazol-5-yl)-2-fluorobenzenesulfonamide, N-[2-(cyclohexyloxy)-4-nitrophenyl]methanesulfonamide, 2-(3,4-difluorophenyl)-4-(3-hydroxy-3-methylbutoxy)-5-[4-(methylsulfonyl)phenyl]-3 (2H)-pyridazinone, and 2-(3,5-difluorophenyl)-3-[4-(methylsulfonyl)phenyl]-2-cyclopenten-1-one). Compounds of the invention may also be use in combination with acetaminophen.

Any of the above combinations can be used to treat any appropriate disease, disorder, or condition. Exemplary uses for combinations of a compound of the invention and another therapeutic agent are described below.

Opioid-NOS Inhibitor Combinations in Chronic, Neuropathic Pain

Nerve injury can lead to abnormal pain states known as neuropathic pain. Some of the clinical symptoms include tactile allodynia (nociceptive responses to normally innocuous mechanical stimuli), hyperalgesia (augmented pain intensity in response to normally painful stimuli), and spontaneous pain. Spinal nerve ligation (SNL) in rats is an animal model of neuropathic pain that produces spontaneous pain, allodynia, and hyperalgesia, analogous to the clinical symptoms observed in human patients (Kim and Chung, *Pain* 50:355-363, 1992; Seltzer, *Neurosciences* 7:211-219, 1995).

Neuropathic pain can be particularly insensitive to opioid treatment (Benedetti et al., *Pain* 74:205-211, 1998) and is still considered to be relatively refractory to opioid analgesics (MacFarlane et al., *Pharmacol. Ther.* 75: 1-19, 1997; Watson, *Clin. J. Pain* 16:S49-S55, 2000). While dose escalation can overcome reduced opioid effectiveness, it is limited by increased side effects and tolerance. Morphine administration is known to activate the NOS system, which limits the analgesic action of this drug (Machelska et al., *NeuroReport* 8:2743-2747, 1997; Wong et al., *Br. J. Anaesth.* 85:587, 2000; Xiangqi and Clark, *Mol. Brain. Res.* 95:96-102, 2001). However, it has been shown that the combined systemic administration of morphine and L-NAME can attenuate mechanical and cold allodynia at subthreshold doses at which neither drug administered alone was effective (Ulugol et al., *Neurosci. Res. Com.* 30(3):143-153, 2002). The effect of L-NAME co-administration on morphine analgesia appears to be mediated by nNOS, as L-NAME loses its ability to potentiate morphine analgesia in nNOS null-mutant mice (Clark and Xiangqi, *Mol. Brain. Res.* 95:96-102, 2001). Enhanced analgesia has been demonstrated in the tail-flick or paw pressure models using coadministration of L-NAME or 7-NI with either a mu-, delta-, or kappa-selective opioid agonist (Machelska et al., *J. Pharmacol. Exp. Ther.* 282:977-984, 1997).

While opioids are an important therapy for the treatment of moderate to severe pain, in addition to the usual side effects that limit their utility, the somewhat paradoxical appearance of opioid-induced hyperalgesia may actually render patients more sensitive to pain and potentially aggravate their pain (Angst and Clark, Anesthesiology, 2006, 104(3), 570-587; Chu et. al. J. Pain 2006, 7(1) 43-48). The development of tolerance and opioid induced hyperalgesia is consistent with increased levels of NO production in the brain. The reduced analgesic response to opioids is due to an NO-induced upregulated hyperalgesic response (Heinzen and Pollack, Brain Res. 2004, 1023, 175-184).

Thus, the combination of an nNOS inhibitor with an opioid (for example, those combinations described above) can enhance opioid analgesia in neuropathic pain and prevent the development of opioid tolerance and opioid-induced hyperalgesia.

Antidepressant-NOS Inhibitor Combinations for Chronic Pain, Neuropathic Pain, Chronic Headache or Migraine Many antidepressants are used for the treatment of neuropathic pain (McQuay et al., *Pain* 68:217-227, 1996) and migraine (Tomkins et al., *Am. J. Med.* 111:54-63, 2001), and act via the serotonergic or noradrenergic system. NO serves as a neuromodulator of these systems (Garthwaite and Boulton, *Annu. Rev. Physiol.* 57:683, 1995). 7-NI has been shown to potentiate the release of noradrenaline (NA) by the nicotinic acetylcholine receptor agonist DMPP via the NA transporter (Kiss et al., *Neuroscience Lett.* 215:115-118, 1996). It has been shown that local administration of antidepressants, such as paroxetine, tianeptine, and imipramine decrease levels of hippocampal NO (Wegener et al., *Brain Res.* 959:128-134, 2003). It is likely that NO is important in the mechanism by which antidepressants are effective for treating pain and depression, and that a combination of an nNOS inhibitor with an antidepressant, such as, for example, those combinations described above, will produce better treatments.

Serotonin $5HT_{1B/1D/1F}$ Agonist or CGRP Antagonist and NOS Inhibitor Combinations in Migraine Administration of Glyceryl trinitrate (GTN), an NO donor, induces immediate headaches in normal individuals and results in delayed migraine attacks in migraineurs with a 4-6 hour latency period (Iversen et al., *Pain* 38:17-24, 1989). In patients with migraine attack, levels of CGRP (Calcitonin Gene Related Peptide), a potent vasodialator, in the carotid artery correlate with the onset and ablation of migraine attack (Durham, *Curr Opin Investig Drugs* 5(7):731-5, 2004). Sumatriptan, an antimigraine drug having affinity at $5HT_{1B}$, $5HT_1D$, and $5HT_{1F}$ receptors, reduces GTN-induced immediate headache and in parallel contracts cerebral and extracerebral arteries (Iversen and Olesen, *Cephalagia* 13(Suppl 13):186, 1993). The antimigraine drug rizatriptan also reduces plasma levels of CGRP following migraine pain reduction (Stepien et al., *Neurol. Neurochir. Pol.* 37(5):1013-23, 2003). Both NO and CGRP have therefore been implicated as a cause for migraine. Serotonin $5HT_{1B/1D}$ agonists have been shown to block NMDA receptor-evoked NO signaling in brain cortex slices (Strosznajder et al., *Cephalalgia* 19(10):859, 1999). These results suggest that a combination of a compound of the invention and a selective or non-selective $5HT_{1B/1D/1F}$ agonist or a CGRP antagonist, such as those combinations described above, would be useful for the treatment of migraine.

Pharmaceutical Compositions

The compounds of the invention are preferably formulated into pharmaceutical compositions for administration to human subjects in a biologically compatible form suitable for administration in vivo. Accordingly, in another aspect, the present invention provides a pharmaceutical composition comprising a compound of the invention in admixture with a suitable diluent, carrier, or excipient.

The compounds of the invention may be used in the form of the free base, in the form of salts, solvates, and as prodrugs. All forms are within the scope of the invention. In accordance with the methods of the invention, the described compounds or salts, solvates, or prodrugs thereof may be administered to a patient in a variety of forms depending on the selected route of administration, as will be understood by those skilled in the art. The compounds of the invention may be administered, for example, by oral, parenteral, buccal, sublingual, nasal, rectal, patch, pump, or transdermal administration and the pharmaceutical compositions formulated accordingly. Parenteral administration includes intravenous, intraperitoneal, subcutaneous, intramuscular, transepithelial, nasal, intrapulmonary, intrathecal, rectal, and topical modes of administration. Parenteral administration may be by continuous infusion over a selected period of time.

A compound of the invention may be orally administered, for example, with an inert diluent or with an assimilable edible carrier, or it may be enclosed in hard or soft shell gelatin capsules, or it may be compressed into tablets, or it may be incorporated directly with the food of the diet. For oral therapeutic administration, a compound of the invention may be incorporated with an excipient and used in the form of ingestible tablets, buccal tablets, troches, capsules, elixirs, suspensions, syrups, wafers, and the like.

A compound of the invention may also be administered parenterally. Solutions of a compound of the invention can be prepared in water suitably mixed with a surfactant, such as hydroxypropylcellulose. Dispersions can also be prepared in glycerol, liquid polyethylene glycols, DMSO and mixtures thereof with or without alcohol, and in oils. Under ordinary conditions of storage and use, these preparations may contain a preservative to prevent the growth of microorganisms. Conventional procedures and ingredients for the selection and preparation of suitable formulations are described, for example, in Remington's Pharmaceutical Sciences (2003-20th edition) and in The United States Pharmacopeia: The National Formulary (USP 24 NF19), published in 1999.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that may be easily administered via syringe.

Compositions for nasal administration may conveniently be formulated as aerosols, drops, gels, and powders. Aerosol formulations typically include a solution or fine suspension of the active substance in a physiologically acceptable aqueous or non-aqueous solvent and are usually presented in single or multidose quantities in sterile form in a sealed container, which can take the form of a cartridge or refill for use with an atomizing device. Alternatively, the sealed container may be a unitary dispensing device, such as a single dose nasal inhaler or an aerosol dispenser fitted with a metering valve, which is intended for disposal after use. Where the dosage form comprises an aerosol dispenser, it will contain a propellant, which can be a compressed gas, such as compressed air or an organic propellant, such as fluorochlorohydrocarbon. The aerosol dosage forms can also take the form of a pump-atomizer.

Compositions suitable for buccal or sublingual administration include tablets, lozenges, and pastilles, where the active ingredient is formulated with a carrier, such as sugar, acacia, tragacanth, or gelatin and glycerine. Compositions for rectal administration are conveniently in the form of suppositories containing a conventional suppository base, such as cocoa butter.

The compounds of the invention may be administered to an animal, e.g., a human, alone or in combination with pharmaceutically acceptable carriers, as noted above, the proportion of which is determined by the solubility and chemical nature of the compound, chosen route of administration, and standard pharmaceutical practice.

The dosage of the compounds of the invention, and/or compositions comprising a compound of the invention, can vary depending on many factors, such as the pharmacodynamic properties of the compound; the mode of administration; the age, health, and weight of the recipient; the nature and extent of the symptoms; the frequency of the treatment, and the type of concurrent treatment, if any; and the clearance rate of the compound in the animal to be treated. One of skill in the art can determine the appropriate dosage based on the above factors. The compounds of the invention may be administered initially in a suitable dosage that may be adjusted as required, depending on the clinical response. In general, satisfactory results may be obtained when the compounds of the invention are administered to a human at a daily dosage of between 0.05 mg and 3000 mg (measured as the solid form). A preferred dose ranges between 0.05-500 mg/kg, more preferably between 0.5-50 mg/kg.

A compound of the invention can be used alone or in combination with other agents that have NOS-inhibiting activity, or in combination with other types of treatment (which may or may not inhibit NOS) to treat, prevent, and/or reduce the risk of stroke, neuropathic or migraine pain, or other disorders that benefit from NOS inhibition. In combination treatments, the dosages of one or more of the therapeutic compounds may be reduced from standard dosages when administered alone. In this case, dosages of the compounds when combined should provide a therapeutic effect.

In addition to the above-mentioned therapeutic uses, a compound of the invention can also be used in diagnostic assays, screening assays, and as a research tool.

In diagnostic assays, a compound of the invention may be useful in identifying or detecting NOS activity. For such a use, the compound may be radiolabeled (as described elsewhere herein) and contacted with a population of cells of an organism. The presence of the radiolabel on the cells may indicate NOS activity.

In screening assays, a compound of the invention may be used to identify other compounds that inhibit NOS, for example, as first generation drugs. As research tools, the compounds of the invention may be used in enzyme assays and assays to study the localization of NOS activity. Such information may be useful, for example, for diagnosing or monitoring disease states or progression. In such assays, a compound of the invention may also be radiolabeled.

NOS In Vitro Inhibition Assays

The compounds of the present invention have been found to exhibit selective inhibition of the neuronal isoform of NOS (nNOS). Compounds may be examined for their efficacy in preferentially inhibiting nNOS over iNOS and/or eNOS by a person skilled in the art, for example, by using the methods described in Examples 19a and 19b and herein below.

The following non-limiting examples are illustrative of the present invention:

EXAMPLES

Example 1

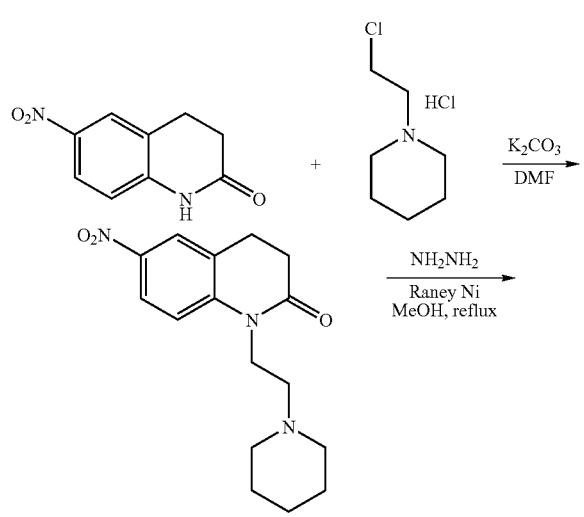

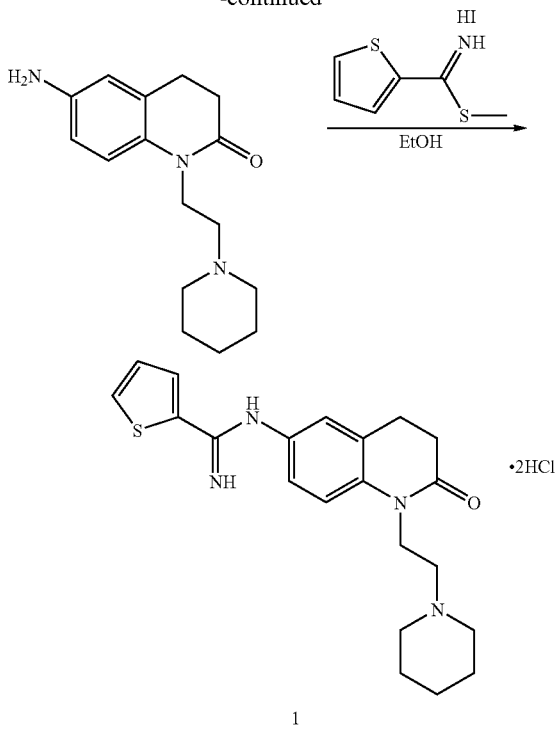

6-nitro-1-(2-(piperidin-1-yl)ethyl)-3,4-dihydroquinolin-2(1H)-one

A suspension of 6-nitro-3,4-dihydroquinolin-2(1H)-one (400 mg, 2.08 mmol), 1-(2-chloroethyl)piperidine hydrochloride(421 mg, 2.29 mmol) and potassium carbonate(862 mg, 6.24 mmol) in 10 mL DMF was stirred at room temperature overnight. After this time, the mixture was poured into 20 mL H$_2$O then extracted with 2×50 mL CH$_2$Cl$_2$. The organic layer was separated, washed with brine and concentrated to give a yellow brown solid which was subjected to flash chromatography on silica gel using 5% MeOH/CH$_2$Cl$_2$ to give a yellow viscous oil (560 mg, 88.7%). $^1$H-NMR (CDCl$_3$) δ: 8.14 (dd, J=2.7, 9 Hz, 1H), 8.06-8.05 (m, 1H), 7.24 (d, J=9.0 Hz, 1H), 4.11 (t, J=7.2 Hz, 2H), 3.02-2.95 (m, 2H), 2.73-2.67 (m, 2H), 2.57-2.48 (m, 6H), 1.59-1.44 (m, 6H).

MS (ESI): 304.2 (M+1, 100%).

6-amino-1-(2-(piperidin-1-yl)ethyl)-3,4-dihydroquinolin-2(1H)-one

A solution of 6-nitro-1-(2-(piperidin-1-yl)ethyl)-3,4-dihydroquinolin-2(1H)-one (500 mg, 1.65 mmol) in 10 mL methanol was added to Raney Nickel (slurry in H$_2$O, 50 mg) in a round bottom flask. The suspension was heated at reflux for 10 minutes then filtered through a pad of celite. The celite pad was washed with 10 mL methanol. The filtrate was concentrated to give a dark brown residue was subjected to flash silica gel chromatography using 5% 2M NH$_3$ in MeOH/CH$_2$Cl$_2$ to give an off-white solid (350 mg, 77.7%). $^1$H-NMR (DMSO-d$_6$) δ: 6.81 (d, J=8.2 Hz, 1H), 6.46-6.41 (m, 2H), 4.84 (br s, 2H), 3.87 (t, J=7.1 Hz, 2H), 2.66 (t, J=6.5 Hz, 2H), 2.40-2.32 (m, 8H), 1.46-1.35 (m, 6H); MS (ESI): 274.2 (M+1, 100%).

N-(2-oxo-1-(2-(piperidin-1-yl)ethyl)-1,2,3,4-tetrahydroquinolin-6-yl)thiophene-2-carboximidamide A solution of 6-amino-1-(2-(piperidin-1-yl)ethyl)-3,4-dihydroquinolin-2(1H)-one (225 mg, 0.82 mmol) in 10 mL EtOH was treated with methyl thiophene-2-carbimidothioate hydroiodide (470 mg, 1.65 mmol) and stirred overnight at room temperature. A TLC analysis indicated that the starting amine is still present. An additional 235 mg of methyl thiophene-2-carbimidothioate hydroiodide was added and stirring was continued for 1 day. Argon was bubbled through the mixture for 20 minutes then it was concentrated to give a brownish oil. This residue was partitioned between CH$_2$Cl$_2$ (50 mL) with 10% MeOH and saturated sodium bicarbonate (20 mL). The aqueous layer was extracted with an additional 50 mL CH$_2$Cl$_2$. The combined organic layers were washed with brine, dried over sodium sulfate and concentrated to give a brown residue which was subjected to flash chromatography on silica gel using 5% MeOH/CH$_2$Cl$_2$ to 10% 2M NH$_3$ in MeOH/CH$_2$Cl$_2$ to give a yellow solid which contained a mixture of starting amine and the desired product. This mixture was then subjected to preparative TLC using 10% MeOH: 10% Et3N:80% EtOAc as eluant. A small amount of product was obtained in pure form (analyzed by HPLC). This compound was converted to the dihydrochloride salt by dissolving in 10 mL of a 10% MeOH/CH$_2$Cl$_2$ solution, cooled to 0° C. and treated with 0.5 mL of a 1M HCl in Et$_2$O solution. The solution was stirred for 20 minutes then concentrated to give a yellow-brown oil. A yellow solid was obtained after drying under high vacuum overnight. Yield: 12 mg of compound 1. HPLC analysis indicated that the product is >99% pure. $^1$H-NMR (MeOH-d$_4$) δ: 8.08-8.05 (m, 2H), 7.40-7.38 (m, 4H), 4.42 (t, J=6.7 Hz, 2H), 3.77-3.73 (m, 2H), 3.41 (t, J=6.7 Hz, 2H), 3.32-3.02 (m, 4H), 2.76-2.72 (m, 2H), 2.00-1.53 (m, 6H); MS (ESI): 383.2 (M+1), 30%, 192.1 (M+2), 100%. ESI-HRMS calculated for C$_{21}$H$_{27}$N$_4$OS (MH$^+$): 383.1900, Observed: 383.1908.

Example 2

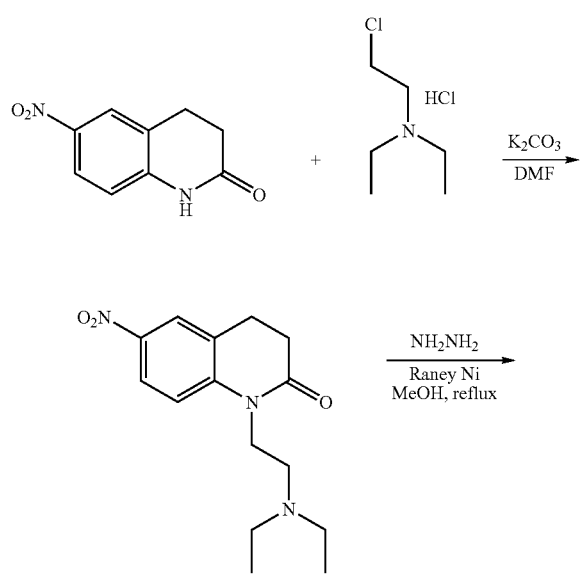

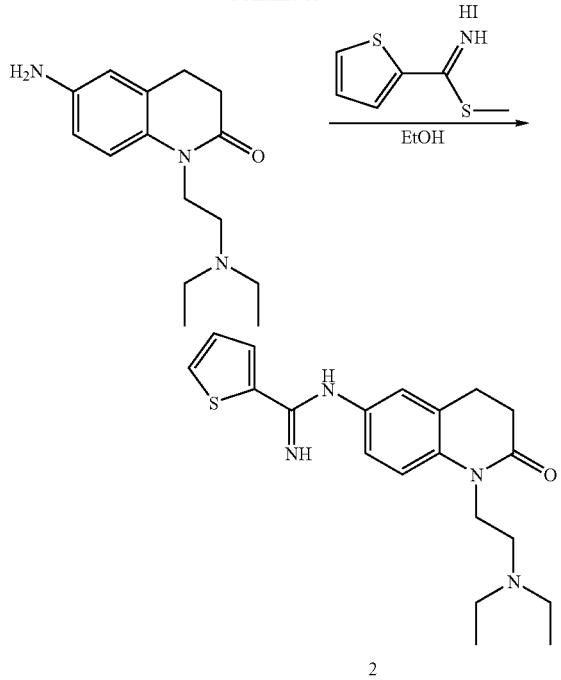

1-(2-(diethylamino)ethyl)-6-nitro-3,4-dihydroquinolin-2(1H)-one

A suspension of 6-nitro-3,4-dihydroquinolin-2(1H)-one (400 mg, 2.08 mmol), 2-chloro-N,N-diethylethanamine hydrochloride (394 mg, 2.29 mmol) and potassium carbonate (862 mg, 6.24 mmol) in 10 mL DMF was stirred at room temperature overnight. After this time, the mixture was poured into 20 mL H$_2$O then extracted with 2×50 mL CH$_2$Cl$_2$. The organic layer was separated, washed with brine and concentrated to give a yellow brown solid which was subjected to flash chromatography on silica gel using 5% MeOH/CH$_2$Cl$_2$ to give a yellow viscous oil (585 mg, 96.5%). $^1$H-NMR (CDCl$_3$) δ: 8.16 (dd, J=2.5, 9 Hz, 1H), 8.06 (d, J=2.5 Hz, 1H), 7.23 (d, J=9.0 Hz, 1H), 4.07 (t, J=7.0 Hz, 2H), 3.00 (t, J=7.0 Hz, 2H), 2.73-2.55 (m, 8H), 1.01 (t, J=7.0 Hz, 6H). MS (ESI): 292.2 (M+1, 100%).

6-amino-1-(2-(diethylamino)ethyl)-3,4-dihydroquinolin-2(1H)-one

A solution of 1-(2-(diethylamino)ethyl)-6-nitro-3,4-dihydroquinolin-2(1H)-one (500 mg, 1.72 mmol) in 10 mL methanol was added to Raney Nickel (slurry in H$_2$O, 50 mg) in a round bottom flask. The suspension was treated with hydrazine hydrate (534 µL, 17.2 mmol) and heated at reflux for 10 minutes then filtered through a pad of celite. The celite pad was rinsed with 10 mL methanol. The filtrate was concentrated to give a dark brown residue which was subjected to flash silica gel chromatography using 5% 2M NH$_3$ in MeOH/ CH$_2$Cl$_2$ to give a colorless oil (365 mg, 81.2%). $^1$H-NMR (CDCl$_3$) δ: 6.88 (d, J=8.4 Hz, 1H), 6.58 (d, J=2.7 Hz, 1H), 6.51 (dd, J=2.7, 9 Hz, 1H), 3.98 (t, J=7.8 Hz, 2H), 3.54 (br s, 2H), 2.78 (t, J=7.8 Hz, 2H), 2.66-2.55 (m, 8H), 1.04 (t, J=7.2 Hz, 6H). MS (ESI): 262.2 (M+1, 100%).

N-(1-(2-(diethylamino)ethyl)-2-oxo-1,2,3,4-tetrahydroquinolin-6-yl)thiophene-2-carboximidamide A solution of 6-amino-1-(2-(diethylamino)ethyl)-3,4-dihydroquinolin-2(1H)-one (275 mg, 1.05 mmol) in 10 mL EtOH was treated with methyl thiophene-2-carbimidothioate hydroiodide (600 mg, 2.10 mmol) and stirred for 4 days at room temperature. Argon was bubbled through the mixture for 20 minutes then the mixture was partitioned between $CH_2Cl_2$ (50 mL) and saturated sodium bicarbonate (10 mL). The aqueous layer was extracted with an additional 20 mL $CH_2Cl_2$. The combined organic layers were dried over sodium sulfate and concentrated to give a yellow residue which was subjected to flash chromatography on silica gel using 5% MeOH/$CH_2Cl_2$ then 5% 2M $NH_3$ in MeOH/$CH_2Cl_2$ to give a yellow solid (170 mg, 43.7%). HPLC analysis indicated that the product is >99% pure. $^1$H-NMR (DMSO-$d_6$) δ: 7.73 (d, J=3.6 Hz, 1H), 7.60 (d, J=4.8 Hz, 1H), 7.11-7.04 (m, 2H), 6.76-6.74 (m, 2H), 6.42 (brs, 2H), 3.92 (t, J=7 Hz, 2H), 2.80 (t, J=7 Hz, 2H), 2.56-2.47 (m, 8H), 0.94 (t, J=7 Hz, 6H).

MS (ESI): 371.2 (M+1). ESI-HRMS calculated for $C_{20}H_{27}N_4SO$ (MH$^+$): 371.1900, Observed: 371.1906.

Example 3

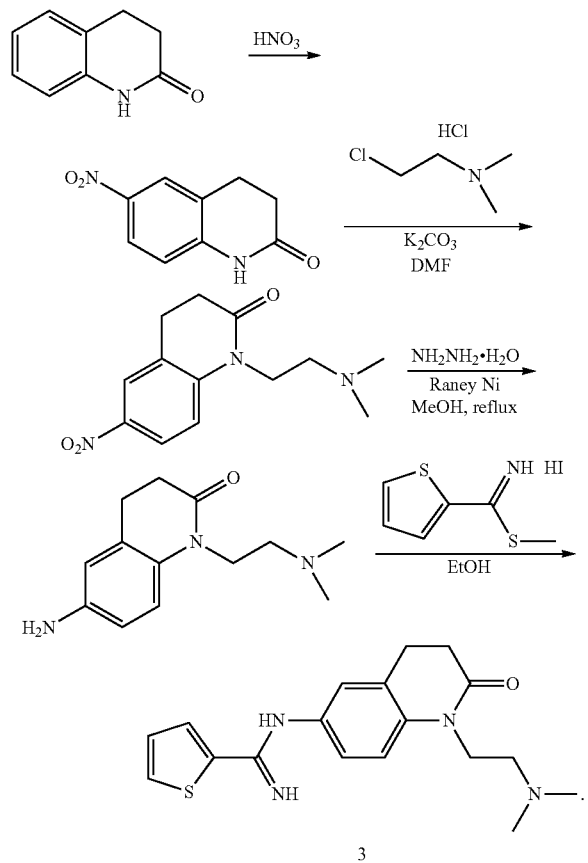

3

6-nitro-3,4-dihydroquinolin-2(1H)-one

To a 250 mL round bottom flask containing 3,4-dihydro-2-(1H)-quinoline (3.00 g, 20.38 mmol) and a magnetic stirbar was added concentrated sulphuric acid (60 mL). The argon purged reaction was placed into an ice-methanol bath (~−10° C.) and stirred to dissolve the solid. Distilled water (15 mL) was added. A 45% solution of fuming nitric acid in water (2.86 mL, 20.43 mmol) was added dropwise to the colorless reaction. The orange-red solution was stirred at −10–0°C. for 25 minutes. The reaction was quenched by pouring onto an ice-water slush (300 mL). The ice was allowed to melt, and the pale yellow solid collected by vacuum filtration. The solid was washed with water (3.50 mL). After drying under suction, the product was washed again with ether (3×30 mL). TLC (1:1 EtOAc:Hexanes) revealed presence of some starting material. The product was washed on the filter with dichloromethane (2×30 mL). TLC revealed the solid was pure desired product, and the filtrate wash contained both starting material and product. Yield: 3.20 g of yellow solid (82%). $^1$H NMR (DMSO-$d_6$) δ: 10.68 (br s, 1H), 8.11 (s, 1H), 8.07 (d, J=8.7 Hz, 1H), 7.00 (d, J=8.7 Hz, 1H), 3.01 (t, J=7.2 Hz, 2H), 2.53 (t, J=7.8 Hz, 2H).

1-(2-(dimethylamino)ethyl)-6-nitro-3,4-dihydroquinolin-2(1H)-one

A suspension of 6-nitro-3,4-dihydroquinolin-2(1H)-one (500 mg, 2.60 mmol), (N,N-dimethylamino)ethyl chloride hydrochloride (412 mg, 2.86 mmol) and potassium carbonate (1.07 g, 7.74 mmol) in 8 mL DMF was stirred at room temperature for 48 hours. Additional (N,N-dimethylamino)ethyl chloride hydrochloride (187 mg, 1.30 mmol) and potassium carbonate (359 mg, 2.60 mmol). Reaction was stirred for an additional 16 hours. After this time, the reaction was transferred to a separatory funnel and diluted with cold water and ethyl acetate. The aqueous was extracted twice more with ethyl acetate and the combined organic fractions were washed with brine, dried over $Na_2SO_4$, filtered and concentrated. The residue was subjected to flash chromatography on silica gel using 5% 2M $NH_3$ in MeOH/$CH_2Cl_2$ to give a yellow solid. Yield: 370 mg (54%). $^1$H NMR (CDCl$_3$) δ: 8.15 (dd, J=2.7, 9.0 Hz, 1H), 8.06 (d, J=2.7 Hz, 1H), 7.17 (d, J=9 Hz, 1H), 4.09 (t, J=7.2 Hz, 2H), 3.00 (t, J=6.6 Hz, 2H), 2.71 (t, J=7.5 Hz, 2H), 2.52 (t, J=7.5 Hz, 2H), 2.32 (s, 6H). MS (ESI): 264.1 (M+1).

6-amino-1-(2-(dimethylamino)ethyl)-3,4-dihydroquinolin-2(1H)-one

A suspension of 1-(2-(dimethylamino)ethyl)-6-nitro-3,4-dihydroquinolin-2(1H)-one (320 mg, 1.215 mmol) in dry methanol (10 mL) was treated with Ra—Ni (~0.05 g) followed by hydrazine hydrate (0.38 mL, 12.2 mmol) at room temperature and the resulting mixture was refluxed for 20 min. The colorless reaction was cooled to room temperature, filtered through a celite pad, washed with methanol (2×10 mL). The combined methanol layer was evaporated and crude was purified by column chromatography (2 M $NH_3$ in MeOH:$CH_2Cl_2$, 5:95). Yield: 280 mg of colorless oil (98%). $^1$H NMR (CDCl$_3$) δ: 6.86 (d, J=8.4 Hz, 1H), 6.57 (dd, J=2.7, 8.4 Hz, 1H), 6.51 (d, J=2.1 Hz, 1H), 4.01 (t, J=7.5 Hz, 2H), 2.78 (t, J=7.2 Hz, 2H), 2.58 (t, J=7.2 Hz, 2H), 2.51 (t, J=7.2 Hz, 2H), 2.31 (s, 6H). MS (ESI): 234.2 (M+1).

N-(1-(2-(dimethylamino)ethyl)-2-oxo-1,2,3,4-tetrahydroquinolin-6-yl)thiophene-2-carboximidamide A solution of 6-amino-1-(2-(dimethylamino)ethyl)-3,4-dihydroquinolin-2(1H)-one (0.280 g, 1.20 mmol) in absolute ethanol (5 mL) was treated with methyl thiophene-2-carbimidothioate hydroiodide (0.684 g, 2.40 mmol) at room temperature and the resulting mixture was stirred overnight (18 h). The reaction was diluted with ether (45 mL) and the precipitate collected by vacuum filtration. The precipitate was washed from the filter with methanol and the solvent was evaporated. The residue was diluted with 1N sodium hydroxide solution (5 mL) and product was extracted into ethyl acetate (3×10 ml). The combined ethyl acetate layer was washed with brine and dried (Na$_2$SO$_4$). Solvent was evaporated and crude was purified by column chromatography (2M ammonia in methanol:dichloromethane, 1:19). Product was dried under high vacuum. Yield: 230 mg of yellow oil 3 (56%).

$^1$H NMR (CDCl$_3$) δ: 7.44 (dd, J=1, 5.4 Hz, 1H), 7.41 (d, J=3.3 Hz, 1H), 7.09 (t, J=4.2 Hz,1H), 7.03 (d, J=8.4 Hz, 1H), 6.88 (dd, J=2.1, 8.4 Hz, 1H), 6.83 (d, J=2.1 Hz, 1H), 4.87 (br s, 2H), 4.06 (t, J=7.5 Hz, 2H), 2.86(t, J=7.2 Hz, 2H), 2.63 (t, J=7.2 Hz, 2H), 2.55 (t, J=7.2 Hz, 2H), 2.33 (s, 6H). MS (ESI): 357.2 (M+1). ESI-HRMS calculated for C$_{18}$H$_{23}$N$_4$SO (MH$^+$): 343.1587, Observed: 343.1598.

Example 4

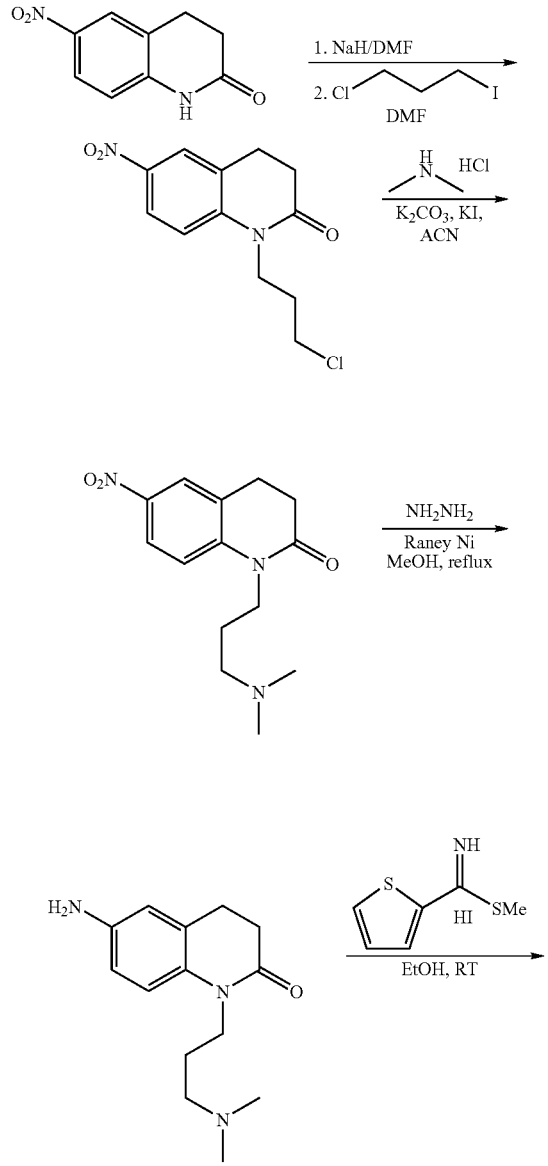

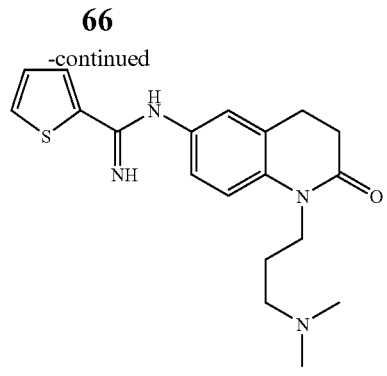

4

1-(3-chloropropyl)-6-nitro-3,4-dihydroquinolin-2(1H)-one 6-nitro-3,4-dihydroquinolin-2(1H)-one (1.50 g, 7.81 mmol) was dissolved in anhydrous DMF (30 mL) in an argon purged round bottom flask. The reaction was stirred in an ice-water bath and 60% sodium hydride in mineral oil (1.25 g, 31.25 mmol) was added in one portion. The reaction became dark red-orange. This solution was transferred using a cannulating needle to a solution of 1-chloro-3-iodopropane (2.52 mL, 23.47 mmol) in DMF (20 mL). The reaction was stirred at room temperature for 5 hours. The reaction was quenched with brine (25 mL), transferred to a separatory funnel and partitioned with ethyl acetate (30 mL). The aqueous was extracted twice more with ethyl acetate (2×20 mL). The combined organic layers were washed with brine, dried with sodium sulphate, decanted and concentrated to afford a yellow solid. Purification by flash column chromatography afforded a yellow solid (Ethyl acetate:hexanes, 30:70-100:0); Yield: 1.58 g (75%).

$^1$H NMR (DMSO-d$_6$) δ: 8.16 (s, 1H), 8.13 (d, J=2.7 Hz, 1H), 7.36(d, J=8.7 Hz, 1H), 4.09-4.04 (m, 2H), 3.71 (t, J=6.3 Hz, 2H), 3.01 (t, J=7.5 Hz, 2H), 2.66-2.61 (m, 2H), 2.04-1.99 (m, 2H). MS (ESI): 291.0 and 293.0 (M+1).

1-(3-(dimethylamino)propyl)-6-nitro-3,4-dihydroquinolin-2(1H)-one 1-(3-chloropropyl)-6-nitro-3,4-dihydroquinolin-2(1H)-one (300 mg, 1.12 mmol), dimethylamine hydrochloride (911 mg, 11.16 mmol), potassium iodide (1.85 g, 11.16 mmol) and potassium carbonate (1.54 g, 11.16 mmol) were weighed into an argon purged vial fitted with a magnetic stirbar. Anhydrous acetonitrile was added, and the yellow suspension stirred at room temperature for 18 hours. The reaction was placed in a heating block at a temperature of 60° C. for 2 hours. After cooling to room temperature, the reaction was filtered through celite and the celite pad washed with methanol and the filtrate concentrated to afford a yellow solid. No further purification was performed. Yield: 520 mg crude material. $^1$H NMR (DMSO) δ: 8.11 (d, J=2.4 Hz, 1H), 8.06 (dd, J=2.7 Hz, 9.3 Hz, 1H), 7.41 (d, J=9 Hz, 1H), 3.94 (t, J=7.2 Hz, 2H), 2.99 (t, J=6.9 Hz, 2H), 2.73 (s, 6H), 2.59 (t, J=8.1 Hz, 2H), 2.45 (t, J=1.5 Hz, 2H), 1.86 (t, J=7.5 Hz, 2H). MS (ESI): 278.1 (M+1).

6-amino-1-(2-(dimethylamino)ethyl)-3,4-dihydroquinolin-2(1H)-one 1-(3-(dimethylamino)propyl)-6-nitro-3,4-dihydroquinolin-2(1H)-one (0.510 g, 1.84 mmol) in dry methanol (10 mL)

was treated with Ra—Ni (~0.05 g) followed by hydrazine hydrate (0.58 mL, 18.4 mmol) at room temperature and the resulting mixture was refluxed for 20 min. The reaction was cooled to room temperature, filtered through a celite bed, washed with methanol (2×10 mL). The combined methanol layer was evaporated and crude was purified by column chromatography (2 M $NH_3$ in $MeOH:CH_2Cl_2$, 5:95). Yield: 90 mg of yellow solid (20%). $^1$H NMR ($CDCl_3$) $^1$H NMR ($CDCl_3$) δ: 6.86 (d, J=8.4 Hz, 1H), 6.56 (dd, J=2.7, 8.4 Hz, 1H), 6.52 (d, J=2.1 Hz, 1H), 3.92 (t, J=7.2 Hz, 2H), 2.79 (t, J=7.2 Hz, 2H), 2.59 (t, J=7.2 Hz, 2H), 2.35 (t, J=7.2 Hz, 2H), 2.23 (s, 6H), 1.85-1.75 (m, 2H). MS (ESI): 248.2 (M+1).

N-(1-(2-(dimethylamino)ethyl)-2-oxo-1,2,3,4-tetrahydroquinolin-6-yl)thiophene-2-carboximidamide A solution of 6-amino-1-(2-(dimethylamino)ethyl)-3,4-dihydroquinolin-2(1H)-one (0.045 g, 0.182 mmol) in dry ethanol (5 mL) was treated with methyl thiophene-2-carbimidothioate hydroiodide (0.103 g, 0.361 mmol) at room temperature and the resulting mixture was stirred over night (18 h). The reaction was diluted with ether (45 mL) and the precipitate collected by vacuum filtration. The precipitate was washed from the filter with methanol and the solvent was evaporated. The residue was diluted with 1N sodium hydroxide solution (5 mL) and product was extracted into ethyl acetate (3×10 mL). The combined ethyl acetate layer was washed with brine and dried ($Na_2SO_4$). The solvent was evaporated and crude was purified by column chromatography (2M ammonia in methanol:dichloromethane, 1:19). Product was dried under high vacuum. Yield: 40 mg of yellow oil 4 (58%) $^1$H NMR ($CDCl_3$) δ 7.44 (dd, J=1, 5.4 Hz, 1H), 7.41 (d, J=3.3 Hz, 1H), 7.09 (t, J=4.2 Hz, 1H), 7.03 (d, J=8.4 Hz, 1H), 6.88 (dd, J=2.1, 8.4 Hz, 1H), 6.83 (d, J=2.1 Hz, 1H), 4.87 (br s, 2H), 3.98 (t, J=7.2 Hz, 2H), 2.87 (t, J=7.2 Hz, 2H), 2.63 (t, J=7.2 Hz, 2H), 2.37 (t, J=7.2 Hz, 2H), 2.25 (s, 6H), 1.89-1.79 (m, 2H). MS (ESI): 357.2 (M+1). ESI-HRMS calculated for $C_{19}H_{25}N_4SO$ ($MH^+$): 357.1743, Observed: 357.1752.

Example 5

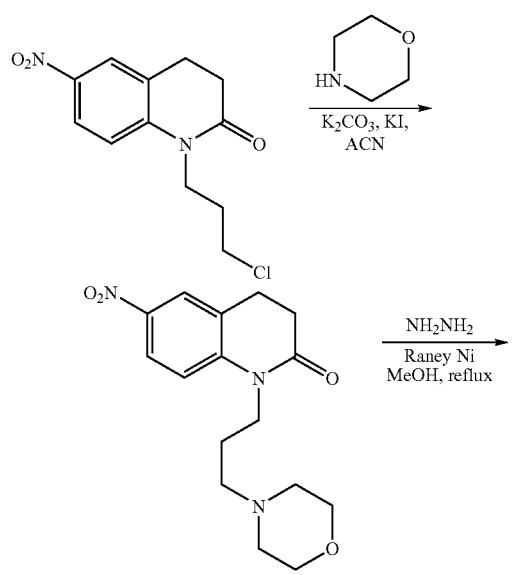

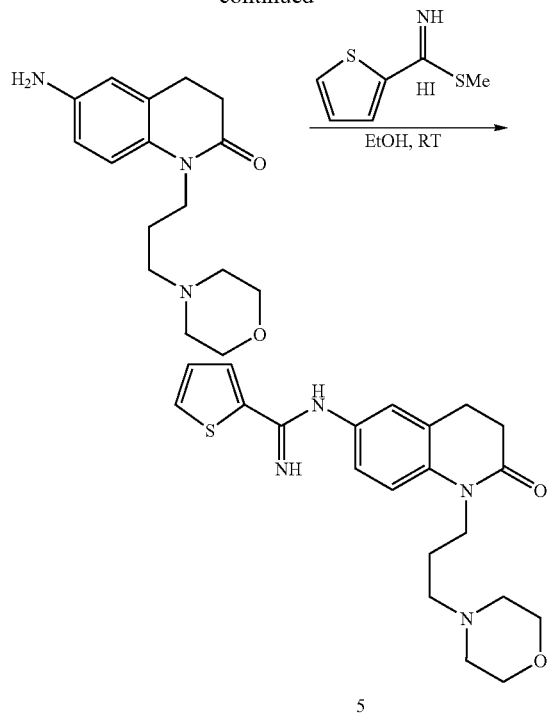

1-(3-morpholinopropyl)-6-nitro-3,4-dihydroquinolin-2(1H)-one 1-(3-chloropropyl)-6-nitro-3,4-dihydroquinolin-2(1H)-one (100 mg, 0.359 mmol), morpholine (313 uL, 3.59 mmol), potassium iodide (596 mg, 3.59 mmol) and potassium carbonate (496 mg, 3.59 mmol) were weighed into an argon purged vial fitted with a magnetic stirbar. Anhydrous acetonitrile (4 mL) was added, and the yellow suspension stirred in a heating block at a temperature of 65° C. for 18 hours. As starting material remained, the reaction was stirred at this temperature for an additional 3 days. After cooling to room temperature, the reaction was diluted with water (10 mL) and dichloromethane (15 mL) and transferred to a separatory funnel. The organic layer was collected, and the aqueous layer extracted twice more with dichloromethane (2×10 mL). The combined organics were washed with brine (15 mL) and dried over sodium sulphate. The solution was decanted and concentrated to afford a yellow oil. The product was purified using flash chromatography (2 M $NH_3$ in $MeOH:CH_2Cl_2$, 2.5-5:95-97.5) to afford a yellow oil. Yield: 88 mg yellow oil (77%). $^1$H-NMR ($CDCl_3$) δ: 8.13 (dd, J=2.7, 9 Hz, 1H), 8.07 (d, J=2.4 Hz, 1H), 7.21 (d, J=9.0 Hz, 1H), 4.04 (t, J=7.5 Hz, 2H), 3.72 (t, J=4.5 Hz, 4H), 3.01 (t, J=7.2 Hz, 2H), 2.73-2.68 (m, 2H), 2.46-2.39 (m, 6H), 1.88-1.79 (m, 2H). MS (EI): 319 (M+).

6-amino-1-(3-morpholinopropyl)-3,4-dihydroquinolin-2(1H)-one 1-(3-morpholinopropyl)-6-nitro-3,4-dihydroquinolin-2(1H)-one (78 mg, 0.244 mmol) in dry methanol (5 mL) was treated with Ra—Ni (~0.05 g) followed by hydrazine hydrate (76 uL, 2.44 mmol) at room temperature and the resulting mixture was refluxed for 30 minutes. The reaction was cooled to room temperature, filtered through a celite bed and the bed washed with methanol (2×10 mL). The combined methanol layer was evaporated and crude was purified by column chromatography (2 M NH₃ in MeOH:CH₂Cl₂, 2.5:97.5). Yield: 64 mg of yellow oil (90%). ¹H NMR (CDCl3) δ: 6.86 (d, J=8.4 Hz, 1H), 6.56 (dd, J=2.7, 8.4 Hz, 1H), 6.52 (d, J=2.1 Hz, 1H), 3.93 (t, J=7.2 Hz, 2H), 3.71 (t, J=4.5 Hz, 4H), 2.81-2.76 (m, 2H), 2.61-2.56 (m, 2H), 2.44-2.36 (m, 6H) 1.83-1.65 (m, 2H). MS (ESI): 290.2 (M+1).

N-(1-(3-morpholinopropyl)-2-oxo-1,2,3,4-tetrahydroquinolin-6-yl)thiophene-2-carboximidamide A solution of 6-amino-1-(3-morpholinopropyl)-3,4-dihydroquinolin-2(1H)-one (0.055 g, 0.190 mmol) in dry ethanol (5 mL) was treated with methyl thiophene-2-carbimidothioate hydroiodide (0.108 g, 0.379 mmol) at room temperature and the resulting mixture was stirred for 64 hours. The reaction was transferred to a separatory funnel and diluted with ethyl acetate (30 mL) and saturated sodium hydrogen carbonate (20 mL). The aqueous was partitioned twice more with ethyl acetate (2×20 mL). The combined organics were washed with brine and dried (Na₂SO₄). Solvent was evaporated and crude was purified by column chromatography (2M ammonia in methanol:dichloromethane, 0-1:10-9). The product was dried under high vacuum to give 5 as a yellow oil. Yield: 36 mg of yellow oil (48%). ¹H NMR (CDCl3) δ: 7.44 (d, J=5.4 Hz, 1H), 7.41 (d, J=3.3 Hz, 1H), 7.09 (t, J=4.2 Hz, 1H), 7.06 (d, J=8.4 Hz, 1H), 6.88 (d, J=2.1 Hz, 1H), 6.84 (d, J=4.2 Hz, 1H), 4.86 (br s, 2H), 4.02-3.97 (m, 2H), 3.73-3.70 (m, 4H), 2.89-2.84 (m, 2H), 2.66-2.61 (m, 2H), 2.46-2.39 (m, 6H), 1.90-1.80 (m, 2H). MS (ESI): 399.2 (M+1). ESI-HRMS calculated for C₂₁H₂₇N₄SO₂ (MH⁺): 399.1849, Observed: 399.1836.

Example 6

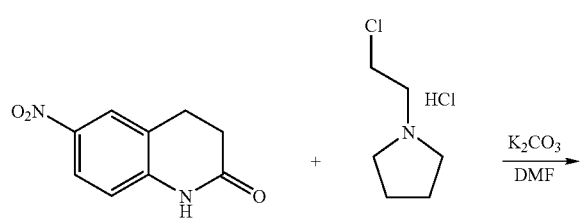

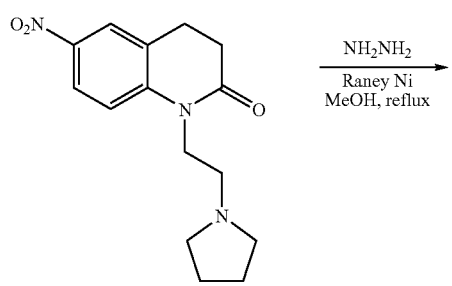

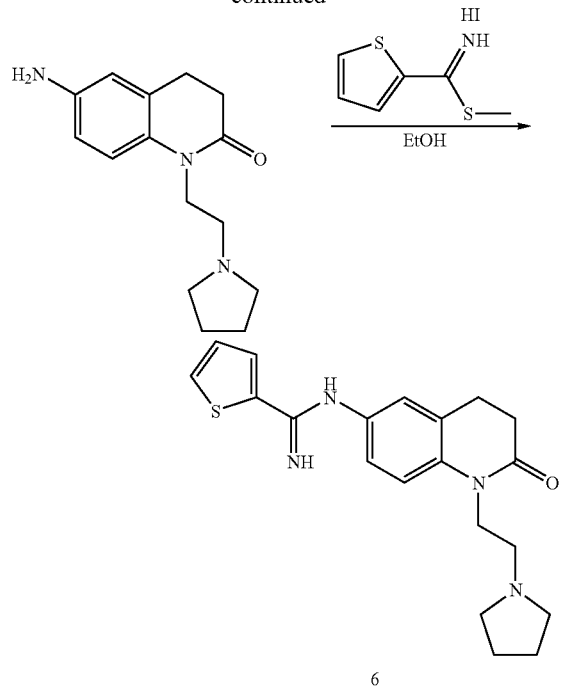

6-nitro-1-(2-(pyrrolidin-1-yl)ethyl)-3,4-dihydroquinolin-2(1H)-one

A suspension of 6-nitro-3,4-dihydroquinolin-2(1H)-one (230 mg, 1.06 mmol), 1-(2-chloroethyl)pyrrolidine hydrochloride (234 mg, 1.37 mmol) and potassium carbonate (440 mg, 3.18 mmol) in 5 mL DMF was stirred at room temperature for 4 days. After this time, the mixture was poured into 20 mL H₂O then extracted with 2×30 mL CH₂Cl₂. The organic layers were combined together, washed with brine (20 mL) and concentrated. Product was subjected to flash chromatography on the biotage using 5% 2M NH3 in MeOH/CH₂Cl₂ to give a yellow solid. Yield: 218 mg of yellow solid (71%). ¹H NMR (CDCl₃) δ: 8.14 (dd, J=2.7, 9 Hz, 1H), 8.06 (d, J=2.4 Hz, 1H), 7.20 (d, J=9.0 Hz, 1H), 4.13 (t, J=7.5 Hz, 2H), 3.00 (t, J=6.9 Hz, 2H), 2.73-2.68 (m, 4H), 2.63-2.60 (m, 4H), 1.82-1.78 (m, 4H). MS (ESI): 290.2 (M+1, 100%).

6-amino-1-(2-(pyrrolidin-1-yl)ethyl)-3,4-dihydroquinolin-2(1H)-one

To solution of 6-nitro-1-(2-(pyrrolidin-1-yl)ethyl)-3,4-dihydroquinolin-2(1H)-one (205 mg, 0.709 mmol) in 5 mL methanol was added to Raney Nickel (slurry in H₂O, 50 mg) in a reaction vial. The suspension was treated with hydrazine hydrate (220 µL, 7.09 mmol) and heated at reflux for 2 hours and then filtered through a pad of celite. The celite pad was rinsed with 10 mL methanol. The filtrate was concentrated and the resulting product was subjected to flash silica gel chromatography using 2.5% 2M NH₃ in MeOH/CH₂Cl₂ to afford a yellow oil. Yield: 180 mg (98%). ¹H NMR (CDCl₃) δ: 6.89 (d, J=8.4 Hz, 1H), 6.56 (dd, J=2.7, 8.4 Hz, 1H), 6.52 (d, J=2.1 Hz, 1H), 4.04 (t, J=7.5 Hz, 2H), 2.81-2.76 (m, 2H), 2.71-2.66 (m, 2H), 2.63-2.56 (m, 6H), 1.81-1.77 (m, 4H). MS (ESI): 260.2 (M+1, 100%).

N-(2-oxo-1-(2-(pyrrolidin-1-yl)ethyl)-1,2,3,4-tetrahydroquinolin-6-yl)thiophene-2-carboximidamide A solution of 6-amino-1-(2-(pyrrolidin-1-yl)ethyl)-3,4-dihydroquinolin-2(1H)-one (165 mg, 0.636 mmol) in 5 mL of ethanol was treated with methyl thiophene-2-carbimidothioate hydroiodide (363 mg, 1.27 mmol) and stirred for 18 hours at room temperature. The mixture was partitioned between CH$_2$Cl$_2$ (50 mL) and saturated sodium bicarbonate (10 mL). The aqueous layer was extracted with an additional 20 mL CH$_2$Cl$_2$. The combined organic layers were dried over sodium sulfate and concentrated to give a yellow residue which was subjected to flash chromatography on a Biotage system using 5-10% 2M NH$_3$ in MeOH/CH$_2$Cl$_2$ to give a yellow solid. Yield: 157 mg of yellow oil (68%). $^1$H NMR (CDCl3) δ: 7.44 (d, J=5.4 Hz, 1H), 7.41 (d, J=3.3 Hz, 1H), 7.09 (t, J=4.2 Hz, 1H), 7.06 (d, J=8.4 Hz, 1H), 6.88 (d, J=2.1 Hz, 1H), 6.84 (d, J=4.2 Hz, 1H), 4.86 (br s, 2H), 4.12-4.06 (m, 2H), 2.88-2.83 (m, 2H), 2.75-2.70 (m, 2H), 2.65-2.60 (m, 6H), 1.82-1.78 (m, 4H). MS (ESI): 369.2 (M+1). ESI-HRMS calculated for C$_{20}$H$_{25}$N$_4$SO (MH$^+$): 369.1743, Observed: 369.1731.

Example 7

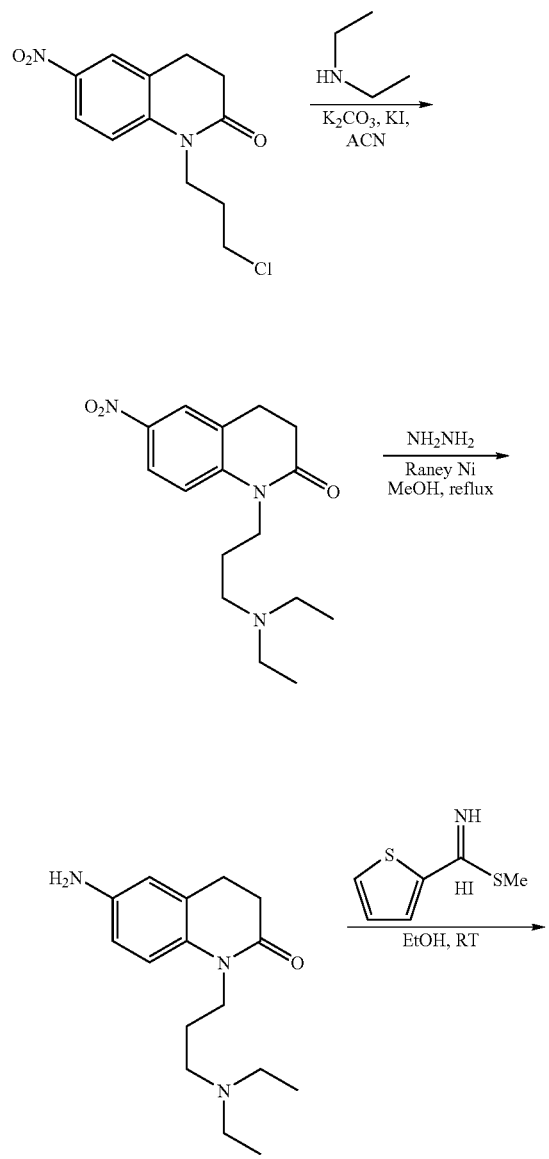

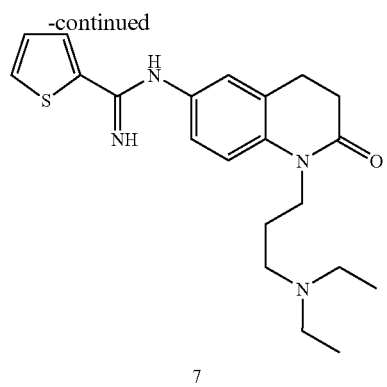

7

1-(3-(diethylamino)propyl)-6-nitro-3,4-dihydroquinolin-2(1H)-one 1-(3-chloropropyl)-6-nitro-3,4-dihydroquinolin-2(1H)-one (100 mg, 0.359 mmol), diethylamine (263 uL, 3.59 mmol), potassium iodide (596 mg, 3.59 mmol) and potassium carbonate (496 mg, 3.59 mmol) were weighed into an argon purged vial fitted with a magnetic stirbar. Anhydrous acetonitrile (4 mL) was added, and the yellow suspension stirred in a heating block at a temperature of 65° C. for 18 hours. As starting material remained, the reaction was stirred at this temperature for an additional 3 days. After cooling to room temperature, the reaction was diluted with water (10 mL) and dichloromethane (15 mL) and transferred to a separatory funnel. The organic layer was collected, and the aqueous layer extracted twice more with dichloromethane (2×10 mL). The combined organic layers were washed with brine (15 mL) and dried over sodium sulphate. The solution was decanted and concentrated to afford a yellow oil. The product was purified using flash chromatography (2 M NH$_3$ in MeOH:CH$_2$Cl$_2$, 2.5-5:95-97.5) to afford a yellow oil. Yield: 102 mg yellow oil (93%). $^1$H NMR (CDCl$_3$) δ: 8.14 (dd, J=2.7, 9 Hz, 1H), 8.06 (d, J=2.4 Hz, 1H), 7.23 (d, J=9.0 Hz, 1H), 4.02 (t, J=7.5 Hz, 2H), 3.01 (t, J=7.2 Hz, 2H), 2.73-2.68 (m, 2H), 2.57-2.48 (m, 6H), 1.83-1.73 (m, 2H), 1.04 (t, J=7.2 Hz, 6H). MS (EI): 305 (M+).

6-Amino-1-(3-diethylamino-propyl)-3,4-dihydro-1H-quinolin-2-one 1-(3-(Diethylamino)propyl)-6-nitro-3,4-dihydroquinolin-2(1H)-one (93 mg, 0.305 mmol) in dry methanol (5 mL) was treated with Ra—Ni (slurry in water, ~0.05 g) followed by hydrazine hydrate (95 uL, 3.05 mmol) at room temperature and the resulting mixture was refluxed for 30 minutes. The reaction was cooled to room temperature, filtered through a celite bed, washed with methanol (2×10 mL). The combined methanol layer was evaporated and crude was purified by column chromatography (2 M NH$_3$ in MeOH:CH$_2$Cl$_2$, 2.5:97.5). Yield: 62 mg of yellow oil (74%). $^1$H NMR (CDCl$_3$) δ: 6.87 (d, J=8.4 Hz, 1H), 6.56 (dd, J=2.7, 8.4 Hz, 1H), 6.52 (d, J=2.1 Hz, 1H), 3.91 (m, 2H), 2.81-2.76 (m, 2H), 2.61-2.54 (m, 2H), 2.52-2.46 (m, 6H), 1.78-1.61 (m, 2H), 1.01 (t, J=7.2 Hz, 6H). MS (ESI): 276.2 (M+1).

N-(1-(3-(diethylamino)propyl)-2-oxo-1,2,3,4-tetrahydroquinolin-6-yl)thiophene-2-carboximidamide A solution of 6-Amino-1-(3-diethylamino-propyl)-3,4-dihydro-1H-quinolin-2-one (0.058 g, 0.211 mmol) in dry ethanol (5 mL) was treated with methyl thiophene-2-carbimidothioate hydroiodide (0.120 g, 0.421 mmol) at room temperature and the resulting mixture was stirred for 64 hours. The reaction was transferred to a separatory funnel and diluted with ethyl acetate (30 mL) and saturated sodium hydrogen carbonate (20 mL). The aqueous was partitioned twice more with ethyl acetate (2×20 mL). The combined organics were washed with brine and dried ($Na_2SO_4$). Solvent was evaporated and crude was purified by column chromatography (2M ammonia in methanol:dichloromethane, 0-1: 10-9). The product 7 was dried under high vacuum. Yield: 35 mg of yellow solid (44%). $^1$H NMR (CDCl3) δ: 7.44 (d, J=5.4 Hz, 1H), 7.41 (d, J=3.3 Hz, 1H), 7.09 (t, J=4.2 Hz, 1H), 7.06 (d, J=8.4 Hz, 1H), 6.88 (d, J=2.1 Hz, 1H), 6.84 (d, J=4.2 Hz, 1H), 4.90 (br s, 2H), 4.03-3.99 (m, 2H), 2.90-2.85 (m, 2H), 2.77-2.62 (m, 8H), 2.03-1.93 (m, 2H), 1.15 (t, J=7.2 Hz, 6H). MS (ESI): 385.2 (M+1). ESI-HRMS calculated for $C_{21}H_{29}N_4SO_2$ (MH$^+$): 385.2056, Observed: 385.2040.

Example 8

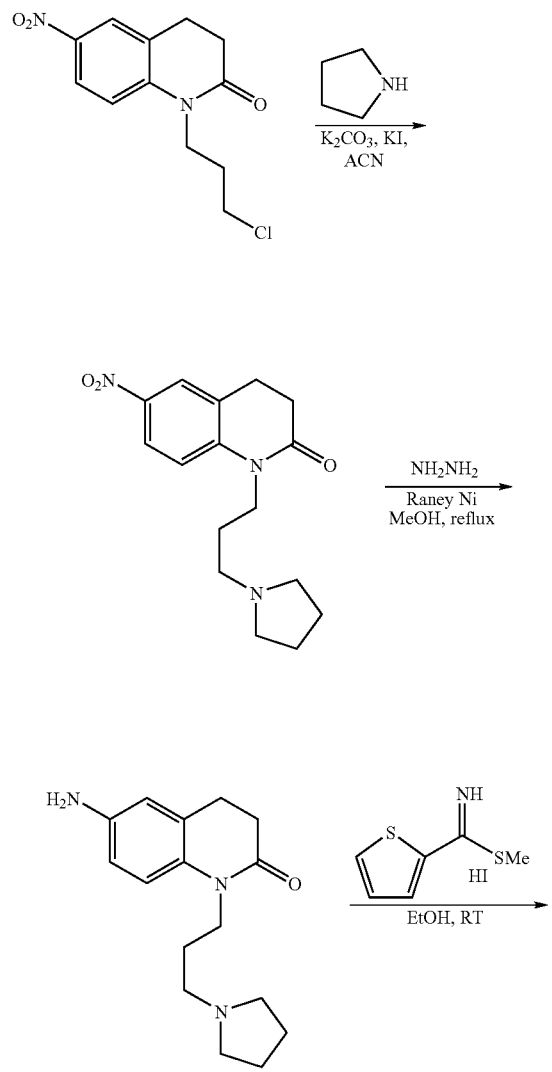

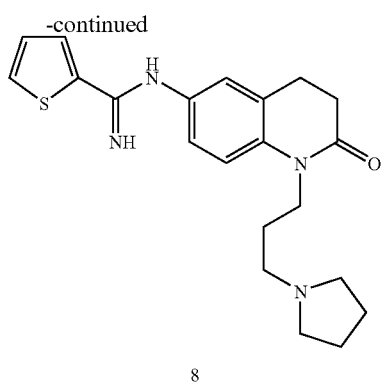

8

6-nitro-1-(3-(pyrrolidin-1-yl)propyl)-3,4-dihydroquinolin-2(1H)-one 1-(3-chloropropyl)-6-nitro-3,4-dihydroquinolin-2(1H)-one (100 mg, 0.359 mmol), pyrrolidine (300 uL, 3.59 mmol), potassium iodide (596 mg, 3.59 mmol) and potassium carbonate (496 mg, 3.59 mmol) were weighed into an argon purged vial fitted with a magnetic stirbar. Anhydrous acetonitrile (4 mL) was added, and the yellow suspension stirred in a heating block at a temperature of 65° C. for 18 hours. As starting material remained, the reaction was stirred at this temperature for an additional 3 days. After cooling to room temperature, the reaction was diluted with water (10 mL) and dichloromethane (15 mL) and transferred to a separatory funnel. The organic layer was collected, and the aqueous layer extracted twice more with dichloromethane (2×10 mL). The combined organics were washed with brine (15 mL) and dried over sodium sulphate. The solution was decanted and concentrated to afford a yellow oil. The product was purified using flash chromatography to afford a yellow oil (2 M $NH_3$ in MeOH:$CH_2Cl_2$, 2.5-5:95-97.5). Yield: 99 mg yellow oil (91%). $^1$H NMR (CDCl$_3$) δ: 8.13 (dd, J=2.7, 9 Hz, 1H), 8.06 (d, J=2.4 Hz, 1H), 7.23 (d, J=9.0 Hz, 1H), 4.05 (t, J=7.5 Hz, 2H), 3.00 (t, J=7.2 Hz, 2H), 2.73-2.68 (m, 2H), 2.56-2.51 (m, 6H), 1.92-1.77 (m, 6H). MS (EI): 303 (M+).

6-amino-1-(3-(pyrrolidin-1-yl)propyl)-3,4-dihydroquinolin-2(1H)-one 6-nitro-1-(3-(pyrrolidin-1-yl)propyl)-3,4-dihydroquinolin-2(1H)-one (89 mg, 0.293 mmol) in dry methanol (5 mL) was treated with Ra—Ni (~0.05 g) followed by hydrazine hydrate (92 uL, 2.95 mmol) at room temperature and the resulting mixture was refluxed for 30 minutes. The reaction was cooled to room temperature, filtered through a celite bed, washed with methanol (2×10 mL). The combined methanol layer was evaporated and crude was purified by column chromatography (2 M $NH_3$ in MeOH:$CH_2Cl_2$, 2.5:97.5). Yield: 58 mg of yellow oil (73%). $^1$H NMR (CDCl3) δ: 6.86 (d, J=8.4 Hz, 1H), 6.55 (dd, J=2.7, 8.4 Hz, 1H), 6.52 (d, J=2.1 Hz, 1H), 3.94 (m, 2H), 2.81-2.76 (m, 2H), 2.61-2.56 (m, 2H), 2.53-2.49 (m, 6H), 1.87-1.82 (m, 2H), 1.79-1.75 (m, 4H). MS (ESI): 274.2 (M+1).

N-(1-(3-(pyrrolidin-1-yl)propyl)-2-oxo-1,2,3,4-tetrahydroquinolin-6-yl)thiophene-2-carboximidamide A solution of 6-amino-1-(3-(pyrrolidin-1-yl)propyl)-3,4-dihydroquinolin-2(1H)-one (0.053 g, 0.194 mmol) in dry ethanol (5 mL) was treated with methyl thiophene-2-carbimidothioate hydroiodide (0.110 g, 0.386 mmol) at room temperature and the resulting mixture was stirred for 64 hours. The reaction was transferred to a separatory funnel and diluted with ethyl acetate (30 mL) and saturated sodium hydrogen carbonate (20 mL). The aqueous was partitioned twice more with ethyl acetate (2×20 mL). The combined organics were washed with brine and dried (Na$_2$SO$_4$). Solvent was evaporated and crude was purified by column chromatography (2M ammonia in methanol:dichloromethane, 0-1:10-9). The product was dried under high vacuum. Yield: 31 mg of yellow solid (42%). $^1$H NMR (CDCl3) δ: 7.44 (d, J=5.4 Hz, 1H), 7.41 (d, J=3.3 Hz, 1H), 7.09 (t, J=4.2 Hz, 1H), 7.06 (d, J=8.4 Hz, 1H), 6.88 (d, J=2.1 Hz, 1H), 6.84 (d, J=4.2 Hz, 1H), 4.91 (br s, 2H), 4.05-4.00 (m, 2H), 2.89-2.85 (m, 2H), 2.70-2.64 (m, 8H), 2.02-1.97 (m, 2H), 1.90-1.82 (m, 4H). MS (ESI): 383.2 (M+1). ESI-HRMS calculated for C$_{21}$H$_{27}$N$_4$SO$_2$ (MH$^+$): 383.1900, Observed: 383.1895.

Example 9

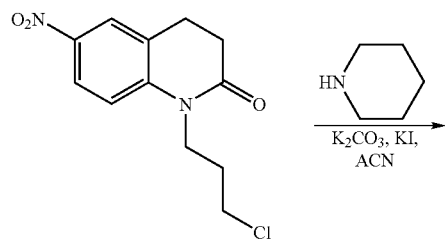

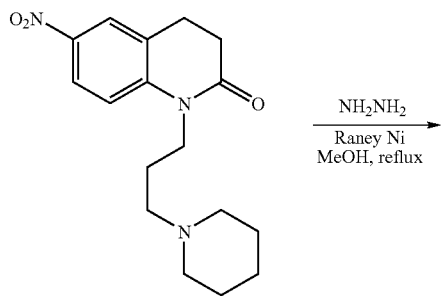

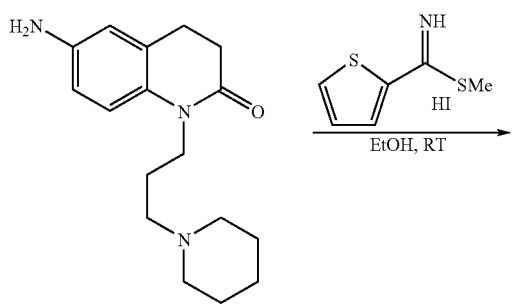

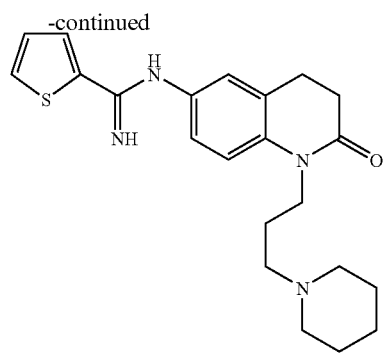

9

6-nitro-1-(3-(piperidin-1-yl)propyl)-3,4-dihydro-quinolin-2(1H)-one 1-(3-chloropropyl)-6-nitro-3,4-dihydroquinolin-2(1H)-one (100 mg, 0.359 mmol), piperidine (355 uL, 3.59 mmol), potassium iodide (596 mg, 3.59 mmol) and potassium carbonate (496 mg, 3.59 mmol) were weighed into an argon purged vial fitted with a magnetic stirbar. Anhydrous acetonitrile (4 mL) was added, and the yellow suspension stirred in a heating block at a temperature of 65° C. for 18 hours. As starting material remained, the reaction was stirred at this temperature for an additional 3 days. After cooling to room temperature, the reaction was diluted with water (10 mL) and dichloromethane (15 mL) and transferred to a separatory funnel. The organic layer was collected, and the aqueous layer extracted twice more with dichloromethane (2×10 mL). The combined organic fractions were washed with brine (15 mL) and dried over sodium sulphate. The solution was decanted and concentrated to afford a yellow oil. The product was purified using flash chromatography (2 M NH$_3$ in MeOH:CH$_2$Cl$_2$, 2.5-5:95-97.5) to afford a yellow oil. Yield: 102 mg yellow oil (89%). $^1$H NMR (CDCl$_3$) δ: 8.13 (dd, J=2.7, 9 Hz, 1H), 8.05 (d, J=2.4 Hz, 1H), 7.29 (d, J=9.0 Hz, 1H), 4.02 (t, J=7.5 Hz, 2H), 3.00 (t, J=7.2 Hz, 2H), 2.73-2.68 (m, 2H), 2.39-2.35 (m, 6H), 1.88-1.79 (m, 2H), 1.64-1.45 (m, 6H). MS (EI): 317 (M+).

6-amino-1-(3-(piperidin-1-yl)propyl)-3,4-dihydro-quinolin-2(1H)-one 6-nitro-1-(3-(piperidin-1-yl)propyl)-3,4-dihydroquinolin-2(1H)-one (98 mg, 0.309 mmol) in dry methanol (5 mL) was treated with Ra—Ni (~0.05 g slurry in water) followed by hydrazine hydrate (96 uL, 3.08 mmol) at room temperature and the resulting mixture was refluxed for 30 minutes. The reaction was cooled to room temperature, filtered through a celite bed, washed with methanol (2×10 mL). The combined methanol layer was evaporated and crude was purified by column chromatography (2 M NH$_3$ in MeOH:CH$_2$Cl$_2$, 2.5:97.5). Yield: 71 mg of yellow oil (80%). $^1$H NMR (CDCl$_3$) δ: 6.90 (d, J=8.4 Hz, 1H), 6.55 (dd, J=2.7, 8.4 Hz, 1H), 6.51 (d, J=2.1 Hz, 1H), 3.91 (m, 2H), 2.80-2.76 (m, 2H), 2.61-2.56 (m, 2H), 2.38-2.33 (m, 6H), 1.84-1.79 (m, 2H), 1.60-1.55 (m, 4H), 1.46-1.42 (m, 2H). MS (ESI): 288.2 (M+1).

N-(1-(3-(piperidin-1-yl)propyl)-2-oxo-1,2,3,4-tetrahydroquinolin-6-yl)thiophene-2-carboximidamide A solution of 6-amino-1-(3-(piperidin-1-yl)propyl)-3,4-dihydroquinolin-2(1H)-one (0.065 g, 0.226 mmol) in dry ethanol (5 mL) was treated with methyl thiophene-2-carbimidothioate hydroiodide (0.129 g, 0.452 mmol) at room temperature and the resulting mixture was stirred for 64 hours. The reaction was transferred to a separatory funnel and diluted with ethyl acetate (30 mL) and saturated sodium hydrogen carbonate (20 mL). The aqueous was partitioned twice more with ethyl acetate (2×20 mL). The combined organics were washed with brine and dried ($Na_2SO_4$). Solvent was evaporated and crude was purified by column chromatography (2M ammonia in methanol:dichloromethane, 0-1:10-9). The product was dried under high vacuum. Yield: 46 mg of yellow solid (51%). $^1$H NMR (DMSO-$d_6$) δ: 8.02 (d, J=3.9 Hz, 1H), 7.99 (d, J=3 Hz, 1H), 7.32 (d, J =4.8 Hz, 1H), 7.28 (d, J=6.3 Hz, 1H), 7.20 (s, 1H), 7.17 (s, 1H), 4.32 (br s, 2H), 3.98–3.93 (m, 2H), 3.45-3.40 (m, 4H), 3.16-3.10 (m, 4H), 2.95-2.90 (m, 4H), 2.61-2.56(m, 2H), 2.01-1.90 (m, 2H). MS (ESI): 397.2 (M+1). ESI-HRMS calculated for $C_{22}H_{29}N_4SO$ (MH$^+$): 397.2056, Observed: 397.2073.

Example 10

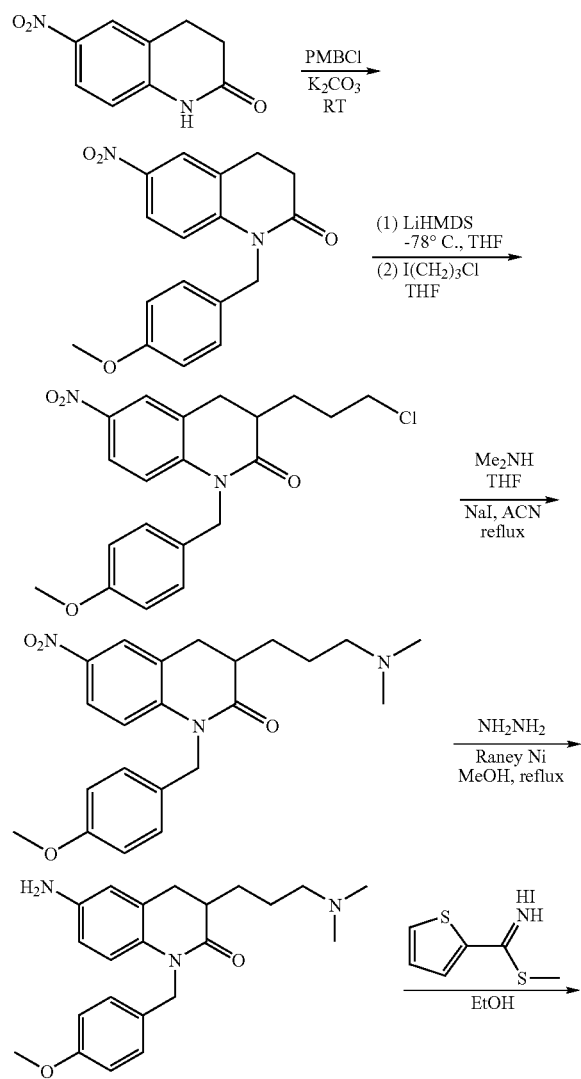

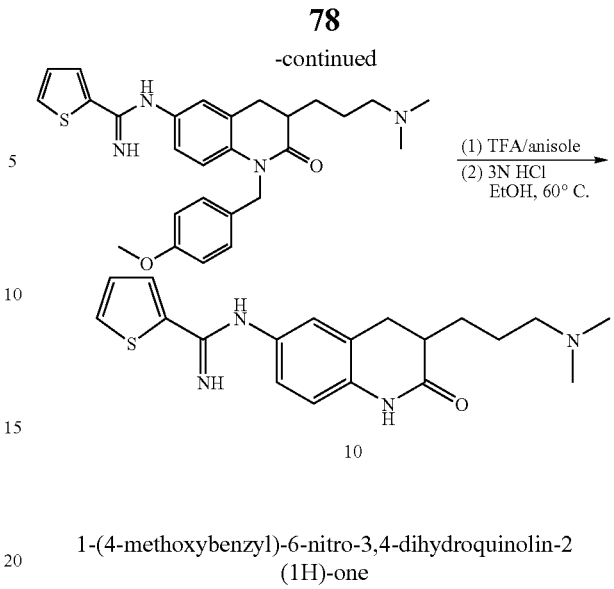

1-(4-methoxybenzyl)-6-nitro-3,4-dihydroquinolin-2(1H)-one

A suspension of 6-nitro-3,4-dihydroquinolin-2(1H)-one (500 mg, 2.60 mmol), 4-methoxybenzyl chloride (388 μL, 2.86 mmol) and potassium carbonate (1.08 g, 7.80 mmol) in 10 mL DMF was stirred at room temperature overnight. After this time, the mixture was poured into 20 mL $H_2O$ then extracted with 2×50 mL $CH_2Cl_2$. The organic layer was separated, washed with brine and concentrated to give a yellow solid which was subjected to flash chromatography on silica gel using 1% MeOH/$CH_2Cl_2$ to give an off-white solid (605 mg, 74.5%). $^1$H-NMR (DMSO-$d_6$) δ: 8.15 (d, J=2.7 Hz, 1H), 8.02 (dd, J=2.7, 9.0 Hz, 1H), 7.15 (dd, J=3.0, 9.0 Hz, 1H), 6.88-6.85 (m, 4H), 5.14 (s, 2H), 3.70 (s, 3H), 3.11-3.06 (m, 2H), 2.80-2.75 (m, 2H).

MS (EI): 312.4 (M$^+$, 10%), 121.3 (100%).

3-(3-chloropropyl)-1-(4-methoxybenzyl)-6-nitro-3,4-dihydroquinolin-2(1H)-one

A solution of 1-(4-methoxybenzyl)-6-nitro-3,4-dihydroquinolin-2(1H)-one (350 mg, 1.12 mmol) in 10 mL THF was cooled to −78° C. (acetone/dry ice bath) then treated with lithium hexamethyldisilazine (1.23 mL of a 1M solution in THF). The resulting dark solution was stirred for 30 minutes then treated with 1-iodo-3-chloropropane dropwise. The mixture was allowed to warm to room temperature and kept at this temperature overnight. The reaction was quenched with brine and extracted with 3×50 mL $CH_2Cl_2$. The combined organic fractions were dried over $MgSO_4$, filtered and concentrated to give a dark residue which was subjected to flash chromatography on silica gel using $CH_2Cl_2$. A yellow viscous oil was obtained (130 mg, 29.8%). $^1$H-NMR (CDCl$_3$) δ: 8.08-8.00 (m, 2H), 7.12-7.09 (m, 2H), 7.00 (d, J=8.7 Hz, 1H), 6.86-6.84 (m, 2H), 5.15 (dd, J=4.2, 20.4 Hz, 2H), 3.76 (s, 3H), 3.60 (t, J=6.3 Hz, 2H), 3.17 (dd, J=5.4, 15.6 Hz, 1H), 2.93-2.71 (m, 2H), 2.05-1.67 (m, 4H).

MS (EI): 388 (M$^+$, 10%), 121.3 (100%).

3-(3-(dimethylamino)propyl)-1-(4-methoxybenzyl)-6-nitro-3,4-dihydroquinolin-2(1H)-one A suspension of 3-(3-chloropropyl)-1-(4-methoxybenzyl)-6-nitro-3,4-dihydroquinolin-2(1H)-one (120 mg, 0.31 mmol), sodium iodide (47 mg, 0.31 mmol) and potassium carbonate in 3 mL acetonitrile was treated with dimethylamine in THF (0.3 mL of a 2M solution, 0.62 mmol). The mixture was heated at 80° C. in a sealed tube for 22 hours. The reaction was cooled to room temperature then filtered through a pad of celite. The filter pad was rinsed with methanol and the filtrate was concentrated to give a brown residue which was used without further purification. Yield: 115 mg (93.5%). $^1$H-NMR (CDCl$_3$) δ: 8.07 (d, J=2.4 Hz, 1H), 8.00 (dd, J=2.7, 9 Hz, 1H), 7.11-7.08 (m, 2H), 6.98 (d, J=9.0 Hz, 1H), 6.87-6.84 (m, 2H), 5.15 (dd, J=4.2, 20.4 Hz, 2H), 3.76 (s, 3H), 3.15 (dd, J=5.4, 15.6 Hz, 1H), 2.95-2.87 (m, 4H), 2.48 (s, 6H), 1.92-1.61 (m, 4H).
MS (ESI): 398.2 (MH$^+$, 100%).

6-amino-3-(3-(dimethylamino)propyl)-1-(4-methoxybenzyl)-3,4-dihydroquinolin-2(1H)-one A solution of 3-(3-(dimethylamino)propyl)-1-(4-methoxybenzyl)-6-nitro-3,4-dihydroquinolin-2(1H)-one (115 mg, 0.29 mmol) in 10 mL methanol was added to Raney Nickel (slurry in H$_2$O, 50 mg) in a round bottom flask. The suspension was treated with hydrazine hydrate (90 μL, 2.90 mmol) and heated at reflux for 10 minutes then filtered through a pad of celite. The celite pad was rinsed with 10 mL methanol. The filtrate was concentrated to give a yellow residue which was subjected to flash silica gel chromatography using 5% 2M NH$_3$ in MeOH/CH$_2$Cl$_2$ to give a yellow semi-solid (77 mg, 72.3%). $^1$H-NMR (CDCl$_3$) δ: 7.13-7.10 (m, 2H), 6.83-6.80 (m, 2H), 6.69 (d, J=8.4 Hz, 1H), 6.50 (d, J=2.4 Hz, 1H), 6.42 (dd, J=2.4, 8.4 Hz, 1H), 5.05 (dd, J=15.6, 29.1 Hz, 2H), 3.76 (s, 3H), 3.48 (br s, 2H), 3.01-2.91 (m, 1H), 2.70-2.58 (m, 2H), 2.28 (t, J=7.2 Hz, 2H), 2.21 (s, 6H), 1.88-1.42 (m, 4H).
MS (ESI): 368.2 (MH$^+$, 100%).

N-(3-(3-(dimethylamino)propyl)-1-(4-methoxybenzyl)-2-oxo-1,2,3,4-tetrahydroquinolin-6-yl) thiophene-2-carboximidamide A solution of 6-amino-3-(3-(dimethylamino)propyl)-1-(4-methoxybenzyl)-3,4-dihydroquinolin-2(1H)-one (70 mg, 0.19 mmol) in 5 mL EtOH was treated with methyl thiophene-2-carbimidothioate hydroiodide (109 mg, 0.38 mmol) and stirred at room temperature for 3 days. Argon was bubbled through the mixture for 20 minutes then it was partitioned between CH$_2$Cl$_2$ (50 mL) and saturated sodium bicarbonate (10 mL). The aqueous layer was extracted with an additional 20 mL CH$_2$Cl$_2$. The combined organic layers were rinsed with brine, dried over sodium sulfate and concentrated to give a yellow residue which was subjected to flash chromatography on silica gel using 2% MeOH/CH$_2$Cl$_2$ then 5% 2M NH$_3$ in MeOH/CH$_2$Cl$_2$ to give a light yellow solid (70 mg, 77.7%). An HPLC analysis indicated that the product is >99% pure. $^1$H-NMR (DMSO-d$_6$) δ: 7.71 (d, J=3.6 Hz, 1H), 7.58 (d, J=5.1 Hz, 1H), 7.16 (d, J=8.7 Hz, 2H), 7.08 (t, J=3.9, 1H), 6.89-6.86 (m, 3H), 6.75 (br s, 1H), 6.64-6.62 (m, 1H), 6.46 (br s, 2H), 5.03 (dd, J=15.9, 5.1 Hz, 2H), 3.71 (s, 3H), 3.00 (dd, J=5.1, 15.2 Hz, 1H), 2.73-2.56 (m, 2H), 2.22 (t, J=6.6 Hz, 2H), 2.14 (s, 6H), 1.78-1.34 (m, 4H). MS (ESI): 477.2 (M+1).

N-(3-(3-(dimethylamino)propyl)-2-oxo-1,2,3,4-tetrahydroquinolin-6-yl)thiophene-2-carboximidamide dihydrochloride A solution of N-(3-(3-(dimethylamino)propyl)-1-(4-methoxybenzyl)-2-oxo-1,2,3,4-tetrahydroquinolin-6-yl) thiophene-2-carboximidamide (50 mg, 0.1 mmol) and anisole (23 μL, 0.2 mmol) in 7.5 mL trifluoroacetic acid was stirred at room temperature for 2 hours then heated at 60° C. for 22 hours. A TLC analysis indicated that only starting material is present. The mixture was concentrated and treated with 3N HCl and ethanol (5 mL) then heated at 60° C. for 4 hours. The yellow solution was treated with saturated NaHCO$_3$ then extracted with 3×20 mL CH$_2$Cl$_2$. The combined organic layers were dried with MgSO$_4$, filtered and concentrated to give a yellow residue. This residue was subjected to flash chromatography on silica gel using 5% 2M NH$_3$ in MeOH/CH$_2$Cl$_2$ to give a light yellow solid. This compound was dissolved in CH$_2$Cl$_2$ (5 mL) and treated with 1 mL of a 1M HCl solution in Et$_2$O to form a precipitate. The slurry was concentrated to give a yellow solid (22 mg, 51.3%). An HPLC analysis indicated that the product is >99% pure. An HPLC analysis indicated that the product is >99% pure. $^1$H-NMR (CD$_3$OD) δ: 7.96-7.95 (d, J=4.5 Hz, 2H), 7.31 (pseudo t, J=4.2 Hz, 1H), 7.24 (br s, 1H), 7.17 (dd, J=1.5, 8.1 Hz, 1H), 7.00 (d, J=5.9 Hz, 1H), 3.17-3.10 (m, 2H), 2.85 (s, 6H), 2.91-2.83 (m, 2H) 2.67-2.60 (m, 1H), 1.91-1.56 (m, 4H).
MS (ESI): 357.2 (M+1). ESI-HRMS calculated for C$_{19}$H$_{24}$N$_4$SO (MH$^+$): 357.1743, Observed: 357.1744.

Example 11

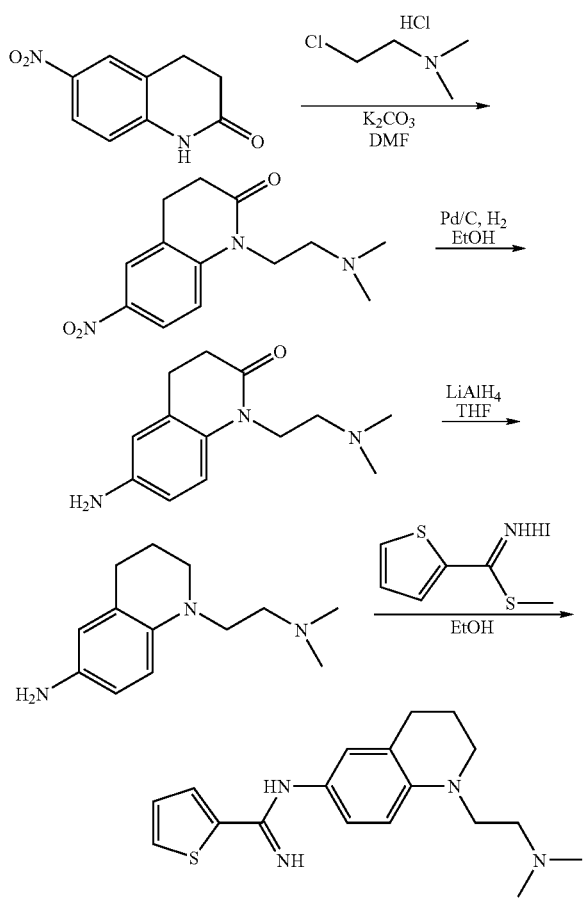

11

1-(2-(dimethylamino)ethyl)-6-nitro-3,4-dihydroquinolin-2(1H)-one

A suspension of 6-nitro-3,4-dihydroquinolin-2(1H)-one (1.5 g, 7.80 mmol), 2-chloro-N,N-dimethylethanamine hydrochloride (2.25 g, 15.60 mmol) and potassium carbonate (6.47 g, 46.80 mmol) in 25 mL DMF was stirred at room temperature for 3 days. After this time, the mixture was poured into 20 mL H$_2$O then extracted with 3×150 mL EtOAc. The combined organic fractions were washed with brine, dried over Na$_2$SO$_4$, filtered and concentrated. The residue was subjected to flash chromatography on silica gel using 5% 2M NH$_3$ in MeOH/CH$_2$Cl$_2$ to give a yellow viscous oil (1.5 g, 73.2%). $^1$H-NMR (CDCl$_3$) δ: 8.14 (dd, J=2.4, 9.0 Hz, 1H), 8.06 (d, J=2.4 Hz, 1H), 7.15 (d, J=9.0 Hz, 1H), 4.09 (t, J=7.5 Hz, 2H), 3.03-2.98 (m, 2H), 2.73-2.68 (m, 2H), 2.51 (t, J=7.5 Hz, 2H), 2.31 (s, 6H).

6-amino-1-(2-(dimethylamino)ethyl)-3,4-dihydro-quinolin-2(1H)-one

A suspension of 1-(2-(dimethylamino)ethyl)-6-nitro-3,4-dihydroquinolin-2(1H)-one (1.48 g, 5.62 mmol) and palladium on activated carbon (10%, 300 mg, 0.28 mmol) in 20 mL ethanol was stirred under a balloon of hydrogen overnight. The suspension was filtered through a pad of celite. The filter pad was rinsed with 50 mL ethanol and the filtrate was concentrated to give a viscous oil. The crude product was used without further purification. (1.3 g, 100%). $^1$H-NMR (CDCl$_3$) δ: 6.85 (d, J=8.7 Hz, 1H), 6.55 (dd, J=2.7, 8.7 Hz, 1H), 6.51 (d, J=2.7 Hz, 1H), 4.00 (t, J=7.5 Hz, 2H), 3.56 (br s, 2H), 2.80-2.75 (m, 2H), 2.60-2.55 (m, 2H), 2.47 (t, J=7.5 Hz, 2H), 2.31 (s, 6H).

1-(2-(dimethylamino)ethyl)-1,2,3,4-tetrahydroquino-lin-6-amine

A solution of 6-amino-1-(2-(dimethylamino)ethyl)-3,4-dihydroquinolin-2(1H)-one (1.3 g, 5.57 mmol) in 10 mL anhydrous THF was added dropwise to a cooled suspension of 1M LiAlH$_4$ in THF (22.3 mL, 22.3 mmol). The suspension was stirred at room temperature for 1 day. After this time, the mixture was cooled to 0° C. and treated with 5 mL 1N NaOH dropwise with rapid stirring. After stirring for 30 minutes, the suspension was treated with Na$_2$SO$_4$ and filtered. The filter cake was rinsed with 10% 2M NH$_3$ in MeOH/CH$_2$Cl$_2$ (100 mL total). The filtrate was concentrated and the dark residue was subjected to flash chromatography on silica gel using 5-10% 2M NH$_3$ in MeOH/CH$_2$Cl$_2$ to give a dark viscous oil (930 mg, 76.2%). $^1$H-NMR (CDCl$_3$) δ: 6.49 (brs, 2H), 6.40 (s, 1H), 3.34-3.30 (m, 2H), 3.30 (br s, 2H), 3.21 (t, J=5.7 Hz, 2H), 2.68 (t, J=5.7 Hz, 2H), 2.49-2.44 (m, 2H), 2.28 (s, 6H), 1.95-1.87 (m, 2H).
MS (ESI): 220.2 (M+1).

N-(1-(2-(dimethylamino)ethyl)-1,2,3,4-tetrahydro-quinolin-6-yl)thiophene-2-carboximidamide A solution of 1-(2-(dimethylamino)ethyl)-1,2,3,4-tetrahydroquinolin-6-amine (900 mg, 4.10 mmol) in 25 mL EtOH was treated with methyl thiophene-2-carbimidothioate hydroiodide (2.34 g, 1.43 mmol) and stirred overnight at room temperature. Argon was bubbled through the mixture for 20 minutes then it was partitioned between CH$_2$Cl$_2$ (100 mL) and saturated sodium bicarbonate (20 mL). The organic layer was separated and the aqueous layer was extracted with an additional 50 mL CH$_2$Cl$_2$. The combined organic layers were rinsed with water, dried over sodium sulfate, filtered and concentrated to give a dark oil which was subjected to flash chromatography on silica gel using 5% MeOH/CH$_2$CH$_2$ then 5% 2M NH$_3$ in MeOH/CH$_2$Cl$_2$ to give an orange solid. $^1$H-NMR (DMSO-d$_6$) δ: 7.66 (d, J=3.6 Hz, 1H), 7.55 (d, J=4.8 Hz, 1H), 7.08-7.05 (m, 1H), 6.57-6.48 (m, 3H), 6.25 (brs, 2H), 3.29-3.21 (m, 4H), 2.65 (t, J=6.3 Hz, 2H), 2.39 (t, J=6.3 Hz, 2H), 2.19 (s, 6H), 1.85-1.82 (m, 2H).
MS (ESI): 329.2 (M+1). ESI-HRMS calculated for C$_{18}$H$_{24}$N$_4$S (MH$^+$): 329.1794, Observed: 329.1804.

Example 12

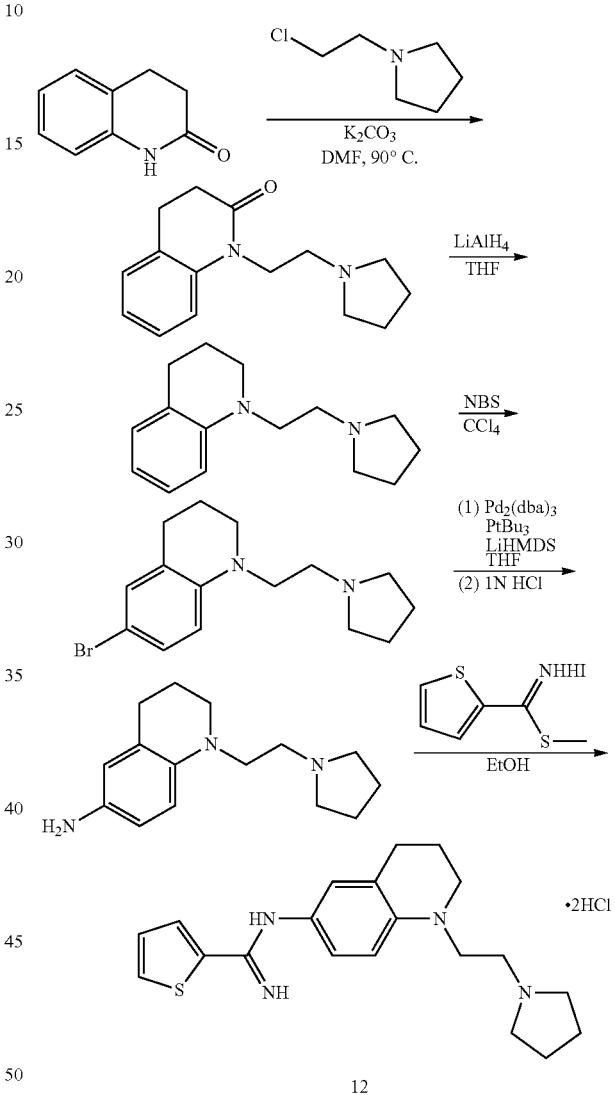

12

1-(2-(pyrrolidin-1-yl)ethyl)-3,4-dihydroquinolin-2 (1H)-one

A suspension of 3,4-dihydroquinolin-2(1H)-one (1.0 g, 6.79 mmol), 1-(2-chloroethyl)pyrrolidine hydrochloride (1.27 g, 7.47 mmol) and potassium carbonate (2.82 g, 20.37 mmol) in 10 mL DMF was stirred at room temperature overnight then heated at 95° C. for 1 day. After this time, the mixture was poured into 20 mL H$_2$O then extracted with 2×100 mL EtOAc. The combined organic fractions were washed with brine, dried over Na$_2$SO$_4$, filtered and concentrated. The residue was dried under reduced pressure for 18 hours then subjected to flash chromatography on silica gel using 5% MeOH/CH$_2$Cl$_2$ then 5% 2M NH$_3$ in MeOH/

CH₂Cl₂ to give a yellow viscous oil (800 mg, 48.2%). ¹H-NMR (CDCl₃) δ: 7.24-7.08 (m, 3H), 7.00 (m, 1H), 4.10 (t, J=7.8 Hz, 2H), 2.89 (psuedo t, J=6.7 Hz, 2H), 2.74-2.60 (m, 8H), 1.82-1.78 (m, 4H).

MS (ESI): 245.2 (M+1).

1-(2-(pyrrolidin-1-yl)ethyl)-1,2,3,4-tetrahydroquinoline

A solution of 1-(2-(pyrrolidin-1-yl)ethyl)-3,4-dihydroquinolin-2(1H)-one (700 mg, 2.87 mmol) in 12 mL anhydrous THF was treated with LiAlH₄ (218 mg, 5.73 mmol) portionwise. The suspension was stirred at room temperature for 1 day. After this time, the mixture was cooled to 0° C. and treated with 2 mL 1N NaOH dropwise with rapid stirring. After stirring for 30 minutes, the suspension was treated with Na₂SO₄ and filtered. The filter cake was rinsed with CH₂Cl₂ (150 mL total). The filtrate was concentrated and the residue was subjected to flash chromatography on silica gel using 5% 2M NH₃ in MeOH/CH₂Cl₂ to give a light yellow oil (563 mg, 85.1%). ¹H-NMR (CDCl₃) δ: 7.06-7.01 (m, 1H), 6.93 (d, J=7.2 Hz, 1H), 6.63-6.52 (m, 2H), 3.44 (t, J=7.5 Hz, 2H), 3.31 (t, J=5.7 Hz, 2H), 2.76-2.56 (m, 8H), 1.97-1.90 (m, 2H), 1.83-1.78 (m, 4H).

MS (ESI): 231.2 (M+1, 100%).

6-bromo-1-(2-(pyrrolidin-1-yl)ethyl)-1,2,3,4-tetrahydroquinoline

A solution of 1-(2-(pyrrolidin-1-yl)ethyl)-1,2,3,4-tetrahydroquinoline (490 mg, 2.13 mmol) in 10 mL of carbontetrachloride was cooled to 0° C. then treated with NBS (378 mg, 2.13 mmol) portionwise. The resulting suspension was stirred at 0° C. for 3.5 hours. The mixture was filtered through celite and the filter pad was rinsed with 3×20 mL hexanes. The filtrate was concentrated to give a light brown residue which was subjected to flash chromatography on silica gel using 5% 2M NH₃ in MeOH/CH₂Cl₂ to give a light brown oil (380 mg, 57.7%). ¹H-NMR (CDCl₃) δ: 7.09 (dd, J=2.4, 8.7 Hz, 1H), 7.02 (d, J=2.4 Hz, 1H), 6.46 (d, J=8.7 Hz, 1H), 3.42 (t, J=7.8 Hz, 2H), 3.29 (t, J=5.7 Hz, 2H), 2.76-2.55 (m, 8H), 1.95-1.89 (m, 2H), 1.82-1.77 (m, 4H).

MS (ESI): 309.1 and 311.1 (M+1, 100%).

1-(2-(pyrrolidin-1-yl)ethyl)-1,2,3,4-tetrahydroquinolin-6-amine

A solution of 6-bromo-1-(2-(pyrrolidin-1-yl)ethyl)-1,2,3,4-tetrahydroquinoline (355 mg, 1.15 mmol) and Pd₂(dba)₃ (52 mg, 0.12 mmol) in 10 mL anhydrous THF was treated with lithium hexamethyldisilizane (2.3 mL of a 1 M solution in THF, 2.3 mmol) followed by PtBu₃ (700 µL of a 10% wt in hexanes solution, 0.23 mmol). The resulting dark brown suspension was heated at 90° C. for 2 hours. The mixture was cooled to room temperature and treated with 7 ml of a 1N HCl solution then stirred at room temperature for 15 minutes. The mixture was partitioned between CH₂Cl₂ (100 mL) and 1N NaOH (20 mL). The organic layer was separated and the aqueous layer was extracted once more with 100 mL CH₂Cl₂. The combined organic fractions were rinsed with brine, dried over Na₂SO₄, treated with ~500 mg activated charcoal, filtered and concentrated to give a dark brown residue. This residue was subjected to flash chromatography on silica gel using 5% MeOH/CH₂Cl₂ then 5-10% 2M NH₃ in MeOH/CH₂Cl₂ to give a viscous dark brown residue (180 mg, 63.8%). ¹H-NMR (CDCl₃) δ: 6.53-6.49 (m, 2H), 6.40 (br s, 1H), 3.37 (t, J=7.5 Hz, 2H), 3.21 (br s, 2H), 3.20 (t, J=5.4 Hz, 2H), 2.70-2.66 (m, 4H), 2.63-2.55 (m, 4H), 1.95-1.86 (m, 2H), 1.81-1.77 (m, 4H).

MS (ESI): 246.2 (M+1).

N-(1-(2-(pyrrolidin-1-yl)ethyl)-1,2,3,4-tetrahydroquinolin-6-yl)thiophene-2-carboximidamide dihydrochloride A solution of 1-(2-(pyrrolidin-1-yl)ethyl)-1,2,3,4-tetrahydroquinolin-6-amine (175 mg, 0.71 mmol) in 10 mL EtOH was treated with methyl thiophene-2-carbimidothioate hydroiodide (407 mg, 1.43 mmol) and stirred overnight at room temperature. Argon was bubbled through the mixture for 20 minutes then it was partitioned between CH₂Cl₂ (100 mL) and saturated sodium bicarbonate (20 mL). The aqueous layer was extracted with an additional 50 mL CH₂Cl₂. The combined organic layers were rinsed with brine, dried over sodium sulfate and concentrated to give a dark oil which was subjected to flash chromatography on silica gel using 5% MeOH/CH₂Cl₂ then 5-10% 2M NH₃ in MeOH/CH₂Cl₂ to give a dark brown residue. This compound (185 mg) was dissolved in CH2Cl2 (5 mL) and treated with 2 mL of a 1M HCl solution in Et2O to form a precipitate. The suspension was diluted with hexanes (15 mL) and the solid was filtered. The solid was hygroscopic, so it was dissolved in methanol (10 mL), concentrated and dried under reduced pressure. A greenish yellow solid 12 was obtained (230 mg, 75.9%). An HPLC analysis indicated that the product is >99% pure. ¹H-NMR (CD₃OD) δ: 8.03-8.00 (m, 2H), 7.36-7.33 (m, 1H), 7.10 (dd, J=2.7, 8.7 Hz, 1H), 7.01 (d, J=2.7 Hz, 1H), 6.89 (d, J=8.7 Hz, 1H), 3.78-3.71 (m, 4H), 3.4-3.39 (m, 4H), 3.21-3.13 (m, 2H), 2.81 (t, J=6.3 Hz, 2H), 2.20-1.96 (m, 6H).

MS (ESI): 355.2 (M+1). ESI-HRMS calculated for C₂₀H₂₇N₄S₁ (MH⁺): 355.1950, Observed: 355.1945.

Example 13

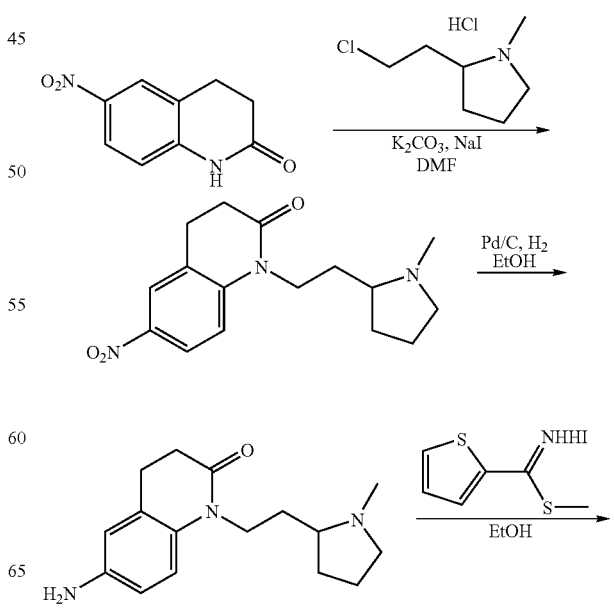

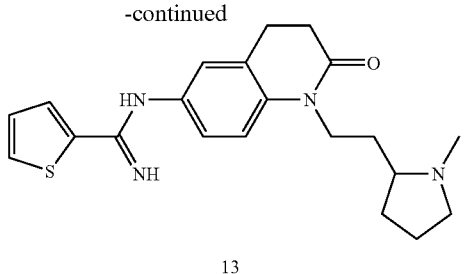

13

1-(2-(1-methylpyrrolidin-2-yl)ethyl)-6-nitro-3,4-dihydroquinolin-2(1H)-one

A suspension of 6-nitro-3,4-dihydroquinolin-2(1H)-one (2.0 g, 10.4 mmol), 2-(2-chloroethyl)-1-methylpyrrolidine hydrochloride (3.83 g, 20.8 mmol), sodium iodide (779 mg, 5.20 mmol) and potassium carbonate (8.63 g, 62.4 mmol) in dimethylformamide (15 mL) was stirred at room temperature overnight. After this time, the mixture was diluted with water (15 mL) then extracted with ethyl acetate (3×75 mL). The combined organic fractions were washed with brine, dried over $Na_2SO_4$, filtered and concentrated. The residue was subjected to flash chromatography on silica gel using 5% 2M $NH_3$ in MeOH/$CH_2Cl_2$ to give an orange oil which solidified upon drying under reduced pressure (2.32 g, 73.7%). $^1$H-NMR ($CDCl_3$) δ: 8.13 (dd, J=2.7, 9 Hz, 1H), 8.05 (d, J=2.4 Hz, 1H), 7.11 (d, J=9.0 Hz, 1H), 4.15-4.05 (m, 1H), 3.97-3.87 (m, 1H), 3.05-3.01 (m, 4H), 2.72-2.70 (m, 2H), 2.28 (s, 3H), 2.17-1.60 (m, 7H).
MS (EI): 303 (M+).

6-amino-1-(2-(1-methylpyrrolidin-2-yl)ethyl)-3,4-dihydroquinolin-2(1H)-one

A suspension of 1-(2-(1-methylpyrrolidin-2-yl)ethyl)-6-nitro-3,4-dihydroquinolin-2(1H)-one (2.25 g, 7.42 mmol) and palladium on activated carbon (10%, 100 mg, 0.09 mmol) in 50 mL ethanol was stirred under a balloon of hydrogen for 2 days. The suspension was filtered through a pad of celite. The filter pad was rinsed with 50 mL ethanol and the filtrate was concentrated to give a viscous oil. The crude product was subjected to Biotage flash chromatography on silica gel using 0-5% 2M $NH_3$ in MeOH/$CH_2Cl_2$ to give a yellow foam (1.48 g, 72.9%). $^1$H-NMR ($CDCl_3$) δ: 6.82 (d, J=8.4 Hz, 1H), 6.55 (dd, J=3.0, 8.4 Hz, 1H), 6.52 (d, J=3.0 Hz, 1H), 4.09-3.99 (m, 1H), 3.86-3.76 (m, 1H), 3.54 (br s, 2H), 3.04-3.01 (m, 1H), 2.81-2.76 (m, 2H), 2.61-2.56 (m, 2H), 2.29 (s, 3H), 2.17-1.60 (m, 8H).
MS (ESI): 274.2 (M+1, 100%).

N-(1-(2-(1-methylpyrrolidin-2-yl)ethyl)-2-oxo-1,2,3,4-tetrahydroquinolin-6-yl)thiophene-2-carboximidamide A solution of 6-amino-1-(2-(1-methylpyrrolidin-2-yl)ethyl)-3,4-dihydroquinolin-2(1H)-one (1.15 g, 4.21 mmol) in absolute ethanol (25 mL) was treated with methyl thiophene-2-carbimidothioate hydroiodide (2.40 g, 8.42 mmol) and stirred at room temperature for 18 hours. The reaction was diluted with diethyl ether (150 mL) and the precipitate collected by vacuum filtration. The precipitate was washed with ether (50 mL). The yellow solid was dissolved in water (50 mL) and transferred to a separatory funnel. The reaction was treated with 1N NaOH (10 mL) and extracted with ethyl acetate (3×15 mL). The combined organic layers were washed with brine, dried over sodium sulfate, filtered and concentrated to give a yellow oil which was subjected to flash chromatography on silica gel using 0-5% 2M $NH_3$ in MeOH/$CH_2Cl_2$ to give a yellow foam. Yield: 1.11 g of yellow foam (69%). $^1$H-NMR (DMSO-$d_6$) δ: 7.73 (d, J=3.0 Hz, 1H), 7.60 (d, J=5.4 Hz, 1H), 7.10-7.02 (m, 2H), 6.72-6.75 (m, 2H), 6.45 (br s, 2H), 3.91-3.80 (m, 2H), 2.96-2.90 (m, 1H), 2.82-2.78 (m, 2H), 2.19 (s, 3H), 2.08-1.80 (m, 6H), 1.66-1.49 (m, 4H).
MS (ESI): 383.2 (M+1). ESI-HRMS calculated for $C_{21}H_{27}N_4OS$ (MH$^+$): 383.1900, Observed: 383.1902.

Example 14

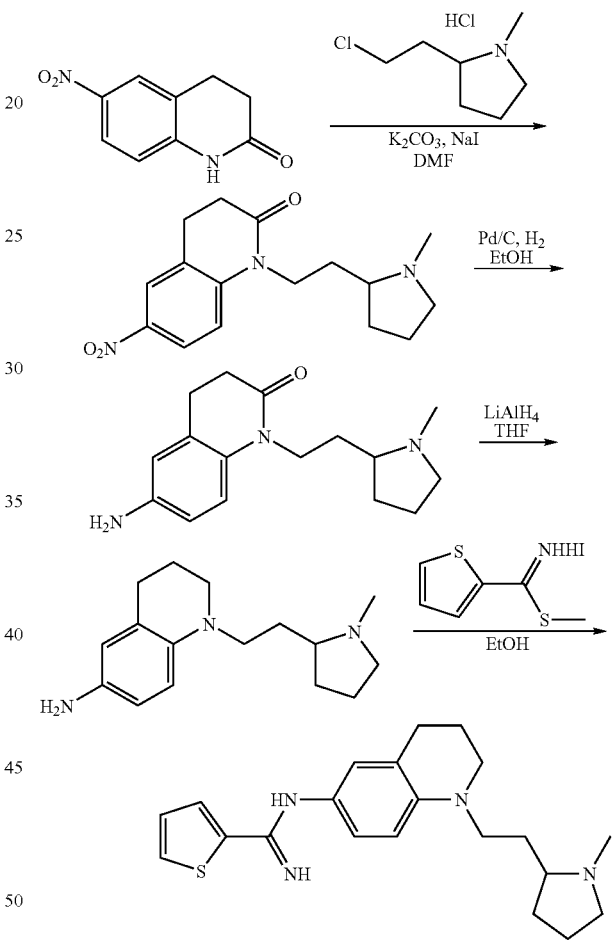

14

1-(2-(1-methylpyrrolidin-2-yl)ethyl)-6-nitro-3,4-dihydroquinolin-2(1H)-one

A suspension of 6-nitro-3,4-dihydroquinolin-2(1H)-one (2.0 g, 10.4 mmol), 2-(2-chloroethyl)-1-methylpyrrolidine hydrochloride (3.83 g, 20.8 mmol), sodium iodide (779 mg, 5.20 mmol) and potassium carbonate (8.63 g, 62.4 mmol) in 15 mL DMF was stirred at room temperature overnight. After this time, the mixture was poured into 50 mL $H_2O$ then extracted with 2×100 mL of EtOAc. The combined organic fractions were washed with brine, dried over $Na_2SO_4$, filtered and concentrated. The residue was dried under reduced pressure for 18 hours then subjected to flash chromatography on silica gel using 5% MeOH/CH$_2$Cl$_2$ then 5% 2M NH$_3$ in MeOH/CH$_2$Cl$_2$ to give an orange oil which solidified upon drying under reduced pressure (2.32 g, 73.7%). $^1$H-NMR (CDCl$_3$) δ: 8.13 (dd, J=2.7, 9 Hz, 1H), 8.05 (d, J=2.4 Hz, 1H), 7.11 (d, J=9.0 Hz, 1H), 4.15-4.05 (m, 1H), 3.97-3.87 (m, 1H), 3.05-3.01 (m, 4H), 2.72-2.70 (m, 2H), 2.28 (s, 3H), 2.17-1.60 (m, 7H).

MS (EI): 303 (M+).

6-amino-1-(2-(1-methylpyrrolidin-2-yl)ethyl)-3,4-dihydroquinolin-2(1H)-one

A suspension of 1-(2-(1-methylpyrrolidin-2-yl)ethyl)-6-nitro-3,4-dihydroquinolin-2(1H)-one (2.25 g, 7.42 mmol) and palladium on activated carbon (10%, 100 mg, 0.09 mmol) in 50 mL ethanol was stirred under a balloon of hydrogen for 2 days. The suspension was filtered through a pad of celite. The filter pad was rinsed with 50 mL ethanol and the filtrate was concentrated to give a viscous oil. The crude product was subjected to Biotage flash chromatography on silica gel using 0-5% 2M NH$_3$ in MeOH/CH$_2$Cl$_2$ to give a yellow foam (1.48 g, 72.9%). $^1$H-NMR (CDCl$_3$) δ: 6.82 (d, J=8.4 Hz, 1H), 6.55 (dd, J=3.0, 8.4 Hz, 1H), 6.52 (d, J=3.0 Hz, 1H), 4.09-3.99 (m, 1H), 3.86-3.76 (m, 1H), 3.54 (br s, 2H), 3.04-3.01 (m, 1H), 2.81-2.76 (m, 2H), 2.61-2.56 (m, 2H), 2.29 (s, 3H), 2.17-1.60 (m, 8H).

MS (ESI): 274.2 (M+1, 100%).

1-(2-(1-methylpyrrolidin-2-yl)ethyl)-1,2,3,4-tetrahydroquinolin-6-amine

A solution of 6-amino-1-(2-(1-methylpyrrolidin-2-yl)ethyl)-3,4-dihydroquinolin-2(1H)-one(1H)-one (350 mg, 1.28 mmol) in 5 mL anhydrous THF was added dropwise to a cooled suspension of 1M LiAlH$_4$ in THF (5.1 mL, 5.1 mmol). The suspension was stirred at room temperature for 1 day. After this time, the mixture was cooled to 0° C. and treated with 1 mL 1N NaOH dropwise with rapid stirring. After stirring for 30 minutes, the suspension was treated with Na$_2$SO$_4$, diluted with 20 mL 10% 2M NH$_3$ in MeOH/CH$_2$Cl$_2$ and filtered. The filter cake was rinsed with 50 mL 10% 2M NH$_3$ in MeOH/CH$_2$Cl$_2$. The filtrate was concentrated and the dark residue was subjected to flash chromatography on silica gel using 5-10% 2M NH$_3$ in MeOH/CH$_2$Cl$_2$ to give a dark viscous oil (172 mg, 52.0%). $^1$H-NMR (CDCl$_3$) δ 6.48 (brs, 2H), 6.41 (brs, 1H), 3.29-3.03 (m, 8H), 2.68 (t, J=6.6 Hz, 2H), 2.30 (s, 3H), 2.18-1.42 (m, 9H).

MS (ESI): 260.2 (M+1, 100%).

N-(1-(2-(1-methylpyrrolidin-2-yl)ethyl)-1,2,3,4-tetrahydroquinolin-6-yl)thiophene-2-carboximidamide A solution of 1-(2-(1-methylpyrrolidin-2-yl)ethyl)-1,2,3,4-tetrahydroquinolin-6-amine (160 mg, 0.61 mmol) in 10 mL EtOH was treated with methyl thiophene-2-carbimidothioate hydroiodide (353 mg, 1.24 mmol) and stirred at room temperature for 2 days. Argon was bubbled through the mixture for 30 minutes then it was partitioned between CH$_2$Cl$_2$ (100 mL) and saturated sodium carbonate (20 mL). The organic layer was separated and the aqueous layer was extracted with an additional 50 mL CH$_2$Cl$_2$. The combined organic layers were dried over sodium sulfate, filtered and concentrated to give a dark oil which was subjected to flash chromatography on silica gel using 2% MeOH/CH$_2$Cl$_2$ then 5-10% 2M NH$_3$ in MeOH/CH$_2$Cl$_2$ to give a dark yellow residue. 1H-NMR (DMSO-d$_6$) δ: 7.67 (d, J=3.9 Hz, 1H), 7.55 (d, J=3.9 Hz, 1H), 7.07 (dd, J=3.9, 5.4 Hz, 1H), 6.57-6.48 (m, 3H), 6.23 (br s, 2H), 3.30-3.17 (m, 4H), 2.97-2.90 (m, 1H), 2.66 (t, J=6.3 Hz, 2H), 2.21 (s, 3H), 2.05-1.37 (m, 10H).

MS (ESI): 369.2 (M+1). ESI-HRMS calculated for C$_{21}$H$_{29}$N$_4$S$_1$ (MH$^+$): 369.2107, Observed: 369.2126.

Example 15

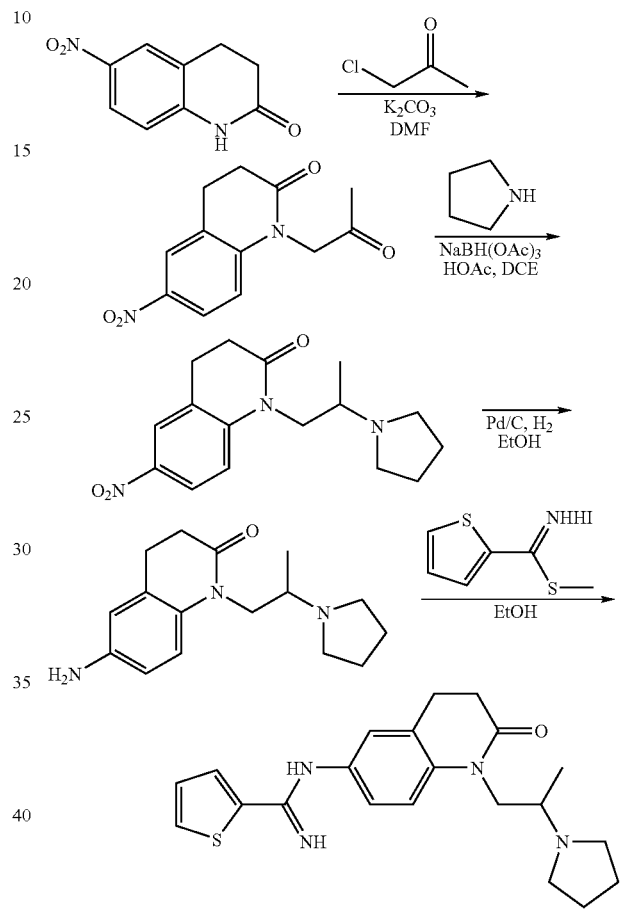

15

6-nitro-1-(2-oxopropyl)-3,4-dihydroquinolin-2(1H)-one

A suspension of 6-nitro-3,4-dihydroquinolin-2(1H)-one (950 mg, 4.94 mmol) and potassium carbonate (4.10 g, 29.64 mmol) in 12 mL DMF was treated with chloroacetone (787 μL, 9.89 mmol) and stirred at room temperature overnight. After this time, the mixture was cooled to 0° C. and treated with 50 mL H$_2$O under rapid stirring. A precipitate formed and it was filtered then washed with 50 mL H$_2$O. The solid was collected and dried under reduced pressure overnight (1.01 g, 82.1%). $^1$H-NMR (DMSO-d$_6$) δ: 8.17 (d, J=2.4 Hz, 1H), 8.05 (dd, J=2.4, 8.7 Hz, 1H), 7.05 (d, J=8.7 Hz, 1H), 3.33 (s, 2H), 3.05 (t, J=7.8 Hz, 2H), 2.66 (t, J=7.8 Hz, 2H), 2.24 (s, 3H). MS (EI): 248 (M+).

6-nitro-1-(2-(pyrrolidin-1-yl)propyl)-3,4-dihydroquinolin-2(1H)-one

A solution of 6-nitro-1-(2-oxopropyl)-3,4-dihydroquinolin-2(1H)-one (500 mg, 2.01 mmol) and pyrrolidine (333 μL, 4.03 mmol) in 10 mL 1,2-dichloroethane (DCE) was treated with acetic acid (228 µL, 4.03 mmol) followed by sodium triacetoxyborohydride (1.27 g, 6.03 mmol). The suspension was stirred at room temperature overnight then quenched with 10 mL 1N NaOH. The mixture was diluted with 15 mL H$_2$O then extracted with 2×100 mL CH$_2$Cl$_2$. The combined organic fractions were rinsed with 50 mL H$_2$O, dried over MgSO$_4$, filtered and concentrated to give a yellow residue which was subjected to flash chromatography on silica gel using 5% 2M NH$_3$ in MeOH/CH$_2$Cl$_2$. A yellow oil was obtained (595 mg, 97.5%). $^1$H-NMR (CDCl$_3$) δ: 8.13 (dd, J=2.7, 9.0 Hz, 1H), 8.07 (d, J=2.7 Hz, 1H), 7.21 (d, J=9.0 Hz, 1H), 4.21 (dd, J=8.7, 14.1 Hz, 1H), 4.02 (dd, J=5.4, 14.4 Hz, 1H), 3.00 (t, J=7.2 Hz, 2H), 2.91-2.62 (m, 7H), 1.92-1.90 (m, 4H), 1.00 (d, J=6.3 Hz, 3H).

MS (ESI): 304.2 (M+1, 100%).

6-amino-1-(2-(pyrrolidin-1-yl)propyl)-3,4-dihydro-quinolin-2(1H)-one

A suspension of 6-nitro-1-(2-(pyrrolidin-1-yl)propyl)-3,4-dihydroquinolin-2(1H)-one (585 mg, 1.93 mmol) and palladium on activated carbon (10%, 103 mg, 0.096 mmol) in 15 mL ethanol was stirred under a balloon of hydrogen overnight. The suspension was filtered through a pad of silica gel. The filter pad was rinsed with 20 mL of 2M NH$_3$ in methanol and the filtrate was concentrated to give a viscous oil. The crude product was used without further purification. (490 mg, 92.9%). $^1$H-NMR (CDCl$_3$) δ: 7.20 (d, J=8.7 Hz, 1H), 6.63 (dd, J=2.4, 8.7 Hz, 1H), 6.51 (d, J=2.4 Hz, 1H), 4.37 (d, J=7.2 Hz, 2H), 3.58 (brs, 2H), 2.82-2.77 (m, 2H), 2.63-2.58 (m, 2H), 2.1 (br s, 4H), 1.80-1.62 (br s, 5H), 1.30 (d, J=6.6 Hz, 3H).

MS (ESI): 274.2 (M+1, 100%).

N-(2-oxo-1-(2-(pyrrolidin-1-yl)propyl)-1,2,3,4-tetrahydroquinolin-6-yl)thiophene-2-carboximidamide A solution of 6-amino-1-(2-(pyrrolidin-1-yl)propyl)-3,4-dihydroquinolin-2(1H)-one (240 mg, 0.88 mmol) in 10 mL EtOH was treated with methyl thiophene-2-carbimidothioate hydroiodide (501 mg, 1.76 mmol) and stirred overnight at room temperature. The mixture was diluted with CH$_2$Cl$_2$ (10 mL) and argon was bubbled through the solution for 20 minutes. The solution was partitioned between CH$_2$Cl$_2$ (100 mL) and saturated sodium carbonate (20 mL). The organic layer was separated and the aqueous layer was extracted with an additional 50 mL CH$_2$Cl$_2$. The combined organic layers were dried over sodium sulfate, filtered and concentrated to give a yellow which was subjected to flash chromatography on silica gel using 2% MeOH/CH$_2$Cl$_2$ then 5-10% 2M NH$_3$ in MeOH/CH$_2$Cl$_2$. A yellow solid was obtained (200 mg, 59.4%). $^1$H-NMR (DMSO-d$_6$) δ: 7.71 (d, J=3.6 Hz, 1H), 7.57 (d, J=5.4 Hz, 1H), 7.08-7.06 (m, 2H), 6.72-6.71 (m, 2H), 6.41 (br s, 2H), 4.05 (dd, J=9.0, 13.8 Hz, 1H), 3.83 (dd, J=4.8, 13.8 Hz, 1H), 2.79-2.75 (m, 3H), 2.54-2.47 (m, 6H), 1.63 (br, 4H), 0.87 (d, J=6.3 Hz, 3H).

MS (ESI): 383.2 (M+1). ESI-HRMS calculated for C$_{21}$H$_{27}$N$_4$SO (MH$^+$): 383.1900, Observed: 355.1896.

Example 16

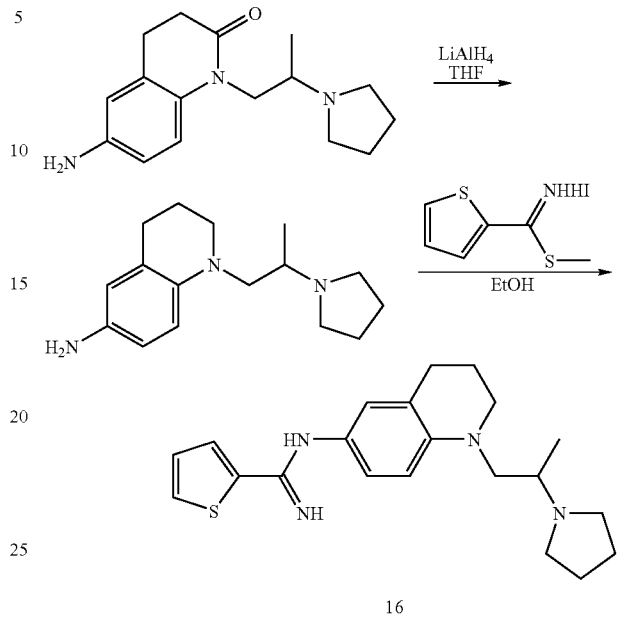

16

1-(2-(pyrrolidin-1-yl)propyl)-1,2,3,4-tetrahydro-quinolin-6-amine

A solution of 6-amino-1-(2-(pyrrolidin-1-yl)propyl)-3,4-dihydroquinolin-2(1H)-one (245 mg, 0.90 mmol) in 10 mL anhydrous THF was cooled to 0° C. and treated with dropwise addition of 1M LiAlH$_4$ in THF (2.7 mL, 2.7 mmol). The suspension was stirred at room temperature overnight. After this time, the mixture was cooled to 0° C. and treated with 1.5 mL 1N NaOH dropwise with rapid stirring. After stirring for 30 minutes, the suspension was diluted with 10 mL CH$_2$Cl$_2$ was treated with Na$_2$SO$_4$. The suspension was filtered and the solid was rinsed with 20 mL 5% 2M NH$_3$ in MeOH/CH$_2$Cl$_2$. The filtrate was concentrated and the dark residue was subjected to flash chromatography on silica gel using 5% 2M NH$_3$ in MeOH/CH$_2$Cl$_2$ to give a dark viscous oil (136 mg, 58.4%). $^1$H-NMR (CDCl$_3$) δ: 6.84 (br, 2H), 6.41 (br, 1H), 3.48 (dd, J=4.2, 14.4 Hz, 1H), 3.24-3.19 (m, 4H), 3.91 (dd, J=14.4, 4.2 Hz, 1H), 2.69-2.67 (m, 6H), 1.95-1.79 (m, 7H), 1.14 (d, J=6.6 Hz, 3H).

MS (ESI): 260.2 (M+1).

N-(1-(2-(pyrrolidin-1-yl)propyl)-1,2,3,4-tetrahydro-quinolin-6-yl)thiophene-2-carboximidamide A solution of 1-(2-(pyrrolidin-1-yl)propyl)-1,2,3,4-tetrahydroquinolin-6-amine (130 mg, 0.50 mmol) in 10 mL EtOH was treated with methyl thiophene-2-carbimidothioate hydroiodide (285 mg, 1.00 mmol) and stirred at room temperature for 3 days. Argon was bubbled through the solution for 20 minutes. The solution was partitioned between CH$_2$Cl$_2$ (100 mL) and saturated sodium carbonate (15 mL). The organic layer was separated and the aqueous layer was extracted with an additional 50 mL CH$_2$Cl$_2$. The combined organic layers were dried over sodium sulfate, filtered and concentrated to give a yellow residue which was subjected to flash chromatography on silica gel using 2.5% MeOH/CH$_2$Cl$_2$ then 5-10% 2M NH$_3$ in MeOH/CH$_2$Cl$_2$. A light orange solid was obtained (100 mg, 54.3%). $^1$H-NMR (DMSO-d$_6$) δ: 7.67 (d, J=3.6 Hz, 1H), 7.55 (d, J=4.2 Hz, 1H), 7.08-7.05 (m, 1H), 6.56-6.48 (m, 3H), 6.25 (br s, 2H), 3.44 (dd, J=4.5, 14.4 Hz, 1H), 3.33-3.25 (m, 2H), 2.95 (dd, J=8.7, 13.8 Hz, 1H), 2.72-2.58 (m, 7H), 1.86-1.82 (m, 2H), 1.67 (br, 4H), 1.03 (d, J=6.3 Hz, 3H).

MS (ESI): 369.2 (M+1). ESI-HRMS calculated for C$_{21}$H$_{29}$N$_4$S (MH$^+$): 369.2107, Observed: 369.2113.

Example 17

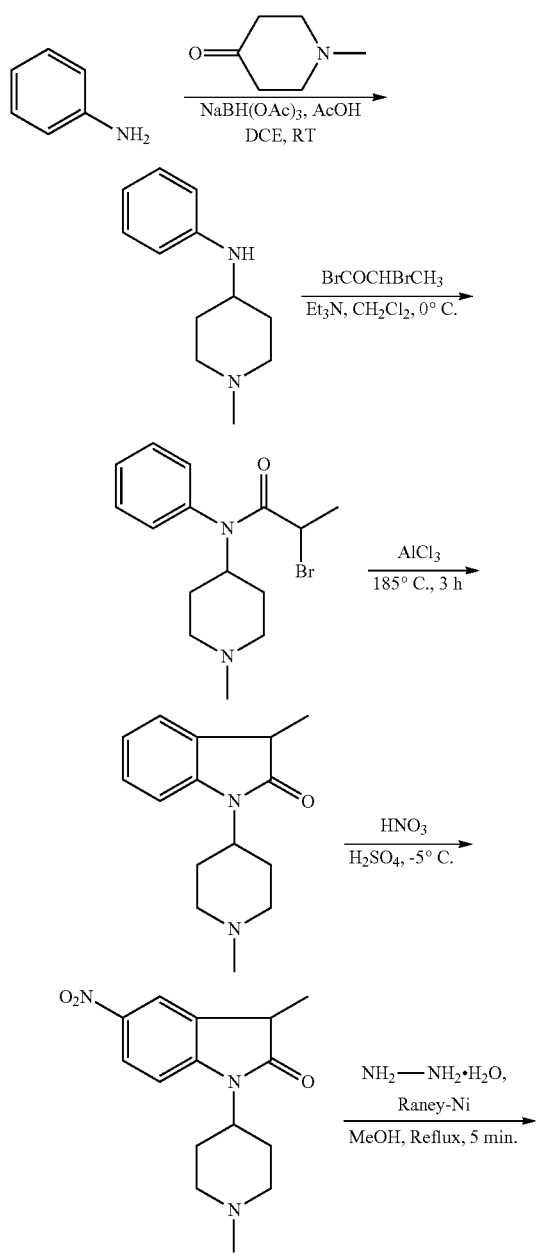

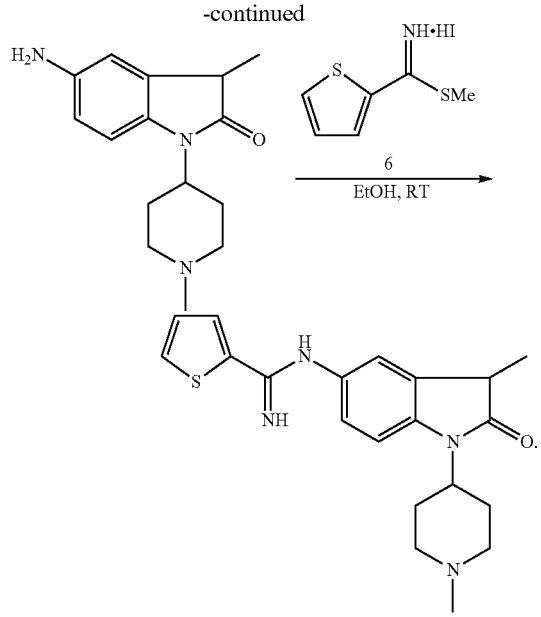

1-Methyl-N-phenylpiperidin-4-amine

A solution of aniline (2.0 g, 1.95 mL, 21.475 mmol), N-methyl-4-piperidone (2.64 mL, 21.475 mmol) and AcOH (1.21 mL, 21.475 mmol) in dry 1,2-dichloroethane (20 mL) was treated with NaBH(OAc)$_3$ (6.82 g, 32.213 mmol) at 0° C. The reaction was brought to room temperature and stirred for overnight (16 h). The reaction was basified with 1 N NaOH solution (40 mL) and product was extracted into CH$_2$Cl$_2$ (2×25 mL). The combined CH$_2$Cl$_2$ layer was washed with brine (15 mL) and dried (Na$_2$SO$_4$). Solvent was evaporated and crude was purified by column chromatography (2 M NH$_3$ in MeOH:CH$_2$Cl$_2$, 5:95) to obtain compound 1-methyl-N-phenylpiperidin-4-amine (4.0 g, 98%) as a solid. $^1$H NMR (DMSO-d$_6$) δ: 1.29-1.42 (m, 2H), 1.82-1.88 (m, 2H), 1.93-2.02 (m, 2H), 2.15 (s, 3H), 2.68-2.74 (m, 2H), 3.08-3.18 (m, 1H), 5.36 (d, 1H, J=8.1 Hz), 6.47 (t, 1H, J=7.2 Hz), 6.54 (d, 2H, J=7.8 Hz), 7.03 (t, 2H, J=7.2 Hz); ESI-MS (m/z, %) 191 (MH$^+$, 100).

2-Bromo-N-(1-methylpiperidin-4-yl)-N-phenylpropanamide

A solution of compound 1-methyl-N-phenylpiperidin-4-amine (1.0 g, 5.255 mmol) in dry CH$_2$Cl$_2$ (10 mL) was treated with Et$_3$N (2.19 mL, 15.766 mmol) followed by 2-bromopropionyl bromide (0.61 mL, 5.780 mmol) at 0° C. and stirred at same temperature for 1 h. The reaction was diluted with water (25 mL) and product was extracted into CH$_2$Cl$_2$ (2×25 mL). The combined CH$_2$Cl$_2$ layer was washed with brine (20 mL) and dried (Na$_2$SO$_4$). Solvent was evaporated and crude was purified by column chromatography (MeOH:CH$_2$Cl$_2$, 5:95) to obtain compound 2-Bromo-N-(1-methylpiperidin-4-yl)-N-phenylpropanamide (1.5 g, 88%) as a solid. $^1$H NMR (DMSO-d$_6$) δ: 1.09-1.33 (m, 2H), 1.59 (d, 3H, J=6.3 Hz), 1.66-1.74 (m, 2H), 1.89-1.98 (m, 2H), 2.09 (s, 3H), 2.68-2.74 (m, 2H), 4.01 (q, 1H), 4.28-4.36 (m, 1H), 7.26-7.30 (m, 2H), 7.46-7.50 (m, 3H); ESI-MS (m/z, %) 327 and 325 (MH$^+$, 100%).

3-Methyl-1-(1-methylpiperidin-4-yl)indolin-2-one

2-Bromo-N-(1-methylpiperidin-4-yl)-N-phenylpropanamide (0.31 g, 0.953 mmol) was treated with anhydrous $AlCl_3$ (0.5 g) and the resulting mixture was stirred at 185° C. for 2.5 h. The reaction was brought to room temperature, diluted with water (20 mL), then basified with 1 N NaOH solution (25 mL) and product was extracted into ethyl acetate (2×20 mL). The combined ethyl acetate layer was washed with brine (15 mL) and dried ($Na_2SO_4$). Solvent was evaporated and crude was purified by column chromatography ($MeOH:CH_2Cl_2$, 5:95) to obtain 3-methyl-1-(1-methylpiperidin-4-yl)indolin-2-one (0.19 g, 82%) a solid. $^1H$ NMR (DMSO-$d_6$) δ: 1.31 (d, 3H, J=7.5 Hz), 1.50-1.58 (m, 2H), 1.99 (t, 2H, J=11.7 Hz), 2.20 (s, 3H), 2.32-2.42 (m, 2H), 2.84-2.90 (m, 2H), 3.44 (q, 1H), 3.99-4.10 (m, 1H), 7.00 (t, 1H, J=7.2 Hz), 7.12 (d, 1H, J=7.8 Hz), 7.23 (t, 1H, J=7.8 Hz), 7.30 (d, 1H, J=7.5 Hz); ESI-MS (m/z, %) 245 (MH$^+$, 100).

3-Methyl-1-(1-methylpiperidin-4-yl)-5-nitroindolin-2-one

A solution of 3-methyl-1-(1-methylpiperidin-4-yl)indolin-2-one(0.18 g, 0.736 mmol) in con. $H_2SO_4$ (2 mL) was treated with fuming $HNO_3$ (0.034 mL, 0.736 mmol) at −5 to −10° C. (ice+salt) and resulting solution was stirred for 30 min. at this same temperature. The reaction was quenched with addition of crushed ice, and then basified with 1 N NaOH and product was extracted into $CH_2Cl_2$ (2×20 mL). The combined $CH_2Cl_2$ layer was washed with brine (10 mL) and dried ($Na_2SO_4$). The solvent was evaporated and crude was purified by column chromatography (2 M $NH_3$ in $MeOH:CH_2Cl_2$, 2.5:97.5) to obtain compound 3-methyl-1-(1-methylpiperidin-4-yl)-5-nitroindolin-2-one (0.13 g, 61%) as a solid. $^1H$ NMR (DMSO-$d_6$) δ: 1.39 (d, 3H, J=7.5 Hz), 1.55-1.62 (m, 2H), 2.01 (t, 2H, J=11.4 Hz), 2.20 (s, 3H), 2.31-2.39 (m, 2H), 2.87 (d, 2H, J=11.4 Hz), 3.63 (q, 1H), 4.06-4.16 (m, 1H), 7.39 (d, 1H, J=9.3 Hz), 8.18-8.22 (m, 2H); ESI-MS (m/z, %) 290 (MH$^+$, 100).

5-Amino-3-methyl-1-(1-methylpiperidin-4-yl)indolin-2-one

A solution of compound 3-methyl-1-(1-methylpiperidin-4-yl)-5-nitroindolin-2-one (0.1 g, 0.345 mmol) in dry methanol (3 mL) was treated with Ra—Ni (0.05 g of wet slurry) followed by hydrazine hydrate (0.1 mL, 3.456 mmol) at room temperature. The resulting mixture was refluxed for 2 min. in a pre-heated oil bath and brought to room temperature. The reaction was filtered through celite bed and washed with methanol (3×10 mL). The combined methanol layer was evaporated and crude was purified by column chromatography (2 M $NH_3$ in $MeOH:CH_2Cl_2$, 5:95) to obtain compound 5-amino-3-methyl-1-(1-methylpiperidin-4-yl)indolin-2-one (0.085 g, 96%) as a syrup. $^1H$ NMR (DMSO-$d_6$) δ: 1.24 (d, 3H, J=7.8 Hz), 1.42-1.54 (m, 2H), 1.96 (t, 2H, J=10.2 Hz), 2.18 (s, 3H), 2.26-2.34 (m, 2H), 2.85 (d, 2H, J=11.1 Hz), 3.25-3.30 (m, 1H), 3.91-4.02 (m, 1H), 4.75 (s, 2H), 6.43 (dd, 1H, J=2.1, 8.4 Hz), 6.56 (d, 1H, J=1.5 Hz), 6.79 (d, 1H, J=8.4 Hz); ESI-MS (m/z, %) 260 (MH$^+$, 100).

N-(3-Methyl-1-(1-methylpiperidin-4-yl)-2-oxoindolin-5-yl)thiophene-2-carboximidamide A solution of 5-amino-3-methyl-1-(1-methylpiperidin-4-yl)indolin-2-one (0.075 g, 0.289 mmol) in dry ethanol (3 mL) was treated with compound 6 (0.16 g, 0.578 mmol) at room temperature and stirred for over night (18 h). The reaction was diluted with sat. $NaHCO_3$ solution (20 mL) and product was extracted into $CH_2Cl_2$ (2×15 mL). The combined $CH_2Cl_2$ layer was washed with brine (10 mL) and dried ($Na_2SO_4$). Solvent was evaporated and crude was purified by column chromatography (2 M $NH_3$ in $MeOH:CH_2Cl_2$, 5:95) to obtain compound 17 (0.095 g, 90%) as a solid. $^1H$ NMR (DMSO-$d_6$) δ; 1.32 (d, 3H, J=7.8 Hz), 1.50-1.60 (m, 2H), 2.00 (t, 2H, J=11.4 Hz), 2.20 (s, 3H), 2.31-2.42 (m, 2H), 2.88 (d, 2H, J=11.1 Hz), 3.36 (q, 1H), 4.01-4.10 (m, 1H), 6.41 (brs, 2H), 6.73 (d, 1H, J=8.1 Hz), 6.85 (s, 1H), 7.05-7.10 (m, 2H), 7.59 (d, 1H, J=5.1 Hz), 7.71 (d, 1H, J=3.3 Hz); ESI-MS (m/z, %) 369 (MH$^+$, 40), 272 (67%), 185 (100), 176 (30); ESI-HRMS calculated for $C_{20}H_{25}N_4OS$ (MH$^+$), calculated: 369.1743; observed: 369.1759.

Example 18

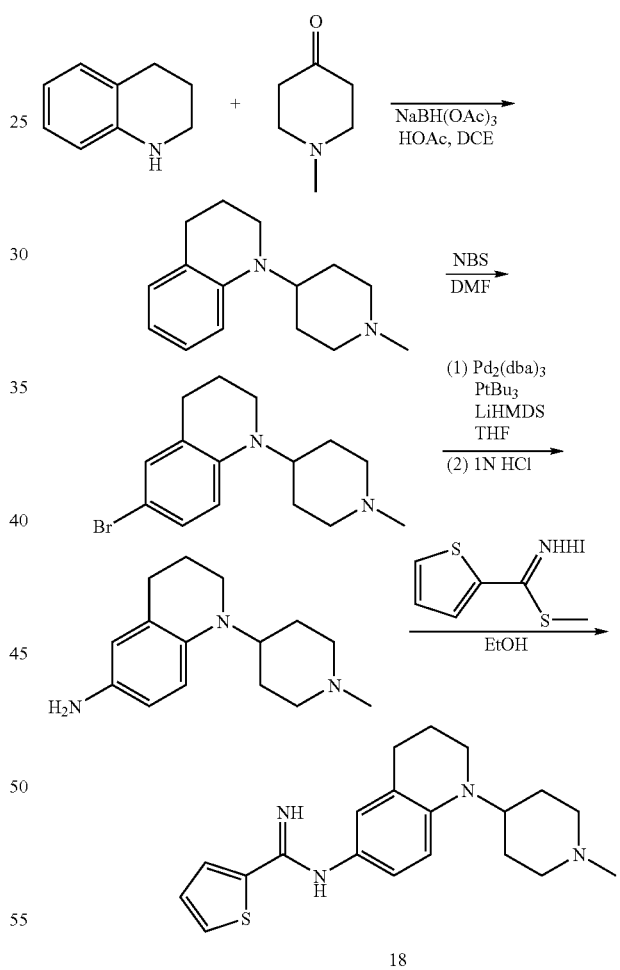

18

1-(1-methylpiperidin-4-yl)-1,2,3,4-tetrahydroquinoline

A solution of 1,2,3,4-tetrahydroquinoline (1.0 mL, 7.94 mmol) in 20 mL 1,2-dichloroethane was treated with 1-methylpiperidin-4-one (2.76 mL, 23.8 mmol) followed by sodium triacetoxyborohydride (8.4 g, 39.7 mmol) then acetic acid (2.25 mL). The suspension was stirred at room temperature for 1 day. After this time, the mixture was cooled to 0° C., quenched with 5 mL 1N NaOH and stirred for 20 minutes. The suspension was extracted with 100 mL $CH_2Cl_2$. The organic layer was dried over $MgSO_4$, filtered and concentrated to give a light residue which was subjected to flash chromatography on silica gel using 5% $MeOH/CH_2Cl_2$ then 5% 2M $NH_3$ in $MeOH/CH_2Cl_2$. A yellow oil was obtained (440 mg, 24.1%). $^1$H-NMR ($CDCl_3$) δ: 7.07-7.02 (m, 1H), 6.95 (d, J=7.5 Hz, 1H), 6.65 (d, J=8.4 Hz, 1H), 6.55 (pseudo t, J=7.8 Hz, 1H), 3.65-3.55 (m, 1H), 3.20 (t, J=5.7 Hz, 2H), 2.99-2.95 (m, 2H), 2.73 (t, J=6.0 Hz, 2H), 2.31 (s, 3H), 2.11-2.05 (m, 2H), 1.93-1.73 (m, 6H).

MS (ESI): 231.2 (M+1, 100%).

6-bromo-1-(1-methylpiperidin-4-yl)-1,2,3,4-tetrahydroquinoline

A solution of 1-(1-methylpiperidin-4-yl)-1,2,3,4-tetrahydroquinoline (500 mg, 2.17 mmol) in 7 mL of DMF was cooled to 0° C. then treated dropwise with NBS (386 mg, 2.17 mmol) in 7 mL DMF. The reaction was stirred at 0° C. for 2 hours then treated with 30 mL $H_2O$. The suspension was extracted with 100 mL EtOAc. The organic layer was dried over $MgSO_4$, filtered and concentrated to give a dark residue, which was filtered through a short plug of silica gel using 5%, 2M $NH_3$ in $MeOH/CH_2Cl_2$ (100 mL). The filtrate was concentrated and subjected to flash chromatography on silica gel using 5% $MeOH/CH_2Cl_2$ then 5% 2M $NH_3$ in $MeOH/CH_2Cl_2$. A light yellow oil was obtained (490 mg, 73.0%). $^1$H-NMR ($CDCl_3$) δ: 7.10 (dd, J=2.1, 10.8 Hz), 7.04-7.03 (m, 1H), 6.50 (d, J=9.0 Hz, 1H), 3.57-3.47 (m, 1H), 3.18 (t, J=5.7 Hz, 2H), 2.98-2.94 (m, 2H), 2.68 (t, J=6.0 Hz, 2H), 2.31 (s, 3H), 2.10-2.02 (m, 2H), 1.91-1.69 (m, 6H).

MS (ESI): 309.1 and 311.1 (M+1, 100%).

1-(1-methylpiperidin-4-yl)-1,2,3,4-tetrahydroquinolin-6-amine

A solution of 6-bromo-1-(1-methylpiperidin-4-yl)-1,2,3,4-tetrahydroquinoline (425 mg, 1.37 mmol) and $Pd_2(dba)_3$ (63 mg, 0.07 mmol) in 10 mL anhydrous THF was treated with lithium hexamethyldisilizane (2.8 mL of a 1 M solution in THF, 2.8 mmol) followed by $PtBu_3$ (830 μL of a 10% wt in hexanes solution, 0.27 mmol). The resulting dark brown suspension was heated at 100° C. for 2 hours. The mixture was cooled to room temperature and treated with 7 ml of a 1N HCl solution then stirred at room temperature for 15 minutes. The mixture was partitioned between $CH_2Cl_2$ (100 mL) and 1N NaOH (20 mL). The organic layer was separated and the aqueous layer was extracted once more with 100 mL $CH_2Cl_2$. The combined organic fractions were rinsed with brine, dried over $Na_2SO_4$, treated with ~500 mg activated charcoal, filtered and concentrated to give a dark brown residue. This residue was subjected to flash chromatography on silica gel using 5% $MeOH/CH_2Cl_2$ then 5-10% 2M $NH_3$ in $MeOH/CH_2Cl_2$ to give a viscous dark brown residue (163 mg, 48.5%). $^1$H-NMR ($CDCl_3$) δ: 6.54 (d, J=8.7 Hz, 1H), 6.49 (dd, J=2.7, 8.7 Hz, 1H), 6.42-6.41 (m, 1H), 3.54-3.44 (m, 1H), 3.20 (brs, 2H), 3.11 (t, J=5.4 Hz, 2H), 2.97-2.93 (m, 2H), 2.66 (t, J=6.0 Hz, 2H), 2.30 (s, 3H), 2.08-2.01 (m, 2H), 1.91-1.71 (m, 6H).

MS (ESI): 246.2 (M+1, 100%).

N-(1-(1-methylpiperidin-4-yl)-1,2,3,4-tetrahydroquinolin-6-yl)thiophene-2-carboximidamide A solution of 1-(1-methylpiperidin-4-yl)-1,2,3,4-tetrahydroquinolin-6-amine (150 mg, 0.61 mmol) in 10 mL EtOH was treated with methyl thiophene-2-carbimidothioate hydroiodide (349 mg, 1.22 mmol) and stirred overnight at room temperature. Argon was bubbled through the mixture for 20 minutes then it was partitioned between $CH_2Cl_2$ (100 mL) and saturated sodium carbonate (20 mL). The aqueous layer was extracted with an additional 50 mL $CH_2Cl_2$. The combined organic layers were dried over sodium sulfate and concentrated to give a dark oil which was subjected to flash chromatography on silica gel using 5% $MeOH/CH_2Cl_2$ then 5-10% 2M $NH_3$ in $MeOH/CH_2Cl_2$ to give 18 as a brown solid. $^1$H-NMR (DMSO-$d_6$) δ: 7.67 (d, J=3.6 Hz, 1H), 7.54 (d, J=5.4 Hz, 1H), 7.06 (pseudo t, J=4.2 Hz, 1H), 6.63-6.48 (m, 3H), 6.21 (br s, 2H), 3.54-3.47 (m, 1H), 3.11 (t, J=5.7 Hz, 2H), 2.86-2.82 (m, 2H), 2.63 (t, J=6.0 Hz, 2H), 2.17 (s, 3H), 2.03-1.96 (m, 2H), 1.84-1.57 (m, 6H).

MS (ESI): 355.2 (M+1, 100%). ESI-HRMS calculated for $C_{20}H_{26}N_4S$ (MH$^+$): 355.1950, Observed: 355.1938.

Example 19a nNOS (Human), eNOS (Human) and iNOS (Human) Enzyme Assay

Recombinant human inducible NOS (iNOS) may be produced in Baculovirus-infected Sf9 cells (ALEXIS). In a radiometric method, NO synthase activity is determined by measuring the conversion of [$^3$H]L-arginine to [$^3$H]L-citrulline. To measure iNOS, 10 μL of enzyme is added to 100 μL of 100 mM HEPES, pH=7,4, containing 1 mM $CaCl_2$, 1 mM EDTA, 1 mM dithiothreitol, 1 μM FMN, 1 μM FAD, 10 μM tetrahydrobiopterin, 120 μM NADPH, and 100 nM CaM.

To measure enzyme inhibition, a 15 μL solution of a test substance is added to the enzyme assay solution, followed by a pre-incubation time of 15 min at RT. The reaction is initiated by addition of 20 μL-arginine containing 0.25 μCi of [$^3$H] arginine/mL and 24 μM L-arginine. The total volume of the reaction mixture is 150 μL in every well. The reactions are carried out at 37° C. for 45 min. The reaction is stopped by adding 20 μL of ice-cold buffer containing 100 mM HEPES, 3 mM EGTA, 3 mM EDTA, pH=5.5. [$^3$H]L-citrulline is separated by DOWEX (ion-exchange resin DOWEX 50 W X 8-400, SIGMA) and the DOWEX is removed by spinning at 12,000 g for 10 min in the centrifuge. An 70 μL aliquot of the supernatant is added to 100 μL of scintillation fluid and the samples are counted in a liquid scintillation counter (1450 Microbeta Jet, Wallac). Specific NOS activity is reported as the difference between the activity recovered from the test solution and that observed in a control sample containing 240 mM of the inhibitor L-NMMA. All assays are performed at least in duplicate. Standard deviations are 10% or less. These results would show the selectivity of the compounds of the invention for nNOS inhibition. Results for exemplary compounds of the invention are also shown in Table 3 and Table 4. Human nNOS and eNOS Protocol:

| Reagents and Materials | |
|---|---|
| Enzymes: | Nitric oxide synthase (neuronal, human recombinant) nNOS I, Cat. No. ALX-201-068, Axxora LLC, CA 92121, USA Nitric oxide synthase (endothelial, human recombinant) eNOS III, Cat. No. ALX-201-070, Axxora LLC |

-continued

| Reagents and Materials | |
|---|---|
| L-NMMA | $N^G$-monomethyl-L-arginine 1/04/05, Cat # A17933, Batch # 04-11-9002, Novabiochem |
| L-NAME | $N^G$-Nitro-L-arginine methyl ester Cat # N5751, Aldrich |
| 2× Reaction Buffer: | 50 mM Tris-HCl (pH 7.4), Cat. No. 93313, Sigma-Aldrich Co. |
| | 6 µM tetrahydrobiopterin (BH$_4$), Cat. No. T4425, Sigma |
| | 2 µM flavin adenine dinucleotide (FAD), Cat. No. F6625, Sigma |
| | 2 µM flavin adenine mononucleotide (FMN), Cat. No. F8399, Sigma |
| Stop Buffer: | 50 mM N-2-hydroxyethylpiperazine-N'-2-ethanesulfonic acid |
| | (HEPES) (pH 5.5), H7523, Sigma and 5 mM Ethylene diamine tetra acetic acid (EDTA), Cat. No. EDS, Sigma |
| NADPH: | 10 mM freshly prepared on day of assay, Cat. No. N7505, Sigma |
| Calcium Chloride: | 6 mM, Cat. No. 21107, Sigma |
| Calmodulin: | 1 mM, Cat. No. P2277, Sigma |
| [$^3$H]-L-Arginine: | 1 µCi/reaction, 40-70 Ci/mmol, Cat. No. TRK-698, Amersham Biosciences |
| L-Arginine: | 2.5 µM (final assay concentration), Cat. No. A5131, Sigma |
| Equilibrated Resin: | AG-50W X8 Resin in HEPES buffer (pH 5.5), Cat. No. 1421441, Bio-Rad Laboratories Ltd. |
| Spin Cups & Holder: | Cat. No. C8163, Fisher Scientific |
| Liquid Scintillation Counter: | Tri-Carb 2000CA/LL, Canberra Packard Canada. |
| Liquid Scintillation Fluid: | Cat. No. 6012239, Ultima Gold, Perkin-Elmer Life and Analytical Sciences, MA |
| CO$_2$ Incubator: | Lab-Line Enviro Shaker. |
| Microcentrifuge: | Mikro 20. |
| Vortex Mixer: | Mini Vortex mixer, IKA |

Procedure for Human nNOS and eNOS

Primary stock solutions of test compounds at a concentration of 6 mM are prepared from the 2 to 5 mg powder. The primary stock solutions of each test compound are prepared freshly in distilled water on the day of study to obtain a final concentration of 6 mM. For determination of IC$_{50}$ values, 12 test compound concentrations are prepared as 3-fold serial dilutions. Concentration range of test compound utilized for nNOS are 0.001 to 300 µM and for eNOS are 0.003 to 1000 µM. The vehicle of the test compound or inhibitor is used as blank control. For non-specific activity, 100 µM L-NMMA is used. The IC$_{50}$ concentration of L-NAME run in parallel as controls.

Procedure

All incubations are performed in duplicate.

Prepare the reaction mixture on ice by adding the following components with a micropipette to a polypropylene microcentrifuge tube:

---

10 µL of test compound, inhibitor or control (vehicle or L-NMMA) solution
25 µL of Reaction Buffer { 25 mM Tris-HCl, 0.6 µM BH4, 0.2 µM FMN, 0.2 µM FAD}
5 µL of 10 mM NADPH solution {1 mM} (freshly prepared in 10 mM Tris-HCl (pH 7.4)
5 µL of 6 mM CaCl$_2$ {600 µM}
5 µL of 1 mM Calmodulin {100 µM}
5 µL of 0.02 µg/µL nNOS or 0.12 µg/µL eNOS

---

Pre-incubate the above reaction mixture at room temperature for 15 mins.

Start the reaction by addition of the substrate (in 5 µL containing 1 µCi of [$^3$H]-L-Arginine+2.5 µM of unlabeled L-Arginine) to the reaction mixture. Total reaction volume is 60 µL.

Mix using a vortex mixer and incubate the above reaction mixture at 37° C. in an incubator for 30 mins.

Add 400 µL of ice-cold Stop Buffer at the end of the incubation period to stop the reaction. (The EDTA in the Stop Buffer chelates all of the available calcium.)

Mix using a vortex mixer and transfer the reaction samples to spin cups and centrifuge using a microcentrifuge, at 13,000 rpm for 30 sec. at room temperature.

Remove the spin cups from the holder and transfer 450 µL of eluate (containing the unbound L-citrulline) to scintillation vials. Add 3 mL of scintillation fluid and quantify the radioactivity in a liquid scintillation counter.

Calculation of IC$_{50}$ Values:

Data is analyzed using a Sigmoidal dose-response (variable slope) curve to determine the IC$_{50}$ value of the test compound.

$$Y = \text{Bottom} + (\text{Top} - \text{Bottom})/(1 + 10^{((\text{Log } IC_{50} - X) * \text{Hill Slope})})$$

X is the logarithm of test compound or inhibitor concentration

Y is the amount of L-citrulline formation (pmol)

Bottom refers to the lowest Y value and Top refers to the highest Y value.

This is identical the "four parameter logistic equation."

The slope factor (also called Hill slope) describes the steepness of a curve. A standard competitive binding curve that follows the law of mass action has a slope of −1.0. If the slope is shallower, the slope factor will be a negative fraction, e.g., −0.85 or −0.60.

Example 19b nNOS (Rat), eNOS (Rat) and iNOS (Mouse) Enzyme Assay

Recombinant rat or mouse NO synthases (iNOS, eNOS, nNOS) were expressed in Sf9 cells (Sigma), 36 mg prot/ml (Bradford). Solution in 50 mM Hepes, pH 7.4 with 10% glycerol.

Inhibition of NOS was determined by measuring the formation of L-[3H] citrulline from L-[3H] arginine. Enzyme assays were performed in the presence of 0,25 µCi [3H] arginine/ml, 120 µM NADPH, 1 µM FAD and FMN, 10 µM BH4, 100 nM, CaM, 100 mM Hepes, 2.4 mM CaCl$_2$, 24 µM L-arginine, 1 mM EDTA, 1 mM DTT. Stop buffer:100 mM Hepes, pH 5.5, 3 mM EDTA, 3 mM EGTA.

Enzyme and inhibitor were pre-incubated for 35 min in the presence of NADPH before addition of arginine to initiate the reaction. Incubation continued for 45 min before the reaction mixture was quenched and [3H] citrulline separated from unreacted substrate on DOWEX 50 W X 8-400 ion-exchange resin in a 96-well format. Results for exemplary compounds of the invention are also shown in Table 3 and Table 4.

TABLE 3

Selective inhibition of human NOS by compounds of the Invention (Rodent data)

| Example | hnNOS IC$_{50}$, µM | HeNOS IC$_{50}$, µM | HiNOS IC$_{50}$, µM | Selectivity eNOS/nNOS |
|---|---|---|---|---|
| 1 | 0.78 (0.022) | 25.2 (52) | 39 (8.5) | 32.3 |

TABLE 3-continued

Selective inhibition of human NOS by compounds of the Invention (Rodent data)

| Example | hnNOS IC$_{50}$, μM | HeNOS IC$_{50}$, μM | HiNOS IC$_{50}$, μM | Selectivity eNOS/nNOS |
|---|---|---|---|---|
| 2 | 2.21 | 73.6 | 22 | 33.3 |
| 3 | 0.58 | 41.1 | 32 | 70.7 |
|   | (0.21) | (65) | (>100) |   |
| 4 | 1.14 | 154 | 13 | 135 |
|   | 0.683 | 69.5 | (>100) |   |
|   | (0.16) | (77) |   |   |
| 5 | 5.46 | 105 |   | 19.2 |
| 6 | 0.165 | 29.8 | >100 | 181 |
| 7 | 0.869 | 13.9 | >100 | 16 |
| 8 | 1.22 | 24.5 |   | 20.1 |
| 9 | 0.798 | 10.2 |   | 12.8 |
| 10 | 0.198 | 10.8 | >100 | 54.5 |
| 11 | 0.253 | 37.7 | 0.85 | 149 |
|   | 0.43 | 58.7 | (>100) | 136 |
|   | (0.46) | (>100) |   |   |
| 12 | 0.31 | 36 | (>100) | 115 |
|   | (1.9) | >100 |   |   |
| 13 | 1.1 | 68.9 | >100 | 62.6 |
| 14 | 0.13 | 17.4 | >100 | 137 |
|   | (0.17) | (35) | (>100) | (206) |
| 15 | 5.8 | 52.6 | >100 | 9.1 |
| 16 | 0.7 | 33.7 | 19.4 | 48.1 |
| 17 | 4.9 | 155 | 57 | 31 |
| 18 | 8.8 | 50 | >100 | 5.7 |

Example 20

Efficacy in Models Predictive of Neuropathic-Like Pain States

The efficacy of the compounds of the invention for the treatment of neuropathic pain was assessed using standard animal models predictive of anti-hyperalgesic and anti-allodynic activity induced by a variety of methods, each described in more detail below.

(a) Chung Model of Injury-induced Neuropathic-like Pain: The experimental designs for the Chung Spinal Nerve Ligation SNL Model assay for neuropathic pain are depicted in FIGS. 1 and 5. Nerve ligation injury was performed according to the method described by Kim and Chung (Kim and Chung, Pain 50:355-363, 1992). This technique produces signs of neuropathic dysesthesias, including tactile allodynia, thermal hyperalgesia, and guarding of the affected paw. Rats were anesthetized with halothane and the vertebrae over the L4 to S2 region were exposed. The L5 and L6 spinal nerves were exposed, carefully isolated, and tightly ligated with 4-0 silk suture distal to the DRG. After ensuring homeostatic stability, the wounds were sutured, and the animals allowed to recover in individual cages. Sham-operated rats were prepared in an identical fashion except that the L5/L6 spinal nerves were not ligated. Any rats exhibiting signs of motor deficiency were euthanized. After a period of recovery following the surgical intervention, rats show enhanced sensitivity to painful and normally non-painful stimuli.

After standard dosings (3, 10, and 30 mg/kg) injected IP according to the published procedure, there is a clear antihyperalgesic effect of nNOS selective compounds 11 (FIG. 2), 23 (FIG. 4), 37 (FIG. 9). 47 (FIG. 10), 54 (FIG. 11), 28 (FIG. 12), or antiallodynic effect of compound 23 (FIG. 6). Compound 3 showed no antihyperalgesic effect (FIG. 3)

Example 21

In another embodiment, compounds of the invention are useful for treating CNS diseases. Preferably, a compound of the invention should be CNS penetrant. A preferred example of a compound of the invention would be Example 11 over less CNS penetrant compounds such as Example 3.

Two compounds delivered at the same dose in the Chung animal model of neuropathic pain (a CNS disorder) differ even though the nNOS values are similar. While other factors are likely involved, activity correlates with lipophilicity.

Example 11. nNOS=0.253 μM, eNOS=37.7 μM

Example 3. nNOS=0.58 μM, eNOS=41.1 μM

Example 22

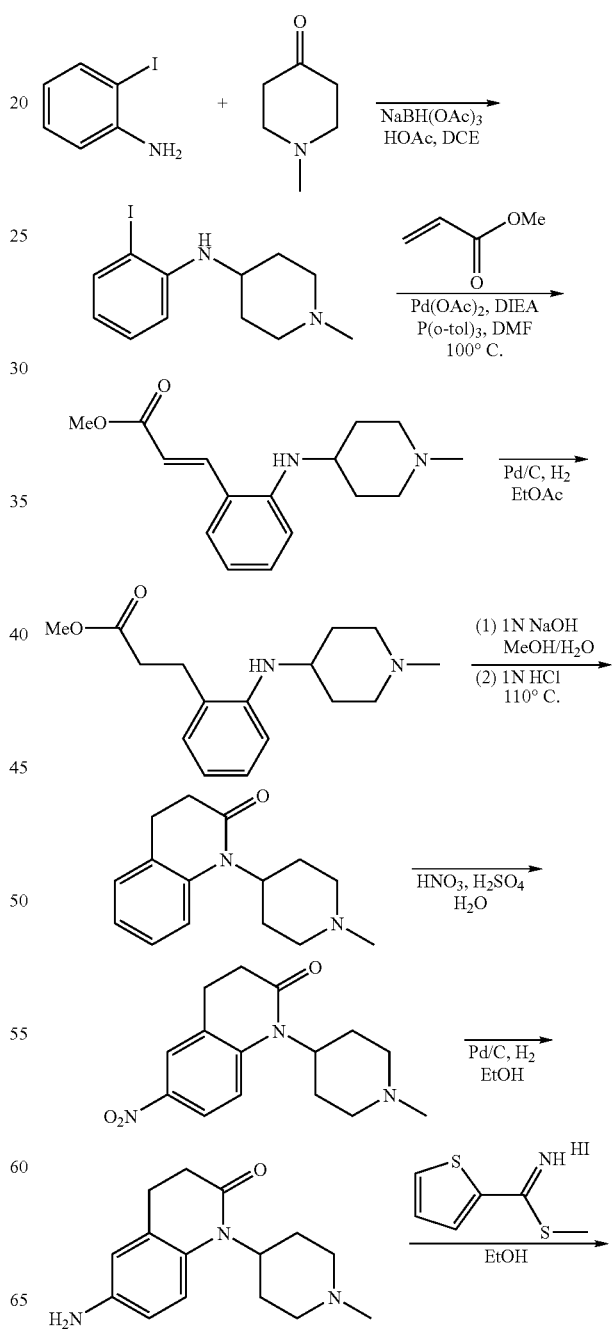

-continued

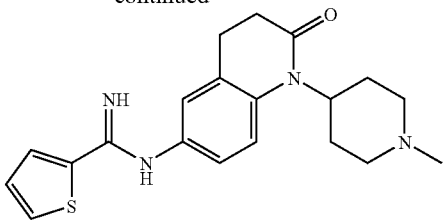

22

N-(2-Iodophenyl)-1-methylpiperidin-4-amine

A solution of 2-iodoaniline (1.0 g, 4.57 mmol) in 15 mL 1,2-dichloroethane was treated with 1-methylpiperidin-4-one (530 µL, 4.57 mmol) followed by sodium triacetoxyborohydride (1.55 g, 7.31 mmol) then acetic acid (259 µL). The suspension was stirred at room temperature for 21 hours. After this time, the mixture was cooled to 0° C., quenched with 20 mL 1N NaOH and extracted with 2×100 mL $CH_2Cl_2$. The combined organic layer was dried over $MgSO_4$, filtered and concentrated. The residue was subjected to flash chromatography on silica gel using 5% 2M $NH_3$ in MeOH/$CH_2Cl_2$. A light yellow oil was obtained (579 mg, 40.2%). $^1$H-NMR ($CDCl_3$) δ 7.64 (dd, J=1.2, 8.1 Hz, 1H), 7.21-7.15 (m, 1H), 6.57 (d, J=8.1 Hz, 1H), 6.44-6.39 (m, 1H), 4.12-4.10 (m, 1H), 3.37-3.35 (m, 1H), 3.79-2.75 (m, 2H), 2.31 (s, 3H), 2.22-2.03 (m, 4H), 1.65-1.53 (m, 2H). MS (ESI): 317.1 (M+1, 100%).

(E)-Methyl 3-(2-(1-methylpiperidin-4-ylamino)phenyl)acrylate

A solution of N-(2-iodophenyl)-1-methylpiperidin-4-amine (550 mg, 1.74 mmol), methyl acrylate (157 µL, 1.74 mmol), palladium acetate (39 mg, 0.17 mmol), tri-o-tolylphosphine (106 mg, 0.35) and diisopropylethylamine (608 µL, 3.48 mmol) in 7 mL DMF was deoxygenated with argon then heated at 100° C. for 5 hours. The mixture was cooled to room temperature then partitioned between EtOAc (150 mL) and $H_2O$ (20 mL). After extraction, the organic layer was separated and rinsed with brine. The organic layer was dried over $Na_2SO_4$, filtered and concentrated to give a yellow residue, which was subjected to flash chromatography on silica gel using 5%, 2M $NH_3$ in MeOH/$CH_2Cl_2$. A viscous yellow oil was obtained (350 mg, 73.4%). $^1$H-NMR ($CDCl_3$) δ 7.85 (d, J=15.9 Hz, 1H), 7.37-7.35 (m, 1H), 7.24-7.21 (m, 1H), 6.72-6.67 (m, 2H), 6.33 (d, J=15.9 Hz, 1H), 3.88-3.85 (m, 1H), 3.81 (s, 3H), 3.36 (brs, 1H), 2.84-2.81 (m, 2H), 2.31 (s, 3H), 2.18-2.05 (m, 4H), 1.63-1.51 (m, 2H). MS (ESI): 275.2 (M+1, 100%).

Methyl 3-(2-(1-methylpiperidin-4-ylamino)phenyl)propanoate

A suspension of (E)-methyl 3-(2-(1-methylpiperidin-4-ylamino)phenyl)acrylate (330 mg, 1.20 mmol) and palladium on carbon (10% wt, 128 mg, 0.12 mmol) in 20 mL EtOAc was stirred under a balloon of hydrogen overnight. The suspension was diluted with MeOH (50 mL) and filtered through a pad of celite. The celite pad was rinsed with 10 mL of MeOH. The filtrate was concentrated and the residue was subjected to flash chromatography on silica gel using 5% 2M $NH_3$ in MeOH/$CH_2Cl_2$. A light yellow oil was obtained (300 mg, 90.4%). $^1$H-NMR ($CDCl_3$) δ 7.14-7.08 (m, 1H), 7.04-7.01 (m, 1H), 6.67-6.63 (m, 2H), 3.76-3.74 (m, 1H), 3.69 (s, 3H), 3.35 (brs, 1H), 2.82-2.77 (m, 4H), 2.65-2.60 (m, 2H), 2.31 (s, 3H), 2.19-2.06 (m, 4H), 1.61-1.49 (m, 2H). MS (ESI): 277.2 (M+1, 100%).

1-(1-Methylpiperidin-4-yl)-3,4-dihydroquinolin-2(1H)-one

A solution of methyl 3-(2-(1-methylpiperidin-4-ylamino)phenyl)propanoate (1.1 g, 3.98 mmol) in 20 mL MeOH/5 mL $H_2O$ was treated with 1N NaOH (8.8 mL, 8.76 mmol) and stirred at room temperature for 2 hours. The mixture was concentrated and made acidic with 6N HCl. Approximately half of this mixture was diluted with 1N HCl (15 mL) and heated at 110° C. overnight. After cooling, the mixture was concentrated on the rotoevaporator then made basic with saturated $Na_2CO_3$. This solution was extracted with 2×100 mL $CH_2Cl_2$. The combined organic fractions were dried over $MgSO_4$, filtered and concentrated to give a light brown residue, which was subjected to flash chromatography on silica gel using 5%, 2M $NH_3$ in MeOH/$CH_2Cl_2$. A light yellow solid was obtained (320 mg, 78.2%). $^1$H-NMR ($CDCl_3$) δ 7.24-7.16 (m, 3H), 7.02-6.97 (m, 1H), 4.47-4.34 (m, 1H), 2.99-2.95 (m, 2H), 2.83-2.70 (m, 2H), 2.68-2.55 (m, 4H), 2.33 (s, 3H), 2.13-2.06 (m, 2H), 1.72-1.69 (m, 2H). MS (ESI): 245.2 (M+1, 100%).

1-(1-Methylpiperidin-4-yl)-6-nitro-3,4-dihydroquinolin-2(1H)-one

A solution of 1-(1-methylpiperidin-4-yl)-3,4-dihydroquinolin-2(1H)-one (305 mg, 1.25 mmol) in conc. $H_2SO_4$ (4 mL) was treated with fuming $HNO_3$ (53 µL, 1.25 mmol) at −5 to −10° C. (ice/MeOH) and the resulting solution was stirred for 30 min. at the same temperature. The reaction was quenched with the addition of crushed ice, and then basified with 1 N NaOH, and the product was extracted into $CH_2Cl_2$ (2×50 mL). The combined $CH_2Cl_2$ layer was dried ($Na_2SO_4$), filtered, and the solvent was evaporated. The crude was triturated with hexanes to afford the title compound (320 mg, 88.4%) as a solid. $^1$H-NMR ($CDCl_3$) δ 8.10-8.05 (m, 2H), 7.33 (d, J=8.7 Hz, 1H), 4.50-4.39 (m, 1H), 3.01-2.90 (m, 4H), 2.67-2.54 (m, 4H), 2.33 (s, 3H), 2.15-2.08 (m, 2H), 1.74-1.70 (m, 2H). MS (ESI): 290.2 (M+1, 100%).

6-Amino-1-(1-methylpiperidin-4-yl)-3,4-dihydroquinolin-2(1H)-one

A suspension of 1-(1-methylpiperidin-4-yl)-6-nitro-3,4-dihydroquinolin-2(1H)-one (300 mg, 1.04 mmol) and palladium on activated carbon (10% wt, 55 mg, 0.05 mmol) in 20 mL ethanol/4 mL THF was stirred under a balloon of hydrogen overnight. The suspension was filtered through a pad of celite. The filter pad was rinsed with 50 mL methanol, and the filtrate was concentrated to give a viscous oil. The crude product was used without further purification. (250 mg, 92.6%). $^1$H-NMR ($CDCl_3$) δ 7.06 (d, J=9.3 Hz, 1H), 6.54-6.49 (m, 2H), 4.46-4.36 (m, 1H), 3.42 (brs, 2H), 2.97-2.94 (m, 2H), 2.73-2.49 (m, 6H), 2.31 (s, 3H), 2.27-2.05 (m, 2H), 1.27-1.21 (m, 2H). MS (ESI): 260.2 (M+1, 100%).

N-(1-(1-Methylpiperidin-4-yl)-2-oxo-1,2,3,4-tetrahydroquinolin-6-yl)thiophene-2-carboximidamide A solution of 6-amino-1-(1-methylpiperidin-4-yl)-3,4-dihydroquinolin-2(1H)-one (240 mg, 0.93 mmol) in 15 mL EtOH was treated with methyl thiophene-2-carbimidothioate hydroiodide (528 mg, 1.85 mmol) and stirred overnight at room temperature. A TLC analysis indicated that starting material (amine) is still present. An additional equivalent of methyl thiophene-2-carbimidothioate hydroiodide (265 mg, 0.93 mmol) was added, and stirring was continued at room temperature overnight. A TLC analysis indicated that starting material (amine) was still present. The reaction was worked up by bubbling argon through the mixture for 20 minutes; then it was partitioned between $CH_2Cl_2$ (100 mL) and saturated sodium carbonate (20 mL). The aqueous layer was extracted with an additional 50 mL $CH_2Cl_2$. The combined organic layers were dried over sodium sulfate and concentrated to give a yellow oil which was subjected to flash chromatography on silica gel using 5% $MeOH/CH_2Cl_2$ then 5-10% 2M $NH_3$ in $MeOH/CH_2Cl_2$ to give a yellow semi-solid. This mixture contained starting amine and the desired product as determined by $^1H$-NMR analysis. The mixture was dissolved in methanol (10 mL) and treated with methyl thiophene-2-carbimidothioate hydroiodide (528 mg, 1.85 mmol) and stirred at room temperature for 2 days. The reaction was worked-up and purified as described above to give the title compound as a yellow solid (100 mg, 29.3%). $^1H$-NMR (DMSO-$d_6$) δ 7.73 (d, J=2.3 Hz, 1H), 7.59 (d, J=4.8 Hz, 1H), 7.16-7.15 (m, 1H), 7.09 (dd, J=5.1, 6.3 Hz, 1H), 6.74-6.70 (m, 2H), 6.44 (brs, 2H), 4.05-3.97 (m, 1H), 2.86-2.50 (m, 8H), 2.18 (s, 3H), 2.00-1.93 (m, 2H), 1.59-1.55 (m, 2H). MS (ESI): 369.2 (M+1, 100%). ESI-HRMS calculated for $C_{20}H_{25}N_4SO$ (MH$^+$): 369.1739, Observed: 369.1743.

Examples 23 and 24

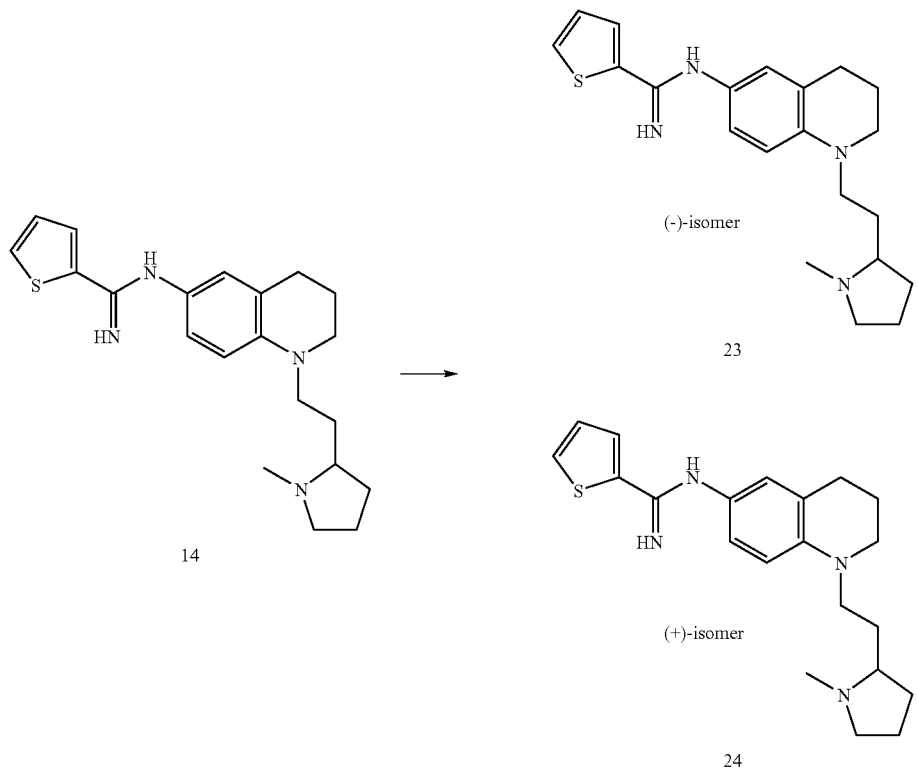

N-(1-(2-(1-Methylpyrrolidin-2-yl)ethyl)-1,2,3,4-tetrahydroquinolin-6-yl)thiophene-2-carboximidamide (Example 14)

Title compound was prepared as described in Example 14.

Separation of (+)-isomer and (−)-isomers: Separation of enantiomers was achieved by chiral HPLC. Column: Chiracel AD-H 20×250 mm (−)-Isomer (23): 1$^{st}$ eluting isomer. The free base was converted to the dihydrochloride salt by standard methods. Optical Rotation: $^{25}[α]_{589}$=−0.18°, c=0.5 in MeOH. $^1$H-NMR (CD$_3$OD) δ 8.02-7.99 (m, 2H), 7.34 (pseudo t, J=4.5 Hz, 1H), 7.11-7.03 (m, 2H), 6.85 (d, J=8.4 Hz, 1H), 3.70-3.65 (m, 1H), 3.51-3.37 (m, 4H), 3.20-3.11 (m, 2H), 2.93 (s, 3H), 2.84-2.80 (m, 2H), 2.50-1.75 (m, 8H). MS (ESI): 369.2 (M+1). ESI-HRMS calculated for $C_{21}H_{29}N_4S$ (MH$^+$): 369.2107, Observed: 369.2118.

(+)-Isomer (24): 2$^{nd}$ eluting isomer. The free base was converted to the dihydrochloride salt by standard methods. Optical Rotation: $^{25}[α]_{589}$=+0.170, c=0.48 in MeOH. $^1$H-NMR (CD$_3$OD) δ 8.03-7.99 (m, 2H), 7.34 (pseudo t, J=4.5 Hz, 1H), 7.12-7.03 (m, 2H), 6.85 (d, J=8.7 Hz, 1H), 3.73-3.65 (m, 1H), 3.51-3.39 (m, 4H), 3.20-3.11 (m, 2H), 2.93 (s, 3H), 2.84-2.80 (m, 2H), 2.50-1.75 (m, 8H). MS (ESI):

369.2 (M+1). ESI-HRMS calculated for $C_{21}H_{29}N_4S$ (MH$^+$): 369.2107, Observed: 369.2113.

Example 25

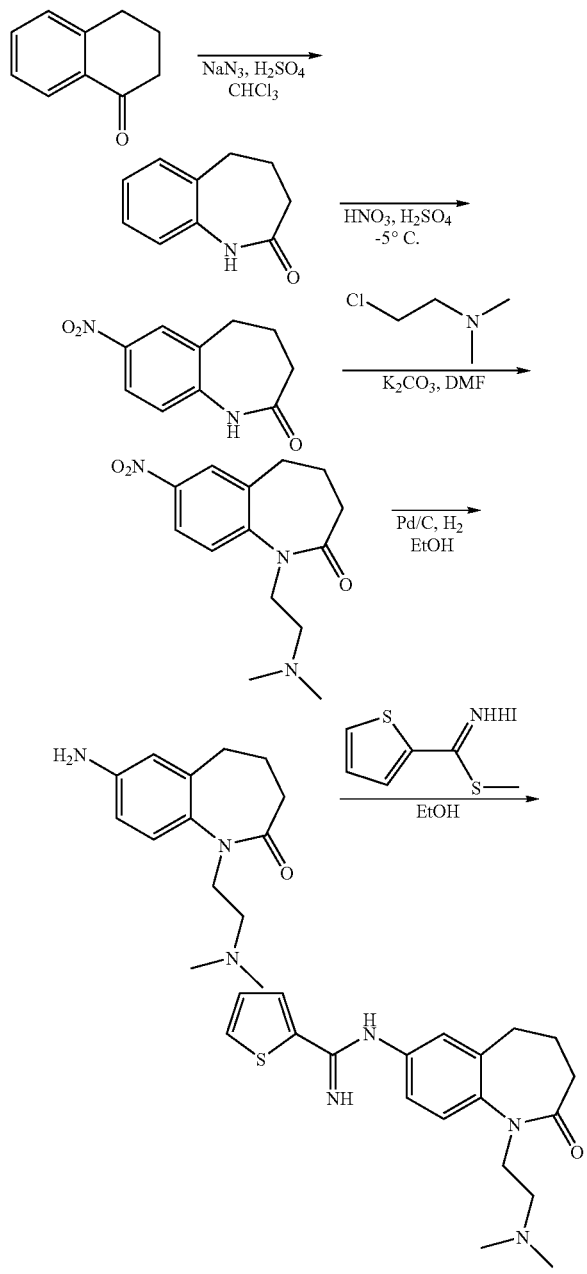

4,5-Dihydro-1H-benzo[b]azepin-2(3H)-one

A suspension of 3,4-dihydronaphthalen-1(2H)-one (2.0 g, 13.68 mmol) and sodium azide (1.11 g, 17.10 mmol) in a mixture of 14 mL CHCl$_3$ and 3 mL H$_2$O was heated at 40° C. then treated with H$_2$SO$_4$ dropwise over 20 minutes. The mixture was diluted with 50 mL H$_2$O and filtered. The solid was slurried in hot H$_2$O, cooled and filtered to give a gray solid (1.45 g, 65.6%). $^1$H-NMR (DMSO-d$_6$) δ 9.49 (s, 1H), 7.25- 7.22 (m, 2H), 7.19-7.21 (m, 1H), 6.95 (d, J=7.8 Hz, 1H), 2.70-2.65 (m, 2H), 2.15-2.07 (m, 4H). MS (EI): 161 (M+).

7-Nitro-4,5-dihydro-1H-benzo[b]azepin-2(3H)-one

A solution of 4,5-dihydro-1H-benzo[b]azepin-2(3H)-one (1.42 g, 8.81 mmol) in conc. H$_2$SO$_4$ (25 mL) was treated with fuming HNO$_3$ (414 μL, 8.81 mmol) at −5 to −10° C. (ice/MeOH). The resulting solution was stirred at the same temperature for 30 minutes. The reaction was quenched with the addition of crushed ice. The resulting suspension was diluted with H$_2$O (50 mL) and filtered. The solid was washed with 4×50 mL H$_2$O, collected and dried under reduced pressure overnight. Yield: 1.0 g, 55.1%. $^1$H-NMR (DMSO-d$_6$) δ 10.08 (s, 1H), 8.19 (d, J=2.4 Hz, 1H), 8.11 (dd, J=2.4, 8.7 Hz, 1H), 7.15 (d, J=8.7 Hz, 1H), 2.83-2.79 (m, 2H), 2.26-2.13 (m, 4H). MS (EI): 206 (M+).

1-(2-(Dimethylamino)ethyl)-7-nitro-4,5-dihydro-1H-benzo[b] azepin-2(3H)-one

A suspension of 7-nitro-4,5-dihydro-1H-benzo[b]azepin-2(3H)-one (490 mg, 2.38 mmol), 2-chloro-N,N-dimethylethanamine hydrochloride (685 mg, 4.75 mmol) and potassium carbonate (1.97 g, 14.28 mmol) in 15 mL DMF was stirred at room temperature for 1 day. A TLC analysis indicated that the starting material was still present. The mixture was treated with 2-chloro-N,N-dimethylethanamine hydrochloride (685 mg, 4.75 mmol) and potassium carbonate (1.97 g, 14.28 mmol) followed by 5 mL DMF and stirring was continued at room temperature for 18 hours. After this time, the mixture was poured into 50 mL H$_2$O, then extracted with 2×100 mL EtOAc. The combined organic fractions were washed with brine, dried over Na$_2$SO$_4$, filtered, and concentrated to give a dark residue. The residue was subjected to flash chromatography on silica gel using 2-5% 2M NH$_3$ in MeOH/CH$_2$Cl$_2$ to give a yellow viscous oil (412 mg, 62.4%). $^1$H-NMR (DMSO-d$_6$) δ 8.21-8.15 (m, 2H), 7.67 (d, J=8.7 Hz, 1H), 3.92-3.90 (m, 2H), 2.87-2.83 (m, 2H), 2.27 (t, J=6.3 Hz, 2H), 2.21-2.11 (m, 4H), 2.03 (s, 6H). MS (EI): 278.1 (M+1).

7-Amino-1-(2-(dimethylamino)ethyl)-4,5-dihydro-11H-benzo[b]azepin-2(3H)-one

A suspension of 1-(2-(dimethylamino)ethyl)-7-nitro-4,5-dihydro-1H-benzo[b]azepin-2(3H)-one (400 mg, 1.44 mmol) and palladium on activated carbon (10% wt, 153 mg, 0.14 mmol) in 20 mL ethanol was stirred under a balloon of hydrogen overnight. The suspension was filtered through a pad of celite. The filter pad was rinsed with 50 mL methanol and the filtrate was concentrated to give an off-white solid (350 mg, 98.3%). $^1$H-NMR (CDCl$_3$) δ 6.99 (d, J=8.4 Hz, 1H), 6.58 (dd, J=2.4, 8.4 Hz, 1H), 6.50 (d, J=2.4 Hz, 1H), 3.73-3.65 (m, 2H), 3.69 (brs, 2H), 2.72-2.55 (m, 2H), 2.39 (t, J=6.9 Hz, 2H), 2.21-2.11 (m, 4H), 2.19 (s, 6H). MS (EI): 248.2 (M+1).

N-(1-(2-(Dimethylamino)ethyl)-2-oxo-2,3,4,5-tetrahydro-1H-benzo[b]azepin-7-yl)thiophene-2-carboximidamide A solution of 7-amino-1-(2-(dimethylamino)ethyl)-4,5-dihydro-1H-benzo[b]azepin-2(3H)-one (100 mg, 0.40 mmol) in 10 mL EtOH was treated with methyl thiophene-2-carbimidothioate hydroiodide (231 mg, 0.81 mmol) and stirred overnight at room temperature. The reaction was worked up by diluting with CH$_2$Cl$_2$ (20 mL) and bubbling argon through the mixture for 20 minutes. The mixture was partitioned between CH$_2$Cl$_2$ (100 mL) and saturated sodium carbonate (15 mL). After extraction, the organic layer was separated and the aqueous layer was extracted with an additional 50 mL CH$_2$Cl$_2$. The combined organic layers were dried over magnesium sulfate, filtered, and concentrated to give a yellow oil which was subjected to flash chromatography on silica gel using 2% MeOH/CH$_2$Cl$_2$ then 5-10% 2M NH$_3$ in MeOH/CH$_2$Cl$_2$ to give a yellow semi-solid (100 mg, 69.9%). $^1$H-NMR (DMSO-d$_6$) δ 7.75 (d, J=3.3 Hz, 1H), 7.60 (d, J=5.1 Hz, 1H), 7.27 (d, J=8.4 Hz, 1H), 7.12-7.09 (m, 1H), 6.79-6.74 (m, 2H), 6.46 (brs, 2H), 3.30-3.28 (m, 2H), 2.65-2.60 (m, 2H), 2.32-2.27 (m, 2H), 2.15-1.98 (m, 4H), 2.09 (s, 6H). MS (EI): 357.2 (M+1). ESI-HRMS calculated for C$_{19}$H$_{25}$N$_4$SO (MH$^+$): 357.1743, Observed: 357.1753.

Example 26

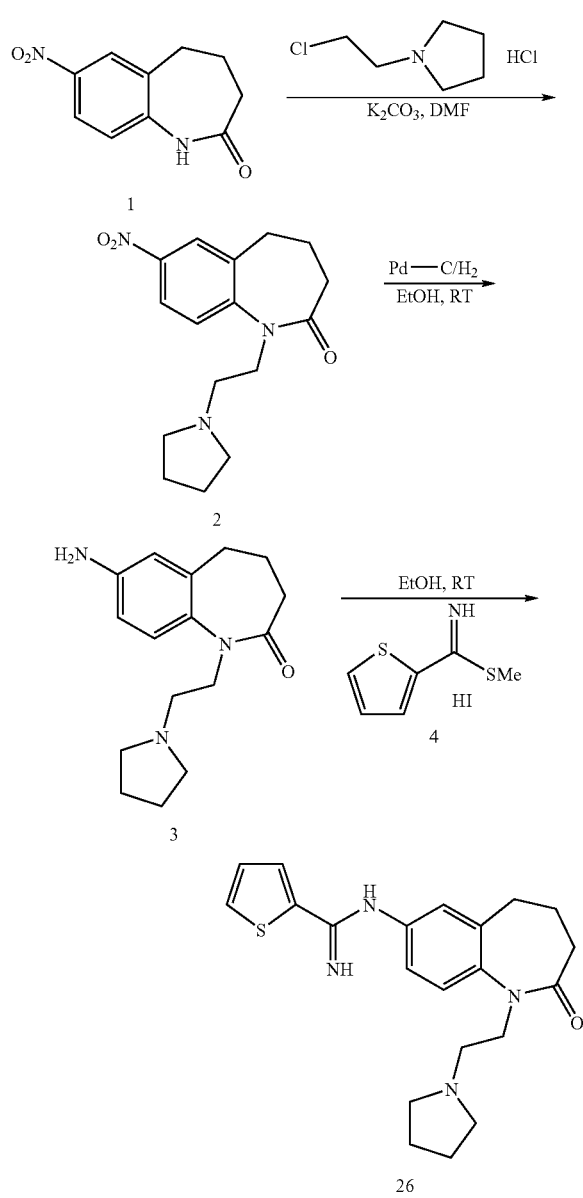

7-Nitro-4,5-dihydro-1H-benzo[b]azepin-2(3H)-one (1)

For complete experimental details and spectral data, please see Example 25.

7-Nitro-1-(2-(pyrrolidin-1-yl)ethyl)-4,5-dihydro-1H-benzo[b]azepin-2(3H)-one (2)

A suspension of compound 1 (0.49 g, 2.38 mmol), 1-(2-chloroethyl)pyrrolidine hydrochloride (0.80 g, 4.75 mmol) and K$_2$CO$_3$ (1.97 g, 14.28 mmol) in dry DMF (15 mL) was stirred at room temperature overnight. At this time starting material was observed; then 1-(2-chloroethyl)pyrrolidine hydrochloride (0.80 g, 4.75 mmol) and K$_2$CO$_3$ (1.97 g, 14.28 mmol) were added and stirred for additional 24 h. The reaction was diluted with water (50 mL), and product was extracted into ethyl acetate (2×100 mL). The combined ethyl acetate layer was washed with brine (2×50 m/L) and dried (Na$_2$SO$_4$). The solvent was evaporated and crude was purified by column chromatography (2M NH$_3$ in MeOH:CH$_2$Cl$_2$, 2:98 to 5:95) to obtain compound 2 (0.35 g, 49%) as a syrup. $^1$H NMR (DMSO-d$_6$) δ 1.50-1.56 (m, 4H), 2.02-2.18 (m, 4H), 2.26-2.34 (m, 4H), 2.45-2.48 (m, 2H, merged with DMSO peak), 2.85 (t, 2H, J=6.6 Hz), 3.96 (brs, 2H), 7.66 (d, 1H, J=8.7 Hz), 8.14-8.20 (m, 2H); ESI-MS (m/z, %): 304 (MH$^+$, 100), 233 (26).

7-Amino-1-(2-(pyrrolidin-1-yl)ethyl)-4,5-dihydro-1H-benzo[b]azepin-2(3H)-one (3)

A solution of compound 2 (0.33 g, 1.087 mmol) in dry ethanol (5 mL) was treated with Pd—C (~0.05 g) and purged with hydrogen gas. The flask was evacuated and purged with hydrogen gas (twice) and stirred under hydrogen atm. (balloon pressure) at room temperature for 3.5 h. The reaction was filtered through celite bed, washed with methanol (3×10 mL). The combined organic layer was evaporated to obtain crude compound 3 (0.283 g, 95%) as a foam. $^1$H NMR (DMSO-d$_6$) δ 1.56-1.60 (m, 4H), 1.90-2.08 (m, 4H), 2.30-2.56 (m, 10H), 5.04 (s, 2H), 6.39 (d, 1H, J=2.4 Hz), 6.46 (dd, 1H, J=2.4, 9.1 Hz), 6.98 (d, 1H, J=8.4 Hz); ESI-MS (m/z, %) 274 (MH$^+$, 100), 203 (36).

N-(2-Oxo-1-(2-(pyrrolidin-1-yl)ethyl)-2,3,4,5-tetrahydro-1H-benzo[b]azepin-7-yl)thiophene-2-carboximidamide (26)

A solution of compound 3 (0.1 g, 0.365 mmol) in dry ethanol (5 mL) was treated with compound 4 (0.2 g, 0.731 mmol), and the mixture was stirred at room temperature for 18 h. The reaction was diluted with sat. NaHCO$_3$ solution (25 mL) and product was extracted into CH$_2$Cl$_2$ (2×20 mL). The combined CH$_2$Cl$_2$ layer was washed with brine (10 mL) and dried (Na$_2$SO$_4$). Solvent was evaporated and crude was purified by column chromatography (2 M NH$_3$ in MeOH:CH$_2$Cl$_2$, 3:97) to obtain compound 5 (0.11 g, 79%) as a solid. $^1$H NMR (DMSO-d$_6$) δ 1.56-1.68 (m, 4H), 1.88-2.06 (m, 2H), 2.10-2.18 (m, 2H), 2.32-2.68 (m, 10H), 6.45 (brs, 2H), 6.73 (d, 1H, J=1.5 Hz), 7.10 (d, 1H, J=4.2 Hz), 7.27 (d, 1H, J=8.4 Hz), 7.61 (d, 1H, J=5.1 Hz), 7.74 (d, 1H, J=3.3 Hz); ESI-MS (m/z, %) 383 (MH$^+$, 100), 312 (52), 156 (90), 148 (76); ESI-HRMS

Example 27

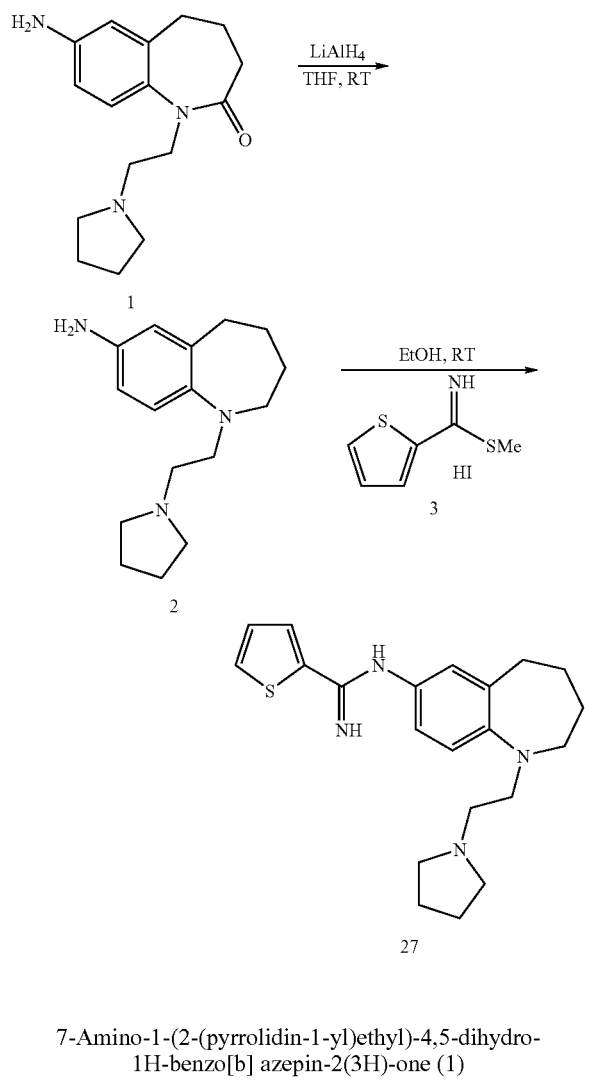

7-Amino-1-(2-(pyrrolidin-1-yl)ethyl)-4,5-dihydro-1H-benzo[b] azepin-2(3H)-one (1)

For complete experimental details and spectral data, please see Example 26.

1-(2-(Pyrrolidin-1-yl)ethyl)-2,3,4,5-tetrahydro-1H-benzo[b]azepin-7-amine (2)

A suspension of LiAlH$_4$ (2.48 mL, 2.487 mmol, 1.0 M suspension in dry THF) was treated with compound 1 (0.17 g, 0.621 mmol) in dry THF (5 mL) at 0° C. over a period of 2 min. The reaction was brought to room temperature and stirred for 18 h. The reaction was quenched with water (0.1 mL), 2 N NaOH solution (0.1 mL) and water (0.1 mL). After stirring for 30 min. at room temperature, the reaction was filtered and washed with CH$_2$Cl$_2$ (3×15 mL). The combined organic layer was evaporated and crude was purified by column chromatography (2 M NH$_3$ in MeOH:CH$_2$Cl$_2$, 5:95) to obtain compound 2 (0.15 g, 94%) as a thick syrup. $^1$H NMR (DMSO-d$_6$) δ 1.40-1.50 (m, 2H), 1.56-1.70 (m, 6H), 2.40-2.60 (m, 8H), 2.74 (t, 2H, J=5.1 Hz), 3.07 (t, 2H, J=7.5 Hz), 4.53 (s, 2H), 6.30-6.34 (m, 2H), 6.65 (d, 1H, J=8.1 Hz); ESI-MS (m/z, %) 260 (MH$^+$, 100), 189 (85).

N-(1-(2-(Pyrrolidin-1-yl)ethyl)-2,3,4,5-tetrahydro-1H-benzo[b]azepin-7-yl)thiophene-2-carboximidamide (27)

A solution of compound 2 (0.13 g, 0.501 mmol) in dry ethanol (5 mL) was treated with compound 3 (0.28 g, 1.002 mmol) and the mixture was stirred at room temperature for 16 h. The reaction was diluted with sat. NaHCO$_3$ solution (25 mL) and product was extracted into CH$_2$Cl$_2$ (2×20 mL). The combined CH$_2$Cl$_2$ layer was washed with brine (10 mL) and dried (Na$_2$SO$_4$). Solvent was evaporated and crude was purified by column chromatography (2 M NH$_3$ in MeOH:CH$_2$Cl$_2$, 5:95) to obtain compound 27 (0.15 g, 83%) as a solid. $^1$H NMR (DMSO-d$_6$) δ 1.48-1.56 (m, 2H), 1.60-1.68 (m, 6H), 2.40-2.55 (m, 4H), 2.58 (t, 2H, J=6.6 Hz), 2.62-2.70 (m, 2H), 2.82-2.90 (m, 2H), 3.19 (t, 2H, J=7.5 Hz), 6.29 (s, 2H), 6.60-6.66 (m, 2H), 6.89 (d, 1H, J=9.0 Hz), 7.07 (dd, 1H, J=3.9, 4.8 Hz), 7.57 (d, 1H, J=4.8 Hz), 7.70 (d, 1H, J=3.6 Hz); ESI-MS (m/z, %) 369 (MH$^+$, 77), 272 (100); ESI-HRMS calculated for C$_{21}$H$_{29}$N$_4$S (MH$^+$), calculated: 369.2107, observed: 369.2121; HPLC purity 98.8% by area.

Example 28

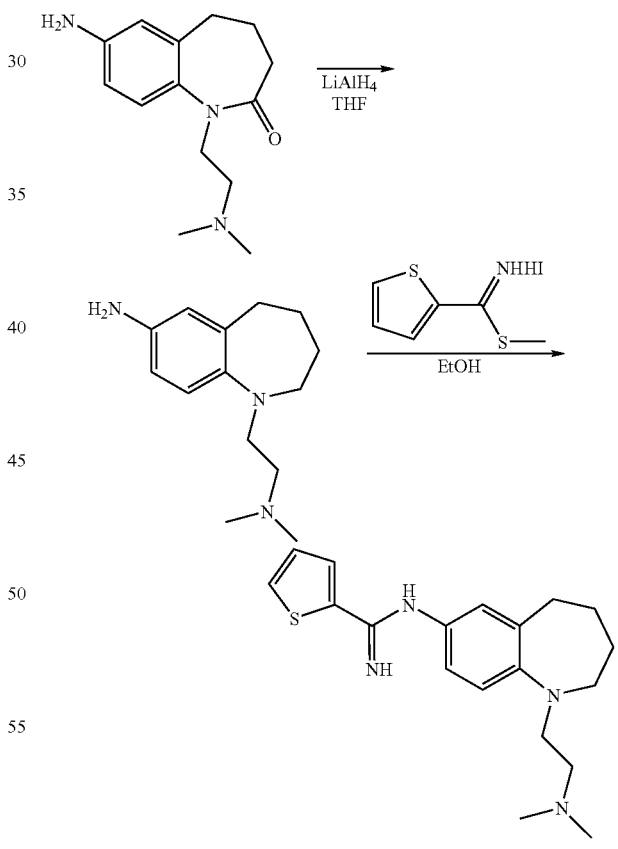

1-(2-(Dimethylamino)ethyl)-2,3,4,5-tetrahydro-1H-benzo[b]azepin-7-amine

A suspension of 1 M LiAlH$_4$ in THF (1.82 mL, 1.82 mmol) was cooled to 0° C. then treated with 7-amino-1-(2-(dimethylamino)ethyl)-4,5-dihydro-1H-benzo[b]azepin-2(3H)-one (225 mg, 0.91 mmol) (see experimental procedure for the synthesis of Example 25) in 10 mL THF dropwise. The suspension was stirred at room temperature overnight. After this time, the mixture was cooled to 0° C. and treated with 1 mL 1N NaOH dropwise with rapid stirring. After stirring for 20 minutes, the suspension was treated with Na$_2$SO$_4$. The suspension was filtered and the solid was rinsed with 50 mL 10% 2M NH$_3$ in MeOH/CH$_2$Cl$_2$. The filtrate was concentrated and the dark residue was subjected to flash chromatography on silica gel using 5% 2M NH$_3$ in MeOH/CH$_2$Cl$_2$ to give a dark viscous oil (75 mg, 35.4%). $^1$H-NMR (CDCl$_3$) δ 6.80-6.78 (m, 1H), 6.52-6.48 (m, 2H), 3.40 (brs, 2H), 3.21-3.17 (m, 2H), 2.87-2.83 (m, 2H), 2.70-2.66 (m, 2H), 2.47-2.43 (m, 2H), 2.27 (s, 6H), 1.72-1.64 (m, 2H), 1.59-1.55 (m, 2H). MS (EI): 234.2 (M+1).

N-(1-(2-(Dimethylamino)ethyl)-2,3,4,5-tetrahydro-1H-benzo[b]azepin-7-yl)thiophene-2-carboximidamide dihydrochloride A solution of 1-(2-(dimethylamino)ethyl)-2,3,4,5-tetrahydro-1H-benzo[b]azepin-7-amine (65 mg, 0.28 mmol) in 5 mL EtOH was treated with methyl thiophene-2-carbimidothioate hydroiodide (159 mg, 0.56 mmol) and stirred overnight at room temperature. The reaction was worked up by diluting with CH$_2$Cl$_2$ (20 mL) and bubbling argon through the mixture for 20 minutes. The mixture was partitioned between CH$_2$Cl$_2$ (100 mL) and saturated sodium carbonate (15 mL). After extraction, the organic layer was separated and the aqueous layer was extracted with an additional 50 mL CH$_2$Cl$_2$. The combined organic layers were dried over magnesium sulfate, filtered and concentrated to give a yellow oil which was subjected to flash chromatography on silica gel using 2% MeOH/CH$_2$Cl$_2$ then 5-10% 2M NH$_3$ in MeOH/CH$_2$Cl$_2$ to give a yellow semi-solid. This residue was converted to the dihydrochloride salt by dissolving in CH$_2$Cl$_2$ and treating with ethereal HCl. A brown solid was obtained (35 mg, 36.5%). $^1$H-NMR (CD$_3$OD) δ 8.05-8.02 (m, 2H), 7.37-7.21 (m, 4H), 3.64 (t, J=6.3 Hz, 2H), 3.39 (t, J=6.0 Hz, 2H), 3.08-3.05 (m, 2H), 2.95-2.85 (m, 2H), 2.94 (s, 6H), 1.90-1.80 (m, 2H), 1.70-1.60 (m, 2H). MS (EI): 343.2 (M+1). ESI-HRMS calculated for C$_{19}$H$_{27}$N$_4$S (MH$^+$): 343.1950, Observed: 343.1949.

Example 29

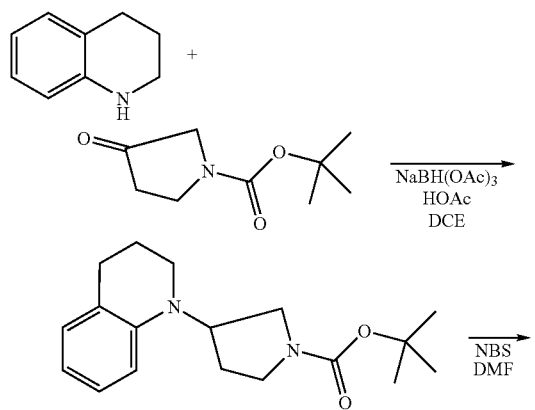

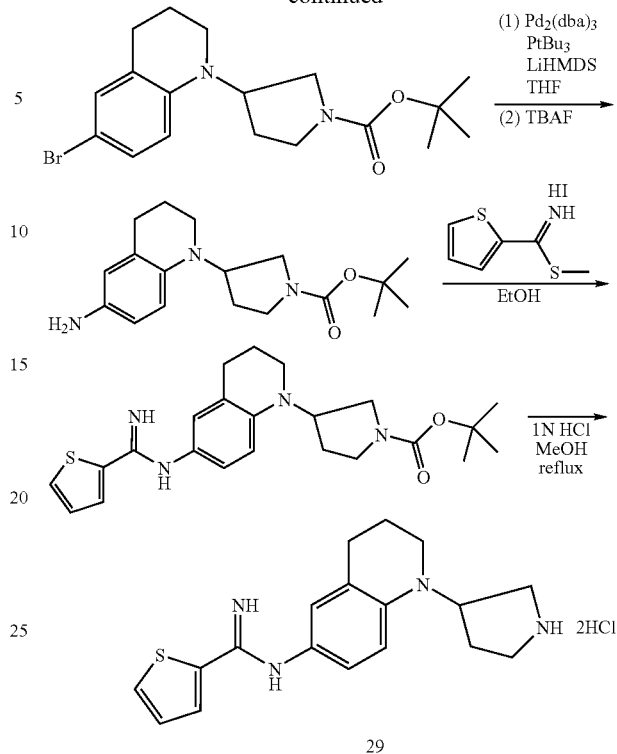

29 tert-Butyl 3-(3,4-dihydroquinolin-1(2H)-yl)pyrrolidine-1-carboxylate

A solution of 1,2,3,4-tetrahydroquinoline (1.0 mL, 7.94 mmol) in 30 mL 1,2-dichloroethane was treated with tert-butyl 3-oxopyrrolidine-1-carboxylate (2.94 g, 15.87 mmol) followed by sodium triacetoxyborohydride (8.4 g, 39.68 mmol) then acetic acid (2.25 mL). The suspension was stirred at room temperature for 1 day. After this time, the mixture was cooled to 0° C., quenched with 20 mL 1N NaOH and stirred for 20 minutes. The suspension was extracted with 2×100 mL CH$_2$Cl$_2$. The organic layer was rinsed with brine, dried over MgSO$_4$, filtered and concentrated to give a yellow residue which was subjected to flash chromatography on silica gel using 15% EtOAc/Hexanes to give a viscous oil (1.89 g, 78.8%). $^1$H-NMR (CDCl$_3$) δ 7.07 (pseudo t, J=7.2 Hz, 1H), 6.97 (d, J=7.2 Hz, 1H), 6.69 (d, J=8.1 Hz, 1H), 6.62 (pseudo t, J=7.5 Hz, 1H), 4.44-4.40 (m, 1H), 3.63-3.20 (m, 6H), 2.75 (t, J=6.3 Hz, 2H), 2.13-2.08 (m, 2H), 1.94-1.90 (m, 2H), 1.48 (s, 9H). MS (ESI): 303.2 (M+1).

tert-Butyl 3-(6-bromo-3,4-dihydroquinolin-1(2H)-yl) pyrrolidine-1-carboxylate

A solution of tert-butyl 3-(3,4-dihydroquinolin-1(2H)-yl) pyrrolidine-1-carboxylate (1.86 g, 6.15 mmol) in 15 mL of DMF was cooled to 0° C. then treated dropwise with NBS (1.09 g, 6.15 mmol) in 15 mL DMF. The reaction was stirred at 0° C. for 1.5 hours then treated with 100 mL H$_2$O. The suspension was extracted with 2×150 mL EtOAc. The combined organic layer was rinsed with brine (3×20 mL), dried over Na$_2$SO$_4$, filtered and concentrated to give a viscous oil. This residue was subjected to flash chromatography on silica gel using 15% EtOAc/Hexanes to give a viscous oil (1.50 g, 63.8%). $^1$H-NMR (CDCl$_3$) δ 7.13 (d, J=9.0 Hz, 1H), 7.07

(brs, 1H), 6.55 (d, J=9.0 Hz, 1H), 4.35-4.33 (m, 1H), 3.58-3.18 (m, 6H), 2.71 (t, J=6.3 Hz, 2H), 2.11-2.04 (m, 2H), 1.91-1.87 (m, 2H), 1.47 (s, 9H). MS (ESI): 325.1 and 327.1 (M+1, 100%).

tert-Butyl 3-(6-amino-3,4-dihydroquinolin-1(2H)-yl)pyrrolidine-1-carboxylate

A suspension of $Pd_2(dba)_3$ (46 mg, 0.05 mmol) in 2 mL anhydrous THF was treated with $P^tBu_3$ (600 μL of a 10% wt in hexanes solution, 0.2 mmol) and stirred at room temperature for 5 minutes. A solution of tert-butyl 3-(6-bromo-3,4-dihydroquinolin-1(2H)-yl)pyrrolidine-1-carboxylate (381 mg, 1.00 mmol) followed by lithium hexamethyldisilizane (2.0 mL of a 1 M solution in THF, 2.0 mmol). The resulting dark brown suspension was heated at 95° C. for 1.5 hours. The mixture was cooled to room temperature and treated with 8 ml of a 1M tetrabutylammonium fluoride solution in THF then stirred at room temperature for 20 minutes. The mixture was partitioned between $Et_2O$ (100 mL) and $H_2O$ (20 mL). After extraction, the organic layer was separated and the aqueous layer was extracted once more with $Et_2O$ (50 mL). The combined organic fractions were dried over $Na_2SO_4$, filtered and concentrated to give a dark brown residue. This residue was subjected to flash chromatography on silica gel using 2.5% 2M $NH_3$ in $MeOH/CH_2Cl_2$ to give a viscous dark brown residue (295 mg, 93.1%). $^1$H-NMR ($CDCl_3$) δ 6.59-6.44 (m, 3H), 4.35-4.23 (m, 1H), 3.59-3.11 (m, 8H), 2.69 (t, J=6.3 Hz, 2H), 2.09-2.04 (m, 2H), 1.93-1.87 (m, 2H), 1.47 (s, 9H). MS (ESI): 318.2 (M+1, 100%).

tert-Butyl-3-(6-(thiophene-2-carboximidamido)-3,4-dihydroquinolin-1(2H)-yl)pyrrolidine-1-carboxylate A solution of tert-butyl 3-(6-amino-3,4-dihydroquinolin-1(2H)-yl)pyrrolidine-1-carboxylate (210 mg, 0.66 mmol) in 12 mL EtOH was treated with methyl thiophene-2-carbimidothioate hydroiodide (377 mg, 1.32 mmol) and stirred overnight at room temperature. Argon was bubbled through the mixture for 20 minutes then it was partitioned between $CH_2Cl_2$ (100 mL) and saturated sodium carbonate (20 mL). The aqueous layer was extracted with an additional 50 mL $CH_2Cl_2$. The combined organic layers were dried over magnesium sulfate, filtered and concentrated to give a dark yellow oil which was subjected to flash chromatography on silica gel using 2% $MeOH/CH_2Cl_2$ then 2.5% 2M $NH_3$ in $MeOH/CH_2Cl_2$ to give a yellow solid (168 mg, 59.6%). $^1$H-NMR (DMSO-$d_6$) δ 7.68 (d, J=3.3 Hz, 1H), 7.57 (d, J=5.1 Hz, 1H), 7.07 (dd, J=3.9, 5.1 Hz, 1H), 6.73 (d, J=8.7 Hz, 1H), 6.59-6.52 (m, 2H), 6.34 (brs, 2H), 4.46-4.34 (m, 1H), 3.51-3.10 (m, 6H), 2.69 (t, J=6.3 Hz, 2H), 2.08-1.99 (m, 2H), 1.85-1.78 (m, 2H), 1.41 (s, 9H). MS (ESI): 427.2 (M+1, 100%).

N-(1-(Pyrrolidin-3-yl)-1,2,3,4-tetrahydroquinolin-6-yl)thiophene-2-carboximidamide dihydrochloride A solution of tert-butyl-3-(6-(thiophene-2-carboximidamido)-3,4-dihydroquinolin-1(2H)-yl)pyrrolidine-1-carboxylate (150 mg, 0.35 mmol) in 5 mL methanol was treated with 10 mL 1N HCl then heated at 70° C. for 30 minutes. The solution was concentrated and dried under reduced pressure to give a yellow solid. This solid was triturated with 5% MeOH/95% $Et_2O$. The yellow solid was collected and dried under reduced pressure. Yield: 125 mg (89.3%). $^1$H-NMR (DMSO-$d_6$) δ 11.23 (s, 1H), 9.78 (brs, 1H), 9.65 (brs, 1H, 9.59 (brs, 1H), 8.61 (s, 1H), 8.15-8.14 (m, 2H), 7.36 (pseudo t, J=4.5 Hz, 1H), 7.09-6.88 (m, 3H), 4.76-4.66 (m, 1H), 3.39-3.06 (m, 6H), 2.72 (t, J=5.4 Hz, 2H), 2.16-2.01 (m, 2H), 1.87-1.83 (m, 2H). MS (EI): 327.2 (M+1). ESI-HRMS calculated for $C_{18}H_{23}N_4S$ (MH$^+$): 327.1637, Observed: 327.1649.

Example 30

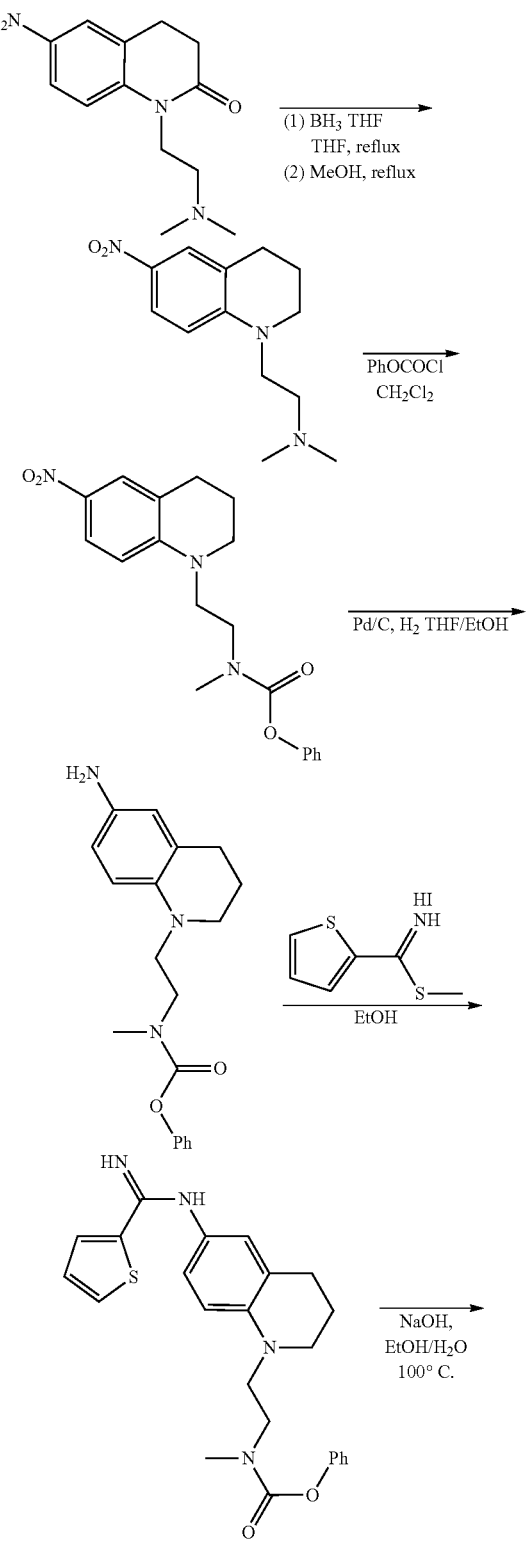

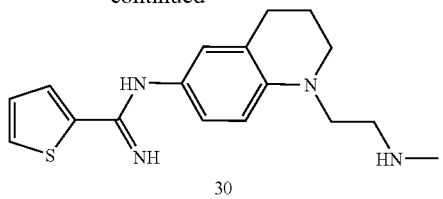

30

1-(2-(Dimethylamino)ethyl)-6-nitro-3,4-dihydro-quinolin-2(1H)-one

A suspension of 6-nitro-3,4-dihydroquinolin-2(1H)-one[1] (1.5 g, 7.80 mmol), 2-chloro-N,N-dimethylethanamine hydrochloride (2.25 g, 15.60 mmol) and potassium carbonate (6.47 g, 46.80 mmol) in 25 mL DMF was stirred at room temperature for 3 days. After this time, the mixture was poured into 20 mL $H_2O$ then extracted with 3×150 mL EtOAc. The combined organic fractions were washed with brine, dried over $Na_2SO_4$, filtered and concentrated. The residue was subjected to flash chromatography on silica gel using 5% 2M $NH_3$ in MeOH/$CH_2Cl_2$ to give a yellow viscous oil (1.5 g, 73.2%). $^1$H-NMR (CDCl$_3$) δ 8.14 (dd, J=2.4, 9.0 Hz, 1H), 8.06 (d, J=2.4 Hz, 1H), 7.15 (d, J=9.0 Hz, 1H), 4.09 (t, J=7.5 Hz, 2H), 3.03-2.98 (m, 2H), 2.73-2.68 (m, 2H), 2.51 (t, J=7.5 Hz, 2H), 2.31 (s, 6H). MS (ESI): 364.1 (M+1).

[1]. Devita et al, WO03/045313

N,N-Dimethyl-2-(6-nitro-3,4-dihydroquinolin-1(2H)-yl)ethanamine

A solution of 1-(2-(dimethylamino)ethyl)-6-nitro-3,4-dihydroquinolin-2(1H)-one (1.0 g, 3.80 mmol) in 10 mL THF was cooled to 0° C. and treated with a solution of 1M borane in THF (21.5 mL, 21.50 mmol). The solution was heated at reflux for 6 hours then stirred at room temperature for 1 day. After this time, the mixture was cooled to 0° C. and quenched with methanol (5 mL). The mixture was concentrated, dissolved in methanol (20 mL), stirred at room temperature for 3 days then heated at reflux for 6 hours. The reaction was concentrated and the residue was subjected to Biotage silica gel chromatography using a gradient of 1-10% 2M $NH_3$ in MeOH/$CH_2Cl_2$ to give a viscous oil (598 mg, 63.1%). $^1$H-NMR (CDCl$_3$) δ 7.96 (dd, J=2.7, 9 Hz, 1H), 7.85 (d, J=2.1 Hz, 1H), 6.48 (d, J=9 Hz, 1H), 3.50-3.43 (m, 4H), 2.78 (t, J=6.3 Hz, 2H), 2.50 (t, J=7.5 Hz, 2H), 2.29 (t, 6H), 1.99-1.94 (m, 2H). MS (ESI): 250.2 (M+1).

Phenyl methyl(2-(6-nitro-3,4-dihydroquinolin-1(2H)-yl)ethyl)carbamate

A solution of N,N-dimethyl-2-(6-nitro-3,4-dihydroquinolin-1(2H)-yl)ethanamine (500 mg, 2.01 mmol) in 10 mL $CH_2Cl_2$ was treated dropwise with phenylchloroformate (378 μL, 3.01 mmol). The reaction was stirred at room temperature for 17 hours then partitioned between $CH_2Cl_2$ 100 mL and 1N NaOH (20 mL). After extraction, the organic layer was separated, dried over $Na_2SO_4$, filtered and concentrated to give a yellow residue. This residue was subjected to flash chromatography on silica gel using 20% EtOAc/$CH_2Cl_2$ to give a yellow residue (610 mg, 85.4%). $^1$H-NMR (CDCl$_3$) δ 7.99-7.92 (m, 1H), 7.87 (d, J=2.1 Hz, 1H), 7.39-7.33 (m, 2H), 7.23-7.19 (m, 1H), 7.06-7.01 (m, 2H), 6.69 (m, 1H), 3.67-3.52 (m, 4H), 3.48 (t, J=5.7 Hz, 2H), 3.14 and 3.07 (2×s, 3H), 2.79 (t, J=6.3 Hz, 2H), 1.99-1.96 (m, 2H). MS (ESI): 356.2 (M+1).

Phenyl 2-(6-amino-3,4-dihydroquinolin-1(2H)-yl)ethyl(methyl)carbamate

A suspension of phenyl methyl(2-(6-nitro-3,4-dihydroquinolin-1(2H)-yl)ethyl)carbamate (500 mg, 1.41 mmol) and palladium on activated carbon (10%, 75 mg, 0.07 mmol) in a 1:1 mixture of THF/EtOH (20 mL) was stirred under a balloon of hydrogen for 4.5 hours. The suspension was filtered through a pad of celite. The filter pad was rinsed with 25 mL methanol and the filtrate was concentrated to give a dark viscous oil. The crude product was used without further purification (460 mg, quantitative). $^1$H-NMR (CDCl$_3$) δ 7.39-7.34 (m, 2H), 7.22-7.17 (m, 1H), 7.12-7.08 (m, 2H), 6.61-6.42 (m, 3H), 3.61-3.45 (m, 4H), 3.26 (t, J=6.0 Hz, 2H), 3.20 (brs, 2H), 3.13 and 3.06 (2×s, 3H), 2.70 (t, J=6.3 Hz, 2H), 1.96-1.87 (m, 2H). MS (ESI): 326.2 (M+1).

Phenyl methyl(2-(6-(thiophene-2-carboximidamido)-3,4-dihydroquinolin-1(2H)-yl)ethyl)carbamate A solution of phenyl 2-(6-amino-3,4-dihydroquinolin-1(2H)-yl)ethyl(methyl)carbamate (445 mg, 1.37 mmol) in 20 mL EtOH was treated with methyl thiophene-2-carbimidothioate hydroiodide (780 mg, 2.73 mmol) and stirred overnight at room temperature. Argon was bubbled through the mixture for 20 minutes then it was partitioned between $CH_2Cl_2$ (100 mL) and saturated sodium carbonate (20 mL). After extraction, the organic layer was separated and the aqueous layer was extracted with an additional 100 mL $CH_2Cl_2$. The combined organic layers were dried over sodium sulfate, filtered and concentrated to give a dark oil which was subjected to flash chromatography on silica gel using 2.5% MeOH/$CH_2Cl_2$ then 2.5-7.5% 2M $NH_3$ in MeOH/$CH_2Cl_2$ to give a yellow-brown solid (400 mg, 67.2%). $^1$H-NMR (DMSO-d$_6$) δ 7.68 (brs, 1H), 7.58 (d, J=5.1 Hz, 1H), 7.42-7.34 (m, 2H), 7.24-7.18 (m, 1H), 7.11-7.03 (m, 3H), 6.68 (d, J=9.0 Hz, 1H), 6.57-6.51 (m, 2H), 6.29 (brs, 2H), 3.58-3.44 (m, 4H), 3.32-3.27 (m, 2H), 3.09 and 2.97 (2×s, 3H), 2.73-2.65 (m, 2H), 1.90-1.83 (m, 2H). MS (ESI): 435.2 (M+1, 100%).

N-(1-(2-(Methylamino)ethyl)-1,2,3,4-tetrahydroquinolin-6-yl)thiophene-2-carboximidamide dihydrochloride A solution of phenyl methyl(2-(6-(thiophene-2-carboximidamido)-3,4-dihydroquinolin-1(2H)-yl)ethyl)carbamate (380 mg, 0.87 mmol) in 15 mL ethanol was treated with NaOH (350 mg, 8.70 mmol) followed by $H_2O$ (8 mL). The mixture was then heated at reflux for 6 hours. The solution was concentrated and partitioned between $CH_2Cl_2$ (100 mL) and brine (20 mL). After extraction, the organic layer was separated, and the aqueous layer was extracted once more $CH_2Cl_2$ (100 mL). The combined organic layers were rinsed with brine, dried over $Na_2SO_4$, filtered and concentrated to give a dark residue. This residue was subjected to flash chromatography on silica gel using 5% 2M $NH_3$ in MeOH/$CH_2Cl_2$ to give a yellow solid 30 (155 mg, 56.8%). The free base was converted to the dihydrochloride salt by dissolving in MeOH and adding 1M HCl in Et$_2$O. $^1$H-NMR (CD$_3$OD) δ 7.98-7.95 (m, 2H), 7.31-7.28 (m, 1H), 7.05 (dd, J=2.4, 8.7 Hz, 1H), 6.97 (d, J=2.4 Hz, 1H), 6.81 (d, J=8.7 Hz, 1H), 3.62 (t, J=6.6 Hz, 2H), 3.34 (t, J=5.4 Hz, 2H), 3.20 (t, J=6.9 Hz, 2H), 2.78 (t, J=6.0 Hz, 2H), 2.72 (s, 3H), 1.99-1.92 (m, 2H). MS (EI): 315.2 (M+1). ESI-HRMS calculated for $C_{17}H_{23}N_4S$ (MH+): 315.1637, Observed: 315.1629.

Example 31

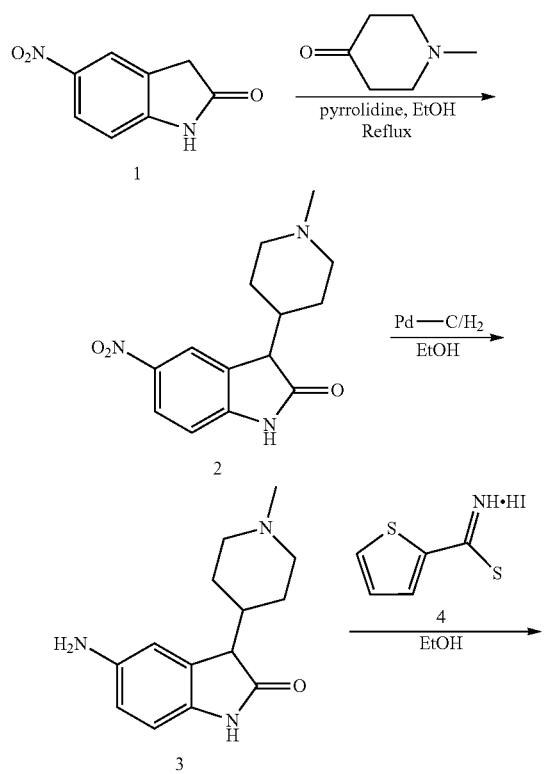

3-(1-Methylpiperidin-4-yl)-5-nitroindolin-2-one (2)

A solution of compound 1 (0.5 g, 2.806 mmol), N-methyl-4-piperidone (0.69 mL, 5.613 mmol) and pyrrolidine (0.7 mL, 8.420 mmol) in dry ethanol (10 mL) was refluxed for 4 h. The reaction was brought to room temperature, diluted with water (20 mL) and product was extracted into $CH_2Cl_2$ (2×25 mL). The combined $CH_2Cl_2$ layer was washed with brine (10 mL) and dried ($Na_2SO_4$). Solvent was evaporated and crude product was purified by column chromatography (2 M $NH_3$ in MeOH:$CH_2Cl_2$, 2.5:97.5) to obtain compound 2 (0.2 g, 26%) as a solid. $^1H$ NMR (DMSO-$d_6$) δ 11.05 (s, 1H), 8.17 (dd, 1H, J=2.1, 8.5 Hz), 8.09 (s, 1H), 6.99 (d, 1H, J=8.7 Hz), 3.59 (d, 1H, J=3.6 Hz), 2.77-2.70 (m, 2H), 2.09 (s, 3H), 2.05-1.96 (m, 1H), 1.84-1.74 (m, 2H), 1.54-1.36 (m, 4H); ESI-MS (m/z, %): 276 (MH+, 100).

5-Amino-3-(1-methylpiperidin-4-yl)indolin-2-one (3)

A solution of compound 2 (0.18 g, 0.654 mmol) in dry ethanol (5 mL) was treated with Pd—C (~0.02 g) and purged with hydrogen gas. The reaction was stirred at room temperature under hydrogen atm. (balloon pressure) overnight (16 h). The reaction was filtered through celite bed, washed with methanol (3×10 mL). The combined organic layer was evaporated and crude was purified by column chromatography (2M $NH_3$ in MeOH:$CH_2Cl_2$, 1:9) to obtain compound 3 (0.08 g, 50%) as a foam. $^1H$ NMR (DMSO-$d_6$) δ 9.89 (s, 1H), 6.57 (s, 1H), 6.48 (d, 1H, J=8.1 Hz), 6.37 (d, 1H, J=8.1 Hz), 4.64 (s, 2H), 2.78-2.67 (m, 2H), 2.09-2.04 (m, 4H), 1.87-1.70 (m, 3H), 1.61-1.52 (m, 2H), 1.37-1.26 (m, 2H); ESI-MS (m/z, %): 246 (MH+, 100).

N-(3-(1-Methylpiperidin-4-yl)-2-oxoindolin-5-yl)thiophene-2-carboximidamide (31)

A solution of compound 3 (0.07 g, 0.285 mmol) in dry ethanol (3 mL) was treated with compound 4 (0.16 g, 0.570 mmol) at room temperature and the resulting mixture was stirred for 2 days. The reaction was diluted with sat. $NaHCO_3$ solution (20 mL) and product was extracted into $CH_2Cl_2$ (2×15 mL). The combined organic layer was washed with brine (15 mL) and dried ($Na_2SO_4$). Solvent was evaporated and crude was purified by column chromatography (2M $NH_3$ in MeOH:$CH_2Cl_2$, 1:9) to obtain compound 31 (0.075 g, 75%) as a solid. $^1H$ NMR (DMSO-$d_6$) δ 10.19 (s, 1H), 7.71 (d, 1H, J=3.3 Hz), 7.59 (d, 1H, J=4.5 Hz), 7.09 (t, 1H, J=4.5 Hz), 6.75-6.65 (m, 3H), 6.34 (brs, 2H), 2.74 (t, 2H, J=10.5 Hz), 2.56-2.46 (m, 1H, merged with DMSO peak), 2.10 (s, 3H), 1.90-1.75 (m, 3H), 1.58-1.32 (m, 4H); ESI-MS (m/z, %): 355 (MH+, 51), 178 (100); ESI-HRMS calculated for $C_{19}H_{23}N_4OS$ (MH+), calculated: 355.1587; observed: 355.1580; HPLC purity 98.34% by area.

Example 32

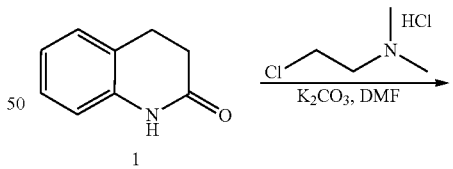

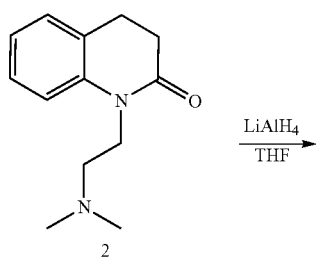

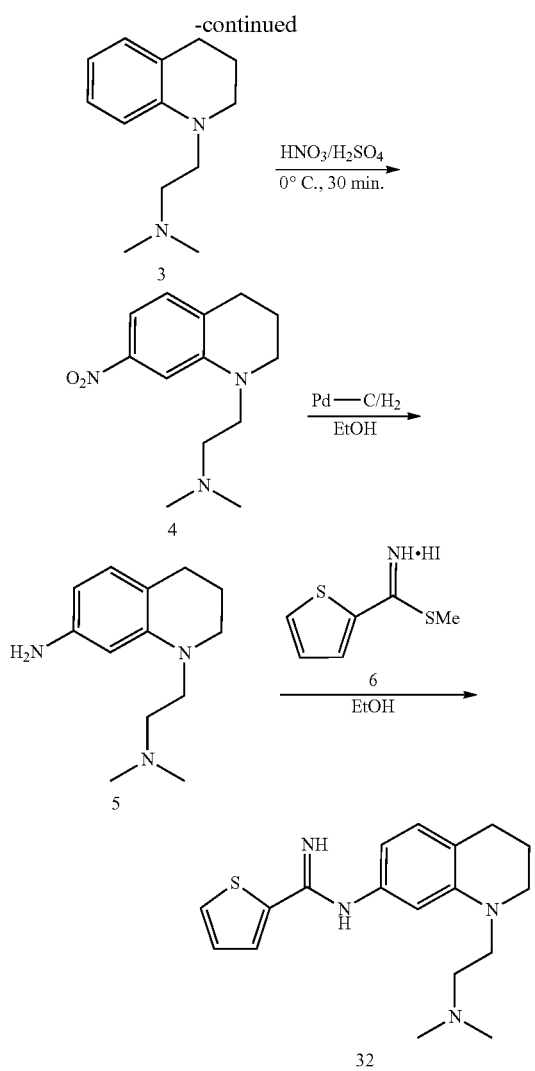

1-(2-(Dimethylamino)ethyl)-3,4-dihydroquinolin-2(1H)-one (2)

A solution of compound 1 (4 g, 27.179 mmol) in dry DMF (50 mL) was treated with $K_2CO_3$ (11.26 g, 81.538 mmol) followed by 2-chloro-N,N-dimethylethanamine hydrochloride (4.30 g, 29.897 mmol) at room temperature. The resulting mixture was stirred at 85° C. for 2.5 days. The reaction was brought room temperature, diluted with water (250 mL) and product was extracted into ethyl acetate (2×50 mL). The combined organic layer was washed with brine (25 mL) and dried ($Na_2SO_4$). The solvent was evaporated and crude was purified by column chromatography (2 M $NH_3$ in MeOH:$CH_2Cl_2$, 5:95) to obtain compound 2 (2.2 g, 37%) as a syrup. $^1$H NMR (DMSO-$d_6$) δ 7.27-7.19 (m, 2H), 7.12 (d, 1H, J=8.1 Hz), 6.98 (t, 1H, J=6.3 Hz), 3.96 (t, 2H, J=7.5 Hz), 2.82 (t, 2H, J=7.8 Hz), 2.51 (t, 2H, J=7.8 Hz), 2.37 (t, 2H, J=7.2 Hz), 2.18 (s, 6H); EI-MS (m/z, %): 218 (MH$^+$, 2), 71 (36), 58 (100).

2-(3,4-Dihydroquinolin-1(2H)-yl)-N,N-dimethylethanamine (3)

A solution of LiAlH$_4$ (39.39 mL, 39.397 mmol, 1 M solution in THF) was treated with compound 2 (2.15 g, 9.849 mmol) in dry THF (25 mL) at 0° C. The reaction was brought to room temperature and stirred for over night (18 h). The reaction was quenched with water (1.5 mL), 2 N NaOH solution (1.5 mL) and water (1.5 mL). After stirring for 30 min. at room temperature, the reaction was filtered, washed with $CH_2Cl_2$ (4×20 mL). The combined organic layer was evaporated and crude was purified by column chromatography (2 M $NH_3$ in MeOH:$CH_2Cl_2$, 2:98 to 5:95) to obtain compound 3 (0.95 g, 47%) as a syrup. $^1$H NMR (DMSO-$d_6$) δ 6.93 (t, 1H, J=8.1 Hz), 6.83 (d, 1H, J=7.2 Hz), 6.51 (d, 1H, J=8.1 Hz), 6.43 (t, 1H, J=7.8 Hz), 3.33-3.24 (m, 4H), 2.64 (t, 2H, J=6.3 Hz), 2.36 (t, 2H, J=7.5 Hz), 2.17 (s, 6H), 1.85-1.77 (m, 2H); ES-MS (m/z, %) 205 (MH$^+$, 22), 160 (100), 132 (65).

N,N-Dimethyl-2-(7-nitro-3,4-dihydroquinolin-1(2H)-yl)ethanamine (4)

A solution of compound 3 (0.87 g, 4.285 mmol) in con. $H_2SO_4$ (10 mL) was treated with fuming HNO$_3$ (0.2 mL, 4.285 mmol, 90%) drop wise over a period of 10 min. at 0° C. and was stirred at same temperature for additional 20 min. The reaction was diluted with water (50 mL), basified to pH ~10 using 2 N NaOH solution and product was extracted into $CH_2Cl_2$ (3×20 mL). The combined organic layer was washed with brine (15 mL) and dried ($Na_2SO_4$). Solvent was evaporated and crude was purified by column chromatography (2 M $NH_3$ in MeOH:$CH_2Cl_2$, 2.5:97.5 to obtain compound 4 (0.85 g, 80%) including some dinitro derivative, which was separated at later stage.

1-(2-(Dimethylamino)ethyl)-1,2,3,4-tetrahydroquinolin-7-amine (5)

A solution of compound 4 (0.8 g, 3.208 mmol) in dry ethanol (20 mL) was treated with Pd—C (~0.08 g) and purged with hydrogen gas. The reaction was stirred at room temperature under hydrogen atm. for 3 h. The reaction was filtered through celite bed and washed with methanol (3×20 mL). The combined organic layer was evaporated and crude was purified by column chromatography (2 M NH$_3$ in MeOH:$CH_2Cl_2$, 5:95) to obtain compound 5 (0.6 g, 86%).

N-(1-(2-(Dimethylamino)ethyl)-1,2,3,4-tetrahydroquinolin-7-yl)thiophene-2-carboximidamide (36)

A solution of compound 5 (0.55 g, 2.507 mmol) in dry ethanol (10 mL) was treated with compound 6 (1.43 g, 5.015 mmol) at room temperature and the resulting mixture was stirred for over night (16 h). The reaction was diluted with sat. NaHCO$_3$ solution (50 mL) and product was extracted into $CH_2Cl_2$ (2×25 mL). The combined organic layer was washed with brine (15 mL) and dried ($Na_2SO_4$). Solvent was evaporated and crude was purified by column chromatography (2 M NH$_3$ in MeOH:$CH_2Cl_2$, 3:97) to obtain compound 32 (0.5 g, 61%) as a solid. $^1$H NMR (DMSO-$d_6$) δ 7.69 (dd, 1H, J=0.9, 3.6 Hz), 7.57 (dd, 1H, J=0.9, 5.1 Hz), 7.07 (dd, 1H, J=3.9, 5.1 Hz), 6.78 (d, 1H, J=7.8 Hz), 6.25 (brs, 2H), 6.01-5.98 (m, 2H), 3.32-3.25 (m, 4H), 2.38 (t, 2H, J=6.9 Hz), 2.16 (s, 6H), 1.86-1.80 (m, 2H); ESI-MS (m/z, %): 329 (MH$^+$, 100), 258 (40); ESI-HRMS calculated for $C_{18}H_{25}N_4S$ (MH$^+$), calculated: 329.1794; observed: 329.2808; HPLC purity 96.37% by area.

Example 33

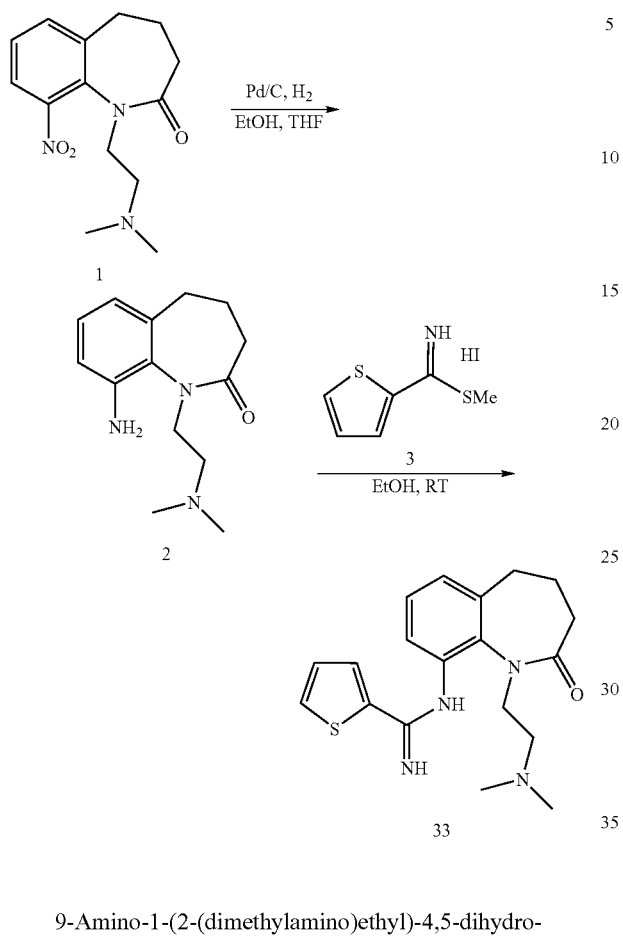

9-Amino-1-(2-(dimethylamino)ethyl)-4,5-dihydro-1H-benzo[b]azepin-2(3H)-one (2)

1-(2-(dimethylamino)ethyl)-9-nitro-4,5-dihydro-1H-benzo[b]azepin-2(3H)-one (100 mg, 0.361 mmol) was stirred to dissolve in a mixture of ethanol (4 mL) and THF (3 mL). To this solution was added palladium on carbon, 10 wt %, (40 mg) as a solid. The black suspension was stirred under hydrogen gas for 3 h. When TLC analysis showed that the starting material was consumed the reaction mixture was filtered through a pad of celite and washed with methanol. The filtrate was concentrated and then chromatographed on silica gel in 10% 2 N $NH_3$/MeOH in dichloromethane. Yield 90 mg (quantitative). $^1$H NMR (DMSO-$d_6$) δ 6.86 (d, 1H, J=8.1 Hz), 6.53 (d, 1H, J=3.0 Hz), 6.38 (dd, 1H, J=8.1, 3.0 Hz), 5.02 (brs, 2H), 2.50 (m, 2H), 2.25 (m, 2H), 1.8-2.2 (m, 10H); ESI-MS (m/z, %): 248 (MH+, 58), 203 (100).

N-(1-(2-(Dimethylamino)ethyl)-2-oxo-2,3,4,5-tetrahydro-1H-benzo[b]azepin-9-yl)thiophene-2-carboximidamide (33)

To a stirred solution of 9-amino-1-(2-(dimethylamino)ethyl)-4,5-dihydro-1H-benzo[b]azepin-2(3H)-one (85 mg, 0.344 mmol) in EtOH (6 mL) was added methyl thiophene-2-carbimidothioate hydroiodide (196 mg, 0.687 mmol). The resulting suspension was stirred overnight at room temperature. The reaction mixture was then diluted with $Na_2CO_3$ (aq, sat) and extracted with dichloromethane (3×). The combined organics were dried, filtered and concentrated, then chromatographed in 2-5% 2M $NH_3$/MeOH in dichloromethane, giving the desired product. Yield: 87 mg, 71%. $^1$H NMR (DMSO-$d_6$) δ 7.75 (d, 1H, J=3.3 Hz), 7.61 (d, 1H, J=4.5 Hz), 7.16 (d, 1H, J=7.8 Hz), 7.10 (m, 1H), 6.82 (s, 1H), 6.66 (d, 1H, J=8.1 Hz), 6.46 (brs, 2H), 2.65 (m, 3H), 2.28 (m, 3H), 2.17 (m, 2H), 1.9-2.15 (m, 8H). ESI-MS (m/z, %): 357 (MH+, 100), 312 (48), 156 (38), 148 (31).

Example 34

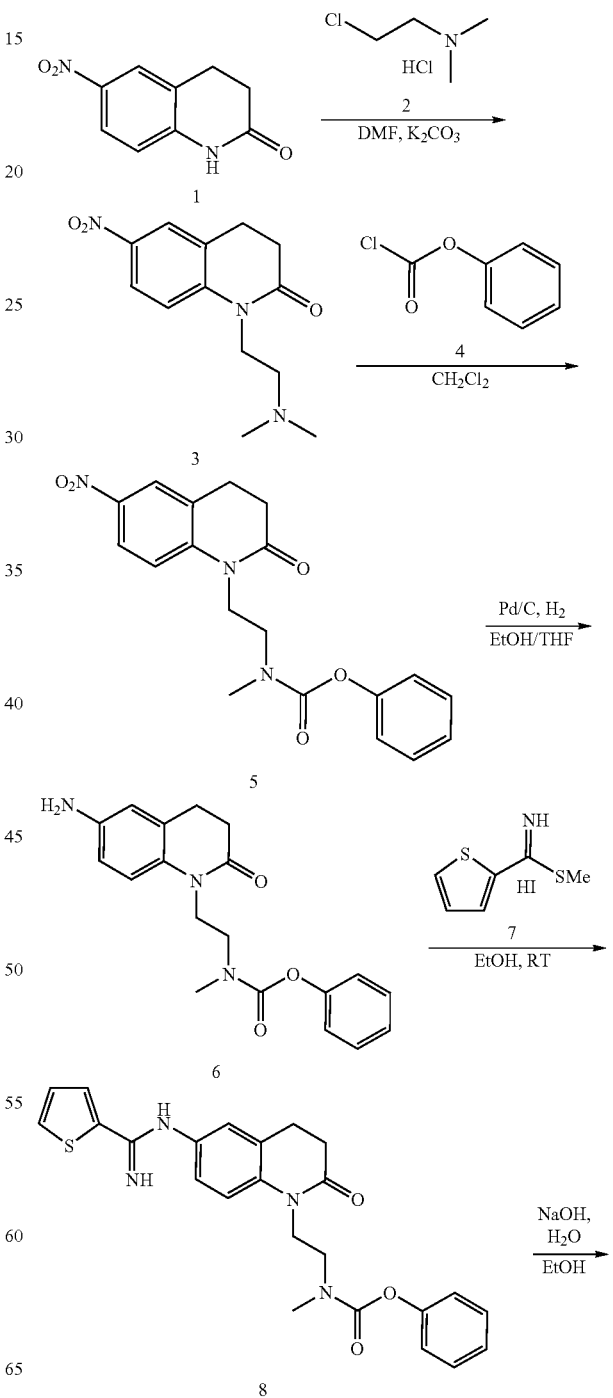

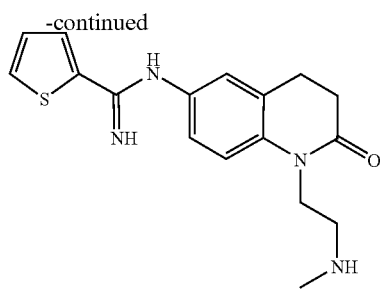

34

1-(2-(Dimethylamino)ethyl)-6-nitro-3,4-dihydroquinolin-2(1H)-one (3)

6-Nitro-3,4-dihydroquinolin-2(1H)-one (5 g, 25.61 mmol) and 2-chloro-N,N-dimethylethanamine hydrochloride (7.38 g, 51.23 mmol) were weighed into a round bottom flask and stirred in DMF (50 mL). To this solution/suspension was added potassium carbonate (21.59 g, 156.2 mmol). The resulting suspension was stirred overnight at room temperature. The reaction mixture was then poured into ice water (150 mL) and extracted with ethyl acetate (2×100 mL). The combined organics were washed with water (1×) and brine (1×). The organic phase was dried over sodium sulfate, filtered and concentrated. The resulting residue was chromatographed in 0-20% (2M $NH_3$ in MeOH) in 1:1 dichloromethane and ethyl acetate, giving a yellow solid. Yield: 5.8 g, 84%. $^1$H NMR ($CDCl_3$) δ 8.14 (dd, 1H, J=9.0, 3.0 Hz) 8.06 (d, 1H, J=3.0 Hz), 7.16 (d, 1H, J=9.0 Hz), 4.08 (t, 1H, J=7.5 Hz), 3.00 (t, 1H, J=7.5 Hz), 2.70 (t, 1H, J=7.5 Hz); 2.51 (t, 1H, J=7.5 Hz), 2.31 (s, 6H).

Phenyl methyl(2-(6-nitro-2-oxo-3,4-dihydroquinolin-1(2H)-yl)ethyl)carbamate (5)

1-(2-(Dimethylamino)ethyl)-6-nitro-3,4-dihydroquinolin-2(1H)-one (1.16 g, 4.40 mmol) was dissolved in dichloromethane (20 mL) in a round bottom flask at room temperature. The solution was cooled to 0° C. and phenyl chloroformate (0.829 mL, 6.61 mmol) was added slowly to avoid an excessive exotherm. The reaction mixture was then warmed to room temperature and stirred overnight. The reaction mixture was then diluted with dichloromethane and quenched with dilute NaOH (~0.5 M). The aqueous phase was extracted with dichloromethane (3×) and the combined organics were dried over sodium sulfate, filtered and concentrated. The resulting residue was then chromatographed in 50-100% ethyl acetate in hexanes. Yield: 1.29 g, 78%. $^1$H NMR ($CDCl_3$) δ 8.13 (dd, 1H, J=9.0, 2.7 Hz), 8.05 (t, 1H, J=3.3 Hz), 7.41 (m, 3H); 7.23 (m, 1H); 7.06 (m, 2H), 4.23 (m, 2H), 3.70 and 3.58 (2t, 2H, J=7.2 Hz), 3.19 and 3.09 (2s, 3H), 3.00 (t, 2H, J=7.4 Hz), 2.72 (t, 2H, J=7.4 Hz); ESI-MS (m/z, %): 392 ($MNa^+$, 100), 370 (MH+, 28).

Phenyl 2-(6-amino-2-oxo-3,4-dihydroquinolin-1 (2H)-yl)ethyl(methyl)carbamate (6)

Phenyl methyl(2-(6-nitro-2-oxo-3,4-dihydroquinolin-1 (2H)-yl)ethyl)carbamate (1.29 g, 3.49 mmol) was dissolved by stirring in ethanol (40 mL) and THF (30 mL) in a round bottom flask. The solution was stirred under an atmosphere of hydrogen for 6 h at room temperature. When TLC confirmed the reaction was completed, the mixture was filtered through celite, and the filtrate was concentrated. The resulting residue was chromatographed on silica gel eluting with ethyl acetate, giving a white/pink foam. Yield: 990 mg, 84%. $^1$H NMR (DMSO-$d_6$) δ 7.36 (m, 2H), 7.20 (m, 1H), 7.01 (m, 2H); 6.91 (d, 1H, J=8.4 Hz), 6.43 (m, 2H), 4.87 (s, 2H), 4.11 and 4.03 (2m, 2H), 3.56 and 3.44 (2t, 2H, J=6.0 Hz), 2.99 and 2.87 (2s, 3H), 2.66 (m, 2H), 2.43 (m, 2H); ESI-MS (m/z, %): 362 ($MNa^+$, 35), 340 ($MH^+$, 100), 202 (44).

Phenyl methyl(2-(2-oxo-6-(thiophene-2-carboximidamido)-3,4-dihydroquinolin-1(2H)-yl)ethyl)carbamate (8)

Methyl thiophene-2-carbimidothioate hydroiodide (1.62 g, 5.71 mmol) was weighed into a round bottom flask with a stirbar. Phenyl 2-(6-amino-2-oxo-3,4-dihydroquinolin-1 (2H)-yl)ethyl(methyl)carbamate (0.969 g, 2.85 mmol) was dissolved in ethanol (50 mL) and added to the flask. The resulting suspension was stirred overnight at room temperature. When the reaction was finished, argon was bubbled through the reaction mixture for 1 h, then the mixture was neutralized with sodium carbonate (sat. aq. solution). The product was extracted with dichloromethane (3×). The combined organics were dried over sodium sulfate, filtered and concentrated. The residue was chromatographed in (1:1) ethyl acetate:$CH_2Cl_2$ then 10% (2M $NH_3$ in methanol) in dichloromethane. Yield: 700 mg, 55%. $^1$H NMR (DMSO-$d_6$) δ 7.91 (m, 2H), 7.38 (m, 2H), 7.26 (m, 3H), 7.04 (m, 4H), 4.23 and 4.14 (2m, 2H), 3.63 and 3.51 (2m, 2H), 3.06 and 2.92 (2s, 3H), 2.84 (t, 2H, J=6.9 Hz), 2.56 (t, 2H, J=6.9 Hz); ESI-MS (m/z, %): 449 ($MH^+$, 100).

N-(1-(2-(Methylamino)ethyl)-2-oxo-1,2,3,4-tetrahydroquinolin-6-yl)thiophene-2-carboximidamide (34)

Phenyl methyl(2-(2-oxo-6-(thiophene-2-carboximidamido)-3,4-dihydroquinolin-1(2H)-yl)ethyl)carbamate (700 mg, 1.56 mmol) was stirred in EtOH (20 mL). To this suspension was added solid NaOH (624 mg, 15.6 mmol), followed by water (10 mL). The flask was then fitted with a condenser and was heated to reflux for 2 h. When TLC analysis showed that the reaction was complete, the mixture was cooled to room temperature and diluted with water. The product was extracted with dichloromethane (3×) and the combined organics were dried, filtered and concentrated, then chromatographed in EtOAc, followed by 10% 2M $NH_3$/MeOH in dichloromethane. The isolated spot was then triturated with methanol and ether. Yield: 223 mg, 43%). $^1$H NMR (DMSO-d6) δ 7.73 (d, 1H, J=3.6 Hz), 7.59 (d, 1H, J=5.4 Hz), 7.10 (m, 2H), 6.73 (m, 2H), 6.45 (brs, 2H), 3.91 (t, 1H, J=7.2 Hz), 2.81 (t, 1H, J=7.2 Hz), 2.65 (t, 1H, J=7.2 Hz), 2.50 (t, 1H, J=7.2 Hz); ESI-MS (m/z, %): 329 ($MH^+$, 70), 149 (100), 141 (80), 127 (96).

Example 35

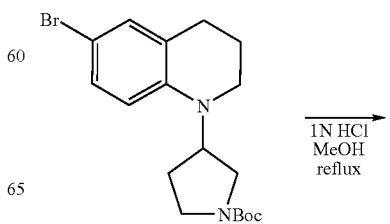

-continued

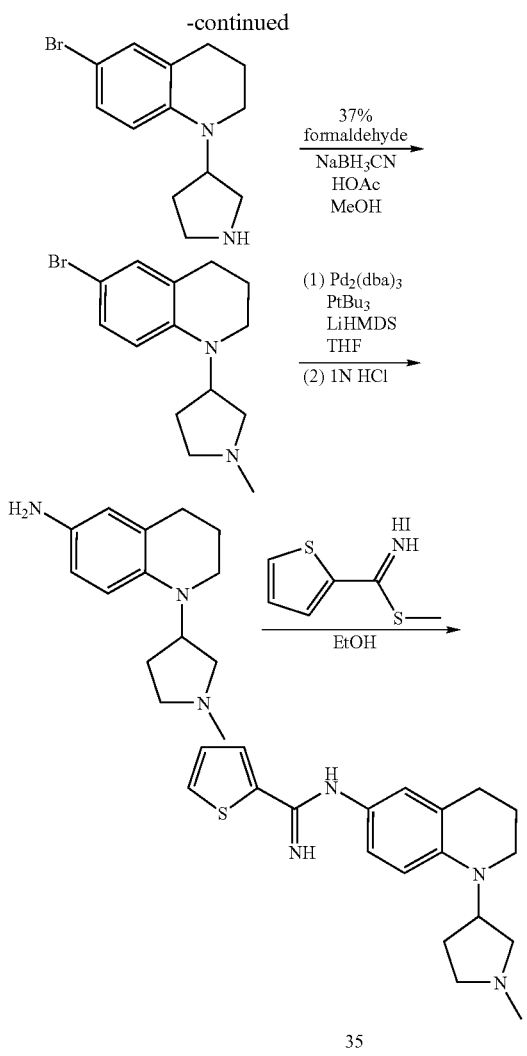

6-Bromo-1-(pyrrolidin-3-yl)-1,2,3,4-tetrahydroquinoline

A solution of tert-butyl 3-(6-bromo-3,4-dihydroquinolin-1(2H)-yl)pyrrolidine-1-carboxylate (see Example 29; 700 mg, 1.83 mmol) in 10 mL methanol was treated with 12 mL 1N aq. HCl. A precipitate formed upon addition of the HCl solution. Additional methanol (10 mL) was added to solubilize the mixture. The solution was then heated at reflux for 30 minutes. The solution was concentrated and extracted with $CH_2Cl_2$ (2×50 mL). The aqueous layer was basified with saturated $Na_2CO_3$ and extracted with $CH_2Cl_2$ (2×100 mL). The combined organic fractions were rinsed with brine, dried over $Na_2SO_4$, filtered and concentrated to give the title compound as an oil. Yield: 404 mg (78.4%). $^1$H-NMR (CDCl$_3$) δ 7.11 (dd, J=2.7, 9.0 Hz, 1H), 7.04 (d, J=2.1 Hz, 1H), 6.57 (d, J=8.7 Hz, 1H), 4.36-4.27 (m, 1H), 3.21 (t, J=5.4 Hz, 2H), 3.16-2.90 (m, 4H), 2.71 (t, J=6.3 Hz, 2H), 2.11-2.00 (m, 1H), 1.93-1.78 (m, 4H). MS(ESI): 281.1 and 283.1 (M+1).

6-Bromo-1-(1-methylpyrrolidin-3-yl)-1,2,3,4-tetrahydroquinoline

A solution of 6-bromo-1-(pyrrolidin-3-yl)-1,2,3,4-tetrahydroquinoline (200 mg, 0.71 mmol) in 7 mL anhydrous methanol was treated with formaldehyde (37% aqueous solution, 79 μL, 1.07 mmol) followed by acetic acid (100 μL, 1.78 mmol). The solution was treated with sodium cyanoborohydride (67 mg, 1.07 mmol). The suspension was stirred at room temperature for 3 hours. The mixture was concentrated to dryness and partitioned between 20 mL 1N NaOH and 100 mL of $CH_2Cl_2$. After extraction, the organic layer was dried over $Na_2SO_4$, filtered and concentrated to give an oily residue which was subjected to flash chromatography on silica gel using 5% 2M $NH_3$ in MeOH/$CH_2Cl_2$. A yellow oil was obtained (153 mg, 72.9%). $^1$H-NMR (CDCl$_3$) δ 7.10 (dd, J=2.4, 8.7 Hz, 1H), 7.04 (d, J=2.4 Hz, 1H), 6.57 (d, J=9.0 Hz, 1H), 4.47-4.38 (m, 1H), 3.26 (t, J=5.7 Hz, 2H), 2.81-2.68 (m, 4H), 2.60-2.55 (m, 1H), 2.40-2.24 (m, 1H), 2.35 (s, 3H), 2.24-2.13 (m, 1H), 1.92-1.79 (m, 3H). MS(ESI): 295.1 and 297.1 (M+1).

1-(1-Methylpyrrolidin-3-yl)-1,2,3,4-tetrahydroquinolin-6-amine

A suspension of $Pd_2(dba)_3$ (22 mg, 0.024 mmol) in 2 mL anhydrous THF was treated P$^t$Bu$_3$ (285 μL of a 10% wt in hexane solution, 0.094 mmol). The mixture was stirred at room temperature for 5 minutes then lithium hexamethyldisililazide (0.95 mL of a 1 M solution in THF, 0.95 mmol) was added. The resulting dark mixture was treated with 6-bromo-1-(1-methylpyrrolidin-3-yl)-1,2,3,4-tetrahydroquinoline (140 mg, 0.47 mmol) in 8 mL THF. The dark brown suspension was heated at 95° C. in a sealed tube for 2 hours. The mixture was concentrated and treated with 5 ml of a 1N HCl solution then stirred at room temperature for 10 minutes. The mixture was partitioned between $CH_2Cl_2$ (100 mL) and 1N NaOH (20 mL). After extraction, the organic layer was separated and dried over $Na_2SO_4$, filtered and concentrated to give a dark brown residue. This residue was subjected to flash chromatography on silica gel using 2.5% MeOH/$CH_2Cl_2$ then 5% 2M $NH_3$ in MeOH/$CH_2Cl_2$ to give a dark brown residue (95 mg, 87.2%). $^1$H-NMR (CDCl$_3$) δ 6.59 (d, J=8.4 Hz, 1H), 6.47 (dd, J=2.7, 8.7 Hz, 1H), 6.42 (d, J=2.4 Hz, 1H), 4.45-4.38 (m, 1H), 3.28 (brs, 2H), 3.23-3.12 (m, 2H), 2.75-2.60 (m, 5H), 2.45-2.39 (m, 1H), 2.34 (s, 3H), 2.19-2.09 (m, 1H), 1.92-1.82 (m, 3H). MS (EI): 232.2 (M+1).

N-(1-(1-Methylpyrrolidin-3-yl)-1,2,3,4-tetrahydroquinolin-6-yl)thiophene-2-carboximidamide A solution of 1-(1-methylpyrrolidin-3-yl)-1,2,3,4-tetrahydroquinolin-6-amine (80 mg, 0.35 mmol) in 8 mL ethanol was treated with methyl thiophene-2-carbimidothioate hydroiodide (197 mg, 0.69 mmol) and stirred overnight at room temperature. The mixture was diluted with $CH_2Cl_2$ (10 mL) and argon was bubbled through the solution for 20 minutes. The solution was partitioned between $CH_2Cl_2$ (100 mL) and 1N NaOH (20 mL). After extraction, the organic layer was separated, dried over sodium sulfate, filtered and concentrated to give a dark residue which was subjected to flash chromatography on silica gel using 2.5% MeOH/$CH_2Cl_2$ then 5% 2M $NH_3$ in MeOH/$CH_2Cl_2$. A light brown solid was obtained. This compound was converted to the dihydrochloride salt (95 mg, 65.6%). $^1$H-NMR (DMSO-d$_6$) δ 7.67 (d, J=3.3 Hz, 1H), 7.55 (d, J=5.1 Hz, 1H), 7.08-7.06 (m, 1H), 6.70 (d, J=8.7 Hz, 1H), 6.55-6.50 (m, 2H), 6.29 (brs, 2H), 4.46-4.37 (m, 1H), 3.21-3.15 (m, 2H), 2.74-2.69 (m, 4H), 2.50-2.43 (m, 2H), 2.25 (s, 3H), 2.15-2.04 (m, 1H), 1.86-1.67

(m, 3H). MS (ESI): 341.2 (M+1). ESI-HRMS calculated for $C_{19}H_{25}N_4S$ (MH$^+$): 341.1794, Observed: 341.1788.

Example 36

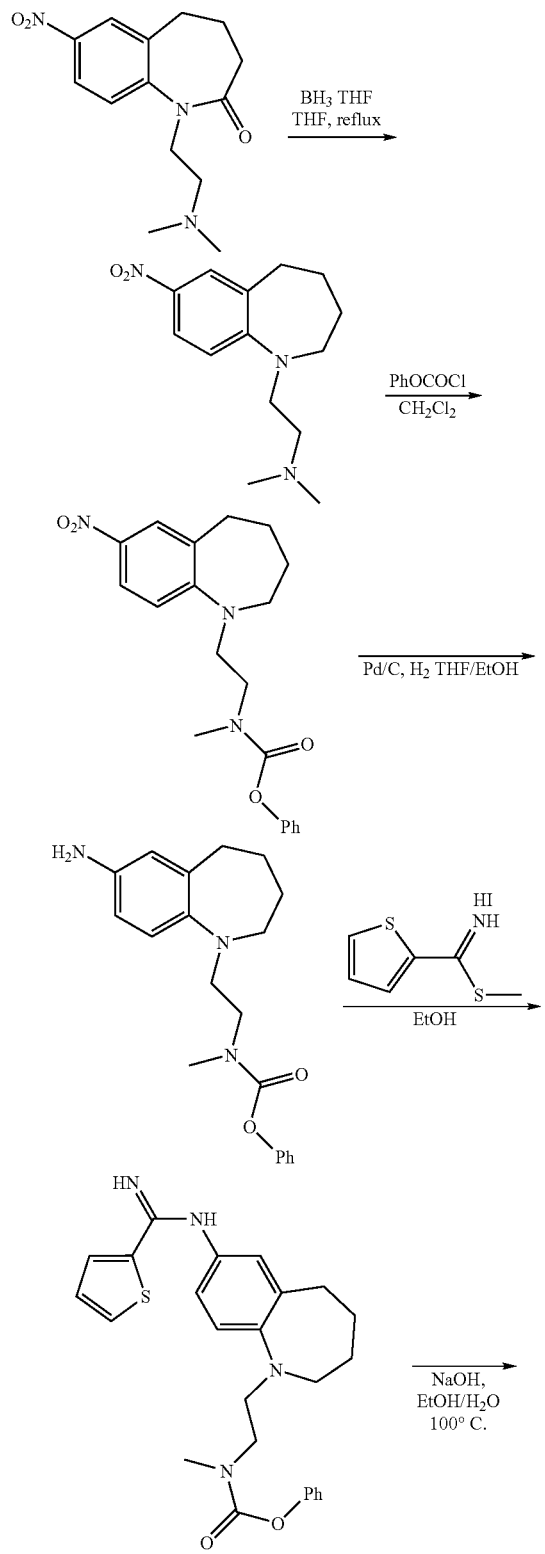

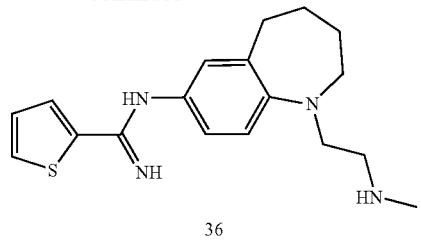

36

1-(2-(Dimethylamino)ethyl)-7-nitro-4,5-dihydro-1H-benzo[b]azepin-2(3H)-one (see Example 25)

A suspension of 7-nitro-4,5-dihydro-1H-benzo[b]azepin-2(3H)-one (490 mg, 2.38 mmol), 2-chloro-N,N-dimethylethanamine hydrochloride (685 mg, 4.75 mmol) and potassium carbonate (1.97 g, 14.28 mmol) in 15 mL DMF was stirred at room temperature for 1 day. A TLC analysis indicated that the starting material is still present. The mixture was treated with 2-chloro-N,N-dimethylethanamine hydrochloride (685 mg, 4.75 mmol) and potassium carbonate (1.97 g, 14.28 mmol) followed by 5 mL DMF and stirring was continued at room temperature for 18 hours. After this time, the mixture was poured into 50 mL $H_2O$ then extracted with 2×100 mL of ethyl acetate. The combined organic fractions were washed with brine, dried over $Na_2SO_4$, filtered and concentrated to give a dark residue. The residue was subjected to flash chromatography on silica gel using 2-5% 2M $NH_3$ in MeOH/$CH_2Cl_2$ to give a yellow viscous oil (412 mg, 62.4%). 1H-NMR (DMSO-d$_6$) δ 8.21-8.15 (m, 2H), 7.67 (d, J=8.7 Hz, 1H), 3.92-3.90 (m, 2H), 2.87-2.83 (m, 2H), 2.27 (t, J=6.3 Hz, 2H), 2.21-2.11 (m, 4H), 2.03 (s, 6H). MS (EI): 278.1 (M+1).

N,N-Dimethyl-2-(7-nitro-2,3,4,5-tetrahydro-1H-benzo[b]azepin-1-yl)ethanamine

A solution of 1-(2-(dimethylamino)ethyl)-7-nitro-4,5-dihydro-1H-benzo[b]azepin-2(3H)-one (0.8 g, 2.88 mmol) was treated with a solution of 1M borane in THF (28.8 mL, 28.80 mmol). The solution was heated at reflux for 6 hours then stirred at room temperature overnight. After this time, the mixture was cooled to 0° C. and quenched with methanol (20 mL). The mixture was concentrated, dissolved in methanol (20 mL), and heated at reflux for 4 hours. The reaction was concentrated and the residue was subjected to silica gel chromatography using a gradient of 1.5-5% 2M $NH_3$ in MeOH/$CH_2Cl_2$ to give a yellow oil (565 mg, 74.6%). $^1$H-NMR (CDCl$_3$) δ 7.96 (dd, J=2.7, 8.7 Hz, 1H), 7.91 (d, J=2.7 Hz, 1H), 6.75 (d, J=9.0 Hz, 1H), 3.44-3.39 (m, 2H), 3.37-3.33 (m, 2H), 2.88-2.85 (m, 2H), 2.55-2.51 (m, 2H), 2.29 (s, 6H), 1.85-1.78 (m, 4H). MS (ESI): 264.2 (M+1).

Phenyl methyl(2-(7-nitro-2,3,4,5-tetrahydro-1H-benzo[b]azepin-1-yl)ethyl)carbamate A solution of N,N-dimethyl-2-(7-nitro-2,3,4,5-tetrahydro-1H-benzo[b]azepin-1-yl)ethanamine (400 mg, 1.52 mmol) in 10 mL $CH_2Cl_2$ was treated dropwise with phenylchloroformate (286 µL, 2.28 mmol). The reaction was stirred at room temperature for 21 hours then partitioned between $CH_2Cl_2$ (100 mL) and 1N NaOH (20 mL). After extraction, the organic layer was separated and the aqueous layer was extracted with additional $CH_2Cl_2$ (50 mL). The combined organic layer was dried over Na$_2$SO$_4$, filtered and concentrated to give a yellow residue. This residue was subjected to flash chromatography on silica gel using CH$_2$Cl$_2$ to give a yellow residue (460 mg, 82.0%). $^1$H-NMR (CDCl$_3$) δ 7.99 (dd, J=2.7, 9.0 Hz, 1H), 7.93 (d, J=2.7 Hz, 1H), 7.40-7.34 (m, 2H), 7.23-7.18 (m, 1H), 7.10-7.04 (m, 2H), 6.87 (dd, J=6.3, 2.7 Hz, 1H), 3.65-3.55 (m, 4H), 3.39-3.31 (m, 2H), 3.11 and 3.05 (2×s, 3H), 2.88-2.85 (m, 2H), 1.85-1.65 (m, 4H). MS (ESI): 370.2 (M+1).

Phenyl 2-(7-amino-2,3,4,5-tetrahydro-11H-benzo[b]azepin-1-yl)ethyl(methyl)carbamate A suspension of phenyl methyl(2-(7-nitro-2,3,4,5-tetrahydro-1H-benzo[b]azepin-1-yl)ethyl)carbamate (450 mg, 1.22 mmol) and palladium on activated carbon (10%, 65 mg, 0.06 mmol) in a 1:1 mixture of THF/EtOH (20 mL) was stirred under a balloon of hydrogen overnight. The suspension was filtered through a pad of celite. The filter pad was rinsed with 20 mL methanol and the filtrate was concentrated to give a dark residue. The crude product was used without further purification (325 mg, 78.5%). $^1$H-NMR (CDCl$_3$) δ 7.38-7.33 (m, 2H), 7.21-7.08 (m, 3H), 6.87-6.81 (m, 1H), 6.53-6.48 (m, 2H), 3.57-3.47 (m, 2H), 3.42 (brs, 2H), 3.37-3.28 (m, 2H), 3.07 and 3.00 (2×s, 3H), 2.89-2.86 (m, 2H), 2.71-2.68 (m, 2H), 1.75-1.60 (m, 2H), 1.63-1.50 (m, 2H). MS (ESI): 340.2 (M+1).

Phenyl-methyl(2-(7-(thiophene-2-carboximidamido)-2,3,4,5-tetrahydro-1H-benzo[b]azepin-1-yl)ethyl)carbamate A solution of phenyl 2-(7-amino-2,3,4,5-tetrahydro-1H-benzo[b]azepin-1-yl)ethyl(methyl)carbamate (300 mg, 0.88 mmol) in 12 mL EtOH was treated with methyl thiophene-2-carbimidothioate hydroiodide (504 mg, 1.77 mmol) and stirred at room temperature overnight. Argon was bubbled through the mixture for 20 minutes then it was partitioned between CH$_2$Cl$_2$ (100 mL) and saturated sodium carbonate (20 mL). After extraction, the organic layer was separated and the aqueous layer was extracted with an additional 50 mL CH$_2$Cl$_2$. The combined organic layers were dried over sodium sulfate, filtered and concentrated to give a yellow residue which was subjected to flash chromatography on silica gel using 2.5% MeOH/CH$_2$Cl$_2$ then 2.5% 2M NH$_3$ in MeOH/CH$_2$Cl$_2$ to give a yellow solid after drying (210 mg, 53.2%). $^1$H-NMR (DMSO-d$_6$) δ 7.71 (dd, J=4.5, 9.3 Hz, 1H), 7.57 (d, J=4.8 Hz, 1H), 7.41-7.35 (m, 2H), 7.23-7.19 (m, 1H), 7.14-7.05 (m, 3H), 7.00-6.97 (m, 1H), 6.64 (m, 2H), 6.33 (brs, 2H), 3.59-3.44 (m, 2H), 3.33-3.26 (m, 2H), 3.06 and 2.94 (2×s, 3H), 2.93-2.88 (m, 2H), 2.72-2.63 (m, 2H), 1.75-1.60 (m, 2H), 1.63-1.50 (m, 2H). MS (ESI): 449.2 (M+1, 100%).

N-(1-(2-(Methylamino)ethyl)-2,3,4,5-tetrahydro-1H-benzo[b]azepin-7-yl)thiophene-2-carboximidamide 36

A solution of phenyl-methyl(2-(7-(thiophene-2-carboximidamido)-2,3,4,5-tetrahydro-1H-benzo[b]azepin-1-yl)ethyl)carbamate (200 mg, 0.45 mmol) in 12 mL ethanol was treated with NaOH (178 mg, 4.46 mmol) followed by H$_2$O (5 mL). The mixture was then heated at reflux for 6 hours. A TLC analysis indicated that starting material is present. At this moment, NaOH (90 mg) was added and heating was continued for 1 hour. The solution was concentrated to about 5 mL and partitioned between CH$_2$Cl$_2$ (100 mL) and brine (20 mL). After extraction, the organic layer was separated and the aqueous layer was extracted once more with CH$_2$Cl$_2$ (50 mL). The combined organic layers were dried over Na$_2$SO$_4$, filtered and concentrated to give a yellow oil. This residue was subjected to flash chromatography on silica gel using 2.5-10% 2M NH$_3$ in MeOH/CH$_2$Cl$_2$ to give a yellow solid (60 mg, 40.5%). $^1$H-NMR (DMSO-d$_6$) δ 7.70 (d, J=3.3 Hz, 1H), 7.57 (d, J=4.8 Hz, 1H), 7.09-7.06 (m, 1H), 6.91-6.88 (m, 1H), 6.64-6.62 (m, 2H), 6.33-6.31 (m, 2H), 3.14 (t, J=6.3 Hz, 2H), 2.85-2.70 (m, 2H), 2.77-2.61 (m, 4H), 2.31 (s, 3H), 1.67-1.62 (m, 2H), 1.50-1.46 (m, 2H). MS (EI): 329.2 (M+1). ESI-HRMS calculated for C$_{18}$H$_{25}$N$_4$S (MH$^+$): 329.1794, Observed: 329.1802.

Example 37

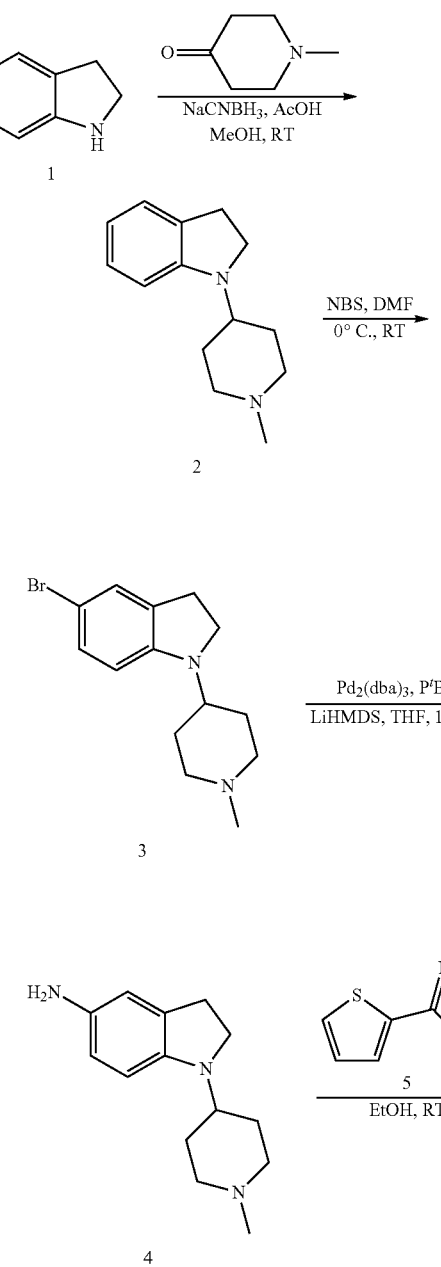

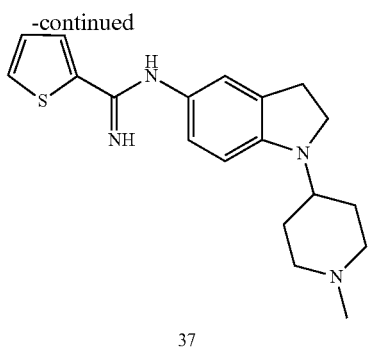

37

1-(1-Methylpiperidin-4-yl)indoline (2)

A solution of compound 1 (1.0 g, 8.391 mmol), N-methyl-4-piperidone (1.23 mL, 10.069 mmol) and glacial acetic acid (1.18 mL, 20.978 mmol) in dry methanol (10 mL) was treated with NaCNBH$_3$ (0.63 g, 10.069 mmol) at 0° C. The resulting mixture was brought to room temperature and stirred for 3 h. The reaction was diluted with 2 N NaOH solution (100 mL) and product was extracted into CH$_2$Cl$_2$ (2×25 mL). The combined CH$_2$Cl$_2$ layer was washed with brine (20 mL) and dried (Na$_2$SO$_4$). The solvent was evaporated and the crude material was purified by silica gel column chromatography (2 M NH$_3$ in MeOH:CH$_2$Cl$_2$, 3:97) to obtain compound 2 (1.15 g, 63.5%) as a syrup. $^1$H NMR (DMSO-d$_6$) δ 7.06-7.01 (m, 2H), 6.59 (t, 1H, J=6.6 Hz), 6.40 (d, 1H, J=7.8 Hz), 3.40-3.34 (m, 3H), 2.97-2.91 (m, 4H), 2.30 (s, 3H), 2.09-2.00 (m, 2H), 1.80-1.72 (m, 4H); ESI-MS (m/z, %): 217 (MH$^+$, 42). 98 (100).

5-Bromo-1-(1-methylpiperidin-4-yl)indoline (3)

A solution of compound 2 (1.12 g, 5.176 mmol) in dry DMF (10 mL) was treated with NBS (0.92 g, 5.176 mmol) in dry DMF (5 mL) at 0° C. over a period of 5 min. and stirring was continued at same temperature for 3 h. The reaction was diluted with water (100 mL) and product was extracted into ethyl acetate (2×25 mL). The combined ethyl acetate layer was washed with brine (20 mL) and dried (Na$_2$SO$_4$). The solvent was evaporated and crude material was purified by column chromatography (2 M NH$_3$ in MeOH:CH$_2$Cl$_2$, 3:97) to obtain compound 3 (1.15 g, 76%) as a syrup. $^1$H NMR (DMSO-d$_6$) δ 7.14-7.06 (m, 2H), 6.37 (d, 1H, J=8.4 Hz), 3.35-3.24 (m, 3H, merged with water peak), 2.93-2.80 (m, 4H), 2.16 (s, 3H), 2.00-1.88 (m, 2H), 1.64-1.55 (m, 4H); EI-MS (m/z, %): 293, 295 (M$^+$, bromine isotope, 47), 98 (59), 97 (100), 71 (47).

1-(1-Methylpiperidin-4-yl)indolin-5-amine (4)

Pd$_2$(dba)$_3$ (0.077 g, 0.084 mmol) in dry THF (3 mL) was treated with P$^t$Bu$_3$ (1.04 mL, 0.338 mmol, 10% wt in hexanes) at room temperature. The mixture was treated with compound 3 (0.5 g, 1.693 mmol) in dry THF (7 mL) followed by LiH-MDS (3.4 mL, 3.387 mmol, 1 M solution in THF) and the resulting mixture was stirred at 100° C. (sealed tube) for 2 h. The reaction was brought to room temperature, quenched with 1 N HCl solution (10 mL) and stirred for 10 min. The solution was made basic with 1 N NaOH solution (50 mL) and product was extracted into ethyl acetate (2×25 mL). The combined ethyl acetate layer was washed with brine (15 mL) and dried (Na$_2$SO$_4$). Solvent was evaporated and crude was purified by column chromatography on silica gel (2 M NH$_3$ in MeOH:CH$_2$Cl$_2$, 2:98 to 5:95) to obtain compound 4 (0.14 g, 36%) as a foam that was used directly in the next step.

N-(1-(1-Methylpiperidin-4-yl)indolin-5-yl)thiophene-2-carboximidamide (37)

A solution of compound 4 (0.12 g, 0.518 mmol) in dry ethanol (3 mL) was treated with compound 5 (0.29 g, 1.037 mmol) at room temperature and resulting mixture was stirred for over night (18 h) at room temperature. The reaction was diluted with sat. NaHCO$_3$ solution (20 mL) and product was extracted into CH$_2$Cl$_2$ (2×15 mL). The combined CH$_2$Cl$_2$ layer was washed with brine (15 mL) and dried (Na$_2$SO$_4$). The solvent was evaporated and the crude product was purified by column chromatography on silica gel (2 M NH$_3$ in MeOH:CH$_2$Cl$_2$, 5:95) to obtain compound 37 (0.1 g, 57%) as a solid. $^1$H NMR (DMSO-d$_6$) δ 7.67 (d, 1H, J=3.6 Hz), 7.54 (d, 1H, J=5.1 Hz), 7.06 (t, 1H, J=3.9 Hz), 6.61 (s, 1H), 6.51 (d, 1H, J=8.1 Hz), 6.39 (d, 1H, J=8.1 Hz), 6.24 (brs, 2H), 3.30-3.24 (m, 3H), 2.86-2.80 (m, 4H), 2.16 (s, 3H), 2.00-1.92 (m, 2H), 1.66-1.56 (m, 4H); ESI-MS (m/z, %): 341 (MH$^+$, 100), 244 (87); ESI-HRMS calculated for C$_{19}$H$_{25}$N$_4$S (MH$^+$), calculated: 341.1794; observed: 4341.1805; HPLC purity 93.24% by area.

Example 38

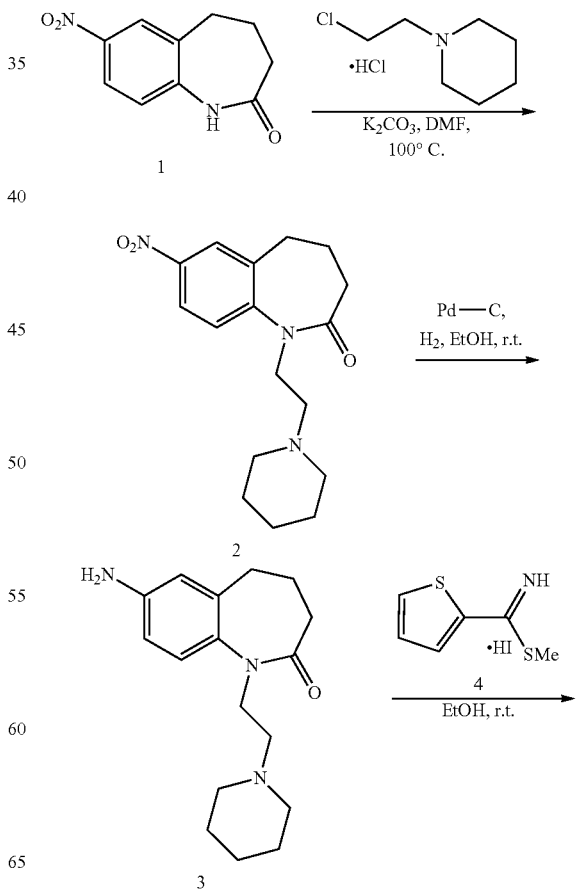

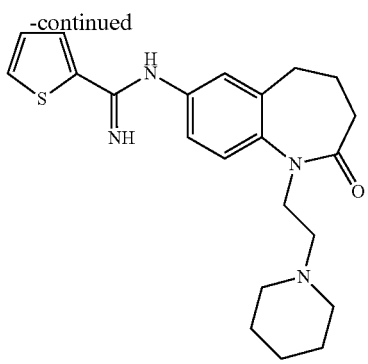

38

7-Nitro-4,5-dihydro-1H-benzo[b]azepin-2(3H)-one (1)

see Example 25 for complete experimental details and spectral data.

7-Nitro-1-(2-(piperidin-1-yl)ethyl)-4,5-dihydro-1H-benzo[b]azepin-2(3H)-one (2)

A suspension of compound 1 (1.0 g, 4.85 mmol), 1-(2-chloroethyl)piperidine monohydrochlorate (1.785 g, 9.70 mmol) and $K_2CO_3$ (4.02 g, 29.10 mmol) in DMF (10 mL) was heated to 100° C. and stirred for overnight (22.5 hours). The reaction mixture was brought to room temperature and diluted with $H_2O$ (100 mL) and extracted with EtOAc (3×50 mL). The combined organic layers were dried ($Na_2SO_4$) and concentrated to give a brown residue. The product was isolated along with the 9-nitro regioisomer by column chromatography (2 N $NH_3$ in MeOH:$CH_2Cl_2$, 3:97) to obtain compound 2 (1.44 g, 93.5%) as a thick brown syrup. ESI-MS (m/z, %): 318.2 (MH+, 100), 233.1 (38).

7-Amino-1-(2-(piperidin-1-yl)ethyl)-4,5-dihydro-1H-benzo[b]azepin-2(3H)-one (3)

A solution of compound 2 (500 mg, 1.56 mmol) in dry ethanol (10 mL) was treated with Pd—C (~0.05 g) and purged with hydrogen gas. The reaction mixture was stirred at room temperature under hydrogen atmosphere (balloon pressure) overnight (18 h). The mixture was filtered through a celite bed and washed with methanol (3×25 mL). The combined organic fractions were dried under reduced pressure to obtain crude compound 3 (0.5 g, quantitative) as a colourless foam. $^1$H-NMR (DMSO-$d_6$) δ 1.34 (m, 6H), 1.87-2.22 (m, 10H), 5.00-5.03 (m, 2H), 6.34-6.52 (m, 2H), 6.98 (d, 1H, J=8.4 Hz); ESI-MS (m/z, %): 288.2 (MH+, 100), 203.1 (37).

N-(2-Oxo-1-(2-(piperidin-1-yl)ethyl)-2,3,4,5-tetrahydro-1H-benzo[b]azepin-7-yl)thiophene-2-carboximidamide (38)

A solution of compound 3 (449 mg, 1.64 mmol) in dry ethanol (10 mL) was treated with compound 4 (0.936 g, 3.28 mmol) and stirred for overnight (16 h) at room temperature. The reaction mixture was diluted with saturated $NaHCO_3$ solution (50 mL) and extracted with $CH_2Cl_2$ (2×50 mL). The combined organic fractions were washed with brine (50 mL), dried ($Na_2SO_4$) and concentrated. The crude product was purified by column chromatography (2N $NH_3$ in MeOH:$CH_2Cl_2$, 2:98 followed by 4:96) to give compound 38 (410.3 mg, 66.2%) as a yellow solid. $^1$H-NMR (DMSO-$d_6$) δ 1.35 (m, 6H), 2.01-2.30 (m, 10H), 2.72 (brs, 2H), 6.44 (brs, 2H), 6.75 (m, 2H), 7.10 (m, 1H), 7.28 (d, 1H, J=8.3 Hz), 7.62 (d, 1H, J=5.1 Hz), 7.74 (d, 1H, J=3.4 Hz). ESI-MS (m/z, %): 397.2 (MH+, 78), 312 (28), 156 (100), 148 (53); ESI-HRMS calculated for $C_{22}H_{29}N_4OS$ (MH+), calculated: 397.2070; observed: 397.2056; HPLC-purity: 93.90% by area.

Example 39

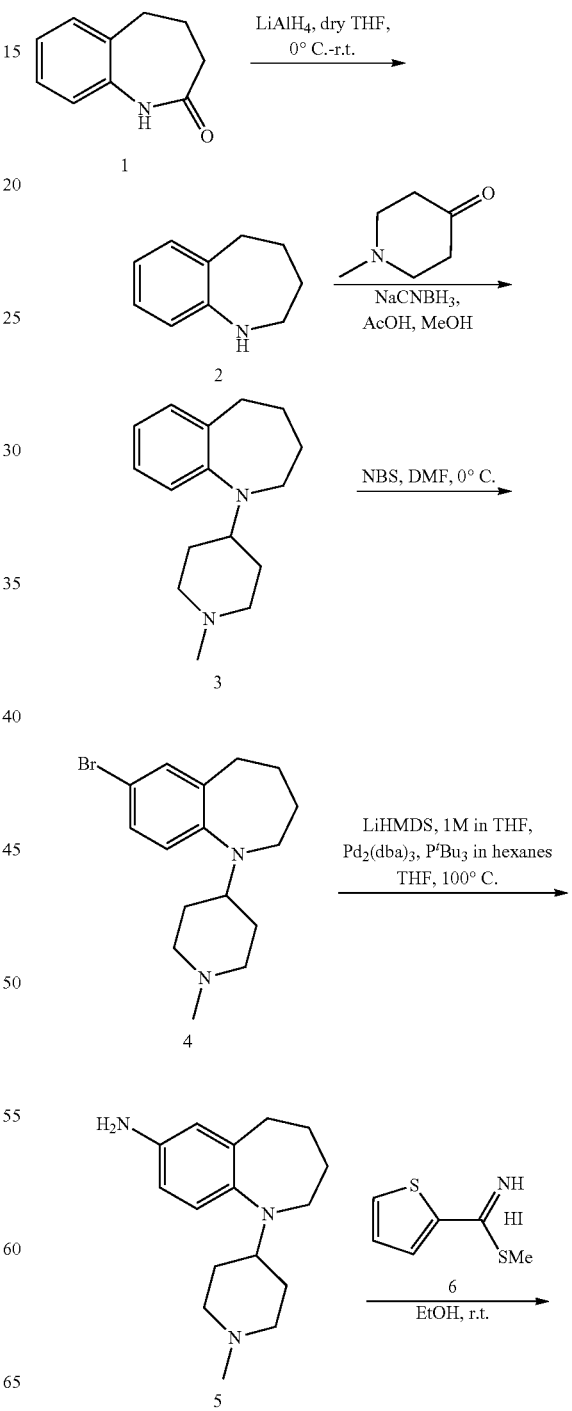

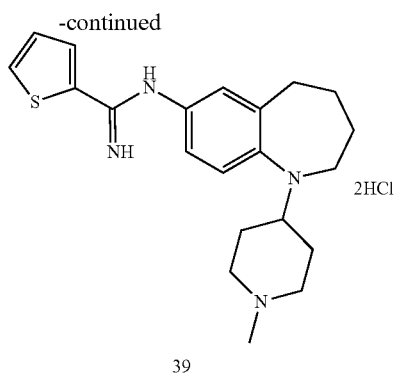

39

4,5-Dihydro-1H-benzo[b]azepin-2(3H)-one (1)

See Example 25 for complete experimental details and spectral data.

2,3,4,5-Tetrahydro-1H-benzo[b]azepine (2)

A suspension of LiAlH$_4$ (49.63 mL, 49.63 mmol) in 1.0 M THF was treated drop wise with a solution of compound 1 (2.0 g, 12.41 mmol) in THF (60 mL) while stirring at 0° C. The resulting reaction mixture was brought to room temperature and stirred for 23 hours. The reaction was quenched with H$_2$O (1.9 mL), 1 N NaOH solution (1.9 mL), and H$_2$O (1.9 mL) upon which a white precipitate formed. The suspension was filtered and the precipitate washed with CH$_2$Cl$_2$ (3×50 mL). The filtrate was dried (Na$_2$SO$_4$), concentrated, and dried under reduced pressure to obtain compound 2 (1.55 g, 84.7%) as a brown solid. $^1$H-NMR (DMSO-d$_6$) δ 1.53 (m, 2H), 1.64 (m, 2H), 2.63 (m, 2H), 2.88 (m, 2H), 5.15 (brs, 1H), 6.66 (td, 1H, J=7.5, 1.2 Hz), 6.78 (dd, 1H, J=7.4, 1.0 Hz), 6.93 (t, 1H, J=7.4 Hz), 7.00 (d, 1H, J=7.0 Hz); EI-MS (m/z, %): 147 (M$^+$, 100), 146 (44), 132 (42), 119 (40), 118 (89).

1-(1-Methylpiperidin-4-yl)-2,3,4,5-tetrahydro-1H-benzo[b]azepine (3)

A solution of compound 2 (1.0 g, 6.79 mmol), N-methyl-4-piperidone (1.00 mL, 8.15 mmol) and acetic acid (0.96 mL, 16.98 mmol) in dry methanol (10 mL) was treated with NaCNBH$_3$ (0.51 g, 8.15 mmol) at 0° C. The reaction mixture was brought to room temperature and stirred overnight (15 hours). The reaction was quenched with 2N NaOH (100 mL) and extracted with CH$_2$Cl$_2$ (2×25 mL). The combined organic fractions were washed with brine (30 mL), dried (Na$_2$SO$_4$) and concentrated. The crude product was purified by column chromatography (2.0 N NH$_3$ in MeOH:CH$_2$Cl$_2$, 3:97) to give compound 3 (0.82 g, 49.4%) as a yellow oil. $^1$H-NMR (DMSO-d$_6$) δ 1.55 (m, 4H), 1.74 (m, 4H), 1.96 (td, 2H, J=11.3, 2.6 Hz), 2.15 (s, 3H), 2.66 (m, 2H), 2.78 (m, 2H), 2.93 (m, 2H), 3.17 (m, 1H), 6.74 (t, 1H, J=7.3 Hz), 6.90 (d, 1H, J=8.2 Hz), 7.01 (m, 2H); EI-MS (m/z, %): 244 (M$^+$, 24), 97 (100), 71 (37).

7-Bromo-1-(1-methylpiperidin-4-yl)-2,3,4,5-tetrahydro-1H-benzo[b]azepine (4)

A solution of compound 3 (0.73 g, 2.99 mmol) in DMF (5 mL) was treated with a solution of NBS (0.53 g, 2.99 mmol) in DMF (5 mL) at 0° C. The reaction mixture was stirred at 0° C. for 2 hours and stored at 0° C. overnight. The reaction mixture was diluted with H$_2$O (100 mL) and extracted with ethyl acetate (3×25 mL). The combined organic layers were washed with brine (25 mL), dried (Na$_2$SO$_4$) and concentrated. The product was filtered through a short plug of silica gel (2.0 N NH$_3$ in MeOH:CH$_2$Cl$_2$, 2.5:97.5) to give compound 4 (0.915 g, 95.3%) as a yellow oil. $^1$H-NMR (DMSO-d$_6$) δ 1.56 (m, 4H), 1.72 (m, 4H), 1.96 (td, 2H, J=10.9, 2.2 Hz), 2.15 (s, 3H), 2.65 (m, 2H), 2.76 (m, 2H), 2.93 (m, 2H), 3.14 (m, 1H), 6.83 (d, 1H, J=8.5 Hz), 7.19 (td, 2H, J=8.6, 2.4 Hz); EI-MS (m/z, %) 324 (M$^+$, 14) 322 (M$^+$, 14), 98 (25), 97 (100), 96 (25), 71 (38).

1-(1-Methylpiperidin-4-yl)-2,3,4,5-tetrahydro-1H-benzo[b]azepin-7-amine (5)

A suspension of Pd$_2$(dba)$_3$ (70 mg, 0.077 mmol) and P$^t$Bu$_3$ 10% wt in hexanes (0.94 m/L, 0.31 mmol) in THF (5.0 mL) was treated with a solution of compound 4 (500.0 mg, 1.55 mmol) in THF (5.0 mL) followed by LiHMDS 1 M in THF (3.1 mL, 3.1 mmol) at room temperature. The resulting brown mixture was stirred at 100° C. for 2 hours then cooled to room temperature and treated with 1 N HCl (10 mL) and stirred for 15 minutes. The mixture was basified with 1 N NaOH (25 mL) and extracted with CH$_2$Cl$_2$ (2×100 mL). The combined organic fractions were washed with brine (100 mL), dried (Na$_2$SO$_4$) and concentrated to give a dark brown residue. The crude product was purified by flash chromatography on silica gel (MeOH:CH$_2$Cl$_2$, 5:95 followed by 2 N NH$_3$ in MeOH: CH$_2$Cl$_2$, 5:95) to give compound 5 (339.6 mg, 84.7%) as a dark viscous oil.

N-(1-(1-Methylpiperidin-4-yl)-2,3,4,5-tetrahydro-1H-benzo[b]azepin-7-yl)thiophene-2-carboximidamide (39)

A solution of compound 8 (321.6 mg, 1.24 mmol) in dry ethanol (10 mL) was treated with compound 6 (707 mg, 2.48 mmol) at room temperature. The reaction mixture was stirred for 16 hours at room temperature then diluted with saturated NaHCO$_3$ solution (50 mL) and extracted with CH$_2$Cl$_2$ (2×50 mL). The combined organic fractions were washed with brine (50 mL), dried (Na$_2$SO$_4$) and concentrated to give a brown residue. The crude product was purified by column chromatography on silica gel (MeOH:CH$_2$Cl$_2$, 2:98 followed by 2 N NH$_3$ in MeOH:CH$_2$Cl$_2$, 4:96 to 5:95) to give compound 39 (374.6 mg, 81.9%) as a yellow residue. $^1$H-NMR (DMSO-d$_6$) δ 1.56-1.79 (m, 9H), 1.97 (t, 2H, J=10.5 Hz), 2.16 (s, 3H), 2.65 (brs, 2H), 2.80 (d, 2H, J=10.2 Hz), 2.91 (brs, 2H), 3.12 (m, 1H), 6.30 (brs, 2H), 6.59 (m, 2H), 6.89 (d, 1H, J=8.9 Hz), 7.07 (t, 1H, J=4.5 Hz), 7.57 (d, 1H, J=5.1), 7.70 (d, 1H, J=3.5 Hz); ESI-MS (m/z, %) 369 (MH$^+$, 35), 272 (100). ESI-HRMS calculated for C$_{21}$H$_{29}$N$_4$S (MH$^+$), calculated: 369.2101; observed: 369.2107; HPLC-purity: 97.31% by area.

Example 40

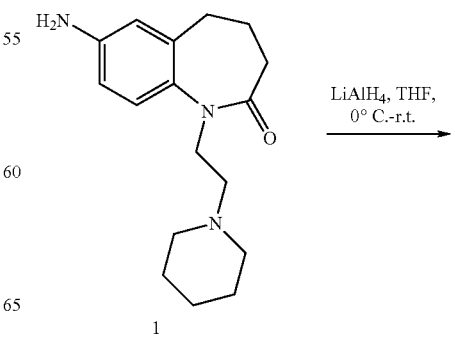

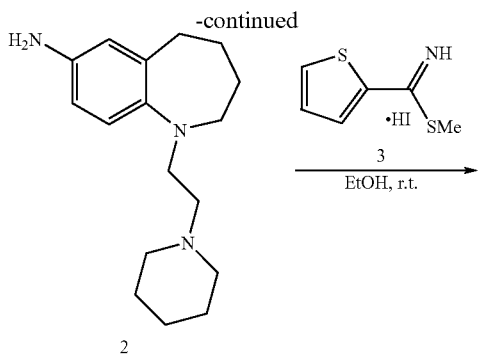

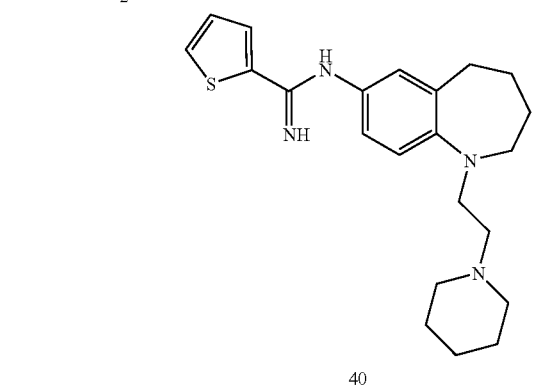

7-Amino-1-(2-(piperidin-1-yl)ethyl)-4,5-dihydro-1H-benzo[b]azepin-2(3H)-one (1)

See Example 38 for complete experimental details and spectral data.

1-(2-(Piperidin-1-yl)ethyl)-2,3,4,5-tetrahydro-1H-benzo[b]azepin-7-amine (2)

A suspension of LiAlH$_4$ (1.0 M in THF, 3.2 mL, 3.20 mmol) was treated dropwise with a solution of compound 1 (230.7 mg, 0.803 mmol) in dry THF (6 m/L) at 0° C. The reaction was brought to room temperature and stirred overnight (16 h) then quenched with H$_2$O (0.1 mL), 1 N NaOH (0.1 mL), then additional H$_2$O (0.1 mL) upon which a white precipitate formed. The precipitate was filtered off and the washed with CH$_2$Cl$_2$ (3×25 mL). The combined organic fractions were concentrated and purified by column chromatography on silica gel (2N NH$_3$ in MeOH:CH$_2$Cl$_2$, 5:95) to give compound 2 (197.7 mg, 90.0%) as a brown residue. $^1$H-NMR (DMSO-d$_6$) δ 1.36 (m, 2H), 1.45 (m, 6H), 1.60 (m, 2H), 2.36 (m, 6H), 2.73 (m, 2H), 3.06 (t, 2H, J=7.3 Hz), 3.33 (s, 3H), 4.55 (brs, 2H), 6.31 (m, 2H), 6.64 (d, 1H, J=8.1 Hz); ESI-MS (m/z, %): 274 (MH$^+$, 100).

N-(1-(2-(Piperidin-1-yl)ethyl)-2,3,4,5-tetrahydro-1H-benzo[b]azepin-7-yl)thiophene-2-carboximidamide (40)

A solution of compound 2 (180 mg, 0.659 mmol) in ethanol (10 mL) at room temperature was treated with 3 (0.376 g, 1.32 mmol). The reaction mixture was stirred overnight (16 h) at room temperature then diluted with sat. NaHCO$_3$ solution (50 mL) and extracted into CH$_2$Cl$_2$ (2×50 mL). The combined organic fractions were washed with brine (50 mL), dried (Na$_2$SO$_4$) and concentrated. The crude product was purified by column chromatography on silica gel (2N NH$_3$ in MeOH: CH$_2$Cl$_2$, 2.5:97.5) to give compound 40 (209 mg, 83.3%) as an orange solid. $^1$H-NMR (DMSO-d$_6$) δ 1.37 (m, 2H), 1.48 (m, 6H), 1.65 (m, 2H), 2.42 (m, 6H), 2.65 (m, 2H), 2.85 (m, 2H), 3.18 (m, 2H), 6.31 (brs, 2H), 6.62 (m, 2H), 6.88 (d, 1H, J=9.0 Hz), 7.08 (t, 1H, J=4.3 Hz), 7.57 (d, 1H, J=5.05 Hz), 7.70 (d, 1H, J=3.5 Hz); ESI-MS (m/z, %): 383 (MH$^+$, 100), 272 (85), 252 (51), 192 (91); ESI-HRMS calculated for C$_{22}$H$_{31}$N$_4$S (MH$^+$), calculated: 383.2279; observed: 383.2263; HPLC-purity: 97.02% by area.

Example 41

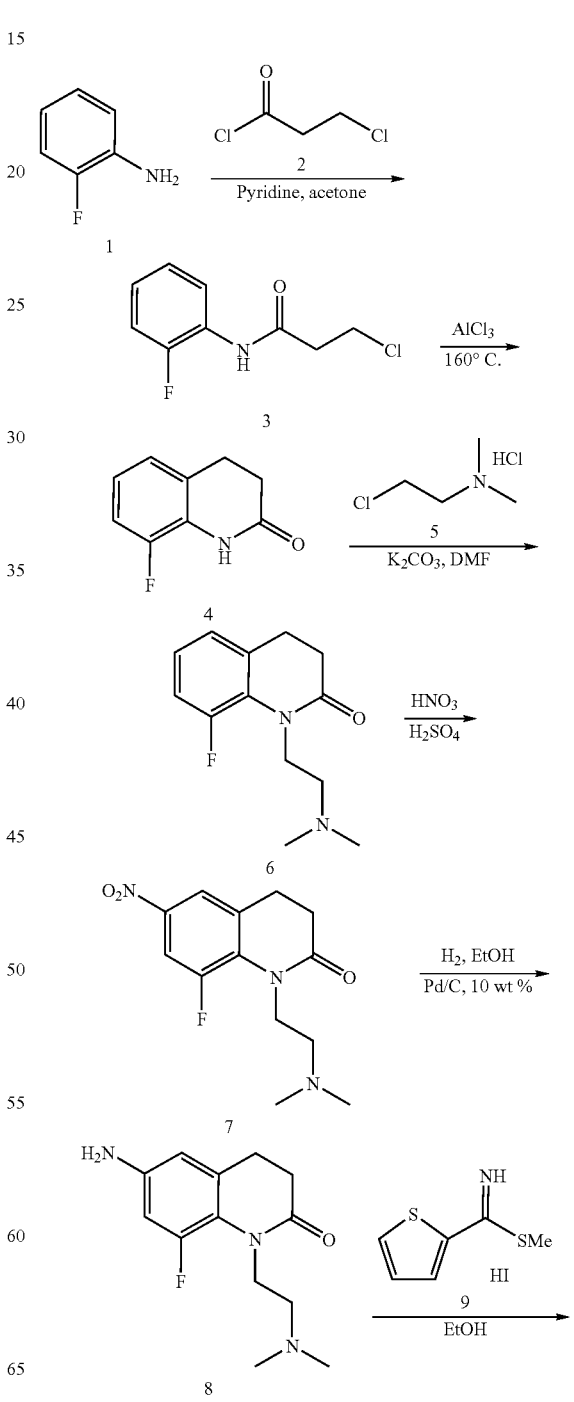

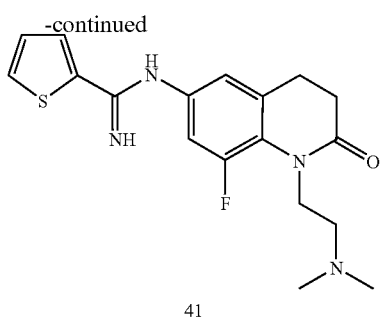

41

3-Chloro-N-(2-fluorophenyl)propanamide (3)

2-Fluoroaniline (2 g, 17.99 mmol) was stirred in acetone (30 mL) and pyridine (2.91 mL, 35.99 mmol) and allowed to dissolve. To this solution was added 3-chloropropanoyl chloride (3.42 g, 26.99 mmol), slowly. The reaction mixture began to reflux, and when the mixture had cooled to room temperature (~30 min) TLC analysis showed that the reaction was complete. The reaction mixture was then diluted with water and HCl$_{(aq)}$ (1N) and extracted with dichloromethane (3×). The combined organic extracts were dried over sodium sulfate, filtered and concentrated, then chromatographed on silica gel in 30% EtOAc in hexanes. Yield: 3.5 g, 97%. $^1$H NMR (CDCl$_3$) δ 2.87 (t, 2H, J=6.7 Hz), 3.89 (t, 2H, J=6.7 Hz), 7.10 (m, 3H), 7.52 (brs, 1H), 8.30 (t, 1H, J=7.5 Hz). EI-MS (m/z, %): 201.1 (M+, 22), 111.1 (100).

8-Fluoro-3,4-dihydroquinolin-2(1H)-one (4)

3-Chloro-N-(2-fluorophenyl)propanamide (3.3 g, 16.4 mmol) and aluminum trichloride (10.9 g, 81.8 mmol) were combined in a RB flask with a stirbar and purged with argon. The mixture of the two solids was heated to 160° C. to form a melt, which was stirred for 1.5 h. The mixture was then removed from the heating bath and when it had cooled to below 100° C., was quenched by careful addition of water. The resulting mixture was cooled to room temperature, neutralized with NaOH, and extracted with dichloromethane (3×). The combined organics were dried, filtered and evaporated, then chromatographed on silica gel using 20% EtOAc in hexanes, giving the desired product. 1H NMR showed some impurities. Yield: 2.35 g, 88%. $^1$H NMR (CDCl$_3$) δ 2.66 (t, 2H, J=7.6 Hz), 3.01 (t, 2H, J=7.6 Hz), 6.96 (m, 3H), 8.11 (brs, 1H).

1-(2-(Dimethylamino)ethyl)-8-fluoro-3,4-dihydro-quinolin-2(1H)-one (6)

8-Fluoro-3,4-dihydroquinolin-2(1H)-one (2.31 g, 13.98 mmol), 2-chloro-N,N-dimethylethanamine hydrochloride (4.03 g, 27.9 mmol) and potassium carbonate (11.78 g, 85.3 mmol) were combined in a round bottom flask containing a stirbar. The flask was purged with argon and DMF was added. The white suspension was stirred overnight at room temperature. The mixture was then diluted with ethyl acetate and washed with water (5×), then brine (2×). The organic phase was then dried, filtered and concentrated, then chromatographed on silica gel using EtOAc eluent. Yield: 2.86 g, 86%. $^1$H NMR 7.0 Hz), 4.09 (t, 2H, J=7.0 Hz), 6.98 (m, 3H). ESI-MS: 237 (MH+, 29), 192 (100). (CDCl$_3$) δ 2.24, (s, 6H), 2.51 (t, 2H, J=7.0 Hz), 2.59 (t, 2H, J=7.0 Hz), 2.87 (t, 2H, J=

1-(2-(Dimethylamino)ethyl)-8-fluoro-6-nitro-3,4-dihydroquinolin-2(1H)-one (7)

1-(2-(Dimethylamino)ethyl)-8-fluoro-3,4-dihydroquinolin-2(1H)-one (2.86 g, 12.11 mmol) was weighed into a round bottom flask equipped a stir bar. To this was added concentrated sulfuric acid (30 mL) and the flask was cooled to −5° C. in an ice/salt bath. To this stirring solution was added nitric acid (90%, 615.5 µL, 13.2 mmol) and the resulting mixture was stirred for 30 min. The reaction mixture was then quenched with ice and NaOH$_{(aq)}$. The product was extracted with CH$_2$Cl$_2$ (3×). The combined organics were dried, filtered and concentrated then chromatographed on silica using 0-10% (2M NH$_3$ in MeOH) in dichloromethane, giving the desired product. Yield: 1.1 g, 32%, product still contains some impurities). $^1$H NMR (CDCl$_3$) δ 2.20 (s, 6H), 2.48 (t, 2H, J=7.0 Hz), 2.67 (t, 2H, J=7.0 Hz), 2.98 (t, 2H, J=7.0 Hz), 4.16 (t, 2H, J=7.0 Hz), 7.89 (m, 2H). ESI-MS: 282 (MH$^+$, 100), 237 (50), 192 (27).

6-Amino-1-(2-(dimethylamino)ethyl)-8-fluoro-3,4-dihydroquinolin-2(1H)-one (8)

1-(2-(Dimethylamino)ethyl)-8-fluoro-6-nitro-3,4-dihydroquinolin-2(1H)-one (500 mg, 1.77 mmol) was weighed into a round bottom flask equipped with a stirbar. Ethanol (10 mL) and THF (2 mL) were added, followed by Pd, 10 wt. % on activated carbon. The flask was fitted with a balloon of hydrogen, evacuated of air and backfilled with hydrogen. The black suspension was stirred for 3 h at room temperature. The solid palladium was then filtered off through a plug of celite and the celite pad washed with methanol. The filtrate was concentrated, then chromatographed on silica gel using 0-10% (2M NH$_3$ in MeOH) in ethyl acetate to give the product. Yield: 325 mg, 72%. EI-MS: 251 (M+, 3), 58 (100).

N-(1-(2-(Dimethylamino)ethyl)-8-fluoro-2-oxo-1,2,3,4-tetrahydroquinolin-6-yl)thiophene-2-carboximidamide (41)

6-Amino-1-(2-(dimethylamino)ethyl)-8-fluoro-3,4-dihydroquinolin-2(1H)-one (312 mg, 1.24 mmol) was stirred to dissolve in ethanol (15 mL). To this solution was added methyl thiophene-2-carbimidothioate hydroiodide (708 mg, 2.48 mmol). The resulting suspension was stirred for 2 days at room temperature. When TLC analysis showed that the reaction was finished, the mixture was diluted with water and aqueous sodium carbonate, then extracted with dichloromethane (3×). The combined organics were dried, filtered and concentrated and the crude product chromatographed on silica gel using 0-10% (2M NH$_3$ in MeOH) in ethyl acetate, then a second time using 20-80% MeCN in an aqueous buffer of ammonium carbonate and ammonium hydroxide adjusted to pH 10.6. Yield: 27 mg). $^1$H NMR (DMSO-d$_6$) δ 2.14 (s, 6H), 2.44 (t, 2H, J=6.7 Hz), 2.49 (m, 2H, masked by DMSO peak), 2.80 (t, 2H, J=6.6 Hz), 3.95 (t, 2H, J=6.5 Hz), 6.61 (m, 4H), 7.09 (m, 1H), 7.62 (m, 1H), 7.75 (m, 1H). ESI-MS: 361 (MH$^+$, 100), 316 (40), 158.6 (57), 136 (37).

Example 42

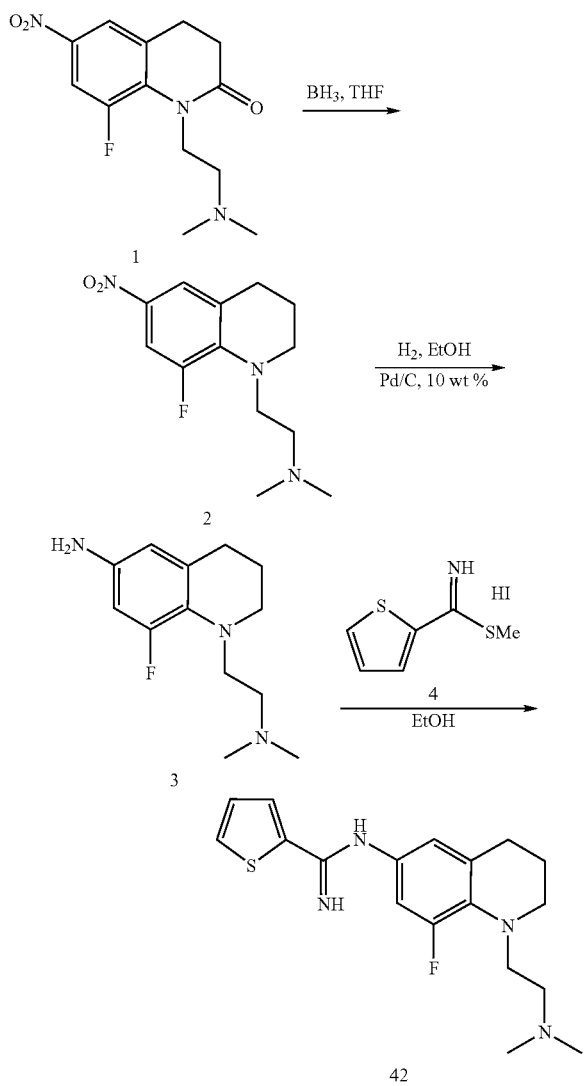

1-(2-(Dimethylamino)ethyl)-8-fluoro-6-nitro-3,4-dihydroquinolin-2(1H)-one (1)

For complete experimental details and spectral data, please see Example 41.

2-(8-Fluoro-6-nitro-3,4-dihydroquinolin-1(2H)-yl)-N,N-dimethylethanamine (2)

1-(2-(Dimethylamino)ethyl)-8-fluoro-6-nitro-3,4-dihydroquinolin-2(1H)-one (600 mg, 2.13 mmol) was added to a round bottom flask equipped with a stir bar. The flask was sealed and purged with argon. Borane.THF (1M solution in THF, 21.3 mL, 21.3 mmol) was added to the starting material and stirred to dissolve. The reaction mixture was heated to reflux overnight. The reaction was cooled to 0° C. and then quenched with methanol (20 mL). The mixture was then concentrated in vacuo, redissolved in methanol and refluxed for 4 h. The mixture was then concentrated onto silica gel and chromatographed using 0-10% (2M $NH_3$ in MeOH) in dichloromethane. Yield: 364 mg, 64%. $^1$H NMR ($CDCl_3$) δ 1.95 (m, 2H), 2.27 (s, 6H), 2.56 (m, 2H), 2.77 (m, 2H), 3.41 (m, 4H), 7.69 (m, 1H), 7.77 (dd, 1H, J=9 Hz, 2.7 Hz). EI-MS: 58 (100).

1-(2-(Dimethylamino)ethyl)-8-fluoro-1,2,3,4-tetrahydroquinolin-6-amine (3)

2-(8-Fluoro-6-nitro-3,4-dihydroquinolin-1(2H)-yl)-N,N-dimethylethanamine (340 mg, 1.27 mmol) was weighed into a round bottom flask equipped with a stir bar. Ethanol (8 mL) was added, followed by Pd (10 wt. % on activated carbon). The flask was fitted with a balloon of hydrogen, evacuated of air and backfilled with hydrogen. The reaction mixture was stirred for 2 h at room temperature under balloon pressure. The reaction mixture was then filtered through a pad of celite and the pad washed with methanol. The filtrate was concentrated, then chromatographed on silica gel using 0-10% (2M $NH_3$ in MeOH) in dichloromethane. Yield: 270 mg, 89%. ESI-MS: 238 (MH+, 100), 193 (37), 147 (31).

N-(1-(2-(Dimethylamino)ethyl)-8-fluoro-1,2,3,4-tetrahydroquinolin-6-yl)thiophene-2-carboximidamide (42)

1-(2-(Dimethylamino)ethyl)-8-fluoro-1,2,3,4-tetrahydroquinolin-6-amine (222 mg, 0.935 mmol) was stirred to dissolve in ethanol in a round bottom flask. To this solution was added methyl thiophene-2-carbimidothioate hydroiodide (533 mg, 1.87 mmol). The resulting suspension was stirred overnight at room temperature. When TLC analysis showed that the reaction was finished, the mixture was diluted with water and aqueous sodium carbonate, then extracted with dichloromethane (3×). The combined organics were dried, filtered and concentrated and the crude product then chromatographed on silica gel using 0-10% (2M $NH_3$ in MeOH) in ethyl acetate, then a second time using 20-80% MeCN in an aqueous buffer of ammonium carbonate and ammonium hydroxide adjusted to pH 10.6. Yield: 46 mg, 15%. $^1$H NMR (DMSO-$d_6$) δ 1.75 (m, 2H), 2.16 (s, 6H), 2.46 (m, 2H), 2.66 (m, 2H), 3.12 (m, 4H), 6.40 (m, 4H), 7.07 (m, 1H), 7.57 (m, 1H), 7.71 (m, 1H). ESI-MS: 347 (MH+, 33), 276 (100), 143 (12).

Example 43

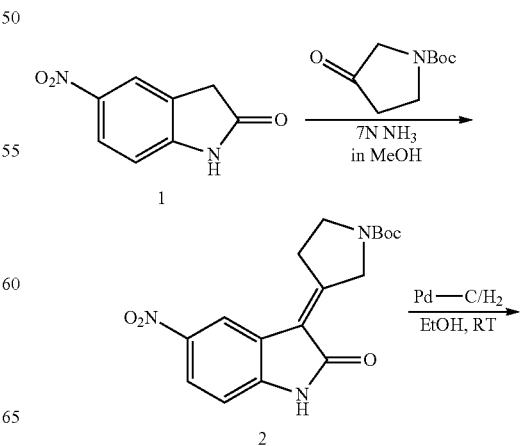

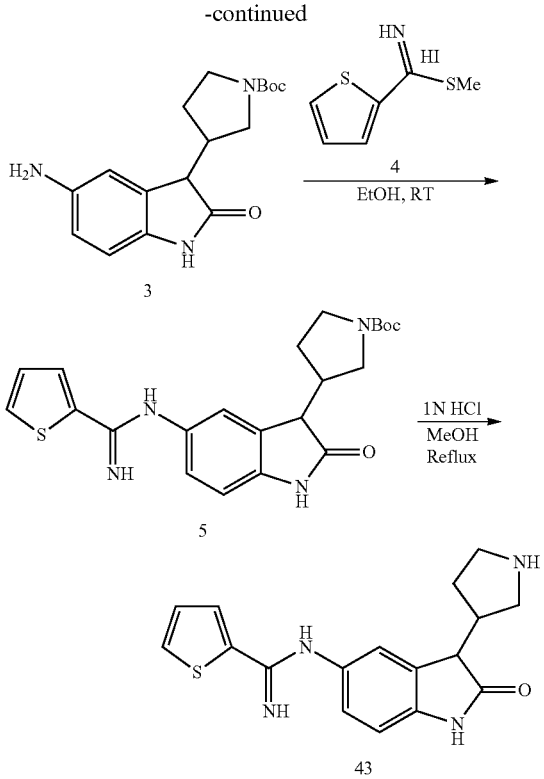

tert-Butyl 3-(5-nitro-2-oxoindolin-3-ylidene)pyrrolidine-1-carboxylate (2)

A solution of compound 1 (1.0 g, 5.613 mmol), N-Boc-3-pyrrolidinone (1.039 mL, 5.613 mmol) in 7 N $NH_3$ in methanol (10 mL) was refluxed for 2 h. The reaction was brought to room temperature, filtered, washed with methanol (2×5 mL) and dried under vacuum to obtain compound 2 as a solid (1.88 g, 97%). $^1$H NMR (DMSO-$d_6$) δ 11.29 (s, 1H), 8.19 (dd, 1H, J=2.1, 8.7 Hz), 8.14 (d, 1H, J=1.8 Hz), 7.05 (d, 1H, J=8.4 Hz), 4.56 (s, 2H), 3.61 (t, 2H, J=7.2 Hz), 3.36-3.30 (m, 2H, merged with DMSO peak), 1.44 (s, 9H); ESI-MS (m/z, %): 368 (M+Na, 23), 272 (48), 246 (MH$^+$-Boc, 100).

tert-Butyl 3-(5-amino-2-oxoindolin-3-yl)pyrrolidine-1-carboxylate (3)

A solution of compound 2 (0.3 g, 0.868 mmol) in 7 N $NH_3$ in methanol (10 mL) was treated with Pd—C (~0.03 g) and purged with hydrogen gas. The reaction was stirred at room temperature under hydrogen atm. (balloon pressure) for 3 h. The reaction was filtered through celite bed, washed with methanol (3×10 mL). The combined organic layer was evaporated and crude was purified by column chromatography (2 M $NH_3$ in MeOH:$CH_2Cl_2$, 5:95) to obtain compound 3 (0.25 g, 91%) as a solid. $^1$H NMR (DMSO-$d_6$) δ 9.99 (s, 1H), 6.57-6.50 (m, 2H), 6.39 (d, 1H, J=8.7 Hz), 4.69 (d, 2H, J=4.2 Hz), 3.56-3.35 (m, 3H), 3.15-3.04 (m, 2H), 2.50-2.49 (m, 1H), 1.98-1.66 (m, 2H), 1.37 (s, 9H); ESI-MS (m/z, %): 340 (M+Na, 5), 244 (100), 218 (MH$^+$-Boc, 84).

tert-Butyl 3-(2-oxo-5-(thiophene-2-carboximidamido)indolin-3-yl)pyrrolidine-1-carboxylate (5)

A solution of compound 3 (0.24 g, 0.756 mmol) in dry ethanol (5 mL) was treated with compound 4 (0.43 g, 1.512 mmol) at room temperature and the resulting mixture was stirred for 16 h. The reaction was diluted with sat. $NaHCO_3$ solution (25 mL) and product was extracted into $CH_2Cl_2$ (2×20 mL). The combined organic layer was dried ($Na_2SO_4$), solvent was evaporated and crude was purified by column chromatography (2 M $NH_3$ in MeOH:$CH_2Cl_2$, 3:97) to obtain compound 5 (0.225 g, 70%) as a solid. $^1$H NMR (DMSO-$d_6$) δ 10.29 (s, 1H), 7.71 (d, 1H, J=2.4 Hz), 7.58 (d, 1H, J=5.1 Hz), 7.08 (t, 1H, J=4.5 Hz), 6.78-6.76 (m, 2H), 6.68 (d, 1H, J=7.8 Hz), 6.39 (s, 2H), 3.59-3.25 (m, 3H), 3.21-3.05 (m, 2H), 2.56-2.50 (m, 1H), 2.03-1.68 (m, 2H), 1.37 (s, 9H); ESI-MS (m/z, %): 427 (MH$^+$, 100).

N-(2-Oxo-3-(pyrrolidin-3-yl)indolin-5-yl)thiophene-2-carboximidamide (43)

A solution of compound 5 (0.21 g, 0.492 mmol) in methanol (10 mL) was treated with 1 N HCl solution (10 mL) and the resulting solution was refluxed for 30 min. The reaction was brought to room temperature and solvent was evaporated. The crude was dissolved into water (10 mL), filtered and washed with water (2×5 mL). The combined water layer was evaporated to obtain compound 43 (0.173 g, 88%) as a solid. $^1$H NMR (DMSO-$d_6$) δ 11.50 (brs, 1H), 10.87 (d, 1H, J=3.0 Hz), 9.79 (s, 1H), 9.69-9.46 (m, 2H), 8.80 (d, 1H, J=7.5 Hz), 8.19-8.16 (m, 2H), 7.43 (s, 1H), 7.37 (t, 1H, J=4.5 Hz), 7.30 (d, 1H, J=8.1 Hz), 7.01 (d, 1H, J=8.1 Hz), 3.50-3.32 (m, 1H), 3.30-3.02 (m, 3H), 2.75-2.50 (m, 2H), 2.18-2.08 (m, 1H), 1.96-1.40 (m, 1H); HPLC purity 95.52% by area.

Example 44

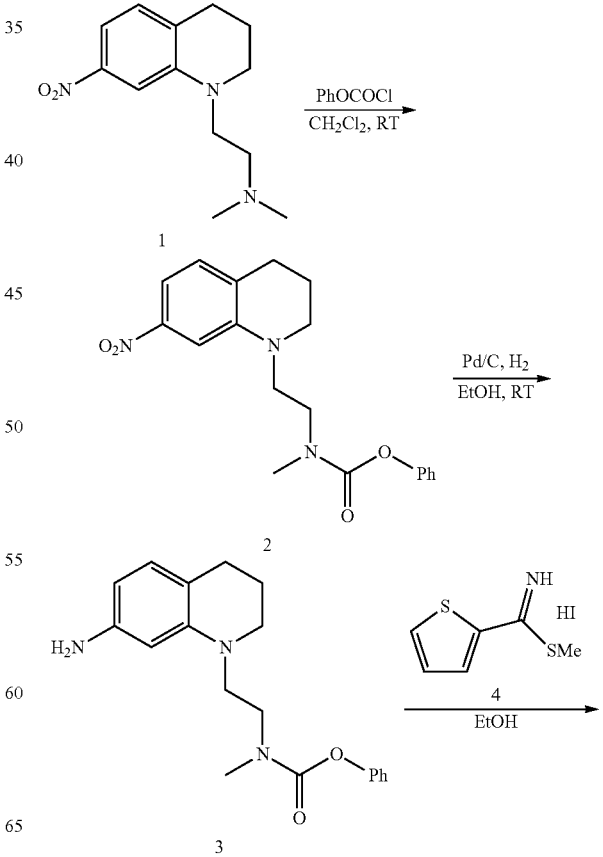

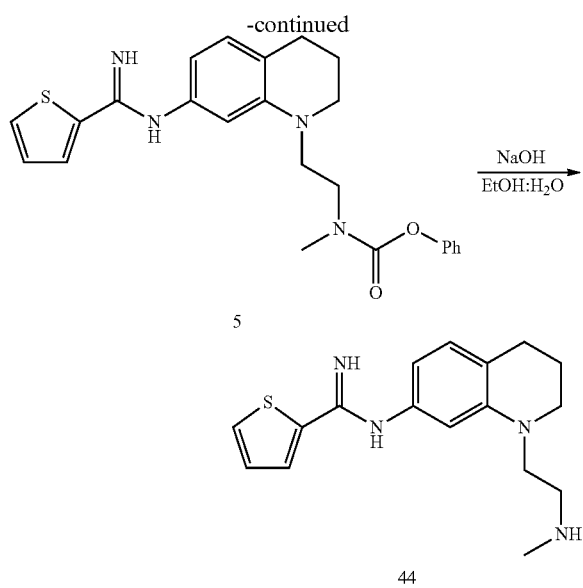

N,N-Dimethyl-2-(7-nitro-3,4-dihydroquinolin-1 (2H)-yl)ethanamine (1)

See Example 32 for complete experimental details and spectral data.

Phenyl methyl(2-(7-nitro-3,4-dihydroquinolin-1 (2H)-yl)ethyl)carbamate (2)

A solution of compound 1 (1.5 g, 6.016 mmol) in dry CH$_2$Cl$_2$ (25 mL) was treated with phenyl chloroformate (1.13 mL, 9.024 mmol) at room temperature and the resulting mixture was stirred for 24 h. The reaction was diluted with 1 N NaOH solution (50 mL) and product was extracted into CH$_2$Cl$_2$ (2×50 mL). The combined organic layer was washed with brine (15 mL) and dried (Na$_2$SO$_4$). Solvent was evaporated and crude was purified by column chromatography on silica gel (CH$_2$Cl$_2$) to obtain compound 2 (1.89 g, 89%) as a syrup. $^1$H NMR (CDCl$_3$) δ 7.49-7.31 (m, 4H), 7.18 (t, 1H, J=7.2 Hz), 7.04-6.90 (m, 3H), 3.68-3.55 (m, 4H), 3.41 (t, 2H, J=5.7 Hz), 3.16-3.07 (m, 3H), 2.79 (t, 2H, J=6.3 Hz), 1.99-1.91 (m, 2H); ESI-MS (m/z, %): 378 (M+Na, 29), 356 (MH$^+$, 100).

Phenyl 2-(7-amino-3,4-dihydroquinolin-1(2H)-yl) ethyl(methyl)carbamate (3)

A solution of compound 2 (1.85 g, 5.205 mmol) in dry ethanol (30 mL) was treated with Pd—C (~0.2 g) and purged with hydrogen gas. The reaction was stirred at room temperature under hydrogen (balloon pressure) for 3 h. The reaction was filtered through celite bed and washed with methanol (3×20 mL). The combined organic layer was evaporated to obtain crude compound 3 (1.67 g, 99%) as a syrup. ESI-MS (m/z, %): 326 (MH$^+$, 100).

Phenyl methyl(2-(7-(thiophene-2-carboximidamido)-3,4-dihydroquinolin-1(2H)-yl)ethyl)carbamate (5)

A solution of compound 3 (1.65 g, 5.070 mmol) in dry ethanol (50 mL) was treated with compound 4 (2.89 g, 10.141 mmol) at room temperature and the resulting mixture was stirred for 24 h. The reaction was diluted with sat. NaHCO$_3$ solution (100 mL) and product was extracted into CH$_2$Cl$_2$ (2×50 mL). The combined organic layer was washed with brine (25 mL) and dried (Na$_2$SO$_4$). The solvent was evaporated and crude product was purified by column chromatography on silica gel (2 M NH$_3$ in MeOH:CH$_2$Cl$_2$, 2.5:97.5) to obtain compound 5 (1.8 g, 82%) as a foam. $^1$H NMR (DMSO-d$_6$) δ 7.53-7.51 (m, 1H), 7.42-7.37 (m, 1H), 7.31-7.27 (m, 1H), 7.23-7.16 (m, 1H), 7.13-7.02 (m, 3H), 6.96 (d, 1H, J=7.5 Hz), 6.91 (d, 1H, J=7.8 Hz), 6.29 (d, 1H, J=4.5 Hz), 6.22 (d, 1H, J=7.8 Hz), 5.71 (brs, 1H), 4.78 (brs, 1H), 3.65-3.52 (m, 4H), 3.35 (t, 2H, J=5.7 Hz), 3.11, 3.03 (2s, 3H), 2.74-2.69 (m, 2H), 1.97-1.89 (m, 2H); ESI-MS (m/z, %): 435 (MH$^+$, 100).

N-(1-(2-(Methylamino)ethyl)-1,2,3,4-tetrahydroquinolin-7-yl)thiophene-2-carboximidamide (44)

A solution of compound 5 (1.30 g, 2.991 mmol) in ethanol:H$_2$O (30 mL, 3:1) was treated with NaOH (1.19 g, 29.916 mmol) at room temperature and the resulting solution was refluxed for 6 h. The reaction was brought to room temperature, diluted with CH$_2$Cl$_2$ (25 mL) and washed with brine (15 mL). The aqueous layer was extracted with more CH$_2$Cl$_2$ (2×20 mL) and combined CH$_2$Cl$_2$ layer was dried (Na$_2$SO$_4$). The solvent was evaporated and crude product was purified by column chromatography on silica gel (2 M NH$_3$ in MeOH:CH$_2$Cl$_2$, 5:95 to 1:9) to obtain compound 44 (0.6 g, 64%) as a solid. $^1$H NMR (DMSO-d$_6$) δ 7.69 (d, 1H, J=3.0 Hz), 7.57 (dd, 1H, J=0.9, 5.1 Hz), 7.07 (dd, 1H, J=3.6, 5.1 Hz), 6.78 (d, 1H, J=7.5 Hz), 6.22 (brs, 2H), 6.08 (d, 1H, J=1.2 Hz), 5.99 (dd, 1H, J=1.5, 7.6 Hz), 3.27-3.23 (m, 4H), 2.68-2.61 (m, 4H), 2.31 (s, 3H), 1.87-1.80 (m, 2H); ESI-MS (m/z, %): 315 (MH$^+$, 100); ESI-HRMS calculated for C$_{17}$H$_{23}$N$_4$S (MH$^+$), calculated: 315.1637; observed: 315.1652; HPLC purity 98.67% by area.

Example 45

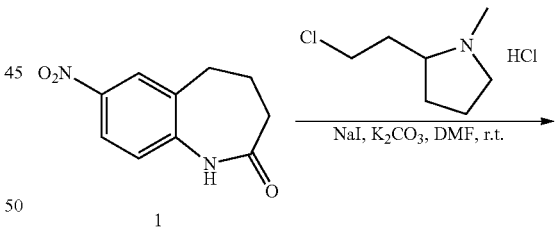

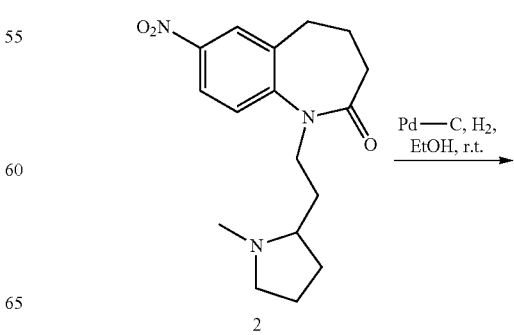

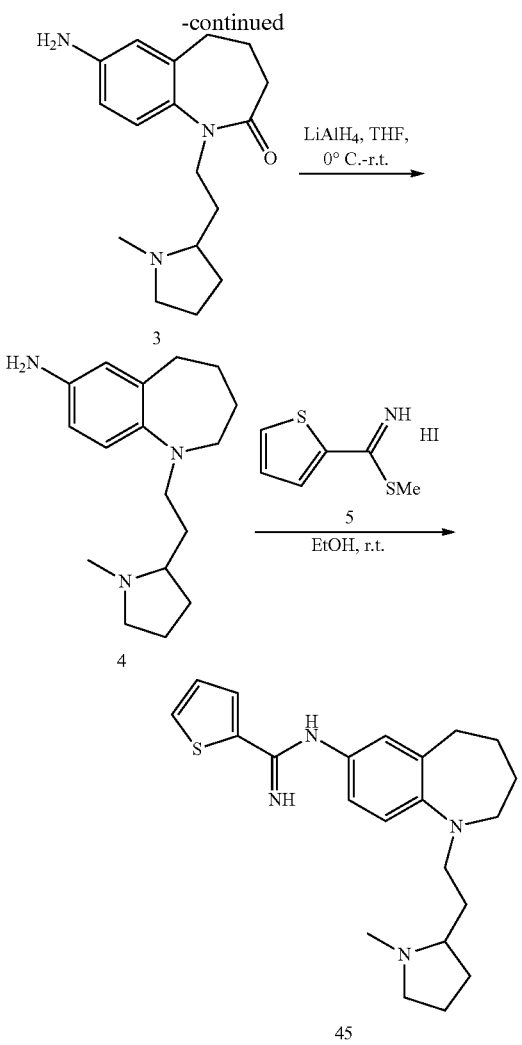

7-Nitro-4,5-dihydro-1H-benzo[b]azepin-2(3H)-one (1)

Refer to the above examples for complete experimental details and spectral data.

1-(2-(1-Methylpyrrolidin-2-yl)ethyl)-7-nitro-4,5-dihydro-1H-benzo[b]azepin-2(3H)-one (2)

A suspension of compound 1 (1.50 g, 7.27 mmol), chloroethyl-1-methylpyrrolidine hydrochloride (2.68 g, 14.55 mmol), NaI (0.545 g, 3.64 mmol) and $K_2CO_3$ (6.03 g, 43.65 mmol) in dry DMF (30 mL) was stirred at room temperature overnight (18 h). The reaction mixture was diluted with $H_2O$ (200 mL) and the product was extracted into EtOAc (2×75 mL). The combined organic fractions were washed with brine (50 mL), dried ($Na_2SO_4$) and concentrated. The product was isolated along with the 9-nitro regioisomer by column chromatography (2.0 N $NH_3$ in MeOH:$CH_2Cl_2$, 3:97) to obtain 2 (1.54 g, 66%) as a thick brown syrup. ESI-MS (m/z, %): 318 (MH$^+$, 100).

7-Amino-1-(2-(1-methylpyrrolidin-2-yl)ethyl)-4,5-dihydro-1H-benzo[b]azepin-2(3H)-one (3)

A solution of 2 (600 mg, 1.89 mmol) in dry ethanol (10 mL) was treated with Pd—C (~0.06 g) and purged with hydrogen gas. The reaction mixture was stirred at room temperature under hydrogen atmosphere (balloon pressure) overnight (18 h). The mixture was filtered through a celite bed and washed with methanol (3×25 mL). The combined organic fractions were concentrated to give a brown residue. The product was purified by dry column chromatography (2 N $NH_3$ in MeOH: $CH_2Cl_2$, 5:95) to give compound 3 (435 mg, 80%) as a colourless foam. $^1$H-NMR (DMSO-$d_6$, 300 MHz) δ: 1.29-1.38 (m, 2H), 1.54-1.60 (m, 2H), 1.66-1.82 (m, 2H), 1.89-2.10 (m, 10H), 2.38-2.45 (m, 2H), 2.84-2.91 (m, 1H), 5.07 (brs, 2H), 6.36-6.52 (m, 2H), 6.85-6.98 (m, 1H).

1-(2-(1-Methylpyrrolidin-2-yl)ethyl)-2,3,4,5-tetrahydro-1H-benzo[b]azepin-7-amine (4)

A solution of compound 3 (825 mg, 2.87 mmol) in anhydrous THF (15 mL) was cooled to 0° C. and treated drop wise with LiAlH$_4$ (1.0 M in THF, 11.5 mL, 11.5 mmol). The reaction mixture was warmed to room temperature and stirred overnight (23 h). The reaction mixture was cooled to 0° C. and quenched with $H_2O$ (0.4 mL), 2 N NaOH (0.4 mL), and additional $H_2O$ (0.4 mL) and stirred for 30 minutes upon, which a white precipitate formed. The solid was filtered off and washed with $CH_2Cl_2$ (2×50 mL) and the filtrate concentrated. The crude product was purified by column chromatography (2N $NH_3$ in MeOH:$CH_2Cl_2$, 5:95) to give compound 4 (590 mg, 75%) as a thick brown syrup.

N-(1-(2-(1-Methylpyrrolidin-2-yl)ethyl)-2,3,4,5-tetrahydro-1H-benzo[b]azepin-7-yl)thiophene-2-carboximidamide (45)

A solution of 4 (170 mg, 0.62 mmol) in dry ethanol (15 mL) was treated with 5 (0.355 g, 1.24 mmol) and stirred for overnight (17 h) at room temperature. The reaction mixture was diluted with saturated NaHCO$_3$ solution (100 mL) and extracted with $CH_2Cl_2$ (2×50 mL). The combined organic fractions were washed with brine (50 mL), dried ($Na_2SO_4$) and concentrated. The crude product was purified by dry column chromatography (MeOH:$CH_2Cl_2$, 2:98 followed by 2 N $NH_3$ in MeOH:$CH_2Cl_2$ 3:97) to give compound 45 (177 mg, 74%) as a yellow solid. $^1$H-NMR (DMSO-$d_6$) δ: 1.38-1.69 (m, 8H), 1.83-1.89 (m, 2H), 2.02-2.12 (m, 2H), 2.19 (s, 3H), 2.65-2.68 (m, 2H), 2.80-3.12 (m, 5H), 6.32 (brs, 2H), 6.62-6.64 (m, 2H), 6.85-6.88 (d, 1H, J=8.9 Hz), 7.06-7.09 (t, 1H, J=3.8 Hz), 7.56-7.58 (d, 1H, J=5.0 Hz), 7.69-7.71 (d, 1H, J=3.6 Hz); ESI-MS (m/z, %): 383 (MH$^+$, 33), 192 (100), 142 (51). ESI-HRMS calculated for $C_{22}H_{30}N_4S$ (MH$^+$), calculated: 383.2253; observed: 383.2263; HPLC-purity: 93.49% by area.

Example 46

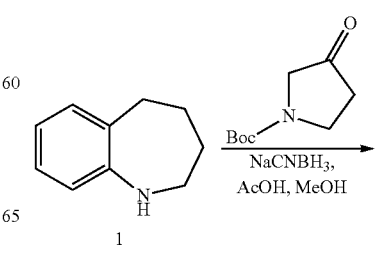

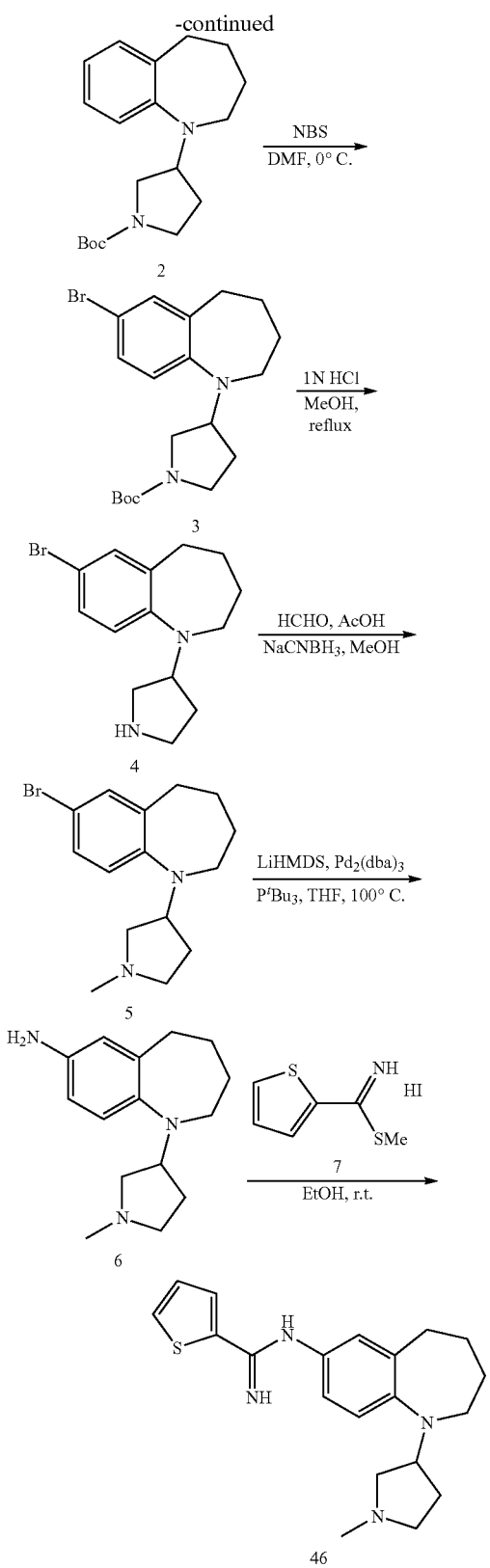

2,3,4,5-Tetrahydro-1H-benzo[b]azepine (1)

See Example 39 for complete experimental details and spectral data.

tert-Butyl 3-(2,3,4,5-tetrahydro-1H-benzo[b]azepin-1-yl)pyrrolidine-1-carboxylate (2)

A solution of compound 1 (1.74 g, 11.82 mmol), N-Boc-3-pyrrolidinone (3.28 g, 17.73 mmol) and acetic acid (1.35 mL, 20.68 mmol) in anhydrous methanol (25 mL) was cooled to 0° C. and treated with a solution of NaCNBH$_3$ (1.67 g, 26.59 mmol) in methanol (5 mL). The reaction was brought to room temperature and stirred overnight (16 h). The reaction was diluted with 2 N NaOH (180 mL) and extracted into EtOAc (2×100 mL). The combined organic fractions were washed with brine (50 mL), dried (Na$_2$SO$_4$) and concentrated. The crude product was purified by column chromatography (EtOAc:Hexanes, 1:4) to obtain compound 2 (3.24 g, 87%) as a syrup. $^1$H NMR (DMSO-d$_6$) δ 1.35-1.39 (m, 9H), 1.44-1.64 (m, 4H), 1.81-1.88 (m, 1H), 2.13-2.18 (m, 1H), 2.67-2.75 (m, 4H), 3.04-3.07 (m, 1H), 3.16-3.22 (m, 1H), 3.38-3.44 (m, 1H), 3.53-3.60 (m, 1H), 4.01-4.04 (m, 1H), 6.83-6.87 (m, 1H), 6.98-7.00 (m, 1H), 7.08-7.13 (m, 2H); ESI-MS (m/z, %): 317 (MH$^+$, 7), 261 (100).

tert-Butyl 3-(7-bromo-2,3,4,5-tetrahydro-1H-benzo[b]azepin-1-yl)pyrrolidine-1-carboxylate (3)

A solution of compound 2 (3.15 g, 9.97 mmol) in DMF (15 mL) was cooled to 0° C. and treated drop wise with a solution of N-bromosuccinimide (1.77 g, 9.97 mmol) in DMF (15 mL). The reaction mixture was stirred at 0° C. for 3 hours then diluted with H$_2$O (100 mL) and extracted into EtOAc (2×100 mL). The combined organic fractions were washed with brine (100 mL), dried (Na$_2$SO$_4$) and concentrated. The crude product was purified by column chromatography (EtOAc:hexanes, 1:9) to obtain compound 3 (3.26 g, 83%) as a foam. $^1$H NMR (DMSO-d$_6$) δ 1.38 (s, 9H), 1.41-1.52 (m, 5H), 1.80-1.87 (m, 1H), 2.12-2.17 (m, 1H), 2.65-2.69 (m, 2H), 2.79-2.92 (m, 2H), 3.00-3.08 (m, 1H), 3.15-3.25 (m, 1H), 3.53-3.59 (m, 1H), 3.96-4.04 (m, 1H), 6.93-6.96 (d, 1H, J=8.4 Hz), 7.23 (dd, 1H, J=2.4, 8.4 Hz), 7.29 (d, 1H, J=2.4 Hz); ESI-MS (m/z, %): 395 (MH$^+$, 7), 341 (92), 339 (100).

7-Bromo-1-(pyrrolidin-3-yl)-2,3,4,5-tetrahydro-1H-benzo[b]azepine (4)

A solution of compound 3 (2.2 g, 5.56 mmol) in methanol (solvent grade, 25 mL) was treated with 1 N HCl (40 mL) and the resulting mixture was refluxed for 30 minutes. The reaction was brought to room temperature, methanol was evaporated and the solution basified with 6 N NaOH (pH ~14). The product was extracted into CH$_2$Cl$_2$ (3×50 mL) and the combined organic layers were dried (Na$_2$SO$_4$) and concentrated to give crude product 4 (1.49 g, 91%) as a syrup. $^1$H NMR (DMSO-d$_6$) δ 1.47-1.62 (m, 6H), 1.97-2.08 (m, 1H), 2.59-2.68 (m, 3H), 2.73-2.79 (m, 2H), 2.84-2.88 (m, 2H), 3.08-3.09 (m, 1H), 3.78-3.87 (m, 1H), 6.85 (d, 1H, J=8.4 Hz), 7.22 (dd, 1H, J=2.4, 8.4 Hz), 7.26 (d, 1H, J=2.4 Hz); ESI-MS (m/z, %): 297, 295 (M$^+$, 100).

7-Bromo-1-(1-methylpyrrolidin-3-yl)-2,3,4,5-tetrahydro-1H-benzo[b]azepine (5)

A solution of compound 4 (0.79 g, 2.68 mmol) in anhydrous methanol (10 mL) was treated with formaldehyde (37% in H$_2$O, 0.26 g, 3.22 mmol) followed by acetic acid (0.38 mL, 6.707 mmol) and NaCNBH$_3$ (0.20 g, 3.22 mmol) at room temperature. The reaction mixture was stirred at room temperature for overnight (16 h). The reaction was basified with 2 N NaOH (50 mL) and the product extracted into CH$_2$Cl$_2$ (2×25 mL). The combined organic layers were washed with brine (25 mL), dried (Na$_2$SO$_4$) and concentrated. The crude product was purified by column chromatography (CH$_2$Cl$_2$, followed by 2 N NH$_3$ in MeOH:CH$_2$Cl$_2$, 5:95) to give compound 5 (0.74 g, 90%) as a brown solid. $^1$H NMR (DMSO-$d_6$) δ 1.48-1.49 (m, 2H), 1.59-1.72 (m, 3H), 2.22 (s, 3H), 2.54-2.66 (m, 5H), 2.89-2.90 (m, 2H), 3.33 (brs, 2H), 3.90-3.94 (m, 1H), 6.78 (d, 1H, J=8.5 Hz), 7.20 (dd, 1H, J=2.5, 8.5 Hz), 7.26 (d, 1H, J=2.5 Hz); ESI-MS (m/z, %): 311 (MH$^+$, 97), 309 (100).

1-(1-Methylpyrrolidin-3-yl)-2,3,4,5-tetrahydro-1H-benzo[b]azepin-7-amine (6)

A suspension of Pd$_2$(dba)$_3$ (105 mg, 0.11 mmol) and P$^t$Bu$_3$ (10% wt in hexanes, 1.40 mL, 0.46 mmol) in anhydrous THF (5 mL) was treated with a solution of compound 5 (713 mg, 2.30 mmol) in THF (10 mL) followed by LiHMDS (1 M in THF, 4.6 mL, 4.60 mmol) at room temperature. The resulting dark brown mixture was heated to 100° C. and stirred for 3 hours in a sealed tube. The reaction mixture was cooled to room temperature and treated with 1 N HCl (20 mL) and stirred for 15 min, then basified with 1 N NaOH (50 mL). The product was extracted into CH$_2$Cl$_2$ (2×50 mL) and the combined organic fractions were washed with brine (25 mL), dried (MgSO$_4$), filtered and concentrated to give a dark brown residue. The crude product was purified by column chromatography (2 N NH$_3$ in MeOH:CH$_2$Cl$_2$, 5:95) to give compound 6 (531 mg, 94%) as a syrup.

N-(1-(1-Methylpyrrolidin-3-yl)-2,3,4,5-tetrahydro-1H-benzo[b]azepin-7-yl)thiophene-2-carboximidamide (46)

A solution of compound 6 (494 mg, 2.01 mmol) in dry ethanol (10 mL) was treated with compound 7 (1.15 g, 4.03 mmol) and stirred for overnight (16 h) at room temperature. The reaction mixture was diluted with saturated NaHCO$_3$ solution (100 mL) and extracted with CH$_2$Cl$_2$ (2×50 mL). The combined organic fractions were washed with brine (25 mL), dried (MgSO$_4$), filtered and concentrated. The crude product was purified by column chromatography (MeOH:CH$_2$Cl$_2$, 2:98 followed by 2 N NH$_3$ in MeOH:CH$_2$Cl$_2$, 2.5:97.5, then 5:95) to give compound 46 (559 mg, 78%) as a solid. $^1$H NMR (DMSO-$d_6$) δ 1.50-1.51 (m, 2H), 1.65-1.72 (m, 3H), 2.13-2.17 (m, 1H), 2.24 (s, 2H), 2.32-2.35 (m, 1H), 2.63-2.70 (m, 5H), 2.83-2.90 (m, 2H), 3.21 (s, 1H), 3.92-3.96 (m, 1H), 6.31 (brs, 2H), 6.60-6.68 (m, 2H), 6.78-6.92 (m, 1H), 7.06-7.11 (m, 1H), 7.56-7.60 (m, 1H), 7.69-7.72 (m, 1H); ESI-MS (m/z, %): 355 (MH$^+$, 83), 272 (100), 178 (82); ESI-HRMS calculated for C$_{20}$H$_{27}$N$_4$S (MH$^+$), calculated: 355.1960; observed: 355.1950; HPLC-purity: 92.12% by area.

Example 47

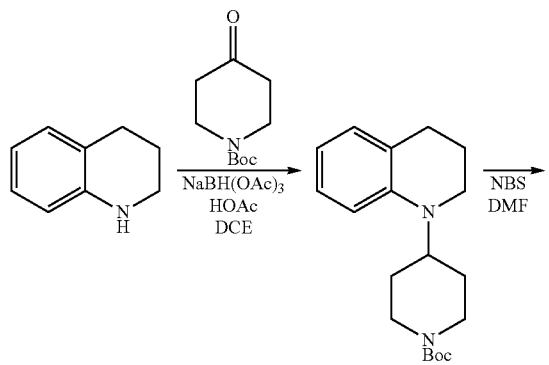

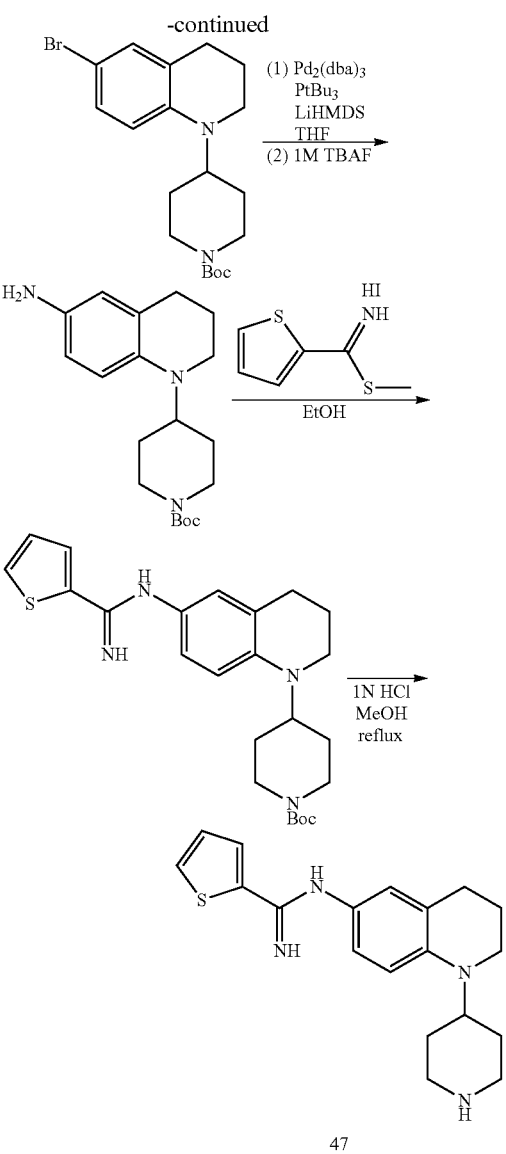

tert-butyl 4-(3,4-dihydroquinolin-1(2H)-yl)piperidine-1-carboxylate

A solution of 1,2,3,4-tetrahydroquinoline (1.06 g, 7.51 mmol) and tert-butyl 4-oxopiperidine-1-carboxylate (2.24 g, 11.26 mmol) in 20 mL 1,2-dichloroethane was treated with sodium triacetoxyborohydride (4.77 g, 22.53 mmol) then acetic acid (1.28 mL, 22.53 mmol). The suspension was stirred at room temperature overnight. At this time, a TLC analysis indicated that 1,2,3,4-tetrahydroquinoline is present along with a more polar spot. To the reaction mixture was added tert-butyl 4-oxopiperidine-1-carboxylate (1.12 g, 5.63 mmol) and sodium triacetoxyborohydride (2.39 g, 11.28 mmol). The suspension was stirred at room temperature for 4 days. After this time, the mixture was cooled to 0° C., quenched with 20 mL 1N NaOH and stirred for 20 minutes. The organic layer was separated and the aqueous layer was extracted with 50 mL CH$_2$Cl$_2$. The combined organic layer was dried over Na$_2$SO$_4$, filtered and concentrated to give a yellow residue. This residue was purified by the Biotage purification system using a silica gel 40M column. A gradient of 5% ethyl acetate:hexanes to 30% ethyl acetate:hexanes over 10 column volumes was used to give the title compound (0.89 g, 37.4%). $^1$H-NMR (CDCl$_3$) δ 7.09-7.03 (m, 1H), 6.97-6.94 (m, 1H), 6.65 (d, J=8.4 Hz, 1H), 6.60-6.55 (m, 1H), 4.30-4.19 (m, 2H), 3.80-3.70 (m, 1H), 3.17 (t, J=5.7 Hz, 2H), 2.84-2.71 (m, 2H), 2.73 (t, J=6.3 Hz, 2H), 1.93-1.85 (m, 2H), 1.78-1.63 (m, 4H), 1.48 (s, 9H). MS (ESI): 317.2 (M+1).

tert-butyl 4-(6-bromo-3,4-dihydroquinolin-1(2H)-yl)piperidine-1-carboxylate

A solution of tert-butyl 4-(3,4-dihydroquinolin-1(2H)-yl)piperidine-1-carboxylate (0.85 g, 2.69 mmol) in 15 mL of DMF was cooled to 0° C. then treated dropwise with NBS (478 mg, 2.69 mmol) in 12 mL DMF. The reaction was stirred at 0° C. for 1 hour then treated with 100 mL H$_2$O. The suspension was extracted with 2×75 mL of ethyl acetate. The combined organic layer was rinsed with brine (2×50 mL), dried over Na$_2$SO$_4$, filtered and concentrated to give a light brown oil. This residue was subjected to silica gel chromatography using the Biotage purification system (25+M column, 0-20% ethyl acetate/hexanes over 10 column volumes) to give a viscous oil which solidified to give a white solid (852 mg, 80.4%). $^1$H-NMR (CDCl$_3$) δ 7.10 (dd, J=2.4 Hz, 8.7 Hz, 1H), 7.05-7.04 (m, 1H), 6.51 (d, J=9.0 Hz, 1H), 4.33-4.19 (m, 2H), 3.71-3.64 (m, 1H), 3.14 (t, J=6.0 Hz, 2H), 2.82-2.74 (m, 2H), 2.69 (t, J=6.3 Hz, 2H), 1.91-1.77 (m, 2H), 1.61-1.57 (m, 4H), 1.47 (s, 9H). MS (ESI): 395.1 and 377.1 (M+1).

tert-butyl 4-(6-amino-3,4-dihydroquinolin-1(2H)-yl)piperidine-1-carboxylate

A suspension of Pd$_2$(dba)$_3$ (29 mg, 0.032 mmol) in 2 mL anhydrous THF was treated with P$^t$Bu$_3$ (400 μL of a 10% wt in hexanes solution, 0.13 mmol) and stirred at room temperature for 5 minutes. To this mixture was added tert-butyl 4-(6-bromo-3,4-dihydroquinolin-1(2H)-yl)piperidine-1-carboxylate (250 mg, 0.63 mmol) followed by lithium hexamethyldisilizane (1.3 mL of a 1 M solution in THF, 1.3 mmol). The resulting dark brown suspension was heated at 95° C. for 3 hours. The mixture was cooled to room temperature and treated with 5 ml of a 1M tetrabutylammonium fluoride solution in THF then stirred at room temperature for 30 minutes. The mixture was partitioned between ethyl acetate (100 mL) and H$_2$O (20 mL). After extraction, the organic layer was separated, dried over Na$_2$SO$_4$, filtered and concentrated to give a dark brown residue. This residue was subjected to flash chromatography on silica gel using 2.5% 2M NH$_3$ in methanol/CH$_2$Cl$_2$ to give a viscous dark brown residue (160 mg, 76.6%). $^1$H-NMR (CDCl$_3$) δ 6.56 (d, J=8.4 Hz, 1H), 6.48 (dd, J=2.7, 8.7 Hz, 1H), 6.43-6.42 (m, 1H), 4.25-4.21 (m, 2H), 3.69-3.59 (m, 1H), 3.24 (br s, 2H), 3.07 (t, J=5.4 Hz, 2H), 2.78-2.72 (m, 2H), 2.66 (t, J=6.6 Hz, 2H), 1.93-1.83 (m, 2H), 1.76-1.55 (m, 4H), 1.47 (s, 9H). MS (ESI): 332.2 (M+1, 100%).

Example 48

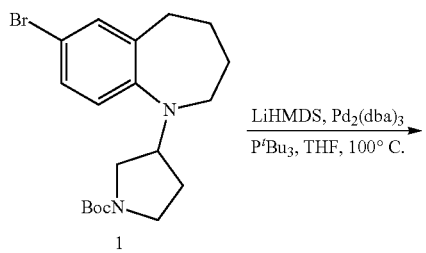

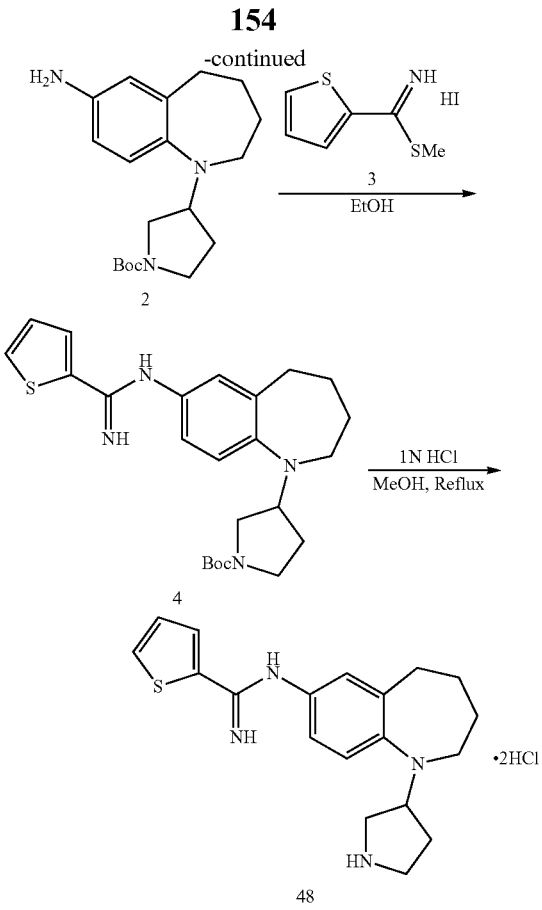

tert-Butyl 3-(7-bromo-2,3,4,5-tetrahydro-1H-benzo[b]azepin-1-yl)pyrrolidine-1-carboxylate (1)

See Example 46 for complete experimental details and spectral data.

tert-Butyl 3-(7-amino-2,3,4,5-tetrahydro-1H-benzo[b]azepin-1-yl)pyrrolidine-1-carboxylate (2)

A suspension of Pd$_2$(dba)$_3$ (0.13 g, 0.145 mmol) and P$^t$Bu$_3$ (1.76 mL, 0.581 mmol, 10% wt in hexane) in anhydrous THF (5 mL) was treated with a solution of compound 1 (1.15 g, 2.908 mmol) in THF (15 mL) followed by LiHMDS (5.81 mL, 5.817 mmol, 1 M solution in THF) at room temperature. The resulting dark brown mixture was heated to 100° C. and stirred for 3 hours in a sealed tube. The reaction mixture was cooled to room temperature and treated with TBAF (5 mL, 1 M solution in THF) and stirred for 20 min. The reaction was diluted with water (25 mL) and product was extracted into ether (3×50 mL) and the combined organic fractions were dried (Na$_2$SO$_4$) and concentrated to give a dark brown residue. The crude product was purified by column chromatography on silica gel (2 N NH$_3$ in methanol:CH$_2$Cl$_2$, 2:98) to obtain compound 2 (0.96 g, quantitative) as a foam. $^1$H NMR (CDCl$_3$) δ 6.77 (d, 1H, J=8.1 Hz), 6.52-6.44 (m, 2H), 3.97-3.86 (m, 1H), 3.70-3.40 (m, 2H), 3.32-3.09 (m, 2H), 2.85-2.77 (m, 2H), 2.70-2.62 (m, 2H), 2.14-2.04 (m, 1H), 1.90-1.72 (m, 1H), 1.68-1.50 (m, 4H), 1.44 (s, 9H); ESI-MS (m/z, %): 332 (MH$^+$, 49), 276 (100).

tert-Butyl 3-(7-(thiophene-2-carboximidamido)-2,3,4,5-tetrahydro-1H-benzo[b]azepin-1-yl)pyrrolidine-1-carboxylate (4)

A solution of compound 2 (0.94 g, 2.836 mmol) in dry ethanol (25 mL) was treated with compound 3 (1.61 g, 5.672 mmol) and stirred for overnight (16 h) at room temperature. The reaction mixture was diluted with saturated NaHCO$_3$ solution (50 mL) and extracted in to CH$_2$Cl$_2$ (2×50 mL). The combined organic fractions were washed with brine (20 mL) and dried (Na$_2$SO$_4$). Solvent was evaporated and crude product was purified by column chromatography (2 N NH$_3$ in MeOH:CH$_2$Cl$_2$, 2.5:97.5) to obtain compound 4 (1.05 g, 85%) as a foam. $^1$H NMR (CDCl$_3$) δ 7.44-7.36 (m, 2H), 7.07 (dd, 1H, J=3.6, 5.1 Hz), 6.93 (d, 1H, J=8.1 Hz), 6.80-6.72 (m, 2H), 4.85 (brs, 2H), 4.03-3.97 (m, 1H), 3.75-3.48 (m, 2H), 3.31-3.18 (m, 2H), 2.90-2.84 (m, 2H), 2.76-2.72 (m, 2H), 2.21-2.11 (m, 1H), 1.98-1.87 (m, 1H), 1.70-1.52 (m, 4H), 1.46 (s, 9H); ESI-MS (m/z, %): 441 (MH$^+$, 100).

N-(1-(Pyrrolidin-3-yl)-2,3,4,5-tetrahydro-1H-benzo[b]azepin-7-yl)thiophene-2-carboximidamide (48)

A solution of compound 4 (0.8 g, 1.815 mmol) in methanol (10 mL) was treated with 1 N HCl (10 mL) and the resulting mixture was refluxed for 30 minutes. The reaction was brought to room temperature and solvent was evaporated. The crude product was dissolved into water (10 mL), filtered and washed. Water was evaporated to obtain compound 48 (0.7 g, 93%) as a solid. $^1$H NMR (DMSO-d$_6$) δ 11.44 (s, 1H), 9.78-9.65 (m, 3H), 8.78 (s, 1H), 8.17-8.15 (m, 2H), 7.37 (t, 1H, J=4.2 Hz), 7.20-7.08 (m, 3H), 3.50-3.40 (m, 1H), 3.38-3.26 (m, 1H), 3.17-2.90 (m, 4H), 2.76 (brt, 2H), 2.30-2.20 (m, 1H), 2.00-1.90 (m, 1H), 1.70-1.50 (m, 4H); ESI-MS (m/z, %): 341 (MH$^+$, 38), 272 (100); ESI-HRMS calculated for C$_{19}$H$_{25}$N$_4$S (MH$^+$, free base), calculated: 341.1794; observed: 341.1801; HPLC-purity: 98.20% by area.

Example 49

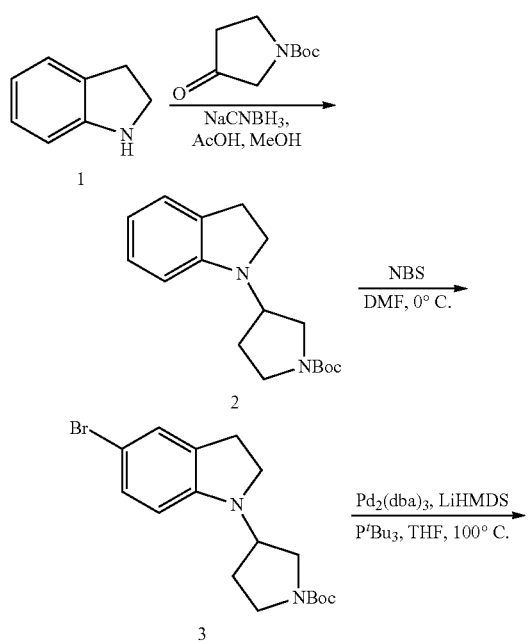

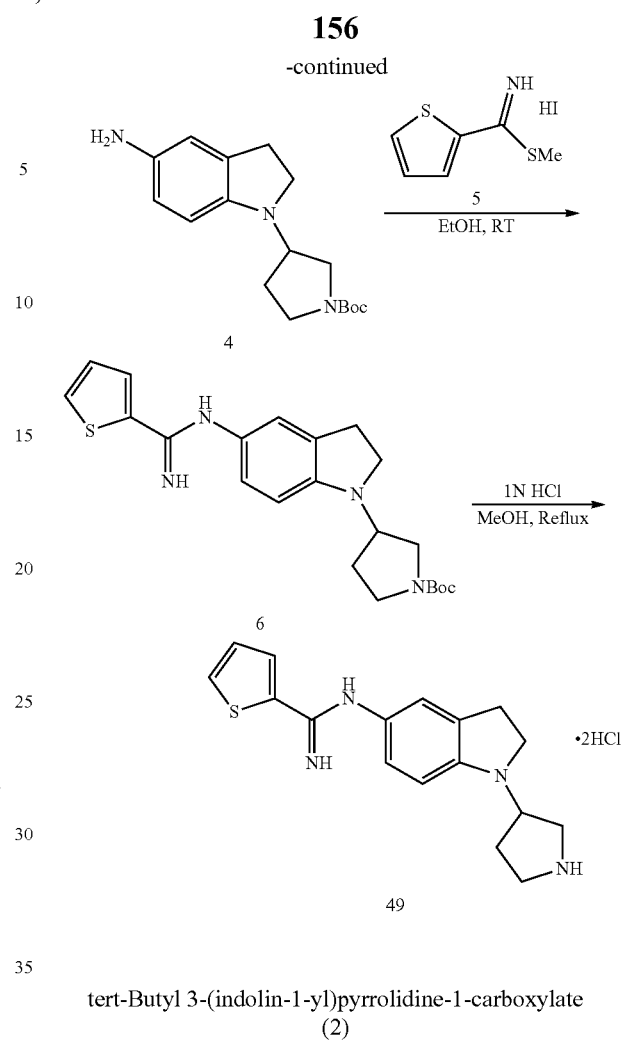

tert-Butyl 3-(indolin-1-yl)pyrrolidine-1-carboxylate (2)

A solution of compound 1 (1.88 mL, 16.782 mmol), N-Boc-3-pyrrolidinone (3.73 g, 20.139 mmol) in dry methanol (20 mL) was treated with acetic acid (2.37 mL, 41.956 mmol) followed by NaCNBH$_3$ (1.26 g, 20.139 mmol) at 0° C. The reaction was brought to room temperature and stirred for 3 h. The reaction was basified with 1 N NaOH solution (100 mL) and product was extracted into CH$_2$Cl$_2$ (3×25 mL). The combined CH$_2$Cl$_2$ layer was dried (Na$_2$SO$_4$) and solvent was evaporated to obtain crude product. The crude was purified by column chromatography (ethyl acetate:hexanes, 1:9) to obtain compound 2 (4.2 g, 87%) as a syrup. $^1$H NMR (CDCl$_3$) δ 7.08-7.02 (m, 2H), 6.66 (t, 1H, J=7.5 Hz), 6.49 (d, 1H, J=7.8 Hz), 4.17-4.05 (m, 1H), 3.70-3.51 (m, 2H), 3.47-3.37 (m, 4H), 2.95 (t, 2H, J=8.4 Hz), 2.18-1.99 (m, 2H), 1.46 (s, 9H); ESI-MS (m/z, %): 289 (MH$^+$, 16), 233 (100).

tert-Butyl 3-(5-bromoindolin-1-yl)pyrrolidine-1-carboxylate (3)

A solution of compound 2 (4.15 g, 14.390 mmol) in dry DMF (30 mL) was treated with NBS (2.56 g, 14.390 mmol) in dry DMF (20 mL) at 0° C. and resulting solution was stirred at same temperature for 3 h. The reaction was diluted with water (150 mL) and product was extracted into ethyl acetate (3×30 mL). The combined ethyl acetate layer was washed with water (2×25 mL), brine (25 mL) and dried (Na$_2$SO$_4$). Solvent was evaporated and crude was purified by column chromatography (ethyl acetate:hexanes, 1:4) to obtain compound 3 (5.12 g, 97%) as a syrup. $^1$H NMR (CDCl$_3$) δ 7.18-7.07 (m, 2H), 6.33 (d, 1H, J=8.7 Hz), 4.13-3.99 (m, 1H), 3.68-3.26 (m, 6H), 2.94 (t, 2H, J=8.1 Hz), 2.17-1.99 (m, 2H), 1.46 (s, 9H); ESI-MS (m/z, %): 390 (MNa$^+$, 6), 368 (MH$^+$, 3), 313, 311(100).

tert-Butyl 3-(5-aminoindolin-1-yl)pyrrolidine-1-carboxylate (4)

A suspension of Pd$_2$(dba)$_3$ (0.124 g, 0.136 mmol) and P$^t$Bu$_3$ (1.65 mL, 0.544 mmol, 10% wt in hexane) in anhydrous THF (5 mL) was treated with a solution of compound 3 (1.0 g, 2.722 mmol) in THF (15 mL) followed by LiHMDS (5.44 mL, 5.445 mmol, 1 M solution in THF) at room temperature. The resulting dark brown mixture was heated to 100° C. and stirred for 3 hours in a sealed tube. The reaction mixture was cooled to room temperature and treated with TBAF (5 mL, 1 M solution in THF) and stirred for 20 min. The reaction was diluted with water (25 mL) and product was extracted into ether (3×30 mL) and the combined organic fractions were dried (Na$_2$SO$_4$) and concentrated to give a dark brown residue. The crude product was purified by column chromatography (2 N NH$_3$ in methanol:CH$_2$Cl$_2$, 3:97) to obtain compound 4 (0.68 g, 82%) as a foam. ESI-MS (m/z, %): 304 (MH$^+$, 16), 248 (100), 134 (25).

tert-Butyl 3-(5-(thiophene-2-carboximidamido)indolin-1-yl)pyrrolidine-1-carboxylate (6)

A solution of compound 4 (0.65 g, 2.142 mmol) in dry ethanol (15 mL) was treated with compound 5 (1.22 g, 4.284 mmol) and stirred for overnight (16 h) at room temperature. The reaction mixture was diluted with saturated NaHCO$_3$ solution (50 mL) and extracted in to CH$_2$Cl$_2$ (2×50 mL). The combined organic fractions were washed with brine (20 mL) and dried (Na$_2$SO$_4$). Solvent was evaporated and crude product was purified by column chromatography (2 N NH$_3$ in methanol:CH$_2$Cl$_2$, 5:95) to obtain compound 6 (0.68 g, 77%) as a foam. $^1$H NMR (DMSO-d$_6$) δ 7.42-7.36 (m, 2H), 7.06 (dd, 1H, J=3.6, 4.9 Hz), 6.79 (brs, 1H), 6.71 (t, 1H, J=5.1 Hz), 6.48 (d, 1H, J=8.1 Hz), 4.89 (brs, 2H), 4.12-4.02 (m, 1H), 3.68-3.35 (m, 6H), 2.93 (t, 2H, J=8.1 Hz), 2.14-2.04 (m, 2H), 1.46 (s, 9H); ESI-MS (m/z, %): 413 (MH$^+$, 100).

N-(1-(Pyrrolidin-3-yl)indolin-5-yl)thiophene-2-carboximidamide (49)

A solution of compound 6 (0.35 g, 0.848 mmol) in methanol (10 mL) was treated with 1 N HCl (10 mL) and the resulting mixture was refluxed for 30 minutes. The reaction was brought to room temperature and solvent was evaporated. The crude product was dissolved into water (10 mL), filtered and washed. Water was evaporated to obtain compound 49 (0.3 g, 92%) as a solid. $^1$H NMR (DMSO-d$_6$) δ11.25 (s, 1H), 9.82-9.60 (m, 3H), 8.63 (s, 1H), 8.15-8.13 (m, 2H), 7.36 (t, 1H, J=4.5 Hz), 7.12-7.06 (m, 2H), 6.68 (d, 1H, J=8.4 Hz), 4.39-4.35 (m, 1H), 3.56-3.06 (m, 6H), 2.96 (t, 2H, J=8.1 Hz), 2.18-2.00 (m, 2H); ESI-MS (m/z, %): 313 (MH$^+$, free base, 100), 244 (61); ESI-HRMS calculated for C$_{17}$H$_{21}$N$_4$S (MH$^+$, free base), calculated: 313.1481; observed: 313.1473; HPLC-purity: 94.05% by area.

Example 50

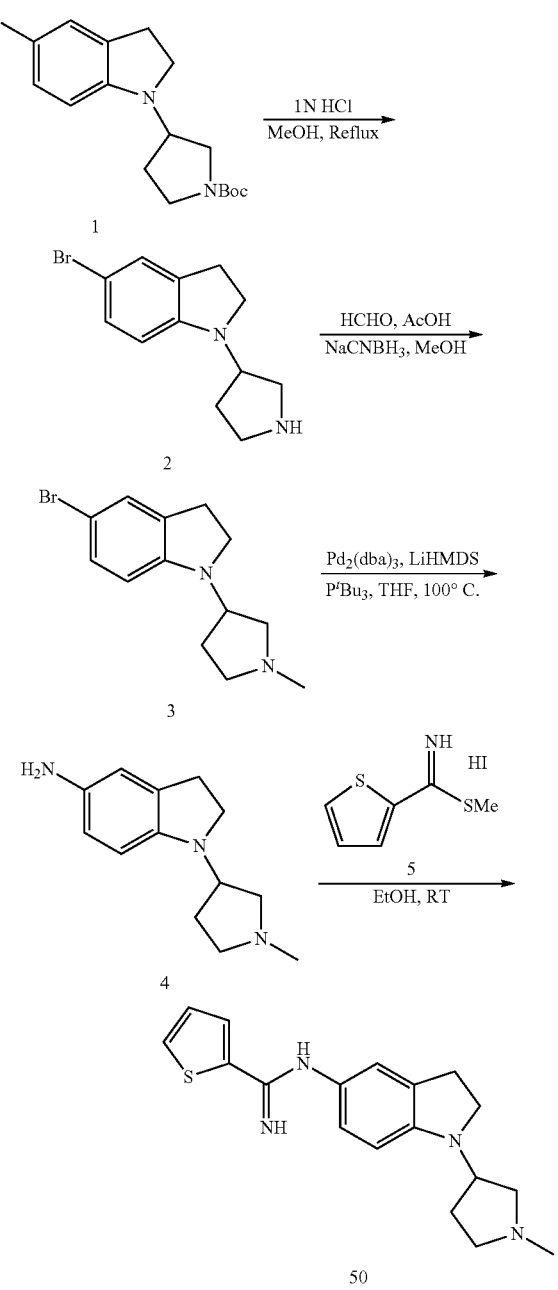

tert-Butyl 3-(5-bromoindolin-1-yl)pyrrolidine-1-carboxylate (1)

See Example 49 for complete experimental details and spectral data.

5-Bromo-1-(pyrrolidin-3-yl)indoline (2)

A solution of compound 1 (3.0 g, 8.168 mmol) in methanol (25 mL) was treated with 1 N HCl (25 mL) and the resulting mixture was refluxed for 1 h. The reaction was brought to room temperature and solvent was evaporated. The crude product was basified with 1 N NaOH solution (pH ~14) and product was extracted into $CH_2Cl_2$ (3×25 mL). The combined $CH_2Cl_2$ layer was dried ($Na_2SO_4$) and solvent was evaporated to obtain compound 2 (1.75 g, 80%) as a syrup. $^1$H NMR (DMSO-$d_6$) δ 7.12-7.06 (m, 2H), 6.45 (d, 1H, J=8.1 Hz), 4.00-3.92 (m, 1H), 3.34 (t, 2H, J=8.4 Hz), 2.96-2.66 (m, 7H), 1.92-1.80 (m, 1H), 1.69-1.60 (m, 1H); ESI-MS (m/z, %): 267, 269 (MH$^+$, 100).

5-Bromo-1-(1-methylpyrrolidin-3-yl)indoline (3)

A solution of compound 2 (1.0 g, 3.743 mmol) in dry methanol (10 mL) was treated with HCHO (0.36 g, 4.491 mmol, 37% in water) followed by acetic acid (0.53 mL, 9.357 mmol) and $NaCNBH_3$ (0.28 g, 4.491 mmol) at room temperature and the resulting mixture was stirred for over night (14 h). The reaction was basified with 2 N NaOH solution (50 mL) and product was extracted into $CH_2Cl_2$ (2×25 mL). The combined organic layer was washed with brine (15 mL) and dried ($Na_2SO_4$). Solvent was evaporated and crude was purified by column chromatography (2 M $NH_3$ in methanol:$CH_2Cl_2$, 5:95) to obtain compound 3 (0.7 g, 66.6%) as a syrup. $^1$H NMR (CDCl$_3$) δ 7.12-7.08 (m, 2H), 6.35 (d, 1H, J=9.0 Hz), 4.19-4.10 (m, 1H), 3.45-3.39 (m, 2H), 2.91 (t, 2H, J=8.1 Hz), 2.70-2.63 (m, 3H), 2.51-2.43 (m, 1H), 2.34 (s, 3H), 2.19-2.07 (m, 1H), 1.93-1.81 (m, 1H); ESI-MS (m/z, %): 281, 283 (MH$^+$, 100).

1-(1-Methylpyrrolidin-3-yl)indolin-5-amine (4)

A suspension of $Pd_2(dba)_3$ (0.1 g, 0.113 mmol) and $P^tBu_3$ (1.38 mL, 0.455 mmol, 10% wt in hexane) in anhydrous THF (3 mL) was treated with a solution of compound 3 (0.64 g, 2.276 mmol) in THF (7 mL) followed by LiHMDS (4.55 mL, 4.552 mmol, 1 M solution in THF) at room temperature. The resulting dark brown mixture was heated to 100° C. and stirred for 3 hours in a sealed tube. The reaction mixture was cooled to room temperature and treated with 1 N HCl solution (5 mL) and stirred for 20 min. The reaction was basified with 2 N NaOH solution (25 mL) and product was extracted into $CH_2Cl_2$ (3×20 mL) and the combined organic fractions were washed with brine (20 mL) and dried ($Na_2SO_4$). The solvent was evaporated and crude product was purified by column chromatography on silica gel (2 N $NH_3$ in MeOH:$CH_2Cl_2$, 5:95) to obtain compound 4 (0.44 g, 89%) as a syrup. $^1$H NMR (DMSO-$d_6$) δ 6.38 (s, 1H), 6.30-6.23 (m, 2H), 4.31 (brs, 2H), 4.01-3.92 (m, 1H), 3.14 (t, 2H, J=8.1 Hz), 2.68 (t, 2H, J=8.1 Hz), 2.56-2.50 (m, 3H), 2.37-2.29 (m, 1H), 2.21 (s, 3H), 2.02-1.90 (m, 1H), 1.76-1.66 (m, 1H); ESI-MS (m/z, %): 218 (MH$^+$, 100).

N-(1-(1-Methylpyrrolidin-3-yl)indolin-5-yl) thiophene-2-carboximidamide (50)

A solution of compound 4 (0.4 g, 1.840 mmol) in dry ethanol (10 mL) was treated with compound 5 (1.04 g, 3.681 mmol) and stirred for overnight (16 h) at room temperature. The reaction mixture was diluted with saturated $NaHCO_3$ solution (25 mL) and extracted in to $CH_2Cl_2$ (2×25 mL). The combined organic fractions were washed with brine (20 mL) and dried ($Na_2SO_4$). Solvent was evaporated and crude product was purified by column chromatography (2 N $NH_3$ in MeOH:$CH_2Cl_2$, 5:95) to obtain compound 50 (0.43 g, 72%) as a solid. $^1$H NMR (DMSO-$d_6$) δ 7.68 (d, 1H, J=3.0 Hz), 7.58 (dd, 1H, J=1.2, 5.1 Hz), 7.07 (dd, 1H, J=3.6, 4.9 Hz), 6.62 (s, 1H), 6.52-6.48 (m, 2H), 6.32 (brs, 2H), 4.16-4.08 (m, 1H), 3.32-3.24 (m, 2H), 2.81 (t, 2H, J=8.1 Hz), 2.63-2.55 (m, 3H), 2.38-2.31 (m, 1H), 2.24 (s, 3H), 2.09-1.97 (m, 1H), 1.82-1.71 (m, 1H); ESI-MS (m/z, %): 327 (MH$^+$, 100), 244 (83); ESI-HRMS calculated for $C_{18}H_{23}N_4S$ (MH$^+$), calculated: 327.1637; observed: 327.1650; HPLC purity: 95.54% by area.

Example 51

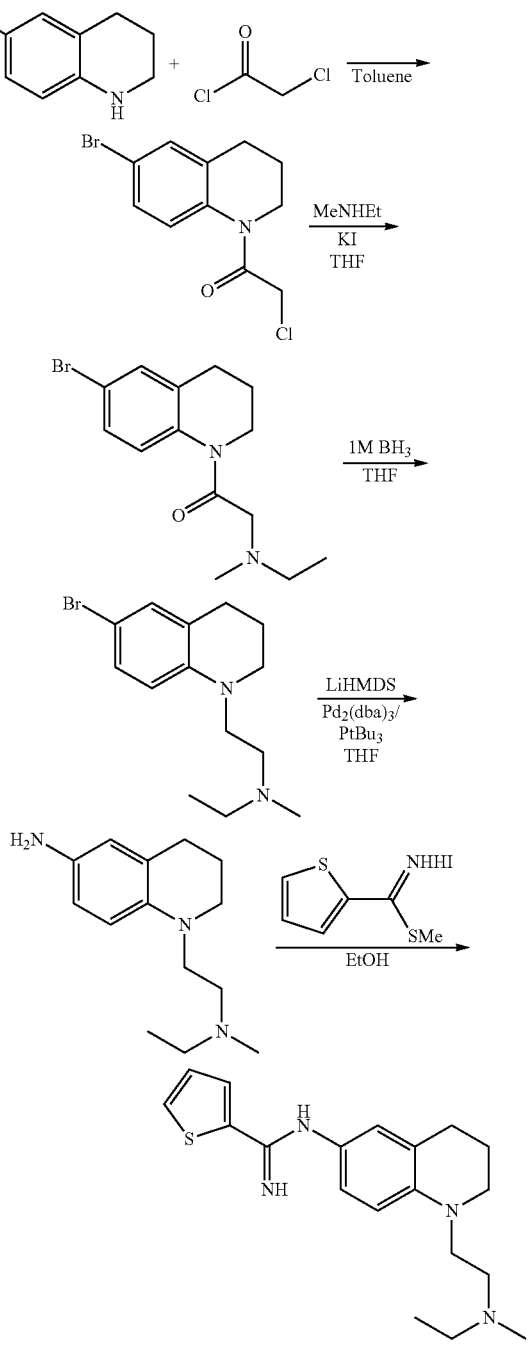

51

1-(6-bromo-3,4-dihydroquinolin-1(2H)-yl)-2-chloroethanone

A solution of 6-bromo-1,2,3,4-tetrahydroquinoline (2.09 g, 9.85 mmol) in 55 mL toluene was treated with 2-chloroacetyl chloride (0.863 mL, 10.84 mmol) dropwise over 10 minutes. The resulting suspension was stirred at room temperature for 1.5 hour then heated at 95° C. for 30 minutes. After cooling to room temperature, the yellow solution was diluted with 20 mL ethyl acetate and treated with 25 mL of a saturated aqueous sodium bicarbonate solution. The mixture was poured into a separatory funnel and extracted. The organic layer was separated, dried over $Na_2SO_4$, filtered and concentrated. The crude product was purified by flash chromatography on silica gel using 30% ethyl acetate:70% hexanes as eluant. A white solid was obtained after drying under reduced pressure (Yield: 2.4 g, 84%). $^1$H-NMR (CDCl$_3$) δ 7.35-7.33 (m, 3H), 4.19 (s, 2H), 3.80 (t, J=6.3 Hz, 2H), 2.74 (t, J=6.6 Hz, 2H), 2.04-1.98 (m, 2H).

1-(6-bromo-3,4-dihydroquinolin-1(2H)-yl)-2-(ethyl(methyl)amino)ethanone

A suspension of 1-(6-bromo-3,4-dihydroquinolin-1(2H)-yl)-2-chloroethanone (1 g, 3.47 mmol) and potassium iodide (0.115 g, 0.693 mmol) in 10 mL THF was treated with N-methylethanamine (1.786 mL, 20.79 mmol). The mixture was stirred at room temperature for 2 hours then heated at 65° C. for 1 hour. The mixture was concentrated and partitioned between $CH_2Cl_2$ (100 mL) and saturated sodium bicarbonate (25 mL). After extraction, the organic layer was separated, dried over $Na_2SO_4$, filtered and concentrated to give a light brown residue. This residue was subjected to flash chromatography on silica gel using 5% 2M $NH_3$ in methanol/95% $CH_2Cl_2$ to give a light brown residue (1.06 g, 98%). $^1$H-NMR (CDCl$_3$) δ 7.52-7.40 (br s, 1H), 7.30-7.27 (m, 2H), 3.80 (t, J=6.0 Hz, 2H), 3.28 (s, 2H), 2.72 (t, J=6.9 Hz, 2H), 2.50 (quart, J=7.2 Hz, 2H), 2.30 (s, 3H), 1.96 (quint, J=6.6 Hz, 2H), 1.03 (t, J=7.2 Hz, 3H). MS (ESI): 311.1 and 313.1 (M+1, 100%).

2-(6-bromo-3,4-dihydroquinolin-1(2H)-yl)-N-ethyl-N-methylethanamine

A solution of 1-(6-bromo-3,4-dihydroquinolin-1(2H)-yl)-2-(ethyl(methyl)amino)ethanone (1.05 g, 3.37 mmol) in THF (10 mL) was cooled to 0° C. then treated with $BH_3$ in THF (1M) (33.7 mL, 33.7 mmol). The clear solution was allowed to warm to room temperature and stirred at this temperature for 3 days. The mixture was cooled to 0° C. and treated with methanol (5 mL) dropwise with caution. After stirring for 15 minutes, the mixture was concentrated to dryness then dissolved in methanol (25 mL) and concentrated again. The residue was dissolved in 25 mL methanol and heated at reflux for 5 hours then stirred at room temperature overnight. The reaction was concentrated to dryness to give a light yellow residue. This residue was subjected to flash chromatography on silica gel using 5% 2M $NH_3$ in MeOH/95% $CH_2Cl_2$ to give a colourless residue (0.89 g, 89%). $^1$H-NMR (CDCl$_3$) δ 7.09 (dd, J=1.8, 6.6 Hz, 1H), 7.02-7.01 (m, 1H), 6.44 (d, J=6.6 Hz, 1H), 3.36 (t, J=5.7 Hz, 2H), 3.29 (t, J=4.2 Hz, 2H), 2.70 (t, J=4.8 Hz, 2H), 2.53-2.43 (m, 4H), 2.28 (s, 3H), 1.94-1.88 (m, 2H), 1.06 (t, J=5.4 Hz, 3H). MS (ESI): 397.1 and 399.1 (M+1, 100%).

1-(2-(ethyl(methyl)amino)ethyl)-1,2,3,4-tetrahydroquinolin-6-amine

A solution of 2-(6-bromo-3,4-dihydroquinolin-1(2H)-yl)-N-ethyl-N-methylethanamine (500 mg, 1.682 mmol) in THF (15 mL) was treated with tris(dibenzylideneacetone)dipalladium(0) (77 mg, 0.084 mmol) followed by Tri-t-butylphosphine in hexanes (10% wt) (0.612 mL, 0.202 mmol). The resulting purple mixture was treated with LiHMDS (Lithium hexamethyldisilazide), 1M in THF (5.05 mL, 5.05 mmol). The reaction vial was sealed and dark mixture was heated at 90° C. for 2 hours. The mixture was transferred to a 125 mL flask, cooled to 0° C. and treated with 10 mL of a 2N HCl solution. After stirring for 10 minutes, the mixture was basified with 1N NaOH and extracted with 2×75 mL $CH_2Cl_2$. After extraction, the combined organic layer was dried over $Na_2SO_4$, filtered and concentrated to give a dark residue. This residue was subjected to flash chromatography on silica gel using 2.5% methanol/97.5% $CH_2Cl_2$ then 5% 2M $NH_3$ in methanol/95% $CH_2Cl_2$ to give a dark brown residue (351 mg, 89%). $^1$H-NMR (CDCl$_3$) δ 6.49-6.48 (2H), 6.41 (br s, 1H), 3.36-3.31 (m, 2H), 3.21 (t, J=5.7 Hz, 2H), 3.20 (br s, 2H), 2.68 (t, J=6.3 Hz, 2H), 2.56-2.43 (m, 4H), 2.28 (s, 3H), 1.95-1.87 (m, 2H), 1.07 (t, J=7.2 Hz, 3H). MS (ESI): 234.2 (M+1).

N-(1-(2-(ethyl(methyl)amino)ethyl)-1,2,3,4-tetrahydroquinolin-6-yl)thiophene-2-carboximidamide (51)

A solution of 1-(2-(ethyl(methyl)amino)ethyl)-1,2,3,4-tetrahydroquinolin-6-amine (335 mg, 1.436 mmol) in ethanol (15 mL) was treated with methyl thiophene-2-carbimidothioate hydroiodide (819 mg, 2.87 mmol) in one portion. The mixture was stirred at room temperature overnight. The mixture was partitioned between 100 mL $CH_2Cl_2$ and 20 mL saturated $Na_2CO_3$ solution. After extraction, the organic layer was separated, dried over $Na_2SO_4$, filtered and concentrated to give a yellow brown residue. This residue was subjected to flash chromatography on silica gel using 2.5% methanol/97.5% $CH_2Cl_2$ then 5% 2M $NH_3$ in methanol/95% $CH_2Cl_2$ to give a dark yellow residue (360 mg, 73.2%). $^1$H-NMR (DMSO-d$_6$) δ 7.67 (d, J=3.6 Hz, 1H), 7.55 (dd, J=0.9, 5.1 Hz, 1H), 7.07 (dd, J=3.6, 4.8 Hz, 1H), 6.58-6.48 (3H), 6.30 (br s, 2H), 3.30-3.22 (m, 4H), 2.65 (t, J=6.0 Hz, 2H), 2.46-2.36 (m, 4H), 2.20 (s, 3H), 1.87-1.80 (m, 2H), 0.97 (t, J=7.2 Hz, 3H). MS (ESI): 343.2 (M+1). ESI-HRMS calculated for $C_{19}H_{27}N_4S(MH^+)$: 343.1950, Observed: 343.1946.

Example 52

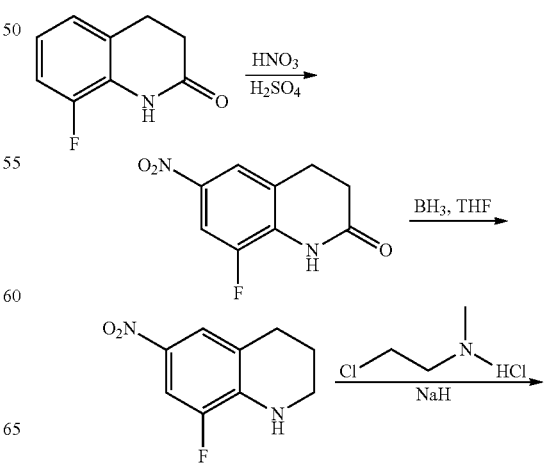

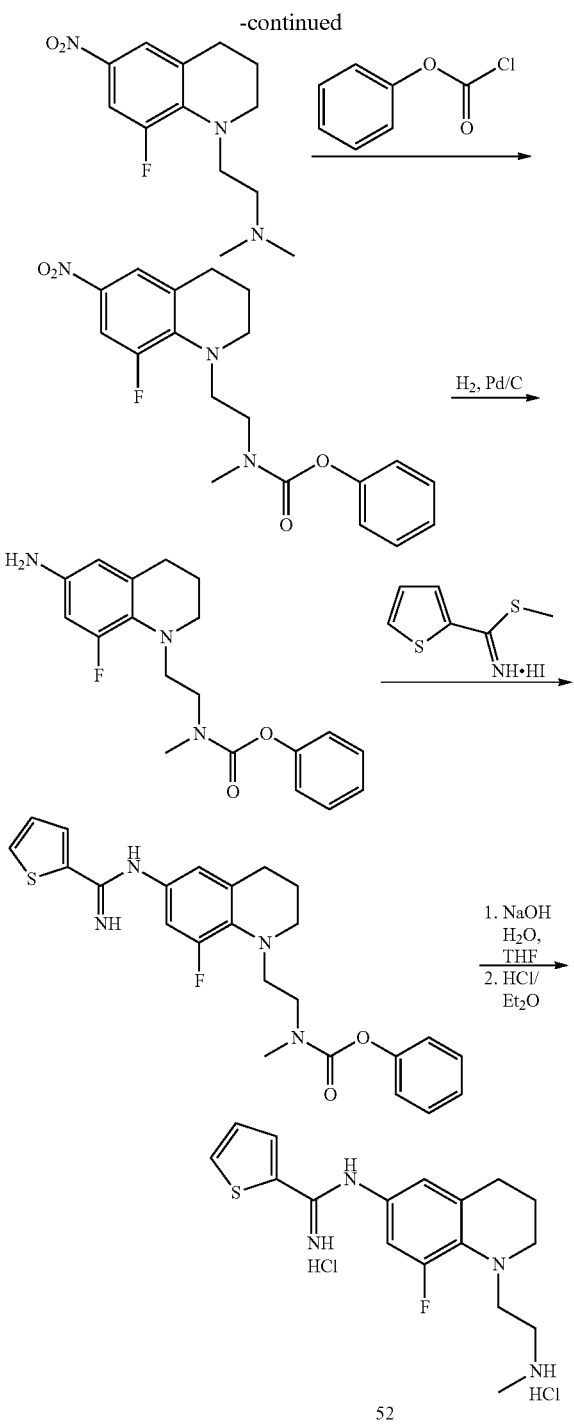

dichloromethane as eluent to give the desired 8-fluoro-6-nitro-3,4-dihydroquinolin-2(1H)-one (2.33 g, 11.09 mmol, 92% yield). ¹H NMR (DMSO-d₆) δ 10.73 (brs, 1H), 8.03 (m, 1H), 8.02 (m, 1H), 3.08 (t, J=7.5 Hz, 2H), 2.57 (t, J=7.5 Hz, 1H).

8-Fluoro-6-nitro-1,2,3,4-tetrahydroquinoline

To a stirred solution of 8-fluoro-6-nitro-3,4-dihydroquinolin-2(1H)-one (950 mg, 4.52 mmol) in tetrahydrofuran (5 ml) was added borane-tetrahydrofuran complex (45.2 ml, 45.2 mmol) as a solution in THF. The reaction mixture was then heated to reflux temperature overnight. The reaction mixture was then cooled to 0° C. and quenched with methanol. The quenched mixture was then concentrated in vacuo, redissolved in methanol and reconcentrated, then refluxed in methanol for 2 h. The mixture was then concentrated onto silica gel, and chromatographed using 0-20% ethyl acetate in hexanes. ¹H NMR (DMSO-d₆) δ 7.77-7.71 (m, 1H), 7.73 (m, 1H), 7.31 (brs, 1H), 3.35-3.28 (m, 2H), 2.77 (t, J=6.2 Hz, 2H), 1.85-1.77 (m, 2H).

2-(8-Fluoro-6-nitro-3,4-dihydroquinolin-1(2H)-yl)-N,N-dimethylethanamine

To a stirred solution of 8-fluoro-6-nitro-1,2,3,4-tetrahydroquinoline (670 mg, 3.42 mmol) in N,N-Dimethylformamide (15 ml), cooled to 0° C. was added sodium hydride, 60% (437 mg, 10.93 mmol) with vigorous stirring. When bubbling subsided, 2-chloro-N,N-dimethylethanamine hydrochloride (984 mg, 6.83 mmol) was added and the reaction mixture (dark red) was stirred at room temperature. After 2 h, no product was observed so the reaction was heated to 90° C. and stirred. After 1 h, TLC showed the reaction to be complete. The mixture was then cooled to room temperature, diluted with water and extracted with ethyl acetate (3×). The combined organics were then washed with 1:1 water:brine (2×), then brine (1×). The organic phase was dried, filtered and concentrated, then chromatographed in 0-10% (2M NH₃ in methanol) in 1:1 ethyl acetate:dichloromethane, giving the desired 2-(8-fluoro-6-nitro-3,4-dihydroquinolin-1(2H)-yl)-N,N-dimethylethanamine (514 mg, 1.923 mmol, 56.3% yield). NMR (DMSO-d₆) δ 7.77 (dd, J=15 Hz, 2.7 Hz, 1H); 7.72 (m, 1H); 3.55-3.48 (m, 2H); 3.43-3.39 (m, 2H); 2.78-2.74 (m, 2H), 2.49-2.44 (m, 2H); 2.16 (s, 6H); 1.88-1.79 (m, 2H). ESI-MS (m/z, %): 268 (MH⁺, 100); 223 (5).

Phenyl 2-(8-fluoro-6-nitro-3,4-dihydroquinolin-1(2H)-yl)ethyl(methyl)carbamate

To a stirred solution of 2-(8-fluoro-6-nitro-3,4-dihydroquinolin-1(2H)-yl)-N,N-dimethylethanamine (500 mg, 1.871 mmol) in Dichloromethane (8 ml) at room temperature was added phenyl chloroformate (0.352 ml, 2.81 mmol) via a syringe dropwise, slowly. The resulting solution was stirred overnight at room temperature. The reaction mixture was then diluted with water and potassium carbonate (dilute) and extracted with dichloromethane (3×). The combined organics were dried, filtered and concentrated, then chromatographed in 0-50% ethyl acetate in hexanes, giving the desired phenyl 2-(8-fluoro-6-nitro-3,4-dihydroquinolin-1(2H)-yl)ethyl(methyl)carbamate (576 mg, 1.543 mmol, 82% yield). ¹H NMR (DMSO-d₆) δ 7.85-7.76 (m, 1H); 7.75-7.70 (m, 1H); 7.34 (t, J=7 Hz, 1H); 7.22-7.16 (m, 1H); 6.99-6.95 (m, 2H); 3.77-3.65 (m, 3H); 3.60-3.54 (m, 1H); 3.43 (t, J=5.5 Hz, 2H); 3.02, 2.93 (2s, 3H); 2.75 (t, J=5.8, 2H); 1.90-1.81 (m, 2H). ESI-MS (m/z, %): 374 (MH+, 100).

8-Fluoro-6-nitro-3,4-dihydroquinolin-2(1H)-one

To a stirred solution of 8-fluoro-3,4-dihydroquinolin-2 (1H)-one (see Example 41 for details) (2 g, 12.11 mmol) in sulfuric acid (12 ml), cooled to −5° C. was added nitric acid, 90% (0.565 ml, 12.11 mmol) as a 1:1 solution in water. The reaction mixture was stirred at −5° C. for 20 min, then quenched via addition of ice, precipitating the product which was collected by filtration. The pale solid was then dissolved in dichloromethane, dried, filtered and concentrated, and then chromatographed on silica gel using 0-10% ethyl acetate in

Phenyl 2-(6-amino-8-fluoro-3,4-dihydroquinolin-1 (2H)-yl)ethyl(methyl)carbamate To a stirred solution of phenyl 2-(8-fluoro-6-nitro-3,4-dihydroquinolin-1(2H)-yl)ethyl(methyl)carbamate (560 mg, 1.500 mmol) was added palladium on activated carbon, 10 wt % (160 mg, 0.150 mmol). The resulting suspension was stirred at room temperature in a balloon pressure atmosphere of hydrogen. After 3 h, most of the starting material was consumed, and the reaction was stopped due to the presence of a minor impurity. The reaction mixture was filtered through a pad of celite, then concentrated to give a brown oil. The residue was dried and use directly in the subsequent reaction. Crude product obtained was phenyl 2-(6-amino-8-fluoro-3,4-dihydroquinolin-1(2H)-yl)ethyl(methyl)carbamate (449 mg, 1.308 mmol, 87% yield). $^1$H NMR (DMSO-$d_6$) δ 7.40-7.35 (m, 2H); 7.23-7.17 (m, 1H); 7.10-7.05 (m, 2H); 6.19 (d, J=14 Hz, 1H); 6.06 (s, 1H); 4.85-4.72 (m, 2H); 3.57-3.53 (m, 1H); 3.46-3.42 (m, 1H); 3.13-2.93 (m, 4H); 3.07, 2.95 (2s, 3H); 2.57 (t, J=6.3 Hz, 1H); 1.74-1.65 (m, 2H). ESI-MS (m/z, %): 344 (MH$^+$).

Phenyl 2-(8-fluoro-6-(thiophene-2-carboximidamido)-3,4-dihydroquinolin-1(2H)-yl)ethyl(methyl) carbamate (52)

To a stirred solution of phenyl 2-(6-amino-8-fluoro-3,4-dihydroquinolin-1(2H)-yl)ethyl(methyl)carbamate (426 mg, 1.241 mmol) in ethanol (12 ml) was added methyl thiophene-2-carbimidothioate hydroiodide (708 mg, 2.481 mmol). The reaction mixture was stirred at room temperature overnight under argon. The reaction mixture was then diluted with water and sodium carbonate, then extracted with dichloromethane (3x). The combined organics were dried, filtered and concentrated, then chromatographed in 40-100% ethyl acetate in hexanes, giving the desired phenyl 2-(8-fluoro-6-(thiophene-2-carboximidamido)-3,4-dihydroquinolin-1(2H)-yl)ethyl(methyl)carbamate 52 (422 mg, 0.933 mmol, 75% yield). $^1$H NMR (DMSO-$d_6$) δ 7.74-7.71 (m, 1H); 7.59-7.57 (m, 1H); 7.41-7.36 (m, 2H); 7.23-7.18 (m, 1H); 7.14-7.07 (m, 3H); 6.50-6.42 (m, 3H); 6.37 (s, 1H); 3.62 (t, J=6 Hz, 1H); 3.51 (t, J=6 Hz, 1H); 3.30 (t, J=6 Hz, 1H); 3.23 (t, J=6 Hz, 1H); 3.15-3.09 (m, 2H); 3.09, 2.97 (2s, 3H); 2.69 (t, J=6 Hz, 2H); 1.83-1.75 (m, 2H). EI-MS (m/z, %): 452 (M+, 8); 288 (60); 179 (100).

N-(8-fluoro-1-(2-(methylamino)ethyl)-1,2,3,4-tetrahydroquinolin-6-yl)thiophene-2-carboximidamide To a stirred solution of phenyl 2-(8-fluoro-6-(thiophene-2-carboximidamido)-3,4-dihydroquinolin-1(2H)-yl)ethyl(methyl)carbamate (400 mg, 0.884 mmol) in Ethanol (11 ml) was added sodium hydroxide (354 mg, 8.84 mmol) as a solution in Water (5.5 ml). The resulting mixture was stirred at reflux and monitored by TLC. After 3 h, the reaction mixture showed some formation of product, and some starting material. Due to the formation of some side product, the reaction was stopped, diluted with water and extracted with dichloromethane (3x). The combined organics were dried, filtered and concentrated, then chromatographed in 0-10% (2M NH$_3$ in MeOH) in dichloromethane, giving the desired N-(8-fluoro-1-(2-(methylamino)ethyl)-1,2,3,4-tetrahydroquinolin-6-yl)thiophene-2-carboximidamide (67 mg, 0.202 mmol, 22.80% yield). $^1$NMR (DMSO-$d_6$) δ 7.71 (d, J=3, 1H); 7.58 (d, J=5 Hz, 1H); 7.07 (dd, J=5 Hz, 3 Hz, 1H); 6.48-6.43 (m, 2H); 6.41 (brd, J=15 Hz, 1H); 6.34 (s, 1H); 3.09 (m, 4H); 2.73-2.64 (m, 4H); 2.31 (s, 3H); 1.77-1.72 (m, 2H). EI-MS (m/z, %): 332 (M+, 9), 288 (100).

N-(8-fluoro-1-(2-(methylamino)ethyl)-1,2,3,4-tetrahydroquinolin-6-yl)thiophene-2-carboximidamide dihydrochloride To a stirred solution of N-(8-fluoro-1-(2-(methylamino)ethyl)-1,2,3,4-tetrahydroquinolin-6-yl)thiophene-2-carboximidamide (57 mg, 0.171 mmol) in Methanol (3 ml) was added hydrogen chloride, 1M in diethyl ether (0.514 ml, 0.514 mmol). The resulting solution was then concentrated to give the desired N-(8-fluoro-1-(2-(methylamino)ethyl)-1,2,3,4-tetrahydroquinolin-6-yl)thiophene-2-carboximidamide dihydrochloride (69 mg, 0.170 mmol, 99% yield). $^1$H NMR (DMSO-$d_6$) δ 9.79 (s, 1H); 9.13 (brs, 2H); 8.84 (s, 1H); 8.16 (d, J=4.8 Hz); 7.37 (t, J=4.3 Hz, 1H); 7.14 (d, J=14 Hz, 1H); 6.94 (s, 1H); 3.47-3.40 (m, 2H); 3.24-3.18 (m, 2H); 3.18-3.10 (m, 2H); 2.76 (t, J=6 Hz, 2H); 2.58 (t, J=5.1 Hz, 3H); 1.85-1.78 (m, 2H). EI-MS (m/z, %): 332 (M+, 9); 288 (100). HRMS calculated for C17H21FN4S (M$^+$), calculated: 332.1477, observed: 332.1471. HPLC purity: 95%.

Example 53

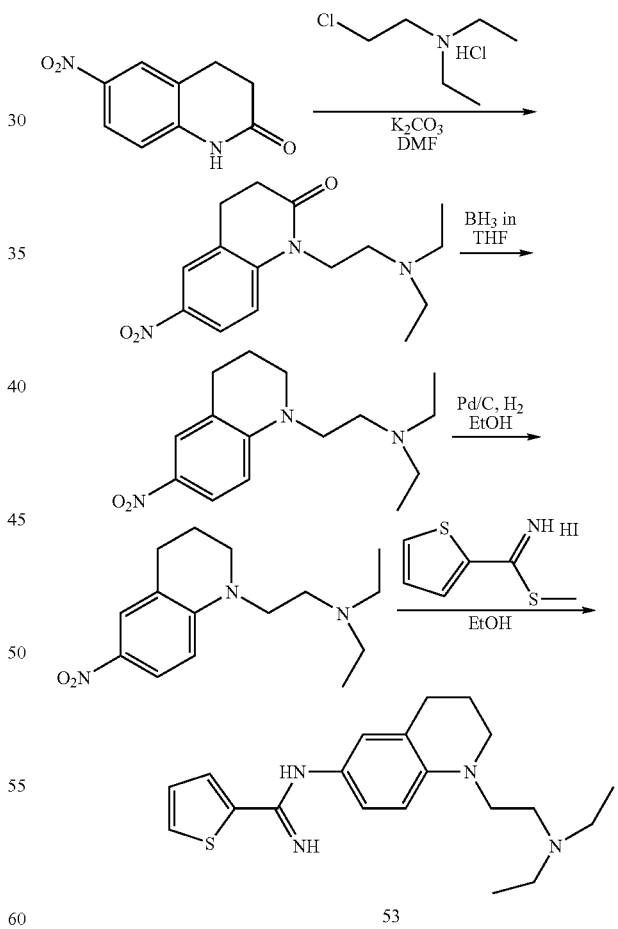

53

1-(2-(diethylamino)ethyl)-6-nitro-3,4-dihydroquinolin-2(1H)-one

A suspension of 6-nitro-3,4-dihydroquinolin-2(1H)-one$^1$ (2 g, 10.41 mmol), 2-(Diethylamino)ethyl chloride hydrochloride (2.69 g, 15.61 mmol), and potassium carbonate (6.47 g, 46.8 mmol) in DMF (25 mL) was stirred at room temperature for 3 days. The mixture was diluted with H₂O (50 mL) then extracted into ethyl acetate (2×75 mL). The combined organic layer was rinsed with brine (2×20 mL), dried over Na₂SO₄, filtered and concentrated to give a viscous yellow residue. This residue was subjected to flash chromatography on silica gel using 2.5% 2M NH₃ in methanol/95% CH₂Cl₂ to give a yellow solid after drying under reduced pressure (2.35 g, 78%). ¹H-NMR (CDCl₃) δ 8.15 (dd, J=2.7, 9.0 Hz, 1H), 8.06-8.05 (m, 1H), 7.30-7.25 (m, 1H), 4.09 (t, J=6.9 Hz, 2H), 3.00 (t, J=6.9 Hz, 2H), 2.73-2.60 (m, 8H), 1.03 (t, J=7.2 Hz, 6H).

[1]. Devita et al, WO03/045313

N,N-diethyl-2-(6-nitro-3,4-dihydroquinolin-1(2H)-yl)ethanamine

A solution of 1-(2-(diethylamino)ethyl)-6-nitro-3,4-dihydroquinolin-2(1H)-one (1 g, 3.43 mmol) and 1M BH₃ in THF (17.16 ml, 17.16 mmol) was stirred at room temperature overnight. After this time, the reaction was cooled to 0° C. then treated with methanol (25 mL) dropwise with caution. The mixture was stirred at 0° C. for 10 minutes then concentrated on the rotovap to give a yellow solid. This compound was dissolved in 40 mL methanol and heated at reflux for 3 hours. After cooling, the solvent was evaporated and the resulting yellow brown residue was subjected to flash chromatography on silica gel using 5% 2M NH₃ in methanol/95% CH₂Cl₂ to give a bright yellow residue (0.87 g, 91%). ¹H-NMR (CDCl₃) δ 7.96 (dd, J=2.7, 9.0 Hz, 1H), 7.85-7.84 (m, 1H), 6.51 (d, J=9.0 Hz, 1H), 3.47 (t, J=5.4 Hz, 4H), 2.74 (t, J=6.3 Hz, 2H), 2.68-2.59 (m, 6H), 1.99-1.91 (m, 2H), 1.05 (t, J=6.9 Hz, 6H). MS (ESI): 278.2 (M+1).

1-(2-(diethylamino)ethyl)-1,2,3,4-tetrahydroquinolin-6-amine

A suspension of N,N-diethyl-2-(6-nitro-3,4-dihydroquinolin-1(2H)-yl)ethanamine (0.85 g, 3.06 mmol) and palladium on charcoal, 10% wt (0.163 g, 0.153 mmol) in ethanol (30 mL) was stirred at room temperature under a balloon of hydrogen overnight. The mixture was filtered through a pad of celite. The celite pad was rinsed with 20 mL of methanol. The filtrate was concentrated and the residue was subjected to flash chromatography on silica gel using 5% 2M NH₃ in methanol/95% CH₂Cl₂ to give a dark brown residue (685 mg, 90%). ¹H-NMR (CDCl₃) δ 6.63-6.32 (m, 3H), 3.37-3.23 (m, 4H), 2.74-2.56 (m, 8H), 1.93 (t, J=5.7 Hz, 2H), 1.08 (t, J=7.2 Hz, 6H). MS (ESI): 248.2 (M+1).

N-(1-(2-(diethylamino)ethyl)-1,2,3,4-tetrahydroquinolin-6-yl)thiophene-2-carboximidamide (53)

A solution of 1-(2-(diethylamino)ethyl)-1,2,3,4-tetrahydroquinolin-6-amine (670 mg, 2.71 mmol) in ethanol (25 mL) was treated with methyl thiophene-2-carbimidothioate hydroiodide (1545 mg, 5.42 mmol) in one portion. The resulting suspension was stirred at room temperature overnight. The mixture was concentrated then partitioned between 150 mL CH₂Cl₂ and 40 mL saturated Na₂CO₃ solution. After extraction, the organic layer was separated, dried over Na₂SO₄, filtered and concentrated to give a yellow brown residue. This residue was subjected to flash chromatography on silica gel using 2.5-5% methanol/97.5-95% CH₂Cl₂ then 5% 2M NH₃ in methanol/95% CH₂Cl₂ to give a dark yellow residue which solidified after drying under reduced pressure (670 mg of 53, 69.4%). ¹H-NMR (DMSO-d₆) δ 7.67 (d, J=3.0 Hz, 1H), 7.54 (d, J=4.8 Hz, 1H), 7.07 (dd, J=3.6, 4.5 Hz, 1H), 6.57-6.48 (m, 3H), 5.76 (br s, 2H), 3.32-3.25 (m, 4H), 2.67-2.63 (m, 2H), 2.52-2.48 (m, 6H), 1.86-1.82 (m, 2H), 0.97 (t, J=6.9 Hz, 6H). MS (ESI): 357.2 (M+1). ESI-HRMS calculated for C₂₀H₂₉N₄S(MH⁺): 357.2107, Observed: 357.2110.

Example 54

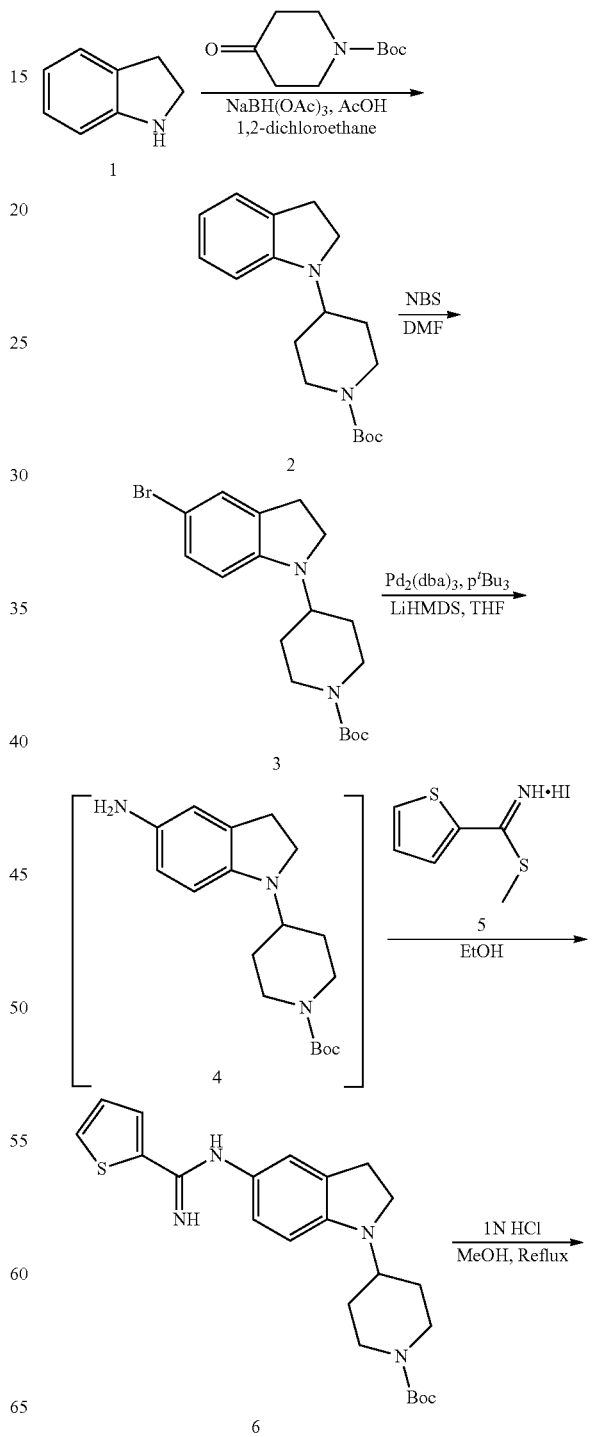

-continued

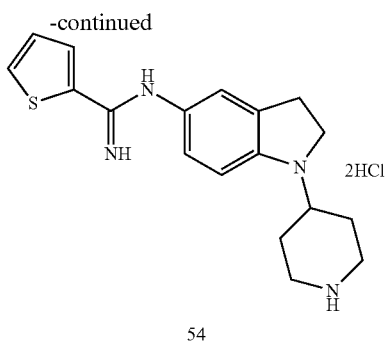

54 tert-Butyl 4-(indolin-1-yl)piperidine-1-carboxylate (2)

A solution of indoline 1 (2.0 g, 16.78 mmol), tert-butyl 4-oxopiperidine-1-carboxylate (3.68 g, 18.46 mmol) in dry 1,2-dichloroethane (30 mL) was treated with acetic acid (2.4 mL, 42.00 mmol) followed by NaBH(OAc)$_3$ (5.34 g, 25.2 mmol) at 0° C. The resulting mixture was brought to room temperature and stirred for 3 h. The reaction was basified with 1 N NaOH solution (50 mL) and product was extracted into ethyl acetate (2×50 mL). The combined ethyl acetate layer was washed with brine (25 mL) and dried (Na$_2$SO$_4$). The solvent was evaporated and crude was purified by column chromatography (ethyl acetate:hexanes, 1:4) to obtain compound 2 (5.0 g, 99%) as a syrup. $^1$H NMR (CDCl$_3$) δ 7.05 (t, 2H, J=7.8 Hz), 6.62 (t, 1H, J=7.2 Hz), 6.43 (d, 11, J=7.5 Hz), 4.25-4.20 (m, 2H), 3.55-3.46 (m, 2H), 3.35 (t, 2H, J=8.4 Hz), 2.95 (t, 2H, J=8.4 Hz), 2.77 (t, 2H, J=12.3 Hz), 1.81-1.77 (m, 2H), 1.63-1.51 (m, 2H), 1.47 (s, 9H); ESI-MS (m/z, %) 303 (MH$^+$, 5), 247 (100).

tert-Butyl 4-(5-bromoindolin-1-yl)piperidine-1-carboxylate (3)

A solution of compound 2 (2.0 g, 6.61 mmol) in dry DMF (10 mL) was treated with N-bromosuccinimide (1.17 g, 6.61 mmol) in DMF (10 mL) at 0° C. over a period of 30 min. The reaction was stirred at same temperature for 3.5 h. The reaction was diluted with water (200 mL) and product was extracted into ethyl acetate (3×25 mL). The combined ethyl acetate layer was washed with water (2×50 mL), brine (25 mL) and dried (Na$_2$SO$_4$). Solvent was evaporated and crude was purified by column chromatography (ethyl acetate:hexanes, 1:4) to obtain compound 3 (2.5 g, 99%) as a syrup. $^1$H NMR (CDCl$_3$) δ 7.13-7.10 (m, 2H), 6.27 (d, 1H, J=9.0 Hz), 4.28-4.20 (m, 2H), 3.50-3.40 (m, 1H), 3.35 (t, 2H, J=8.4 Hz), 2.93 (t, 2H, J=8.4 Hz), 2.75 (t, 2H, J=12.9 Hz), 1.78-1.72 (m, 2H), 1.60-1.49 (m, 2H), 1.46 (s, 9H); ESI-MS (m/z, %) 381, 383 (MH$^+$, 3), 325, 327 (100).

tert-Butyl 4-(5-(thiophene-2-carboximidamido)indolin-1-yl)piperidine-1-carboxylate (6)

A solution of Pd$_2$(dba)$_3$ (0.08 g, 0.087 mmol) in dry THF (5 mL) was treated with P$^t$Bu$_3$ (1.06 mL, 0.351 mmol, 10% in hexanes), followed by compound 3 (0.67 g, 1.757 mmol) in dry THF (5 mL) and LiHMDS (3.51 mL, 3.514 mmol) at room temperature. The resulting mixture was stirred at 100° C. in a seal tube for 3 h. The reaction was brought to room temperature and quenched with TBAF (5 mL, 1 M solution in THF). After stirring for 15 min., solution was basified with 1 N NaOH solution (50 mL) and product was extracted into CH$_2$Cl$_2$ (3×20 mL). The combined CH$_2$Cl$_2$ layer was dried (Na$_2$SO$_4$) and evaporated to obtain the crude product. The crude was purified by column chromatography (2 M NH$_3$ in MeOH:CH$_2$Cl$_2$, 2.5:97.5) to obtain compound 4 (0.4 g, 72%) as a foam.

A solution of compound 4 (0.38 g, 0.683 mmol) in dry ethanol (10 mL) was treated with compound 5 (0.68 g, 2.394 mmol) at room temperature and the resulting mixture was stirred for overnight. The reaction was basified with sat. NaHCO$_3$ solution (50 mL), product was extracted into CH$_2$Cl$_2$ (2×25 mL) and dried (Na$_2$SO$_4$). Solvent was evaporated and crude was purified by column chromatography (2 M NH$_3$ in MeOH:CH$_2$Cl$_2$, 5:95) to obtain compound 6 (0.43 g, 85%) as a solid. $^1$H NMR (DMSO-d$_6$) δ 7.72 (d, 1H, J=3.0 Hz), 7.62 (d, 1H, J=4.8 Hz), 7.10 (dd, 1H, J=3.6, 4.9 Hz), 6.68 (s, 1H), 6.59 (d, 1H, J=8.1 Hz), 6.47 (d, 1H, J=8.4 Hz), 4.05 (d, 2H, J=12.3 Hz), 3.58-3.50 (m, 1H), 3.28-3.24 (m, 2H), 2.90-2.78 (m, 4H), 1.68 (d, 2H, J=11.1 Hz), 1.50-1.36 (m, 1H); ESI-MS (m/z, %) 427 (MH$^+$, 100).

N-(1-(Piperidin-4-yl)indolin-5-yl)thiophene-2-carboximidamide dihydrochloride (54)

A solution of compound 6 (0.23 g, 0.539 mmol) in methanol (10 mL) was treated with 1 N HCl solution (10 mL) and the resulting mixture was refluxed for 30 min. The reaction was brought to room temperature and solvent was evaporated. The crude was dissolved into water (10 mL), filtered and washed with water (2×5 mL). The combined water layer was evaporated to obtain compound 54 (0.18 g, 84%) as dihydrochloride salt. $^1$H NMR (DMSO-d$_6$) δ 11.21 (s, 1H), 9.64 (s, 1H), 9.20-9.04 (m, 2H), 8.60 (s, 1H), 8.15-8.12 (m, 2H), 7.36 (t, 1H, J=4.5 Hz), 7.11-7.03 (m, 2H), 6.66 (d, 1H, J=8.4 Hz), 3.86-3.74 (m, 1H), 3.44-3.32 (m, 4H), 3.06-2.92 (m, 4H), 1.98-1.78 (m, 4H); ESI-MS (m/z, %) 327 (MH$^+$, 100), 244 (81); ESI-HRMS calculated for C$_{18}$H$_{23}$N$_4$S (MH$^+$), calculated: 327.1637; observed: 327.1636; HPLC purity: 98.86% by area.

Example 55

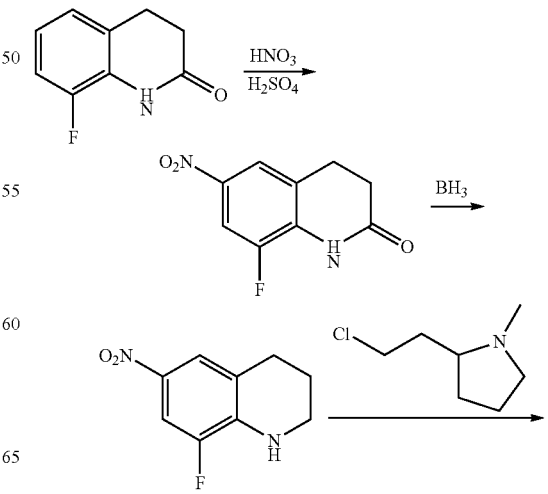

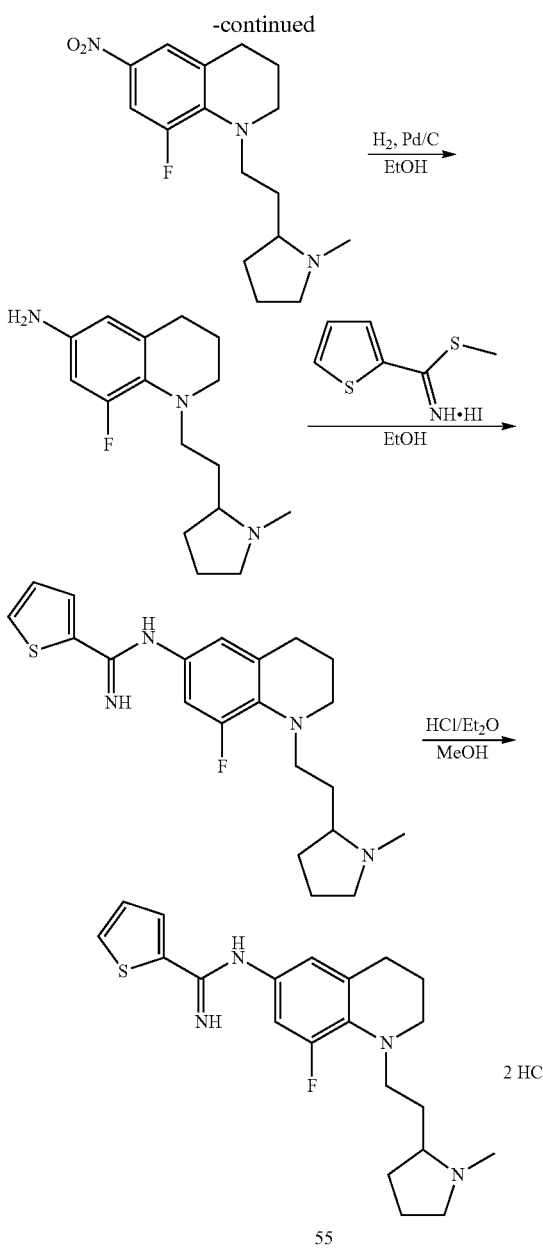

8-Fluoro-6-nitro-3,4-dihydroquinolin-2(1H)-one

To a stirred solution of 8-fluoro-3,4-dihydroquinolin-2 (1H)-one (see Example 41 for details), (5 g, 30.3 mmol) in sulfuric acid, cooled to −5° C. was added nitric acid, fuming (1.413 ml, 30.3 mmol) as a 1:1 mixture in water. The resulting mixture was stirred at −5° C. for 20 min. After 20 min the reaction was quenched via addition of ice, precipitating the product which was collected by filtration. The filter cake was dissolved in dichloromethane and a minimal amount of methanol, dried, filtered and concentrated onto silica gel then chromatographed using 0-10% ethyl acetate in dichloromethane to give the desired 8-fluoro-6-nitro-3,4-dihydroquinolin-2(1H)-one (5.9 g, 28.1 mmol, 93% yield). $^1$H NMR (DMSO-d$_6$) δ 10.73 (brs, 1H), 8.03 (m, 1H), 8.02 (m, 1H), 3.08 (t, J=7.5 Hz, 2H), 2.57 (t, J=7.5 Hz, 1H).

8-Fluoro-6-nitro-1,2,3,4-tetrahydroquinoline

8-Fluoro-6-nitro-3,4-dihydroquinolin-2(1H)-one (5.9 g, 28.1 mmol) was stirred in borane-THF complex, 1M in THF (140 ml, 140 mmol). The solution was heated to 60° C. and stirred overnight. The mixture was then cooled in an ice bath and quenched via addition of methanol (30 mL). The quenched solution was concentrated, then dissolved in methanol and refluxed for 1 h. The solution was then concentrated onto silica gel and chromatographed using 5-30% ethyl acetate in hexanes to give the desired 8-fluoro-6-nitro-1,2,3, 4-tetrahydroquinoline (4.34 g, 22.12 mmol, 79% yield). $^1$H NMR (DMSO-d$_6$) δ 7.77-7.71 (m, 1H), 7.73 (m, 1H), 7.31 (brs, 1H), 3.35-3.28 (m, 2H), 2.77 (t, J=6.2 Hz, 2H), 1.85-1.77 (m, 2H).

8-Fluoro-1-(2-(1-methylpyrrolidin-2-yl)ethyl)-6-nitro-1,2,3,4-tetrahydroquinoline To a stirred solution of 8-fluoro-6-nitro-1,2,3,4-tetrahydroquinoline (500 mg, 2.55 mmol) in N,N-dimethylformamide (11 ml), cooled to 0° C. was added sodium hydride, 60% (326 mg, 8.16 mmol) with vigorous stirring. When the bubbling subsided, 2-(2-chloroethyl)-1-methylpyrrolidine hydrochloride (938 mg, 5.10 mmol) was added and the reaction mixture (dark red) was stirred at 90° C. for 1 h. TLC analysis showed that the reaction mixture was complete. The mixture was then cooled to room temperature, diluted with water and extracted with ethyl acetate (3×). The combined organics were then washed with a 1:1 mixture of brine and water (3×), then brine (1×), dried over sodium sulfate, filtered and concentrated. The residue was chromatographed in ethyl acetate, then 10% methanol in 1:1 ethyl acetate:dichloromethane, giving the desired 8-fluoro-1-(2-(1-methylpyrrolidin-2-yl)ethyl)-6-nitro-1,2,3,4-tetrahydroquinoline (665 mg, 2.164 mmol, 85% yield). $^1$H NMR (DMSO-d$_6$) δ 7.77 (dd, J=15, 2.7 Hz, 1H), 7.71 (d, J=2.4 Hz, 1H), 3.43-3.32 (m, 4H), 2.94-2.88 (m, 1H), 2.78-2.73 (m, 2H), 2.19 (s, 3H), 2.06-1.97 (m, 2H), 1.91-1.83 (m, 4H); 1.64-1.56 (m, 4H).

8-Fluoro-1-(2-(1-methylpyrrolidin-2-yl)ethyl)-1,2,3,4-tetrahydroquinolin-6-amine To a stirred solution of 8-fluoro-1-(2-(1-methylpyrrolidin-2-yl)ethyl)-6-nitro-1,2,3,4-tetrahydroquinoline (660 mg, 2.147 mmol) in tetrahydrofuran (6 ml) and ethanol (6.00 ml) was added palladium on carbon, 10 wt % (229 mg, 0.215 mmol). The suspension was stirred under balloon pressure of hydrogen and monitored by TLC. After 4 h, the reaction was complete. The mixture was then filtered through a pad of celite which was washed with methanol. The filtrate was then concentrated and dried on a high vacuum pump. The residue (8-fluoro-1-(2-(1-methylpyrrolidin-2-yl)ethyl)-1,2,3,4-tetrahydroquinolin-6-amine (590 mg, 2.127 mmol, 99% yield)) was used directly in the subsequent reaction. $^1$H NMR (DMSO-d$_6$) δ 6.16 (dd, J=14.7, 2.4 Hz, 1H); 6.04 (m, 1H), 4.70 (brs, 1H), 2.99-2.93 (m, 3H), 2.88-2.82 (m, 2H), 2.57-2.53 (m, 2H), 2.24 (s, 3H), 2.15-2.05 (m, 2H); 1.93-1.87 (m, 2H), 1.69-1.60 (m, 4H), 1.44-1.35 (m, 2H).

N-(8-Fluoro-1-(2-(1-methylpyrrolidin-2-yl)ethyl)-1,2,3,4-tetrahydroquinolin-6-yl)thiophene-2-carboximidamide To a stirred solution of 8-fluoro-1-(2-(1-methylpyrrolidin-2-yl)ethyl)-1,2,3,4-tetrahydroquinolin-6-amine (580 mg, 2.091 mmol) in ethanol (15 ml) was added methyl thiophene-2-carbimidothioate hydroiodide (1193 mg, 4.18 mmol) as a solid. The resulting suspension was stirred overnight at room temperature under argon. The reaction mixture was then quenched with water and sodium carbonate (sat) and extracted with dichloromethane (3×). The combined organics were dried, filtered and concentrated. The residue was then chromatographed in ethyl acetate, followed by 0-10% (2M NH3 in methanol) in dichloromethane, giving the desired N-(8-fluoro-1-(2-(1-methylpyrrolidin-2-yl)ethyl)-1,2,3,4-tetrahydroquinolin-6-yl)thiophene-2-carboximidamide (485 mg, 1.255 mmol, 60.0% yield). $^1$H NMR (DMSO-$d_6$) δ 7.71 (d, J=3 Hz, 1H), 7.57 (d, J=4.5 Hz, 1H), 7.07 (dd, J=4.8, 3.9 Hz, 1H), 6.44 (brs, 2H), 6.39-6.34 (m, 2H), 3.07-3.02 (m, 4H), 2.95-2.89 (m, 1H), 2.69-2.65 (m, 2H), 2.21 (s, 3H), 2.03-1.99 (m, 2H), 1.94-1.87 (m, 2H), 1.76-1.74 (m, 2H), 1.63-1.59 (m, 2H), 1.46-1.40 (m, 2H).

N-(8-Fluoro-1-(2-(1-methylpyrrolidin-2-yl)ethyl)-1,2,3,4-tetrahydroquinolin-6-yl)thiophene-2-carboximidamide dihydrochloride N-(8-fluoro-1-(2-(1-methylpyrrolidin-2-yl)ethyl)-1,2,3,4-tetrahydroquinolin-6-yl)thiophene-2-carboximidamide (485 mg, 1.255 mmol) was dissolve in a mixture of methanol (2.5 ml) and hydrogen chloride, 1.0 M in diethyl ether (2.510 ml, 2.510 mmol). The solution was then concentrated, giving the desired N-(8-fluoro-1-(2-(1-methylpyrrolidin-2-yl)ethyl)-1,2,3,4-tetrahydroquinolin-6-yl)thiophene-2-carboximidamide dihydrochloride 55 (575 mg, 1.251 mmol, 100% yield). $^1$H NMR (DMSO-$d_6$) δ 11.44 (brs, 1H), 11.07 (m, 1H), 9.79 (brs, 1H), 8.82 (brs, 1H), 8.16 m, 2H), 7.36 (t, J=4.4 Hz, 1H), 7.10 (d, J=13 Hz, 1H), 6.91 (brs, 1H), 4.19 (brs, 2H), 3.54-3.47 (m, 1H), 3.25-3.16 (m, 5H), 3.02-2.96 (m, 1H), 2.77-2.73 (m, 5H), 2.29-2.22 (m, 2H), 1.97-1.91 (m, 3H), 1.85-1.81 (m, 2H), 1.72-1.64 (m, 1H). MS-EI+ (m/z, %) 386 (100, M+), 288 (55), 275 (82), 111 (68), 84 (64). EI+-HRMS calculated for $C_{21}H_{27}FN_4S^+$ (M+) calculated: 386.1938, observed: 386.1940.

Example 56 and Example 57

N-(1-(1-Methylpyrrolidin-3-yl)-1,2,3,4-tetrahydroquinolin-6-yl)thiophene-2-carboximidamide (56 and 57)

The enantiomeric mixture of 35 was separated by using preparative chiral HPLC column chromatography to obtain 56 and 57.

Column: Chiralpak AS-H (0.46×25 cm) S/N 07-8314

Solvent: 40% isopropanol (0.1% DEA)/$CO_2$ 100 bar

Wavelength: 220 nm

Flow rate: 3 mL/min.

First eluting isomer at 3.36 min. (56): ESI-MS (m/z, %) 341.2 (MH$^+$, 100); ESI-HRMS calculated for $C_{19}H_{25}N_4S$ (MH$^+$), Calculated: 341.1794; Observed: 341.1798; Chiral purity: 100%; Chemical purity: 97.0%.

Second eluting isomer at 4.17 min. (57): ESI-MS (m/z, %) 341.2 (MH$^+$, 100); ESI-HRMS calculated for $C_{19}H_{24}N_4S$ (MH$^+$), Calculated: 341.1794; Observed: 341.1790; Chiral purity: 99.86%; Chemical purity: 97.1%.

Example 58

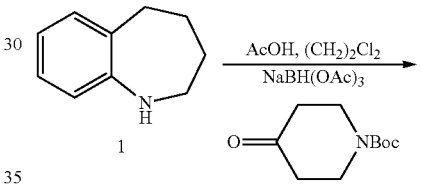

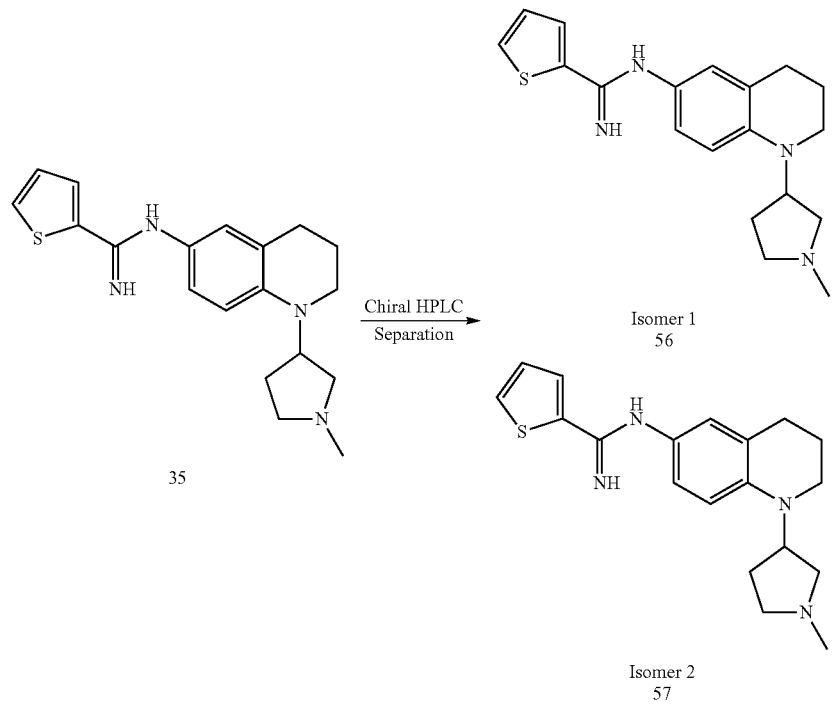

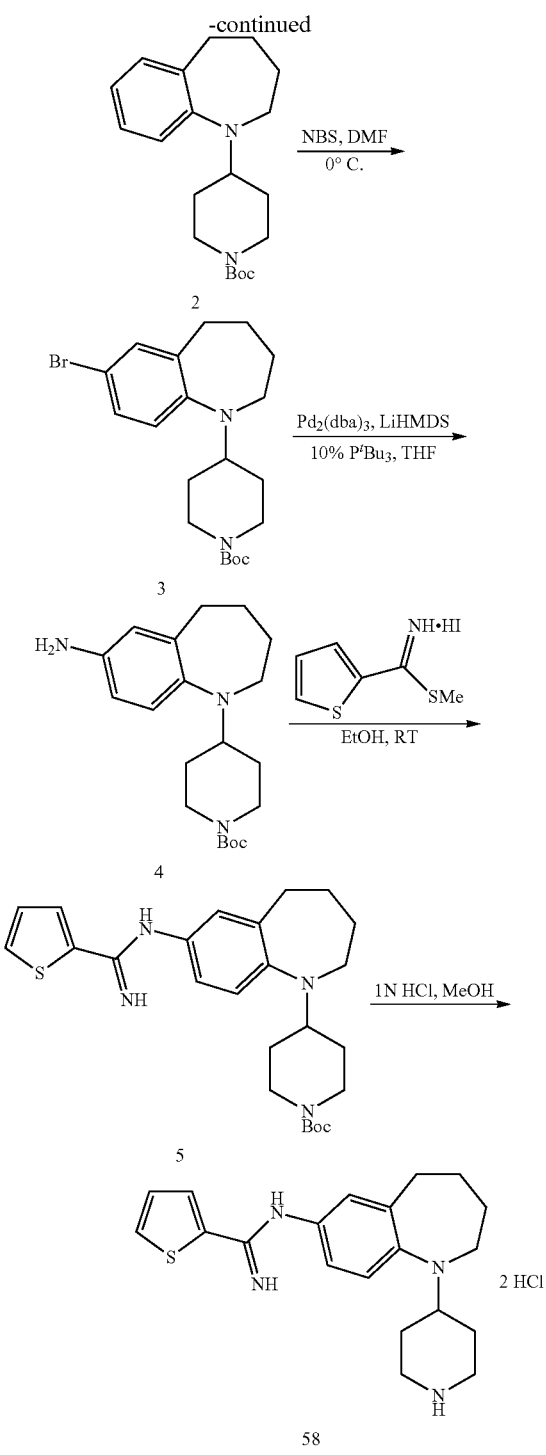

NaOH solution (125 mL) and extracted with ethyl acetate (200 mL). The organic layer was washed with brine (50 mL), dried (Na$_2$SO$_4$) and was concentrated. The crude product was subject to flash chromatography on silica gel using 5% ethyl acetate/hexanes. The sample was concentrated and dried resulting in a colourless viscous liquid, compound 2 (2.12 g, 94%). $^1$H NMR (CDCl$_3$) δ 7.12-7.08 (m, 2H), 6.93 (d, J=7.8 Hz, 1H), 6.83 (t, J=14.7 Hz, 1H), 4.16-4.13 (m, 2H), 3.42 (tt, J=7.2, 22.2 Hz, 1H), 2.98 (brs, 2H), 2.85-2.75 (m, 4H), 1.88 (d, J=12.0 Hz, 2H), 1.73-1.60 (m, 6H), 1.47 (s, 9H); MS-ESI (m/z, %): 331 (MH$^+$, 17), 275 (100).

tert-Butyl 4-(7-bromo-2,3,4,5-tetrahydro-1H-benzo[b]azepin-1-yl)piperidine-1-carboxylate (3)

A solution of compound 2 (1.004 g, 3.026 mmol) in DMF (15 mL) was cooled to 0° C. and was treated dropwise with NBS (0.5408 g, 3.026 mmol) in DMF (15 mL). The reaction mixture was stirred for 1.5 hours at 0° C. The reaction was diluted with H$_2$O (100 mL) and extracted with ethyl acetate (200 mL). The organic layer was washed with brine and dried (Na$_2$SO$_4$). The crude product was purified by flash chromatography on silica gel using 5% EtOAc/Hexanes, which resulted in a white solid, compound 3 (1.26, 101%). $^1$H NMR (CDCl$_3$) δ 7.21-7.15 (m, 2H), 6.78 (d, J=8.4 Hz, 1H), 4.15-4.12 (m, 2H), 3.35 (tt, J=7.2, 18.3 Hz, 1H), 2.95 (brs, 2H), 2.90-2.69 (m, 4H), 1.84 (d, J=12.3 Hz, 2H), 1.71-1.62 (m, 6H), 1.46 (s, 9H); MS-ESI (m/z, %): 411 (MH$^+$, 15), 409 (M$^+$, 15), 355 (96), 353 (100).

tert-Butyl-4-(7-amino-2,3,4,5-tetrahydro-1H-benzo[b]azepin-1-yl)piperidine-1-carboxylate (4)

A solution of Pd$_2$(dba)$_3$ (0.107 g, 0.1172 mmol) in dry THF (5 mL) was treated with P$^t$Bu$_3$ (10% in Hexanes, 1.42 mL, 0.4688 mmol). The mixture was then treated with compound 3 (0.9594 g, 2.344 mmol) in dry THF (15 mL) and LiHMDS (4.69 mL, 4.688 mmol) at room temperature. The solution was stirred at 100° C. for 3 hours. At room temperature, the solution was quenched with 1M TBAF in THF solution (5 mL) and was stirred for 20 minutes. The reaction was the diluted with 3N NaOH solution (50 mL) and was extracted with ethyl acetate (150 mL). The organic layer was dried (Na$_2$SO$_4$) and was concentrated. The crude product was subject to flash chromatography on silica gel using 2.5% 2M NH$_3$ methanol/CH$_2$Cl$_2$, which resulted in a dark brown foam, compound 4 (0.691 g, 85%). $^1$H NMR (CDCl$_3$) δ 6.79 (d, J=5.1 Hz, 1H), 6.51-6.44 (m, 2H), 4.06-4.03 (m, 2H), 3.56-3.51 (m, 1H), 3.28 (tt, J=7.2, 21.3 Hz, 1H), 2.92-2.77 (m, 4H), 2.68-2.64 (m, 2H), 1.82 (d, J=11.1 Hz, 2H), 1.66-1.40 (m, 7H), 1.36 (s, 9H).

tert-Butyl 4-(7-(thiophene-2-carboximidamido)-2,3,4,5-tetrahydro-1H-benzo[b]azepin-1-yl)piperidine-1-carboxylate (5)

A solution of compound 4 (0.6586 g, 1.906 mmol) in dry ethanol (20 mL) was treated with methyl thiophene-2-carbimidothioate hydroiodide (1.087 g, 3.812 mmol) at room temperature and was stirred for 3 hours. The mixture was diluted with saturated sodium bicarbonate solution (50 mL) and was extracted with CH$_2$Cl$_2$ (100 mL). The organic layer was washed with brine (20 mL) and dried (Na$_2$SO$_4$). The concentrated crude product was subject to flash chromatography on silica gel using 2.5-5% MeOH/CH$_2$Cl$_2$, which resulted in a brown foam, compound 5 (0.42 g, 48%). $^1$H NMR (CDCl$_3$) δ 7.42-7.40 (m, 2H), 7.08-7.05 (t, J=9.0 Hz, tert-Butyl 4-(2,3,4,5-tetrahydro-1H-benzo[b]azepin-1-yl)piperidine-1-carboxylate 4,5-dihydro-1H-benzo[b]azepin-2(3H)-one (2)

A mixture of compound 1 (1 g, 6.793 mmol), N-tert-Butoxycarbonyl-4-piperidone (1.35 g, 6.793 mmol) and acetic acid (0.44 mL, 6.793 mmol) in 25 mL of 1,2-dichloroethane was cooled to 0° C. and treated with NaBH(OAc)$_3$ (2.16 g, 10.19 mmol). The reaction was brought to room temperature and was stirred for 2 days. The solution was diluted with 3N 1H), 6.92 (d, J=8.1 Hz, 1H), 6.77-6.73 (m, 2H), 4.13-4.09 (m, 2H), 3.37 (tt, J=7.2, 21.9 Hz, 1H), 2.95-2.71 (m, 6H), 1.87 (d, J=12.9 Hz, 2H), 1.77-1.53 (m, 7H), 1.47 (s, 9H); MS-ESI (m/z, %): 457 (MH+, 14), 455 (M+, 100), 219 (18).

N-(1-(piperidin-4-yl)-2,3,4,5-tetrahydro-1H-benzo[b]azepin-7-yl)thiophene-2-carboximidamide (58)

A solution containing compound 5 (0.4199 g, 0.9236 mmol) in methanol (12 mL) was treated with 1N HCl solution (12 mL) and the mixture was refluxed for 30 minutes. The reaction was brought to room temperature, concentrated and dried under reduced pressure. The product was filtered and recrystallized resulting in a beige dihydrochloride salt, compound 58 (0.323 g, 79%). $^1$H NMR (CDCl$_3$) δ 7.69 (d, J=3.3 Hz, 1H), 7.57 (d, J=4.2 Hz, 1H), 7.07 (t, J=8.7, 1H), 6.90 (d, J=9.0 Hz, 1H), 6.59 (d, J=6.9 Hz, 2H), 6.36-6.20 (m, 2H), 3.42-3.20 (m, 4H), 3.03-2.91 (m, 4H), 2.64-2.57 (m, 4H), 1.78 (d, J=11.4 Hz, 2H), 1.57-1.54 (m, 6H); MS-ESI (m/z, %): 355 (MH+, 72), 272 (100), 219 (48); ESI-HRMS calculated for $C_{20}H_{27}N_4S$ (MH+): Calculated: 355.1950, Observed: 355.1968.

Example 59

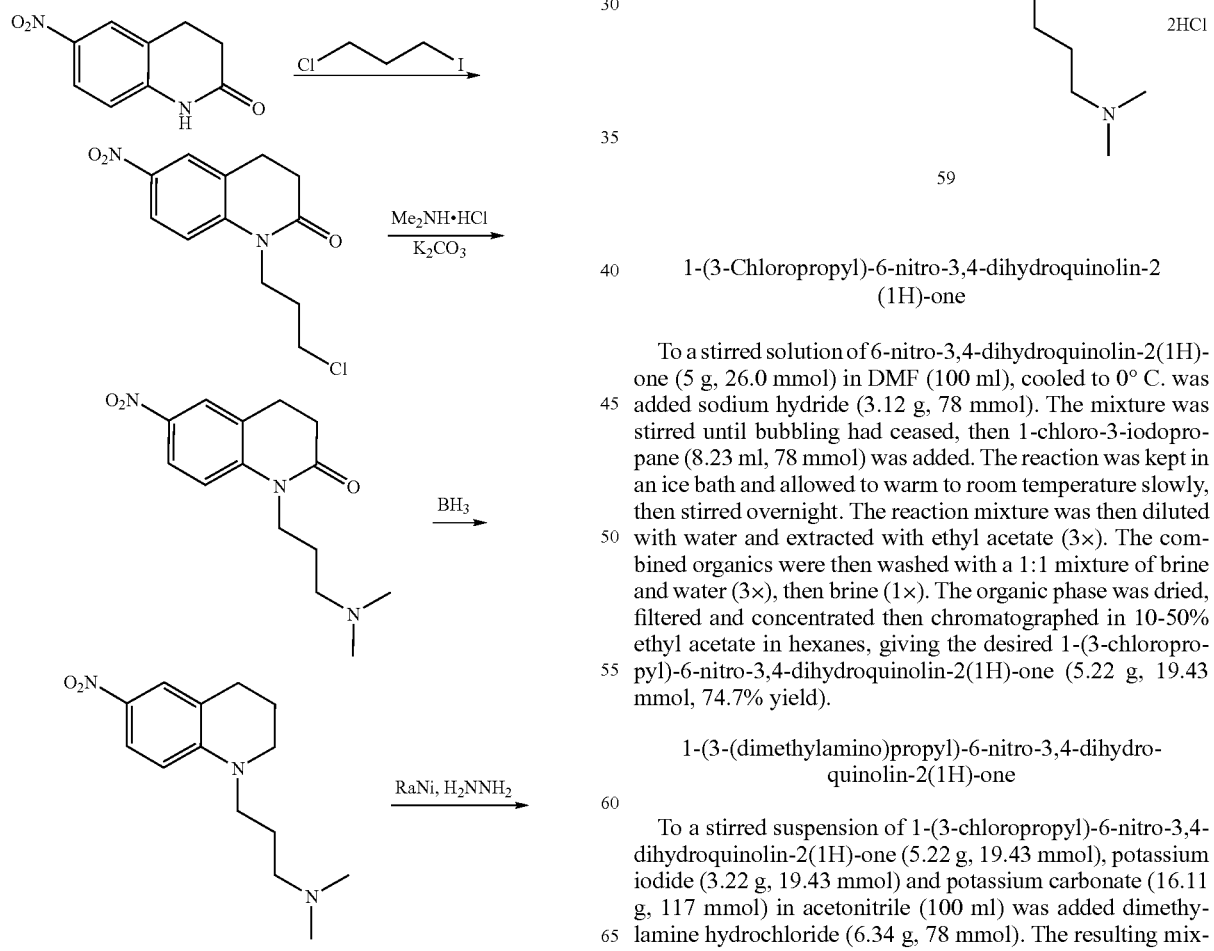

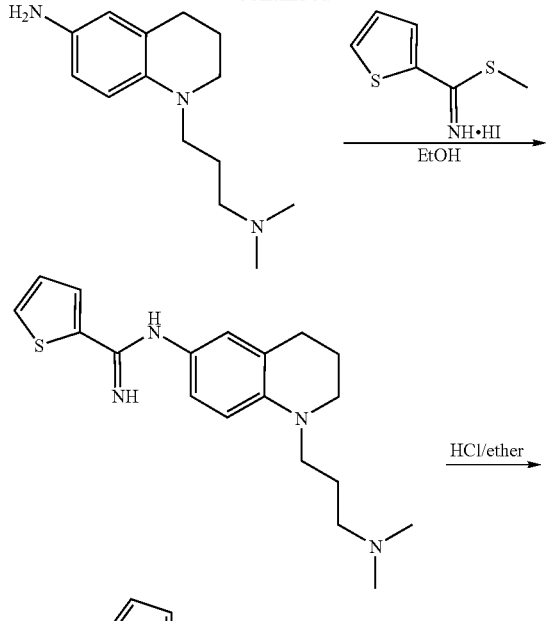

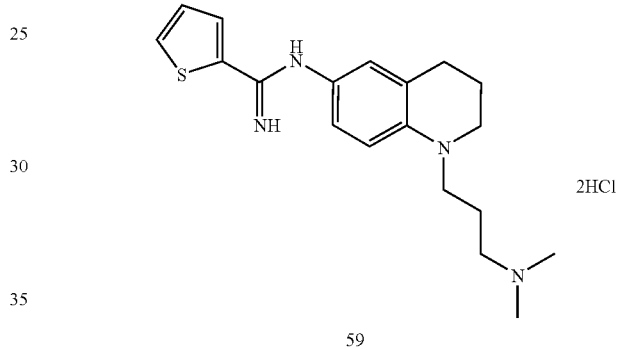

59

1-(3-Chloropropyl)-6-nitro-3,4-dihydroquinolin-2(1H)-one

To a stirred solution of 6-nitro-3,4-dihydroquinolin-2(1H)-one (5 g, 26.0 mmol) in DMF (100 ml), cooled to 0° C. was added sodium hydride (3.12 g, 78 mmol). The mixture was stirred until bubbling had ceased, then 1-chloro-3-iodopropane (8.23 ml, 78 mmol) was added. The reaction was kept in an ice bath and allowed to warm to room temperature slowly, then stirred overnight. The reaction mixture was then diluted with water and extracted with ethyl acetate (3×). The combined organics were then washed with a 1:1 mixture of brine and water (3×), then brine (1×). The organic phase was dried, filtered and concentrated then chromatographed in 10-50% ethyl acetate in hexanes, giving the desired 1-(3-chloropropyl)-6-nitro-3,4-dihydroquinolin-2(1H)-one (5.22 g, 19.43 mmol, 74.7% yield).

1-(3-(dimethylamino)propyl)-6-nitro-3,4-dihydroquinolin-2(1H)-one

To a stirred suspension of 1-(3-chloropropyl)-6-nitro-3,4-dihydroquinolin-2(1H)-one (5.22 g, 19.43 mmol), potassium iodide (3.22 g, 19.43 mmol) and potassium carbonate (16.11 g, 117 mmol) in acetonitrile (100 ml) was added dimethylamine hydrochloride (6.34 g, 78 mmol). The resulting mixture was stirred overnight at 50° C. The mixture was then cooled to room temperature, diluted with water and extracted with dichloromethane (3x). The combined organics were dried, filtered and concentrated, then chromatographed on silica gel using 0-10% (2M NH₃ in MeOH) in dichloromethane as the eluent. ¹H NMR (DMSO-d₆) δ 8.14-8.10 (m, 2H), 7.37 (d, J=9.6 Hz, 1H), 3.94 (t, J=7.5 Hz, 2H), 3.00 (t, J=7.5 Hz, 2H), 2.62 (t, J=7.5 Hz, 1H), 2.27 (t, J=7 Hz, 2H), 2.13 (s, 6H), 1.66 (quint, J=7.5 Hz, 1H). ESI-MS (m/z, %) 278 (MH⁺, 100).

N,N-dimethyl-3-(6-nitro-3,4-dihydroquinolin-1(2H)-yl)propan-1-amine 1-(3-(Dimethylamino)propyl)-6-nitro-3,4-dihydroquinolin-2(1H)-one (4.23 g, 15.25 mmol) was stirred in borane tetrahydrofuran complex, 1M (76 ml, 76 mmol) at 60° C. overnight. The reaction mixture was then cooled to 0° C. and quenched via addition of methanol. The resulting suspension was concentrated and then stirred in refluxing methanol (50 mL). To this solution was added sodium hydroxide (6.10 g, 153 mmol) as a solution in a minimal amount of water. The resulting mixture was refluxed at 90° C. After 1 h, no free product was observed, only product borane complex. The solution was then diluted with water and acidified with conc HCl and refluxed at 90° C. After 1 h, TLC analysis showed free product, and no borane complex. The mixture was then neutralized via addition of NaOH (3N) and extracted with dichloromethane (3x). ¹H NMR (DMSO-d₆) δ 7.87 (dd, J=9.3, 3 Hz, 1H), 7.77 (d, J=3 Hz, 1H), 6.68 (d, J=9.6 Hz, 1H), 3.43-3.38 (m, 4H), 2.74 (t, J=6 Hz, 2H), 2.23 (t, J=6.5 Hz, 2H), 2.13 (s, 6H), 1.85 (quint, J=6 Hz, 2H), 1.68 (quint, J=7 Hz, 2H). ESI-MS (m/z, %) 264 (MH⁺, 100).

1-(3-(Dimethylamino)propyl)-1,2,3,4-tetrahydroquinolin-6-amine

To a stirred solution of N,N-dimethyl-3-(6-nitro-3,4-dihydroquinolin-1(2H)-yl)propan-1-amine (600 mg, 2.278 mmol) in methanol (12 ml) was added Raney nickel (60 mg, 2.278 mmol) followed by hydrazine hydrate (1.108 ml, 22.78 mmol). The resulting mixture was then stirred at 60° C. and monitored by TLC for consumption of the starting material. The reaction mixture was then filtered through celite and the filtrate was concentrated. The residue was then dissolved in dichloromethane, dried, filtered and concentrated to give a dark oil. ¹H NMR (DMSO-d₆) δ 6.37-6.34 (m, 1H), 6.30-6.26 (m, 1H), 6.22-6.20 (m, 1H), 4.17 (brs, 2H), 3.12-3.03 (m, 4H), 2.55 (t, J=6.45 Hz, 2H), 2.20 (t, J=6.9 Hz, 2H), 2.11 (s, 6H), 1.79 (quint, J=6 Hz, 2H), 1.56 (quint, J=7.12 Hz, 2H). ESI-MS (m/z, %) 234 (MH+, 100), 161 (60).

N-(1-(3-(Dimethylamino)propyl)-1,2,3,4-tetrahydroquinolin-6-yl)thiophene-2-carboximidamide To a stirred solution of 1-(3-(dimethylamino)propyl)-1,2,3,4-tetrahydroquinolin-6-amine (490 mg, 2.100 mmol) in ethanol (30 ml) was added methyl thiophene-2-carbimidothioate hydroiodide (1198 mg, 4.20 mmol). The reaction mixture was stirred overnight at room temperature. The mixture was then diluted with water and aqueous sodium carbonate (saturated), then extracted with dichloromethane (3x). The combined organics were dried, filtered and concentrated. The crude product was chromatographed on silica gel using ethyl acetate as solvent followed by 5-10% (2M NH3 in methanol) in dichloromethane to give the desired N-(1-(3-(dimethylamino)propyl)-1,2,3,4-tetrahydroquinolin-6-yl)thiophene-2-carboximidamide 59 after treatment with 1M HCl ether solution (613 mg, 1.790 mmol, 85% yield). ¹H NMR (DMSO-d₆) δ 7.67 (d, J=3 Hz, 1H), 7.55 (d, J=5.1 Hz, 1H), 7.07 (dd, J=5.1, 3 Hz, 1H), 6.55 (m, 2H), 6.48 (m, 1H), 6.31 (brs, 2H), 3.24-3.17 (m, 4H), 2.66 (t, J=6.3 Hz, 2H), 2.25 (t, J=6.9 Hz, 2H), 1.88-1.82 (m, 2H), 1.67-1.60 (m, 2H). ESI-MS (m/z, %) 343 (MH+, 89), 258 (100), 135 (48), 127 (60). ESI-HRMS calculated for C19H27N4S (MH+), calculated: 343.1963, observed: 343.195. HPLC purity: 97%.

Example 60

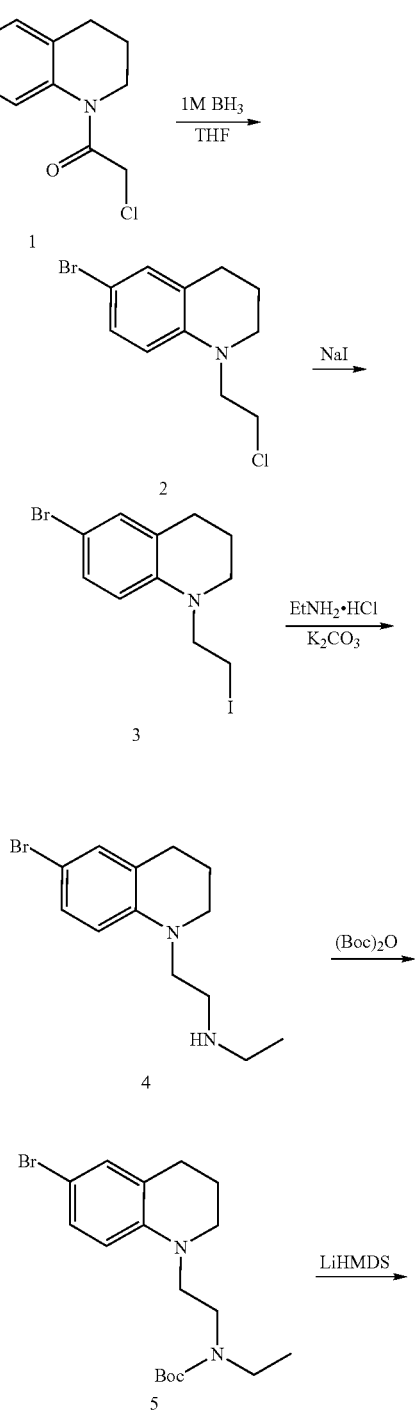

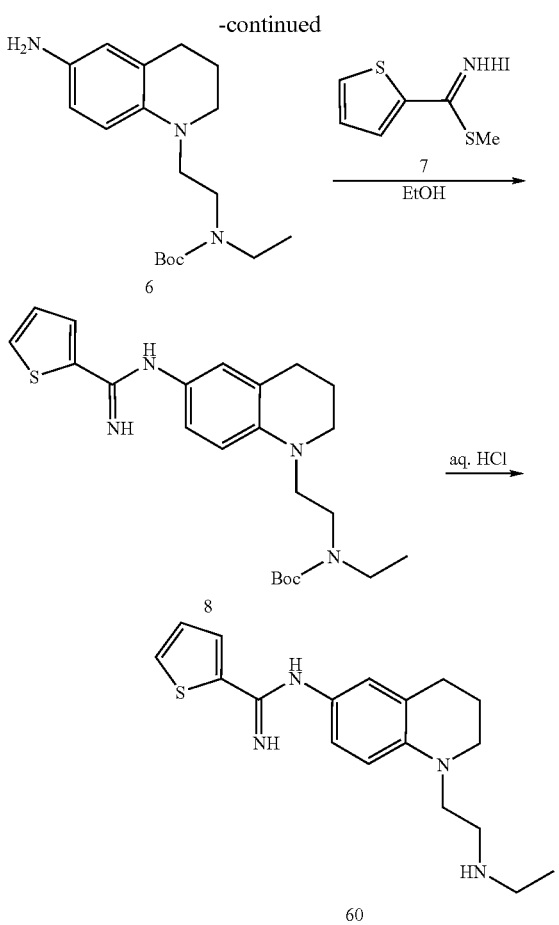

1-(6-Bromo-3,4-dihydroquinolin-1(2H)-yl)-2-chloroethanone (1)

See Example 51 for complete experimental details and spectral data.

6-Bromo-1-(2-chloroethyl)-1,2,3,4-tetrahydroquinoline (2)

A round bottom flask was charged with 1-(6-bromo-3,4-dihydroquinolin-1(2H)-yl)-2-chloroethanone (compound 1, 0.546 g, 1.892 mmol) and treated with borane-THF complex (1M in THF, 18.9 mL, 18.9 mmol, 10 equivalents) and the resulting mixture stirred overnight at room temperature. After cooling to 0° C., the reaction was quenched by dropwise addition of methanol (5 mL) and stirred for 10 minutes at 0° C. The mixture was concentrated under reduced pressure and purified directly on silica gel eluting with 10% ethyl acetate/90% hexanes to yield a viscous residue, 2 (0.519 g, 100%). $^1$H-NMR (CDCl$_3$) δ 7.11 (dd, 1H, J=8.7, 2.4 Hz), 7.08-7.04 (m, 1H), 6.42 (d, 1H, J=8.7), 3.64-3.56 (m, 4H), 3.35 (t, 2H, J=5.6 Hz), 2.73 (t, 2H, J=6.3 Hz), 1.97-1.89 (m, 2H). MS (ESI+): 274/276 (MH$^+$, 100).

6-Bromo-1-(2-iodoethyl)-1,2,3,4-tetrahydroquinoline (3)

A suspension of 6-bromo-1-(2-chloroethyl)-1,2,3,4-tetrahydroquinoline (compound 2, 1.80 g, 6.56 mmol) and sodium iodide (9.83 g, 65.6 mmol) in acetone (50 mL) was heated to reflux for 2 days at which time TLC analysis showed residual starting material 2. At this time a further portion of sodium iodide (19.66 g, 132.0 mmol) was added and the suspension refluxed for 5 days. The mixture was cooled to room temperature, filtered through a pad of celite and the filtrate concentrated to yield a yellow solid. The solid was taken up in a mixture of ethyl acetate/hexanes (150 mL) and filtered through a pad of silica gel, and the pad rinsed further with EtOAc/Hexanes. The filtrate was concentrated to yield a yellow oil, 3 (2.19 g, 91%). $^1$H-NMR (CDCl$_3$) δ 7.12 (dd, 1H, J=8.7, 2.5 Hz), 7.09-7.04 (m, 1H), 6.42 (d, 1H, J=8.7), 3.65-3.60 (m, 2H), 3.33 (t, 2H, J=5.6 Hz), 3.25-3.19 (m, 2H), 2.72 (t, 2H, J=6.3 Hz), 1.98-1.90 (m, 2H). MS (ESI+): 366/368 (MH$^+$, 100).

2-(6-Bromo-3,4-dihydroquinolin-1(2H)-yl)-N-ethylethanamine (4)

A solution of 6-bromo-1-(2-iodoethyl)-1,2,3,4-tetrahydroquinoline (compound 3, 100 mg, 0.273 mmol) in acetonitrile (4.75 mL) and water (0.25 mL) in a 20 mL pressure vessel fitted with a stir-bar is treated with potassium carbonate (0.378 g, 2.73 mmol) and ethylamine hydrochloride (0.223 g, 2.73 mmol) and the sealed vessel stirred at 70° C. overnight. After 18 hours the mixture was partitioned between CH$_2$Cl$_2$ (50 mL) and water (10 mL) and transferred to a separatory funnel. The organic layer was separated and the aqueous layer extracted further with CH$_2$Cl$_2$. The combined organic layer was washed with brine, dried over Na$_2$SO$_4$, filtered and concentrated to give a yellow residue. The residue was purified on silica gel eluting with 7.5% 2M NH$_3$ in methanol/92.5% dichloromethane to yield a yellow oil/residue, 4 (55 mg, 71.1%). $^1$H-NMR (CDCl$_3$) δ 7.09 (dd, 1H, J=8.7, 2.4 Hz), 7.06-7.01 (m, 1H), 6.51 (d, 1H, J=8.7), 3.36 (t, 2H, J=6.8 Hz), 3.29 (t, 2H, J=5.5 Hz), 2.82 (t, 2H, J=6.8 Hz), 2.80-2.65 (2×m, 4H), 1.96-1.88 (m, 2H), 1.11 (t, 3H, J=7.1 Hz).

tert-Butyl 2-(6-bromo-3,4-dihydroquinolin-1(2H)-yl)ethyl(ethyl)carbamate (5)

A solution of 2-(6-bromo-3,4-dihydroquinolin-1(2H)-yl)-N-ethylethanamine (compound 4, 0.250 g, 0.883 mmol) in anhydrous dioxane (15 mL) was treated with triethylamine (0.248 mL, 1.765 mmol) and di-tert-butyl dicarbonate (0.202 g, 0.927 mmol) and the resulting mixture stirred overnight at room temperature. The mixture was concentrated to residue and purified directly on silica gel eluting with 10% ethyl acetate/90% hexanes to yield a colorless oil, 5 (0.280 g, 83%). $^1$H-NMR (CDCl$_3$) δ 7.09 (dd, 1H, J=8.7, 2.3 Hz), 7.03 (br s, 1H), 6.50 (d, 1H, J=8.7), 3.48-3.11 (m, 8H), 2.70 (t, 2H, J=6.3 Hz), 2.05-1.87 (m, 2H), 1.47 (s, 9H), 1.10 (br s, 3H). MS (ESI+): 383/385 (MH$^+$, 38), 327/329 (100).

tert-Butyl 2-(6-amino-3,4-dihydroquinolin-1(2H)-yl)ethyl(ethyl)carbamate (6)

A suspension of tris(dibenzylideneacetone)dipalladium(0) (66 mg, 0.072 mmol) in anhydrous THF (3 mL) was treated with tri-t-butylphosphine in hexane (10% wt) (0.435 mL, 0.143 mmol) and the mixture stirred for 5 minutes at room temperature. A solution of tert-butyl 2-(6-bromo-3,4-dihydroquinolin-1(2H)-yl)ethyl(ethyl)carbamate (compound 5, 0.275 g, 0.717 mmol) in THF (7 mL) was added followed by Lithium bis(trimethylsilyl)amide (1M in THF, 1.435 mL, 1.435 mmol) and the mixture heated in a sealed reaction vial at 90° C. for 3 hours. The mixture was cooled to room temperature and treated with TBAF (1M in THF, 4 mL, 4 mmol) for 30 minutes. The mixture was partitioned between water (10 mL) and ethyl acetate (100 mL), transferred to a separatory funnel and the organic layer separated. The aqueous layer (pH=10) was further extracted with ethyl acetate and the combined organic layers washed with brine, dried over Na$_2$SO$_4$, filtered and concentrated to give a dark brown residue. Purification on silica gel eluting with 2.5% 2M NH$_3$ in methanol/97.5% dichloromethane yielded a brown residue, 6 (171 mg, 74.6%). $^1$H-NMR ((DMSO-d$_6$) δ 6.42 (d, 1H, J=8.5 Hz), 6.31-6.26 (m, 1H), 6.22 (br s, 1H), 4.20 (br s, 2H), 3.26-3.08 (m, 8H), 2.55 (t, 2H, J=6.3 Hz), 1.82-1.74 (m, 2H), 1.41 (s, 9H), 1.02 (t, 3H, J=7.0 Hz). MS (ESI+): 320 (MH$^+$, 90), 264 (100).

tert-Butyl ethyl(2-(6-(thiophene-2-carboximidamido)-3,4-dihydroquinolin-1(2H)-yl)ethyl)carbamate (8)

A solution of tert-butyl 2-(6-amino-3,4-dihydroquinolin-1(2H)-yl)ethyl(ethyl)carbamate (compound 6, 165 mg, 0.517 mmol) in anhydrous EtOH (10 mL) was treated with methyl thiophene-2-carbimidothioate hydroiodide (compound 7, 295 mg, 1.033 mmol) in one portion and the mixture stirred at room temperature for 20 hours. The mixture was partitioned between CH$_2$Cl$_2$ (100 mL) and sat. Na$_2$CO$_3$ (20 mL) and transferred to a separatory funnel. The organic layer was separated, and the aqueous layer (pH=9) was further extracted with CH$_2$Cl$_2$. The combined organic layers were washed with brine, dried over MgSO$_4$, filtered and concentrated to give a yellow residue. Purification on silica gel eluting with 1% methanol/99% dichloromethane then 2.5% 2M NH$_3$ in methanol/97.5% dichloromethane yielded a yellow-orange solid, 8 (120 mg, 54.2%).
$^1$H-NMR (DMSO-d$_6$) δ 7.69 (d, 1H, J=3.2 Hz), 7.58 (d, 1H, J=5.0 Hz), 7.08 (dd, 1H, J=5.0, 3.7 Hz), 6.68-6.59 (m, 1H), 6.59-6.47 (m, 2H), 6.50-6.20 (br s, 2H), 3.33-3.16 (m, 8H), 2.66 (t, 2H, J=6.2 Hz), 1.91-1.79 (m, 2H), 1.41 (s, 9H), 1.04 (t, 3H, J=7.0 Hz). MS (ESI+): 429 (MH$^+$, 100).

N-(1-(2-(Ethylamino)ethyl)-1,2,3,4-tetrahydroquinolin-6-yl)thiophene-2-carboximidamide (9)

A solution of tert-butyl ethyl(2-(6-(thiophene-2-carboximidamido)-3,4-dihydroquinolin-1(2H)-yl)ethyl)carbamate (compound 8, 115 mg, 0.268 mmol) in HPLC grade methanol (10 mL) was treated with 2N aq. HCl (1.35 mL, 2.7 mmol) and the mixture heated to reflux for 90 minutes. After cooling to room temperature, the solution was concentrated and dried briefly on high-vac pump. The residue was purified directly on silica gel eluting with 10% 2M NH$_3$ in methanol/90% dichloromethane to yield a yellow solid, 9 (78 mg, 88%).
$^1$H-NMR (DMSO-d$_6$) δ 7.66 (d, 1H, J=3.0 Hz), 7.54 (dd, 1H, J=5.0, 0.9 Hz), 7.06 (dd, 1H, J=5.0, 3.7 Hz), 6.59-6.52 (m, 2H), 6.47 (br s, 1H), 6.21 (br s, 2H), 3.32-3.20 (m, 4H), 2.70-2.64 (m, 4H), 2.56 (q, 2H, J=7.1 Hz), 1.88-1.80 (m, 2H), 1.04 (t, 3H, J=7.0 Hz). MS (ESI+): 329 (MH$^+$, 100), 258 (100); ESI-HRMS calculated for C$_{18}$H$_{25}$N$_4$S (MH$^+$): 329.1794; observed: 329.1798.

Example 61

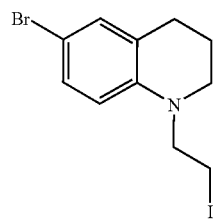

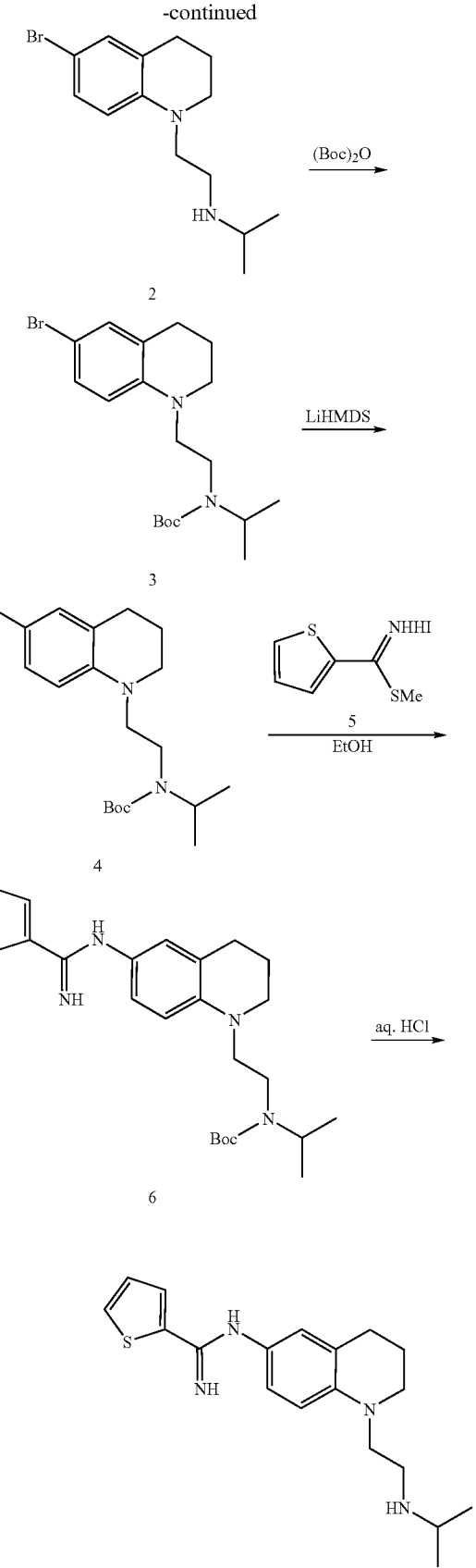

6-bromo-1-(2-iodoethyl)-1,2,3,4-tetrahydroquinoline (1)

See Example 60 for complete experimental details and spectral data.

N-(2-(6-bromo-3,4-dihydroquinolin-1(2H)-yl)ethyl)propan-2-amine (2)

A solution of 6-bromo-1-(2-iodoethyl)-1,2,3,4-tetrahydroquinoline (compound 1, 0.400 g, 1.093 mmol) in acetonitrile (19 mL) and water (1 mL) in a 50 mL pressure vessel fitted with a stir-bar was treated with potassium carbonate (0.755 g, 5.46 mmol) and isopropylamine (0.646 g, 10.93 mmol) and the sealed vessel stirred at 75° C. overnight. After 24 hours the mixture was partitioned between $CH_2Cl_2$ (50 mL) and water (10 mL) and transferred to a separatory funnel. The organic layer was separated and the aqueous layer (pH=12); extracted further with $CH_2Cl_2$. The combined organic layer was washed with brine, dried over $Na_2SO_4$, filtered and concentrated to a yellow oil. Purification on silica gel eluting with 5% 2M $NH_3$ in methanol/95% dichloromethane yielded a pale yellow oil, 2 (270 mg, 83%). $^1$H-NMR (DMSO-$d_6$) δ 7.06 (dd, 1H, J=8.8, 2.5 Hz), 6.99 (d, 1H, J=2.5 Hz), 6.52 (d, 1H, J=8.8), 3.31-3.20 (m, 4H), 2.78-2.67 (m, 1H), 2.67-2.59 (m, 4H), 1.84-1.76 (m, 2H), 0.96 (d, 6H, J=6.2 Hz). MS (ESI+): 297/299 (MH$^+$, 10), 238/240 (20), 159 (100).

tert-Butyl-2-(6-bromo-3,4-dihydroquinolin-1(2H)-yl)ethyl(isopropyl)-carbamate (3)

A solution of N-(2-(6-bromo-3,4-dihydroquinolin-1(2H)-yl)ethyl)propan-2-amine (compound 2, 0.140 g, 0.471 mmol) in anhydrous dioxane (10 mL) was treated with triethylamine (0.132 mL, 0.942 mmol) and di-tert-butyl dicarbonate (0.108 g, 0.495 mmol) and the resulting mixture stirred overnight at room temperature. The mixture was concentrated to residue and purified directly on silica gel eluting with 10% ethyl acetate/90% hexanes to yield a colorless oil, 3 (0.150 g, 80%). $^1$H-NMR (CDCl$_3$) δ 7.09 (dd, 1H, J=8.7, 2.0 Hz), 7.05-7.00 (m, 1H), 6.55 (d, 1H, J=8.7), 4.50-4.00 (br m, 1H), 3.42-3.27 (m, 4H), 3.24-3.11 (m, 2H), 2.70 (t, 2H, J=6.2 Hz), 1.97-1.86 (m, 2H), 1.53-1.51 (2×s, 9H), 1.13 (d, 6H, J=6.8 Hz). MS (ESI+): 397/399 (MH$^+$, 80), 341/343 (100).

tert-Butyl-2-(6-amino-3,4-dihydroquinolin-1(2H)-yl)ethyl(isopropyl)-carbamate (4)

A suspension of tris(dibenzylideneacetone)dipalladium(0) (35 mg, 0.038 mmol in anhydrous THF (3 mL) was treated with tri-t-butylphosphine in hexane (10% wt) (0.229 mL, 0.076 mmol) and the mixture stirred for 5 minutes at room temperature. A solution of tert-butyl-2-(6-bromo-3,4-dihydroquinolin-1(2H)-yl)ethyl(isopropyl)carbamate (compound 3, 0.150 g, 0.378 mmol) in THF (7 mL) was added followed by lithium bis(trimethylsilyl)amide (1M in THF, 0.755 mL, 0.755 mmol) and the mixture heated in a sealed reaction vial at 90° C. for 3 hours. The mixture was cooled to room temperature and treated with TBAF (1M in THF, 3 mL, 3 mmol) for 30 minutes. The mixture was partitioned between water (10 mL) and ethyl acetate (100 mL), transferred to a separatory funnel and the organic layer separated. The aqueous layer (pH=10) was further extracted with ethyl acetate and the combined organic layers washed with brine, dried over $Na_2SO_4$, filtered and concentrated to give a dark brown-red residue. Purification on silica gel eluting with 2.5% 2M $NH_3$ in methanol/97.5% dichloromethane yielded a dark brown residue, 4 (85 mg, 67.5%). $^1$H-NMR (DMSO-$d_6$) δ 6.44 (d, 1H, J=8.0 Hz), 6.28 (dd, 1H, J=8.3, 2.1 Hz), 6.24-6.18 (m, 1H), 4.33-3.91 (br m+br s, 3H), 3.24-3.04 (m, 6H), 2.60-2.50 (m, 2H), 1.85-1.74 (m, 2H), 1.44 (s, 9H), 1.07 (d, 6H, J=6.8 Hz). MS (ESI+): 334 (MH$^+$, 100).

tert-Butyl-isopropyl(2-(6-(thiophene-2-carboximidamido)-3,4-dihydro-quinolin-1(2H)-yl)ethyl)carbamate (6)

A solution of tert-butyl-2-(6-amino-3,4-dihydroquinolin-1(2H)-yl)ethyl(isopropyl) carbamate (compound 4, 85 mg, 0.255 mmol) in anhydrous ethanol (10 mL) was treated with methyl thiophene-2-carbimidothioate hydroiodide (compound 5, 127 mg, 0.446 mmol) in one portion and the mixture stirred at room temperature for 18 hours. TLC analysis showed approximately 80% consumption of the starting material thus a further portion of methyl thiophene-2-carbimidothioate hydroiodide (compound 5, 18.1 mg, 0.063 mmol) was added and the mixture stirred at room temperature for 4 hours. The mixture was partitioned between $CH_2Cl_2$ (100 mL) and sat. $Na_2CO_3$ (20 mL) and transferred to a separatory funnel. The organic layer was separated, and the aqueous layer (pH=9) was further extracted with $CH_2Cl_2$. The combined organic layers were washed with brine, dried over $MgSO_4$, filtered and concentrated to give a brown residue. Purification on silica gel eluting with 1% methanol/99% dichloromethane then 2.5% 2M $NH_3$ in methanol/97.5% dichloromethane yielded a yellow solid, 6 (54 mg, 47.9%). $^1$H-NMR (DMSO-$d_6$) δ 7.70 (d, 1H, J=3.4 Hz), 7.59 (d, 1H, J=5.0 Hz), 7.09 (dd, 1H, J=5.0, 3.6 Hz), 6.71-6.51 (2×m, 3H), 6.51-6.28 (br s, 2H), 4.29-3.94 (br m, 1H), 3.43-3.18 (2×m, 6H), 2.66 (t, 2H, J=5.8 Hz), 1.91-1.80 (m, 2H), 1.46 (s, 9H), 1.11 (d, 6H, J=6.8 Hz). MS (ESI+): 443 (MH$^+$, 100).

N-(1-(2-(Isopropylamino)ethyl)-1,2,3,4-tetrahydroquinolin-6-yl)thiophene-2-carboximidamide (61)

A solution of tert-butyl-isopropyl(2-(6-(thiophene-2-carboximidamido)-3,4-dihydro-quinolin-1(2H)-yl)ethyl)carbamate (compound 6, 50 mg, 0.113 mmol) in HPLC grade methanol (10 mL) was treated with 2N aq. HCl (0.565 mL, 1.13 mmol) and the mixture heated to reflux for 2 hours then cooled to room temperature overnight. The solution was concentrated and dried briefly on high-vac pump. The residue was taken up in 7.5% 2M $NH_3$ in methanol/92.5% dichloromethane (5 mL), reconcentrated then purified directly on silica gel eluting with 7.5% 2M $NH_3$ in methanol/92.5% dichloromethane to yield a yellow solid, 61 (40 mg, quantitative). $^1$H-NMR (DMSO-$d_6$) δ 7.66 (d, 1H, J=3.1 Hz), 7.54 (d, 1H, J=5.1 Hz), 7.06 (dd, 1H, J=5.0, 3.7 Hz), 6.61-6.50 (m, 2H), 6.47 (br s, 1H), 6.21 (br s, 2H), 3.30-3.18 (m, 4H), 2.79-2.70 (m, 1H), 2.70-2.61 (m, 4H), 1.88-1.80 (m, 2H), 0.97 (d, 6H, J=6.2 Hz). MS (ESI+): 343 (MH$^+$, 100); ESI-HRMS calculated for $C_{19}H_{27}N_4S$ (MH$^+$): 343.1950; observed: 343.1953.

Example 62

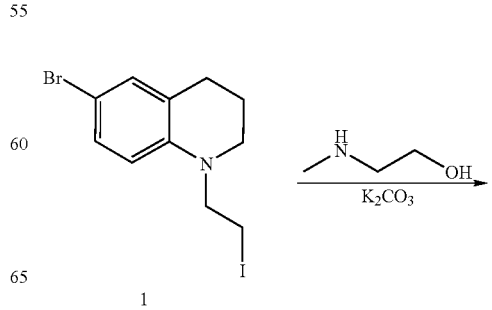

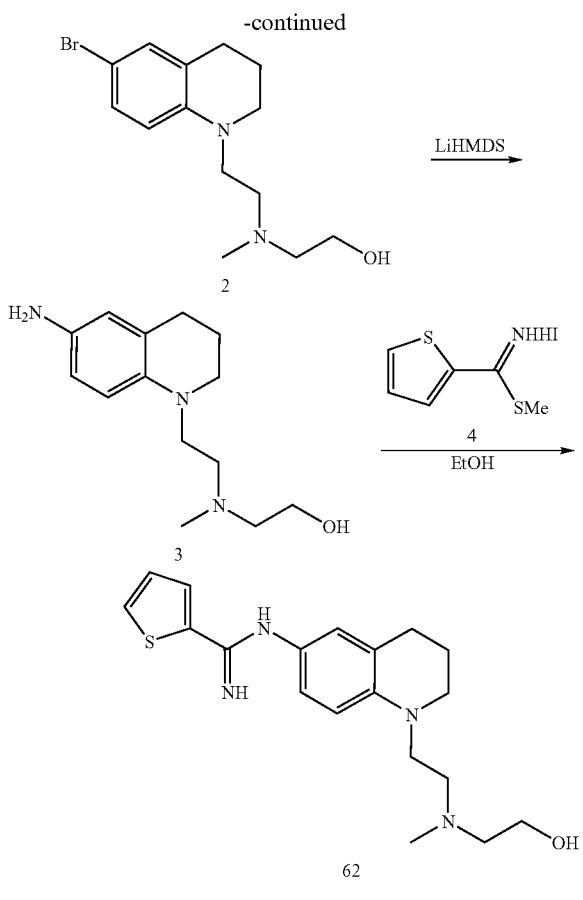

6-Bromo-1-(2-iodoethyl)-1,2,3,4-tetrahydroquinoline (1)

See Example 60 for complete experimental details and spectral data.

2-((2-(6-Bromo-3,4-dihydroquinolin-1(2H)-yl)ethyl)(methyl)amino)ethanol (2)

A solution of 6-bromo-1-(2-iodoethyl)-1,2,3,4-tetrahydroquinoline (compound 1, 0.475 g, 1.298 mmol) in acetonitrile (19 mL) and water (1 mL) in a 50 mL pressure vessel fitted with a stir-bar was treated with potassium carbonate (1.793 g, 12.98 mmol) and 2-(methylamino)ethanol (0.975 g, 12.98 mmol) and the sealed vessel stirred at 80° C. overnight. After 18 hours the mixture was partitioned between $CH_2Cl_2$ (100 mL) and water (20 mL) and transferred to a separatory funnel. The organic layer was separated and the aqueous layer (pH=12); extracted further with $CH_2Cl_2$. The combined organic layer was washed with brine, dried over $Na_2SO_4$, filtered and concentrated to a brown residue. Purification on silica gel eluting with 5% 2M $NH_3$ in methanol/95% dichloromethane yielded a pale yellow oil, 2 (341 mg, 84%). $^1$H-NMR (DMSO-$d_6$) δ 7.06 (dd, 1H, J=8.8, 2.5 Hz), 6.99 (d, 1H, J=2.4 Hz), 6.48 (d, 1H, J=8.8), 4.34 (t, 1H, J=5.3 Hz), 3.44 (q, 2H, J=6.2 Hz), 3.32-3.25 (m, 4H), 2.64 (t, 2H, J=6.2 Hz), 2.47-2.41 (m, 4H), 2.23 (s, 3H), 1.83-1.76 (m, 2H). MS (ESI$^+$): 313/315 (MH$^+$, 100).

2-((2-(6-Amino-3,4-dihydroquinolin-1(2H)-yl)ethyl)(methyl)amino)ethanol (3)

A suspension of tris(dibenzylideneacetone)dipalladium(0) (48 mg, 0.053 mmol) in anhydrous THF (3 mL) was treated with tri-t-butylphosphine in hexane (10% wt) (0.320 mL, 0.105 mmol) and the mixture stirred for 5 minutes at room temperature. A solution of 2-((2-(6-bromo-3,4-dihydroquinolin-1(2H)-yl)ethyl)(methyl)amino)ethanol (compound 2, 0.165 g, 0.527 mmol) in THF (7 mL) was added followed by lithium bis(trimethylsilyl)amide (1M in THF, 1.58 mL, 1.58 mmol) and the mixture heated in a sealed reaction vial at 90° C. for 3 hours. The mixture was cooled to room temperature then to 0° C. and quenched with 3N aq. HCl (1.5 mL) and stirred for 30 minutes slowly warming to room temperature. The mixture was diluted with ethyl acetate, basified to pH ~10 by the addition of 1N aq NaOH and transferred to a separatory funnel. The organic layer was separated and the aqueous layer further extracted with ethyl acetate (×3) and the combined organic layers washed with brine, dried over $Na_2SO_4$, filtered and concentrated to give a dark brown residue. Purification on silica gel eluting with 7.5% 2M $NH_3$ in methanol/92.5% dichloromethane yielded an orange-red residue, 3 (57 mg, 43.4%). $^1$H-NMR (DMSO-$d_6$) δ 6.36-6.27 (m, 2H), 6.21 (br s, 1H), 4.31 (t, 1H, J=5.4 Hz, exch. $D_2O$), 4.18 (br s, 2H, exch. $D_2O$), 3.44 (q, 2H, J=6.3 Hz), 3.18 (t, 2H, J=7.3 Hz), 3.10 (t, 2H, J=5.3 Hz), 2.56-2.40 (2×m, 6H), 2.22 (s, 3H), 1.84-1.72 (m, 2H). MS (ESI+): 250 (MH$^+$, 100).

N-(1-(2-((2-Hydroxyethyl)(methyl)amino)ethyl)-1,2,3,4-tetrahydroquinolin-6-yl)thiophene-2-carboximidamide (62)

A solution of 2-((2-(6-amino-3,4-dihydroquinolin-1(2H)-yl)ethyl)(methyl)amino)ethanol (compound 3, 52 mg, 0.209 mmol) in anhydrous EtOH (10 mL) was treated with methyl thiophene-2-carbimidothioate hydroiodide (compound 4, 119 mg, 0.417 mmol) in one portion and the mixture stirred at room temperature for 20 hours. The solution was concentrated and the residue was taken up in 7.5% 2M $NH_3$ in methanol/92.5% dichloromethane (5 mL), reconcentrated then purified directly on silica gel eluting with 7.5% 2M $NH_3$ in methanol/92.5% dichloromethane to yield a yellow solid, 62 (44 mg, 58.9%). $^1$H-NMR (DMSO-$d_6$) δ 7.67 (d, 1H, J=3.0 Hz), 7.55 (dd, 1H, J=5.0, 0.9 Hz), 7.07 (dd, 1H, J=5.0, 3.7 Hz), 6.60-6.51 (m, 2H), 6.48 (br s, 1H), 6.29 (br s, 2H, exch. $D_2O$), 4.34 (t, 1H, J=5.3 Hz, exch. $D_2O$), 3.46 (q, 2H, J=6.2 Hz), 3.32-3.22 (m, 4H), 2.65 (t, 2H, J=6.2 Hz), 2.50-2.44 (m, 4H), 2.25 (s, 3H), 1.88-1.80 (m, 2H). MS (ESI+): 359 (MH$^+$, 100). ESI-HRMS calculated for $C_{19}H_{27}N_4OS$ (MH$^+$): 359.1900; observed: 359.1908.

Example 63

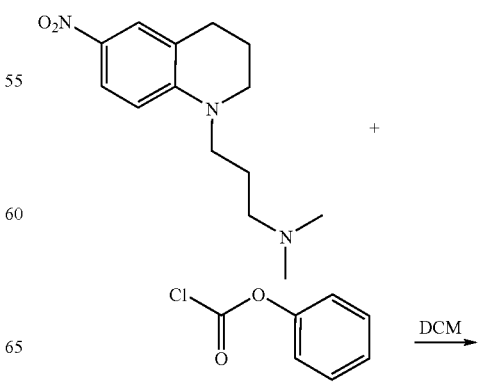

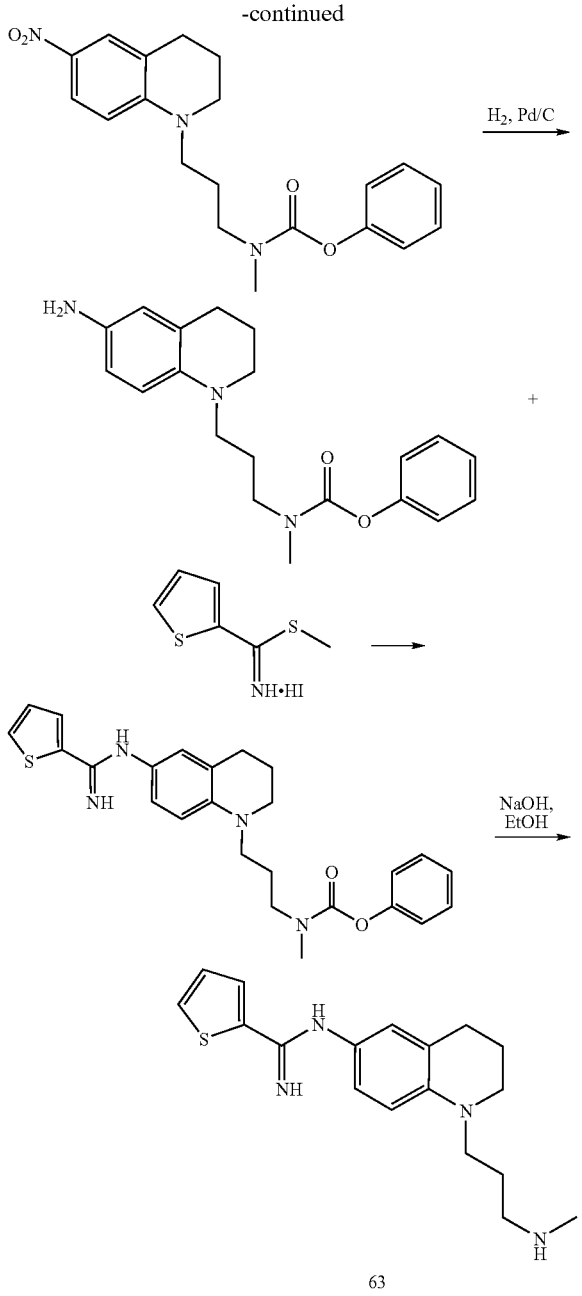

63

N,N-Dimethyl-3-(6-nitro-3,4-dihydroquinolin-1 (2H)-yl)propan-1-amine

See Example 59 for details.

Phenyl methyl(3-(6-nitro-3,4-dihydroquinolin-1 (2H)-yl)propyl)carbamate

To a stirred solution of N,N-dimethyl-3-(6-nitro-3,4-dihydroquinolin-1(2H)-yl)propan-1-amine (1 g, 3.80 mmol) in dichloromethane (20 ml) was added phenyl carbonochloridate (0.715 ml, 5.70 mmol). The resulting solution was stirred at room temperature overnight. The reaction mixture was then diluted with water and extracted with dichloromethane (3×). The combined organics were dried, filtered and concentrated, then chromatographed in 50-100% ethyl acetate in hexanes, giving the desired phenyl methyl(3-(6-nitro-3,4-dihydroquinolin-1(2H)-yl)propyl)carbamate (1.02 g, 2.76 mmol, 72.7% yield). $^1$H NMR (DMSO-d$_6$) δ 7.88 (t, J=7 Hz, 1H), 7.78 (s, 1H), 7.37 (t, J=7 Hz, 2H), 7.20 (t, J=7 Hz, 1H), 7.12-7.06 (m, 2H), 6.70 (d, J=9 Hz, 1H), 3.50-3.33 (m, 6H), 3.06, 2.93 (2s, 3H), 2.76-2.71 (m, 2H), 1.92-1.81 (m, 4H). ESI-MS (m/z, %) 370 (MH$^+$, 100).

Phenyl 3-(6-amino-3,4-dihydroquinolin-1(2H)-yl) propyl(methyl)carbamate

To a stirred solution of phenyl methyl(3-(6-nitro-3,4-dihydroquinolin-1(2H)-yl)propyl)carbamate (1.02 g, 2.76 mmol) in THF (15.00 ml) and ethanol (15 ml) was added palladium 10 wt. % on activated carbon (0.294 g, 0.276 mmol). The reaction mixture was stirred under an atmosphere of hydrogen (balloon pressure) for 3 h. The mixture was then filtered through celite and concentrated, giving a dark oil. The crude product (phenyl 3-(6-amino-3,4-dihydroquinolin-1(2H)-yl) propyl(methyl)carbamate (830 mg, 2.445 mmol, 89% yield)) was used directly in the subsequent reaction. ESI-MS (m/z, %) 340 (MH$^+$, 100).

Phenyl methyl(3-(6-(thiophene-2-carboximidamido)-3,4-dihydroquinolin-1(2H)-yl)propyl)carbamate To a stirred solution of phenyl 3-(6-amino-3,4-dihydroquinolin-1(2H)-yl)propyl(methyl)carbamate (830 mg, 2.445 mmol) in ethanol (35 ml) under argon was added methyl thiophene-2-carbimidothioate hydroiodide (1395 mg, 4.89 mmol). The resulting suspension was stirred overnight at room temperature. The reaction mixture was then diluted with water and sodium carbonate (sat) and extracted with dichloromethane. The combine organics were dried, filtered and concentrated, then chromatographed in 1:1 ethyl acetate in hexanes, then ethyl acetate, followed by 5% (2M NH3 in methanol) in 1:1 ethyl acetate dichloromethane, giving the desired phenyl methyl(3-(6-(thiophene-2-carboximidamido)-3,4-dihydroquinolin-1(2H)-yl)propyl)carbamate (630 mg, 1.404 mmol, 57.4% yield). $^1$H NMR (DMSO-d$_6$) δ 7.67 (d, J=3 Hz, 1H), 7.55 (d, J=4.8 Hz, 1H), 7.41-7.35 (m, 2H), 7.23-7.21 (m, 1H), 7.13-7.05 (m, 3H), 6.56 (m, 2H), 6.49 (brs, 1H), 6.25 (brs, 2H), 3.50-3.45 (m, 2H), 3.38-3.32 (m, 2H), 3.23-3.19 (m, 2H), 3.06, 2.93 (2s, 3H), 2.69-2.64 (m, 2H), 1.89-1.81 (m, 4H).

N-(1-(3-(methylamino)propyl)-2,3,4-tetrahydroquinolin-6-yl)thiophene-2-carboximidamide To a stirred solution of phenyl methyl(3-(6-(thiophene-2-carboximidamido)-3,4-dihydroquinolin-1(2H)-yl)propyl) carbamate (630 mg, 1.404 mmol) in ethanol (20 ml) was added sodium hydroxide (562 mg, 14.04 mmol) as a solution in water (10 ml). The resulting mixture was stirred at 80° C. overnight. The reaction mixture was then cooled to room temperature, diluted with water and extracted with dichloromethane (3×). The combined organics were dried, filtered and concentrated, then chromatographed in a 1:1 mixture of ethyl acetate and dichloromethane, then 5% (2M NH3 in methanol) in 1:1 ethyl acetate:dichloromethane, then 5-15% (2M NH3 in methanol) in dichloromethane. Yield 130 mg (28.2%). $^1$H NMR (DMSO-d$_6$) δ 7.66 (d, J=3.3 Hz, 1H), 7.54 (d, J=5.1 Hz, 1H), 7.06 (dd, J=5.1, 3.6 Hz, 1H), 6.54 (brs, 2H), 6.47 (s, 1H), 6.21 (brs, 2H), 3.26-3.16 (m, 4H), 2.66 (t, J=6.4 Hz, 2H), 2.53-2.48 (m, 2H), 2.28 (s, 3H), 1.85 (quint, J=5.5 Hz, 2H), 1.64 (quint, J=7.2 Hz, 2H).

Salt Formation:

To a solution of N-(1-(3-(methylamino)propyl)-1,2,3,4-tetrahydroquinolin-6-yl)thiophene-2-carboximidamide (120.5 mg, 0.367 mmol) in methanol (3 mL) was added HCl, 1M in diethyl ether (0.734 mL, 0.734 mmol). The resulting solution was concentrated to give a yellow orange solid 63 as the dihydrochloride salt. Yield 163 mg.

Example 64

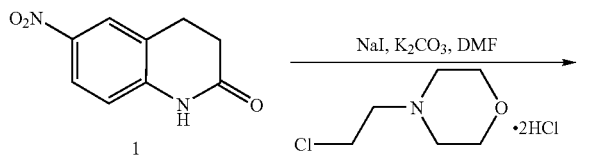

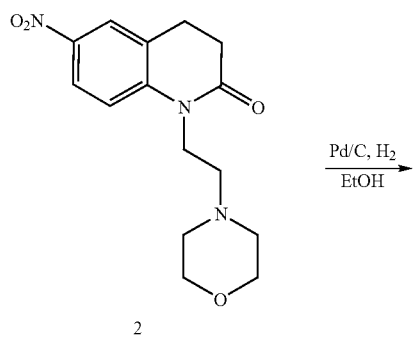

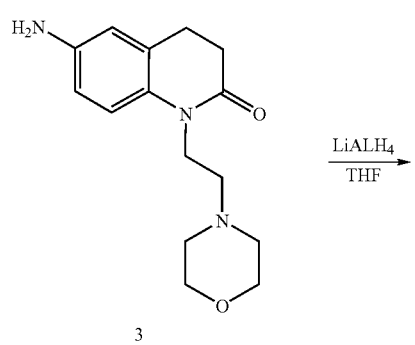

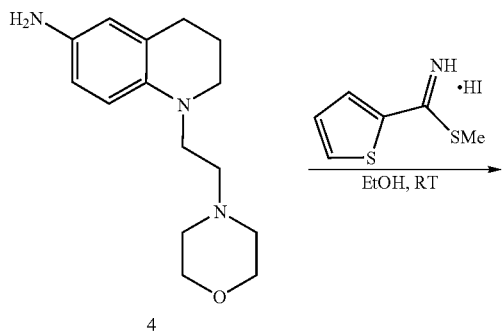

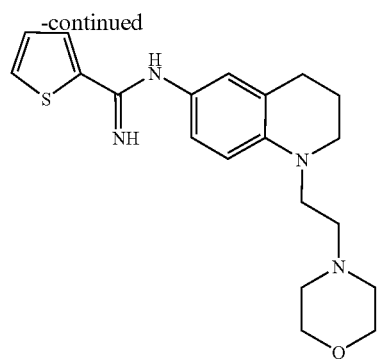

1-(2-morpholinoethyl)-6-nitro-3,4-dihydroquinolin-2(1H)-one (2)

A suspension of 6-nitro-3,4-dihydroquinolin-2(1H)-one (1.00 g, 5.20 mmol), 4-(2-chloroethyl)morpholine hydrochloride (1.94 g, 10.40 mmol), sodium iodide (390 mg, 2.61 mmol) and potassium carbonate (4.32 g, 31.3 mmol) in DMF (5 mL) was stirred at room temperature for 60 hours. The mixture was transferred to a separatory funnel, diluted with water (45 mL) then extracted with ethyl acetate (3×35 mL). The combined organic fractions were washed with brine, dried ($Na_2SO_4$), filtered and concentrated. The crude product was subject to flash chromatography on silica gel using 2.5% 2M $NH_3$ methanol/$CH_2Cl_2$, which resulted in a yellow solid, compound 2 (0.9211 g, 58%).

$^1$H NMR (DMSO-$d_6$) δ 8.15 (brs, 1H), 8.12 (d, J=2.7 Hz, 1H), 7.40 (d, J=9.0 Hz, 1H), 4.06 (t, J=14.1 Hz, 2H), 3.52 (t, J=9.0 Hz, 4H), 2.99 (t, J=14.7 Hz, 2H), 2.64-2.59 (m, 2H), 2.45-2.40 (m, 6H); MS-ESI (m/z, %): 306 (MH$^+$, 100), 219 (16).

6-amino-1-(2-morpholinoethyl)-3,4-dihydroquinolin-2(1H)-one (3)

A suspension of compound 2 (0.9211 g, 3.017 mmol) and palladium on carbon (10% wt, 0.092 g) in ethanol (10 mL) was stirred and fitted with a hydrogen balloon overnight. The suspension was filtered through a pad of celite and was rinsed with methanol (100 mL). The crude product was subject to flash chromatography on silica gel 2.5% 2M $NH_3$ methanol/$CH_2Cl_2$, which resulted in a light brown solid, compound 3 (0.802 g, 96%).

$^1$H NMR (DMSO-$d_6$) δ 6.82 (d, J=8.4 Hz, 1H), 6.45 (d, J=2.4 Hz, 1H), 6.41 (brs, 1H), 4.85 (s, 2H), 3.89 (t, J=14.7 Hz, 2H), 3.54 (t, J=9.0 Hz, 4H), 2.66 (t, J=14.4 Hz, 2H), 2.43-2.37 (m, 8H); MS-ESI (m/z, %): 277 (11), 276 (MH$^+$, 100), 189 (37).

1-(2-morpholinoethyl)-1,2,3,4-tetrahydroquinolin-6-amine (4)

A mixture of compound 3 (0.800 g, 2.905 mmol) in THF (25 mL) was stirred at 0° C. and was treated with solid lithium aluminum hydride (0.4352 g, 11.62 mmol). The mixture was brought to room temperature at which point it was heated to reflux for 1 hour. The reaction was quenched with $H_2O$ (1 mL), 3N NaOH solution (1 mL) and an additional aliquot of $H_2O$ (1 mL). The solution was filtered over celite and was rinsed with diethyl ether. The concentrated crude product was subject to flash chromatography on silica gel 5% 2M $NH_3$ methanol/CH$_2$Cl$_2$, which resulted in a dark brown viscous liquid, compound 4 (0.27 g, 36%).

$^1$H NMR (DMSO-d$_6$) δ 6.35 (d, J=8.4 Hz, 1H), 6.28 (dd, J=2.7, 8.4 Hz, 1H), 6.21 (brs, 1H), 4.18 (s, 2H), 3.55 (t, J=9.3 Hz, 4H), 3.22 (t, J=14.4 Hz, 2H), 3.11 (t, J=11.1 Hz, 2H), 2.55 (m, 2H), 2.41-2.37 (m, 6H), 1.81-1.73 (m, 2H); MS-ESI (m/z, %): 262 (MH$^+$, 96), 147 (30), 114 (100).

N-(1-(2-morpholinoethyl)-1,2,3,4-tetrahydroquinolin-6-yl)thiophene-2-carboximidamide (64)

A solution of compound 4 (0.23 g, 0.88 mmol) in dry ethanol (20 mL) was treated with methyl thiophene-2-carbimidothioate hydroiodide (0.502 g, 1.76 mmol) at room temperature and was stirred for 3 hours. The mixture was diluted with saturated sodium bicarbonate solution (50 mL) and was extracted with CH$_2$Cl$_2$ (100 mL). The organic layer was washed with brine (20 mL) and dried (Na$_2$SO$_4$). The concentrated crude product was subject to flash chromatography on silica gel using 5% methanol/CH$_2$Cl$_2$, which resulted in a brown foam, compound 64 (0.194 g, 59%). $^1$H NMR (CDCl$_3$) δ 7.66 (d, J=3.9 Hz, 1H), 7.54 (d, J=4.5 Hz, 1H), 7.06 (dd, J=3.6, 5.1 Hz, 1H), 6.53 (s, 2H), 6.46 (s, 1H), 6.21 (brs, 2H), 3.57 (t, J=9.3 Hz, 4H), 3.24 (t, J=11.4 Hz, 2H), 3.65 (t, J=12.6 Hz, 2H), 2.45-2.41 (m, 6H), 1.88-1.80 (m, 2H); MS-ESI (m/z, %): 372 (11), 371 (MH$^+$, 100), 258 (9); ESI-HRMS calculated for C$_{20}$H$_{27}$N$_4$OS (MH$^+$): Calculated: 371.1914, Observed: 371.1900.

Examples 65 and 66

Separated Enantiomers of Example 29

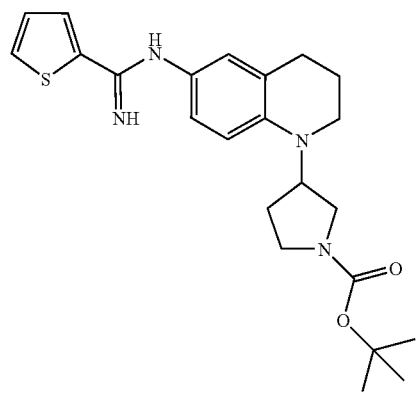

Isomer 1

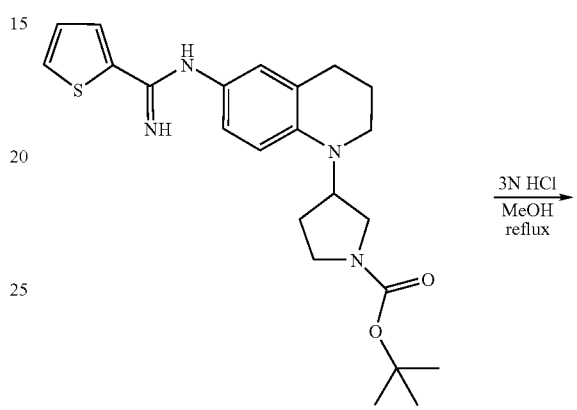

Isomer 2

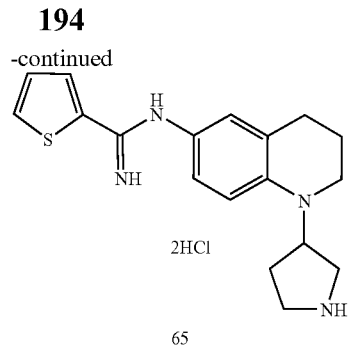

65

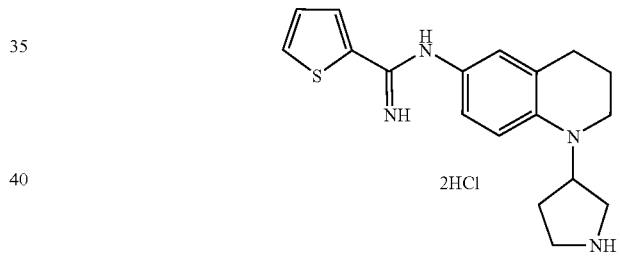

66

The enantiomeric mixture of tert-butyl 3-(6-(thiophene-2-carboximidamido)-3,4-dihydroquinolin-1(2H)-yl)pyrrolidine-1-carboxylate (Example 29) was separated by using preparative chiral HPLC column chromatography to obtain Isomer 1 and Isomer 2.

| | |
|---|---|
| Column: | Chiralcel OJ-H (0.46 × 25 cm) S/N 06-6079 |
| Solvent: | 40% isopropanol (0.1% DEA)/CO$_2$ 100 bar |
| Wavelength: | 220 nm |
| Flow rate: | 3 mL/min. |

First eluting isomer at 4.44 min. (Isomer 1): ESI-MS (m/z, %) 427.2 (MH$^+$, 100%); ESI-HRMS calculated for C$_{23}$H$_{31}$N$_4$O$_2$S (MH$^+$), Calculated: 427.2162; Observed: 427.2206; Chiral purity: 99.42%; Chemical purity: 98.2%.

Second eluting isomer at 5.08 min. (Isomer 2): ESI-MS (m/z, %) 427.2 (MH$^+$, 100%); ESI-HRMS calculated for C$_{23}$H$_{31}$N$_4$O$_2$S (MH$^+$), Calculated: 427.2162; Observed: 427.2177; Chiral purity: 99.57%; Chemical purity: 97.6%.

(−)-N-(1-(pyrrolidin-3-yl)-1,2,3,4-tetrahydroquinolin-6-yl)thiophene-2-carboximidamide dihydrochloride (65)

A solution of tert-butyl 3-(6-(thiophene-2-carboximidamido)-3,4-dihydroquinolin-1(2H)-yl)pyrrolidine-1-carboxylate (Isomer 1) (520 mg, 1.219 mmol) in MeOH (26 ml) was treated with 3N HCl (4.06 ml, 12.19 mmol) then heated at 90° C. for 30 minutes. After cooling, the mixture was concentrated to dryness and dried under reduced pressure overnight. The solid was triturated with 5% isopropanol/95% hexanes (50 mL), collected and dried under reduced pressure (450 mg, 92%). ESI-MS (m/z, %) 327.2 (MH$^+$, 65%), 258.1 (100%); ESI-HRMS calculated for $C_{18}H_{23}N_4S$ (MH$^+$), Calculated: 327.1637; Observed: 326.1650; Chemical purity: 97.7%; Optical Rotation: $^{25}[\alpha]_{589}$=−0.19°, c=1.05 in MeOH.

(+)-N-(1-(pyrrolidin-3-yl)-1,2,3,4-tetrahydroquinolin-6-yl)thiophene-2-carboximidamide dihydrochloride (66)

A solution of tert-butyl 3-(6-(thiophene-2-carboximidamido)-3,4-dihydroquinolin-1(2H)-yl)pyrrolidine-1-carboxylate (Isomer 2) (520 mg, 1.219 mmol) in MeOH (26 ml) was treated with 3N HCl (4.06 ml, 12.19 mmol) then heated at 90° C. for 30 minutes. After cooling, the mixture was concentrated to dryness and dried under reduced pressure overnight. The solid was triturated with 5% isopropanol/95% hexanes (50 mL), collected and dried under reduced pressure (391 mg, 80%). ESI-MS (m/z, %) 327.2 (MH$^+$, 90%), 258.1 (100%); ESI-HRMS calculated for $C_{18}H_{23}N_4S$ (MH$^+$), Calculated: 327.1637; Observed: 326.1635; Chemical purity: 97.3%; Optical Rotation: $^{25}[\alpha]_{589}$=+0.19°, c=0.95 in methanol.

Example 67

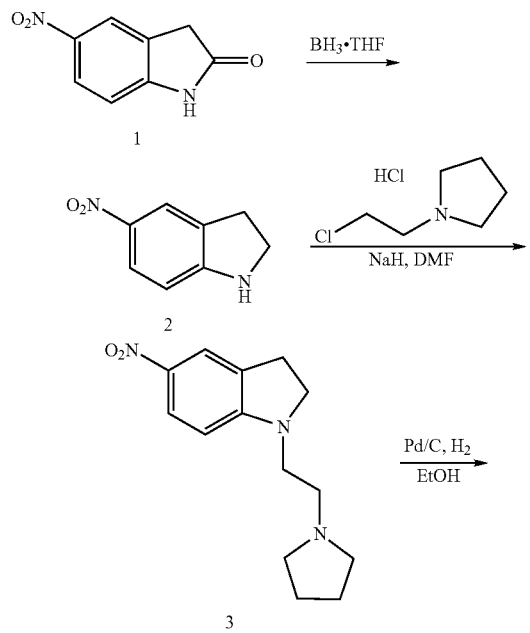

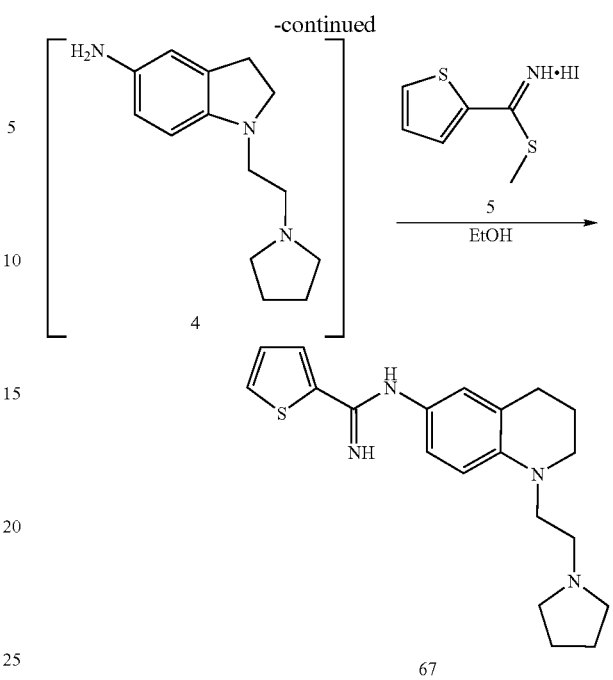

5-Nitro-indoline (2)

A suspension of compound 1 (5 g, 28.1 mmol) in THF (10 mL) was treated with a BH$_3$-THF complex (84 mL, 84 mmol, 1.0 M in THF) and the resulting brown red suspension was refluxed overnight. The reaction was cooled in an ice-bath and methanol (125 mL) was added resulting in orange/red solution which was stirred for half an hour and then concentrated. Methanol (200 mL) was added again and the solution was refluxed for 2 hrs and then concentrated. The residue was subjected to a large silica gel filter with methanol as eluent resulting in a brown solid (2.5 g, 54% yield). $^1$H-NMR (DMSO-d$_6$) δ 7.90 (dd, J=8.7, 2.4 Hz, 1H), 7.83 (s, 1H), 7.26 (s, 1H), 6.44 (d, J=8.7 Hz, 1H), 3.66 (t, J=9.0 Hz, 2H), 3.04 (t, J=9.0 Hz, 2H).

5-Nitro-1-(2-(pyrrolidin-1-yl)ethyl)indoline (3)

A solution of compound 2 (500 mg, 3.05 mmol) in DMF (10 mL) was treated with NaH (390 mg, 9.75 mmol, 60% wt in mineral oil) at 0° C. resulting in a bright orange suspension. The mixture stirred for 10 minutes, then 2-chloroethyl-pyrrolidine hydrochloride (566 mg, 3.33 mmol) was added and the reaction turned into a bright red suspension. The reaction was heated to 90° C. for 1 hour. After 1 hour, the reaction was allowed to cool to room temperature. Then it was diluted with water (20 mL), transferred to a separatory funnel and extracted with ethyl acetate (2×15 mL). The combined the organic layers were washed with brine (3×5 mL), dried (Na$_2$SO$_4$), filtered and concentrated. The residue was subjected to flash chromatography on silica gel using: 2.5% 2M NH$_3$ in methanol: 97.5% CH$_2$Cl$_2$ to give a brown solid (400 mg, 50%). $^1$H-NMR (DMSO-d$_6$) δ 7.96 (dd, J=2.4, 9.0 Hz, 1H), 7.80 (d, J=2.1 Hz, 1H), 6.47 (d, J=9.0 Hz, 1H), 3.73 (t, J=9.0 Hz, 2H), 3.41 (t, J=6.9 Hz, 2H), 3.04 (t, J=8.1 Hz, 2H), 2.62 (t, J=6.9 Hz, 2H), 2.58-2.48 (m, 4H), 1.70-1.64 (m, 4H).

N-(1-(2-(Pyrrolidin-1-yl)ethyl)indolin-5-yl)thiophene-2-carboximidamide (6)

A solution of compound 3 (0.40 g, 1.531 mmol) and Pd—C (0.162 g, 0.153 mmol, 10% wt) in dry ethanol (5 mL) was purged with hydrogen gas. The reaction was stirred at room temperature over night under hydrogen atm. (balloon pressure). Then the reaction mixture was filtered through a celite pad and washed with ethanol (35 mL). The filtrate (compound 4) was treated with imidate 5 (0.873 g, 3.06 mmol) and stirred over night at room temperature. The reaction was diluted with saturated NaHCO$_3$ solution (50 mL) and product was extracted into CH$_2$Cl$_2$ (3×25 mL). The combined organic layers were dried (Na$_2$SO$_4$) and concentrated. The residue was subjected to flash chromatography on silica gel: 2% methanol: 98% CH$_2$Cl$_2$ followed by 5% 2M NH$_3$ in methanol: 95% CH$_2$Cl$_2$, to give a greenish/yellow solid (230 mg, 44%). $^1$H-NMR (DMSO-d$_6$) δ 7.68 (dd, J=0.9, 3.6 Hz, 1H), 7.55 (dd, J=0.9, 5.1 Hz, 1H), 7.07 (dd, J=3.6, 4.8 Hz, 1H), 6.62 (s, 1H), 6.50-6.45 (m, 2H), 6.23 (s, 2H), 3.33-3.27 (m, 2H), 3.11 (t, J=6.9 Hz, 2H), 2.84 (t, J=8.1 Hz, 2H), 2.62 (t, J=7.5, 2H), 2.55-2.45 (m, 4H), 1.70-1.65 (m, 4H); ESI-MS (m/z, %): 341 (MH$^+$, 100), 244 (45), 127 (57), 98 (38); ESI-HRMS calculated for C$_{19}$H$_{25}$N$_4$S (MH$^+$): Calculated: 341.1794, Observed: 341.1788; HPLC purity: 95.3%.

Example 68

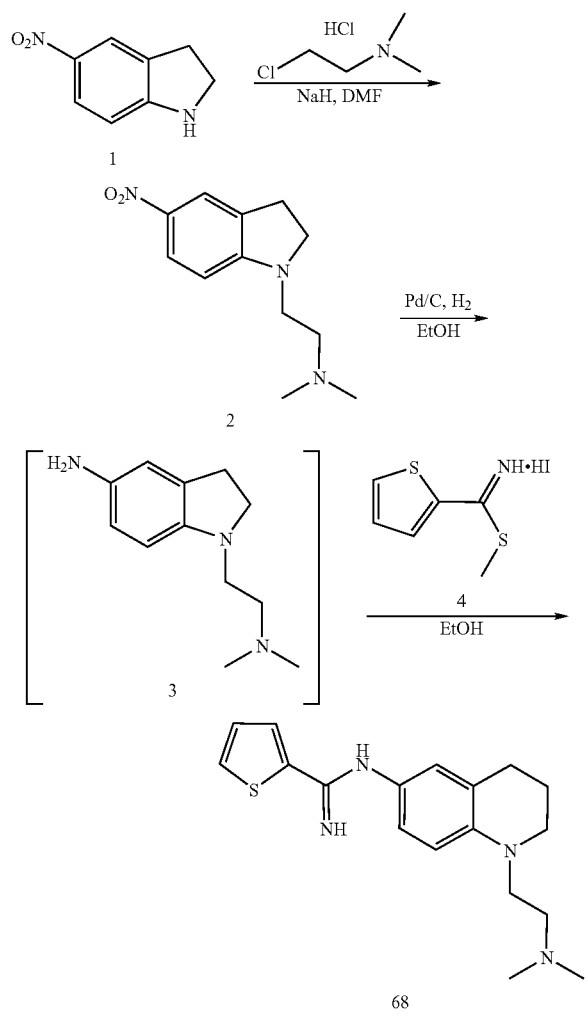

198

5-Nitro-indoline (1)

For complete experimental details and spectral data, please see Example 67.

N,N-Dimethyl-2-(5-nitroindolin-1-yl)ethanamine (2)

A solution of compound 1 (500 mg, 3.05 mmol) in DMF (10 mL) was treated with NaH (390 mg, 9.75 mmol, 60% wt in mineral oil) at 0° C. resulting in an orange mixture. It was then treated with 2-chloro-N,N-dimethylethanamine hydrochloride (877 mg, 6.09 mmol) resulting in a dark red mixture. The reaction was heated to 90° C. and stirred for 1.5 hours. After allowing the reaction to cool to room temperature, water (80 mL) was added, and the reaction was extracted into ethyl acetate (3×25 mL). The combined organic layers were washed with water (2×15 mL) and then with brine (10 mL), dried (Na$_2$SO$_4$), filtered, and concentrated. The residue was subjected to flash chromatography on silica gel:CH$_2$Cl$_2$ and then 2.5% 2M NH$_3$ in methanol: 97.5% CH$_2$Cl$_2$ to give a brownish/red solid (400 mg, 56% yield). $^1$H-NMR (DMSO-d$_6$) δ 7.96 (dd, J=2.1, 8.7 Hz, 1H), 7.79 (d, J=2.1 Hz, 1H), 6.49 (d, J=9.0 Hz, 1H), 3.72 (t, J=8.7 Hz, 2H), 3.39 (t, J=6.6 Hz, 2H), 3.04 (t, J=8.7 Hz, 2H), 2.44 (t, J=6.3, 2H), 2.18 (s, 6H).

N-(1-(2-(Dimethylamino)ethyl)indolin-5-yl) thiophene-2-carboximidamide (68)

A solution of compound 2 (183 mg, 0.778 mmol) and Pd—C (82 mg, 0.078 mmol, 10% wt) in dry ethanol (5 mL) was purged with hydrogen gas. The reaction was stirred at room temperature over night under hydrogen atm. (balloon pressure). Then the reaction mixture was filtered through a celite pad and washed with ethanol (35 mL). The filtrate (compound 3) was treated with imidate 4 (444 mg, 1.559 mmol) and stirred over night at room temperature. The reaction was diluted with saturated NaHCO$_3$ solution (50 mL) and product was extracted into CH$_2$Cl$_2$ (3×25 mL). The combined organic layers were dried (Na$_2$SO$_4$) and concentrated. The residue was subjected to flash chromatography on silica gel: 2% methanol: 98% CH$_2$Cl$_2$ followed by 2.5% 2M NH$_3$ in methanol: 97.5% CH$_2$Cl$_2$ followed by 5% 2M NH$_3$ in methanol: 95% CH$_2$Cl$_2$, to give a greenish/yellow solid (90 mg, yield). $^1$H-NMR (DMSO-d$_6$) δ 7.68 (d, J=2.7 Hz, 1H), 7.56 (dd, J=5.1, 1.2 Hz, 1H), 7.07 (dd, J=3.6, 5.1 Hz, 1H), 6.62 (s, 1H), 6.55-6.46 (m, 2H), 6.28 (s, 2H), 3.32-3.27 (m, 2H), 3.09 (t, J=6.6 Hz, 2H), 2.84 (t, J=8.1 Hz, 2H), 2.45 (t, J=6.9 Hz, 2H), 2.20 (s, 6H). ESI-MS (m/z, %): 315 (MH$^+$, 100), 244 (29), 127 (38); ESI-HRMS calculated for C$_{17}$H$_{23}$N$_4$S (MH$^+$): calculated 315.1637, Observed: 315.1645: HPLC purity: 95.3%.

Example 69

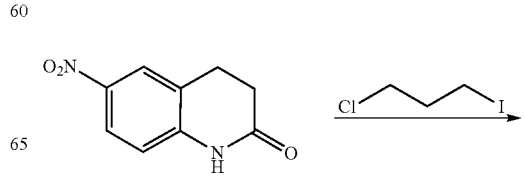

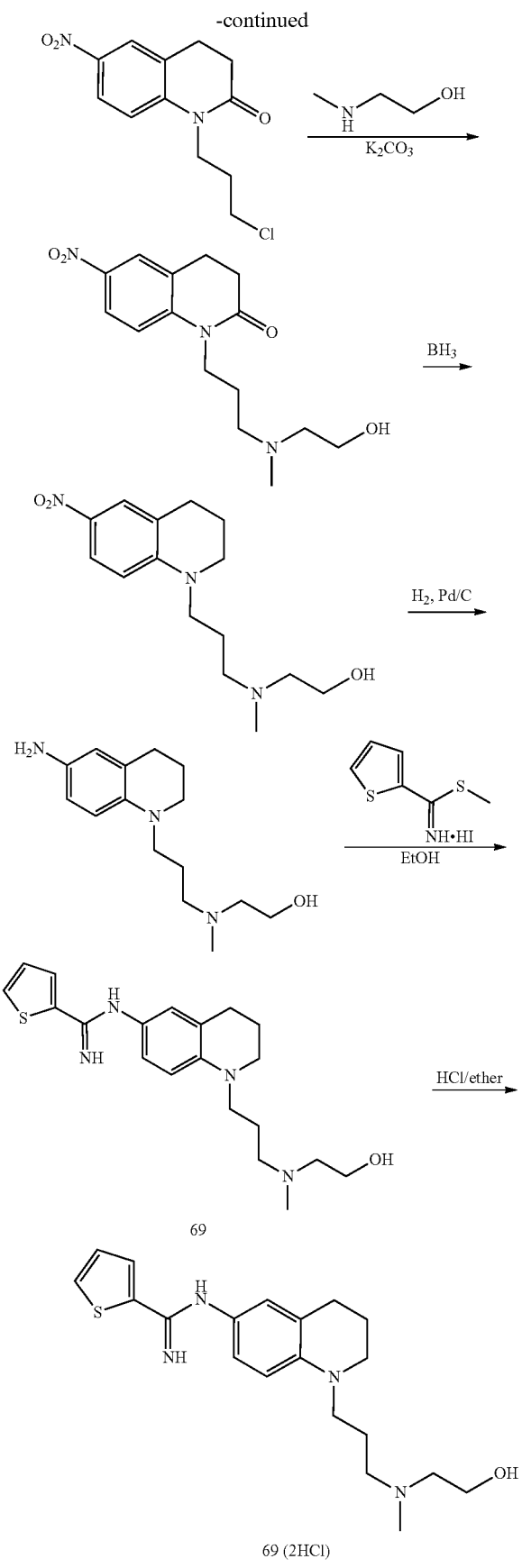

1-(3-Chloropropyl)-6-nitro-3,4-dihydroquinolin-2(1H)-one

To a stirred solution of 6-nitro-3,4-dihydroquinolin-2(1H)-one (2 g, 10.41 mmol) at 0° C. under argon was added sodium hydride, 60% (0.624 g, 15.61 mmol). The mixture was stirred at 0° C. until bubbling ceased, approximately 30 min. To this mixture was then added 1-chloro-3-iodopropane (3.29 ml, 31.2 mmol). The mixture was then allowed to warm slowly to room temperature and stirred overnight. The reaction mixture was then diluted with water and extracted with ethyl acetate (2×). The combined organics were then washed with a 1:1 mixture of water and brine (3×) then brine (1×). The organic phase was then dried, filtered and concentrated on to silica gel, then chromatographed in 10-50% ethyl acetate in hexanes, giving the desired 1-(3-chloropropyl)-6-nitro-3,4-dihydroquinolin-2(1H)-one (2.05 g, 7.63 mmol, 73.3% yield) as a yellow solid. $^1$H NMR (DMSO-$d_6$) δ 8.15 (m, 1H), 8.13 (dd, J=9, 2.7 Hz, 1H), 7.36 (d, J=9 Hz, 1H), 4.07 (t, J=7.4 Hz, 2H), 3.71 (t, J=6.5 Hz, 2H), 3.02 (t, J=7.4 Hz, 2H), 2.63 (t, J=7.4 Hz, 2H), 1.99 (quint, J=7.2 Hz, 2H).

1-(3-((2-Hydroxyethyl)(methyl)amino)propyl)-6-nitro-3,4-dihydroquinolin-2(1H)-one To a stirred mixture of 1-(3-chloropropyl)-6-nitro-3,4-dihydroquinolin-2(1H)-one (500 mg, 1.861 mmol) and potassium carbonate (1286 mg, 9.30 mmol) in acetonitrile (5 ml) was added 2-(methylamino)ethanol (0.447 ml, 5.58 mmol). The resulting mixture was stirred overnight at room temperature under argon. The reaction mixture was then diluted with water and extracted with dichloromethane (3×). The combined organics were dried, filtered and concentrated, then chromatographed on silica gel using ethyl acetate as eluent, followed by 10% (2M NH3 in methanol) in dichloromethane. A large amount of starting material was recovered and resubjected to the reaction conditions, using potassium iodide, and heating overnight at 80° C. followed by workup and repurification.

$^1$H NMR (DMSO-$d_6$) δ 8.15-8.10 (m, 2H), 7.41 (d, J=8.7 Hz, 1H), 4.37 (t, J=5.3 Hz, 1H), 3.95 (t, J=7.4 Hz, 2H), 3.49-3.43 (m, 2H), 3.00 (t, J=7.4 Hz, 2H), 2.62 (t, J=7.4 Hz, 2H), 2.39-2.35 (m, 4H), 2.15 (s, 3H), 1.66 (quint, J=7.4 Hz, 2H).

2-(Methyl(3-(6-nitro-3,4-dihydroquinolin-1(2H)-yl)propyl)amino)ethanol 1-(3-((2-Hydroxyethyl)(methyl)amino)propyl)-6-nitro-3,4-dihydroquinolin-2(1H)-one (200 mg, 0.651 mmol) was stirred in borane-tetrahydrofuran complex, 1M sol'n in THF (6.507 mL, 6.51 mmol) until the material dissolved. The resulting solution was then heated at 60° C. overnight. The reaction mixture was then cooled in an ice bath and quenched with methanol (slowly). The solution was then concentrated, redissolved in methanol (5 mL) and stirred with 1M HCl (5 mL) at reflux for 1 h. The mixture was then basified with 1M NaOH and extracted with dichloromethane (3×). The combined organics were dried, filtered and concentrated, then chromatographed on silica gel eluting with ethyl acetate, followed by 5% (2M NH3/methanol) in dichloromethane. $^1$H NMR (DMSO-$d_6$) δ 7.88 (dd, J=9.3, 2.7 Hz, 1H), 7.77 (d, J=2.7 Hz, 1H), 6.72 (d, J=9.3 Hz, 1H), 4.40 (t, J=5.4 Hz, 1H), 3.51-3.32 (m, 6H), 2.74 (t, J=6 Hz, 2H), 2.41-2.33 (m, 4H), 1.89-1.81 (m, 2H), 1.72-1.64 (m, 2H).

2-((3-(6-Amino-3,4-dihydroquinolin-1(2H)-yl)propyl)(methyl)amino)ethanol

To a stirred solution of 2-(methyl(3-(6-nitro-3,4-dihydroquinolin-1(2H)-yl)propyl)amino)ethanol (76 mg, 0.259 mmol) in ethanol (2 mL) and tetrahydrofuran (2.0 mL) was added palladium, 10 wt % on activated carbon (27.6 mg, 0.026 mmol). The reaction mixture was stirred under an atmosphere of hydrogen (balloon pressure) for 2 h. The reaction mixture was then filtered through a pad of celite (washed with methanol) and concentrated to give a dark oil. The crude product was used directly in the subsequent reaction.

N-(1-(3-((2-Hydroxyethyl)(methyl)amino)propyl)-1,2,3,4-tetrahydroquinolin-6-yl)thiophene-2-carboximidamide (69)

To a stirred solution of 2-((3-(6-amino-3,4-dihydroquinolin-1(2H)-yl)propyl)(methyl)amino)ethanol (67 mg, 0.254 mmol) in ethanol (4 ml) under argon was added methyl thiophene-2-carbimidothioate hydroiodide (145 mg, 0.509 mmol). The resulting suspension was stirred overnight at room temperature. The reaction mixture was then diluted with water and aqeuous sodium carbonate (sat.) then extracted with dichloromethane (3×). The combined organics were dried, filtered and concentrated, then chromatographed on silica gel eluting with ethyl acetate, followed by 5-10% (2M NH3 in methanol) in a 1:1 mixture of ethyl acetate and dichloromethane. $^1$H NMR (DMSO-$d_6$) δ 7.67 (d, J=3.3 Hz, 1H), 7.55 (d, J=5.1 Hz, 7.07 (t, J=4.4 Hz, 1H), 6.55 (m, 2H), 6.48 (s, 1H), 6.23 (brs, 2H), 4.35 (t, J=5.4 Hz, 1H), 3.51-3.44 (m, 2H), 3.24-3.17 (m, 4H), 2.66 (t, J=6.45, 2H), 2.41-2.33 (m, 4H), 2.17 (s, 3H), 1.89-1.81 (m, 2H), 1.63 (quint, J=7 Hz, 2H). ESI-MS (m/z, %) 373 (MH$^+$, 100), 258 (31), 187 (49), 127 (42). ESI-HRMS calculated for C20H29N4OS (MH+), calculated: 373.2056, observed: 373.2052.

Examples 70 and 71

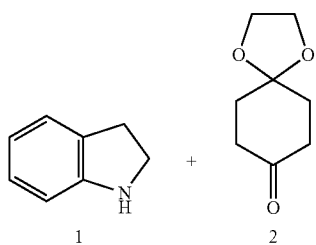

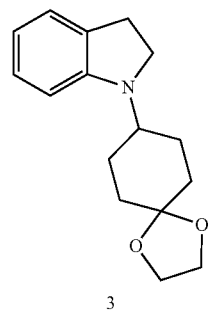

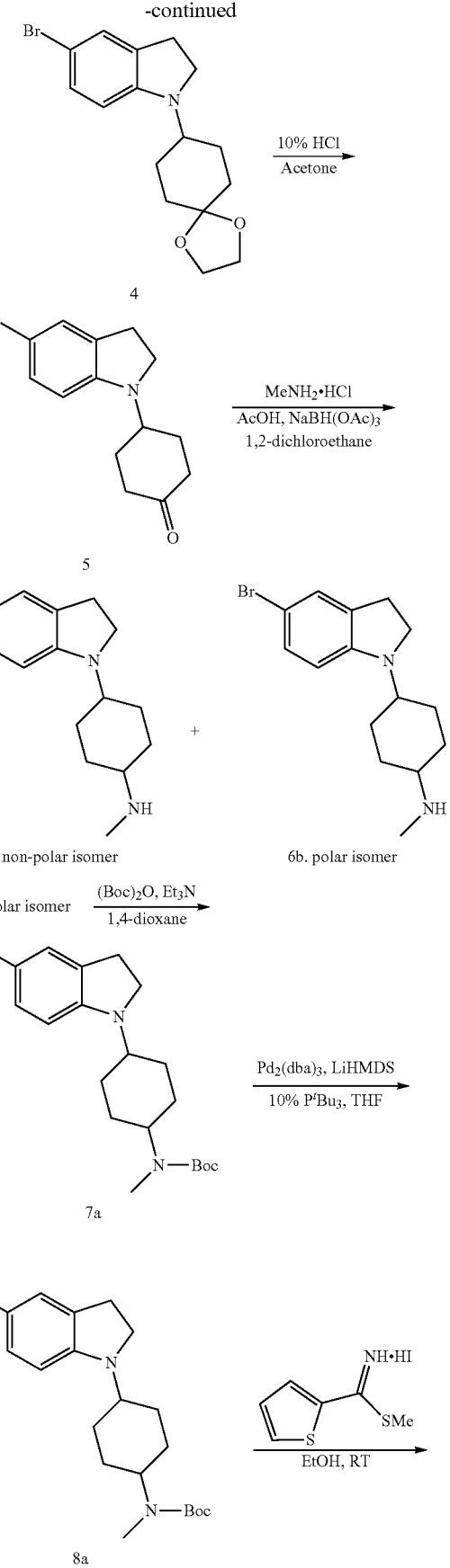

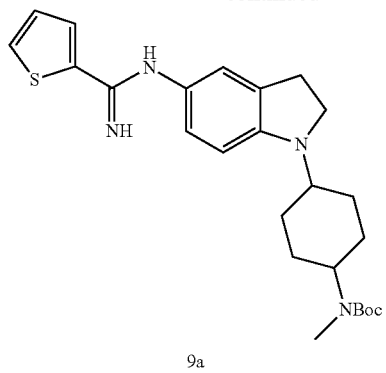

9a

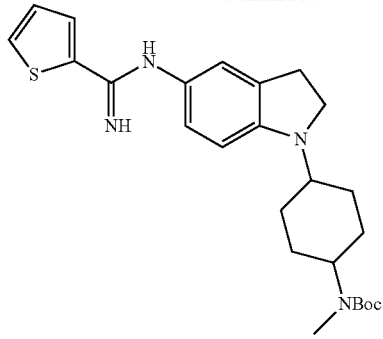

9b

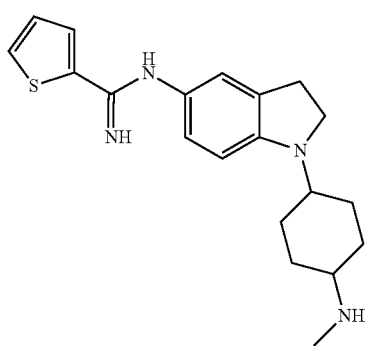

70

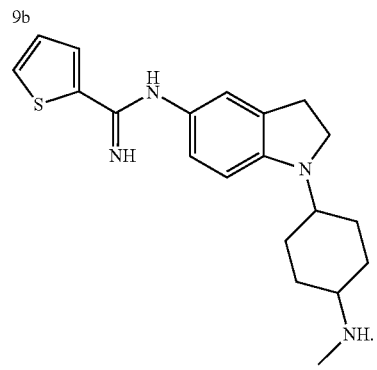

71

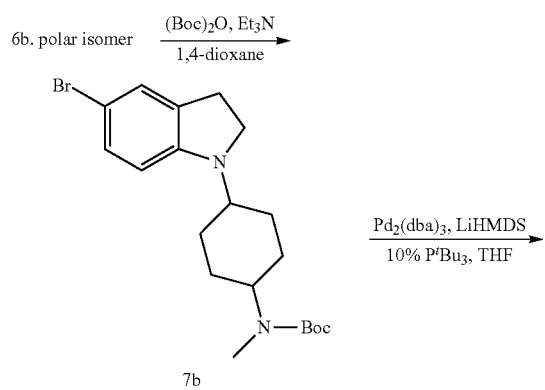

7b

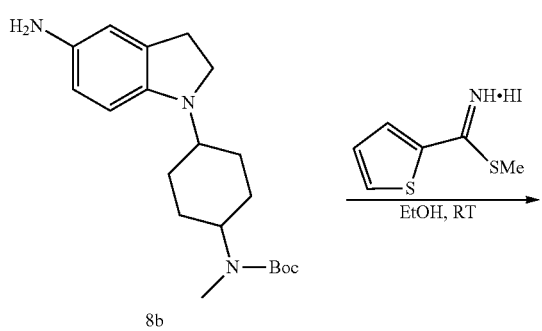

8b 1-(1,4-Dioxaspiro[4.5]decan-8-yl)indoline (3)

A solution of compound 1 (2.0 g, 16.78 mmol) and compound 2 (3.15 g, 20.139 mmol) in dry methanol (20 mL) was treated with acetic acid (2.4 mL, 42.00 mmol) followed by NaCNBH$_3$ (1.26 g, 20.14 mmol) at 0° C. The resulting mixture was brought to room temperature and stirred for 3 h. The reaction was basified with 1 N NaOH solution (50 mL) and product was extracted into ethyl acetate (2×50 mL). The combined ethyl acetate layer was washed with brine (25 mL) and dried (Na$_2$SO$_4$). The solvent was evaporated and the crude product was purified by column chromatography (ethyl acetate:hexanes, 1:4) to obtain compound 3 (3.52 g, 81%) as a solid. $^1$H NMR (CDCl$_3$) δ 7.06-7.02 (m, 2H), 6.59 (t, J=14.7 Hz, 1H), 6.42 (d, J=8.1 Hz, 1H), 3.46 (s, 4H), 3.46-3.35 (m, 3H), 2.93 (t, J=16.5 Hz, 2H), 1.87-1.60 (m, 8H). MS-ESI (m/z, %): 262 (8), 260 (MH$^+$, 100), 120 (28).

5-Bromo-1-(1,4-dioxaspiro[4.5]decan-8-yl)indoline (4)

A solution of compound 3 (3.45 g, 13.30 mmol) in dry DMF (30 mL) was treated with N-bromosuccinimide (2.36 g, 13.30 mmol) in DMF (20 mL) at 0° C. over a period of 30 min. The reaction was stirred at same temperature for 3.5 h. The reaction was diluted with water (200 mL) and product was extracted into ethyl acetate (3×25 mL). The combined ethyl acetate layer was washed with water (2×50 mL), brine (25 mL) and dried (Na$_2$SO$_4$). The solvent was evaporated and the crude product was purified by column chromatography on silica gel (ethyl acetate:hexanes, 1:4) to obtain compound 4 (4.05 g, 90%) as a syrup. $^1$H NMR (CDCl$_3$) δ 7.12-7.10 (m, 2H), 6.25 (d, J=9.0 Hz, 1H), 3.95 (s, 4H), 3.38 (t, J=16.8 Hz, 3H), 2.91 (t, J=16.8 Hz, 2H), 1.86-1.57 (m, 8H). MS-ESI (m/z, %): 340 (98), 338 (M$^+$, 100), 198 (18).

4-(5-Bromoindolin-1-yl)cyclohexanone (5)

A solution of compound 4 (4.0 g, 11.83 mmol) in acetone (50 mL) was treated with 10% HCl solution (50 mL) and the resulting mixture was stirred for over night (16 h). Acetone was evaporated, crude was basified with 2 N NaOH solution and product was extracted into $CH_2Cl_2$ (3×25 mL). The combined $CH_2Cl_2$ layer was washed with brine (20 mL) and dried ($Na_2SO_4$). The solvent was evaporated and the crude product was purified by column chromatography on silica gel (ethyl acetate:hexanes, 1:4) to obtain compound 5 (2.9 g, 83%) as a solid. $^1H$ NMR ($CDCl_3$) δ 7.15 (d, J=6.6 Hz, 2H), 6.32 (d, J=8.7 Hz, 1H), 3.81 (tt, J=7.2, 23.4 Hz, 1H), 3.37 (t, J=16.8 Hz, 2H), 2.95 (t, J=16.5 Hz, 2H), 2.51-2.41 (m, 4H), 2.18-2.11 (m, 2H), 1.92-1.78 (m, 2H). MS-ESI (m/z, %): 296 (96), 294 ($M^+$, 100), 200 (30).

4-(5-Bromoindolin-1-yl)-N-methylcyclohexanamine (6a and b)

A solution of compound 5 (0.5 g, 1.70 mmol), methylamine hydrochloride (0.11 g, 1.70 mmol) in dry 1,2-dichloroethane (10 mL) was treated with acetic acid (0.097 mL, 1.70 mmol) followed by sodium triacetoxyborohydride (0.54 g, 2.55 mmol) at 0° C. The resulting mixture was brought to room temperature and stirred for 3 h. The reaction was basified with 1 N NaOH solution (50 mL) and product was extracted into ethyl acetate (2×50 mL). The combined ethyl acetate layer was washed with brine (25 mL) and dried ($Na_2SO_4$). The solvent was evaporated and the crude product was purified by column chromatography on silica gel (2 M $NH_3$ in MeOH:$CH_2Cl_2$, 2:98) to obtain compounds 6a (0.35 g, 94%) and 6b (0.43 g, 92%) as partially separable mixture of diastereomers. Compound 6a (non-polar isomer, higher rf): $^1H$ NMR (DMSO-d6) δ 7.09-7.04 (m, 2H), 6.35 (d, J=8.1 Hz, 1H), 3.36-3.26 (m, 2H), 2.85 (t, J=16.8 Hz, 2H), 2.59 (t, 1H), 2.23 (s, 3H), 1.80-1.63 (m, 5H), 1.51-1.33 (m, 5H). MS-ESI (m/z, %): 311 ($MH^+$, 94), 309 ($M^+$, 100), 112 (8). Compound 6b (polar-isomer, lower rf): $^1H$ NMR (DMSO-d6) δ 7.09-7.05 (m, 2H), 6.36 (d, J=8.1 Hz, 1H), 3.34-3.29 (m, 3H), 2.85 (t, J=16.8 Hz, 2H), 2.30-2.16 (m, 5H), 1.93 (d, J=12.0 Hz, 2H), 1.67 (d, J=11.1 Hz, 2H), 1.45-1.32 (m, 2H), 1.32-1.02 (m, 2H). MS-ESI (m/z, %): 311 (13), 309 ($M^+$, 8), 280 (93), 278 (100).

tert-Butyl 4-(5-bromoindolin-1-yl)cyclohexyl(methyl)carbamate (7a, non-polar isomer)

A solution of compound 6a (0.28 g, 0.905 mmol) in dry 1,4-dioxane (5 mL) was treated with triethylamine (0.25 mL, 1.811 mmol) followed by di-tert-butyl dicarbonate (0.20 g, 0.951 mmol) at room temperature and stirred for overnight. The reaction was diluted with 1 N NaOH solution (20 mL) and product was extracted into $CH_2Cl_2$ (2×20 mL). The combined $CH_2Cl_2$ layer was washed with brine (20 mL) and dried ($Na_2SO_4$). The solvent was evaporated and the crude product was purified by column chromatography on silica gel (2 M $NH_3$ in methanol:$CH_2Cl_2$, 2.5:97.5) to obtain compound 7a (0.35 g, 94%) as a syrup. $^1H$ NMR ($CDCl_3$) δ 7.14-7.10 (m, 2H), 6.32 (d, J=8.1 Hz, 1H), 4.02-3.98 (m, 1H), 3.70 (s, 2H), 3.56 (t, J=16.2 Hz, 2H), 3.31 (t, J=6.6 Hz, 1H) 2.94 (t, J=16.2 Hz, 2H), 2.79-2.74 (m, 3H), 2.13 (d, J=13.2 Hz, 2H), 1.81-1.67 (m, 4H), 1.46 (s, 9H). MS-ESI (m/z, %): 411 (61), 409 ($M^+$, 58), 331 (100), 275 (37).

tert-Butyl 4-(5-bromoindolin-1-yl)cyclohexyl(methyl)carbamate (7b, polar-isomer)

A solution of compound 6b (0.355 g, 1.148 mmol) in dry 1,4-dioxane (5 mL) was treated with triethylamine (0.32 mL, 2.296 mmol) followed by di-tert-butyl dicarbonate (0.26 g, 1.205 mmol) at room temperature and stirred for overnight. The reaction was diluted with 1 N NaOH solution (20 mL) and product was extracted into $CH_2Cl_2$ (2×20 mL). The combined $CH_2Cl_2$ layer was washed with brine (20 mL) and dried ($Na_2SO_4$). The solvent was evaporated and the crude product was purified by column chromatography on silica gel (2 M $NH_3$ in MeOH:$CH_2Cl_2$, 2.5:97.5) to obtain compound 7b (0.43 g, 92%) as a syrup. $^1H$ NMR ($CDCl_3$) δ 7.12 (brs, 2H), 6.27 (d, J=7.8 Hz, 1H), 3.96-3.92 (m, 1H), 3.70 (s, 2H), 3.37 (t, J=16.8 Hz, 2H), 3.32-3.23 (m, 1H), 2.93 (t, J=16.8 Hz, 2H), 2.80-2.74 (m, 4H), 1.91-1.73 (m, 5H), 1.52 (s, 9H). MS-ESI (m/z, %): 411 ($MH^+$, 14), 409 ($M^+$, 14), 331 (100), 275 (37), 156 (85).

tert-Butyl 4-(5-aminoindolin-1-yl)cyclohexyl(methyl)carbamate (8a, non-polar isomer)

A solution of $Pd_2(dba)_3$ (0.040 g, 0.04397 mmol) in dry THF (5 mL) was treated with $P^tBu_3$ (10% in hexanes, 0.534 mL, 0.1759 mmol). The mixture was then treated with compound 7a (0.36 g, 0.8794 mmol) in dry THF (15 mL) and LiHMDS (1.76 mL, 1.759 mmol) at room temperature. The solution was stirred at 100° C. for 3 hours. At room temperature, the solution was quenched with 1M TBAF in THF solution (2 mL) and was stirred for 20 minutes. The reaction was the diluted with 3N NaOH solution (50 mL) and was extracted with ethyl acetate (150 mL). The organic layer was dried ($Na_2SO_4$) and was concentrated. The crude product was subjected to flash chromatography on silica gel using 2.5% 2M $NH_3$ MeOH/$CH_2Cl_2$, which resulted in a dark brown foam, compound 8a (0.283 g, 93%).

tert-Butyl 4-(5-aminoindolin-1-yl)cyclohexyl(methyl)carbamate (8b, polar-isomer)

A solution of $Pd_2(dba)_3$ (0.047 g, 0.0513 mmol) in dry THF (5 mL) was treated with $P^tBu_3$ (10% in hexanes, 0.622 mL, 0.2052 mmol). The mixture was then treated with compound 7b (0.42 g, 1.026 mmol) in dry THF (15 mL) and LiHMDS (2.05 mL, 2.052 mmol) at room temperature. The solution was stirred at 100° C. for 3 hours. At room temperature, the solution was quenched with 1M TBAF in THF solution (2 mL) and was stirred for 20 minutes. The reaction was the diluted with 3N NaOH solution (50 mL) and was extracted with ethyl acetate (150 mL). The organic layer was dried ($Na_2SO_4$) and was concentrated. The crude product was subjected to flash chromatography on silica gel using 2.5% 2M $NH_3$ MeOH/$CH_2Cl_2$, which resulted in a dark brown foam, compound 8b (0.3495 g, 98%).

tert-Butylmethyl(4-(5-(thiophene-2-carboximidamido)indolin-1-yl)cyclohexyl)carbamate (9a, non-polar isomer)

A solution of compound 8a (0.283 g, 0.8192 mmol) in dry ethanol (20 mL) was treated with methyl thiophene-2-carbimidothioate hydroiodide (1.6345 g, 5.7344 mmol) at room temperature and was stirred for 3 hours. The mixture was diluted with saturated sodium bicarbonate solution (50 mL) and was extracted with $CH_2Cl_2$ (100 mL). The organic layer was washed with brine (20 mL) and dried ($Na_2SO_4$). The concentrated crude product was subject to flash chromatography on silica gel using 2.5% methanol/$CH_2Cl_2$, which resulted in a brown foam, compound 9a (0.2507 g, 67%).

$^1H$ NMR (DMSO-$d_6$) δ 7.68 (d, J=3.6 Hz, 1H), 7.56 (d, J=5.1 Hz, 1H), 7.07 (dd, J=3.9, 8.7 Hz, 1H), 6.63 (brs, 1H), 6.51 (d, J=7.5 Hz, 1H), 6.42 (d, J=8.4 Hz, 1H), 6.28 (brs, 2H), 3.88-3.81 (m, 1H), 3.45 (t, J=15.9 Hz, 2H), 3.26-3.24 (m, 1H), 2.84 (t, J=15.6 Hz, 2H), 2.72 (s, 3H), 2.10-2.06 (m, 2H), 1.81-1.74 (m, 2H), 1.66-1.57 (m, 2H), 1.51-1.46 (m, 2H), 1.40 (s, 9H). MS-ESI (m/z, %): 455 (MH$^+$, 100).

tert-Butylmethyl(4-(5-(thiophene-2-carboximidamido)indolin-1-yl)cyclohexyl)carbamate (9b, polar-isomer)

A solution of compound 8b (0.3316 g, 0.9598 mmol) in dry ethanol (20 mL) was treated with methyl thiophene-2-carbimidothioate hydroiodide (1.642 g, 5.760 mmol) at room temperature and was stirred for 3 hours. The mixture was diluted with saturated sodium bicarbonate solution (50 mL) and was extracted with $CH_2Cl_2$ (100 mL). The organic layer was washed with brine (20 mL) and dried ($Na_2SO_4$). The concentrated crude product was subject to flash chromatography on silica gel using 2.5% MeOH/$CH_2Cl_2$, which resulted in a brown foam, compound 9b (0.3768 g, 86%).

$^1$H NMR (DMSO-$d_6$) δ 7.68 (d, J=3.0 Hz, 1H), 7.56 (d, J=5.1 Hz, 1H), 7.07 (t, J=9.0 Hz, 1H), 6.62 (brs, 1H), 6.54 (d, J=8.4 Hz, 1H), 6.41 (d, J=8.4 Hz, 1H), 6.30 (brs, 2H), 3.81-3.77 (m, 1H), 3.28-3.25 (m, 2H), 2.83 (t, J=16.2 Hz, 2H), 2.68 (s, 3H), 1.78 (d, J=10.8 Hz, 2H), 1.64-1.62 (m, 4H), 1.50-1.46 (m, 2H), 1.40 (s, 9H). MS-ESI (m/z, %): 455 (MH$^+$, 100).

N-(1-(4-(Methylamino)cyclohexyl)indolin-5-yl)thiophene-2-carboximidamide (70, non-polar isomer)

A solution containing compound 9a (0.2314 g, 0.5090 mmol) in methanol (12 mL) was treated with 1N HCl solution (12 mL) and the mixture was refluxed for 30 minutes. The reaction was brought to room temperature, concentrated and dried under reduced pressure. The product, compound 70, as a dihydrochloride salt was made into a freebase and was subject to flash chromatography on silica gel using 10% methanol/$CH_2Cl_2$ (0.1451 g, 81%).

$^1$H NMR (DMSO-$d_6$) δ 7.67 (d, J=3.0 Hz, 1H), 7.54 (d, J=5.1 Hz, 1H), 7.06 (t, J=8.7 Hz, 1H), 6.60 (brs, 1H), 6.51 (d, J=8.1 Hz, 1H), 6.38 (d, J=8.1, 1H), 6.21 (brs, 2H), 3.32-3.25 (m, 4H), 2.82 (t, J=16.8 Hz, 2H), 2.62 (brs, 1H), 2.25 (s, 3H), 1.81-1.66 (m, 4H), 1.53-1.39 (m, 4H). MS-ESI (m/z, %): 355 (MH$^+$, 82), 324 (100), 244 (17), 133 (21); ESI-HRMS calculated for $C_{20}H_{27}N_4S$ (MH$^+$): Calculated: 355.1949, Observed: 355.1950.

N-(1-(4-(Methylamino)cyclohexyl)indolin-5-yl)thiophene-2-carboximidamide (71, polar-isomer)

A solution containing compound 9b (0.3768 g, 0.8288 mmol) in methanol (12 mL) was treated with 1N HCl solution (12 mL) and the mixture was refluxed for 30 minutes. The reaction was brought to room temperature, concentrated and dried under reduced pressure. The product, compound 71, as a dihydrochloride salt was made into a freebase and was subject to flash chromatography on silica gel using 10% MeOH/$CH_2Cl_2$ (0.1933 g, 66%).

$^1$H NMR (DMSO-$d_6$) δ 7.67 (d, J=3.3 Hz, 1H), 7.54 (d, J=5.1 Hz, 1H), 7.06 (t, J=8.7 Hz, 1H), 6.60 (brs, 1H), 6.52 (d, J=8.1 Hz, 1H), 6.21 (brs, 2H), 3.31-3.24 (m, 4H), 3.16 (s, 1H), 2.82 (t, J=16.5 Hz, 2H), 2.31-2.19 (m, 4H), 1.95 (d, J=11.4 Hz, 2H), 1.73 (d, J=11.4 Hz, 2H), 1.47-1.35 (m, 2H), 1.16-1.04 (m, 2H). MS-ESI (m/z, %): 355 (MH$^+$, 100), 324 (81), 141 (26), 133 (35); ESI-HRMS calculated for $C_{20}H_{27}N_4S$ (MH$^+$): Calculated: 355.1935, Observed: 355.1950.

Example 72

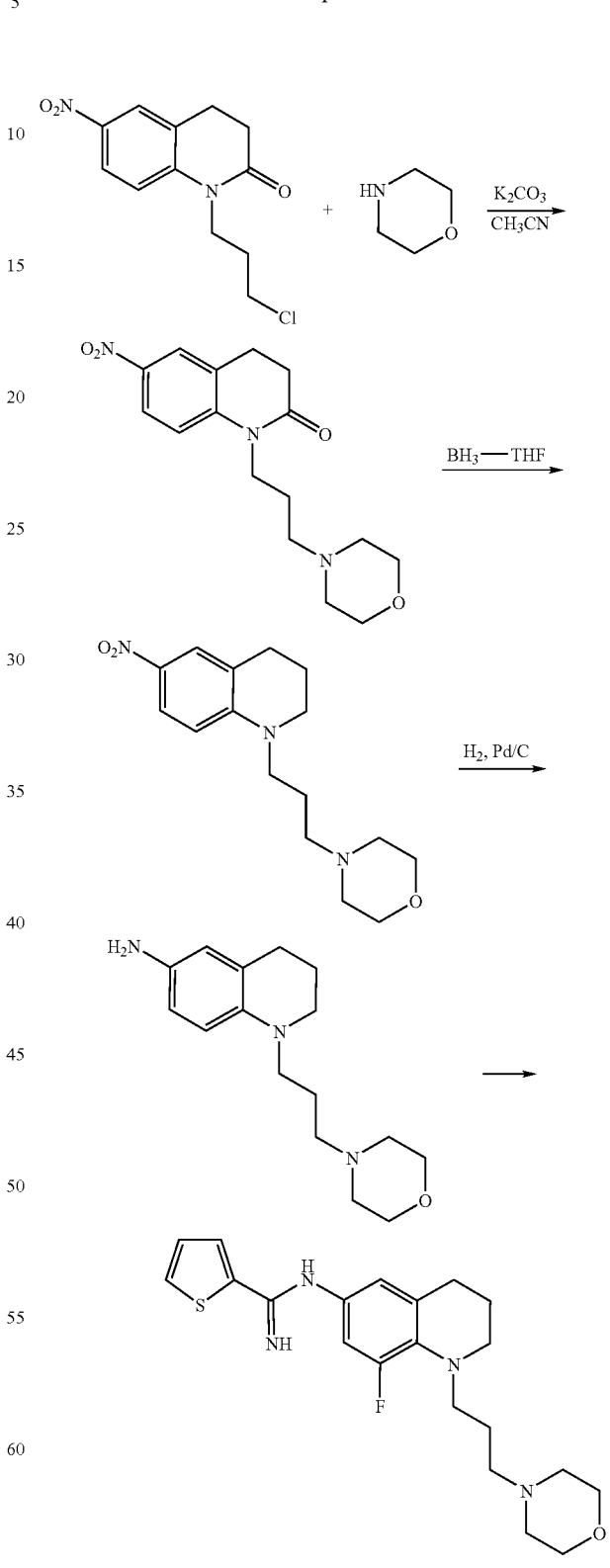

72

1-(3-morpholinopropyl)-6-nitro-3,4-dihydroquinolin-2(1H)-one

To a stirred suspension of 1-(3-chloropropyl)-6-nitro-3,4-dihydroquinolin-2(1H)-one (500 mg, 1.861 mmol) and potassium carbonate (1286 mg, 9.30 mmol) in acetonitrile (10 ml) was added morpholine (0.814 ml, 9.30 mmol) via a syringe. The resulting suspension was then stirred overnight at 75° C. in a sealed tube. The reaction mixture was then cooled to room temperature, diluted with water and extracted with dichloromethane (3×). The combined organics were dried, filtered and concentrated, then chromatographed in ethyl acetate, followed by 5% (2M NH3 in methanol) in dichloromethane, giving the desired 1-(3-morpholinopropyl)-6-nitro-3,4-dihydroquinolin-2(1H)-one (560 mg, 1.754 mmol, 94% yield). $^1$H NMR (DMSO-$d_6$) δ 8.14-8.10 (m, 2H), 7.40 (d, J=9 Hz, 1H), 3.95 (t, J=7.4 Hz, 2H), 3.58-3.54 (m, 4H), 3.03-2.97 (m, 2H), 2.64-2.59 (m, 2H), 2.33-2.28 (m, 6H), 1.74-1.64 (m, 2H).

4-(3-(6-Nitro-3,4-dihydroquinolin-1(2H)-yl)propyl)morpholine 1-(3-Morpholinopropyl)-6-nitro-3,4-dihydroquinolin-2(1H)-one (550 mg, 1.722 mmol) was stirred in borane tetrahydrofuran complex, 1M in THF (17.200 mL, 17.20 mmol) overnight at reflux temperature. The reaction mixture was then cooled to 0° C. and quenched via addition of methanol (10 mL). The solution was then concentrated, and the residue was redissolved in a small amount of methanol and stirred at reflux with 2N HCl for 2 h. The mixture was then neutralized and basified with 3N NaOH and extracted with dichloromethane (3×). The combined organics were dried, filtered and concentrated, then chromatographed in ethyl acetate, followed by 5-10% (2M NH3 in methanol) in dichloromethane, giving the desired 4-(3-(6-nitro-3,4-dihydroquinolin-1(2H)-yl)propyl)morpholine (260 mg, 0.851 mmol, 49.4% yield). $^1$H NMR (DMSO-$d_6$) δ 7.87 (dd, J=9.3, 2.7 Hz, 1H), 7.77 (d, J=2.7 Hz, 1H), 6.72 (d, J=9.3 Hz, 1H), 3.60-3.56 (m, 4H), 3.45-3.39 (m, 4H), 2.74 (t, J=6 Hz, 2H), 2.35-2.26 (m, 6H), 1.88-1.80 (m, 2H), 1.76-1.66 (m, 2H).

1-(3-Morpholinopropyl)-1,2,3,4-tetrahydroquinolin-6-amine

To a stirred solution of 4-(3-(6-nitro-3,4-dihydroquinolin-1(2H)-yl)propyl)morpholine (250 mg, 0.819 mmol) in Ethanol (4 ml) and Tetrahydrofuran (4.00 ml) was added Palladium on activated carbon, 10 wt. % (87 mg, 0.082 mmol). The reaction was then stirred under a hydrogen atmosphere (balloon pressure) for 2 h. When TLC analysis showed that the starting material was consumed, the mixture was filtered through a pad of celite which was then washed with methanol. The filtrate was concentrated, giving the desired 1-(3-morpholinopropyl)-1,2,3,4-tetrahydroquinolin-6-amine (190 mg, 0.690 mmol, 84% yield) as a dark oil.

N-(1-(3-morpholinopropyl)-1,2,3,4-tetrahydroquinolin-6-yl)thiophene-2-carboximidamide To a stirred solution of 1-(3-morpholinopropyl)-1,2,3,4-tetrahydroquinolin-6-amine (190 mg, 0.690 mmol) in ethanol (10 ml) under argon was added methyl thiophene-2-carbimidothioate hydroiodide (393 mg, 1.380 mmol). The resulting suspension was then stirred overnight at room temperature. The mixture was then diluted with water and sodium carbonate and extracted with dichloromethane (3×). The combined organics were dried, filtered and concentrated, then chromatographed in ethyl acetate, followed by 5-10% (2M NH3 in MeOH) in dichloromethane, giving the desired N-(1-(3-morpholinopropyl)-1,2,3,4-tetrahydroquinolin-6-yl)thiophene-2-carboximidamide 72 (132 mg, 0.343 mmol, 49.8% yield). $^1$H NMR (DMSO-$d_6$) δ 7.67 (d, J=3 Hz, 1H), 7.56 (d, J=4.8 Hz, 1H), 7.09-7.06 (m, 1H), 6.56 (brs, 2H), 6.49 (s, 1H), 6.33 (brs, 2H), 3.60-3.56 (m, 4H), 3.26-3.17 (m, 4H), 2.66 (t, J=6.3 Hz, 2H), 2.34-2.28 (m, 6H), 1.89-1.81 (m, 2H), 1.69-1.63 (m, 2H). EI-MS (m/z, %) 384 (100, MH+), 270 (52). HPLC purity: 99%.

Example 73

Isomer 1

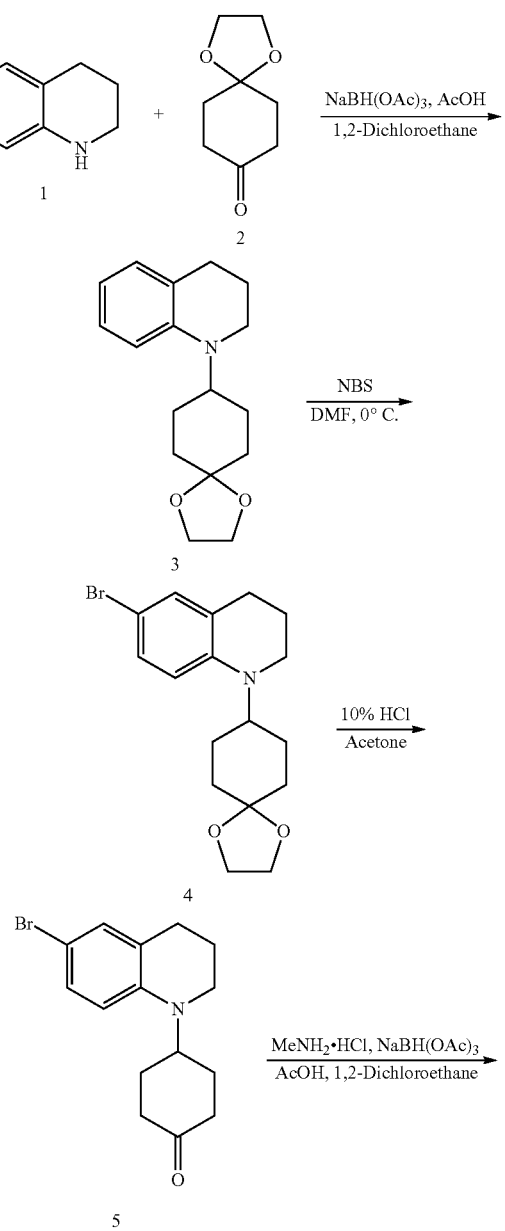

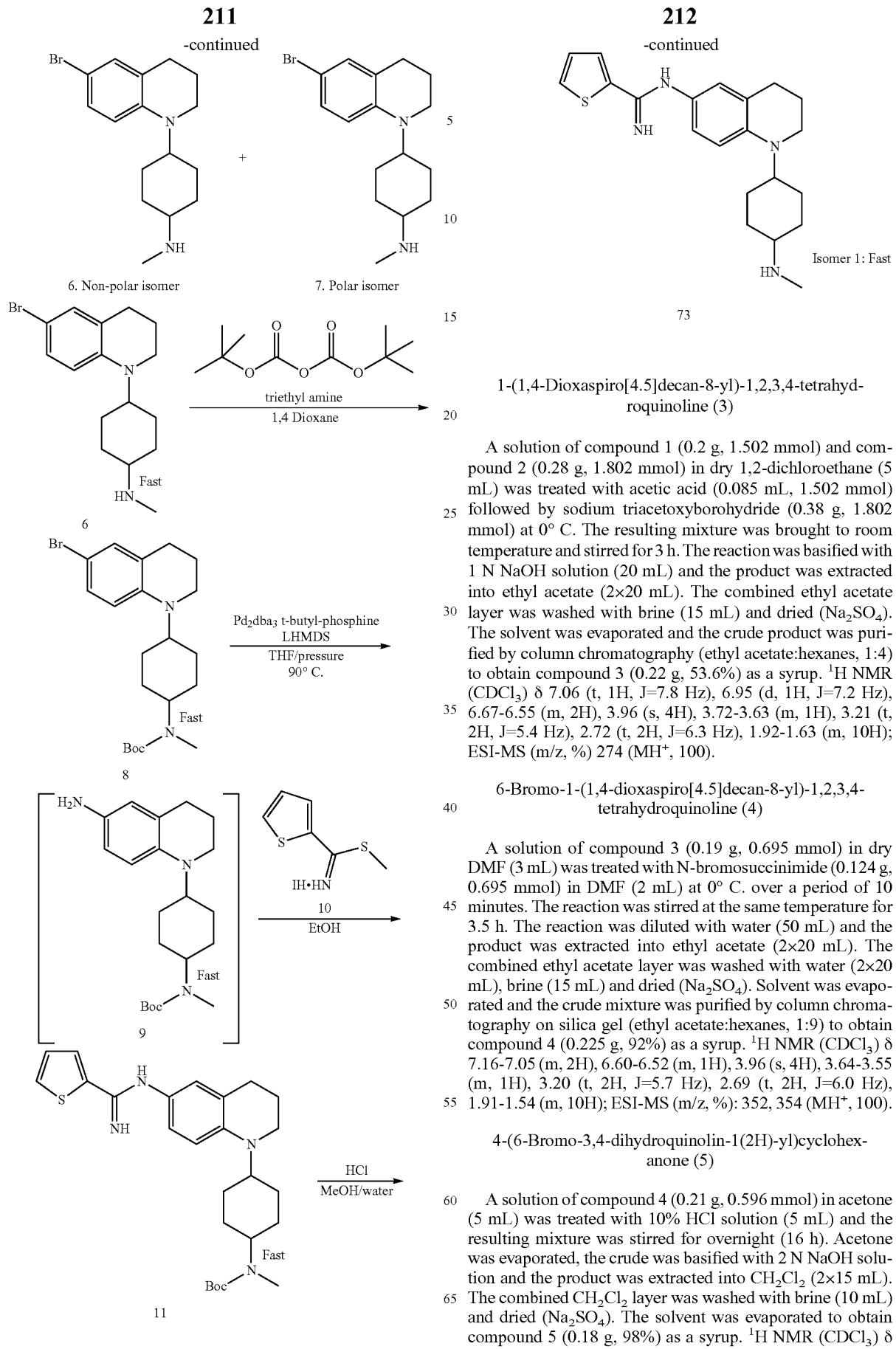

1-(1,4-Dioxaspiro[4.5]decan-8-yl)-1,2,3,4-tetrahydroquinoline (3)

A solution of compound 1 (0.2 g, 1.502 mmol) and compound 2 (0.28 g, 1.802 mmol) in dry 1,2-dichloroethane (5 mL) was treated with acetic acid (0.085 mL, 1.502 mmol) followed by sodium triacetoxyborohydride (0.38 g, 1.802 mmol) at 0° C. The resulting mixture was brought to room temperature and stirred for 3 h. The reaction was basified with 1 N NaOH solution (20 mL) and the product was extracted into ethyl acetate (2×20 mL). The combined ethyl acetate layer was washed with brine (15 mL) and dried ($Na_2SO_4$). The solvent was evaporated and the crude product was purified by column chromatography (ethyl acetate:hexanes, 1:4) to obtain compound 3 (0.22 g, 53.6%) as a syrup. $^1$H NMR ($CDCl_3$) δ 7.06 (t, 1H, J=7.8 Hz), 6.95 (d, 1H, J=7.2 Hz), 6.67-6.55 (m, 2H), 3.96 (s, 4H), 3.72-3.63 (m, 1H), 3.21 (t, 2H, J=5.4 Hz), 2.72 (t, 2H, J=6.3 Hz), 1.92-1.63 (m, 10H); ESI-MS (m/z, %) 274 (MH$^+$, 100).

6-Bromo-1-(1,4-dioxaspiro[4.5]decan-8-yl)-1,2,3,4-tetrahydroquinoline (4)

A solution of compound 3 (0.19 g, 0.695 mmol) in dry DMF (3 mL) was treated with N-bromosuccinimide (0.124 g, 0.695 mmol) in DMF (2 mL) at 0° C. over a period of 10 minutes. The reaction was stirred at the same temperature for 3.5 h. The reaction was diluted with water (50 mL) and the product was extracted into ethyl acetate (2×20 mL). The combined ethyl acetate layer was washed with water (2×20 mL), brine (15 mL) and dried ($Na_2SO_4$). Solvent was evaporated and the crude mixture was purified by column chromatography on silica gel (ethyl acetate:hexanes, 1:9) to obtain compound 4 (0.225 g, 92%) as a syrup. $^1$H NMR ($CDCl_3$) δ 7.16-7.05 (m, 2H), 6.60-6.52 (m, 1H), 3.96 (s, 4H), 3.64-3.55 (m, 1H), 3.20 (t, 2H, J=5.7 Hz), 2.69 (t, 2H, J=6.0 Hz), 1.91-1.54 (m, 10H); ESI-MS (m/z, %): 352, 354 (MH$^+$, 100).

4-(6-Bromo-3,4-dihydroquinolin-1(2H)-yl)cyclohexanone (5)

A solution of compound 4 (0.21 g, 0.596 mmol) in acetone (5 mL) was treated with 10% HCl solution (5 mL) and the resulting mixture was stirred for overnight (16 h). Acetone was evaporated, the crude was basified with 2 N NaOH solution and the product was extracted into $CH_2Cl_2$ (2×15 mL). The combined $CH_2Cl_2$ layer was washed with brine (10 mL) and dried ($Na_2SO_4$). The solvent was evaporated to obtain compound 5 (0.18 g, 98%) as a syrup. $^1$H NMR ($CDCl_3$) δ

7.16 (dd, 1H, J=2.4, 4.3 Hz), 7.08 (s, 1H), 6.60 (d, 1H, J=9.0 Hz), 4.11-4.01 (m, 1H), 3.17 (t, 2H, J=5.7 Hz), 2.71 (t, 2H, J=6.3 Hz), 2.52-2.48 (m, 4H), 2.14-1.85 (m, 6H); ESI-MS (m/z, %): 308, 310 (MH$^+$, 100).

4-(6-Bromo-3,4-dihydroquinolin-1(2H)-yl)-N-methylcyclohexanamine (6 and 7)

A solution of compound 5 (0.16 g, 0.519 mmol) and methylamine hydrochloride (0.035 g, 0.519 mmol) in dry 1,2-dichloroethane (3 mL) was treated with acetic acid (0.03 mL, 0.519 mmol) followed by sodium triacetoxyborohydride (0.165 g, 0.779 mmol) at 0° C. The resulting mixture was brought to room temperature and stirred overnight. The reaction was basified with 1 N NaOH solution (25 mL) and the product was extracted into CH$_2$Cl$_2$ (2×20 mL). The combined CH$_2$Cl$_2$ layer was washed with brine (15 mL) and dried (Na$_2$SO$_4$). The solvent was evaporated and the crude product was purified by column chromatography (ethyl acetate:hexanes, 1:4) to obtain compounds 6 and 7 (0.14 g, 83%) as partially separable mixture of diastereomers. Compound 6: Syrup, $^1$H NMR (DMSO-d$_6$) δ 7.04 (dd, 1H, J=2.4, 8.8 Hz), 6.99 (d, 1H, J=2.4 Hz), 6.58 (d, 1H, J=9.0 Hz), 3.54-3.48 (m, 1H), 3.14 (t, 2H, J=5.7 Hz), 2.67-2.60 (m, 3H), 2.26 (s, 3H), 1.88-1.71 (m, 7H), 1.57-1.47 (m, 2H), 1.38-1.32 (m, 2H); ESI-MS (m/z, %): 323, 325 (MH$^+$, 100). Compound 7: Syrup, $^1$H NMR (DMSO-d$_6$) δ 7.05 (dd, 1H, J=2.7, 8.8 Hz), 6.99 (d, 1H, J=2.4 Hz), 6.57 (d, 1H, J=9.0 Hz), 3.54-3.47 (m, 1H), 3.12 (t, 2H, J=5.7 Hz), 2.62 (t, 2H, J=6.3 Hz), 2.27 (s, 3H), 2.24-2.18 (m, 1H), 1.93 (d, 2H, J=12.0 Hz), 1.79-1.45 (m, 7H), 1.23-1.06 (m, 2H); ESI-MS (m/z, %): 325, 323 (MH$^+$, 30), 292, 294 (100).

tert-Butyl 4-(6-bromo-3,4-dihydroquinolin-1(2H) yl)cyclohexyl(methyl) carbamate (8)

A solution of compound 6 (0.408 g, 1.262 mmol) in dioxane (10 mL) was treated with triethylamine (0.532 mL, 3.79 mmol), and Boc$_2$O (0.303 g, 1.388 mmol) to give an orange-yellow suspension and was stirred overnight at room temperature. The reaction mixture was diluted with 1N NaOH (20 mL) and the product was extracted into CH$_2$Cl$_2$ (3×20 mL). The combined organic layers were washed with brine (15 mL), dried (Na$_2$SO$_4$), and concentrated. The residue was subjected to flash chromatography on silica gel: 2.5% 2M NH$_3$ in methanol: 97.5% CH$_2$Cl$_2$, resulting in a solid. (435 mg, 81% yield). $^1$H NMR (DMSO-d$_6$) δ 7.07 (dd, J=8.7, 2.4 Hz, 1H), 7.02 (d, J=2.4 Hz, 1H), 6.54 (d, J=9.0 Hz, 1H), 3.93-3.85 (m, 1H), 3.72-3.66 (m, 1H), 3.32-3.24 (m, 2H), 2.80 (s, 3H), 2.65 (t, J=6.3 Hz, 2H), 1.95-1.73 (m, 6H), 1.67-1.54 (m, 4H), 1.40 (s, 9H).

tert-Butyl methyl(4-(6-(thiophene-2-carboximidamido-)-3,4-dihydroquinolin-1(2H)-yl)cyclohexyl) carbamate (11)

In a microwave vial, a suspension of Pd$_2$dba$_3$ (0.047 g, 0.051 mmol) and tri-t-butylphosphine (10% wt in hexanes, 0.868 ml, 0.203 mmol) in THF (3 mL) was charged with compound 8 (0.430 g, 1.016 mmol) in THF (7 mL) resulting in a black-red suspension. The mixture was then treated with lithium bis(trimethylsilyl)amide (1M in THF, 2.031 ml, 2.031 mmol) resulting in a black-brown suspension. The microwave vial was sealed with a cap and heated to 90° C. for 3 hours. Tetra-butylammonium fluoride (1M in THF, 4 mL) was added and the solution was stirred for half an hour. The reaction mixture was diluted with 1N NaOH (50 mL) and the product was extracted into CH$_2$Cl$_2$ (3×25 mL). The combined organic layers were dried (Na$_2$SO$_4$), and concentrated. The residue was subjected to flash chromatography on silica gel: CH$_2$Cl$_2$ followed by 2.5% 2M NH$_3$ in MeOH: 97.5% CH$_2$Cl$_2$, resulting in a solid (compound 9). A suspension of compound 9 and compound 10 (0.678 g, 2.377 mmol) in ethanol (10 mL) was stirred overnight at room temperature. The reaction was diluted with saturated NaHCO$_3$ solution (50 mL) and the product was extracted into CH$_2$Cl$_2$ (3×25 mL). The combined organic layers were dried (Na$_2$SO$_4$) and concentrated. The residue was subjected to flash chromatography on silica gel: 50% ethyl acetate: 50% hexanes followed by 2.5% methanol: 97.5% CH$_2$Cl$_2$ to give a solid (250 mg, 52.5% yield). $^1$H NMR (DMSO-d$_6$) δ 7.67 (d, J=3.9 Hz, 1H), 7.55 (d, J=5.1 Hz, 1H), 7.07 (dd, J=4.8, 3.9 Hz, 1H), 6.61-6.50 (m, 3H), 6.24 (s, 2H), 3.92-3.89 (m, 1H), 3.67-3.65 (m, 1H), 3.24 (t, J=5.7 Hz, 2H), 2.80 (s, 3H), 2.66 (t, J=6.3 Hz, 2H), 1.99-1.70 (m, 6H), 1.65-1.54 (m, 4H), 1.40 (s, 9H).

N-(1-(4-(methylamino)cyclohexyl)-1,2,3,4-tetrahydroquinolin-6-yl)thiophene-2-carboximidamide (73)

A solution of compound 11 (250 mg, 0.533 mmol) in methanol (10 mL) and 1M HCl (10 mL) was refluxed for 30 minutes and then concentrated. The residue was partitioned between 3N NaOH (50 mL) and CH$_2$Cl$_2$ (25 mL) and the product was extracted into CH$_2$Cl$_2$ (2×25 mL). The combined organic layers were dried (Na$_2$SO$_4$) and concentrated. This residue was subjected to flash chromatography on silica gel: 2% MeOH: 98% CH$_2$Cl$_2$ followed by 2.5% 2M ammonia in methanol; 97.5% CH$_2$Cl$_2$ to give a yellow-brown solid. (156 mg, 79% yield) $^1$H NMR (DMSO-d$_6$) δ 7.66 (d, J=2.7 Hz, 1H), 7.54 (dd, J=0.9, 5.1 Hz, 1H), 7.06 (dd, J=3.6, 4.8 Hz, 1H), 6.63-6.41 (m, 3H), 6.21 (s, 2H), 3.55-3.46 (m, 1H), 3.35-3.30 (m, 1H) 3.13 (t, J=5.7 Hz, 2H), 2.63 (t, J=6.0 Hz, 2H), 2.26 (s, 3H), 2.10-1.75 (m, 6H), 1.60-1.45 (m, 2H), 1.39-1.32 (m, 2H). ESI-MS (m/z, %): 369 (MH$^+$, 96), 338 (48), 258 (100), 185 (20), 148 (24), 140 (20); ESI-HRMS calculated for C$_{21}$H$_{29}$N$_4$S (MH$^+$): 369.2107, Observed: 369.2112; HPLC purity: 95.3%.

Example 74

Isomer 2

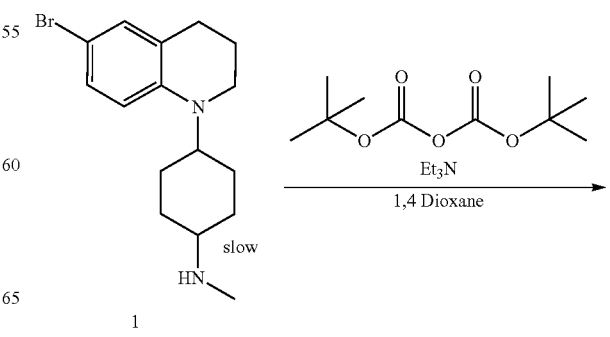

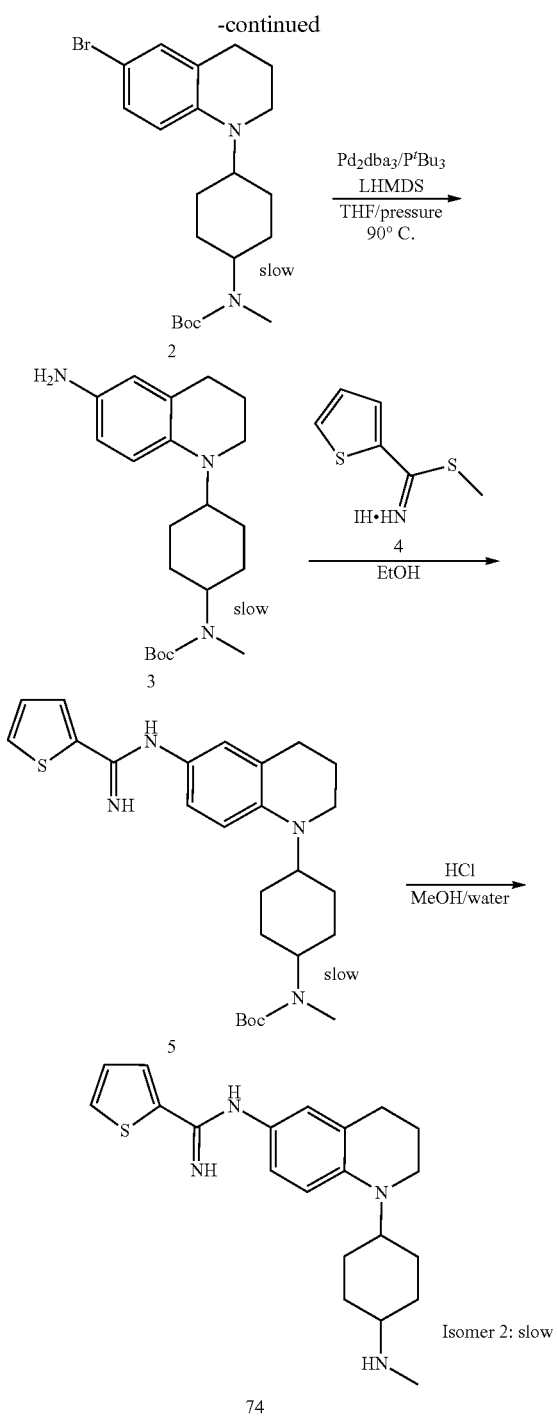

4-(6-Bromo-3,4-dihydroquinolin-1(2H)-yl)-N-methylcyclohexanamine (1)

Refer to Example 73 (compound 7).

tert-Butyl 4-(6-bromo-3,4-dihydroquinolin-1(2H)-yl)cyclohexyl(methyl) carbamate (2)

A solution of compound 1 (0.38 g, 1.175 mmol) in dioxane (10 mL) was treated with triethylamine (0.495 mL, 3.53 mmol), and Boc$_2$O (0.282 g, 1.293 mmol) to give an orange-yellow suspension and was stirred overnight at room temperature. The reaction mixture was diluted with 1N NaOH (20 mL) and the product was extracted into CH$_2$Cl$_2$ (3×20 mL). The combined organic layers were washed with brine (15 mL), dried (Na$_2$SO$_4$), and concentrated. The residue was subjected to flash chromatography on silica gel: 2.5% 2M NH$_3$ in methanol: 97.5% CH$_2$Cl$_2$, resulting in a solid. (456 mg, 92% yield). $^1$H NMR (DMSO-d$_6$) δ 7.07 (dd, J=2.7, 9.0 Hz, 1H), 7.00 (d, J=2.7 Hz, 1H), 6.62 (d, J=9.0 Hz, 1H), 3.62-3.53 (m, 2H), 3.134 (t, J=5.7 Hz, 2H), 2.69 (s, 3H), 2.63 (t, J=6.3 Hz, 2H), 1.80-1.53 (m, 10H), 1.40 (s, 9H).

tert-Butyl methyl(4-(6-(thiophene-2-carboximidamido-)-3,4-dihydroquinolin-1(2H)-yl)cyclohexyl) carbamate (5)

In a microwave vial, a suspension of Pd$_2$ dba$_3$ (0.049 g, 0.053 mmol) and tri-t-butylphosphine (10% wt in hexanes, 0.91 mL, 0.203 mmol) in THF (3 mL) was charged with compound 2 (0.430 g, 1.016 mmol) in THF (7 mL) resulting in a black-red suspension. The mixture was then treated with lithium bis(trimethylsilyl)amide (1M in THF, 2.031 ml, 2.031 mmol) resulting in a black-brown suspension. The microwave vial was sealed with a cap and heated to 90° C. for 3 hours. TBAF (1M in THF, 4 mL) was added and the solution was stirred for half an hour. Then the reaction mixture was diluted with 1N NaOH (50 mL) and the product was extracted into CH$_2$Cl$_2$ (3×25 mL). The combined organic layers were dried (Na$_2$SO$_4$), and concentrated. The residue was subjected to flash chromatography on silica gel:CH$_2$Cl$_2$ followed by 2.5% 2M NH$_3$ in methanol: 97.5% CH$_2$Cl$_2$, resulting in a solid (compound 3). A suspension of compound 3 and compound 4 (0.606 g, 2.125 mmol) in ethanol (10 mL) was stirred overnight at room temperature. The reaction was diluted with saturated NaHCO$_3$ solution (50 mL) and the product was extracted into CH$_2$Cl$_2$ (3×25 mL). The combined organic layers were dried (Na$_2$SO$_4$) and concentrated. The residue was subjected to flash chromatography on silica gel: 50% ethyl acetate: 50% hexanes followed by 2.5% methanol: 97.5% CH$_2$Cl$_2$ to give a solid (250 mg, 50.0% yield). $^1$H NMR (DMSO-d$_6$) δ 7.67 (d, J=4.2 Hz, 1H), 7.55 (dd, J=0.6, 4.8 Hz, 1H), 7.07 (dd, J=3.9, 5.1 Hz, 1H), 4.03-4.01 (m, 1H), 3.60-3.57 (m, 1H), 3.12 (t, J=5.4 Hz, 2H), 2.70 (s, 3H), 2.64 (t, J=6.3 Hz, 2H), 1.84-1.60 (m, 10H), 1.40 (s, 9H).

N-(1-(4-(Methylamino)cyclohexyl)-1,2,3,4-tetrahydroquinolin-6-yl)thiophene-2-carboximidamide (74)

A solution of compound 5 (250 mg, 0.533 mmol) in MeOH (10 mL) and 1M HCl (10 mL) was refluxed for half an hour and then concentrated. The residue was partitioned between 3N NaOH (50 mL) and CH$_2$Cl$_2$ (25 mL) and the product was extracted into CH$_2$Cl$_2$ (2×25 mL). The combined organic layers were dried (Na$_2$SO$_4$), and concentrated. This residue was subjected to flash chromatography on silica gel: 2% methanol: 98% CH$_2$Cl$_2$ followed by 2.5% 2M ammonia in methanol; 97.5% CH$_2$Cl$_2$ to give a yellow-brown solid. (108 mg, 55% yield) $^1$H NMR (DMSO-d$_6$) δ 7.67 (d, J=3.0 Hz, 1H), 7.54 (d, J=5.1 Hz, 1H), 7.07 (dd, J=3.9, 5.1 Hz), 6.62-6.47 (m, 3H), 6.21 (s, 2H), 3.57-3.50 (m, 1H), 3.11 (t, J=5.4 Hz, 2H), 2.63 (t, J=6.3 Hz, 2H), 2.28 (s, 3H), 2.24-2.20 (m, 1H), 1.98-1.92 (m, 2H), 1.82-1.77 (m, 2H), 1.70-1.65 (m, 2H), 1.59-1.47 (m, 2H), 1.24-1.11 (m, 2H). ESI-MS (m/z, %): 369 (MH$^+$, 82), 338 (100), 258 (21), 185 (50), 148 (64), 140

(46); ESI-HRMS calculated for $C_{21}H_{29}N_4S$ (MH+): 369.2107, Observed: 369.2104; HPLC purity: 95.3%.

Example 75

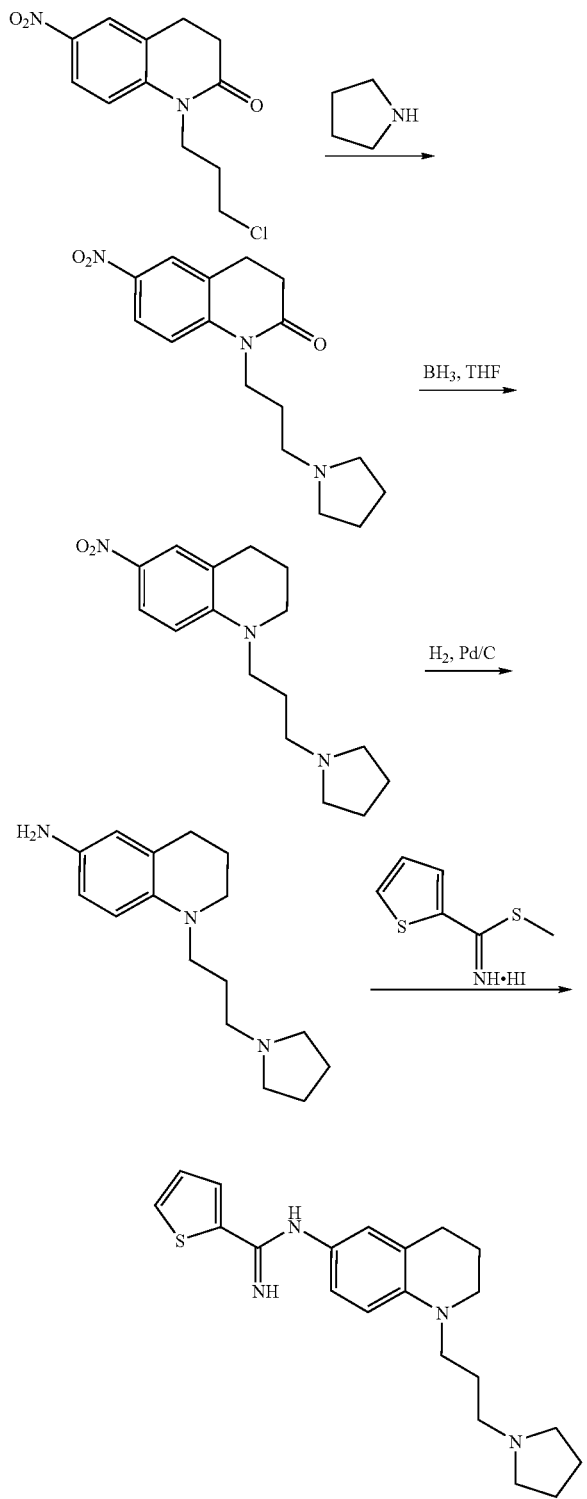

75

6-Nitro-1-(3-(pyrrolidin-1-yl)propyl)-3,4-dihydroquinolin-2(1H)-one

To a stirred suspension of 6-nitro-1-(3-(pyrrolidin-1-yl)propyl)-3,4-dihydroquinolin-2(1H)-one (516 mg, 1.701 mmol, 91% yield) and potassium carbonate (1286 mg, 9.30 mmol) in acetonitrile (10 ml) was added pyrrolidine (0.777 ml, 9.30 mmol) via a syringe. The reaction vessel was sealed and heated at 80° C. overnight. The reaction mixture was then cooled to room temperature, diluted with water and extracted with dichloromethane (3×). The combined organics were dried, filtered and concentrated, then chromatographed on silica gel using ethyl acetate, followed by 5% (2M $NH_3$ in MeOH) in dichloromethane as eluent to give the desired 6-nitro-1-(3-(pyrrolidin-1-yl)propyl)-3,4-dihydroquinolin-2 (1H)-one (516 mg, 1.701 mmol, 91% yield). $^1$H NMR (DMSO-$d_6$) δ 8.15-8.10 (m, 2H), 7.39 (d, J=8.7 Hz, 1H), 3.97 (t, J=7.4 Hz, 2H), 3.00 (t, J=7.5 Hz, 1H), 2.64-2.59 (m, 2H), 2.44-2.39 (m, 6H), 1.72-1.65 (m, 6H).

6-Nitro-1-(3-(pyrrolidin-1-yl)propyl)-1,2,3,4-tetrahydroquinoline

A solution of 6-nitro-1-(3-(pyrrolidin-1-yl)propyl)-3,4-dihydroquinolin-2(1H)-one (500 mg, 1.648 mmol) in borane tetrahydrofuran complex, 1 M in THF (16.500 mL, 16.50 mmol) was stirred overnight at 60° C. The reaction mixture was then cooled to 0° C., and quenched with methanol. The resulting solution was concentrated, and the residue was stirred in refluxing methanol and 1N HCl for 1 h. The mixture was then neutralized with 1N sodium hydroxide, then extracted with dichloromethane (3×). The combined organics were dried, filtered and concentrated then chromatographed on silica gel using ethyl acetate, followed by 5-10% (2M $NH_3$ in MeOH) in dichloromethane as eluent to give the desired 6-nitro-1-(3-(pyrrolidin-1-yl)propyl)-1,2,3,4-tetrahydroquinoline (270 mg, 0.933 mmol, 56.6% yield). $^1$H NMR (DMSO-$d_6$) δ 7.87 (dd, J=9.3, 2.7 Hz, 1H), 7.77 (d, J=2.7 Hz, 1H), 6.70 (d, J=9.3 Hz, 1H), 3.46-3.38 (m, 4H), 2.74 (t, J=6 Hz, 2H), 2.43-2.38 (m, 6H), 1.86-1.82 (m, 2H), 1.74-1.67 (m, 6H).

1-(3-(Pyrrolidin-1-yl)propyl)-1,2,3,4-tetrahydroquinolin-6-amine

To a stirred solution of 6-nitro-1-(3-(pyrrolidin-1-yl)propyl)-1,2,3,4-tetrahydroquinoline (270 mg, 0.933 mmol) in ethanol (5 ml) and tetrahydrofuran (5.00 ml) was added palladium on activated carbon, 10 wt. % (99 mg, 0.093 mmol). The resulting suspension was stirred under an atmosphere of hydrogen (balloon pressure) and monitored by TLC. After 2 h, the reaction mixture was filtered through a pad of celite, which was then washed with methanol. The filtrate was then concentrated, giving the desired 1-(3-(pyrrolidin-1-yl)propyl)-1,2,3,4-tetrahydroquinolin-6-amine (238 mg, 0.918 mmol, 98% yield) as a dark oil.

N-(1-(3-(pyrrolidin-1-yl)propyl)-1,2,3,4-tetrahydroquinolin-6-yl)thiophene-2-carboximidamide To a stirred solution of 1-(3-(pyrrolidin-1-yl)propyl)-1,2,3,4-tetrahydroquinolin-6-amine (115 mg, 0.443 mmol) in ethanol (6 ml) under argon was added methyl thiophene-2-carbimidothioate hydroiodide (253 mg, 0.887 mmol). The reaction mixture was stirred overnight at room temperature. The mixture was then diluted with water and sodium carbonate and extracted with dichloromethane (3×). The combined organics were dried, filtered and concentrated, then chromatographed on silica gel using ethyl acetate, followed by 5-10% (2M NH₃ in methanol) in dichloromethane as eluent to give the desired N-(1-(3-(pyrrolidin-1-yl)propyl)-1,2,3,4-tetrahydroquinolin-6-yl)thiophene-2-carboximidamide (119 mg, 0.323 mmol, 72.8% yield). $^1$H NMR (DMSO-d$_6$) δ 7.67 (d, J=3.6 Hz, 1H), 7.55 (d, J=5 Hz, 1H), 7.06 (dd, J=5, 3.6 Hz, 1H), 6.58 (brs, 2H), 6.48 (s, 1H), 6.27 (brs, 2H), 3.26-3.17 (m, 4H), 2.66 (t, J=6.3 Hz, 2H), 2.45-2.40 (m, 6H), 1.89-1.81 (m, 2H), 1.70-1.62 (m, 6H). ESI-MS (m/z, %) 369 (MH$^+$, 47), 185 (100). ESI-HRMS calculated for C21H29N4S (MH+), calculated: 369.2122, observed: 369.2107. HPLC purity: >95%.

Example 76

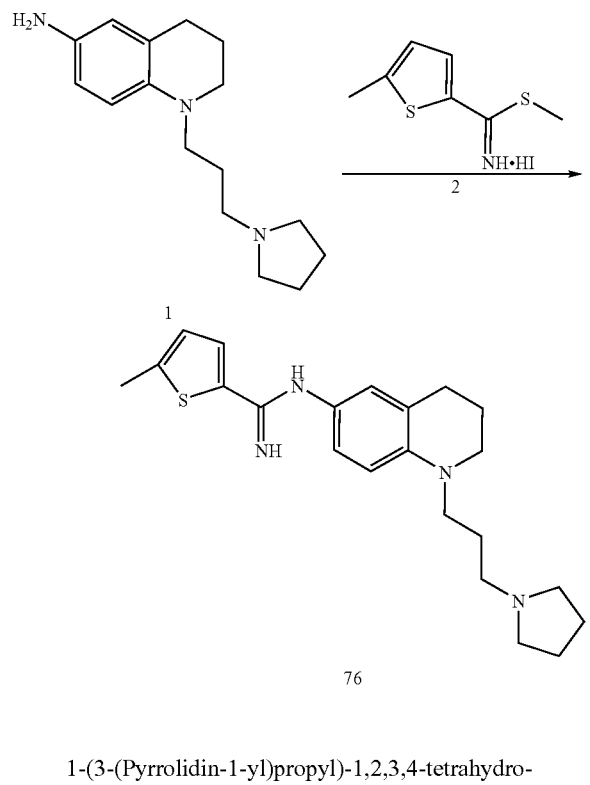

1-(3-(Pyrrolidin-1-yl)propyl)-1,2,3,4-tetrahydroquinolin-6-amine

See Example 75

5-Methyl-N-(1-(3-(pyrrolidin-1-yl)propyl)-1,2,3,4-tetrahydroquinolin-6-yl)thiophene-2-carboximidamide To a stirred solution of 1-(3-(pyrrolidin-1-yl)propyl)-1,2,3,4-tetrahydroquinolin-6-amine (115 mg, 0.443 mmol) in ethanol (6 ml) was added methyl 5-methylthiophene-2-carbimidothioate hydroiodide (265 mg, 0.887 mmol). The resulting suspension was stirred overnight at room temperature. The mixture was then diluted with water and sodium carbonate and extracted with dichloromethane. The combined organics were dried, filtered and concentrated, then chromatographed on silica gel with ethyl acetate, followed by 5-10% (2M NH3 in MeOH) in dichloromethane as eluent to give the desired 5-methyl-N-(1-(3-(pyrrolidin-1-yl)propyl)-1,2,3,4-tetrahydroquinolin-6-yl)thiophene-2-carboximidamide (98 mg, 0.256 mmol, 57.8% yield). $^1$H NMR (DMSO-d$_6$) δ 7.45 (d, J=3.3 Hz, 1H), 6.74 (d, J=2.4 Hz, 1H), 6.53 (m, 2H), 6.45 (s, 1H), 6.13 (brs, 2H), 3.26-3.16 (m, 4H), 2.68-2.63 (m, 2H), 2.43-2.39 (m, 6H), 2.41 (s, 3H), 1.86-1.82 (m, 2H), 1.68-1.64 (m, 6H). ESI-MS (m/z, %) 383 (MH+, 39), 272 (49), 192 (100). ESI-HRMS calculated for C22H31N4S (MH+), calculated: 383.2264, observed:

Example 77

Data were obtained using the methods of Examples 19a-b.

Table 4. Selective inhibition of human NOS and rat NOS by compounds of the Invention

| Example | hnNOS IC$_{50}$, μM | heNOS IC$_{50}$, μM | hiNOS IC$_{50}$, μM | Selectivity eNOS/nNOS |
|---|---|---|---|---|
| 22 | 1.72 | 151 | >100 | 87.8 |
| 23 | 0.26 (0.23) | 41.0 (>100) | >100 | 157 (>434) |
| 24 | 0.17 (0.12) | 15.4 (22) | 33.2 (>100) | 91.7 (183) |
| 25 | 12.3 | 151 | >100 | 12.3 |
| 26 | 9.91 | 80.1 | >100 | 8.1 |
| 27 | 0.35 (0.092) | 48.7 (42.1) | 54.4 (>100) | 138 (523) |
| 28 | 0.44 (0.12) | 99.1 (62.7) | 35.7 (>100) | 225 (321) |
| 29 | 0.25 (0.15) | 23.5 (>100) | 15.6 6.94 (>100) | 94.8 (321) |
| 30 | 0.57 0.38 0.18 (0.192) | 24.7 29 40.7 (inactive) | >100 (>100) | 43.6 76.3 226 |
| 31 | 0.6 (0.99) | 22.9 (>100) | 5.52 (>100) | 38.3 |
| 32 | 0.45 (0.94) | 37.7 (>100) | 0.26 (>100) | 83.2 |
| 33 | 2.2 | 193 | >100 | 90 |
| 34 | 0.39 | 45.1 | 1.28 | 115 |
| 35 | 0.36 | 27.5 | 4.9 | 75.8 |
| 36 | 0.38 | 47.1 | >100 | 123 |
| 37 | 1.22 | 50.3 | 4.35 | 41.2 |
| 38 | 10.0 | 148 | 8.21 | 14.8 |
| 39 | 2.96 | 20 | 1.34 | 6.8 |
| 40 | 1.9 | 56.3 | >100 | 29.6 |
| 41 | 3.3 | 194 | 3.27 | 58.8 |
| 42 | 0.09 | 24.3 | >100 | 270 |
| 43 | 0.18 | 27.4 | 7.03 | 152 |
| 44 | 0.12 (0.48) | 22.4 (0.63) | >100 (4.3) | 187 |
| 45 | 1.8 | 30.8 | >100 | 17 |
| 46 | 0.08 | 60.5 | >100 | 756 |
| 47 | 0.6 (3.8) | 156 (>100) | 6.57 (0.34) | 260 |
| 48 | 0.33 | 75 | 0.61 | 227 |
| 49 | 0.08 | 5.45 | | 68.1 |
| 50 | 0.43 | 21.2 | | 49 |
| 51 | 0.09 | 33.3 | | 370 |
| 52 | 0.3 | 13.5 | | 45 |
| 53 | 0.25 | 64.4 | | 256 |
| 54 | 0.27 (2.6) | 46.0 (12) | >100 (7.53) | 170 |
| 55 | 0.08 | 14.5 | >100 | 181 |
| 56 | 0.09 | 18.3 | 34 | 203 |
| Isomer 1 | (0.087) | (4.5) | | (51) |
| 57 | 0.32 | 199 | 40.4 | 622 |
| Isomer 2 | (0.504) | (>100) | | (>198) |
| 58 | 2.3 | 66.3 | >100 | 29 |
| 59 | 0.27 | 22.4 | 34.5 | 83 |
| 60 | 0.39 (0.44) | 52.8 (>100) | 16.6 | 135 (>227) |

-continued

| Example | hnNOS IC$_{50}$, µM | heNOS IC$_{50}$, µM | hiNOS IC$_{50}$, µM | Selectivity eNOS/nNOS |
|---|---|---|---|---|
| 61 | 0.26 | 30.2 | 2.9 | 116 |
|  | (1.1) | (6.2) | (8.0) | (5.6) |
| 62 | 0.13 | 63.9 | (7.0) | 492 |
|  | (0.94) |  |  |  |
| 63 | 0.235 | 22.5 |  | 95.7 |
| 64 | 0.68 | 82.5 |  | 121 |
| 65 | 0.31 | 22.5 | (7.5) | 73 |
| Isomer 1 | (0.28) | (9.08) |  | (32.4) |
| 66 | 0.01 | 14.2 | (2.9) | 1420 |
| Isomer 2 | (0.1) |  |  |  |
| 67 | 0.092 | 26.9 |  | 292 |
| 68 | 0.041 | 12.9 |  | 316 |
| 69 | 0.078 | 39.9 |  | 511 |
| 70 | 0.21 | 17.9 |  | 86.5 |
| 71 | 0.105 | 34.1 |  | 325 |

Rodent data in parentheses.

Example 78

Sciatic Cuff Model of Neuropathic Pain

Peripheral neuropathy resulting from nerve injury from postherpetic neuralgia, diabetes, cancer or trauma etc. in humans (or other species) can produce persistent pain characterized by symptoms of spontaneous pain and allodynia (pain or nociceptive response provoked by a normally innocuous mechanical stimulus). Several theories have been proposed to explain the mechanisms underlying basis for peripheral neuropathic pain including changes in the central nervous system particularly in the spinal dorsal horn including altered signal transduction mechanisms, central sensitization and decreased inhibitor mechanisms (G. M. Pitcher and J. L. Henry, Exp. Neurol. 2004, 186, 173-197 and references therein). In contrast to central mechanisms in peripheral neuropathy, modifications in peripheral sensory pathways (e.g. altered gene expression in large diameter non-nociceptive sensory neurons) resulting in expanded peripheral receptive fields and a persistent slowly decaying afterdischarge in spinal neurons may also contribute to neuropathic pain.

The Sciatic Nerve Cuff model in rats (Mosconi and Kruger, 1996, Pain 64, 37-57) involves implantation of a plastic cuff around the sciatic nerve that results in painful neuropathy several days after surgery and induction of nociceptive afterdischarge in spinal neurons after innocuous peripheral mechanical stimulation (G. M. Pitcher and J. L. Henry). Mechanical allodynia is measured in the ipsilateral paw using calibrated von Frey hair testing. A single acute application of the drug (i.p. dosing) reverses the post-cuff pain thresholds to mechanical stimulus towards normal threshold levels.

The study utilized a cuff model (Mosconi T, Kruger L. Fixed-diameter polyethylene cuffs applied to the rat sciatic nerve induce a painful neuropathy: ultrastructural morphometric analysis of axonal alterations. Pain 64: 37-57, 1996) to examine the therapeutic effectiveness of the test compound 11 on a battery of behavioural endpoints in rats.

Mechanical Allodynia—von Frey Hair

The testing chamber consists of a 30×30×30 cm Plexiglas box with a clear Plexiglas floor. This floor contained 0.5 cm diameter holes that are spaced 1.5 cm apart, and is positioned over a mirror, which allows an unobstructed view of the rat paws. Animals are placed in the testing chamber and allowed to acclimatize for 30 min prior to testing. von Frey filaments (Stoelting Co., Illinois, USA) are applied to the soft tissue of the plantar surface of the hind paw to determine the withdrawal threshold. The first filament applied corresponds to a force of 4.31 grams. If a negative response (no movement) is observed, a filament exerting greater force is applied, and if a positive response (paw withdrawal from platform) is observed, a filament of lesser force is used. Each filament is applied three times, at 3 sec intervals. A 50% response threshold is calculated according to the response pattern observed (described by Chaplan et al. 1994). The maximum score possible is 15 grams, and the minimum is 0.25 grams.

A baseline reading with von Frey hairs is taken before model induction. Thus rats are acclimatized to the testing chamber and readings are taken for at least three days for the baseline before any surgery. After the surgery von Frey hair testing for any development of mechanical sensitivity is assessed.

Open-Closed Elevated Platform

The testing apparatus consists of a long, narrow, rectangular platform (79 cm×17.5 cm or 31 in.×7 in.) that is elevated off the ground (1.1 m. or 43 in.). Half of the platform is enclosed by three walls and a ceiling, while the other half is open. There are no barriers between the two compartments, therefore the rat may move freely between them. A typical test consists of placing the rat on the open platform, and observing how much time it spends in each compartment, during a ten minutes observation period. The test is usually performed once with both compartments at room temperature for acclimatization purpose. A normal rat prefers to stay in the closed chamber. The test is performed a second time with the platform of the closed compartment at 1° C.-10° C. to study temperature and surrounding preferences in rats induced with various pain models. The test is performed a second time with the platform of the closed compartment at 0 C. Thus the preferred chamber becomes an aversive situation. A normal rat still prefers the closed cold chamber to an open space. This is different in the rats that develop cold sensitivity. Thus, time spent in each chamber is noted and the difference before and after surgery is indicative of the development of pain sensitivity. This test is designed to determine and measure any cold hypersensitivity on the feet. People with neuropathic pain typically feel cold as painful.

The animal will be placed into a box of approximately 12×12×12 inches. The bottom is filled with an ice-saline mixture and a metal plate is placed just on top of this mixture. The time taken to lift or lick a paw is taken as an inverse measure of the cold sensitivity.

This test will take approximately 2 minutes to run. Post-testing treatment—the feet will be wiped with a soft cloth or paper towel and the animal will be placed back in its home cage for five minutes. An allowance will be made for the time necessary to transfer to as well as adaptation to the next testing apparatus.

Model Induction

The method of inducing peripheral neuropathy is by implantation of a single cuff around the sciatic nerve, modified from the method described by Mosconi and Kruger (1996), where two to four cuffs were used. Rats are anaesthetized with a combination of ketamine (5 mg/100 g) and xylazine (0.5 mg/100 g), i.p. The left sciatic nerve is exposed after blunt dissection of overlying muscle and freed from surrounding tissue. A cuff made of a 2 mm segment of polyethylene (PE-90) tubing (Intramedic PE-90, Clay Adams, Division of Becton Dickinson, Parsippany, N.J.) slit longitudinally is fit around the nerve. Subsequently the muscle is sutured, and skin closed using suture clips. Antibiotic ointment (Nitrofurazone 0.2%) is applied over the wound, and 0.03 ml of the antibiotic Tribrissen 24% (trimethoprim-sulfadiazine) is injected subcutaneously. Animals are placed under a heating lamp until they recovered from the anaesthetic and then returned to their home cage.

Results from the testing of Compound 11 are shown in FIGS. 14 through 17. Thus an nNOS inhibitor of the invention is useful for the treatment of neuropathic pain associated with peripheral neuropathies.

After sciatic nerve injury with an implanted cuff, the animals exhibited tactile hypersensitivity that was stable over a period of at least four weeks after induction. Example 11 administration (i.p 30 mg/kg) reversed the tactile hypersensitivity at two and four hours after the first injection. The pre-injection reading on the second drug-administration day revealed sustained reversal of the tactile hypersensitivity—i.e. there was a full latent effect of the first dose. There was no further overt effect of Example 11 administration on tactile sensitivity on successive days.

The development of cold allodynia is associated with peripheral neuropathy and neuropathic pain (Seung Keun Back et. al. Neuroscience Lett. 2004, 368, 341-344). Naïve control rats do not display paw lifts in the cold plate test (4±2° C.) whereas sciatic nerve cuff-implanted rats exhibit a mean of approximately 18 paw lifts during the 10-minute test period averaged over the four test days. Daily administration of Example 11 (i.p. 30 mg/kg) decreases paw lifts to an average of approximately nine lifts during the 10-minute test period (FIG. 16).

After sciatic cuff implantation in the hind leg, the differential distribution of hind paw weight (prior to drug administration on each day) revealed a preferential placement on the contralateral hind paw—i.e. there was an avoidance of standing on the neuropathic paw. Administration of Example 11 on the first day produced a shift in weight placement toward even distribution between the two hind paws. This effect of Example 11 was observed at two hours and at four hours after drug administration whereas 24 hours after the first dose, the distribution of hind paw weight exhibited preferential placement on the contralateral hind paw. Drug administration on successive days produced a shift in hind paw weight placement toward even distribution on each day (FIG. 17).

Example 79

Irritable bowel syndrome (IBS), characterized by abdominal pain and bloating, is often poorly treated. Rectal instillation of butyrate provides a clinically relevant model of non-inflammatory colonic hypersensitivity in rats (Bourdu et. al. 2005) (FIG. 18). Referred lumbar hypersensitivity in the colonic hypersensitivity model was quantified by applying von Frey hairs to the lumbar dermatomes of rats (Bourdu S, Gastroenterology. 2005 June; 128(7)). Thus colonic administration of butyrate results in a tactile hypersensitivity in the abdominal area that can be reversed by the administration of a compound of the invention. FIG. 19 shows the effect of administration of compound 11 on visceral pain.

Example 80

FIG. 7 shows a schematic diagram of the Porreca model for allodynia (US 2008/0031822).
Animals. Male, Sprague Dawley rats (275-300 g) were purchased from Harlan Sprague Dawley (Indianapolis, Ind.). Animals were given free access to food and water. Animals were maintained on a 12 hour light (7 am to 7 pm) and 12 hour dark cycle (7 pm to 7 am). All procedures were in accordance with the policies and recommendations of the International Association for the Study of Pain and the National Institutes of Health guidelines and use of laboratory animals as well as approved by the Animal Care and Use Committee of the University of Arizona.
Surgical Preparation.
Migraine cannulation: Male Sprague Dawley rats were anesthetized using ketamine/xylazine (80 mg/kg, i.p.), the top of the head was shaved using a rodent clipper (Oster Golden A5 w/size 50 blade), and the shaved area was cleaned with betadine and 70% ethanol. Animals were placed into a stereotaxic apparatus (Stoelting model 51600) and the body core temperatures of 37° C. were maintained using a heating pad placed below the animals. Within the shaved and cleaned area on the head, a 2 cm incision was made using a scalpel with a #10 blade and any bleeding was cleaned using sterile cotton swabs. Location of bregma and midline bone sutures were identified as references and a small hole 1 mm in diameter was made using a hand drill without breaking the dura but deep enough to expose the dura. Two additional holes (1 mm in diameter) 4 to 5 mm from the previous site were made in order to mount stainless steel screws (Small Parts #A-MPX-080-3F) securing the cannula through which an inflammatory soup could be delivered to induce experimental migraine. A modified intracerebroventricular (ICV) cannula (Plastics One #C313G) was placed into the hole without penetrating into or through the dura. The ICV cannula was modified by cutting it to a length of 1 mm from the bottom of the plastic threads using a Dremel mototool and a file to remove any steel burrs. Once the modified migraine cannula was in place, dental acrylic was placed around the migraine cannula and stainless steel screws in order to assure that the cannula was securely mounted. Once the dental acrylic was dry (i.e., after 10-15 min) the cap of the cannula was secured on top to avoid contaminants entering the cannula and the skin was sutured back using 3-0 silk suture. Animals were given an antibiotic injection (Amikacin C, 5 mg/kg, i.m.) and removed from the stereotaxic frame and allowed to recover from anesthesia on a heated pad. Animals were placed in a clean separate rat cage for a 5 day recovery period.
Injections. Subcutaneous injections: Subcutaneous (s.c.) injections were performed by manually holding the animal and inserting a 25 gauge disposable needle on a disposable 1 cc syringe into the abdominal region of the animal assuring that the needle remained between the muscle and the skin of the animal. Injections of compounds were performed over a 5 sec period and were noted as positive by the development of an out-pocketing of the skin at the site of injection. Oral delivery was accomplished by using an 18 gauge gavage needle attached to a 1 cc syringe.
Migraine cannula injections: An injection cannula (Plastics One, C313I cut to fit the modified ICV cannulas) connected to a 25 μl Hamilton Syringe (1702SN) by tygon tubing (Cole-Palmer, 95601-14) was used to inject 10 μl of the inflammatory mediators solution onto the dura.
Behavioral Testing. Naïve animals prior to the day of migraine surgery are placed in suspended plexiglass chambers (30 cm L×15 cm W×20 cm H) with a wire mesh bottom (1 cm²) and acclimated to the testing chambers for 30 minutes.
Hindpaw Sensory Thresholds to Non-Noxious Tactile Stimuli in Rats
The paw withdrawal thresholds to tactile stimuli were determined in response to probing with calibrated von Frey filaments (Stoelting, 58011). The von Frey filaments were applied perpendicularly to the plantar surface of the hind paw of the animal until it buckles slightly, and is held for 3 to 6 sec. A positive response was indicated by a sharp withdrawal of the paw. The 50% paw withdrawal threshold was determined by the non-parametric method of Dixon (1980). An initial probe equivalent to 2.00 g was applied and if the response was negative the stimulus was increased one increment, otherwise a positive response resulted in a decrease of one increment. The stimulus was incrementally increased until a positive response was obtained, then decreased until a negative result was observed. This "up-down" method was repeated until three changes in behavior were determined. The pattern of positive and negative responses was tabulated. The 50% paw withdrawal threshold is determined as $(10^{[Xf+kM]})/10,000$, where Xf=the value of the last von Frey filament employed, k=Dixon value for the positive/negative pattern, and M=the mean (log) difference between stimuli. Only naïve animals with baselines of 11 to 15 g were used in the experiment. Fifteen grams was used as the maximal cut-off. Five days post migraine surgery animals paw withdrawal thresholds were re-tested using the same habituation and von Frey procedure as stated above. Data were converted to % "antiallodynia" by the formula: % activity=100×(post-migraine value−baseline value)/(15 g−baseline value). Only animals that demonstrated no difference in their tactile hypersensitivity as compared to their pre-migraine surgery values were used in all studies.

After establishing baseline paw withdrawal thresholds, individual animals were removed from the testing chamber, the cap of the migraine cannula was removed and animals received an injection of either a mixture of inflammatory mediators (1 mM Histamine, 1 mM 5-HT [Serotonin], 1 mM Bradykinin, 1 mM $PGE_2$) or vehicle at 10 uL volume via the migraine cannula over a 5 to 10 second period. The inflammatory mediator (IM) cocktail was made fresh on the day of each experiment. The cap of the migraine cannula was replaced, individual animals were placed back into their corresponding testing chamber and paw withdrawal thresholds were measured at 1 hour intervals over a 6 hour time course. Data were converted to % "antiallodynia" by the formula: % activity=100×(post-IM value−pre-IM baseline value)/(15 g−pre-IM baseline value).

Data on selected compounds of the invention obtained using this model are shown in FIGS. 8 (Compound 23) and 13 (Compound 28). Application of an inflammatory soup (IS) onto the dura results in a decrease in the hindpaw withdrawal threshold upon stimulation with von Frey filaments. Administration of Sumatriptan succinate (1 mg/kg s.c.) 5 minutes prior to the addition of the soup results in the prevention of the development of hindpaw allodynia as measured two hours after IS administration. Similarly the non-selective NOS inhibitor L-NMMA (10 mg/kg i.v) or 23 and 28 (30 mg/kg p.o.) 15 minutes prior to IS reverses the development of hindpaw allodynia. Thus non selective NOS inhibitors such as L-NMMA, or more selective nNOS inhibitors (e.g., compounds 23 and 28) should be effective for the treatment of migraine.

Other Embodiments

While the present invention has been described with reference to what are presently considered to be the preferred examples, it is to be understood that the invention is not limited to the disclosed examples. To the contrary, the invention is intended to cover various modifications and equivalent arrangements included within the spirit and scope of the appended claims.

All publications, patents and patent applications are herein incorporated by reference in their entirety to the same extent as if each individual publication, patent or patent application was specifically and individually indicated to be incorporated by reference in its entirety. Where a term in the present application is found to be defined differently in a document incorporated herein by reference, the definition provided herein is to serve as the definition for the term.

Other embodiments are in the claims.

What is claimed is:
1. A compound having the formula:

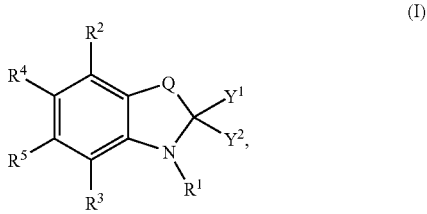

wherein,
Q is $(CHR^6)_{1-3}$;
$R^1$ and each $R^6$ is, independently, H, optionally substituted $C_{1-6}$ alkyl, optionally substituted $C_{1-4}$ alkaryl, optionally substituted $C_{1-4}$ alkheterocyclyl, optionally substituted $C_{2-9}$ heterocyclyl, or optionally substituted $C_{3-8}$ cycloalkyl;
wherein $Y^1$ and $Y^2$ are each H, or $Y^1$ and $Y^2$ together are =O, or $Y^1$ and $Y^2$ are independently H, optionally substituted $C_{1-6}$ alkyl, optionally substituted $C_{6-10}$ aryl, optionally substituted $C_{1-6}$ alkaryl, optionally substituted $C_{2-9}$ heterocyclyl, hydroxy, optionally substituted $C_{1-6}$ alkoxy, optionally substituted $C_{1-6}$ thioalkoxy, or optionally substituted $C_{1-4}$ alkheterocyclyl;
one and only one of $R^2$, $R^3$, $R^4$, and $R^5$ is $(CH_2)_{r2}NHC(NH)R^{24}$;
wherein r2 is 0;
$R^{24}$ is 2-thienyl;
and each of the remaining $R^2$, $R^3$, $R^4$, and $R^5$ is, independently, H or fluoro;
or a pharmaceutifully acceptable salt thereof.

2. The compound of claim 1,
wherein,
Q is $(CHR^6)_{1-3}$;
$R^1$ and each $R^6$ is, independently, H, optionally substituted $C_{1-6}$ alkyl, optionally substituted $C_{1-4}$ alkaryl, optionally substituted $C_{1-4}$ alkheterocyclyl, optionally substituted $C_{2-9}$ heterocyclyl, or optionally substituted $C_{3-8}$ cycloalkyl;
each of $R^2$ and $R^3$ is, independently, H or fluoro;
each of $R^4$ and $R^5$ is, independently, H or $(CH_2)_{r2}NHC(NH)R^{24}$;
wherein $Y^1$ and $Y^2$ are each H, or $Y^1$ and $Y^2$ together are =O;
wherein one, but not both, of $R^4$ and $R^5$ is H;
or a pharmaceutically acceptable salt or thereof.

3. The compound of claim 1, wherein $Y^1$ and $Y^2$ together are =O, and Q is $(CHR^6)_2$.

4. The compound of claim 1, wherein $Y^1$ and $Y^2$ are each H, and Q is $(CHR^6)_2$.

5. The compound of claim 1, wherein $Y^1$ and $Y^2$ together are =O, and Q is $CHR^6$.

6. The compound of claim 1, wherein $Y^1$ and $Y^2$ are each H, and Q is $CHR^6$.

7. The compound of claim 1, wherein $Y^1$ and $Y^2$ together are =O, and Q is $(CHR^6)_3$.

8. The compound of claim 1, wherein $Y^1$ and $Y^2$ are each H, and Q is $(CHR^6)_3$.

9. The compound of claim 1, wherein $R^4$ or $R^5$ has the formula:
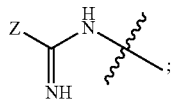 (II)
wherein Z is $R^{2A}$.
10. The compound of claim 1, wherein $R^2$ or $R^3$ has the formula:
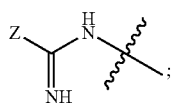 (II)
wherein Z is $R^{2A}$.
11. A compound of the formula:
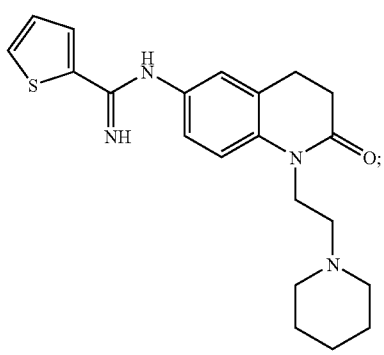
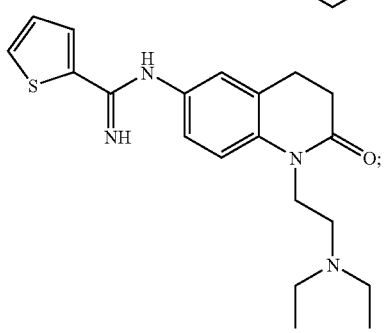
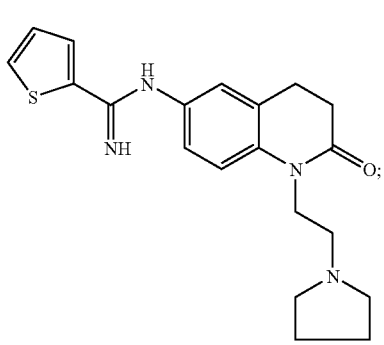
-continued
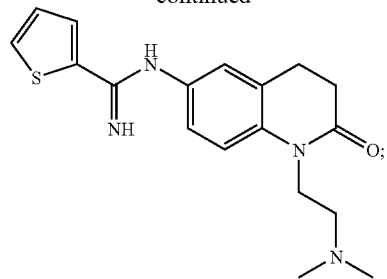
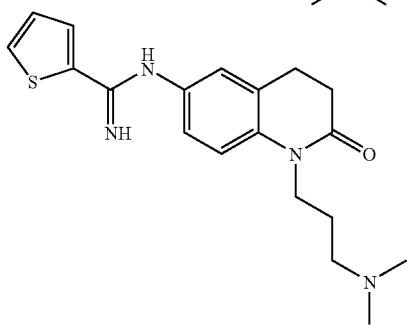
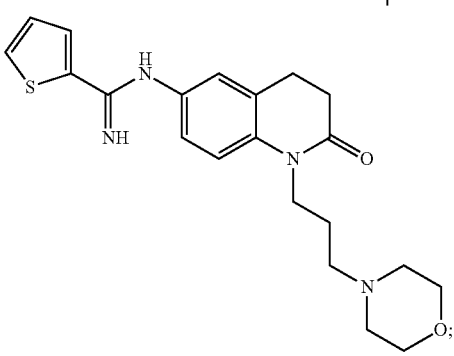
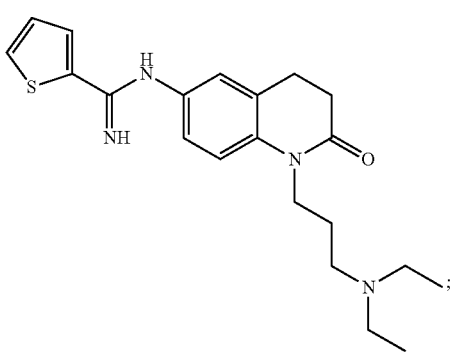
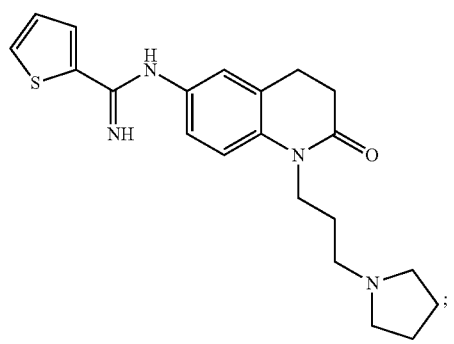

229
-continued
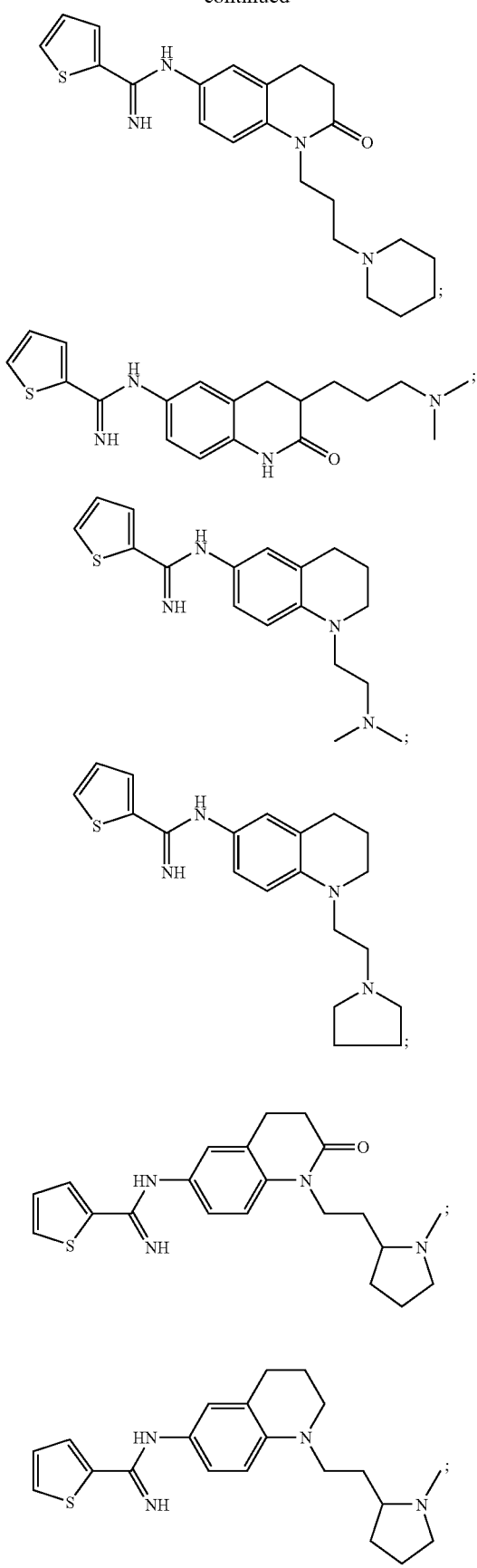
230
-continued
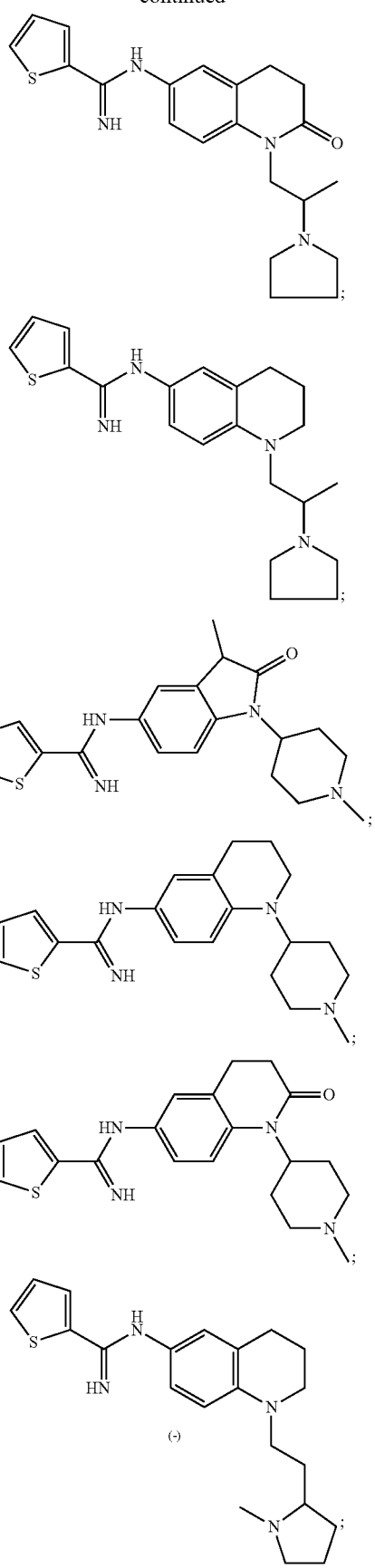

231
-continued
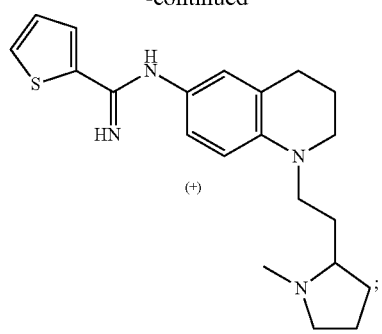
(+)
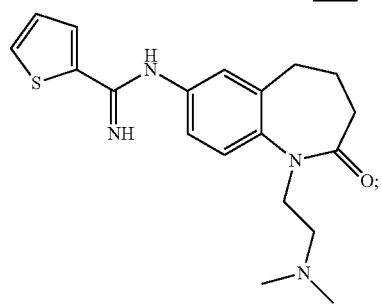
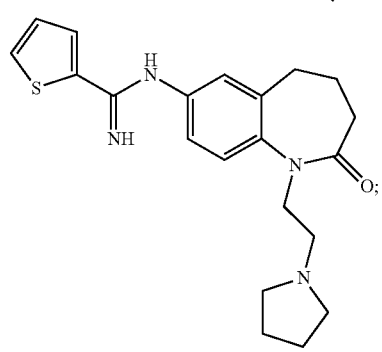
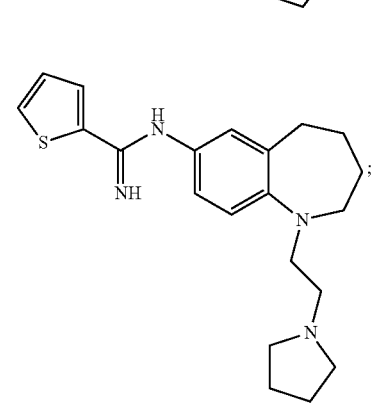
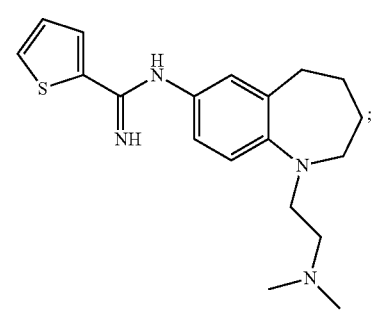
232
-continued
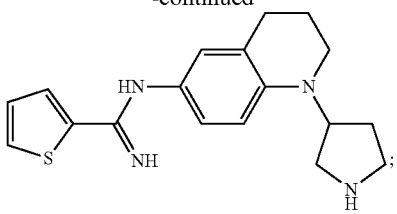
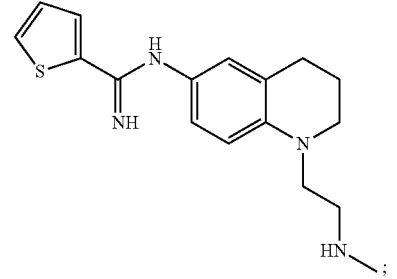
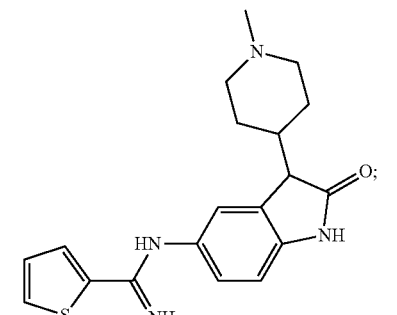
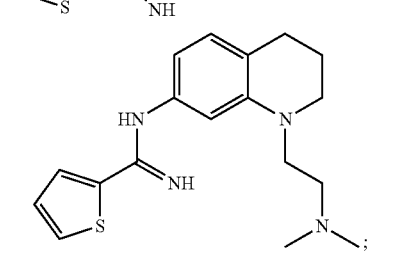
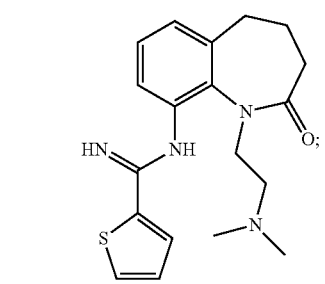
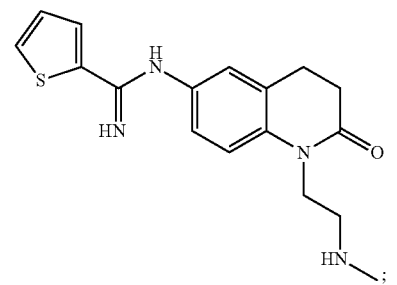

233
-continued
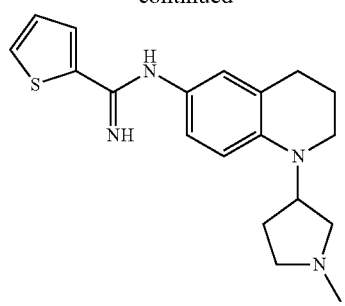
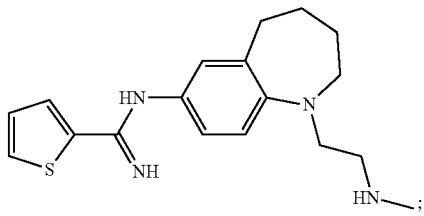
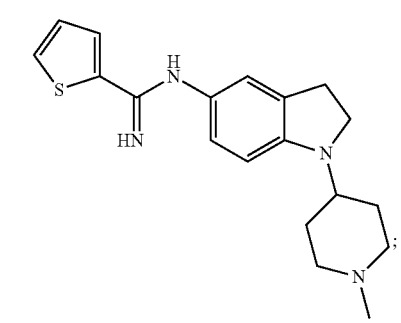
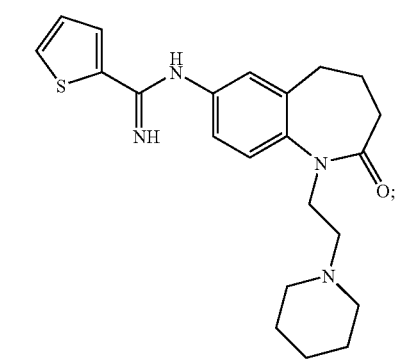
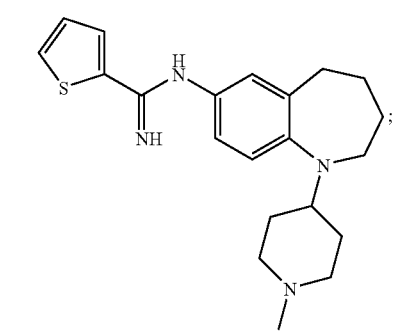
234
-continued
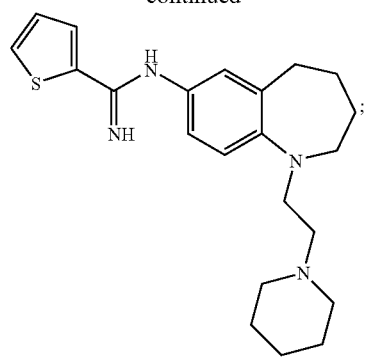
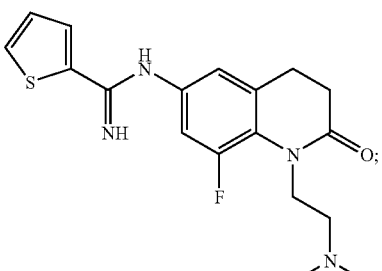
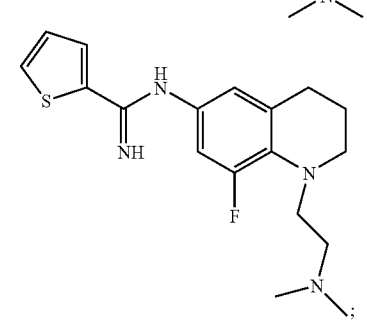
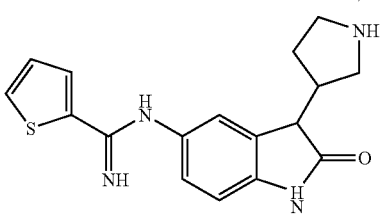
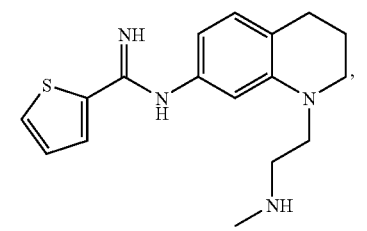
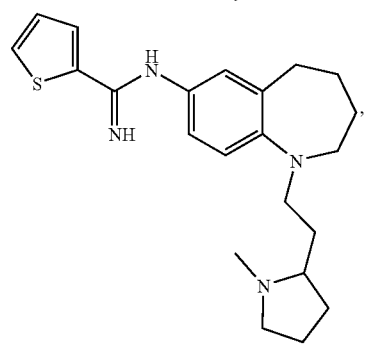

235
-continued
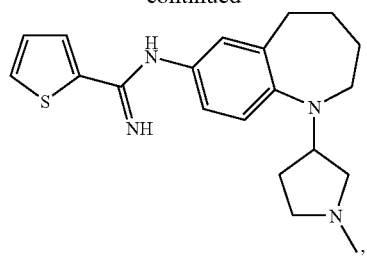
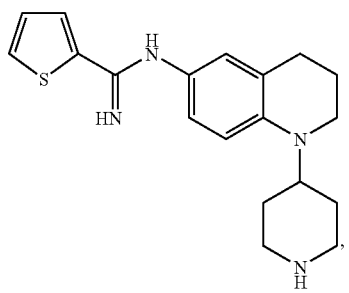
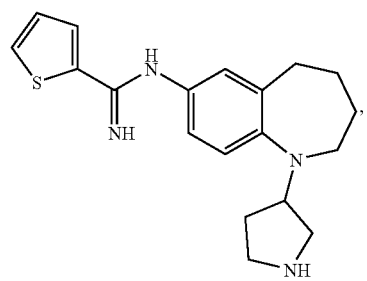
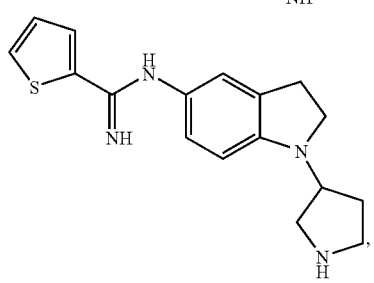
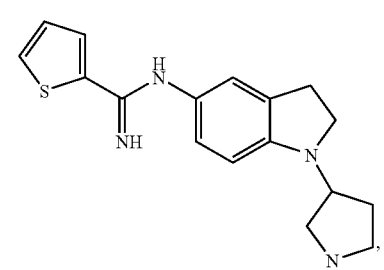
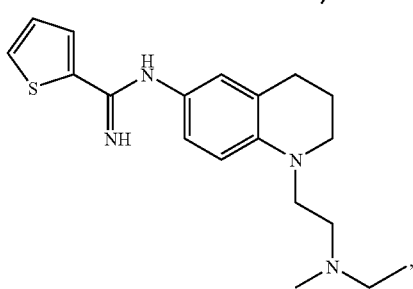
236
-continued
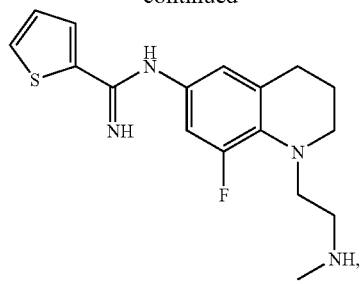
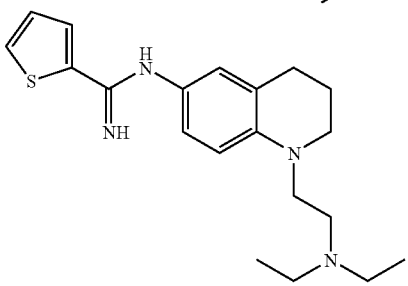
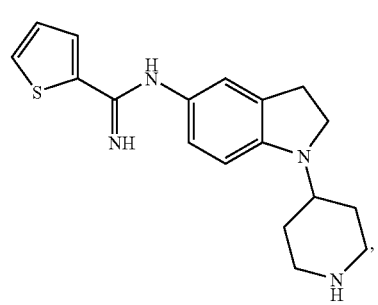
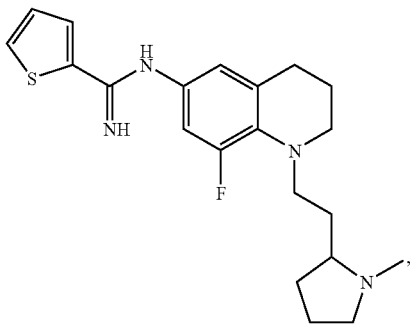
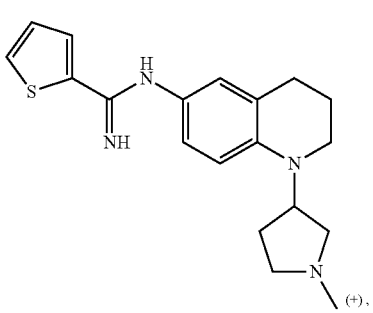

237
-continued
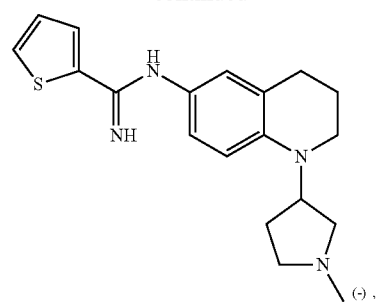
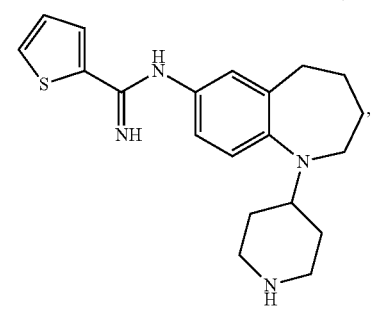
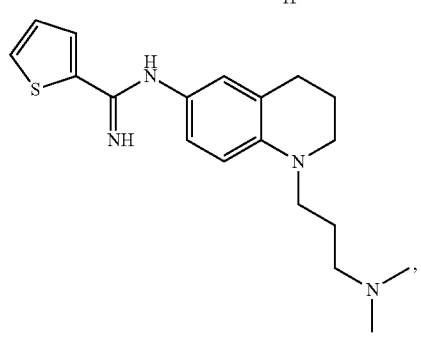
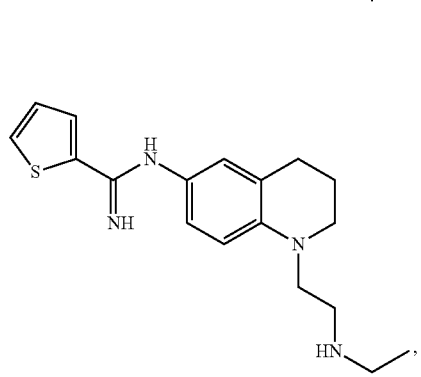
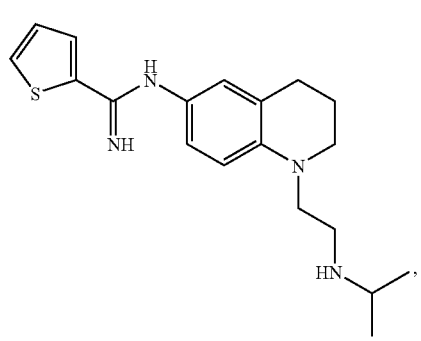
238
-continued
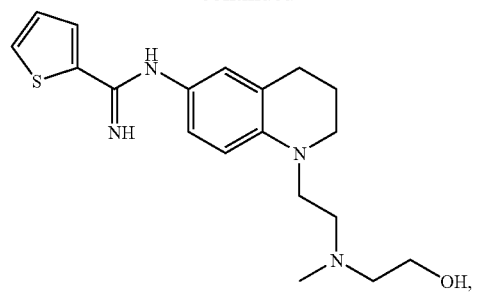
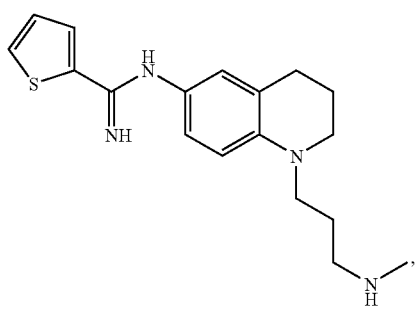
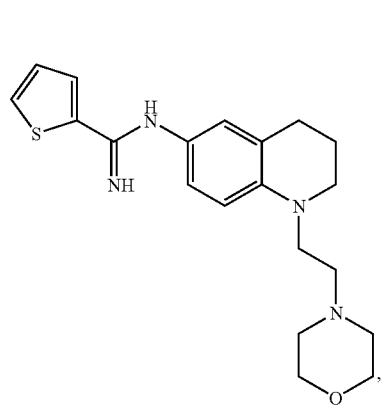
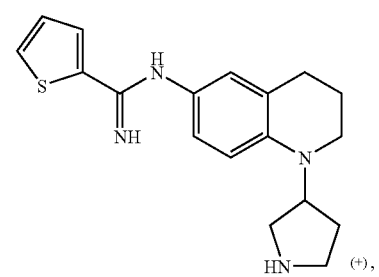
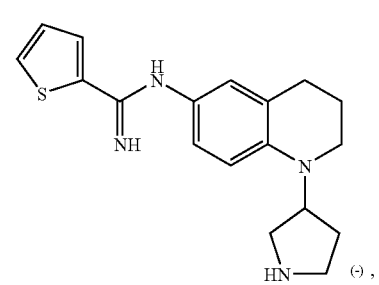

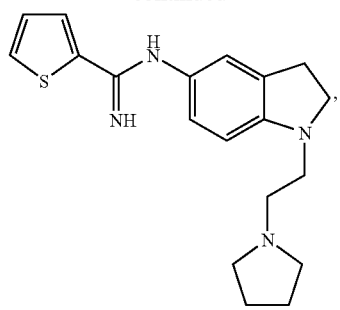
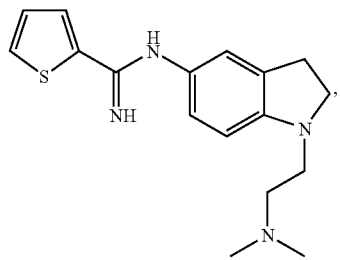
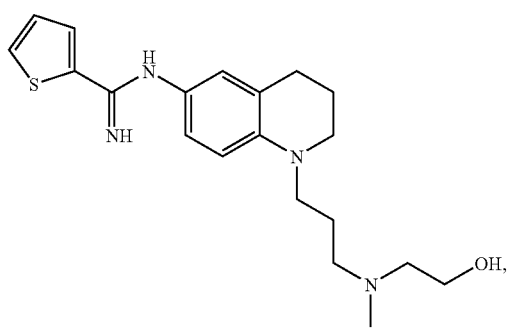
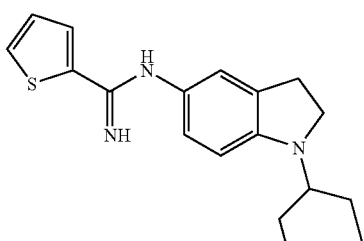, Diastereomer 1,
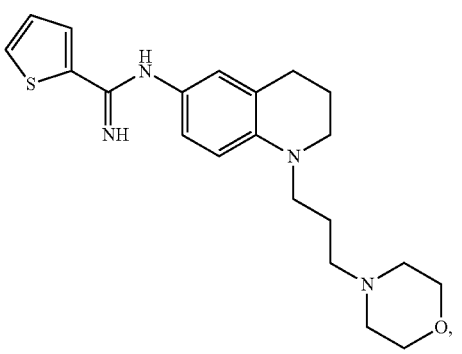
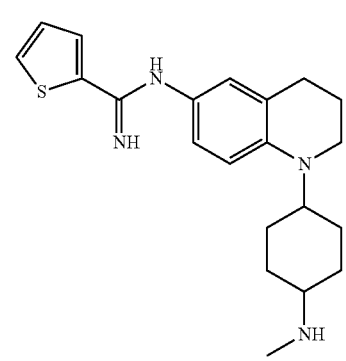 Isomer 1,
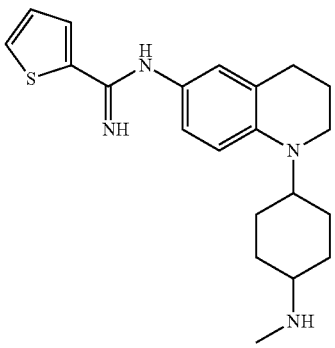 Isomer 2,
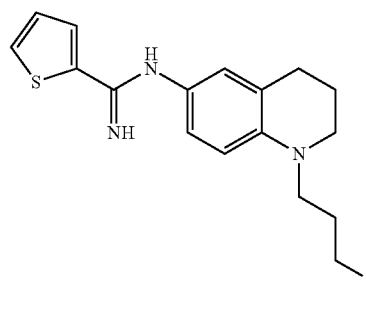

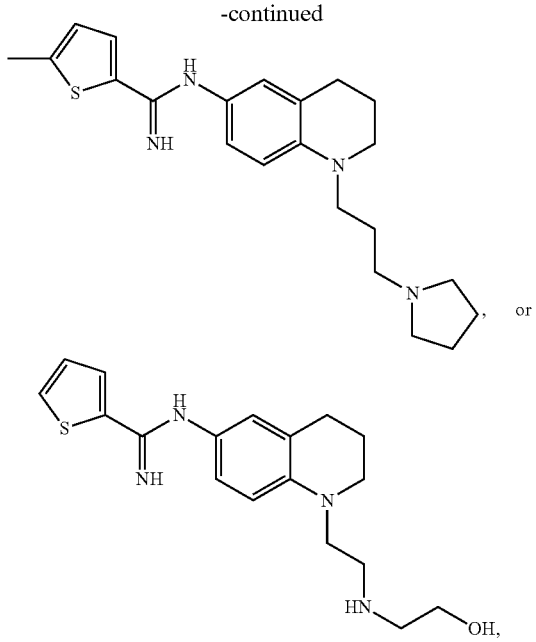

or a pharmaceutically acceptable salt thereof.

12. A pharmaceutical composition comprising a compound of claim 1 or a a pharmaceutically acceptable salt thereof, and a pharmaceutically acceptable excipient.

13. The compound of claim 1, wherein $R^1$ or $R^6$ is optionally substituted $C_{1-6}$ alkyl comprising —$NR^G R^H$, where each of $R^G$ and $R^H$ is, independently, (a) hydrogen, (b) optionally substituted $C_{1-6}$ alkyl, or (c) optionally substituted $C_{3-8}$ cycloalkyl.

14. The compound of claim 13, wherein said optionally substituted $C_{1-6}$ alkyl of (b) is hydroxyalkyl or unsubstituted $C_{1-6}$ alkyl.

15. A compound having the formula

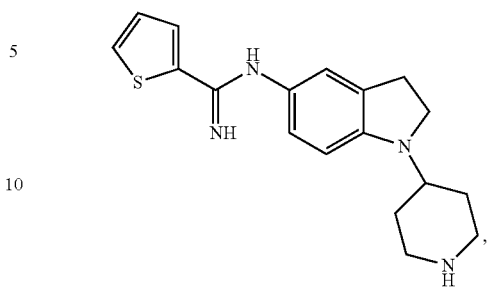

or a pharmaceutically acceptable salt thereof.

16. A pharmaceutical composition comprising a compound having the formula

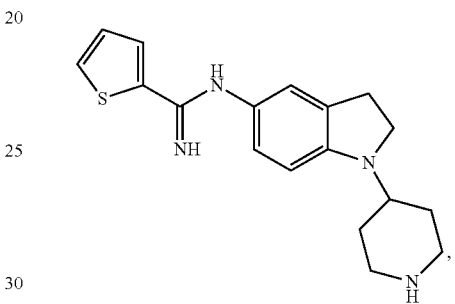

or a pharmaceutically acceptable salt thereof, and a pharmaceutically acceptable excipient.

17. The pharmaceutical composition of claim 16, wherein said composition is formulated for topical administration.

* * * * *